(12) United States Patent
Lin et al.

(10) Patent No.: US 10,351,834 B2
(45) Date of Patent: *Jul. 16, 2019

(54) GH61 POLYPEPTIDE VARIANTS AND POLYNUCLEOTIDES ENCODING SAME

(71) Applicants: NOVOZYMES, INC., Davis, CA (US); NOVOZYMES A/S, Bagsvaerd (DK)

(72) Inventors: Janine Lin, Davis, CA (US); Doreen Bohan, Fairfield, CA (US); Michelle Maranta, Davis, CA (US); Leslie Beresford, Woodland, CA (US); Michael Lamsa, Woodland, CA (US); Bjarne Gram Hansen, Frederiksberg (DK); Frank Winther Rasmussen, Roskilde (DK); Matt Sweeney, Sacramento, CA (US); Douglas J. Boyle, III, Davis, CA (US)

(73) Assignees: Novozymes, Inc., Davis, CA (US); Novozymes A/S, Bagsvaerd (DK)

( * ) Notice: Subject to any disclaimer, the term of this patent is extended or adjusted under 35 U.S.C. 154(b) by 715 days.

This patent is subject to a terminal disclaimer.

(21) Appl. No.: 14/358,642

(22) PCT Filed: Nov. 21, 2012

(86) PCT No.: PCT/US2012/066278
§ 371 (c)(1),
(2) Date: May 15, 2014

(87) PCT Pub. No.: WO2013/119302
PCT Pub. Date: Aug. 15, 2013

(65) Prior Publication Data
US 2015/0007369 A1    Jan. 1, 2015

Related U.S. Application Data

(60) Provisional application No. 61/562,277, filed on Nov. 21, 2011.

(51) Int. Cl.
| | | |
|---|---|---|
| *C12N 9/02* | (2006.01) |
| *C12N 9/24* | (2006.01) |
| *D21C 5/00* | (2006.01) |
| *C11D 3/386* | (2006.01) |
| *C12P 19/02* | (2006.01) |
| *D21H 17/00* | (2006.01) |

(52) U.S. Cl.
CPC ............ *C12N 9/2402* (2013.01); *C11D 3/386* (2013.01); *C12N 9/0004* (2013.01); *C12N 9/0071* (2013.01); *C12P 19/02* (2013.01); *D21C 5/005* (2013.01); *D21H 17/005* (2013.01)

(58) Field of Classification Search
CPC ....... C12N 9/2402; C12N 9/14; C12N 9/0071
See application file for complete search history.

(56) References Cited

U.S. PATENT DOCUMENTS

| | | | | |
|---|---|---|---|---|
| 8,541,651 B2 * | 9/2013 | Wogulis | ................ | C12P 19/14 800/284 |
| 2015/0082493 A1 * | 3/2015 | Lin | ...................... | C12N 9/0071 800/298 |

FOREIGN PATENT DOCUMENTS

| | | | |
|---|---|---|---|
| WO | 2005074647 A2 | 8/2005 | |
| WO | 2005074656 A2 | 8/2005 | |
| WO | 2006074435 A2 | 7/2006 | |
| WO | 2007089290 A2 | 8/2007 | |
| WO | 2008148131 A1 | 12/2008 | |
| WO | 2008151043 A1 | 12/2008 | |
| WO | 2009085859 A2 | 7/2009 | |
| WO | 2009085864 A2 | 7/2009 | |
| WO | 2009085868 A1 | 7/2009 | |
| WO | 2009085935 A2 | 7/2009 | |
| WO | 2010065830 A1 | 6/2010 | |
| WO | 2010138754 A1 | 12/2010 | |
| WO | 2011005867 A1 | 1/2011 | |
| WO | 2011035027 A2 | 3/2011 | |
| WO | 2011039319 A1 | 4/2011 | |
| WO | 2011041397 A1 | 4/2011 | |
| WO | 2011041504 A1 | 4/2011 | |
| WO | 2011050037 A1 | 4/2011 | |
| WO | WO 2011/050037 * | 4/2011 | ............... C12N 9/42 |
| WO | 2011123505 A1 | 10/2011 | |
| WO | 2012000892 A1 | 1/2012 | |
| WO | 2012044835 A1 | 4/2012 | |
| WO | 2012068509 A1 | 5/2012 | |

OTHER PUBLICATIONS

NCBI Reference Sequence: XP_002559170.1, available Aug. 14, 2009.*
NCBI Reference Sequence XP_001271679.1, available online Feb. 21, 2008.*
Quinlan et al (PNAS, Sep. 13, 2011, 108(37) pp. 15079-15084).*
Langston et al (Applied and Environmental Microbiology, Oct. 2011, p. 7007-7015).*
Horn et al. Biotechnology for Biofuels 2012, 5:45.*
Dimarogona et al (Bioresourse Technology 110 (202) 480-487.*
Harris et al, 2010, Biochem 49(15), 3305-3316 (Year: 2010).*
WO 2012-068509—Geneseq Access No. AZW46086.
Vaillancourt et al, 2010—Genbank Acces No. EFQ351701.
US 2011-099671—EBI Access No. AZH97000.
Harris et al, 2010, Biochem 49(15), 3305-3316.

* cited by examiner

*Primary Examiner* — Lee A Visone
(74) *Attorney, Agent, or Firm* — Robert L. Starnes

(57) ABSTRACT

The present invention relates to GH61 polypeptide variants. The present invention also relates to polynucleotides encoding the variants; nucleic acid constructs, vectors, and host cells comprising the polynucleotides; and methods of using the variants.

34 Claims, 10 Drawing Sheets

Specification includes a Sequence Listing.

```
        M  T  L  S  K  I  T  S  I  A  G  L  L  A  S  A  S  L  V  A  G  H  G  F  V  S  G
  1 ATGACTTTGT CCAAGATCAC TTCCATTGCT GGCCTTCTGG CCTCAGCGTC TCTCGTGGCT GGCCACGGCT TTGTTTCTGG
        I  V  A  D  G  K  Y                                                              Y  G
 81 CATTGTTGCT GATGGGAAAT AGTATGTGCT TGAACCACAC AAATGACAGC TGCAACAGCT AACTTCTATT CCAGTTACGG
        G  Y  L  V  N  Q  Y  P  Y  M  S  N  P  P  D  T  I  A  W  S  T  T  A  T  D  L
161 AGGGTACCTT GTTAACCAAT ACCCCTACAT GAGCAACCCT CCCGACACCA TTGCCTGGTC CACCACCGCC ACCGACCTCG
        G  F  V  D  G  T  G  Y  Q  S  P  D  I  I  C  H  R  D  A  K  N  G  K  L  T  A  T
241 GCTTTGTGGA CGGCACCGGC TACCAGTCTC CGGATATTAT CTGCCACAGA GACGCAAAGA ATGGCAAGTT GACCGCAACC
        V  A  A  G  S  Q  I  E  F  Q  W  T  T  W  P  E  S  H  H  G  P
321 GTTGCAGCCG GTTCACAGAT CGAATTCCAG TGGACGACGT GGCCAGAGTC TCACCATGGA CCGGTACGAC GCCGAAGAGA
                                                              L  I  T  Y  L  A  P  C  N  G  D  C  A  T
401 AGAGAACATA TTGTGACCAG ATAGGCTAAC ATAGCATAGT TGATTACTTA CCTCGCTCCA TGCAACGGCG ACTGTGCCAC
        V  D  K  T  T  L  K  F  V  K  I  A  A  Q  G  L  I  D  G  S  N  P  P  G  V  W
481 CGTGGACAAG ACCACCCTGA AGTTTGTCAA GATCGCCGCT CAAGGCTTGA TCGACGGCTC CAACCCACCT GGTGTTTGGG
        A  D  D  E  M  I  A  N  N  N  T  A  T  V  T  I  P  A  S  Y  A  P  G  N  Y  V  L
561 CTGATGATGA AATGATCGCC AACAACAACA CGGCCACAGT GACCATTCCT GCCTCCTATG CCCCCGGAAA CTACGTCCTT
        R  H  E  I  I  A  L  H  S  A  G  N  L  N  G  A  Q  N  Y  P  Q  C  F  N  I  Q  I
641 CGCCACGAGA TCATCGCCCT TCACTCTGCG GGTAACCTGA ACGGCGCGCA GAACTACCCC CAGTGTTTCA ACATCCAAAT
        T  G  G  G  S  A  Q  G  S  G  T  A  G  T  S  L  Y  K  N  T  D  P  G  I  K  F
721 CACCGGTGGC GGCAGTGCTC AGGGATCTGG CACCGCTGGC ACGTCCCTGT ACAAGAATAC TGATCCTGGC ATCAAGTTTG
        D  I  Y  S  D  L  S  G  G  Y  P  I  P  G  P  A  L  F  N  A  *
801 ACATCTACTC GGATCTGAGC GGTGGATACC CTATTCCTGG TCCTGCACTG TTCAACGCTT AA
```

Fig. 1

SEQUENCE LISTING

<160> NUMBER OF SEQ ID NOS: 346

<210> SEQ ID NO 1
<211> LENGTH: 1846
<212> TYPE: DNA
<213> ORGANISM: Thielavia terrestris

<400> SEQUENCE: 1

| | | | | | |
|---|---|---|---|---|---|
| aattgaagga | gggagtggcg | gagtggccac | caagtcaggc | ggctgtcaac | taaccaagga | 60 |
| tgggaacagt | tcggctcgcc | ttgcccgagg | gcagcgttcc | ctgatgggga | cgaaccatgg | 120 |
| gactggggtc | agctgctgta | taaaagttca | aatcgatgat | ctctcagatg | gcgctgctgg | 180 |
| ggtgttctgc | gcttttccat | cctcgcaacc | tggtatccca | ctagtccagc | gttcggcacc | 240 |
| atgaagtcgt | tcaccattgc | cgccttggca | gccctatggg | cccaggaggc | cgccgcccac | 300 |
| gcgaccttcc | aggacctctg | gattgatgga | gtcgactacg | gctcgcaatg | tgtccgcctc | 360 |
| ccggcgtcca | actcccccgt | caccaatgtt | gcgtccgacg | atatccgatg | caatgtcggc | 420 |
| acctcgaggc | ccaccgtcaa | gtgcccggtc | aaggccggct | ccacggtcac | gatcgagatg | 480 |
| caccaggttc | gcacgcctct | ctgcgtaggc | cccccagcta | ctatatggca | ctaacacgac | 540 |
| ctccagcaac | ctggcgaccg | gtcttgcgcc | aacgaggcta | tcggcggcga | ccactacggc | 600 |
| cccgtaatgg | tgtacatgtc | caagtcgat | gacgcggtga | cagccgacgg | ttcatcgggc | 660 |
| tggttcaagg | tgttccagga | cagctgggcc | aagaacccgt | cgggttcgac | gggcgacgac | 720 |
| gactactggg | gcaccaagga | cctcaactcg | tgctgcggca | agatgaacgt | caagatcccc | 780 |
| gaagacatcg | agccgggcga | ctacctgctc | cgcgccgagg | ttatcgcgct | gcacgtggcc | 840 |
| gccagctcgg | gcggcgcgca | gttctacatg | tcctgctacc | agctgaccgt | gacgggctcc | 900 |
| ggcagcgcca | cccccctcgac | cgtgaatttc | ccgggcgcct | actcggccag | cgacccgggc | 960 |
| atcctgatca | acatccacgc | gcccatgtcg | acctacgtcg | tcccgggccc | gaccgtgtac | 1020 |
| gcgggcggct | cgaccaagtc | ggctggcagc | tcctgctccg | gctgcgaggc | gacctgcacg | 1080 |
| gttggttccg | gccccagcgc | gacactgacg | cagcccacct | ccaccgcgac | cgcgaccctcc | 1140 |
| gcccctggcg | gcggcggctc | cggctgcacg | gcggccaagt | accagcagtg | cggcggcacc | 1200 |
| ggctacactg | ggtgcaccac | ctgcgctgta | agttccctcg | tgatatgcag | cggaacaccg | 1260 |
| tctggactgt | tttgctaact | cgcgtcgtag | tccgggtcta | cctgcagcgc | cgtctcgcct | 1320 |
| ccgtactact | cgcagtgcct | ctaagccggg | agcgcttgct | cagcgggctg | ctgtgaagga | 1380 |
| gctccatgtc | cccatgccgc | catggccgga | gtaccgggct | gagcgcccaa | ttcttgtata | 1440 |
| tagttgagtt | ttcccaatca | tgaatacata | tgcatctgca | tggactgttg | cgtcgtcagt | 1500 |
| ctacatcctt | tgctccactg | aactgtgaga | ccccatgtca | tccggaccat | tcgatcggtg | 1560 |
| ctcgctctac | catctcggtt | gatgggtctg | ggcttgagag | tcactggcac | gtcctcggcg | 1620 |
| gtaatgaaat | gtggaggaaa | gtgtgagctg | tctgacgcac | tcggcgctga | tgagacgttg | 1680 |
| agcgcggccc | acactggtgt | tctgtaagcc | agcacacaaa | agaatactcc | aggatggccc | 1740 |
| atagcggcaa | atatacagta | tcagggatgc | aaaaagtgca | aaagtaaggg | gctcaatcgg | 1800 |
| ggatcgaacc | cgagacctcg | cacatgactt | atttcaagtc | agggt | | 1846 |

<210> SEQ ID NO 2
<211> LENGTH: 326
<212> TYPE: PRT
<213> ORGANISM: Thielavia terrestris

<400> SEQUENCE: 2

```
Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
            20                  25                  30

Tyr Gly Ser Gln Cys Val Arg Leu Pro Ala Ser Asn Ser Pro Val Thr
        35                  40                  45

Asn Val Ala Ser Asp Asp Ile Arg Cys Asn Val Gly Thr Ser Arg Pro
    50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
                100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Tyr Trp Gly
    130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
        180                 185                 190

Tyr Gln Leu Thr Val Thr Gly Ser Gly Ser Ala Thr Pro Ser Thr Val
    195                 200                 205

Asn Phe Pro Gly Ala Tyr Ser Ala Ser Asp Pro Gly Ile Leu Ile Asn
210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
        260                 265                 270

Thr Ser Thr Ala Thr Ala Thr Ser Ala Pro Gly Gly Gly Ser Gly
    275                 280                 285

Cys Thr Ala Ala Lys Tyr Gln Gln Cys Gly Gly Thr Gly Tyr Thr Gly
290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 3
<211> LENGTH: 880
<212> TYPE: DNA
<213> ORGANISM: Thielavia terrestris

<400> SEQUENCE: 3
accccgggat cactgcccct aggaaccagc acacctcggt ccaatcatgc ggttcgacgc    60
cctctccgcc ctcgctcttg cgccgcttgt ggctggccac ggcgccgtga ccagctacat   120
catcggcggc aaaaacctat ccggctacga gggcttctcg cctgcctcga gcccgccgac   180
gatccagtac cagtggcccg actacaaccc gaccctgagc gtgaccgacc cgaagatgcg   240
```

-continued

```
ctgcaacggc ggcacctcgg cagagctcag cgcgcccgtc caggccggcg agaacgtgac    300
ggccgtctgg aagcagtgga cccaccagca aggccccgtc atggtctgga tgttcaagtg    360
ccccggcgac ttctcgtcgt gccacggcga cggcaagggc tggttcaaga tcgaccagct    420
gggcctgtgg ggcaacaacc tcaactcgaa caactgggc accgcgatcg tctacaagac     480
cctccagtgg agcaacccga tccccaagaa cctcgcgccg ggcaactacc tcatccgcca    540
cgagctgctc gccctgcacc aggccaacac gccgcagttc tacgccgagt gcgcccagct    600
ggtcgtctcc ggcagcggct ccgccctgcc cccgtccgac tacctctaca gcatccccgt    660
ctacgcgccc cagaacgacc ccggcatcac cgtgagtggg cttccgttcc gcggcgagct    720
ctgtggaaat cttgctgacg atgggctagg ttgacatcta caacggcggg cttacctcct    780
acaccccgcc cggcggcccc gtctggtctg gcttcgagtt ttaggcgcat tgagtcgggg    840
gctacgaggg gaaggcatct gttcgcatga gcgtgggtac                         880
```

<210> SEQ ID NO 4
<211> LENGTH: 239
<212> TYPE: PRT
<213> ORGANISM: Thielavia terrestris

<400> SEQUENCE: 4

```
Met Arg Phe Asp Ala Leu Ser Ala Leu Ala Leu Ala Pro Leu Val Ala
1               5                   10                  15

Gly His Gly Ala Val Thr Ser Tyr Ile Ile Gly Gly Lys Thr Tyr Pro
                20                  25                  30

Gly Tyr Glu Gly Phe Ser Pro Ala Ser Ser Pro Thr Ile Gln Tyr
            35                  40                  45

Gln Trp Pro Asp Tyr Asn Pro Thr Leu Ser Val Thr Asp Pro Lys Met
        50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Asn Trp Gly Thr Ala Ile Val Tyr Lys
130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
    210                 215                 220

Ser Tyr Thr Pro Pro Gly Gly Pro Val Trp Ser Gly Phe Glu Phe
225                 230                 235
```

<210> SEQ ID NO 5
<211> LENGTH: 1000

```
<212> TYPE: DNA
<213> ORGANISM: Thielavia terrestris

<400> SEQUENCE: 5
ctcctgttcc tgggccaccg cttgttgcct gcactattgg tagagttggt ctattgctag      60
agttggccat gcttctcaca tcagtcctcg gctcggctgc cctgcttgct agcggcgctg     120
cggcacacgg cgccgtgacc agctacatca tcgccggcaa gaattacccg ggtgggtag     180
ctgattattg agggcgcatt caaggttcat accggtgtgc atggctgaca accggctggc     240
agataccaag gcttttctcc tgcgaactcg ccgaacgtca tccaatggca atggcatgac     300
tacaaccccg tcttgtcgtg cagcgactcg aagcttcgct gcaacggcgg cacgtcggcc     360
accctgaacg ccacggccgc accgggcgac accatcaccg ccatctgggc gcagtggacg     420
cacagccagg gccccatcct ggtgtggatg tacaagtgcc cgggctcctt cagctcctgt     480
gacggctccg gcgctggctg gttcaagatc gacgaggccg gcttccacgg cgacggcgtc     540
aaggtcttcc tcgacaccga gaacccgtcc ggctgggaca tcgccaagct cgtcggcggc     600
aacaagcagt ggagcagcaa ggtccccgag ggcctcgccc ccggcaacta cctcgtccgc     660
cacgagttga tcgccctgca ccaggccaac aacccgcagt tctacccgga gtgcgcccag     720
gtcgtcatca ccggctccgg caccgcgcag ccggatgcct catacaaggc ggctatcccc     780
ggctactgca accagaatga cccgaacatc aaggtgagat ccaggcgtaa tgcagtctac     840
tgctggaaag aaagtggtcc aagctaaacc gcgctccagg tgcccatcaa cgaccactcc     900
atccctcaga cctacaagat tcccggcccct cccgtcttca agggcaccgc cagcaagaag     960
gcccgggact tcaccgcctg aagttgttga atcgatggag                           1000

<210> SEQ ID NO 6
<211> LENGTH: 258
<212> TYPE: PRT
<213> ORGANISM: Thielavia terrestris

<400> SEQUENCE: 6

Met Leu Leu Thr Ser Val Leu Gly Ser Ala Ala Leu Leu Ala Ser Gly
1               5                   10                  15

Ala Ala Ala His Gly Ala Val Thr Ser Tyr Ile Ile Ala Gly Lys Asn
                20                  25                  30

Tyr Pro Gly Tyr Gln Gly Phe Ser Pro Ala Asn Ser Pro Asn Val Ile
            35                  40                  45

Gln Trp Gln Trp His Asp Tyr Asn Pro Val Leu Ser Cys Ser Asp Ser
        50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
        115                 120                 125

Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175
```

| Leu | Ile | Ala | Leu | His | Gln | Ala | Asn | Asn | Pro | Gln | Phe | Tyr | Pro | Glu | Cys |
|---|---|---|---|---|---|---|---|---|---|---|---|---|---|---|---|
| | | | 180 | | | | | 185 | | | | | 190 | | |

| Ala | Gln | Val | Val | Ile | Thr | Gly | Ser | Gly | Thr | Ala | Gln | Pro | Asp | Ala | Ser |
|---|---|---|---|---|---|---|---|---|---|---|---|---|---|---|---|
| | | | 195 | | | | | 200 | | | | | 205 | | |

| Tyr | Lys | Ala | Ala | Ile | Pro | Gly | Tyr | Cys | Asn | Gln | Asn | Asp | Pro | Asn | Ile |
|---|---|---|---|---|---|---|---|---|---|---|---|---|---|---|---|
| | | | 210 | | | | | 215 | | | | | 220 | | |

| Lys | Val | Pro | Ile | Asn | Asp | His | Ser | Ile | Pro | Gln | Thr | Tyr | Lys | Ile | Pro |
|---|---|---|---|---|---|---|---|---|---|---|---|---|---|---|---|
| 225 | | | | | 230 | | | | | 235 | | | | | 240 |

| Gly | Pro | Pro | Val | Phe | Lys | Gly | Thr | Ala | Ser | Lys | Lys | Ala | Arg | Asp | Phe |
|---|---|---|---|---|---|---|---|---|---|---|---|---|---|---|---|
| | | | | 245 | | | | | 250 | | | | | 255 | |

Thr Ala

<210> SEQ ID NO 7
<211> LENGTH: 681
<212> TYPE: DNA
<213> ORGANISM: Thielavia terrestris

<400> SEQUENCE: 7

```
atgctcgcaa acggtgccat cgtcttcctg gccgccgccc tcggcgtcag tggccactac      60
acctggccac gggttaacga cggcgccgac tggcaacagg tccgtaaggc ggacaactgg     120
caggacaacg gctacgtcgg ggatgtcacg tcgccacaga tccgctgttt ccaggcgacc     180
ccgtccccgg ccccatccgt cctcaacacc acggccggct cgaccgtgac ctactgggcc     240
aaccccgacg tctaccaccc cgggcctgtg cagttttaca tggcccgcgt gcccgatggc     300
gaggacatca actcgtggaa cggcgacggc gccgtgtggt tcaaggtgta cgaggaccat     360
cctacctttg cgctcagct cacatggccc agcacgggca agagctcgtt cgcggttccc      420
atccccccgt gcatcaagtc cggctactac ctcctccggg cggagcaaat cggcctgcac     480
gtcgcccaga gcgtaggcgg agcgcagttc tacatctcat cgcccagct cagcgtcacc     540
ggcggcggca gcaccgagcc gccgaacaag gtggccttcc ccggcgctta cagtgcgacg     600
gacccgggca ttctgatcaa catctactac cctgttccca cgtcctacca gaaccccggc     660
ccggccgtct tcagctgctg a                                              681
```

<210> SEQ ID NO 8
<211> LENGTH: 226
<212> TYPE: PRT
<213> ORGANISM: Thielavia terrestris

<400> SEQUENCE: 8

| Met | Leu | Ala | Asn | Gly | Ala | Ile | Val | Phe | Leu | Ala | Ala | Ala | Leu | Gly | Val |
|---|---|---|---|---|---|---|---|---|---|---|---|---|---|---|---|
| 1 | | | | 5 | | | | | 10 | | | | | 15 | |

| Ser | Gly | His | Tyr | Thr | Trp | Pro | Arg | Val | Asn | Asp | Gly | Ala | Asp | Trp | Gln |
|---|---|---|---|---|---|---|---|---|---|---|---|---|---|---|---|
| | | | 20 | | | | | 25 | | | | | 30 | | |

| Gln | Val | Arg | Lys | Ala | Asp | Asn | Trp | Gln | Asp | Asn | Gly | Tyr | Val | Gly | Asp |
|---|---|---|---|---|---|---|---|---|---|---|---|---|---|---|---|
| | | | 35 | | | | | 40 | | | | | 45 | | |

| Val | Thr | Ser | Pro | Gln | Ile | Arg | Cys | Phe | Gln | Ala | Thr | Pro | Ser | Pro | Ala |
|---|---|---|---|---|---|---|---|---|---|---|---|---|---|---|---|
| | | | | 50 | | | | | 55 | | | | | 60 | |

| Pro | Ser | Val | Leu | Asn | Thr | Thr | Ala | Gly | Ser | Thr | Val | Thr | Tyr | Trp | Ala |
|---|---|---|---|---|---|---|---|---|---|---|---|---|---|---|---|
| 65 | | | | | 70 | | | | | 75 | | | | | 80 |

| Asn | Pro | Asp | Val | Tyr | His | Pro | Gly | Pro | Val | Gln | Phe | Tyr | Met | Ala | Arg |
|---|---|---|---|---|---|---|---|---|---|---|---|---|---|---|---|
| | | | | 85 | | | | | 90 | | | | | 95 | |

| Val | Pro | Asp | Gly | Glu | Asp | Ile | Asn | Ser | Trp | Asn | Gly | Asp | Gly | Ala | Val |
|---|---|---|---|---|---|---|---|---|---|---|---|---|---|---|---|
| | | | 100 | | | | | 105 | | | | | 110 | | |

```
Trp Phe Lys Val Tyr Glu Asp His Pro Thr Phe Gly Ala Gln Leu Thr
    115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Ser Thr Glu Pro Pro Asn Lys Val Ala
                180                 185                 190

Phe Pro Gly Ala Tyr Ser Ala Thr Asp Pro Gly Ile Leu Ile Asn Ile
            195                 200                 205

Tyr Tyr Pro Val Pro Thr Ser Tyr Gln Asn Pro Gly Pro Ala Val Phe
    210                 215                 220

Ser Cys
225
```

<210> SEQ ID NO 9
<211> LENGTH: 960
<212> TYPE: DNA
<213> ORGANISM: Thielavia terrestris

<400> SEQUENCE: 9

```
atgaagggac ttttcagtgc cgccgccctc tccctggccg tcggccaggc ttcggcccat    60
tacatcttcc agcaactctc catcaacggg aaccagtttc cggtgtacca atatattcgc   120
aagaacacca attataacag tcccgttacc gatctcacgt ccgacgatct tcggtgcaat   180
gtcggcgccc agggtgctgg gacagacacc gtcacggtga aggccggcga ccagttcacc   240
ttcacccttg acaccctgt ttaccaccag gggcccatct ccatctacat gtccaaggcc    300
ccgggcgcgg cgtcagacta cgatggcagc ggcggctggt tcaagatcaa ggactgggc    360
ccgactttca cgccgacgg cacggccacc tgggacatgg ccggctcata cacctacaac   420
atcccgacct gcattccga cggcgactat ctgctccgca tccagtcgct ggccatccac   480
aaccctggc cggcgggcat cccgcagttc tacatctcct cgccagat caccgtgacc    540
ggcggcggca acggcaaccc tggcccgacg gccctcatcc ccggcgcctt caaggacacc   600
gacccgggct acacggtgaa catctacacg aacttccaca actacaccgg tcccggcccg   660
gaggtcttca gctgcaacgg cggcggctcg aacccgcccc gccggtgag tagcagcacg   720
cccgcgacca cgacgctggt cacgtcgacg cgcaccacgt cctccacgtc ctccgcctcg   780
acgccggcct cgaccggcgg ctgcaccgtc gccaagtggg gccagtgcgg cggcaacggg   840
tacaccggct gcacgacctg cgcggccggg tccacctgca gcaagcagaa cgactactac   900
tcgcagtgct gtaagggag gccgcaaagc atgaggtgtt tgaagaggag gagagggggtc  960
```

<210> SEQ ID NO 10
<211> LENGTH: 304
<212> TYPE: PRT
<213> ORGANISM: Thielavia terrestris

<400> SEQUENCE: 10

```
Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
```

```
                35                  40                  45
Val Thr Asp Leu Thr Ser Asp Asp Leu Arg Cys Asn Val Gly Ala Gln
 50                  55                  60

Gly Ala Gly Thr Asp Thr Val Thr Val Lys Ala Gly Asp Gln Phe Thr
 65                  70                  75                  80

Phe Thr Leu Asp Thr Pro Val Tyr His Gln Gly Pro Ile Ser Ile Tyr
                 85                  90                  95

Met Ser Lys Ala Pro Gly Ala Ser Asp Tyr Asp Gly Ser Gly Gly
             100                 105                 110

Trp Phe Lys Ile Lys Asp Trp Gly Pro Thr Phe Asn Ala Asp Gly Thr
             115                 120                 125

Ala Thr Trp Asp Met Ala Gly Ser Tyr Thr Tyr Asn Ile Pro Thr Cys
 130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                 165                 170                 175

Ile Thr Val Thr Gly Gly Gly Asn Gly Asn Pro Gly Pro Thr Ala Leu
             180                 185                 190

Ile Pro Gly Ala Phe Lys Asp Thr Asp Pro Gly Tyr Thr Val Asn Ile
             195                 200                 205

Tyr Thr Asn Phe His Asn Tyr Thr Val Pro Gly Pro Glu Val Phe Ser
 210                 215                 220

Cys Asn Gly Gly Gly Ser Asn Pro Pro Pro Val Ser Ser Ser Thr
225                 230                 235                 240

Pro Ala Thr Thr Thr Leu Val Thr Ser Thr Arg Thr Thr Ser Ser Thr
                 245                 250                 255

Ser Ser Ala Ser Thr Pro Ala Ser Thr Gly Gly Cys Thr Val Ala Lys
             260                 265                 270

Trp Gly Gln Cys Gly Gly Asn Gly Tyr Thr Gly Cys Thr Thr Cys Ala
             275                 280                 285

Ala Gly Ser Thr Cys Ser Lys Gln Asn Asp Tyr Tyr Ser Gln Cys Leu
 290                 295                 300
```

<210> SEQ ID NO 11
<211> LENGTH: 954
<212> TYPE: DNA
<213> ORGANISM: Thielavia terrestris

<400> SEQUENCE: 11

```
atgaagggcc tcagcctcct cgccgctgcg tcggcagcga ctgctcatac catcttcgtg    60
cagctcgagt caggggggaac gacctatccg gtatcctacg gcatccggga ccctagctac   120
gacggtccca tcaccgacgt cacctccgac tcactggctt gcaatggtcc cccgaacccc   180
acgacgccgt ccccgtacat catcaacgtc accgccggca ccacggtcgc ggcgatctgg   240
aggcacaccc tcacatccgg ccccgacgat gtcatggacg ccagccacaa ggggccgacc   300
ctggcctacc tcaagaaggt cgatgatgcc ttgaccgaca cgggtatcgg cggcggctgg   360
ttcaagatcc aggaggccgg ttacgacaat ggcaattggg ctaccagcac ggtgatcacc   420
aacggtggct ccaatatatt tgacatcccc gcctgcattc ccaacggcca gtatctgctc   480
cgcgccgaga tgatcgcgct ccacgccgcc agcacgcagg tggtgcccca gctctacatg   540
gagtgcgcgc agatcaacgt ggtgggcggc tccggcagcg ccagcccgca gacgtacagc   600
atcccgggca tctaccaggc aaccgacccg ggcctgctga tcaacatcta ctccatgacg   660
```

```
ccgtccagcc agtacaccat tccgggtccg cccctgttca cctgcagcgg cagcggcaac    720
aacggcggcg gcagcaaccc gtcgggcggg cagaccacga cggcgaagcc cacgacgacg    780
acggcggcga cgaccacctc ctccgccgct cctaccagca gccagggggg cagcagcggt    840
tgcaccgttc cccagtggca gcagtgcggt ggcatctcgt tcaccggctg caccacctgc    900
gcggcgggct acacctgcaa gtatctgaac gactattact cgcaatgcca gtaa          954
```

<210> SEQ ID NO 12
<211> LENGTH: 317
<212> TYPE: PRT
<213> ORGANISM: Thielavia terrestris

<400> SEQUENCE: 12

```
Met Lys Gly Leu Ser Leu Leu Ala Ala Ser Ala Ala Thr Ala His
1               5                   10                  15

Thr Ile Phe Val Gln Leu Glu Ser Gly Gly Thr Thr Tyr Pro Val Ser
            20                  25                  30

Tyr Gly Ile Arg Asp Pro Ser Tyr Asp Gly Pro Ile Thr Asp Val Thr
        35                  40                  45

Ser Asp Ser Leu Ala Cys Asn Gly Pro Pro Asn Pro Thr Thr Pro Ser
50                  55                  60

Pro Tyr Ile Ile Asn Val Thr Ala Gly Thr Thr Val Ala Ala Ile Trp
65                  70                  75                  80

Arg His Thr Leu Thr Ser Gly Pro Asp Asp Val Met Asp Ala Ser His
                85                  90                  95

Lys Gly Pro Thr Leu Ala Tyr Leu Lys Lys Val Asp Asp Ala Leu Thr
            100                 105                 110

Asp Thr Gly Ile Gly Gly Gly Trp Phe Lys Ile Gln Glu Ala Gly Tyr
        115                 120                 125

Asp Asn Gly Asn Trp Ala Thr Ser Thr Val Ile Thr Asn Gly Gly Phe
130                 135                 140

Gln Tyr Ile Asp Ile Pro Ala Cys Ile Pro Asn Gly Gln Tyr Leu Leu
145                 150                 155                 160

Arg Ala Glu Met Ile Ala Leu His Ala Ala Ser Thr Gln Gly Gly Ala
                165                 170                 175

Gln Leu Tyr Met Glu Cys Ala Gln Ile Asn Val Val Gly Gly Ser Gly
            180                 185                 190

Ser Ala Ser Pro Gln Thr Tyr Ser Ile Pro Gly Ile Tyr Gln Ala Thr
        195                 200                 205

Asp Pro Gly Leu Leu Ile Asn Ile Tyr Ser Met Thr Pro Ser Ser Gln
210                 215                 220

Tyr Thr Ile Pro Gly Pro Pro Leu Phe Thr Cys Ser Gly Ser Gly Asn
225                 230                 235                 240

Asn Gly Gly Gly Ser Asn Pro Ser Gly Gly Gln Thr Thr Ala Lys
                245                 250                 255

Pro Thr Thr Thr Thr Ala Ala Thr Thr Thr Ser Ser Ala Ala Pro Thr
            260                 265                 270

Ser Ser Gln Gly Gly Ser Ser Gly Cys Thr Val Pro Gln Trp Gln Gln
        275                 280                 285

Cys Gly Gly Ile Ser Phe Thr Gly Cys Thr Cys Ala Ala Gly Tyr
    290                 295                 300

Thr Cys Lys Tyr Leu Asn Asp Tyr Tyr Ser Gln Cys Gln
305                 310                 315
```

<210> SEQ ID NO 13
<211> LENGTH: 799
<212> TYPE: DNA
<213> ORGANISM: Thermoascus aurantiacus

<400> SEQUENCE: 13

| | | | | | |
|---|---|---|---|---|---|
| atgtcctttt | ccaagataat | tgctactgcc | ggcgttcttg | cctctgcttc | tctagtggct | 60 |
| ggccatggct | tcgttcagaa | catcgtgatt | gatggtaaaa | agtatgtcat | tgcaagacgc | 120 |
| acataagcgg | caacagctga | caatcgacag | ttatggcggg | tatctagtga | accagtatcc | 180 |
| atacatgtcc | aatcctccag | aggtcatcgc | ctggtctact | acggcaactg | atcttggatt | 240 |
| tgtggacggt | actggatacc | aaaccccaga | tatcatctgc | cataggggcg | ccaagcctgg | 300 |
| agccctgact | gctccagtct | ctccaggagg | aactgttgag | cttcaatgga | ctccatggcc | 360 |
| tgattctcac | catggcccag | ttatcaacta | ccttgctccg | tgcaatggtg | attgttccac | 420 |
| tgtggataag | acccaattag | aattcttcaa | aattgccgag | agcggtctca | tcaatgatga | 480 |
| caatcctcct | gggatctggg | cttcagacaa | tctgatagca | gccaacaaca | gctggactgt | 540 |
| caccattcca | accacaattg | cacctggaaa | ctatgttctg | aggcatgaga | ttattgctct | 600 |
| tcactcagct | cagaaccagg | atggtgccca | gaactatccc | cagtgcatca | atctgcaggt | 660 |
| cactggaggt | ggttctgata | cccctgctgg | aactcttgga | acggcactct | accacgatac | 720 |
| cgatcctgga | attctgatca | acatctatca | gaaactttcc | agctatatca | tccctggtcc | 780 |
| tcctctgtat | actggttaa | | | | | 799 |

<210> SEQ ID NO 14
<211> LENGTH: 249
<212> TYPE: PRT
<213> ORGANISM: Thermoascus aurantiacus

<400> SEQUENCE: 14

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
                20                  25                  30

Lys Tyr Tyr Gly Gly Tyr Leu Val Asn Gln Tyr Pro Tyr Met Ser Asn
            35                  40                  45

Pro Pro Glu Val Ile Ala Trp Ser Thr Thr Ala Thr Asp Leu Gly Phe
        50                  55                  60

Val Asp Gly Thr Gly Tyr Gln Thr Pro Asp Ile Ile Cys His Arg Gly
65                  70                  75                  80

Ala Lys Pro Gly Ala Leu Thr Ala Pro Val Ser Pro Gly Gly Thr Val
                85                  90                  95

Glu Leu Gln Trp Thr Pro Trp Pro Asp Ser His Gly Pro Val Ile
            100                 105                 110

Asn Tyr Leu Ala Pro Cys Asn Gly Asp Cys Ser Thr Val Asp Lys Thr
        115                 120                 125

Gln Leu Glu Phe Phe Lys Ile Ala Glu Ser Gly Leu Ile Asn Asp Asp
    130                 135                 140

Asn Pro Pro Gly Ile Trp Ala Ser Asp Asn Leu Ile Ala Ala Asn Asn
145                 150                 155                 160

Ser Trp Thr Val Thr Ile Pro Thr Thr Ile Ala Pro Gly Asn Tyr Val
                165                 170                 175

Leu Arg His Glu Ile Ile Ala Leu His Ser Ala Gln Asn Gln Asp Gly
            180                 185                 190

```
Ala Gln Asn Tyr Pro Gln Cys Ile Asn Leu Gln Val Thr Gly Gly Gly
        195                 200                 205

Ser Asp Asn Pro Ala Gly Thr Leu Gly Thr Ala Leu Tyr His Asp Thr
    210                 215                 220

Asp Pro Gly Ile Leu Ile Asn Ile Tyr Gln Lys Leu Ser Ser Tyr Ile
225                 230                 235                 240

Ile Pro Gly Pro Pro Leu Tyr Thr Gly
            245

<210> SEQ ID NO 15
<211> LENGTH: 1172
<212> TYPE: DNA
<213> ORGANISM: Trichoderma reesei

<400> SEQUENCE: 15
```

| | | |
|---|---|---|
| ggatctaagc cccatcgata tgaagtcctg cgccattctt gcagcccttg gctgtcttgc | 60 |
| cgggagcgtt ctcggccatg gacaagtcca aaacttcacg atcaatggac aatacaatca | 120 |
| gggtttcatt ctcgattact actatcagaa gcagaatact ggtcacttcc caacgttgc | 180 |
| tggctggtac gccgaggacc tagacctggg cttcatctcc cctgaccaat acaccacgcc | 240 |
| cgacattgtc tgtcacaaga acgcggcccc aggtgccatt tctgccactg cagcggccgg | 300 |
| cagcaacatc gtcttccaat ggggccctgg cgtctggcct cacccctacg gtcccatcgt | 360 |
| tacctacgtg gctgagtgca gcggatcgtg cacgaccgtg aacaagaaca acctgcgctg | 420 |
| ggtcaagatt caggaggccg gcatcaacta taacacccaa gtctgggcgc agcaggatct | 480 |
| gatcaaccag ggcaacaagt ggactgtgaa gatcccgtcg agcctcaggc ccggaaacta | 540 |
| tgtcttccgc catgaacttc ttgctgccca tggtgcctct agtgcgaacg gcatgcagaa | 600 |
| ctatcctcag tgcgtgaaca tcgccgtcac aggctcgggc acgaaagcgc tccctgccgg | 660 |
| aactcctgca actcagctct acaagcccac tgacctggc atcttgttca acccttacac | 720 |
| aacaatcacg agctacacca tccctggccc agccctgtgg caaggctaga tccaggggta | 780 |
| cggtgttggc gttcgtgaag tcggagctgt tgacaaggat atctgatgat gaacggagag | 840 |
| gactgatggg cgtgactgag tgtatatatt tttgatgacc aaattgtata cgaaatccga | 900 |
| acgcatggtg atcattgttt atccctgtag tatattgtct ccaggctgct aagagcccac | 960 |
| cgggtgtatt acggcaacaa agtcaggaat ttgggtggca atgaacgcag gtctccatga | 1020 |
| atgtatatgt gaagaggcat cggctggcat gggcattacc agatataggc cctgtgaaac | 1080 |
| atatagtact tgaacgtgct actggaacgg atcataagca agtcatcaac atgtgaaaaa | 1140 |
| acactacatg taaaaaaaaa aaaaaaaaaa aa | 1172 |

```
<210> SEQ ID NO 16
<211> LENGTH: 249
<212> TYPE: PRT
<213> ORGANISM: Trichoderma reesei

<400> SEQUENCE: 16

Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
            20                  25                  30

Asn Gln Gly Phe Ile Leu Asp Tyr Tyr Tyr Gln Lys Gln Asn Thr Gly
        35                  40                  45

His Phe Pro Asn Val Ala Gly Trp Tyr Ala Glu Asp Leu Asp Leu Gly
```

```
            50                  55                  60
Phe Ile Ser Pro Asp Gln Tyr Thr Thr Pro Asp Ile Val Cys His Lys
 65                  70                  75                  80

Asn Ala Ala Pro Gly Ala Ile Ser Ala Thr Ala Ala Gly Ser Asn
                 85                  90                  95

Ile Val Phe Gln Trp Gly Pro Gly Val Trp Pro His Pro Tyr Gly Pro
                100                 105                 110

Ile Val Thr Tyr Val Val Glu Cys Ser Gly Ser Cys Thr Thr Val Asn
                115                 120                 125

Lys Asn Asn Leu Arg Trp Val Lys Ile Gln Glu Ala Gly Ile Asn Tyr
130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
                180                 185                 190

Gln Asn Tyr Pro Gln Cys Val Asn Ile Ala Val Thr Gly Ser Gly Thr
                195                 200                 205

Lys Ala Leu Pro Ala Gly Thr Pro Ala Thr Gln Leu Tyr Lys Pro Thr
210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245

<210> SEQ ID NO 17
<211> LENGTH: 924
<212> TYPE: DNA
<213> ORGANISM: Myceliophthora thermophila

<400> SEQUENCE: 17
atgaagttca cctcgtccct cgctgtcctg gccgctgccg gcgcccaggc tcactgttag     60
tcgaccctcg aacccaacac ccccctcccc ccttttctcc tccatctcct cggcctcact    120
tagtagccgc tgacaacgac tagatacctt ccctagggcc ggcactggtg gctcgctctc    180
tggcgagtgg gaggtggtcc gcatgaccga gaaccattac tcgcacggcc cggtcaccga    240
tgtcaccagc cccgagatga cctgctatca gtccggcgtg cagggtgcgc cccagaccgt    300
ccaggtcaag gcgggctccc aattcacctt cagcgtggat ccctcgatcg ccaccccgg    360 ccctctccag ttctacatgg ctaaggtgcc gtcgggccag acggccgcca cctttgacgg    420
cacgggagcc gtgtggttca agatctacca gacggcccg aacggcctcg caccgacag     480 cattacctgg cccagcgccg gttcgtgact tcctccccac tcgcttttt tttttattt    540 tttattttt tttctttcgg aactcaagaa tctttctctc tctctcccgt ctttggcctt     600
gaacaacact aaaactcttc cttactgtat taattaggca aaaccgaggt ctcggtcacc    660
atccccagct gcatcgatga tggcgagtac ctgctccggg tcgagcacat cgcgctccac    720
agcgccagca gcgtgggcgg cgctcagttc tacattgcct gcgcccagct ctccgtcacc    780
ggcggctccg gcaccctcaa cacgggctcg ctcgtctccc tgcccggcgc ctacaaggcc    840
accgacccgg gcatcctctt ccagctctac tggcccatcc cgaccgagta catcaacccc    900
ggcccggccc ccgtctcttg ctaa                                            924
```

```
<210> SEQ ID NO 18
<211> LENGTH: 232
<212> TYPE: PRT
<213> ORGANISM: Myceliophthora thermophila

<400> SEQUENCE: 18

Met Lys Phe Thr Ser Ser Leu Ala Val Leu Ala Ala Gly Ala Gln
1               5                   10                  15

Ala His Tyr Thr Phe Pro Arg Ala Gly Thr Gly Ser Leu Ser Gly
                20                  25                  30

Glu Trp Glu Val Val Arg Met Thr Glu Asn His Tyr Ser His Gly Pro
            35                  40                  45

Val Thr Asp Val Thr Ser Pro Glu Met Thr Cys Tyr Gln Ser Gly Val
    50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
                100                 105                 110

Gly Ala Val Trp Phe Lys Ile Tyr Gln Asp Gly Pro Asn Gly Leu Gly
            115                 120                 125

Thr Asp Ser Ile Thr Trp Pro Ser Ala Gly Lys Thr Glu Val Ser Val
130                 135                 140

Thr Ile Pro Ser Cys Ile Asp Asp Gly Glu Tyr Leu Leu Arg Val Glu
145                 150                 155                 160

His Ile Ala Leu His Ser Ala Ser Ser Val Gly Gly Ala Gln Phe Tyr
                165                 170                 175

Ile Ala Cys Ala Gln Leu Ser Val Thr Gly Gly Ser Gly Thr Leu Asn
            180                 185                 190

Thr Gly Ser Leu Val Ser Leu Pro Gly Ala Tyr Lys Ala Thr Asp Pro
        195                 200                 205

Gly Ile Leu Phe Gln Leu Tyr Trp Pro Ile Pro Thr Glu Tyr Ile Asn
    210                 215                 220

Pro Gly Pro Ala Pro Val Ser Cys
225                 230

<210> SEQ ID NO 19
<211> LENGTH: 854
<212> TYPE: DNA
<213> ORGANISM: Myceliophthora thermophila

<400> SEQUENCE: 19
atgaaggccc tctctctcct tgcggctgcc tcggcagtct ctgcgcatac catcttcgtc     60
cagctcgaag cagacggcac gaggtacccg gtctcgtacg ggatccggga cccaagctac    120
gacggcccca tcaccgacgt cacatccaac gacgttgctt gcaacggcgg gccgaacccg    180 acgacccct ccagcgacgt catcaccgtc accgcgggca ccacggtcaa ggccatctgg    240
aggcacaccc tccaatccgg cccggacgat gtcatggacg ccagccacaa gggcccgacc    300
ctggcctacc tcaagaaggt cggcgatgcc accaaggact cgggcgtcgg cggtggctgg    360
ttcaagattc aggaggacgg ctacaacaac ggccagtggg gcaccagcac cgttatctcc    420
aacggcggcg agcactacat gtgagccatt cctccgagag aagaccaaga ctcttgacga    480
tctcgctgac ccgtgcaaca agtgacatcc cggcctgcat ccccgagggt cagtacctcc    540
tccgcgccga gatgatcgcc ctccacgcgg ccgggtcccc cggcggtgcc cagctctacg    600
```

```
taagcctctg cccttccccc cttcctcttg atcgaatcgg actgcccacc cccctttttcg    660 actccgacta acaccgttgc cagatggaat gtgcccagat caacatcgtc ggcggctccg    720
gctcggtgcc cagctcgacc gtcagcttcc ccggcgcgta cagccccaac gacccgggtc    780
tcctcatcaa catctattcc atgtcgccct cgagctcgta caccatcccg ggcccgcccg    840
tcttcaagtg ctag                                                      854
```

<210> SEQ ID NO 20
<211> LENGTH: 235
<212> TYPE: PRT
<213> ORGANISM: Myceliophthora thermophila

<400> SEQUENCE: 20

```
Met Lys Ala Leu Ser Leu Leu Ala Ala Ala Ser Ala Val Ser Ala His
1               5                  10                  15

Thr Ile Phe Val Gln Leu Glu Ala Asp Gly Thr Arg Tyr Pro Val Ser
            20                  25                  30

Tyr Gly Ile Arg Asp Pro Ser Tyr Asp Gly Pro Ile Thr Asp Val Thr
        35                  40                  45

Ser Asn Asp Val Ala Cys Asn Gly Gly Pro Asn Pro Thr Thr Pro Ser
    50                  55                  60

Ser Asp Val Ile Thr Val Thr Ala Gly Thr Thr Val Lys Ala Ile Trp
65                  70                  75                  80

Arg His Thr Leu Gln Ser Gly Pro Asp Asp Val Met Asp Ala Ser His
                85                  90                  95

Lys Gly Pro Thr Leu Ala Tyr Leu Lys Lys Val Gly Asp Ala Thr Lys
            100                 105                 110

Asp Ser Gly Val Gly Gly Gly Trp Phe Lys Ile Gln Glu Asp Gly Tyr
        115                 120                 125

Asn Asn Gly Gln Trp Gly Thr Ser Thr Val Ile Ser Asn Gly Gly Glu
    130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Asn Ile Val Gly Gly Ser Gly
            180                 185                 190

Ser Val Pro Ser Ser Thr Val Ser Phe Pro Gly Ala Tyr Ser Pro Asn
        195                 200                 205

Asp Pro Gly Leu Leu Ile Asn Ile Tyr Ser Met Ser Pro Ser Ser Ser
    210                 215                 220

Tyr Thr Ile Pro Gly Pro Pro Val Phe Lys Cys
225                 230                 235
```

<210> SEQ ID NO 21
<211> LENGTH: 1242
<212> TYPE: DNA
<213> ORGANISM: Myceliophthora thermophila

<400> SEQUENCE: 21

```
atgaagtcct tcgccctcac cactctggcc gccctggccg gcaacgccgc cgctcacgcg    60
accttccagg ccctctgggt cgacggcgtc gactacggcg cgcagtgtgc ccgtctgccc    120
gcgtccaact cccggtcac cgacgtgacc tccaacgcga tccgctgcaa cgccaacccg    180
tcgcccgctc ggggcaagtg cccggtcaag gccggctcga ccgttacggt cgagatgcat    240
```

```
caggtacgtt ggatgaatga aaggggaaag gaagcagagg cagaagggga aggcgaaggg    300
aaagaaaaag aaaagaaat  ggaaaagaaa agaaatgga  aaagaaaaag aaaaatgaaa    360
aagaaagtgg aaaccgtcag actaactggg gctcctcccc cccaccccte ctttgatatc    420
agcaacccgg tgaccggtcg tgcagcagcg aggcgatcgg cggggcgcac tacggccccg    480
tcatggtgta catgtccaag gtgtcggacg cggcgtcggc ggacgggtcg tcgggctggt    540
tcaaggtgtt cgaggacggc tgggccaaga cccgtccgg  cgggtcgggc gacgacgact    600
actgggcac  caaggacctg aactcgtgct gcgggaagat gaacgtcaag atccccgccg    660
acctgccctc gggcgactac ctgctccggg ccgaggccct cgcgctgcac acggcgggca    720
gcgccggcgg cgcccagttc tacatgacgt gctaccagct caccgtgacg ggctccggca    780
gcgccagccc gcccaccgtc tccttcccgg gcgcctacaa ggccaccgac ccgggcatcc    840
tcgtcaacat ccacgccccg ctgtccggct acaccgtgcc cggcccggcc gtctactccg    900
gcggctccac caagaaggcc ggcagcgcct gcaccggctg cgagtccacc tgcgccgtcg    960
gctccggccc caccgccacc gtctcccagt cgcccggttc caccgccacc tccgcccccg   1020
gcggcggcgc cggctgcacc gtccagaagt accagcagtg cggcggcgag ggctacaccg   1080
gctgcaccaa ctgcgcggta cgttttttcaa ccccgttttt ttttttcctt ccctaccta   1140
tttggttacc taattaatta cttteegget getgactttt tgetttagte eggetctace   1200
tgcagcgccg tctcgccgcc ctactactcg cagtgcgtct aa                      1242
```

<210> SEQ ID NO 22
<211> LENGTH: 323
<212> TYPE: PRT
<213> ORGANISM: Myceliophthora thermophila

<400> SEQUENCE: 22

```
Met Lys Ser Phe Ala Leu Thr Thr Leu Ala Ala Leu Ala Gly Asn Ala
1               5                   10                  15

Ala Ala His Ala Thr Phe Gln Ala Leu Trp Val Asp Gly Val Asp Tyr
            20                  25                  30

Gly Ala Gln Cys Ala Arg Leu Pro Ala Ser Asn Ser Pro Val Thr Asp
        35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Gly Ala
                85                  90                  95

His Tyr Gly Pro Val Met Val Tyr Met Ser Lys Val Ser Asp Ala Ala
            100                 105                 110

Ser Ala Asp Gly Ser Ser Gly Trp Phe Lys Val Phe Glu Asp Gly Trp
        115                 120                 125

Ala Lys Asn Pro Ser Gly Gly Ser Gly Asp Asp Tyr Trp Gly Thr
    130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190
```

Gln Leu Thr Val Thr Gly Ser Gly Ser Ala Ser Pro Pro Thr Val Ser
        195                 200                 205

Phe Pro Gly Ala Tyr Lys Ala Thr Asp Pro Gly Ile Leu Val Asn Ile
    210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
            260                 265                 270

Gly Ser Thr Ala Thr Ser Ala Pro Gly Gly Gly Gly Cys Thr Val
        275                 280                 285

Gln Lys Tyr Gln Gln Cys Gly Gly Glu Gly Tyr Thr Gly Cys Thr Asn
    290                 295                 300

Cys Ala Ser Gly Ser Thr Cys Ser Ala Val Ser Pro Pro Tyr Tyr Ser
305                 310                 315                 320

Gln Cys Val

<210> SEQ ID NO 23
<211> LENGTH: 1253
<212> TYPE: DNA
<213> ORGANISM: Myceliophthora thermophila

<400> SEQUENCE: 23
atgaagcctt ttagcctcgt cgccctggcg accgccgtga gcggccatgc catcttccag     60
cgggtgtcgg tcaacgggca ggaccagggc cagctcaagg gggtgcgggc gccgtcgagc    120
aactccccga tccagaacgt caacgatgcc aacatggcct gcaacgccaa cattgtgtac    180
cacgacagca ccatcatcaa ggtgcccgcg ggagcccgcg tcggcgcgtg gtggcagcac    240
gtcatcggcg ggccgcaggg cgccaacgac ccggacaacc cgatcgcggc ctcccacaag    300
ggtatgatga tcgatgatgc ctctctcttc ccccgttctt gatggacagg cgatggctcc    360
caggaacacg cgtgactgac caccgaatcc aggccccatc caggtctacc tggccaaggt    420
ggacaacgcg gcgacggcgt cgccgtcggg cctcaggtgg ttcaaggtgg ccgagcgcgg    480
cctgaacaac ggcgtgtggg ccgtcgatga gctcatcgcc aacaacggct ggcactactt    540
cgacctgccg tcgtgcgtgg cccccggcca gtacctgatg cgcgtcgagc tgctcgccct    600
gcacagcgcc tcaagccccg gcggcgccca gttctacatg ggctgcgcac agatcgaagg    660
tgcgtcgatc tttgttctcc ttccgtgtcc tctctgatcc tttctctctt ctttttcttt    720
cttttactcc ctttccttcc atcttcggag aagcaacgaa gggggaaagg gatagaagag    780
aggaatgaga gacgacgaaa gagaggattg gggaaagaca agacagggaa aaaaagacaa    840
gaaaaaaaaa aaaaaaaaaa aacagagtga gctaacaaga caatcagtc actggctccg    900
gcaccaactc gggctccgac tttgtctcgt tccccggcgc ctactcggcc aacgatccgg    960
gcatcttgct aagcatctac gacagctcgg gcaagcccac caacggcggg cgctcgtacc   1020
cgatccccgg cccgcgcccc atctcctgct ccggcagcgg cgacggcggc aacaacggcg   1080
gcggcggcga cgacaacaac aataacaacg tggtggcaa caacgcggc ggcggcggcg   1140
gcagcgtccc cctgtacggg cagtgcggcg gcatcggcta cacgggcccg accacctgtg   1200
cccagggaac ttgcaaggtg tcgaacgaat actacagcca gtgcctcccc tag           1253

<210> SEQ ID NO 24
<211> LENGTH: 310

<212> TYPE: PRT
<213> ORGANISM: Myceliophthora thermophila

<400> SEQUENCE: 24

```
Met Lys Pro Phe Ser Leu Val Ala Leu Ala Thr Ala Val Ser Gly His
1               5                   10                  15
Ala Ile Phe Gln Arg Val Ser Val Asn Gly Gln Asp Gln Gly Gln Leu
            20                  25                  30
Lys Gly Val Arg Ala Pro Ser Ser Asn Ser Pro Ile Gln Asn Val Asn
        35                  40                  45
Asp Ala Asn Met Ala Cys Asn Ala Asn Ile Val Tyr His Asp Ser Thr
    50                  55                  60
Ile Ile Lys Val Pro Ala Gly Ala Arg Val Gly Ala Trp Trp Gln His
65                  70                  75                  80
Val Ile Gly Gly Pro Gln Gly Ala Asn Asp Pro Asp Asn Pro Ile Ala
                85                  90                  95
Ala Ser His Lys Gly Pro Ile Gln Val Tyr Leu Ala Lys Val Asp Asn
            100                 105                 110
Ala Ala Thr Ala Ser Pro Ser Gly Leu Arg Trp Phe Lys Val Ala Glu
        115                 120                 125
Arg Gly Leu Asn Asn Gly Val Trp Ala Val Asp Glu Leu Ile Ala Asn
    130                 135                 140
Asn Gly Trp His Tyr Phe Asp Leu Pro Ser Cys Val Ala Pro Gly Gln
145                 150                 155                 160
Tyr Leu Met Arg Val Glu Leu Leu Ala Leu His Ser Ala Ser Ser Pro
                165                 170                 175
Gly Gly Ala Gln Phe Tyr Met Gly Cys Ala Gln Ile Glu Val Thr Gly
            180                 185                 190
Ser Gly Thr Asn Ser Gly Ser Asp Phe Val Ser Phe Pro Gly Ala Tyr
        195                 200                 205
Ser Ala Asn Asp Pro Gly Ile Leu Leu Ser Ile Tyr Asp Ser Ser Gly
    210                 215                 220
Lys Pro Thr Asn Gly Gly Arg Ser Tyr Pro Ile Pro Gly Pro Arg Pro
225                 230                 235                 240
Ile Ser Cys Ser Gly Ser Gly Asp Gly Gly Asn Gly Gly Gly Gly Gly
                245                 250                 255
Asp Asp Asn Asn Asn Asn Asn Gly Gly Gly Asn Asn Gly Gly Gly Gly
            260                 265                 270
Gly Gly Ser Val Pro Leu Tyr Gly Gln Cys Gly Gly Ile Gly Tyr Thr
        275                 280                 285
Gly Pro Thr Thr Cys Ala Gln Gly Thr Cys Lys Val Ser Asn Glu Tyr
    290                 295                 300
Tyr Ser Gln Cys Leu Pro
305                 310
```

<210> SEQ ID NO 25
<211> LENGTH: 814
<212> TYPE: DNA
<213> ORGANISM: Myceliophthora thermophila

<400> SEQUENCE: 25

```
atgaagctct ccctcttctc cgtcctggcc actgccctca ccgtcgaggg catgccatc     60 ttccagaagg tctccgtcaa cggagcggac cagggctccc tcaccggcct ccgcgctccc   120
aacaacaaca accccgtgca ggatgtcaac agccaggaca tgatctgcgg ccagtcggga   180
```

```
tcgacgtcga acactatcat cgaggtcaag gccggcgata ggatcggtgc ctggtatcag    240
catgtcatcg gcggtgccca gttccccaac gacccagaca acccgattgc caagtcgcac    300
aagggccccg tcatggccta cctcgccaag gttgacaatg ccgcaaccgc cagcaagacg    360
ggcctgaagt ggtatgtatt cccgcggccc gagggacatc gggttgggca agtcgagact    420
gacggagctc gcttctccgt ataggttcaa gatttgggag gataccttta atcccagcac    480
caagacctgg ggtgtcgaca acctcatcaa taacaacggc tgggtgtact tcaacctccc    540
gcagtgcatc gccgacggca actacctcct ccgcgtcgag gtcctcgctc tgcactcggc    600
ctactctcag ggccaggctc agttctacca gtcctgcgcc agatcaacg tatcggcgg     660 cggctccttc acaccgccgt cgactgtcag cttcccgggt gcctacagcg ccagcgaccc    720
cggtatcctg atcaacatct acggcgccac cggccagccc gacaacaacg gccagccgta    780
cactgcccct gggcccgcgc ccatctcctg ctga                                814

<210> SEQ ID NO 26
<211> LENGTH: 246
<212> TYPE: PRT
<213> ORGANISM: Myceliophthora thermophila

<400> SEQUENCE: 26

Met Lys Leu Ser Leu Phe Ser Val Leu Ala Thr Ala Leu Thr Val Glu
1               5                   10                  15

Gly His Ala Ile Phe Gln Lys Val Ser Val Asn Gly Ala Asp Gln Gly
                20                  25                  30

Ser Leu Thr Gly Leu Arg Ala Pro Asn Asn Asn Pro Val Gln Asp
            35                  40                  45

Val Asn Ser Gln Asp Met Ile Cys Gly Gln Ser Gly Ser Thr Ser Asn
        50                  55                  60

Thr Ile Ile Glu Val Lys Ala Gly Asp Arg Ile Gly Ala Trp Tyr Gln
65                  70                  75                  80

His Val Ile Gly Gly Ala Gln Phe Pro Asn Asp Pro Asp Asn Pro Ile
                85                  90                  95

Ala Lys Ser His Lys Gly Pro Val Met Ala Tyr Leu Ala Lys Val Asp
            100                 105                 110

Asn Ala Ala Thr Ala Ser Lys Thr Gly Leu Lys Trp Phe Lys Ile Trp
        115                 120                 125

Glu Asp Thr Phe Asn Pro Ser Thr Lys Thr Trp Gly Val Asp Asn Leu
130                 135                 140

Ile Asn Asn Asn Gly Trp Val Tyr Phe Asn Leu Pro Gln Cys Ile Ala
145                 150                 155                 160

Asp Gly Asn Tyr Leu Leu Arg Val Glu Val Leu Ala Leu His Ser Ala
                165                 170                 175

Tyr Ser Gln Gly Gln Ala Gln Phe Tyr Gln Ser Cys Ala Gln Ile Asn
            180                 185                 190

Val Ser Gly Gly Gly Ser Phe Thr Pro Pro Ser Thr Val Ser Phe Pro
        195                 200                 205

Gly Ala Tyr Ser Ala Ser Asp Pro Gly Ile Leu Ile Asn Ile Tyr Gly
    210                 215                 220

Ala Thr Gly Gln Pro Asp Asn Asn Gly Gln Pro Tyr Thr Ala Pro Gly
225                 230                 235                 240

Pro Ala Pro Ile Ser Cys
            245
```

```
<210> SEQ ID NO 27
<211> LENGTH: 1115
<212> TYPE: DNA
<213> ORGANISM: Thermoascus aurantiacus

<400> SEQUENCE: 27
atgtcgttct cgaagattgc tgcgatcacc ggggccatta cctatgcgtc tctggccgcc      60
gctcacggtt atgttacagg aatcgtagcc gatggcacct agtatgtaac gctcatgcca     120
agatccgcat tgctgtacta acaattagca gctacggggg ctatatcgtg acccaatacc     180
cctacatgtc gacaccgccg gatgtcatcg cctggtctac caaagcaact gatcttggtt     240
tcgtggatcc cagtagctat gcttcgtctg atattatctg ccacaagggt gctgagcctg     300
gtgccctgag cgccaaggtg gctgctggag ggaccgtcga gctgcagtgg acggattggc     360
ctgagagtca aagggcccg tcattgact acctcgccgc tgtaacggg gactgctcga      420 ctgtcgacaa gaccaaacta gagttcttca agattgatga gagtggccta attgacggca     480
gcagcgcccc aggcacatgg gcctctgaca cttgattgc caataacaac agctggaccg      540
tcaccatccc gagcacgatt gctcccggca actatgtcct gagacatgaa atcattgccc     600
tccactccgc cggaaataca aatggtgctc agaactaccc ccagtgtatc aaccttgagg     660
tcacaggcag tggcaccgac acccctgccg gcaccctcgg aacggagctt tataaggcaa     720
cggaccctgg cattctggtc aacatctacc agacctgac cagctacgat attcccggcc     780
ctgctctgta caccggtggt agctctggta gctctggttc ctccaacacc gccaaggca      840 ccacttcgac ggcttctagc tctatcgtga ccccgacgcc tgttaacaac ccaaccgtta     900
ctcagactgc cgttgttgat gtcacccaga ctgtttccca gaatgctgcc gtcgccacca     960
cgactccggc ctccactgca gttgctacag ctgtcccaac gggaaccacc tttagctttg    1020
attcgatgac ctcggatgaa ttcgtcagcc tgatgcgtgc gaccgtgaat tggctgcttt    1080
ctaacaagaa gcatgcccgg gatctttctt actaa                                1115

<210> SEQ ID NO 28
<211> LENGTH: 354
<212> TYPE: PRT
<213> ORGANISM: Thermoascus aurantiacus

<400> SEQUENCE: 28

Met Ser Phe Ser Lys Ile Ala Ala Ile Thr Gly Ala Ile Thr Tyr Ala
1               5                   10                  15

Ser Leu Ala Ala Ala His Gly Tyr Val Thr Gly Ile Val Ala Asp Gly
            20                  25                  30

Thr Tyr Tyr Gly Gly Tyr Ile Val Thr Gln Tyr Pro Tyr Met Ser Thr
        35                  40                  45

Pro Pro Asp Val Ile Ala Trp Ser Thr Lys Ala Thr Asp Leu Gly Phe
    50                  55                  60

Val Asp Pro Ser Ser Tyr Ala Ser Ser Asp Ile Ile Cys His Lys Gly
65                  70                  75                  80

Ala Glu Pro Gly Ala Leu Ser Ala Lys Val Ala Ala Gly Gly Thr Val
                85                  90                  95

Glu Leu Gln Trp Thr Asp Trp Pro Glu Ser His Lys Gly Pro Val Ile
            100                 105                 110

Asp Tyr Leu Ala Ala Cys Asn Gly Asp Cys Ser Thr Val Asp Lys Thr
        115                 120                 125

Lys Leu Glu Phe Phe Lys Ile Asp Glu Ser Gly Leu Ile Asp Gly Ser
    130                 135                 140
```

```
Ser Ala Pro Gly Thr Trp Ala Ser Asp Asn Leu Ile Ala Asn Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Thr Asn Gly
            180                 185                 190

Ala Gln Asn Tyr Pro Gln Cys Ile Asn Leu Glu Val Thr Gly Ser Gly
        195                 200                 205

Thr Asp Thr Pro Ala Gly Thr Leu Gly Thr Glu Leu Tyr Lys Ala Thr
    210                 215                 220

Asp Pro Gly Ile Leu Val Asn Ile Tyr Gln Thr Leu Thr Ser Tyr Asp
225                 230                 235                 240

Ile Pro Gly Pro Ala Leu Tyr Thr Gly Gly Ser Ser Gly Ser Ser Gly
                245                 250                 255

Ser Ser Asn Thr Ala Lys Ala Thr Thr Ser Thr Ala Ser Ser Ser Ile
            260                 265                 270

Val Thr Pro Thr Pro Val Asn Asn Pro Thr Val Thr Gln Thr Ala Val
        275                 280                 285

Val Asp Val Thr Gln Thr Val Ser Gln Asn Ala Ala Val Ala Thr Thr
    290                 295                 300

Thr Pro Ala Ser Thr Ala Val Ala Thr Ala Val Pro Thr Gly Thr Thr
305                 310                 315                 320

Phe Ser Phe Asp Ser Met Thr Ser Asp Glu Phe Val Ser Leu Met Arg
                325                 330                 335

Ala Thr Val Asn Trp Leu Leu Ser Asn Lys Lys His Ala Arg Asp Leu
            340                 345                 350

Ser Tyr

<210> SEQ ID NO 29
<211> LENGTH: 862
<212> TYPE: DNA
<213> ORGANISM: Aspergillus fumigatus

<400> SEQUENCE: 29
atgactttgt ccaagatcac ttccattgct ggccttctgg cctcagcgtc tctcgtggct      60
ggccacggct tgtttctgg cattgttgct gatgggaaat agtatgtgct gaaccacac      120 aaatgacagc tgcaacagct aacttctatt ccagttacgg agggtacctt gttaaccaat     180 accctacat gagcaaccct cccgacacca ttgcctggtc caccaccgcc accgacctcg      240
gctttgtgga cggcaccggc taccagtctc cggatattat ctgccacaga gacgcaaaga     300
atggcaagtt gaccgcaacc gttgcagccg gttcacagat cgaattccag tggacgacgt     360
ggccagagtc tcaccatgga ccggtacgac gccgaagaga agagaacata ttgtgaccag     420
ataggctaac atagcatagt tgattactta cctcgctcca tgcaacggcg actgtgccac     480
cgtggacaag accaccctga gtttgtcaa gatcgccgct caaggcttga tcgacggctc     540
caacccacct ggtgtttggg ctgatgatga atgatcgcc aacaacaaca cggccacagt      600
gaccattcct gcctcctatg cccccggaaa ctacgtcctt cgccacgaga tcatcgccct     660
tcactctgcg ggtaacctga acggcgcgca gaactacccc cagtgtttca acatccaaat     720
caccggtggc ggcagtgctc agggatctgg caccgctggc acgtccctgt acaagaatac     780
tgatcctggc atcaagtttg acatctactc ggatctgagc ggtggatacc ctattcctgg     840
tcctgcactg ttcaacgctt aa                                             862
```

<210> SEQ ID NO 30
<211> LENGTH: 250
<212> TYPE: PRT
<213> ORGANISM: Aspergillus fumigatus

<400> SEQUENCE: 30

```
Met Thr Leu Ser Lys Ile Thr Ser Ile Ala Gly Leu Leu Ala Ser Ala
1               5                   10                  15

Ser Leu Val Ala Gly His Gly Phe Val Ser Gly Ile Val Ala Asp Gly
            20                  25                  30

Lys Tyr Tyr Gly Gly Tyr Leu Val Asn Gln Tyr Pro Tyr Met Ser Asn
        35                  40                  45

Pro Pro Asp Thr Ile Ala Trp Ser Thr Thr Ala Thr Asp Leu Gly Phe
    50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95

Glu Phe Gln Trp Thr Thr Trp Pro Glu Ser His His Gly Pro Leu Ile
            100                 105                 110

Thr Tyr Leu Ala Pro Cys Asn Gly Asp Cys Ala Thr Val Asp Lys Thr
        115                 120                 125

Thr Leu Lys Phe Val Lys Ile Ala Ala Gln Gly Leu Ile Asp Gly Ser
    130                 135                 140

Asn Pro Pro Gly Val Trp Ala Asp Asp Glu Met Ile Ala Asn Asn Asn
145                 150                 155                 160

Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
    210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250
```

<210> SEQ ID NO 31
<211> LENGTH: 1021
<212> TYPE: DNA
<213> ORGANISM: Penicillium pinophilum

<400> SEQUENCE: 31

```
atgccttcta ctaaagtcgc tgcccttcct gctgttctag ctttggcctc cacggttgct      60
ggccatggtt ttgtgcaaaa catcgttatc gacggtaaat cgtaagcagt gatgcatcca     120
ttattaaact agacatgctt acaaaaaaat cagttactct ggataccttg tgaatcagtt     180
cccctacgag tccaacccac cagctgttat tgggtgggca caactgcaa ccgacctggg     240 attcgtcgct cccagtgagt acaccaatgc agacattatc tgccacaaga acgccacacc     300
tggcgcgctt tctgctccag ttgctgcagg gggcactgtc gagctccagt ggactacatg     360
gcccgatagt catcacggtc ctgtcatcag ctacctcgcc aactgcaatg gcaattgttc     420
```

```
taccgtggat aagactaagc tagactttgt caagattgac caaggtggtt tgatcgacga    480 tactacccc ccgggtacat gggcttccga caaacttatc gctgccaaca acagctggac    540
tgtaactatc ccctccacca tcgcgcctgg aaactacgtt ttgcgccacg aaatcattgc    600
tcttcactcc gctggaaacg cagacggtgc ccaaaactac cctcaatgca tcaacttgga    660
gatcaccggc agcggaaccg ccgctccctc tggtaccgct ggcgaaaagc tctacacctc    720
tactgacccc ggtatcttgg tcaatatcta ccaatccttg tcgacctacg ttattcccgg    780
accaactctg tggagcggtg ctgccaatgg cgctgttgcc actggttctg ctactgcggt    840
tgctacgact gccactgctt ctgcgaccgc tactcctacc acacttgtta cctctgtcgc    900
tccagcttca tctaccttg ccactgctgt tgtgaccact gtcgctcctg cagtaactga    960
tgtcgtgact gtcaccgatg tagttaccgt gaccaccgtc atcaccacta ctgtcctttg    1020
a                                                                    1021
```

<210> SEQ ID NO 32
<211> LENGTH: 322
<212> TYPE: PRT
<213> ORGANISM: Penicillium pinophilum

<400> SEQUENCE: 32

```
Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
                20                  25                  30

Lys Ser Tyr Ser Gly Tyr Leu Val Asn Gln Phe Pro Tyr Glu Ser Asn
            35                  40                  45

Pro Pro Ala Val Ile Gly Trp Ala Thr Thr Ala Thr Asp Leu Gly Phe
        50                  55                  60

Val Ala Pro Ser Glu Tyr Thr Asn Ala Asp Ile Ile Cys His Lys Asn
65                  70                  75                  80

Ala Thr Pro Gly Ala Leu Ser Ala Pro Val Ala Gly Gly Thr Val
                85                  90                  95

Glu Leu Gln Trp Thr Thr Trp Pro Asp Ser His His Gly Pro Val Ile
            100                 105                 110

Ser Tyr Leu Ala Asn Cys Asn Gly Asn Cys Ser Thr Val Asp Lys Thr
        115                 120                 125

Lys Leu Asp Phe Val Lys Ile Asp Gln Gly Gly Leu Ile Asp Asp Thr
    130                 135                 140

Thr Pro Pro Gly Thr Trp Ala Ser Asp Lys Leu Ile Ala Ala Asn Asn
145                 150                 155                 160

Ser Trp Thr Val Thr Ile Pro Ser Thr Ile Ala Pro Gly Asn Tyr Val
                165                 170                 175

Leu Arg His Glu Ile Ile Ala Leu His Ser Ala Gly Asn Ala Asp Gly
            180                 185                 190

Ala Gln Asn Tyr Pro Gln Cys Ile Asn Leu Glu Ile Thr Gly Ser Gly
        195                 200                 205

Thr Ala Ala Pro Ser Gly Thr Ala Gly Glu Lys Leu Tyr Thr Ser Thr
    210                 215                 220

Asp Pro Gly Ile Leu Val Asn Ile Tyr Gln Ser Leu Ser Thr Tyr Val
225                 230                 235                 240

Ile Pro Gly Pro Thr Leu Trp Ser Gly Ala Ala Asn Gly Ala Val Ala
                245                 250                 255

Thr Gly Ser Ala Thr Ala Val Ala Thr Thr Ala Thr Ala Ser Ala Thr
```

```
              260                 265                 270
Ala Thr Pro Thr Thr Leu Val Thr Ser Val Ala Pro Ala Ser Ser Thr
            275                 280                 285

Phe Ala Thr Ala Val Val Thr Thr Val Ala Pro Ala Val Thr Asp Val
        290                 295                 300

Val Thr Val Thr Asp Val Val Thr Val Thr Thr Val Ile Thr Thr Thr
305                 310                 315                 320

Val Leu

<210> SEQ ID NO 33
<211> LENGTH: 1486
<212> TYPE: DNA
<213> ORGANISM: Thermoascus sp.

<400> SEQUENCE: 33
atgttgtcgt tcgcttctgc caagtcagct gtgctgacga cccttctact tcttggatcc     60
gctcaggctc acactttgat gaccaccctg tttgtggatg cgtcaatca gggagatggt    120 gtctgtattc gcatgaacaa caacggtagt actgccaaca cctatatcca gcctgtcacg    180
agcaaggata ttgcctgcgg taagtacagt accggtccag atatcatact ctatttcaat    240
ccgacaacag tcagagctgg agagcaatgc taaacatccc caggcattca aggcgaaatt    300
ggcgccgctc gagtctgtcc agccaaggct tcatccaccc tcacgttcca attccgagag    360
cagccatcca acccgaattc cgctcctctc gatccctcgc acaaaggccc cgctgcggtg    420
tacctgaaaa aggtagactc cgccatcgcg agcaacaacg ccgctggaga cggctggttc    480
aagatctggg agtccgtcta cgacgagtcc acgggcaaat ggggtacgac caagatgatc    540
gagaacaacg ggcacatctc tgtcaaggtc cccgacgata tcgagggtgg gtattatctc    600
gcgcgtacgg agcttctggc gctgcacgcg gcgaacgaag gggatccgca gttctacgtt    660
ggctgcgcgc agctgttcat cgattcagcg gggacagcga aaccgcctac tgtctctatt    720
ggagagggga cctacgatct gagcatgcct gccatgacgt acaatatcta ccagactccg    780
ttggctctac catacccgat gtatgggcct cctgtctaca cacctggctc tggctcgggt    840
tctggctctg gttccgggtc agcttctgca acgagatctt ctgctattcc tactgccacc    900
gctgttacgg actgttcttc gaagaggac agggaagact cagtcatggc aaccggtgtt    960
cccgttgcaa gaagcacact cagaacctgg gttgacagac tgtcatggca tggtaaggcc    1020
cgtgagaacg tgaaaccagc cgccaggaga agcgcccttg tccagaccga gggtctgaag    1080
ccggaaggct gcatcttcgt caacggcaac tggtgcggtt tcgaggtccc cgattacaac    1140
gatgcggaaa gctgctgggc tgtacgttcc cgtctaatta cttaaaacga aataaaagct    1200
aacagtactt ttcttttct aatcccaggc ctccgacaac tgctggaaac agtccgactc    1260
gtgctggaac cagacccagc ccaccggcta caacaactgc cagatctggc aagaccagaa    1320
atgcaagccc atccaggact cgtgtagcca atccaacccg actggaccgc cgaacaaggg    1380
caaggatata actccaacgt ggccgcccct ggagggctcg atgaagacct tcaccaagcg    1440
cactgtcagt taccgtgatt ggattatgaa aaggaaagga gcataa                  1486

<210> SEQ ID NO 34
<211> LENGTH: 444
<212> TYPE: PRT
<213> ORGANISM: Thermoascus sp.

<400> SEQUENCE: 34
```

-continued

```
Met Leu Ser Phe Ala Ser Ala Lys Ser Ala Val Leu Thr Thr Leu Leu
1               5                   10                  15

Leu Leu Gly Ser Ala Gln Ala His Thr Leu Met Thr Thr Leu Phe Val
            20                  25                  30

Asp Gly Val Asn Gln Gly Asp Gly Val Cys Ile Arg Met Asn Asn Asn
            35                  40                  45

Gly Ser Thr Ala Asn Thr Tyr Ile Gln Pro Val Thr Ser Lys Asp Ile
        50                  55                  60

Ala Cys Gly Ile Gln Gly Glu Ile Gly Ala Ala Arg Val Cys Pro Ala
65                  70                  75                  80

Lys Ala Ser Ser Thr Leu Thr Phe Gln Phe Arg Glu Gln Pro Ser Asn
                85                  90                  95

Pro Asn Ser Ala Pro Leu Asp Pro Ser His Lys Gly Pro Ala Ala Val
            100                 105                 110

Tyr Leu Lys Lys Val Asp Ser Ala Ile Ala Ser Asn Asn Ala Ala Gly
            115                 120                 125

Asp Gly Trp Phe Lys Ile Trp Glu Ser Val Tyr Asp Glu Ser Thr Gly
            130                 135                 140

Lys Trp Gly Thr Thr Lys Met Ile Glu Asn Asn Gly His Ile Ser Val
145                 150                 155                 160

Lys Val Pro Asp Asp Ile Glu Gly Gly Tyr Tyr Leu Ala Arg Thr Glu
                165                 170                 175

Leu Leu Ala Leu His Ala Ala Asn Glu Gly Asp Pro Gln Phe Tyr Val
            180                 185                 190

Gly Cys Ala Gln Leu Phe Ile Asp Ser Ala Gly Thr Ala Lys Pro Pro
            195                 200                 205

Thr Val Ser Ile Gly Glu Gly Thr Tyr Asp Leu Ser Met Pro Ala Met
            210                 215                 220

Thr Tyr Asn Ile Tyr Gln Thr Pro Leu Ala Leu Pro Tyr Pro Met Tyr
225                 230                 235                 240

Gly Pro Pro Val Tyr Thr Pro Gly Ser Gly Ser Gly Ser Gly Ser Gly
                245                 250                 255

Ser Gly Ser Ala Ser Ala Thr Arg Ser Ser Ala Ile Pro Thr Ala Thr
            260                 265                 270

Ala Val Thr Asp Cys Ser Ser Glu Glu Asp Arg Glu Asp Ser Val Met
            275                 280                 285

Ala Thr Gly Val Pro Val Ala Arg Ser Thr Leu Arg Thr Trp Val Asp
            290                 295                 300

Arg Leu Ser Trp His Gly Lys Ala Arg Glu Asn Val Lys Pro Ala Ala
305                 310                 315                 320

Arg Arg Ser Ala Leu Val Gln Thr Glu Gly Leu Lys Pro Glu Gly Cys
            325                 330                 335

Ile Phe Val Asn Gly Asn Trp Cys Gly Phe Glu Val Pro Asp Tyr Asn
            340                 345                 350

Asp Ala Glu Ser Cys Trp Ala Ser Asp Asn Cys Trp Lys Gln Ser
            355                 360                 365

Asp Ser Cys Trp Asn Gln Thr Gln Pro Thr Gly Tyr Asn Asn Cys Gln
            370                 375                 380

Ile Trp Gln Asp Gln Lys Cys Lys Pro Ile Gln Asp Ser Cys Ser Gln
385                 390                 395                 400

Ser Asn Pro Thr Gly Pro Pro Asn Lys Gly Lys Asp Ile Thr Pro Thr
                405                 410                 415

Trp Pro Pro Leu Glu Gly Ser Met Lys Thr Phe Thr Lys Arg Thr Val
```

```
              420                 425                 430
Ser Tyr Arg Asp Trp Ile Met Lys Arg Lys Gly Ala
        435                 440
```

<210> SEQ ID NO 35
<211> LENGTH: 835
<212> TYPE: DNA
<213> ORGANISM: Penicillium sp.

<400> SEQUENCE: 35

```
atgctgtctt cgacgactcg caccctcgcc tttacaggcc ttgcgggcct tctgtccgct    60
cccctggtca aggcccatgg ctttgtccag ggcattgtca tcggtgacca attgtaagtc   120
cctctcttgc agttctgtcg attaactgct ggactgcttg cttgactccc tgctgactcc   180
caacagctac agcgggtaca tcgtcaactc gttcccctac gaatccaacc cacccccgt    240
catcggctgg ccacgaccg ccaccgacct gggcttcgtc gacggcacag ataccaagg     300
cccggacatc atctgccacc ggaatgcgac gcccgcgccg ctgacagccc cgtggccgc    360
cggcggcacc gtcgagctgc agtggacgcc gtggccggac agccaccacg gacccgtcat   420
cacctacctg gcgccgtgca acggcaactg ctcgaccgtc gacaagacga cgctggagtt   480
cttcaagatc gaccagcagg gcctgatcga cgacacgagc ccgccgggca cctgggcgtc   540
ggacaacctc atcgccaaca caatagctg accgtcacc attcccaaca gcgtcgcccc     600
cggcaactac gtcctgcgcc acgagatcat cgccctgcac tcggccaaca caaggacgg    660
cgcccagaac taccccagt gcatcaacat cgaggtcacg gcggcggct ccgacgcgcc     720
tgagggtact ctgggcgagg atctctacca tgacaccgac ccgggcattc tggtcgacat   780
ttacgagccc attgcgacgt ataccattcc ggggccgcct gagccgacgt tctag        835
```

<210> SEQ ID NO 36
<211> LENGTH: 253
<212> TYPE: PRT
<213> ORGANISM: Penicillium sp.

<400> SEQUENCE: 36

```
Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160
```

-continued

```
Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250
```

<210> SEQ ID NO 37
<211> LENGTH: 878
<212> TYPE: DNA
<213> ORGANISM: Thielavia terrestris

<400> SEQUENCE: 37

```
atgaagttct cactggtgtc tctgctggct tacggcctct cggtcgaggc gcactccatc    60
ttccaggttc gtctcgcaca tcacgctcaa ctcggctcgt ggcgtaaggg caaggattaa   120
cacggccggc agagagtctc ggtcaacggc aagaccaag gcctgctcac cggcctccgc    180
gctccaagca acaacaaccc agtgcaagat gtcaacagcc agaacatgat ttgcggccag   240
tcgggctcca agtcgcagac cgttatcaac gtcaaggccg cgacaggat cggctcgctc    300
tggcagcatg tcatcggcgg cgcccagttt tcgggtgacc cggacaaccc gatcgcccac   360
tcgcacaagg gccccgtgat ggcgtacctt gctaaggtcg acaatgccgc gtccgcgagc   420
caaacgggtc tgaagtggta agtagcgggc gacgctcagg ggacggggat cggggggcctg   480
ctccatccga gactaacacc gtggacaggt tcaagatctg gcaggacggg ttcgatacca   540
gcagcaagac atgggggcgtc gacaacctga tcaagaacaa cggctgggtg tacttccacc   600
tgccgcagtg cctcgctccg ggccagtatc tcctgcgcgt cgaggttctg gcgctgcact   660
cggcgtacca gcagggccag gcccagttct accagtcctg cgcccagatc aacgtctccg   720
gctccgggtc cttcagcccg tcccagacgg tcagcatccc gggcgtctac agcgccaccg   780
acccgagcat cctcatcaac atctacggca gcacgggggca gcccgacaac ggcggcaagg   840
cttacaaccc ccctggaccc gccccgatct cctgctga                            878
```

<210> SEQ ID NO 38
<211> LENGTH: 246
<212> TYPE: PRT
<213> ORGANISM: Thielavia terrestris

<400> SEQUENCE: 38

```
Met Lys Phe Ser Leu Val Ser Leu Leu Ala Tyr Gly Leu Ser Val Glu
1               5                   10                  15

Ala His Ser Ile Phe Gln Arg Val Ser Val Asn Gly Gln Asp Gln Gly
            20                  25                  30

Leu Leu Thr Gly Leu Arg Ala Pro Ser Asn Asn Pro Val Gln Asp
        35                  40                  45

Val Asn Ser Gln Asn Met Ile Cys Gly Gln Ser Gly Ser Lys Ser Gln
    50                  55                  60

Thr Val Ile Asn Val Lys Ala Gly Asp Arg Ile Gly Ser Leu Trp Gln
65                  70                  75                  80
```

His Val Ile Gly Gly Ala Gln Phe Ser Gly Asp Pro Asp Asn Pro Ile
            85                  90                  95

Ala His Ser His Lys Gly Pro Val Met Ala Tyr Leu Ala Lys Val Asp
            100                 105                 110

Asn Ala Ala Ser Ala Ser Gln Thr Gly Leu Lys Trp Phe Lys Ile Trp
            115                 120                 125

Gln Asp Gly Phe Asp Thr Ser Ser Lys Thr Trp Gly Val Asp Asn Leu
130                 135                 140

Ile Lys Asn Asn Gly Trp Val Tyr Phe His Leu Pro Gln Cys Leu Ala
145                 150                 155                 160

Pro Gly Gln Tyr Leu Leu Arg Val Glu Val Leu Ala Leu His Ser Ala
                165                 170                 175

Tyr Gln Gln Gly Gln Ala Gln Phe Tyr Gln Ser Cys Ala Gln Ile Asn
            180                 185                 190

Val Ser Gly Ser Gly Ser Phe Ser Pro Ser Gln Thr Val Ser Ile Pro
            195                 200                 205

Gly Val Tyr Ser Ala Thr Asp Pro Ser Ile Leu Ile Asn Ile Tyr Gly
            210                 215                 220

Ser Thr Gly Gln Pro Asp Asn Gly Gly Lys Ala Tyr Asn Pro Pro Gly
225                 230                 235                 240

Pro Ala Pro Ile Ser Cys
                245

<210> SEQ ID NO 39
<211> LENGTH: 1253
<212> TYPE: DNA
<213> ORGANISM: Thielavia terrestris

<400> SEQUENCE: 39
atgaggacga cattcgccgc cgcgttggca gccttcgctg cgcaggaagt ggcaggccat      60
gccatcttcc aacagctctg ggtggacggc accgactata tacgtgctcc ccttttcctt     120
ttgtgtttgc ccatcctcga ttgataaccc gaggccatcc aatgctgact cttacagcac     180
ggctcctcct gcgtccgcat gccgctgtcg aactcgcccg tcacgaacgt cggcagcagg     240
gacatgatct gcaacgccgg cacgcgcccc gtcagcggga agtgccccgt caaggccggc     300
ggcaccgtga cggttgagat gcaccaggtg ggctgatttc ctgagcgtcc tattcctccc     360
ggaagcccct ttcccatcct ttgccctggc taaccccctcc gccctcccca gcaacccggg     420
gatcggtcgt gtaacaacga agccatcggc ggcgcccact ggggaccggt gcaggtgtac     480
ctcagcaagg tggaggacgc gagcacggcg gacgggtcga cgggctggtt caagatcttc     540
gcggacacgt ggtccaagaa ggcgggcagc tcggtggggg acgacgacaa ctggggcacg     600
cgcgacctca acgcgtgctg cggcaagatg caggtcaaga tcccggcgga catcccgtcg     660
ggcgactacc tgctgcgggc ggaggcgctg gcgctgcaca cggcgggcca ggtgggcggc     720
gcgcagttct acatgagctg ctaccagatc accgtgtcgg gcggcggcag cgccagcccg     780
gccaccgtca agttccccgg cgcctacagc gccaacgacc cgggcatcca catcaacatc     840
cacgcggccg tgtccaacta cgtcgcgccc ggcccggccg tctattccgg cggcacgacc     900
aaggtggccg gtccgggtg ccaaggctgc gagaacacgt gcaaggtcgg ctcgtcgccc     960
acggcgacgg cgccgtcggg caagagcggc gcgggttccg acggcggcgc tgggaccgac    1020
ggcgggtctt cgtcttcgag ccccgacacg gcagcgcgt gcagcgtgca ggcctacggg    1080
cagtgcggcg ggaacgggta ctcgggttgc acccagtgcg cggtaagttc ggggtcgtct    1140

```
gtcttttgta ggaacatccg agaggcttgg ctgacgaggc gttgttgtag cccggctata    1200
cttgcaaggc ggtctctccg ccgtactatt cgcagtgcgc cccttcttct tag           1253
```

<210> SEQ ID NO 40
<211> LENGTH: 334
<212> TYPE: PRT
<213> ORGANISM: Thielavia terrestris

<400> SEQUENCE: 40

```
Met Arg Thr Thr Phe Ala Ala Leu Ala Ala Phe Ala Ala Gln Glu
1               5                   10                  15

Val Ala Gly His Ala Ile Phe Gln Gln Leu Trp His Gly Ser Ser
            20                  25                  30

Val Arg Met Pro Leu Ser Asn Ser Pro Val Thr Asn Val Gly Ser Arg
        35                  40                  45

Asp Met Ile Cys Asn Ala Gly Thr Arg Pro Val Ser Gly Lys Cys Pro
    50                  55                  60

Val Lys Ala Gly Gly Thr Val Thr Val Glu Met His Gln Gln Pro Gly
65                  70                  75                  80

Asp Arg Ser Cys Asn Asn Glu Ala Ile Gly Gly Ala His Trp Gly Pro
                85                  90                  95

Val Gln Val Tyr Leu Ser Lys Val Glu Asp Ala Ser Thr Ala Asp Gly
            100                 105                 110

Ser Thr Gly Trp Phe Lys Ile Phe Ala Asp Thr Trp Ser Lys Lys Ala
        115                 120                 125

Gly Ser Ser Val Gly Asp Asp Asn Trp Gly Thr Arg Asp Leu Asn
    130                 135                 140

Ala Cys Cys Gly Lys Met Gln Val Lys Ile Pro Ala Asp Ile Pro Ser
145                 150                 155                 160

Gly Asp Tyr Leu Leu Arg Ala Glu Ala Leu Ala Leu His Thr Ala Gly
                165                 170                 175

Gln Val Gly Gly Ala Gln Phe Tyr Met Ser Cys Tyr Gln Ile Thr Val
            180                 185                 190

Ser Gly Gly Gly Ser Ala Ser Pro Ala Thr Val Lys Phe Pro Gly Ala
        195                 200                 205

Tyr Ser Ala Asn Asp Pro Gly Ile His Ile Asn Ile His Ala Ala Val
    210                 215                 220

Ser Asn Tyr Val Ala Pro Gly Pro Ala Val Tyr Ser Gly Gly Thr Thr
225                 230                 235                 240

Lys Val Ala Gly Ser Gly Cys Gln Gly Cys Glu Asn Thr Cys Lys Val
                245                 250                 255

Gly Ser Ser Pro Thr Ala Thr Ala Pro Ser Gly Lys Ser Gly Ala Gly
            260                 265                 270

Ser Asp Gly Gly Ala Gly Thr Asp Gly Gly Ser Ser Ser Ser Pro
        275                 280                 285

Asp Thr Gly Ser Ala Cys Ser Val Gln Ala Tyr Gln Cys Gly Gly
    290                 295                 300

Asn Gly Tyr Ser Gly Cys Thr Gln Cys Ala Pro Gly Tyr Thr Cys Lys
305                 310                 315                 320

Ala Val Ser Pro Pro Tyr Tyr Ser Gln Cys Ala Pro Ser Ser
                325                 330
```

<210> SEQ ID NO 41
<211> LENGTH: 798
<212> TYPE: DNA

<213> ORGANISM: Thielavia terrestris

<400> SEQUENCE: 41

```
atgaagctga gcgttgccat cgccgtgctg cgtcggctc ttgccgaggc tcactgtgag      60
tgcatcgtct cactccagct actgcgaagc ttgctgacga tggtccctag acaccttccc    120
cagcatcgga aacaccgctg actggcagta tgtgcggatt acaacgaact accagagcaa    180
cgggccggtg acggacgtca cctcggatca aattcggtgc tacgaacgga acccaggcac    240
gggagcgcag ggcatataca acgtcaccgc cggccagacc atcaactaca acgcgaaggc    300
gtccatctcc cacccggggc ccatgtcctt ctacattgct aaggttcccg ccggccaaac    360
cgctgcgacc tgggacggta aggggctgt gtggaccaag atctaccagg acatgcccaa    420
gttcggcagc agcctgacct ggcccaccat gggtaagaat tctcaccctg gaaatgaacg    480
cacatttgca cagatctaac atggcctaca ggcgccaagt ctgtccccgt caccatccct    540
cgttgcctcc agaacggcga ttaccttctg cgagccgagc acatcgctct acacagcgcg    600
agcagcgtcg gtggcgccca gttctacctc tcgtgcgccc agcttactgt cagcggcggc    660
agtggcacct ggaaccccaa gaaccgggtc tccttccccg cgcttacaa ggcaacagac    720
ccgggcatct tgatcaacat ctactacccc gtgccgacca gctactcgcc gcccggcccg    780
ccggctgaga cgtgctaa                                                 798
```

<210> SEQ ID NO 42
<211> LENGTH: 227
<212> TYPE: PRT
<213> ORGANISM: Thielavia terrestris

<400> SEQUENCE: 42

```
Met Lys Leu Ser Val Ala Ile Ala Val Leu Ala Ser Ala Leu Ala Glu
1               5                   10                  15

Ala His Tyr Thr Phe Pro Ser Ile Gly Asn Thr Ala Asp Trp Gln Tyr
            20                  25                  30

Val Arg Ile Thr Thr Asn Tyr Gln Ser Asn Gly Pro Val Thr Asp Val
        35                  40                  45

Thr Ser Asp Gln Ile Arg Cys Tyr Glu Arg Asn Pro Gly Thr Gly Ala
    50                  55                  60

Gln Gly Ile Tyr Asn Val Thr Ala Gly Gln Thr Ile Asn Tyr Asn Ala
65                  70                  75                  80

Lys Ala Ser Ile Ser His Pro Gly Pro Met Ser Phe Tyr Ile Ala Lys
                85                  90                  95

Val Pro Ala Gly Gln Thr Ala Ala Thr Trp Asp Gly Lys Gly Ala Val
            100                 105                 110

Trp Thr Lys Ile Tyr Gln Asp Met Pro Lys Phe Gly Ser Ser Leu Thr
        115                 120                 125

Trp Pro Thr Met Gly Ala Lys Ser Val Pro Val Thr Ile Pro Arg Cys
    130                 135                 140

Leu Gln Asn Gly Asp Tyr Leu Leu Arg Ala Glu His Ile Ala Leu His
145                 150                 155                 160

Ser Ala Ser Ser Val Gly Gly Ala Gln Phe Tyr Leu Ser Cys Ala Gln
                165                 170                 175

Leu Thr Val Ser Gly Gly Ser Gly Thr Trp Asn Pro Lys Asn Arg Val
            180                 185                 190

Ser Phe Pro Gly Ala Tyr Lys Ala Thr Asp Pro Gly Ile Leu Ile Asn
        195                 200                 205
```

```
Ile Tyr Tyr Pro Val Pro Thr Ser Tyr Ser Pro Gly Pro Pro Ala
    210                 215                 220

Glu Thr Cys
225

<210> SEQ ID NO 43
<211> LENGTH: 977
<212> TYPE: DNA
<213> ORGANISM: Thielavia terrestris

<400> SEQUENCE: 43
atgaagctgt catcccagct cgccgccctc acgctggccg cggcctccgt gtcaggccac      60
tacatcttcg agcagattgc ccatggcggc accaagttcc caccttacga gtacatccga     120
agaaacacga actataacag ccctgtcacc agtctctcgt cgaacgacct gcgatgcaac     180
gtaggcggcg agacggctgg caacacgacc gtcctcgacg tgaaggcggg cgactccttc     240
accttctact cggacgtggc cgtgtaccac caggggccca tctcactgtg cgtgccccgg     300
gccaactttg atcagtccca gcggactgt ccgctcgcct ggataaccac aattgactga     360
cagcccgcac agctacatgt ccaaggctcc cggctccgtc gtggactacg acggctccgg     420
cgactggttc aagatccacg actggggccc gaccttcagc aacggccagg cctcgtggcc     480
gctgcggggt gcgtcccttc cctttccctc cccttcctc ccccccttc                  540
ccccctttc tgtctggtcg cacgcccgc tgacgtcccc gtagcaact accagtacaa         600
catcccgacg tgcatcccga acggcgagta cctgctgcgc atccagtcgc tggcgatcca     660
caaccccgg gccacgccgc agttctacat cagctgcgcg caggtccggg tctcgggcgg     720
cggcagcgcc tccccctccc aacggccaa gatccccggc gcgttcaagg cgaccgatcc     780
cgggtatacc gcgaatgtga gtgccctatg ttccttgcgc tccttgttcc ttgctccttg     840
ctcggcgtgc ttgaacgcta cgggctgtgg agggagggat ggatggatga ataggatgct     900
gactgatggt gggacaccag atttacaata acttccactc gtatacggtg ccgggtccgg     960
cggtctttca gtgctag                                                    977

<210> SEQ ID NO 44
<211> LENGTH: 223
<212> TYPE: PRT
<213> ORGANISM: Thielavia terrestris

<400> SEQUENCE: 44

Met Lys Leu Ser Ser Gln Leu Ala Ala Leu Thr Leu Ala Ala Ala Ser
1               5                   10                  15

Val Ser Gly His Tyr Ile Phe Glu Gln Ile Ala His Gly Gly Thr Lys
                20                  25                  30

Phe Pro Pro Tyr Glu Tyr Ile Arg Arg Asn Thr Asn Tyr Asn Ser Pro
            35                  40                  45

Val Thr Ser Leu Ser Ser Asn Asp Leu Arg Cys Asn Val Gly Gly Glu
        50                  55                  60

Thr Ala Gly Asn Thr Thr Val Leu Asp Val Lys Ala Gly Asp Ser Phe
65                  70                  75                  80

Thr Phe Tyr Ser Asp Val Ala Val Tyr His Gln Gly Pro Ile Ser Leu
                85                  90                  95

Tyr Met Ser Lys Ala Pro Gly Ser Val Val Asp Tyr Asp Gly Ser Gly
            100                 105                 110

Asp Trp Phe Lys Ile His Asp Trp Gly Pro Thr Phe Ser Asn Gly Gln
        115                 120                 125
```

```
Ala Ser Trp Pro Leu Arg Asp Asn Tyr Gln Tyr Asn Ile Pro Thr Cys
    130                 135                 140

Ile Pro Asn Gly Glu Tyr Leu Leu Arg Ile Gln Ser Leu Ala Ile His
145                 150                 155                 160

Asn Pro Gly Ala Thr Pro Gln Phe Tyr Ile Ser Cys Ala Gln Val Arg
                165                 170                 175

Val Ser Gly Gly Gly Ser Ala Ser Pro Ser Pro Thr Ala Lys Ile Pro
            180                 185                 190

Gly Ala Phe Lys Ala Thr Asp Pro Gly Tyr Thr Ala Asn Ile Tyr Asn
        195                 200                 205

Asn Phe His Ser Tyr Thr Val Pro Gly Pro Ala Val Phe Gln Cys
    210                 215                 220

<210> SEQ ID NO 45
<211> LENGTH: 1107
<212> TYPE: DNA
<213> ORGANISM: Thielavia terrestris

<400> SEQUENCE: 45
atgccttctt tcgcctccaa gactctcctt tccaccctgg cgggtgccgc atccgtggcc      60
gcccacgggc acgtgtcgaa catcgtcatc aacggggtct cgtaccaggg ttacgatccg     120
acctccttcc cttacatgca gaacccgccc atcgtggtcg gctggactgc cgccgacacg     180
gacaacggct tgttgccccc ggatgccttc gccagtggcg atatcatctg ccacaagaac     240
gccaccaacg ccaagggcca cgccgtggtc gccgcgggag acaagatctt catccagtgg     300
aacacatggc ccgagtccca ccacggcccc gtcatcgact acctcgcgag ctgcggcagc     360
gcgtcctgcg agaccgtcga caagaccaag ctcgagttct tcaagatcga cgaggtcggc     420
ctggtcgacg cagctcggc gcccggtgtg tggggctccg accagctcat cgccaacaac     480
aactcgtggc tcgtcgagat cccgccacc atcgcgccgg caactacgt cctgcgccac     540
gagatcatcg cgctgcacag cgccgaaaac gccgacggcg cccagaacta cccgcagtgc     600
ttcaacctgc agatcaccgg caccggcacc gccaccccct ccggcgtccc cggcacctcg     660
ctctacaccc cgaccgaccc gggcatcctc gtcaacatct cagcgcccc gatcacctac     720
accgtcccgg ggccggccct catctccggc gccgtcagca tcgcccagtc ctcctccgcc     780
atcaccgcct ccggcaccgc cctgaccggc tctgccaccg cacccgccgc cgccgctgct     840
accacaactt ccaccaccaa cgccgcggct gctgctacct gctgctgctg tgctgctggt     900
acttccacaa ccaccaccag cgccgcggcc gtggtccaga cctcctcctc ctcctcctcc     960
gccccgtcct tgccgccgc cgccgccacc accaccgcgg ctgccagcgc ccgcccgacc    1020
ggctgctcct ctggccgctc caggaagcag ccgcgccgcc acgcgcggga tatggtggtt    1080
gcgcgagggg ctgaggaggc aaactga                                       1107

<210> SEQ ID NO 46
<211> LENGTH: 368
<212> TYPE: PRT
<213> ORGANISM: Thielavia terrestris

<400> SEQUENCE: 46

Met Pro Ser Phe Ala Ser Lys Thr Leu Leu Ser Thr Leu Ala Gly Ala
1               5                   10                  15

Ala Ser Val Ala Ala His Gly His Val Ser Asn Ile Val Ile Asn Gly
            20                  25                  30
```

```
Val Ser Tyr Gln Gly Tyr Asp Pro Thr Ser Phe Pro Tyr Met Gln Asn
    35                  40                  45

Pro Pro Ile Val Val Gly Trp Thr Ala Ala Asp Thr Asp Asn Gly Phe
50                  55                  60

Val Ala Pro Asp Ala Phe Ala Ser Gly Asp Ile Ile Cys His Lys Asn
65                  70                  75                  80

Ala Thr Asn Ala Lys Gly His Ala Val Val Ala Gly Asp Lys Ile
                85                  90                  95

Phe Ile Gln Trp Asn Thr Trp Pro Glu Ser His Gly Pro Val Ile
            100                 105                 110

Asp Tyr Leu Ala Ser Cys Gly Ser Ala Ser Cys Glu Thr Val Asp Lys
            115                 120                 125

Thr Lys Leu Glu Phe Phe Lys Ile Asp Glu Val Gly Leu Val Asp Gly
    130                 135                 140

Ser Ser Ala Pro Gly Val Trp Gly Ser Asp Gln Leu Ile Ala Asn Asn
145                 150                 155                 160

Asn Ser Trp Leu Val Glu Ile Pro Pro Thr Ile Ala Pro Gly Asn Tyr
                165                 170                 175

Val Leu Arg His Glu Ile Ile Ala Leu His Ser Ala Glu Asn Ala Asp
            180                 185                 190

Gly Ala Gln Asn Tyr Pro Gln Cys Phe Asn Leu Gln Ile Thr Gly Thr
            195                 200                 205

Gly Thr Ala Thr Pro Ser Gly Val Pro Gly Thr Ser Leu Tyr Thr Pro
    210                 215                 220

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
                245                 250                 255

Ser Ser Ser Ala Ile Thr Ala Ser Gly Thr Ala Leu Thr Gly Ser Ala
            260                 265                 270

Thr Ala Pro Ala Ala Ala Ala Thr Thr Ser Thr Thr Asn Ala
    275                 280                 285

Ala Ala Ala Ala Thr Ser Ala Ala Ala Ala Gly Thr Ser Thr Thr
290                 295                 300

Thr Thr Ser Ala Ala Val Val Gln Thr Ser Ser Ser Ser Ser
305                 310                 315                 320

Ala Pro Ser Ser Ala Ala Ala Ala Thr Thr Ala Ala Ala Ser
            325                 330                 335

Ala Arg Pro Thr Gly Cys Ser Gly Arg Ser Arg Lys Gln Pro Arg
            340                 345                 350

Arg His Ala Arg Asp Met Val Val Ala Arg Gly Ala Glu Glu Ala Asn
    355                 360                 365
```

<210> SEQ ID NO 47
<211> LENGTH: 993
<212> TYPE: DNA
<213> ORGANISM: Thielavia terrestris

<400> SEQUENCE: 47

```
atgccgcccg cactccctca actcctaacc acgtcctga ccgccctcac cctcggttcc      60
accgccctcg cccactcaca cctcgcgtac attatcgtta acggcaagct ctaccagggc     120
ttcgacccgc gccgcacca ggccaactac ccttcccggg tcgggtggtc caccggcgcc     180
gtcgacgacg gcttcgtcac gccggccaac tactccaccc cggacatcat ttgccacatc    240
```

```
gccggcacca gcccggccgg ccacgcgccc gtgcgcccgg gcgaccgcat ccacgtccag    300
tggaacggct ggccggtcgg ccacatcggt cccgtgctgt cgtacctcgc ccgctgcgag    360
tcggacacgg gctgcacggg ccagaacaag accgcgctgc ggtggaccaa gatcgacgac    420
tccagcccga ccatgcagaa cgtcgccggc gcgggcaccc agggcgaggg cacccccggc    480
aagcgctggg ccaccgacgt gctgatcgcc gccaacaaca gctggcaggt cgccgtgccg    540
gcggggctgc cgaccggcgc gtacgtgctg cgcaacgaga tcatcgcgct gcactacgcg    600
gcgaggaaga acggggcgca gaactatccg ctctgcatga acctgtgggt ggacgccagt    660
ggtgataata gtagtgtggc tgcaacgacg cggcggtgac ggcgggggg tctgcagatg     720 gatgcgtatg acgcgcgcgg gttctacaag gagaacgatc cggcgtgct ggtcaatgtc     780 acggccgcgc tgtcgtcgta tgtcgtgccc gggccgacgg tggcggcggg cgccacgccg    840
gtgccgtacg cgcagcagag cccgagcgtg tcgacggcgg cgggcacgcc cgtcgtcgtt    900
acaaggacta gcgagacggc gccgtacacg ggcgccatga cgccgacggt tgcggcgagg    960
atgaagggga gggggtatga tcggcggggt tag                                 993
```

<210> SEQ ID NO 48
<211> LENGTH: 330
<212> TYPE: PRT
<213> ORGANISM: Thielavia terrestris

<400> SEQUENCE: 48

```
Met Pro Pro Ala Leu Pro Gln Leu Leu Thr Thr Val Leu Thr Ala Leu
1               5                   10                  15

Thr Leu Gly Ser Thr Ala Leu Ala His Ser His Leu Ala Tyr Ile Ile
            20                  25                  30

Val Asn Gly Lys Leu Tyr Gln Gly Phe Asp Pro Arg Pro His Gln Ala
        35                  40                  45

Asn Tyr Pro Ser Arg Val Gly Trp Ser Thr Gly Ala Val Asp Asp Gly
    50                  55                  60

Phe Val Thr Pro Ala Asn Tyr Ser Thr Pro Asp Ile Ile Cys His Ile
65                  70                  75                  80

Ala Gly Thr Ser Pro Ala Gly His Ala Pro Val Arg Pro Gly Asp Arg
                85                  90                  95

Ile His Val Gln Trp Asn Gly Trp Pro Val Gly His Ile Gly Pro Val
            100                 105                 110

Leu Ser Tyr Leu Ala Arg Cys Glu Ser Asp Thr Gly Cys Thr Gly Gln
        115                 120                 125

Asn Lys Thr Ala Leu Arg Trp Thr Lys Ile Asp Asp Ser Ser Pro Thr
    130                 135                 140

Met Gln Asn Val Ala Gly Ala Gly Thr Gln Gly Glu Gly Thr Pro Gly
145                 150                 155                 160

Lys Arg Trp Ala Thr Asp Val Leu Ile Ala Ala Asn Asn Ser Trp Gln
                165                 170                 175

Val Ala Val Pro Ala Gly Leu Pro Thr Gly Ala Tyr Val Leu Arg Asn
            180                 185                 190

Glu Ile Ile Ala Leu His Tyr Ala Ala Arg Lys Asn Gly Ala Gln Asn
        195                 200                 205

Tyr Pro Leu Cys Met Asn Leu Trp Val Asp Ala Ser Gly Asp Asn Ser
    210                 215                 220

Ser Val Ala Ala Thr Thr Ala Val Thr Ala Gly Gly Leu Gln Met
225                 230                 235                 240
```

```
Asp Ala Tyr Asp Ala Arg Gly Phe Tyr Lys Glu Asn Asp Pro Gly Val
            245                 250                 255

Leu Val Asn Val Thr Ala Ala Leu Ser Ser Tyr Val Pro Gly Pro
        260                 265                 270

Thr Val Ala Ala Gly Ala Thr Pro Val Pro Tyr Ala Gln Gln Ser Pro
            275                 280                 285

Ser Val Ser Thr Ala Ala Gly Thr Pro Val Val Val Thr Arg Thr Ser
        290                 295                 300

Glu Thr Ala Pro Tyr Thr Gly Ala Met Thr Pro Thr Val Ala Ala Arg
305                 310                 315                 320

Met Lys Gly Arg Gly Tyr Asp Arg Arg Gly
            325                 330
```

<210> SEQ ID NO 49
<211> LENGTH: 1221
<212> TYPE: DNA
<213> ORGANISM: Thielavia terrestris

<400> SEQUENCE: 49

```
atgaagacat tcaccgccct cctggccgca gccggcctcg tcgccggcca tggatatgtc     60
gacaacgcca ccattggcgg ccagtttat  caggtactct accgcttcac ccaaggtccg    120
ctggccacaa ctctataggt gtcataaatt aacaagccac cgtcccgcag ttctatcagg    180
tgtgctcgct accgaccatg tggtcccgtc tcagcaagcc actcacacgc ccatgatccc    240
ctagccttac gtcgacccgt atttagcaac cttggcacgt agtatttatt gtcccaaata    300
ttgagctgaa ctgcacctcc ctagaatccc gcggtgctaa cattctttca gcccgacagg    360
gtctctcgat ccatcccggg caacggcccg gtcacggacg tcactctcat cgacctgcag    420
tgcaacgcca attccacccc ggccaagctc acgccactg  ccgctgccgg tcggacgtg     480
attctccgct ggacgctctg gcctgagtcg cacgttggcc ccgtcatcac ctacatggcc    540
cgctgccccg acacgggctg ccaggactgg atgccgggca cttcgtagga gcccatcttg    600
caccatatcc atttcaaccg ccacacgca  ctgacccata tgtctgtcta ccctgcagt     660
gcggtctggt tcaagatcaa ggagggcggc cgcgacggca cttccaacac ctgggccgac    720
gtacgtgtac cccgtcccag agagccaaag cccccccttc aacaaagcaa acatctcaat    780
agcccgagcc tacgcactaa ccctctcct  tcccctcga  aaacacagac cccgctgatg    840
acggcgccca cctcgtacac gtacacgatc ccctcctgcc tgaagaaggg ctactacctg    900
gtccgccacg agatcatcgc gctgcacgcc gcctacacct accccggcgc gcagttctac    960
ccgggctgcc accagctcaa cgtcacgggc ggcgggtcca ccgtaccgtc gagcggcctg   1020
gtggcctttc ccggggcgta caagggcagt gaccccggga ttacgtacga tgcgtataaa   1080
ggtgggttgg ctggttggcc caggtcttgg tgatggggga atgtggtgat gaggtttatt   1140
atttgggatc ccgtggctaa cgtaaccctg ggtgtagcgc aaacgtacca gattcctggg   1200
ccggcggtct ttacttgctg a                                             1221
```

<210> SEQ ID NO 50
<211> LENGTH: 236
<212> TYPE: PRT
<213> ORGANISM: Thielavia terrestris

<400> SEQUENCE: 50

```
Met Lys Thr Phe Thr Ala Leu Leu Ala Ala Ala Gly Leu Val Ala Gly
1               5                   10                  15
```

```
His Gly Tyr Val Asp Asn Ala Thr Ile Gly Gly Gln Phe Tyr Gln Asn
            20                  25                  30

Pro Ala Val Leu Thr Phe Phe Gln Pro Asp Arg Val Ser Arg Ser Ile
        35                  40                  45

Pro Gly Asn Gly Pro Val Thr Asp Val Thr Leu Ile Asp Leu Gln Cys
    50                  55                  60

Asn Ala Asn Ser Thr Pro Ala Lys Leu His Ala Thr Ala Ala Ala Gly
65                  70                  75                  80

Ser Asp Val Ile Leu Arg Trp Thr Leu Trp Pro Glu Ser His Val Gly
                85                  90                  95

Pro Val Ile Thr Tyr Met Ala Arg Cys Pro Asp Thr Gly Cys Gln Asp
            100                 105                 110

Trp Met Pro Gly Thr Ser Ala Val Trp Phe Lys Ile Lys Glu Gly Gly
        115                 120                 125

Arg Asp Gly Thr Ser Asn Thr Trp Ala Asp Thr Pro Leu Met Thr Ala
    130                 135                 140

Pro Thr Ser Tyr Thr Tyr Thr Ile Pro Ser Cys Leu Lys Lys Gly Tyr
145                 150                 155                 160

Tyr Leu Val Arg His Glu Ile Ile Ala Leu His Ala Ala Tyr Thr Tyr
                165                 170                 175

Pro Gly Ala Gln Phe Tyr Pro Gly Cys His Gln Leu Asn Val Thr Gly
            180                 185                 190

Gly Gly Ser Thr Val Pro Ser Ser Gly Leu Val Ala Phe Pro Gly Ala
        195                 200                 205

Tyr Lys Gly Ser Asp Pro Gly Ile Thr Tyr Asp Ala Tyr Lys Ala Gln
    210                 215                 220

Thr Tyr Gln Ile Pro Gly Pro Ala Val Phe Thr Cys
225                 230                 235

<210> SEQ ID NO 51
<211> LENGTH: 933
<212> TYPE: DNA
<213> ORGANISM: Thielavia terrestris

<400> SEQUENCE: 51
atggccttgc tgctcttggc aggcttggcc attctggccg gccggctca tgcccacggc      60 ggcctcgcca actacacagt gggcaacacc tggtataggg ggtgcgtaag gggggcaccg    120
acaacgcctg cttagtaact ccaccatttc gagcgggcta acaccgggcg cagctacgac    180
cccttcacgc cggcgccga ccagatcggc cagccgtgga tgatccaacg cgcgtgggac     240
tcgatcgacc cgatcttcag cgtcaacgac aaggcgctcg cctgcaacac cccggccacg    300
gcgccgacct cttacattcc catccgcgcg ggcgagaaca tcacggccgt gtactggtac    360
tggctgcacc cggtgggccc catgacggcg tggctggcgc ggtgcgacgg cgactgccgc    420
gacgccgacg tcaacgaggc gcgctggttc aagatctggg aggccggcct gctcagcggg    480
ccgaacctgg ccgagggcat gtggtaccag aaggcgttcc agaactggga cggcagcccg    540
gacctgtggc ccgtcacgat cccggccggg ctgaagagcg cctgtacat gatccggcac     600 gagatcttgt cgatccacgt cgaggataaa ccgcagtttt atcccgagtg tgcgcatctg    660
aatgtgaccg ggggtgggga cctgctgccg cctgatgagt ttttggtgaa gttcccgggc    720
gcttacaaag aagatagtga gtgaaacgcg aagcttcggt agccattggg ttgcgctgat    780
ggaggttaga cccgtcgatc aagatcaata tctactcgga ccagtacgcc aatcaacgg    840 tgagtgtaac aggtcgagca aaaccaaaca gatgccgatg actgatgatc tcagaattac    900
```
acaattcccg gagggccgat atgggatggg tga                          933

<210> SEQ ID NO 52
<211> LENGTH: 250
<212> TYPE: PRT
<213> ORGANISM: Thielavia terrestris

<400> SEQUENCE: 52

Met Ala Leu Leu Leu Ala Gly Leu Ala Ile Leu Ala Gly Pro Ala
1               5                   10                  15

His Ala His Gly Gly Leu Ala Asn Tyr Thr Val Gly Asn Thr Trp Tyr
            20                  25                  30

Arg Gly Tyr Asp Pro Phe Thr Pro Ala Ala Asp Gln Ile Gly Gln Pro
        35                  40                  45

Trp Met Ile Gln Arg Ala Trp Asp Ser Ile Asp Pro Ile Phe Ser Val
    50                  55                  60

Asn Asp Lys Ala Leu Ala Cys Asn Thr Pro Ala Thr Ala Pro Thr Ser
65                  70                  75                  80

Tyr Ile Pro Ile Arg Ala Gly Glu Asn Ile Thr Ala Val Tyr Trp Tyr
                85                  90                  95

Trp Leu His Pro Val Gly Pro Met Thr Ala Trp Leu Ala Arg Cys Asp
            100                 105                 110

Gly Asp Cys Arg Asp Ala Asp Val Asn Glu Ala Arg Trp Phe Lys Ile
        115                 120                 125

Trp Glu Ala Gly Leu Leu Ser Gly Pro Asn Leu Ala Glu Gly Met Trp
    130                 135                 140

Tyr Gln Lys Ala Phe Gln Asn Trp Asp Gly Ser Pro Asp Leu Trp Pro
145                 150                 155                 160

Val Thr Ile Pro Ala Gly Leu Lys Ser Gly Leu Tyr Met Ile Arg His
                165                 170                 175

Glu Ile Leu Ser Ile His Val Glu Asp Lys Pro Gln Phe Tyr Pro Glu
            180                 185                 190

Cys Ala His Leu Asn Val Thr Gly Gly Gly Asp Leu Leu Pro Pro Asp
        195                 200                 205

Glu Phe Leu Val Lys Phe Pro Gly Ala Tyr Lys Glu Asp Asn Pro Ser
    210                 215                 220

Ile Lys Ile Asn Ile Tyr Ser Asp Gln Tyr Ala Asn Thr Thr Asn Tyr
225                 230                 235                 240

Thr Ile Pro Gly Gly Pro Ile Trp Asp Gly
                245                 250

<210> SEQ ID NO 53
<211> LENGTH: 1584
<212> TYPE: DNA
<213> ORGANISM: Thielavia terrestris

<400> SEQUENCE: 53
atgatgccgt cccttgttcg cttctcaatg ggtctggcga ccgccttcgc ctcgctgtcc    60
acagcacata ccgtcttcac cacgcttttc atcaacggcg tcgaccaagg ggacgggacc    120
tgcatccgca tggccaagaa gggcagcgtt gcacccatc ccattgctgg tggcctcgac    180
agcccagaca tggcttgtgg tatgccctct gcgtttcccc tgcgagagct ttcctcgagc    240
taacccaatg ccgcgttgcc caggccgaga cggacaacaa gccgtggcat tcacctgccc    300
agccccggcg ggctccaagt tgagcttcga gttccgcatg tgggccgacg cctctcagcc    360

-continued

```
cggctctatc gacccatccc acctcggctc gacggcaatc tacctcaaac aagtctccaa    420
catcagctcc gactcggctg ccggccctgg ctggttcaag atctacgccg agggctacga    480
cacagccgcc aagaagtggg ccacagagaa gctcatcgac aacggcggcc tgctgagcat    540
cgagcttccg cccactctgc cggcgggata ctacctcgcc cgcagcgaga tcgtcaccat    600
ccagaacgtc accaacgacc acgtcgaccc gcagttctac gttggctgcg cacagctctt    660
cgtccagggg cctccgacca cccccaccgt cccgccagac agactcgtct ccatcccggg    720
ccacgtccat gcctccgacc cggggctgac cttcaacatc tggcgcgacg accctccaa    780
gacggcctac accgtcgtcg gcccggcccc cttctccccc accgccgccc caccccccac    840
ctccaccaac accaacgggc agcaacaaca acaacagcaa caggcgataa agcagacgga    900
cggcgtgatc cccgccgact gccagctcaa gaacgccaac tggtgcggcg ccgaggtgcc    960
cgcgtacgcc gacgaggccg gctgctgggc gtcgtcggcc gactgcttcg cccagctgga   1020
cgcctgctac acgtcggcgc cgcccacggg cagccgcggc tgccggctgt gggaggactg   1080
gtgcaccggc attcagcagg gctgccgcgc ggggcggtgg cggggccgc cgcccttca    1140
tggggagggg gcagcagcgg aggtgtgaac ggttcgggga cgggtggcgg tggtggtggt   1200
ggtggtggtg gcactggctc ttcttcggct tctgccccga cggagacggc ctctgctggc   1260
cggggggcg caagaatagc tgccgtggcc ggctgcggag cgggacagg agacatggtt    1320
gaagaggttt tcctcttta ttgggacgct tgcagcggct ggcgacgag ccgtggtggt    1380
ggttcgattc ttgcgaggct tatccttcat gtccttcttc cactttttgag accgaggcga   1440
gccctcgag tccatttact tctcttccac ctgtacctca acttctgtta tccaggaacc   1500
agtggtttct ataatcgcct gagcattaaa ctaggcatat ggccaagcaa aatgtcgcct   1560
gatgtagcgc attacgtgaa ataa                                           1584
```

<210> SEQ ID NO 54
<211> LENGTH: 478
<212> TYPE: PRT
<213> ORGANISM: Thielavia terrestris

<400> SEQUENCE: 54

```
Met Met Pro Ser Leu Val Arg Phe Ser Met Gly Leu Ala Thr Ala Phe
1               5                   10                  15

Ala Ser Leu Ser Thr Ala His Thr Val Phe Thr Thr Leu Phe Ile Asn
            20                  25                  30

Gly Val Asp Gln Gly Asp Gly Thr Cys Ile Arg Met Ala Lys Lys Gly
        35                  40                  45

Ser Val Cys Thr His Pro Ile Ala Gly Gly Leu Asp Ser Pro Asp Met
    50                  55                  60

Ala Cys Gly Arg Asp Gly Gln Gln Ala Val Ala Phe Thr Cys Pro Ala
65                  70                  75                  80

Pro Ala Gly Ser Lys Leu Ser Phe Glu Phe Arg Met Trp Ala Asp Ala
                85                  90                  95

Ser Gln Pro Gly Ser Ile Asp Pro Ser His Leu Gly Ser Thr Ala Ile
            100                 105                 110

Tyr Leu Lys Gln Val Ser Asn Ile Ser Ser Asp Ser Ala Ala Gly Pro
        115                 120                 125

Gly Trp Phe Lys Ile Tyr Ala Glu Gly Tyr Asp Thr Ala Ala Lys Lys
    130                 135                 140

Trp Ala Thr Glu Lys Leu Ile Asp Asn Gly Gly Leu Leu Ser Ile Glu
145                 150                 155                 160
```

```
Leu Pro Pro Thr Leu Pro Ala Gly Tyr Tyr Leu Ala Arg Ser Glu Ile
                165                 170                 175

Val Thr Ile Gln Asn Val Thr Asn Asp His Val Asp Pro Gln Phe Tyr
            180                 185                 190

Val Gly Cys Ala Gln Leu Phe Val Gln Gly Pro Pro Thr Thr Pro Thr
        195                 200                 205

Val Pro Pro Asp Arg Leu Val Ser Ile Pro Gly His Val His Ala Ser
    210                 215                 220

Asp Pro Gly Leu Thr Phe Asn Ile Trp Arg Asp Pro Ser Lys Thr
225                 230                 235                 240

Ala Tyr Thr Val Val Gly Pro Ala Pro Phe Ser Pro Thr Ala Ala Pro
                245                 250                 255

Thr Pro Thr Ser Thr Asn Thr Asn Gly Gln Gln Gln Gln Gln Gln Gln
                260                 265                 270

Gln Ala Ile Lys Gln Thr Asp Gly Val Ile Pro Ala Asp Cys Gln Leu
            275                 280                 285

Lys Asn Ala Asn Trp Cys Gly Ala Glu Val Pro Ala Tyr Ala Asp Glu
        290                 295                 300

Ala Gly Cys Trp Ala Ser Ser Ala Asp Cys Phe Ala Gln Leu Asp Ala
305                 310                 315                 320

Cys Tyr Thr Ser Ala Pro Pro Thr Gly Ser Arg Gly Cys Arg Leu Trp
                325                 330                 335

Glu Asp Trp Cys Thr Gly Ile Gln Gln Gly Cys Arg Ala Gly Arg Trp
                340                 345                 350

Arg Gly Pro Pro Pro Phe His Gly Glu Gly Ala Ala Ala Glu Thr Ala
            355                 360                 365

Ser Ala Gly Arg Gly Gly Ala Arg Ile Ala Ala Val Ala Gly Cys Gly
        370                 375                 380

Gly Gly Thr Gly Asp Met Val Glu Glu Val Phe Leu Phe Tyr Trp Asp
385                 390                 395                 400

Ala Cys Ser Gly Trp Arg Arg Ser Arg Gly Gly Ser Ile Leu Ala
                405                 410                 415

Arg Leu Ile Leu His Val Leu Leu Pro Leu Leu Arg Pro Arg Arg Ala
            420                 425                 430

Pro Arg Val His Leu Leu Leu Phe His Leu Tyr Leu Asn Phe Cys Tyr
        435                 440                 445

Pro Gly Thr Ser Gly Phe Tyr Asn Arg Leu Ser Ile Lys Leu Gly Ile
    450                 455                 460

Trp Pro Ser Lys Met Ser Pro Asp Val Ala His Tyr Val Lys
465                 470                 475

<210> SEQ ID NO 55
<211> LENGTH: 868
<212> TYPE: DNA
<213> ORGANISM: Thielavia terrestris

<400> SEQUENCE: 55
atgcagctcc tcgtgggctt gctgcttgca gccgtggctg ctcgagcaca ttgtatttct      60 accccttttcc gcgtgcctcc cagcctcaag gcaagaagac gcacgcagca gctaacggac    120
cctatcagac acatttccca gactcgtggt aaatgggcag cccgaggaca aggactggtc    180
ggttacgcgc atgaccaaga acgcgcagag caagcaggga gtccaggacc cgaccagtcc    240
cgacattcgc tgctacacgt cgcagacggc gcctaacgtg gctacggtcc ctgccggagc    300
```

```
caccgtccat tacatatcga ctcagcagat caaccacccg ggcccgacgc agtactacct   360
cgccaaggta ccggcggggt cgtcggccaa gacgtgggac gggtcagggg ccgtctggtt   420
caagatctcg accaccatgc cttacttgga caacaacaag cagcttgtct ggccgaatca   480
gagtaggaac aattcccgct ccaatcttcg atttggcctt gagctacggc cgattgcatg   540
ggagagaccg ttgactgacg gggcaaccca accttcatca gacacgtaca cgacggtcaa   600
cacgaccatc cccgccgata cgcccagtgg ggaatacctc ctccgggtcg agcagatcgc   660
gctgcacctg gcctcgcagc ccaacggggc tcagttctac ctggcctgct cgcagatcca   720
gattacgggc ggcggcaacg gcacgcccgg cccgctagtc gcgttgccgg gggcgtacaa   780
gagcaacgac ccgggcattt tggtcaacat ctactctatg cagcccggcg attacaagcc   840
gcccgggccg ccggtgtgga gtggctga                                      868
```

```
<210> SEQ ID NO 56
<211> LENGTH: 230
<212> TYPE: PRT
<213> ORGANISM: Thielavia terrestris

<400> SEQUENCE: 56

Met Gln Leu Leu Val Gly Leu Leu Leu Ala Ala Val Ala Ala Arg Ala
1               5                  10                  15

His Tyr Thr Phe Pro Arg Leu Val Val Asn Gly Gln Pro Glu Asp Lys
            20                  25                  30

Asp Trp Ser Val Thr Arg Met Thr Lys Asn Ala Gln Ser Lys Gln Gly
        35                  40                  45

Val Gln Asp Pro Thr Ser Pro Asp Ile Arg Cys Tyr Thr Ser Gln Thr
    50                  55                  60

Ala Pro Asn Val Ala Thr Val Pro Ala Gly Ala Thr Val His Tyr Ile
65                  70                  75                  80

Ser Thr Gln Gln Ile Asn His Pro Gly Pro Thr Gln Tyr Tyr Leu Ala
                85                  90                  95

Lys Val Pro Ala Gly Ser Ser Ala Lys Thr Trp Asp Gly Ser Gly Ala
            100                 105                 110

Val Trp Phe Lys Ile Ser Thr Thr Met Pro Tyr Leu Asp Asn Asn Lys
        115                 120                 125

Gln Leu Val Trp Pro Asn Gln Asn Thr Tyr Thr Thr Val Asn Thr Thr
    130                 135                 140

Ile Pro Ala Asp Thr Pro Ser Gly Glu Tyr Leu Leu Arg Val Glu Gln
145                 150                 155                 160

Ile Ala Leu His Leu Ala Ser Gln Pro Asn Gly Ala Gln Phe Tyr Leu
                165                 170                 175

Ala Cys Ser Gln Ile Gln Ile Thr Gly Gly Gly Asn Gly Thr Pro Gly
            180                 185                 190

Pro Leu Val Ala Leu Pro Gly Ala Tyr Lys Ser Asn Asp Pro Gly Ile
        195                 200                 205

Leu Val Asn Ile Tyr Ser Met Gln Pro Gly Asp Tyr Lys Pro Pro Gly
    210                 215                 220

Pro Pro Val Trp Ser Gly
225                 230

<210> SEQ ID NO 57
<211> LENGTH: 1068
<212> TYPE: DNA
<213> ORGANISM: Thielavia terrestris
```

<400> SEQUENCE: 57

```
atgaagctgt acctggcggc ctttctaggc gccgtcgcca ccccgggagc gttcgctcat      60
cgtaggttcc ccgtctatct ccctaggggt agcaccacga ctaatttctc gtcgtccccc     120
tgtagaaatc cacgggattc tacttgtcaa cggcaccgaa acgccggaat ggaaatacgt     180
ccggtaatat ctaccttgct ctccttcttc cacaaccagc ctaacacatc atcagtgacg     240
tggcctggga gggcgcctac gaaccggaaa aataccccaa caccgagttc tttaagacgc     300
ccccgcagac ggacatcaac aacccgaaca tcacctgcgg caggaacgcg ttcgactcgg     360
ccagcaagac tgagacggcc gacatactgg ccggctcaga ggtcggcttc cgcgtctcgt     420
gggacggcaa cggcaagtac ggcgtgttct ggcatcccgg gccggggcag atctacctct     480
ctcgtgctcc gaacgacgac ctggaggact accgcggcga cggagactgg ttcaagatcg     540
caaccggcgc cgccgtctcc aataccgagt ggctgctgtg gaacaagcat gacgtgagcc     600
ccaacattcc tcgcccaatc gatcccaac ctggtcacca tggcggcgtc cgggatgcaa      660
agagactaac tccagaggaa cctacctagt tcaacttcac catccccaag acgacgccgc     720
cgggcaagta cctgatgcgc atcgagcagt tcatgccctc cacggtcgaa tacagccagt     780
ggtacgtcaa ctgcgcccac gtcaacatca tcggccccgg cggaggcacg ccgacgggct     840
tgccaggtt cccggcacc tacactgttg acgatcccgg taagccggac ctaccggaca       900
cagaggcctc gggatagctt gctaaccttg tttgctctct ctcttttct ctcccgacta      960
ggcatcaagg tgccgttgaa ccagatcgtc aacagcggag agttgccgca ggaccaactg    1020
aggctgctcg agtacaagcc cccgggccca gcgctgtgga ctggttga                 1068
```

<210> SEQ ID NO 58
<211> LENGTH: 257
<212> TYPE: PRT
<213> ORGANISM: Thielavia terrestris

<400> SEQUENCE: 58

```
Met Lys Leu Tyr Leu Ala Ala Phe Leu Gly Ala Val Ala Thr Pro Gly
1               5                   10                  15

Ala Phe Ala His Gln Ile His Gly Ile Leu Leu Val Asn Gly Thr Glu
            20                  25                  30

Thr Pro Glu Trp Lys Tyr Val Arg Asp Val Ala Trp Glu Gly Ala Tyr
        35                  40                  45

Glu Pro Glu Lys Tyr Pro Asn Thr Glu Phe Phe Lys Thr Pro Pro Gln
    50                  55                  60

Thr Asp Ile Asn Asn Pro Asn Ile Thr Cys Gly Arg Asn Ala Phe Asp
65                  70                  75                  80

Ser Ala Ser Lys Thr Glu Thr Ala Asp Ile Leu Ala Gly Ser Glu Val
                85                  90                  95

Gly Phe Arg Val Ser Trp Asp Gly Asn Gly Lys Tyr Gly Val Phe Trp
            100                 105                 110

His Pro Gly Pro Gly Gln Ile Tyr Leu Ser Arg Ala Pro Asn Asp Asp
        115                 120                 125

Leu Glu Asp Tyr Arg Gly Asp Gly Asp Trp Phe Lys Ile Ala Thr Gly
    130                 135                 140

Ala Ala Val Ser Asn Thr Glu Trp Leu Leu Trp Asn Lys His Asp Phe
145                 150                 155                 160

Asn Phe Thr Ile Pro Lys Thr Thr Pro Pro Gly Lys Tyr Leu Met Arg
                165                 170                 175
```

```
Ile Glu Gln Phe Met Pro Ser Thr Val Glu Tyr Ser Gln Trp Tyr Val
            180                 185                 190

Asn Cys Ala His Val Asn Ile Ile Gly Pro Gly Gly Thr Pro Thr
        195                 200                 205

Gly Phe Ala Arg Phe Pro Gly Thr Tyr Thr Val Asp Asp Pro Gly Ile
    210                 215                 220

Lys Val Pro Leu Asn Gln Ile Val Asn Ser Gly Glu Leu Pro Gln Asp
225                 230                 235                 240

Gln Leu Arg Leu Leu Glu Tyr Lys Pro Pro Gly Pro Ala Leu Trp Thr
                245                 250                 255

Gly

<210> SEQ ID NO 59
<211> LENGTH: 871
<212> TYPE: DNA
<213> ORGANISM: Thermoascus crustaceus

<400> SEQUENCE: 59 atggccttt  cccagataat  ggctattacc  ggcgttttc  ttgcctctgc  ttccctggtg     60
gctggccatg  ctttgttca  gaatatcgtg  attgatggta  aaggtaccct  aactacctac    120
cttactatct  gatgtcattt  acaagaaagg  gcacagacac  aagcggcaaa  aaaaagaaag    180
aaagaaagaa  agaaagaaag  ctgacaaaaa  ttcaacaagt  tatggcgggt  acatcgtgaa    240
ccaatatcca  tacatgtcag  atcctccgga  ggtcgtcggc  tggtctacca  ccgcaaccga    300
cctcggattc  gtggacggta  ccggatacca  aggacctgat  atcatctgcc  acaggggcgc    360
caagcctgca  gccctgactg  cccaagtggc  cgccggagga  accgtcaagc  tggaatggac    420
tccatggcct  gattctcacc  acggcccggt  gatcaactac  cttgctcctt  gcaacggtga    480
ctgttccacc  gtggacaaga  cccaattgaa  attcttcaag  atcgcccagg  ccggtctcat    540
cgatgacaac  agtcctcctg  gtatctgggc  ctcagacaat  ctgatagcgg  ccaacaacag    600
ctggactgtc  accatcccaa  ccacaactgc  acctggaaac  tatgttctaa  ggcatgagat    660
cattgctctc  cactcagctg  gaacaaggga  tggtgcgcag  aactatcccc  agtgcatcaa    720
cctgaaggtc  actggaaatg  gttctggcaa  tcctcctgct  ggtgctcttg  aacggcact    780 ctacaaggat  acagatccgg  gaattctgat  caatatctac  cagaaacttt  ccagctatgt    840
tattcctggt  cctgctttgt  acactggtta  g                                    871

<210> SEQ ID NO 60
<211> LENGTH: 251
<212> TYPE: PRT
<213> ORGANISM: Thermoascus crustaceus

<400> SEQUENCE: 60

Met Ala Phe Ser Gln Ile Met Ala Ile Thr Gly Val Phe Leu Ala Ser
1               5                   10                  15

Ala Ser Leu Val Ala Gly His Gly Phe Val Gln Asn Ile Val Ile Asp
            20                  25                  30

Gly Lys Ser Tyr Gly Gly Tyr Ile Val Asn Gln Tyr Pro Tyr Met Ser
        35                  40                  45

Asp Pro Pro Glu Val Val Gly Trp Ser Thr Thr Ala Thr Asp Leu Gly
    50                  55                  60

Phe Val Asp Gly Thr Gly Tyr Gln Gly Pro Asp Ile Ile Cys His Arg
65                  70                  75                  80

Gly Ala Lys Pro Ala Ala Leu Thr Ala Gln Val Ala Ala Gly Gly Thr
```

|  | 85 | 90 | 95 |  |
|---|---|---|---|---|

Val Lys Leu Glu Trp Thr Pro Trp Pro Asp Ser His His Gly Pro Val
        100                105                110

Ile Asn Tyr Leu Ala Pro Cys Asn Gly Asp Cys Ser Thr Val Asp Lys
        115                120              125

Thr Gln Leu Lys Phe Phe Lys Ile Ala Gln Ala Gly Leu Ile Asp Asp
130                135              140

Asn Ser Pro Pro Gly Ile Trp Ala Ser Asp Asn Leu Ile Ala Ala Asn
145                150              155              160

Asn Ser Trp Thr Val Thr Ile Pro Thr Thr Thr Ala Pro Gly Asn Tyr
        165                170              175

Val Leu Arg His Glu Ile Ile Ala Leu His Ser Ala Gly Asn Lys Asp
        180                185              190

Gly Ala Gln Asn Tyr Pro Gln Cys Ile Asn Leu Lys Val Thr Gly Asn
        195                200              205

Gly Ser Gly Asn Pro Pro Ala Gly Ala Leu Gly Thr Ala Leu Tyr Lys
        210                215              220

Asp Thr Asp Pro Gly Ile Leu Ile Asn Ile Tyr Gln Lys Leu Ser Ser
225                230              235              240

Tyr Val Ile Pro Gly Pro Ala Leu Tyr Thr Gly
        245                250

```
<210> SEQ ID NO 61
<211> LENGTH: 1102
<212> TYPE: DNA
<213> ORGANISM: Thermoascus crustaceus

<400> SEQUENCE: 61
atgtcattct cgaagatact tgctatcgct ggggccatta cctacgcatc ttcagctgcc      60
gctcatggtt atgtccaggg aattgttgtc gatggcagct agtatgtcac tctggatgga     120
accttcagca cgtactgtac taacaatcag cagctacggg ggatatatgg tgacccaata     180
tccctacacc gctcaaccte cggaactcat cgcctggtcc actaaagcaa ccgatcttgg     240
gtttgtggac ggcagtggct atacttctcc tgatatcatc tgccataagg gtgctgagcc     300
tggtgcccag agcgccaaag tggcagctgg agggaccgtt gagctgcagt ggacggcatg     360
gcccgagtct cacaagggcc cagttattga ctacctcgcc gcctgcgacg gggactgctc     420
atctgttgat aagactgcac taaagttctt taagattgac gagagtggtc tgattgacgg     480
caacggtgct ggaacatggg cctctgatac gttgatcaaa aataacaaca gctggactgt     540
caccatccca agcacaattg cttccggaaa ctacgtacta agacacgaaa taattgcgct     600
ccattctgcc ggaaacaaag atggtgctca gaactatccc cagtgtatca acctcgaggt     660
cactggtagt ggcaccgaaa accctgctgg cactctcgga acagcgcttt acacagacac     720
tgatcctggc cttctggtca acatctacca gggtctgtcc aactattcaa tccctggtcc     780
tgctctgtat agcggcaaca gtgataacgc tggttccctc aaccctacca ccacgccgtc     840
aattcagaat gctgctgctg ctccctccac ttccacagca tctgttgtca ctgattcttc     900
gtcagccacc cagactgcta gtgtcgccgc cacgactcca gcctccactt cggctgttac     960
agcctcacca gctcccgata ctggaagcga cgtaaccaaa tatctggatt cgatgagctc    1020
ggatgaggtc ctcaccctgg tgcgcgggac cctgtcttgg ctggtttcta acaagaaaca    1080
tgcgcgggat ctttctcact ga                                             1102
```

<210> SEQ ID NO 62
<211> LENGTH: 349
<212> TYPE: PRT
<213> ORGANISM: Thermoascus crustaceus

<400> SEQUENCE: 62

Met Ser Phe Ser Lys Ile Leu Ala Ile Ala Gly Ala Ile Thr Tyr Ala
1               5                   10                  15

Ser Ser Ala Ala Ala His Gly Tyr Val Gln Gly Ile Val Val Asp Gly
            20                  25                  30

Ser Tyr Tyr Gly Gly Tyr Met Val Thr Gln Tyr Pro Tyr Thr Ala Gln
        35                  40                  45

Pro Pro Glu Leu Ile Ala Trp Ser Thr Lys Ala Thr Asp Leu Gly Phe
50                  55                  60

Val Asp Gly Ser Gly Tyr Thr Ser Pro Asp Ile Ile Cys His Lys Gly
65                  70                  75                  80

Ala Glu Pro Gly Ala Gln Ser Ala Lys Val Ala Ala Gly Thr Val
                85                  90                  95

Glu Leu Gln Trp Thr Ala Trp Pro Glu Ser His Lys Gly Pro Val Ile
                100                 105                 110

Asp Tyr Leu Ala Ala Cys Asp Gly Asp Cys Ser Ser Val Asp Lys Thr
            115                 120                 125

Ala Leu Lys Phe Phe Lys Ile Asp Glu Ser Gly Leu Ile Asp Gly Asn
130                 135                 140

Gly Ala Gly Thr Trp Ala Ser Asp Thr Leu Ile Lys Asn Asn Asn Ser
145                 150                 155                 160

Trp Thr Val Thr Ile Pro Ser Thr Ile Ala Ser Gly Asn Tyr Val Leu
                165                 170                 175

Arg His Glu Ile Ile Ala Leu His Ser Ala Gly Asn Lys Asp Gly Ala
            180                 185                 190

Gln Asn Tyr Pro Gln Cys Ile Asn Leu Glu Val Thr Gly Ser Gly Thr
        195                 200                 205

Glu Asn Pro Ala Gly Thr Leu Gly Thr Ala Leu Tyr Thr Asp Thr Asp
210                 215                 220

Pro Gly Leu Leu Val Asn Ile Tyr Gln Gly Leu Ser Asn Tyr Ser Ile
225                 230                 235                 240

Pro Gly Pro Ala Leu Tyr Ser Gly Asn Ser Asp Asn Ala Gly Ser Leu
                245                 250                 255

Asn Pro Thr Thr Thr Pro Ser Ile Gln Asn Ala Ala Ala Pro Ser
            260                 265                 270

Thr Ser Thr Ala Ser Val Val Thr Asp Ser Ser Ala Thr Gln Thr
275                 280                 285

Ala Ser Val Ala Ala Thr Thr Pro Ala Ser Thr Ser Ala Val Thr Ala
    290                 295                 300

Ser Pro Ala Pro Asp Thr Gly Ser Asp Val Thr Lys Tyr Leu Asp Ser
305                 310                 315                 320

Met Ser Ser Asp Glu Val Leu Thr Leu Val Arg Gly Thr Leu Ser Trp
                325                 330                 335

Leu Val Ser Asn Lys Lys His Ala Arg Asp Leu Ser His
            340                 345

<210> SEQ ID NO 63
<211> LENGTH: 1493
<212> TYPE: DNA
<213> ORGANISM: Thermoascus crustaceus

<400> SEQUENCE: 63

```
atgttgtcat tcattcccac caagtcagct gcgctgacga ctcttctact tcttggaaca      60
gctcatgctc acactttgat gaccaccatg tttgtggacg gcgtcaacca gggagatggt     120
gtctgcattc gcatgaacaa tgacggcgga actgccaata cctatatcca gcctatcacg     180
agcaaggata tcgcctgcgg taagtaccca gatgtcatca tactctgcca taacatccgt     240
catatctact agaatcggag caatgttaag tatttccagg catccaaggc gaaatcggcg     300
cctcccgagt ctgcccagtc aaggcatctt ccaccctaac cttccaattc cgcgagcaac     360
ccaacaaccc aaactcctcc cctctcgatc catcgcacaa aggccccgcc gcggtgtacc     420
tgaaaaggt cgactccgcc atcgcgagca acaacgccgc cggagacagc tggttcaaga      480
tctgggagtc cgtctacgac gagtccacgg gcaaatgggg cacgaccaag atgatcgaga     540
acaacgggca catctccgtc aaggtgcccg atgatatcga gggtggttac tatcttgccc     600
ggacggagct gctggcgcta cattctgcgg atcaggggga tccgcagttc tatgttggct     660
gtgcgcagct gtttatcgat tcggatggga cggcgaaacc gcccactgtt tctattggag     720
agggacgta cgatctgagc atgcctgcca tgacgtataa tatctgggag acaccgttgg      780
ctctgccgta tccgatgtat gggcctcctg tctatacgcc tggctctggt tctggatcag     840
tccgtgcgac gagctcttct gctgtcccta ctgcaaccga atcctctttt gtagaggaaa     900
gagcaaaccc cgtcacggca acagtgtttt attctgcaag gggcaaattc aaaacctgga     960
ttgataaact gtcatggcgc gggaaggtcc gtgagaacgt cagacaagcc gcgggaagaa    1020
gaagcactct cgtccagact gtgggtctaa agccaaaagg ctgcatcttc gtcaatggaa    1080
actggtgcgg cttcgaggtt cccgactaca acgatgcgga gagctgctgg gctgtatgtt    1140
cccctcctta gcctcttaca tccctaagta ctacatttga aaacaacaaa aagaaatgta    1200
tatactaact acgtacgctc tactctaggc ctccgacaac tgctggaaac agtccgacgc    1260
ctgctggaac aagacccaac ccacgggcta caataactgc cagatctggc aggacaagaa    1320
atgcaaggtc atccaggatt cctgtagcgg acccaacccg catggaccac cgaataaggg    1380
caaggatttg actccggagt ggccgccact gaagggctcg atggatacgt tctccaagcg    1440
tactatcggt taccgcgatt ggattgttag aaggagaggt gcatgagggt gta           1493
```

<210> SEQ ID NO 64
<211> LENGTH: 436
<212> TYPE: PRT
<213> ORGANISM: Thermoascus crustaceus

<400> SEQUENCE: 64

```
Met Leu Ser Phe Ile Pro Thr Lys Ser Ala Ala Leu Thr Thr Leu Leu
1               5                   10                  15

Leu Leu Gly Thr Ala His Ala His Thr Leu Met Thr Thr Met Phe Val
            20                  25                  30

Asp Gly Val Asn Gln Gly Asp Gly Val Cys Ile Arg Met Asn Asn Asp
        35                  40                  45

Gly Gly Thr Ala Asn Thr Tyr Ile Gln Pro Ile Thr Ser Lys Asp Ile
    50                  55                  60

Ala Cys Gly Ile Gln Gly Glu Ile Gly Ala Ser Arg Val Cys Pro Val
65                  70                  75                  80

Lys Ala Ser Ser Thr Leu Thr Phe Gln Phe Arg Glu Gln Pro Asn Asn
                85                  90                  95

Pro Asn Ser Ser Pro Leu Asp Pro Ser His Lys Gly Pro Ala Ala Val
```

```
            100                 105                 110
Tyr Leu Lys Lys Val Asp Ser Ala Ile Ala Ser Asn Asn Ala Ala Gly
                115                 120                 125

Asp Ser Trp Phe Lys Ile Trp Glu Ser Val Tyr Asp Glu Ser Thr Gly
            130                 135                 140

Lys Trp Gly Thr Thr Lys Met Ile Glu Asn Asn Gly His Ile Ser Val
145                 150                 155                 160

Lys Val Pro Asp Ile Glu Gly Gly Tyr Tyr Leu Ala Arg Thr Glu
                165                 170                 175

Leu Leu Ala Leu His Ser Ala Asp Gln Gly Asp Pro Gln Phe Tyr Val
            180                 185                 190

Gly Cys Ala Gln Leu Phe Ile Asp Ser Asp Gly Thr Ala Lys Pro Pro
                195                 200                 205

Thr Val Ser Ile Gly Glu Gly Thr Tyr Asp Leu Ser Met Pro Ala Met
            210                 215                 220

Thr Tyr Asn Ile Trp Glu Thr Pro Leu Ala Leu Pro Tyr Pro Met Tyr
225                 230                 235                 240

Gly Pro Pro Val Tyr Thr Pro Gly Ser Gly Ser Val Arg Ala
                245                 250                 255

Thr Ser Ser Ser Ala Val Pro Thr Ala Thr Glu Ser Ser Phe Val Glu
            260                 265                 270

Glu Arg Ala Asn Pro Val Thr Ala Asn Ser Val Tyr Ser Ala Arg Gly
                275                 280                 285

Lys Phe Lys Thr Trp Ile Asp Lys Leu Ser Trp Arg Gly Lys Val Arg
            290                 295                 300

Glu Asn Val Arg Gln Ala Ala Gly Arg Arg Ser Thr Leu Val Gln Thr
305                 310                 315                 320

Val Gly Leu Lys Pro Lys Gly Cys Ile Phe Val Asn Gly Asn Trp Cys
                325                 330                 335

Gly Phe Glu Val Pro Asp Tyr Asn Asp Ala Glu Ser Cys Trp Ala Ala
                340                 345                 350

Ser Asp Asn Cys Trp Lys Gln Ser Asp Ala Cys Trp Asn Lys Thr Gln
            355                 360                 365

Pro Thr Gly Tyr Asn Asn Cys Gln Ile Trp Gln Asp Lys Lys Cys Lys
            370                 375                 380

Val Ile Gln Asp Ser Cys Ser Gly Pro Asn Pro His Gly Pro Pro Asn
385                 390                 395                 400

Lys Gly Lys Asp Leu Thr Pro Glu Trp Pro Pro Leu Lys Gly Ser Met
                405                 410                 415

Asp Thr Phe Ser Lys Arg Thr Ile Gly Tyr Arg Asp Trp Ile Val Arg
            420                 425                 430

Arg Arg Gly Ala
        435

<210> SEQ ID NO 65
<211> LENGTH: 1035
<212> TYPE: DNA
<213> ORGANISM: Aspergillus aculeatus

<400> SEQUENCE: 65
atgaagtata ttcctctcgt tattgcagtt gctgccggcc tggcacgtcc ggctactgcc    60
cactacatct tcagcaagct cgtgctgaac ggagaggcat ctgcggactg caatacatc    120 cgcgagacta ctcgcagcat agtctatgag ccgaccaagt acacctctac cttcgataac    180
```

```
ctaacaccca gcgatagcga cttccgctgt aatctcggtt ccttcagcaa tgctgcgaag    240
accgaggtcg ctgaggttgc ggcaggcgat accatcgcaa tgaagctatt ctacgacacc    300
agtattgcgc atcctggccc gggacaagtt tatatgtcca aggcaccgac cggcaatgtt    360
caggaatacc aaggagacgg ggattggttc aaaatctggg aaaagacccT ttgcaacacg    420
gatggtgatc tgactacaga ggcctggtgc acctggggca tgtcacagtt tgaatttcaa    480
atcccagctg cgaccccggc aggagagtac ctagtgcgcg ccgagcatat aggcctgcat    540
ggcgctcaag cgaacgaggc cgaattcttc tacagctgtg cgcagatcaa ggttacaggc    600
tcgggaactg gatctcccag tctcacgtat caaattcctg gtctctataa cgacactatg    660
accctgttca atggcctcaa tctttggact gattcagccg agaaggtgca gctggatttc    720
ctggagacgc caattgggga cgacgtgtgg agcggagcag gctcggggag cccatctgct    780
gccacctctt cgaccagcgg tgcaactctt gcagctcagg tacaactac ctctgccgcg    840 catgctcagg cccagaccac cattaccacc agcaccagca ccatcacgtc tctcgaatca    900
gccagctcaa ccgatctcgt tgcgcagtat ggtcagtgcg gaggccttaa ctggtccggt    960
ccaaccgagt gtgagacacc ttatacctgt gtgcagcaga accctactac ccatcaatgc   1020
gtgaattcgt gctga                                                     1035
```

<210> SEQ ID NO 66
<211> LENGTH: 344
<212> TYPE: PRT
<213> ORGANISM: Aspergillus aculeatus

<400> SEQUENCE: 66

```
Met Lys Tyr Ile Pro Leu Val Ile Ala Val Ala Ala Gly Leu Ala Arg
1               5                   10                  15

Pro Ala Thr Ala His Tyr Ile Phe Ser Lys Leu Val Leu Asn Gly Glu
            20                  25                  30

Ala Ser Ala Asp Trp Gln Tyr Ile Arg Glu Thr Thr Arg Ser Ile Val
        35                  40                  45

Tyr Glu Pro Thr Lys Tyr Thr Ser Thr Phe Asp Asn Leu Thr Pro Ser
    50                  55                  60

Asp Ser Asp Phe Arg Cys Asn Leu Gly Ser Phe Ser Asn Ala Ala Lys
65                  70                  75                  80

Thr Glu Val Ala Glu Val Ala Ala Gly Asp Thr Ile Ala Met Lys Leu
                85                  90                  95

Phe Tyr Asp Thr Ser Ile Ala His Pro Gly Pro Gly Gln Val Tyr Met
            100                 105                 110

Ser Lys Ala Pro Thr Gly Asn Val Gln Glu Tyr Gln Gly Asp Gly Asp
        115                 120                 125

Trp Phe Lys Ile Trp Glu Lys Thr Leu Cys Asn Thr Asp Gly Asp Leu
    130                 135                 140

Thr Thr Glu Ala Trp Cys Thr Trp Gly Met Ser Gln Phe Glu Phe Gln
145                 150                 155                 160

Ile Pro Ala Ala Thr Pro Ala Gly Glu Tyr Leu Val Arg Ala Glu His
                165                 170                 175

Ile Gly Leu His Gly Ala Gln Ala Asn Glu Ala Glu Phe Phe Tyr Ser
            180                 185                 190

Cys Ala Gln Ile Lys Val Thr Gly Ser Gly Thr Gly Ser Pro Ser Leu
        195                 200                 205

Thr Tyr Gln Ile Pro Gly Leu Tyr Asn Asp Thr Met Thr Leu Phe Asn
    210                 215                 220
```

```
Gly Leu Asn Leu Trp Thr Asp Ser Ala Glu Lys Val Gln Leu Asp Phe
225                 230                 235                 240

Leu Glu Thr Pro Ile Gly Asp Asp Val Trp Ser Gly Ala Gly Ser Gly
                245                 250                 255

Ser Pro Ser Ala Ala Thr Ser Ser Thr Ser Gly Ala Thr Leu Ala Ala
            260                 265                 270

Gln Gly Thr Thr Thr Ser Ala Ala His Ala Gln Ala Gln Thr Thr Ile
        275                 280                 285

Thr Thr Ser Thr Ser Thr Ile Thr Ser Leu Glu Ser Ala Ser Ser Thr
    290                 295                 300

Asp Leu Val Ala Gln Tyr Gly Gln Cys Gly Gly Leu Asn Trp Ser Gly
305                 310                 315                 320

Pro Thr Glu Cys Glu Thr Pro Tyr Thr Cys Val Gln Gln Asn Pro Tyr
                325                 330                 335

Tyr His Gln Cys Val Asn Ser Cys
            340

<210> SEQ ID NO 67
<211> LENGTH: 1203
<212> TYPE: DNA
<213> ORGANISM: Aspergillus aculeatus

<400> SEQUENCE: 67
atgtctgttg ctaagtttgc tggtgttatc ctcggttcgg ccgctctcgt cgctggccac        60
ggttacgtgt cgggtgctgt tgtcgacgga acctactatg gcggctacat tgtcacttcc       120 taccctatt  ccagcgatcc cccggagacc attggatggt ctaccgaggc gaccgacttg       180
ggtttcgtcg atggtagcga gtatgctgat gccgacatca tttgccacaa gagtgccaag       240
cccggtgcca tctctgctga ggtcaaggcc ggtggtactg ttgagctcca gtggactacc       300
tggcccgaca gccaccacgg ccctgtcctg acctaccttg ccaactgcaa tggtgactgc       360
agcagcgtca ccaagaccga cctcgagttt ttcaagattg acgagagcgg tctcatcaac       420
gacgacgacg tccccggtac ctgggccagt gataacttga tcgccaacaa caacagctgg       480
actgtgacca tccctctga  cattgcggct ggcaactacg tcctccgtca cgaaatcatt       540
gcccttcact ctgctggtaa caaggatggt gctcagaact accctcagtg cctcaacttg       600
aaggtcactg gcggcggtga tctcgctcct tctggcactg ctggtgagag cctgtacaag       660 acaccgatg  ctggtatcct cgtcaacatc taccagtctc tttcctccta cgatattccc       720
ggacctgcta tgtacaacgc tacctccagc tcctccagct cctccagctc cagctccagc       780
tccagctcca gctccagctc cggctcttcc agctccgccg ccgcctccag cagctccagc       840
agctccagca ctactgccgc cgccgccgcc gctaccagcg ctgcttcttc cgtcacctct       900
gctgctggct ccgtcgttac tcagactgct accgctgttg agactgatac tgccactgcc       960
taccagacct ccactgaggt tgcgcaagtc accgtcaccg gtagcgctcc ccagcagacc      1020
tacgttgcca ctcccagcag ctccagctct gcctccagca gctccagtgc ttccgtatcc      1080
accagcacca gcctcaccag ctacttcgag tccctgagcg ctgatcagtt cctcagcgtt      1140
ctcaagcaga ctttcacctg gttggtcagc gagaagaagc acgcccgtga cctctccgcc      1200
taa                                                                    1203

<210> SEQ ID NO 68
<211> LENGTH: 400
<212> TYPE: PRT
```

<213> ORGANISM: Aspergillus aculeatus

<400> SEQUENCE: 68

| | | | | | | | | | | | | | | |
|---|---|---|---|---|---|---|---|---|---|---|---|---|---|---|
|Met|Ser|Val|Ala|Lys|Phe|Ala|Gly|Val|Ile|Leu|Gly|Ser|Ala|Ala|Leu|
|1| | | |5| | | |10| | | |15| | |
|Val|Ala|Gly|His|Gly|Tyr|Val|Ser|Gly|Ala|Val|Val|Asp|Gly|Thr|Tyr|
| | | |20| | | |25| | | |30| | | | |
|Tyr|Gly|Gly|Tyr|Ile|Val|Thr|Ser|Tyr|Pro|Tyr|Ser|Ser|Asp|Pro|Pro|
| | |35| | | |40| | | |45| | | | | |
|Glu|Thr|Ile|Gly|Trp|Ser|Thr|Glu|Ala|Thr|Asp|Leu|Gly|Phe|Val|Asp|
| |50| | | |55| | | |60| | | | | | |
|Gly|Ser|Glu|Tyr|Ala|Asp|Ala|Asp|Ile|Ile|Cys|His|Lys|Ser|Ala|Lys|
|65| | | |70| | | |75| | | |80| | | |
|Pro|Gly|Ala|Ile|Ser|Ala|Glu|Val|Lys|Ala|Gly|Gly|Thr|Val|Glu|Leu|
| | | |85| | | |90| | | |95| | | | |
|Gln|Trp|Thr|Thr|Trp|Pro|Asp|Ser|His|His|Gly|Pro|Val|Leu|Thr|Tyr|
| | | |100| | | |105| | | |110| | | | |
|Leu|Ala|Asn|Cys|Asn|Gly|Asp|Cys|Ser|Ser|Val|Thr|Lys|Thr|Asp|Leu|
| | |115| | | |120| | | |125| | | | | |
|Glu|Phe|Phe|Lys|Ile|Asp|Glu|Ser|Gly|Leu|Ile|Asn|Asp|Asp|Asp|Val|
| |130| | | |135| | | |140| | | | | | |
|Pro|Gly|Thr|Trp|Ala|Ser|Asp|Asn|Leu|Ile|Ala|Asn|Asn|Asn|Ser|Trp|
|145| | | |150| | | |155| | | |160| | | |
|Thr|Val|Thr|Ile|Pro|Ser|Asp|Ile|Ala|Ala|Gly|Asn|Tyr|Val|Leu|Arg|
| | | |165| | | |170| | | |175| | | | |
|His|Glu|Ile|Ile|Ala|Leu|His|Ser|Ala|Gly|Asn|Lys|Asp|Gly|Ala|Gln|
| | |180| | | |185| | | |190| | | | | |
|Asn|Tyr|Pro|Gln|Cys|Leu|Asn|Leu|Lys|Val|Thr|Gly|Gly|Asp|Leu|
| |195| | | |200| | | |205| | | | | |
|Ala|Pro|Ser|Gly|Thr|Ala|Gly|Glu|Ser|Leu|Tyr|Lys|Asp|Thr|Asp|Ala|
|210| | | |215| | | |220| | | | | | | |
|Gly|Ile|Leu|Val|Asn|Ile|Tyr|Gln|Ser|Leu|Ser|Ser|Tyr|Asp|Ile|Pro|
|225| | | |230| | | |235| | | |240| | | |
|Gly|Pro|Ala|Met|Tyr|Asn|Ala|Thr|Ser|Ser|Ser|Ser|Ser|Ser|Ser|Ser|
| | | |245| | | |250| | | |255| | | | |
|Ser|Ser|Ser|Ser|Ser|Ser|Ser|Ser|Ser|Ser|Gly|Ser|Ser|Ser|Ser|
| | |260| | | |265| | | |270| | | | | |
|Ala|Ala|Ala|Ser|Ser|Ser|Ser|Ser|Ser|Thr|Thr|Ala|Ala|Ala|
| |275| | | |280| | | |285| | | | | |
|Ala|Ala|Ala|Thr|Ser|Ala|Ala|Ser|Ser|Val|Thr|Ser|Ala|Ala|Gly|Ser|
| |290| | | |295| | | |300| | | | | | |
|Val|Val|Thr|Gln|Thr|Ala|Thr|Ala|Val|Glu|Thr|Asp|Thr|Ala|Thr|Ala|
|305| | | |310| | | |315| | | |320| | | |
|Tyr|Gln|Thr|Ser|Thr|Glu|Val|Ala|Gln|Val|Thr|Val|Thr|Gly|Ser|Ala|
| | | |325| | | |330| | | |335| | | | |
|Pro|Gln|Gln|Thr|Tyr|Val|Ala|Thr|Pro|Ser|Ser|Ser|Ser|Ser|Ala|Ser|
| | | |340| | | |345| | | |350| | | | |
|Ser|Ser|Ser|Ser|Ala|Ser|Val|Ser|Thr|Ser|Thr|Ser|Leu|Thr|Ser|Tyr|
| | |355| | | |360| | | |365| | | | | |
|Phe|Glu|Ser|Leu|Ser|Ala|Asp|Gln|Phe|Leu|Ser|Val|Leu|Lys|Gln|Thr|
| |370| | | |375| | | |380| | | | | | |
|Phe|Thr|Trp|Leu|Val|Ser|Glu|Lys|Lys|His|Ala|Arg|Asp|Leu|Ser|Ala|
|385| | | |390| | | |395| | | |400| | | |

<210> SEQ ID NO 69
<211> LENGTH: 1170
<212> TYPE: DNA
<213> ORGANISM: Aspergillus aculeatus

<400> SEQUENCE: 69

```
atgaagtcct ctactttcgg tatgctcgct ctggcagcag cagccaagat ggtcgatgcc      60
cacaccaccg tcttcgccgt ctggatcaac ggcgaggacc agggtctggg caacagtgcc     120
agtggctaca tccggtctcc ccccagcaac agccccgtca aggacgtgac ctcgaccgac     180
atcacctgca acgtcaacgg cgaccaggcg gcggctaaga ccctctccgt caagggcggc     240
gacgtcgtca ccttcgagtg gcaccacgac agccgggacg cctccgacga catcatcgcc     300
tcctcccaca agggccccgt catggtctac atggccccga ccaccgccgg cagcagcggc     360
aagaactggg tcaagatcgc cgaggacgga tactccgacg gcacctgggc cgtcgacacc     420
ctgatcgcca acagcggcaa gcacaacatc accgtccccg acgtccccgc cggcgactac     480
ctcttccgcc cggagatcat cgccctccac gaggccgaga acgagggcgg cgcccagttc     540
tacatggagt gtgtccagtt caaggtcacc tccgacggtg ccaacactct gcccgacggt     600
gtcagcctgc ccgcgcccta ctccgccact gaccccggta tcctcttcaa catgtacggc     660
tccttcgaca gctatcccat ccccggtccc tccgtctggg atggcactag ctctggctct     720
tcctcttctt cctcttcttc ctcttccagc tcttccgccg ccgctgccgt tgttgccacc     780
tcctcttcct cttcctctgc ttccatcgag gccgtgacca ccaagggtgc cgtcgccgcc     840
gtctccaccg ccgccgccgt ggctcctacc accaccaccg ctgcccccac caccttcgcc     900
acggccgtcg cctccaccaa gaaggccact gcctgccgca caagaccaa gtcctcctcc     960
gctgccacca ccgccgccgc cgtcgccgag accacctctt ccaccgctgc cgccaccgct    1020
gctgcttcct ctgcctcttc cgcctccggc accgccggca agtacgagcg ctgcggtggc    1080
cagggctgga ccggtgccac cacctgcgtt gatggctgga cctgcaagca gtggaaccct    1140
tactactacc agtgcgttga gtctgcctag                                     1170
```

<210> SEQ ID NO 70
<211> LENGTH: 389
<212> TYPE: PRT
<213> ORGANISM: Aspergillus aculeatus

<400> SEQUENCE: 70

```
Met Lys Ser Ser Thr Phe Gly Met Leu Ala Leu Ala Ala Ala Lys
1               5                   10                  15

Met Val Asp Ala His Thr Thr Val Phe Ala Val Trp Ile Asn Gly Glu
            20                  25                  30

Asp Gln Gly Leu Gly Asn Ser Ala Ser Gly Tyr Ile Arg Ser Pro Pro
        35                  40                  45

Ser Asn Ser Pro Val Lys Asp Val Thr Ser Thr Asp Ile Thr Cys Asn
    50                  55                  60

Val Asn Gly Asp Gln Ala Ala Ala Lys Thr Leu Ser Val Lys Gly Gly
65                  70                  75                  80

Asp Val Val Thr Phe Glu Trp His His Asp Ser Arg Asp Ala Ser Asp
                85                  90                  95

Asp Ile Ile Ala Ser Ser His Lys Gly Pro Val Met Val Tyr Met Ala
            100                 105                 110

Pro Thr Thr Ala Gly Ser Ser Gly Lys Asn Trp Val Lys Ile Ala Glu
        115                 120                 125
```

Asp Gly Tyr Ser Asp Gly Thr Trp Ala Val Asp Thr Leu Ile Ala Asn
            130                 135                 140

Ser Gly Lys His Asn Ile Thr Val Pro Asp Val Pro Ala Gly Asp Tyr
145                 150                 155                 160

Leu Phe Arg Pro Glu Ile Ile Ala Leu His Glu Ala Glu Asn Glu Gly
                165                 170                 175

Gly Ala Gln Phe Tyr Met Glu Cys Val Gln Phe Lys Val Thr Ser Asp
            180                 185                 190

Gly Ala Asn Thr Leu Pro Asp Gly Val Ser Leu Pro Gly Ala Tyr Ser
            195                 200                 205

Ala Thr Asp Pro Gly Ile Leu Phe Asn Met Tyr Gly Ser Phe Asp Ser
210                 215                 220

Tyr Pro Ile Pro Gly Pro Ser Val Trp Asp Gly Thr Ser Ser Gly Ser
225                 230                 235                 240

Ser Ser Ser Ser Ser Ser Ser Ser Ser Ser Ala Ala Ala Ala
            245                 250                 255

Val Val Ala Thr Ser Ser Ser Ser Ser Ala Ser Ile Glu Ala Val
            260                 265                 270

Thr Thr Lys Gly Ala Val Ala Ala Val Ser Thr Ala Ala Ala Val Ala
            275                 280                 285

Pro Thr Thr Thr Ala Ala Pro Thr Thr Phe Ala Thr Ala Val Ala
            290                 295                 300

Ser Thr Lys Lys Ala Thr Ala Cys Arg Asn Lys Thr Lys Ser Ser Ser
305                 310                 315                 320

Ala Ala Thr Thr Ala Ala Val Ala Glu Thr Thr Ser Ser Thr Ala
            325                 330                 335

Ala Ala Thr Ala Ala Ala Ser Ser Ala Ser Ser Ala Ser Gly Thr Ala
            340                 345                 350

Gly Lys Tyr Glu Arg Cys Gly Gly Gln Gly Trp Thr Gly Ala Thr Thr
            355                 360                 365

Cys Val Asp Gly Trp Thr Cys Lys Gln Trp Asn Pro Tyr Tyr Tyr Gln
370                 375                 380

Cys Val Glu Ser Ala
385

<210> SEQ ID NO 71
<211> LENGTH: 1221
<212> TYPE: DNA
<213> ORGANISM: Aspergillus aculeatus

<400> SEQUENCE: 71
atgcgtcagg ctcagtcttt gtccctcttg acagctcttc tgtctgccac gcgtgtggct      60
ggacacggtc acgtcactaa cgttgtcgtc aacggtgttt actacgaggg cttcgatatc     120
aacagcttcc cctacgagtc cgatccccct aaggtggcgg cttggaccac tcctaacact     180
ggcaacggtt tcatttcccc cagcgactac ggtaccgatg acattatttg ccaccagaat     240
gccaccaacg cccaggccca cattgttgtt gcggctggtg acaagatcaa catccagtgg     300
accgcgtggc ccgattccca ccacggtcct gtccttgact acctcgctcg ctgcgacggt     360
gagtgtgaga cggttgataa gaccactctt gagttttttca agatcgacgg cgtcggtctc     420
atcagtgaca ccgaagtgcc cggtacctgg ggagatgacc agctgatcgc caacaacaac     480
agctggttgg tcgagatccc cccgaccatt gctcctggca actatgttct cgccacgag     540 cttatcgctc tccacagcgc cggcactgaa gatggtgctc agaactaccc ccagtgtttc     600

```
aacctccagg tcactggctc cggtactgac gagcccgctg gtaccctcgg caccaagctc    660
tacactgagg atgaggctgg tatcgttgtg aacatctaca cctctctgtc ttcctatgcc    720
gtccccggcc ccacccagta cagcggcgcc gtctctgtca gccaatccac ttcggccatt    780
acctccaccg gaactgctgt tgtcggtagc ggcagcgctg ttgccacctc tgccgccgcg    840
gctaccacca gcgctgctgc ttcttctgcc gctgctgcta ccaccgctgc tgccgttacc    900
agcgccaatg ccaacactca gattgcccag cccagcagca gctcttctta ctcccagatc    960
gccgtgcagg tgccctcctc ctggaccacc cttgtgaccg tcactcctcc gccgccgcc    1020 gccaccaccc ctgctgccgt ccctgagcct cagacccct ctgccagctc tggagccacc    1080
actaccagca gcagcagcgg cgccgcccag tctctctacg ccagtgcgg tggtatcaac    1140 tggaccggag ctacctcttg cgttgagggc gctacttgct accagtacaa cccttactac    1200
taccagtgca tctctgccta a                                              1221

<210> SEQ ID NO 72
<211> LENGTH: 406
<212> TYPE: PRT
<213> ORGANISM: Aspergillus aculeatus

<400> SEQUENCE: 72

Met Arg Gln Ala Gln Ser Leu Ser Leu Leu Thr Ala Leu Leu Ser Ala
1               5                   10                  15

Thr Arg Val Ala Gly His Gly His Val Thr Asn Val Val Asn Gly
            20                  25                  30

Val Tyr Tyr Glu Gly Phe Asp Ile Asn Ser Phe Pro Tyr Glu Ser Asp
        35                  40                  45

Pro Pro Lys Val Ala Ala Trp Thr Thr Pro Asn Thr Gly Asn Gly Phe
    50                  55                  60

Ile Ser Pro Ser Asp Tyr Gly Thr Asp Ile Ile Cys His Gln Asn
65                  70                  75                  80

Ala Thr Asn Ala Gln Ala His Ile Val Val Ala Ala Gly Asp Lys Ile
                85                  90                  95

Asn Ile Gln Trp Thr Ala Trp Pro Asp Ser His Gly Pro Val Leu
            100                 105                 110

Asp Tyr Leu Ala Arg Cys Asp Gly Glu Cys Glu Thr Val Asp Lys Thr
        115                 120                 125

Thr Leu Glu Phe Phe Lys Ile Asp Gly Val Gly Leu Ile Ser Asp Thr
    130                 135                 140

Glu Val Pro Gly Thr Trp Gly Asp Asp Gln Leu Ile Ala Asn Asn Asn
145                 150                 155                 160

Ser Trp Leu Val Glu Ile Pro Pro Thr Ile Ala Pro Gly Asn Tyr Val
                165                 170                 175

Leu Arg His Glu Leu Ile Ala Leu His Ser Ala Gly Thr Glu Asp Gly
            180                 185                 190

Ala Gln Asn Tyr Pro Gln Cys Phe Asn Leu Gln Val Thr Gly Ser Gly
        195                 200                 205

Thr Asp Glu Pro Ala Gly Thr Leu Gly Thr Lys Leu Tyr Thr Glu Asp
    210                 215                 220

Glu Ala Gly Ile Val Val Asn Ile Tyr Thr Ser Leu Ser Ser Tyr Ala
225                 230                 235                 240

Val Pro Gly Pro Thr Gln Tyr Ser Gly Ala Val Ser Val Ser Gln Ser
                245                 250                 255
```

```
Thr Ser Ala Ile Thr Ser Thr Gly Thr Ala Val Val Gly Ser Gly Ser
            260                 265                 270

Ala Val Ala Thr Ser Ala Ala Ala Ala Thr Thr Ser Ala Ala Ala Ser
            275                 280                 285

Ser Ala Ala Ala Ala Thr Thr Ala Ala Ala Val Thr Ser Ala Asn Ala
            290                 295                 300

Asn Thr Gln Ile Ala Gln Pro Ser Ser Ser Ser Tyr Ser Gln Ile
305                 310                 315                 320

Ala Val Gln Val Pro Ser Ser Trp Thr Thr Leu Val Thr Val Thr Pro
                325                 330                 335

Pro Ala Ala Ala Thr Thr Pro Ala Ala Val Pro Glu Pro Gln Thr
            340                 345                 350

Pro Ser Ala Ser Ser Gly Ala Thr Thr Thr Ser Ser Ser Gly Ala
            355                 360                 365

Ala Gln Ser Leu Tyr Gly Gln Cys Gly Gly Ile Asn Trp Thr Gly Ala
            370                 375                 380

Thr Ser Cys Val Glu Gly Ala Thr Cys Tyr Gln Tyr Asn Pro Tyr Tyr
385                 390                 395                 400

Tyr Gln Cys Ile Ser Ala
            405

<210> SEQ ID NO 73
<211> LENGTH: 1284
<212> TYPE: DNA
<213> ORGANISM: Aspergillus aculeatus

<400> SEQUENCE: 73
atgtctcttt ccaagattgc cactcttctg ctgggctcgg tctcgctggt cgctggtcat      60
gggtatgtct cgagcatcga ggtggacggt accacctatg agggtacttg gtcgacact     120 tattactacg aatccgaccc gcccgagtta atcgcctggt ccacaaatgc cacgatgat     180 ggctatgtat cgccctccga ctacgagagc gtgaacatca tctgccacaa ggggtctgcg     240
cccggcgcgt tgtcggcccc tgtcgcgccc ggaggctggg tgcagatgac ctggaacacc     300
tggcccaccg accatcacgg ccctgtcatc acgtatatgg ccaattgcca cggttcttgc     360
gcagatgtgg acaagaccac cctcgagttc ttcaagatcg atgctggcgg cttgatcgat     420
gacacggacg tgcctggaac ttgggcgacc gatgagctca ttgaagatag ctatagtcgc     480
aacatcacta tccccagcga tattgccccc gggtactatg ttttgcgaca cgagatcatt     540
gctctgcaca cgccgagaa cctggacgga gcccagaact accccagtg catcaatctg      600 gaagtcaccg gcagcgagac agcaaccccg agtggcacct ggggcactgc tctgtacaag     660
gagaccgacc ccggcatcta tgttgacatc tggaacacgt tgagcacgta tactattccc     720
ggccccgcgc tgtacactgc tggtagcact gcgaccgcag ccgctgctgc cgataccacc     780
actacttctg ctggcaccac cgctgaggcc accaccgctg ccgccgccgt gagtaccacc     840
gcggacgctg ttccgaccga gtcttcagct ccttccgaga ccagcgcgac taccgcgaac     900
cctgctcggc ccactgccgg cagcgacatc cgcttccagc ccggtcaggt caaggctggt     960
gcttcagtca caactcggc tactgagact tcctctggtg agtctgccac gacgaccaca    1020
acatcagtgg ccactgcggc ttcgagcgcg gattcgtcga cgacttctgg ggttttgagt    1080
ggcgcctgca gccaggaggg ctactggtac tgcaacgggg gcactgcgtt ccagcgctgt    1140
gtcaacgggg aatgggatgc gtcccagagt gtggctgcgg gcacggtctg caccgccggt    1200
atctcggaga ccatcaccat ttcagccgcc gccacgcgcc gggatgccat cgtcgtcat    1260
```
ctggcgcgtc ccaagcgtca ctga                                                        1284

<210> SEQ ID NO 74
<211> LENGTH: 427
<212> TYPE: PRT
<213> ORGANISM: Aspergillus aculeatus

<400> SEQUENCE: 74

Met Ser Leu Ser Lys Ile Ala Thr Leu Leu Gly Ser Val Ser Leu
1               5                   10                  15

Val Ala Gly His Gly Tyr Val Ser Ser Ile Glu Val Asp Gly Thr Thr
            20                  25                  30

Tyr Gly Gly Tyr Leu Val Asp Thr Tyr Tyr Glu Ser Asp Pro Pro
        35                  40                  45

Glu Leu Ile Ala Trp Ser Thr Asn Ala Thr Asp Asp Gly Tyr Val Ser
    50                  55                  60

Pro Ser Asp Tyr Glu Ser Val Asn Ile Ile Cys His Lys Gly Ser Ala
65                  70                  75                  80

Pro Gly Ala Leu Ser Ala Pro Val Ala Pro Gly Gly Trp Val Gln Met
                85                  90                  95

Thr Trp Asn Thr Trp Pro Thr Asp His His Gly Pro Val Ile Thr Tyr
            100                 105                 110

Met Ala Asn Cys His Gly Ser Cys Ala Asp Val Asp Lys Thr Thr Leu
        115                 120                 125

Glu Phe Phe Lys Ile Asp Ala Gly Gly Leu Ile Asp Asp Thr Asp Val
    130                 135                 140

Pro Gly Thr Trp Ala Thr Asp Glu Leu Ile Glu Asp Ser Tyr Ser Arg
145                 150                 155                 160

Asn Ile Thr Ile Pro Ser Asp Ile Ala Pro Gly Tyr Tyr Val Leu Arg
                165                 170                 175

His Glu Ile Ile Ala Leu His Ser Ala Glu Asn Leu Asp Gly Ala Gln
            180                 185                 190

Asn Tyr Pro Gln Cys Ile Asn Leu Glu Val Thr Gly Ser Glu Thr Ala
        195                 200                 205

Thr Pro Ser Gly Thr Leu Gly Thr Ala Leu Tyr Lys Glu Thr Asp Pro
    210                 215                 220

Gly Ile Tyr Val Asp Ile Trp Asn Thr Leu Ser Thr Tyr Thr Ile Pro
225                 230                 235                 240

Gly Pro Ala Leu Tyr Thr Ala Gly Ser Thr Ala Thr Ala Ala Ala
                245                 250                 255

Ala Asp Thr Thr Thr Thr Ser Ala Gly Thr Thr Ala Glu Ala Thr Thr
            260                 265                 270

Ala Ala Ala Ala Val Ser Thr Thr Ala Asp Ala Val Pro Thr Glu Ser
        275                 280                 285

Ser Ala Pro Ser Glu Thr Ser Thr Thr Ala Asn Pro Ala Arg Pro
    290                 295                 300

Thr Ala Gly Ser Asp Ile Arg Phe Gln Pro Gly Gln Val Lys Ala Gly
305                 310                 315                 320

Ala Ser Val Asn Asn Ser Ala Thr Glu Thr Ser Ser Gly Glu Ser Ala
                325                 330                 335

Thr Thr Thr Thr Thr Ser Val Ala Thr Ala Ala Ser Ser Ala Asp Ser
            340                 345                 350

Ser Thr Thr Ser Gly Val Leu Ser Gly Ala Cys Ser Gln Glu Gly Tyr
        355                 360                 365

```
Trp Tyr Cys Asn Gly Gly Thr Ala Phe Gln Arg Cys Val Asn Gly Glu
    370                 375                 380

Trp Asp Ala Ser Gln Ser Val Ala Ala Gly Thr Val Cys Thr Ala Gly
385                 390                 395                 400

Ile Ser Glu Thr Ile Thr Ile Ser Ala Ala Thr Arg Arg Asp Ala
            405                 410                 415

Met Arg Arg His Leu Ala Arg Pro Lys Arg His
                420                 425
```

<210> SEQ ID NO 75
<211> LENGTH: 804
<212> TYPE: DNA
<213> ORGANISM: Aspergillus aculeatus

<400> SEQUENCE: 75

```
atgcttgtca aactcatctc ttttctttca gctgctacca gcgtagctgc tcatggtcat      60
gtgtcaaaca ttgtgatcaa cggggtgtcc taccgcggat gggacatcaa ttcggaccct     120
tacaattcca accctccggt ggtggttgca tggcaaacac ccaacacagc taatggcttc     180
atctcccctg atgcatacga cacagatgat gttatttgcc atctgagcgc tacgaatgcc     240
agaggccacg cagtcgtcgc tgctggcgac aagatcagcc tccagtggac gacctggcct     300
gacagtcacc atggccctgt catcagctac tagccaact gcggctccag ctgcgagaca     360
gtcgataaga ccaccctcga gttcttcaag atcgatggtg ttggcttggt ggatgagagc     420
aatcccctg gtatctgggg agacgatgag ctcattgcca caacaactc ttggctggta     480
gagattccag ctagtatcgc gccaggatac tatgtgctgc gtcacgagtt gatcgctctg     540
catggagcag ggagtgagaa tggagcccag aattacatgc aatgtttcaa ccttcaggtt     600
actgggactg gcacggtcca gccttccggg gtcctgggca cggagctgta caaacccaca     660
gacgctggaa ttcttgtcaa tatctaccag tcgctctcca cctatgttgt tcctggcccg     720
accctgatcc cccaggccgt ttccctcgtt cagtcgagct ccaccattac cgcctcgggc     780
acggcagtga caaccacggc ttga                                             804
```

<210> SEQ ID NO 76
<211> LENGTH: 267
<212> TYPE: PRT
<213> ORGANISM: Aspergillus aculeatus

<400> SEQUENCE: 76

```
Met Leu Val Lys Leu Ile Ser Phe Leu Ser Ala Ala Thr Ser Val Ala
1               5                   10                  15

Ala His Gly His Val Ser Asn Ile Val Ile Asn Gly Val Ser Tyr Arg
                20                  25                  30

Gly Trp Asp Ile Asn Ser Asp Pro Tyr Asn Ser Asn Pro Val Val
            35                  40                  45

Val Ala Trp Gln Thr Pro Asn Thr Ala Asn Gly Phe Ile Ser Pro Asp
    50                  55                  60

Ala Tyr Asp Thr Asp Asp Val Ile Cys His Leu Ser Ala Thr Asn Ala
65                  70                  75                  80

Arg Gly His Ala Val Val Ala Ala Gly Asp Lys Ile Ser Leu Gln Trp
                85                  90                  95

Thr Thr Trp Pro Asp Ser His His Gly Pro Val Ile Ser Tyr Leu Ala
            100                 105                 110

Asn Cys Gly Ser Ser Cys Glu Thr Val Asp Lys Thr Thr Leu Glu Phe
```

```
                    115                 120                 125
Phe Lys Ile Asp Gly Val Gly Leu Val Asp Glu Ser Asn Pro Pro Gly
                130                 135                 140

Ile Trp Gly Asp Asp Glu Leu Ile Ala Asn Asn Ser Trp Leu Val
145                 150                 155                 160

Glu Ile Pro Ala Ser Ile Ala Pro Gly Tyr Tyr Val Leu Arg His Glu
                    165                 170                 175

Leu Ile Ala Leu His Gly Ala Gly Ser Glu Asn Gly Ala Gln Asn Tyr
                180                 185                 190

Met Gln Cys Phe Asn Leu Gln Val Thr Gly Thr Gly Thr Val Gln Pro
                    195                 200                 205

Ser Gly Val Leu Gly Thr Glu Leu Tyr Lys Pro Thr Asp Ala Gly Ile
                210                 215                 220

Leu Val Asn Ile Tyr Gln Ser Leu Ser Thr Tyr Val Val Pro Gly Pro
225                 230                 235                 240

Thr Leu Ile Pro Gln Ala Val Ser Leu Val Gln Ser Ser Ser Thr Ile
                    245                 250                 255

Thr Ala Ser Gly Thr Ala Val Thr Thr Thr Ala
                260                 265

<210> SEQ ID NO 77
<211> LENGTH: 822
<212> TYPE: DNA
<213> ORGANISM: Aspergillus aculeatus

<400> SEQUENCE: 77
atgaagtatc ttgcgatctt cgcggcagca gcagctggac tggcccgccc gacagcagcg      60
cactacatct tcagcaagct gattctggac ggcgaagtct ctgaggactg cagtatatt     120 cgtaaaacca cccgggagac atgctatttg ccgaccaagt tcaccgacac cttcgacaac     180
ttgactccga cgaccaggga tttccggtgc aatctcggct cgttcagcaa cgccgccaag     240
accgaagtgg ccgaggtgga agcgggctcc acgattggca tgcagctttt cgctggtagc     300
cacatgcgtc acccgggacc tgcgcaagtc ttcatgtcta aggccccgtc cggcaacgta     360
cagagctacg agggtgacgg ctcctggttc aagatctggg agcgtacact ctgcgacaaa     420
agtggcgatc tgactggaga tgcgtggtgt acatacggcc agaccgagat cgagtttcaa     480
atccccgagg cgaccccgac gggcgaatac ctggtccgag cggagcacat cggtcttcac     540
cgcgcacaga gtaatcaagc cgagttctac tacagctgcg cccaggtcaa ggtcacgggc     600
aatggtaccg gggtgccgag ccagacatat cagatccctg catgtacaa tgaccgctcg     660 gagcttttca acgggctgaa cttgtggtcc tactcggtgg agaacgtcga ggcagccatg     720
aagaattcta tcgtgggtga tgaaatttgg aatggaagtt ctgttccctc tgagtcccat     780
gtcccgaagt ataagaagag tcatgcttgt cgtgtttatt ga                        822

<210> SEQ ID NO 78
<211> LENGTH: 273
<212> TYPE: PRT
<213> ORGANISM: Aspergillus aculeatus

<400> SEQUENCE: 78

Met Lys Tyr Leu Ala Ile Phe Ala Ala Ala Ala Gly Leu Ala Arg
1               5                   10                  15

Pro Thr Ala Ala His Tyr Ile Phe Ser Lys Leu Ile Leu Asp Gly Glu
                20                  25                  30
```

Val Ser Glu Asp Trp Gln Tyr Ile Arg Lys Thr Thr Arg Glu Thr Cys
            35                  40                  45

Tyr Leu Pro Thr Lys Phe Thr Asp Thr Phe Asp Asn Leu Thr Pro Asn
 50                  55                  60

Asp Gln Asp Phe Arg Cys Asn Leu Gly Ser Phe Ser Asn Ala Ala Lys
 65                  70                  75                  80

Thr Glu Val Ala Glu Val Ala Gly Ser Thr Ile Gly Met Gln Leu
                 85                  90                  95

Phe Ala Gly Ser His Met Arg His Pro Gly Pro Ala Gln Val Phe Met
                100                 105                 110

Ser Lys Ala Pro Ser Gly Asn Val Gln Ser Tyr Glu Gly Asp Gly Ser
            115                 120                 125

Trp Phe Lys Ile Trp Glu Arg Thr Leu Cys Asp Lys Ser Gly Asp Leu
130                 135                 140

Thr Gly Asp Ala Trp Cys Thr Tyr Gly Gln Thr Glu Ile Glu Phe Gln
145                 150                 155                 160

Ile Pro Glu Ala Thr Pro Thr Gly Glu Tyr Leu Val Arg Ala Glu His
                165                 170                 175

Ile Gly Leu His Arg Ala Gln Ser Asn Gln Ala Glu Phe Tyr Tyr Ser
                180                 185                 190

Cys Ala Gln Val Lys Val Thr Gly Asn Gly Thr Gly Val Pro Ser Gln
            195                 200                 205

Thr Tyr Gln Ile Pro Gly Met Tyr Asn Asp Arg Ser Glu Leu Phe Asn
            210                 215                 220

Gly Leu Asn Leu Trp Ser Tyr Ser Val Glu Asn Val Glu Ala Ala Met
225                 230                 235                 240

Lys Asn Ser Ile Val Gly Asp Glu Ile Trp Asn Gly Ser Ser Val Pro
                245                 250                 255

Ser Glu Ser His Val Pro Lys Tyr Lys Lys Ser His Ala Cys Arg Val
                260                 265                 270

Tyr

<210> SEQ ID NO 79
<211> LENGTH: 872
<212> TYPE: DNA
<213> ORGANISM: Thermomyces lanuginosus

<400> SEQUENCE: 79

```
atgaagggct ccagcgctgc gtcggtgctt cttaccttcc tcgcgggcat ctcccgtacc      60
tctgcgcacg ggtatgtctc caacctcgtt atcaacggcg tctactatcg gggctggctc     120
cccggcgaag acccctacaa ccctgacccc ccgattggcg ttggctggga gacgcccaac     180
ctgggcaacg gcttcgtgac gccgtcggaa gcgtcgaccg acgccgtcat ctgccacaag     240
gaagccacac cagcccgcgg tcatgtctcc gtgaaggccg tgacaagat ctacatccaa      300
tggcagccga atccatggcc ggattccac acggtgcgt caaacttctg cccgaaagct       360
gttcacactc actaacaaca cttttaggcc ccgtcctgga ctatctggcc ccttgcaacg     420
ggccctgtga gtccgtcgac aagaccagcc tgcgcttctt caagatcgac ggagtgggtc     480
ttatcgacgg ctcttctcct ccgggctact gggccgacga cgaactcatt gcaacggca     540
acgggtggct ggttcagatc cccgaggaca tcaagccggg taactacgtc ctgcgacacg     600
agatcatcgc cttgcacagc gccgggaacc ggacggcgc ccagctgtac ccgcagtgct     660
tcaaccttga gattacggga tccggcaccg tcgagccgga gggcgtgcca gccaccgagt    720
```

```
tctactcgcc cgatgacccg ggcatcctgg tcaacatcta cgagcccctg tccacgtatg      780
aggtgccggg tccctcgctc atcccgcagg cggttcagat cgagcagtct tcgtctgcga      840
ttacggcgac gggcacgccg acgccggcat ga                                    872
```

<210> SEQ ID NO 80
<211> LENGTH: 272
<212> TYPE: PRT
<213> ORGANISM: Thermomyces lanuginosus

<400> SEQUENCE: 80

```
Met Lys Gly Ser Ser Ala Ala Ser Val Leu Leu Thr Phe Leu Ala Gly
1               5                  10                  15

Ile Ser Arg Thr Ser Ala His Gly Tyr Val Ser Asn Leu Val Ile Asn
            20                  25                  30

Gly Val Tyr Tyr Arg Gly Trp Leu Pro Gly Glu Asp Pro Tyr Asn Pro
        35                  40                  45

Asp Pro Pro Ile Gly Val Gly Trp Glu Thr Pro Asn Leu Gly Asn Gly
    50                  55                  60

Phe Val Thr Pro Ser Glu Ala Ser Thr Asp Ala Val Ile Cys His Lys
65                  70                  75                  80

Glu Ala Thr Pro Ala Arg Gly His Val Ser Val Lys Ala Gly Asp Lys
                85                  90                  95

Ile Tyr Ile Gln Trp Gln Pro Asn Pro Trp Pro Asp Ser His His Gly
            100                 105                 110

Pro Val Leu Asp Tyr Leu Ala Pro Cys Asn Gly Pro Cys Glu Ser Val
        115                 120                 125

Asp Lys Thr Ser Leu Arg Phe Phe Lys Ile Asp Gly Val Gly Leu Ile
    130                 135                 140

Asp Gly Ser Ser Pro Pro Gly Tyr Trp Ala Asp Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Ser Ala Gly Asn
            180                 185                 190

Pro Asp Gly Ala Gln Leu Tyr Pro Gln Cys Phe Asn Leu Glu Ile Thr
        195                 200                 205

Gly Ser Gly Thr Val Glu Pro Glu Gly Val Pro Ala Thr Glu Phe Tyr
    210                 215                 220

Ser Pro Asp Asp Pro Gly Ile Leu Val Asn Ile Tyr Glu Pro Leu Ser
225                 230                 235                 240

Thr Tyr Glu Val Pro Gly Pro Ser Leu Ile Pro Gln Ala Val Gln Ile
                245                 250                 255

Glu Gln Ser Ser Ser Ala Ile Thr Ala Thr Gly Thr Pro Thr Pro Ala
            260                 265                 270
```

<210> SEQ ID NO 81
<211> LENGTH: 1039
<212> TYPE: DNA
<213> ORGANISM: Thermomyces lanuginosus

<400> SEQUENCE: 81

```
atggcattct ctacggttac agtttttgtt acgttcctgg ccttcatctc catagcttct      60
gctcatggct tcgtgacaaa aatcaccgta ctcggagata taataagga gtacgtctca      120 gtctcgctag gttgctaaca caggagagat cgctgaccat tgcagctacc ccggctttga     180
```

```
cccgagcact cccaaggagg ttcctccggg tctcgatgtc gcttggtcta ctagtgccag    240
tgatcaggga tacatgagca gttcaaatgc ctcgtatcac agtaaggact ttatctgcca    300
cagaaacgcc aaacctgctc cagacgcagc tcaagttcat gcgggcgaca aggtgcagct    360
tcactggact caatgcctg gacctgagga tcaccaggt cctatccttg attacctcgc      420
gagctgcaac ggaccctgct caaacgtgga aaggcgagc cttaagtgga cgaagattga    480
cgaggcaggg cgctttccca acggaacgtg ggcaacggac ctgctcagga atggggggaaa   540
cacgtggaat gtgacgattc catcggatct tgctcctgga gaatatgtcc tccgcaacga   600
gatcattgca cttcactcgg cgagaaatat gggtggagct cagcactaca tgcaatgtgt   660
caatctgaac gtcactggca ccggccatag agagctacag ggcgtctccg ccgcagaatt   720
ttacaatcct acggatcctg gaattttgat taacgtctgg caaactcaaa gcctttcctc   780
ctaccatatt cccggaccta cactgttagc cgccgatacc ggcaacgacg gtggccattc   840
tgcatcatct accttggcga ctgtgacaag cagacgtctt ccactccga gcgacgccat   900
gcccgggaat ggttcatacg gtgcaatttc gccgccctc aaacctgcta aaggattcca     960
tcctgtttgt aacgcccgat tcagacatgg cagcactttc actttgacta ccctggtcgc   1020
accaccagcc aggacctaa                                                1039
```

<210> SEQ ID NO 82
<211> LENGTH: 327
<212> TYPE: PRT
<213> ORGANISM: Thermomyces lanuginosus

<400> SEQUENCE: 82

```
Met Ala Phe Ser Thr Val Thr Val Phe Val Thr Phe Leu Ala Phe Ile
1               5                   10                  15

Ser Ile Ala Ser Ala His Gly Phe Val Thr Lys Ile Thr Val Leu Gly
            20                  25                  30

Asp Asn Asn Lys Asp Tyr Pro Gly Phe Asp Pro Ser Thr Pro Lys Glu
        35                  40                  45

Val Pro Pro Gly Leu Asp Val Ala Trp Ser Thr Ser Ala Ser Asp Gln
    50                  55                  60

Gly Tyr Met Ser Ser Ser Asn Ala Ser Tyr His Ser Lys Asp Phe Ile
65                  70                  75                  80

Cys His Arg Asn Ala Lys Pro Ala Pro Asp Ala Ala Gln Val His Ala
                85                  90                  95

Gly Asp Lys Val Gln Leu His Trp Thr Gln Trp Pro Gly Pro Glu Asp
            100                 105                 110

His Gln Gly Pro Ile Leu Asp Tyr Leu Ala Ser Cys Asn Gly Pro Cys
        115                 120                 125

Ser Asn Val Glu Lys Ala Ser Leu Lys Trp Thr Lys Ile Asp Glu Ala
    130                 135                 140

Gly Arg Phe Pro Asn Gly Thr Trp Ala Thr Asp Leu Leu Arg Asn Gly
145                 150                 155                 160

Gly Asn Thr Trp Asn Val Thr Ile Pro Ser Asp Leu Ala Pro Gly Glu
                165                 170                 175

Tyr Val Leu Arg Asn Glu Ile Ile Ala Leu His Ser Ala Arg Asn Met
            180                 185                 190

Gly Gly Ala Gln His Tyr Met Gln Cys Val Asn Leu Asn Val Thr Gly
        195                 200                 205

Thr Gly His Arg Glu Leu Gln Gly Val Ser Ala Ala Glu Phe Tyr Asn
    210                 215                 220
```

Pro Thr Asp Pro Gly Ile Leu Ile Asn Val Trp Gln Thr Gln Ser Leu
225                 230                 235                 240

Ser Ser Tyr His Ile Pro Gly Pro Thr Leu Ala Ala Asp Thr Gly
            245                 250                 255

Asn Asp Gly Gly His Ser Ala Ser Thr Leu Ala Thr Val Thr Ser
        260                 265                 270

Arg Arg Leu Ser Thr Pro Ser Asp Ala Met Pro Gly Asn Gly Ser Tyr
            275                 280                 285

Gly Ala Ile Ser Pro Pro Leu Lys Pro Ala Lys Gly Phe His Pro Val
        290                 295                 300

Cys Asn Ala Arg Phe Arg His Gly Ser Thr Phe Thr Leu Thr Thr Leu
305                 310                 315                 320

Val Ala Pro Pro Ala Arg Thr
                325

<210> SEQ ID NO 83
<211> LENGTH: 881
<212> TYPE: DNA
<213> ORGANISM: Thermomyces lanuginosus

<400> SEQUENCE: 83
atgaaaggct ccaccactgc gtctttgctt cttccgctcc tggcgagcgt tactcgcacc      60
tctgcgcacg ggtttgtctc caacctcgtc atcaatggcg tcttctatcg gggctggctc     120
ccgaccgagg acccctacaa ggctgacccc cgattggcg tcggctggga gacgcctaac      180
ctgggcaacg gcttcgtgct gcccgaagaa gcgtcgaccg atgccatcgt ctgccacaaa     240
gaggccgagc cggcccgcgg ctatgccagc gtcgctgccg gtgacaagat ctacattcag     300
tggcagccga acccatggcc ggagtctcat cacggtacgt caaactgccc attgttgcaa     360
ttcagaatca tctactaaca actcttcaag gccccgtcat tgactacctg ccccttgca      420
acggtgactg ctcgactgtc aacaagacca gtttggagtt cttcaagatc gacggcgtgg    480
gcctcatcga cggctcctcc ccgccgggta agtgggctga cgacgagctc attgccaacg    540
gcaacggctg gctggtccag atccccgagg acatcaagcc gggcaactac gtcctgcgcc    600
atgagatcat cgccttgcac gaggcgttca accagaacgg cgctcagatc tacccgcagt    660
gcttcaacct ccagattacc ggctccggca ctgtcgagcc cgagggcacg ccggctaccg    720
agctgtattc gcccaccgat ccgggcattc tggttgacat ctacaacccc ttgagcacgt    780
acgtcgtgcc cggcccgacg ctcatcccgc aggcggttga gattgagcag tcttcgtcgg    840
ctgtcacggc gactggtacg ccgacgccgg cggcggcgta a                       881

<210> SEQ ID NO 84
<211> LENGTH: 274
<212> TYPE: PRT
<213> ORGANISM: Thermomyces lanuginosus

<400> SEQUENCE: 84

Met Lys Gly Ser Thr Thr Ala Ser Leu Leu Leu Pro Leu Leu Ala Ser
1               5                   10                  15

Val Thr Arg Thr Ser Ala His Gly Phe Val Ser Asn Leu Val Ile Asn
            20                  25                  30

Gly Val Phe Tyr Arg Gly Trp Leu Pro Thr Glu Asp Pro Tyr Lys Ala
        35                  40                  45

Asp Pro Pro Ile Gly Val Gly Trp Glu Thr Pro Asn Leu Gly Asn Gly
    50                  55                  60

Phe Val Leu Pro Glu Glu Ala Ser Thr Asp Ala Ile Val Cys His Lys
65                  70                  75                  80

Glu Ala Glu Pro Ala Arg Gly Tyr Ala Ser Val Ala Ala Gly Asp Lys
                85                  90                  95

Ile Tyr Ile Gln Trp Gln Pro Asn Pro Trp Pro Glu Ser His His Gly
            100                 105                 110

Pro Val Ile Asp Tyr Leu Ala Pro Cys Asn Gly Asp Cys Ser Thr Val
            115                 120                 125

Asn Lys Thr Ser Leu Glu Phe Phe Lys Ile Asp Gly Val Gly Leu Ile
    130                 135                 140

Asp Gly Ser Ser Pro Pro Gly Lys Trp Ala Asp Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Glu Ala Phe Asn
            180                 185                 190

Gln Asn Gly Ala Gln Ile Tyr Pro Gln Cys Phe Asn Leu Gln Ile Thr
        195                 200                 205

Gly Ser Gly Thr Val Glu Pro Glu Gly Thr Pro Ala Thr Glu Leu Tyr
    210                 215                 220

Ser Pro Thr Asp Pro Gly Ile Leu Val Asp Ile Tyr Asn Pro Leu Ser
225                 230                 235                 240

Thr Tyr Val Val Pro Gly Pro Thr Leu Ile Pro Gln Ala Val Glu Ile
                245                 250                 255

Glu Gln Ser Ser Ser Ala Val Thr Ala Thr Gly Thr Pro Thr Pro Ala
            260                 265                 270

Ala Ala

<210> SEQ ID NO 85
<211> LENGTH: 969
<212> TYPE: DNA
<213> ORGANISM: Aurantiporus alborubescens

<400> SEQUENCE: 85
atgcgaacca tcgccacgtt tgttacgctt gtagcctcag ttctccctgc ggtcctcgca        60
cacggaggtg tcctctccta ttcsaacggg gggaattggt actggggatg gaagccttac       120
aattcacctg acgggcagac caccatccaa cgcccgtggg caacatacaa tccgatcact       180
gatgcgacgg atcctaccat tgcttgcaac aacgacggga catctggagc tctgcagttg       240
actgcgacag tcgcggcggg atctgccatc acggcgtatt ggaaccaggt gtggccgcat       300
gataaagggc cgatgacgac ataccctcgca caatgccccg gcagtacctg cacaggagtc       360
aacgcgaaga ctctgaaatg gttcaagatc gatcacgccg ggttgctttc tggtactgtc       420
tacagtggct cgtgggcatc aggcaagatg attgcacaga actcgacctg gacaactacc       480
attccagcga cggtgccttc agggaactat ctgatacgtt tcgagactat tgccctgcac       540
tctttgccag cgcaatttta ccctgagtgc gcacaaattc aaatcacggg cggaggttcc       600
cgtgctccaa ccgctgcaga gcttgttagc ttccctggcg cgtacagcaa caatgatcct       660
ggtgtcaaca ttgacatcta ctccaatgcc gcgcagagtg caaccacata cgtaatacca       720
ggacctccat tgtacggcgg tgcttccgga tctggtccat cttccgcgcc tccatcaagt       780 acccaggta gttcgtccac ttcccacggt cccacgtccg tcagcacgtc cagcagtgct       840
gcaccatcga cgacaggaac cgtgacgcag tacggtcagt gcggtggcat tggttgggct       900

```
ggagctaccg gctgtatctc accattcaag tgcacggtca tcaacgatta ttactaccag    960
tgcctctga                                                             969
```

<210> SEQ ID NO 86
<211> LENGTH: 322
<212> TYPE: PRT
<213> ORGANISM: Aurantiporus alborubescens

<400> SEQUENCE: 86

```
Met Arg Thr Ile Ala Thr Phe Val Thr Leu Val Ala Ser Val Leu Pro
1               5                   10                  15

Ala Val Leu Ala His Gly Gly Val Leu Ser Tyr Ser Asn Gly Gly Asn
            20                  25                  30

Trp Tyr Trp Gly Trp Lys Pro Tyr Asn Ser Pro Asp Gly Gln Thr Thr
        35                  40                  45

Ile Gln Arg Pro Trp Ala Thr Tyr Asn Pro Ile Thr Asp Ala Thr Asp
    50                  55                  60

Pro Thr Ile Ala Cys Asn Asn Asp Gly Thr Ser Gly Ala Leu Gln Leu
65                  70                  75                  80

Thr Ala Thr Val Ala Ala Gly Ser Ala Ile Thr Ala Tyr Trp Asn Gln
                85                  90                  95

Val Trp Pro His Asp Lys Gly Pro Met Thr Thr Tyr Leu Ala Gln Cys
            100                 105                 110

Pro Gly Ser Thr Cys Thr Gly Val Asn Ala Lys Thr Leu Lys Trp Phe
        115                 120                 125

Lys Ile Asp His Ala Gly Leu Leu Ser Gly Thr Val Tyr Ser Gly Ser
    130                 135                 140

Trp Ala Ser Gly Lys Met Ile Ala Gln Asn Ser Thr Trp Thr Thr Thr
145                 150                 155                 160

Ile Pro Ala Thr Val Pro Ser Gly Asn Tyr Leu Ile Arg Phe Glu Thr
                165                 170                 175

Ile Ala Leu His Ser Leu Pro Ala Gln Phe Tyr Pro Glu Cys Ala Gln
            180                 185                 190

Ile Gln Ile Thr Gly Gly Gly Ser Arg Ala Pro Thr Ala Ala Glu Leu
        195                 200                 205

Val Ser Phe Pro Gly Ala Tyr Ser Asn Asn Asp Pro Gly Val Asn Ile
    210                 215                 220

Asp Ile Tyr Ser Asn Ala Ala Gln Ser Ala Thr Thr Tyr Val Ile Pro
225                 230                 235                 240

Gly Pro Pro Leu Tyr Gly Gly Ala Ser Gly Ser Gly Pro Ser Ser Ala
                245                 250                 255

Pro Pro Ser Ser Thr Pro Gly Ser Ser Ser Thr Ser His Gly Pro Thr
            260                 265                 270

Ser Val Ser Thr Ser Ser Ser Ala Ala Pro Ser Thr Thr Gly Thr Val
        275                 280                 285

Thr Gln Tyr Gly Gln Cys Gly Gly Ile Gly Trp Ala Gly Ala Thr Gly
    290                 295                 300

Cys Ile Ser Pro Phe Lys Cys Thr Val Ile Asn Asp Tyr Tyr Tyr Gln
305                 310                 315                 320

Cys Leu
```

<210> SEQ ID NO 87
<211> LENGTH: 705
<212> TYPE: DNA

<213> ORGANISM: Aurantiporus alborubescens

<400> SEQUENCE: 87

```
atgaaggcta tcttggctat tttctcggcc cttgctccac ttgccgctgc gcattatacc      60
ttccctgatt ttattgtcaa cggaacaaca actgccgatt gggtctacat ccgagagacc     120
gcgaaccact actcgaatgg tcctgtaacc aacgtgaacg atccagaatt ccgatgctac     180
gagctggacc tgcaaaacac ggcagcgagt accctcaccg ccacggtctc tgcaggctcc     240
agcgtcggct ttaaagctaa cagcgccctt taccatcctg gttatctcga tgtgtatatg     300
tccaaagcga ccccagctgc taattcaccc agtgctggaa cggaccaaag ctggttcaag     360
gtctatgaat ccgctccggt cttcgcgaat ggggccctaa gcttcccttc ggagaacatc     420
caatctttca cgttcacaat cccgaagtcc cttcccagtg ccaatatctc atccgtgtg     480
gaacacatcg ctctccactc cgccagtagc tacgaggtg cacaattcta catcagctgc     540
gctcaagtca atgtcgtcaa cggcgggaac ggaaacccag accgttagt caagattccc     600
ggcgtttaca ctgggaacga gcctggcatc ctcatcaaca tctacagctt cccaccgggt     660
ttcagtggct accaatcccc gggacctgct gtgtggcgtg gttga                     705
```

<210> SEQ ID NO 88
<211> LENGTH: 234
<212> TYPE: PRT
<213> ORGANISM: Aurantiporus alborubescens

<400> SEQUENCE: 88

```
Met Lys Ala Ile Leu Ala Ile Phe Ser Ala Leu Ala Pro Leu Ala Ala
1               5                   10                  15

Ala His Tyr Thr Phe Pro Asp Phe Ile Val Asn Gly Thr Thr Thr Ala
            20                  25                  30

Asp Trp Val Tyr Ile Arg Glu Thr Ala Asn His Tyr Ser Asn Gly Pro
        35                  40                  45

Val Thr Asn Val Asn Asp Pro Glu Phe Arg Cys Tyr Glu Leu Asp Leu
    50                  55                  60

Gln Asn Thr Ala Ala Ser Thr Leu Thr Ala Thr Val Ser Ala Gly Ser
65                  70                  75                  80

Ser Val Gly Phe Lys Ala Asn Ser Ala Leu Tyr His Pro Gly Tyr Leu
                85                  90                  95

Asp Val Tyr Met Ser Lys Ala Thr Pro Ala Ala Asn Ser Pro Ser Ala
            100                 105                 110

Gly Thr Asp Gln Ser Trp Phe Lys Val Tyr Glu Ser Ala Pro Val Phe
        115                 120                 125

Ala Asn Gly Ala Leu Ser Phe Pro Ser Glu Asn Ile Gln Ser Phe Thr
    130                 135                 140

Phe Thr Ile Pro Lys Ser Leu Pro Ser Gly Gln Tyr Leu Ile Arg Val
145                 150                 155                 160

Glu His Ile Ala Leu His Ser Ser Ser Tyr Gly Gly Ala Gln Phe
                165                 170                 175

Tyr Ile Ser Cys Ala Gln Val Asn Val Val Asn Gly Asn Gly Asn
            180                 185                 190

Pro Gly Pro Leu Val Lys Ile Pro Gly Val Tyr Thr Gly Asn Glu Pro
        195                 200                 205

Gly Ile Leu Ile Asn Ile Tyr Ser Phe Pro Pro Gly Phe Ser Gly Tyr
    210                 215                 220

Gln Ser Pro Gly Pro Ala Val Trp Arg Gly
```

<210> SEQ ID NO 89
<211> LENGTH: 702
<212> TYPE: DNA
<213> ORGANISM: Trichophaea saccata

<400> SEQUENCE: 89

```
atgacgcccc tgaaactccg ccccttctc ctcctggtgc tttccacgac cctcagcctc      60
gtgcacgcgc actatcgctt ctacgaactg atcgccaacg gggccaccca cgcttccttc    120
gaatacatcc gccaatgggt gcccatctac agcaactctc ccgtaaccga cgtcaccagc    180
gtcaacctcc gctgcaacgt caacgccact cccgccgccg aggtgatcac cgttgctgcc    240
ggtagcaccg tcggcttcgt agcagacaca acagtaacgc accccggtgc gttcaccgcg    300
tacatggcga aagcgcccga agacatcacg gaatgggatg gcaacgggga ctggttcaag    360
atctgggaga agggtccaac gagtataacc agtagcggga taacctggga cgtcacggat    420
acccaatgga ccttcaccat cccttccgcg acaccaaacg gtcaatacct actccgcttc    480
gagcacatag cgctccacgc cgccagcacc gtgggggtg ctcaattcta catgtcgtgc    540
gcgcagatac aagtaacgaa cggcggcaac gggagtcccg ggccaccat caagttcccg    600
ggcggataca gcgccacaga ccccggtatc ctgatcaata tctattatcc catccccact    660
agttacacta ttcctggtcc accggtttgg accggtaagt aa                       702
```

<210> SEQ ID NO 90
<211> LENGTH: 233
<212> TYPE: PRT
<213> ORGANISM: Trichophaea saccata

<400> SEQUENCE: 90

Met Thr Pro Leu Lys Leu Arg Pro Leu Leu Leu Val Leu Ser Thr
1               5                   10                  15

Thr Leu Ser Leu Val His Ala His Tyr Arg Phe Tyr Glu Leu Ile Ala
            20                  25                  30

Asn Gly Ala Thr His Ala Ser Phe Glu Tyr Ile Arg Gln Trp Val Pro
        35                  40                  45

Ile Tyr Ser Asn Ser Pro Val Thr Asp Val Thr Ser Val Asn Leu Arg
    50                  55                  60

Cys Asn Val Asn Ala Thr Pro Ala Ala Glu Val Ile Thr Val Ala Ala
65                  70                  75                  80

Gly Ser Thr Val Gly Phe Val Ala Asp Thr Thr Val Thr His Pro Gly
                85                  90                  95

Ala Phe Thr Ala Tyr Met Ala Lys Ala Pro Glu Asp Ile Thr Glu Trp
            100                 105                 110

Asp Gly Asn Gly Asp Trp Phe Lys Ile Trp Glu Lys Gly Pro Thr Ser
        115                 120                 125

Ile Thr Ser Ser Gly Ile Thr Trp Asp Val Thr Asp Gln Trp Thr
    130                 135                 140

Phe Thr Ile Pro Ser Ala Thr Pro Asn Gly Gln Tyr Leu Leu Arg Phe
145                 150                 155                 160

Glu His Ile Ala Leu His Ala Ala Ser Thr Val Gly Gly Ala Gln Phe
                165                 170                 175

Tyr Met Ser Cys Ala Gln Ile Gln Val Thr Asn Gly Gly Asn Gly Ser
            180                 185                 190

Pro Gly Pro Thr Ile Lys Phe Pro Gly Gly Tyr Ser Ala Thr Asp Pro

```
            195                 200                 205
Gly Ile Leu Ile Asn Ile Tyr Tyr Pro Ile Pro Thr Ser Tyr Thr Ile
    210                 215                 220

Pro Gly Pro Pro Val Trp Thr Gly Lys
225                 230
```

<210> SEQ ID NO 91
<211> LENGTH: 714
<212> TYPE: DNA
<213> ORGANISM: Trichophaea saccata

<400> SEQUENCE: 91

```
atgaaatgcc ttctctccct ccttctcgcc gcgacagcgg tctccgctca cacgatcttc     60
caagaaatcg gcataaacgg ggtgatgcaa gctcgctacg actacatgcg gctgccgtcc    120
tacgacggtc ccattacgga cgtaacgagc acctacatgg cgtgcaacgg tggtcccaat    180
ccattggtcc aaatctcgaa cgacgtcgct ttcgtaaaag ccggcgacag catcacgctg    240
caatgggcgc aaacgttgac gacagatttc aacacggggc tgatcatcga tccatcgcac    300
ttgggtcctg tgatggtcta catggccaaa gtaccctccg ccaccggtcc gatccccaac    360
agcggctggt tcaaaatcta cgaagacggc tacgacccga caacaaagac atgggcggta    420
accaagctca tcaacaacaa gggaaaagtg accgtcacca tcccatcgtg tctaccggca    480
ggggactact gctgcgcggg tgaaatcatt gccttgcacg cggctagtac ctatccaggc    540
gcacagtttt acatggagtg tgcgcagttg cggcttacca gtggcggcac taagatgcct    600
accacgtata acattccggg gatctattcg cccactgatc cgggtgttac gttcaatctt    660
tacaatggat tcacgagtta taccattcct ggcccaaggc cgtttacatg ctag          714
```

<210> SEQ ID NO 92
<211> LENGTH: 237
<212> TYPE: PRT
<213> ORGANISM: Trichophaea saccata

<400> SEQUENCE: 92

```
Met Lys Cys Leu Leu Ser Leu Leu Ala Ala Thr Ala Val Ser Ala
1               5                   10                  15

His Thr Ile Phe Gln Glu Ile Gly Ile Asn Gly Val Met Gln Ala Arg
                20                  25                  30

Tyr Asp Tyr Met Arg Leu Pro Ser Tyr Asp Gly Pro Ile Thr Asp Val
            35                  40                  45

Thr Ser Thr Tyr Met Ala Cys Asn Gly Gly Pro Asn Pro Leu Val Gln
    50                  55                  60

Ile Ser Asn Asp Val Ala Phe Val Lys Ala Gly Asp Ser Ile Thr Leu
65                  70                  75                  80

Gln Trp Ala Gln Thr Leu Thr Thr Asp Phe Asn Thr Gly Leu Ile Ile
                85                  90                  95

Asp Pro Ser His Leu Gly Pro Val Met Val Tyr Met Ala Lys Val Pro
            100                 105                 110

Ser Ala Thr Gly Pro Ile Pro Asn Ser Gly Trp Phe Lys Ile Tyr Glu
        115                 120                 125

Asp Gly Tyr Asp Pro Thr Thr Lys Thr Trp Ala Val Thr Lys Leu Ile
    130                 135                 140

Asn Asn Lys Gly Lys Val Thr Val Thr Ile Pro Ser Cys Leu Pro Ala
145                 150                 155                 160

Gly Asp Tyr Leu Leu Arg Gly Glu Ile Ile Ala Leu His Ala Ala Ser
```

|     | 165 |     |     |     | 170 |     |     |     | 175 |     |     |
| --- | --- | --- | --- | --- | --- | --- | --- | --- | --- | --- | --- |
Thr Tyr Pro Gly Ala Gln Phe Tyr Met Glu Cys Ala Gln Leu Arg Leu
          180                     185                     190

Thr Ser Gly Gly Thr Lys Met Pro Thr Thr Tyr Asn Ile Pro Gly Ile
            195                     200                     205

Tyr Ser Pro Thr Asp Pro Gly Val Thr Phe Asn Leu Tyr Asn Gly Phe
            210                     215                     220

Thr Ser Tyr Thr Ile Pro Gly Pro Arg Pro Phe Thr Cys
225                 230                     235

<210> SEQ ID NO 93
<211> LENGTH: 1455
<212> TYPE: DNA
<213> ORGANISM: Penicillium thomii

<400> SEQUENCE: 93

```
atgtctctgt ctaagatttc tggattgatc ctcggatctg ctgccttggt ggctggccac      60
ggttacgtga gcggaatcgt cgttgacgat acctactatg tgggatacct tgtcacccag     120
taccccttatg agagtgacgc cccagagctc attgcctggt cggagcaaga gaccgatctg     180
ggttacatcg atggctctga gtatgccaac tccaacatca tctgtcacaa ggaggccaaa     240
cctggtgctt tggaagcacc cgttaaggct ggtggctccg tcgagctcca gtggaccact     300
tggcctacca gccaccacgg tcctgtcatt acctacatgg ccaactgtaa cggcgactgt     360
gacgacgttg acaagactac tttgcagttc ttcaagattg accagggtgg tttgatcagc     420
gataccaccg agcccggtac ctgggcaact gacaacctca tcgccaacaa caatagccgt     480
actgtcaccg tccccagcga cattgccgat ggaaactacg tcctccgtca cgagatcatt     540
gccctccact ccgccgggga gaccaacggt gcccagaact cccccaatg tatcaacttg     600
aaggtcactg gcggcggtag cgctactcct tctggtaccc tgggtaccgc cctgtacaag     660
aacaccgacc ccggtatcct gatcaacatc tacacttccc tcagcaccta cgatatcccc     720
ggcccaaccc tgtacactgc cggcgccgcc gctgctaccg ctgcctccac ggctgcctct     780
tccaccgccg ctgccgttac tactgccgac gccgtcacta ccgccgctgc cgtcaccagc     840
agctctgcat ccgtggaagt tgtgcccaca actactccca gctcatcaat cgtcagtgcc     900
ttcccaacct ggagccctcc ttctaccccca cccttctcca actcttccaa cggatggcgt     960
ccgtcattca gccgcggacc tggtggcccc cgcttcacat ctgctcctgc tcctcagttc    1020
tccgctccta gcggcgctca gcagaagcag tctgccactg ctaccccat cgtggctacc    1080
cctgtcgtga tcaccatgac cgagaccagc acctcctggg tcaccgaaat ggttactctt    1140
actgacaagt ctgttgtgca gaccaccagc gctgtcccag tcgtcgtcgc cgccaccact    1200
acccttaccg agggaagcga gcctgctcag acagcctccc cagcgttgt ctccggctcc    1260
tctagctccg gctctagctc ctcatctacc accaccacct caaagacctc aactggatcc    1320
gactacgtct ccagcgactg gatgtcttac ctcagctcct gagcgctgc tgaggtcctc    1380
cagatgctgc gccagacctt ccgttggatg gtcagcaacg acaaggtgca cgctcgtgat    1440
attaccatca actag                                                    1455
```

<210> SEQ ID NO 94
<211> LENGTH: 484
<212> TYPE: PRT
<213> ORGANISM: Penicillium thomii

<400> SEQUENCE: 94

```
Met Ser Leu Ser Lys Ile Ser Gly Leu Ile Leu Gly Ser Ala Ala Leu
1               5                   10                  15

Val Ala Gly His Gly Tyr Val Ser Gly Ile Val Asp Asp Thr Tyr
            20                  25                  30

Tyr Gly Gly Tyr Leu Val Thr Gln Tyr Pro Tyr Glu Ser Asp Ala Pro
        35                  40                  45

Glu Leu Ile Ala Trp Ser Glu Gln Thr Asp Leu Gly Tyr Ile Asp
50                      55                  60

Gly Ser Glu Tyr Ala Asn Ser Asn Ile Ile Cys His Lys Glu Ala Lys
65                  70                  75                  80

Pro Gly Ala Leu Glu Ala Pro Val Lys Ala Gly Gly Ser Val Glu Leu
                85                  90                  95

Gln Trp Thr Thr Trp Pro Thr Ser His His Gly Pro Val Ile Thr Tyr
                100                 105                 110

Met Ala Asn Cys Asn Gly Asp Cys Asp Val Asp Lys Thr Thr Leu
            115                 120                 125

Gln Phe Phe Lys Ile Asp Gln Gly Gly Leu Ile Ser Asp Thr Thr Glu
130                 135                 140

Pro Gly Thr Trp Ala Thr Asp Asn Leu Ile Ala Asn Asn Asn Ser Arg
145                 150                 155                 160

Thr Val Thr Val Pro Ser Asp Ile Ala Asp Gly Asn Tyr Val Leu Arg
                165                 170                 175

His Glu Ile Ile Ala Leu His Ser Ala Gly Glu Thr Asn Gly Ala Gln
                180                 185                 190

Asn Tyr Pro Gln Cys Ile Asn Leu Lys Val Thr Gly Gly Ser Ala
            195                 200                 205

Thr Pro Ser Gly Thr Leu Gly Thr Ala Leu Tyr Lys Asn Thr Asp Pro
210                 215                 220

Gly Ile Leu Ile Asn Ile Tyr Thr Ser Leu Ser Thr Tyr Asp Ile Pro
225                 230                 235                 240

Gly Pro Thr Leu Tyr Thr Ala Gly Ala Ala Ala Thr Ala Ala Ser
            245                 250                 255

Thr Ala Ala Ser Ser Thr Ala Ala Val Thr Thr Ala Asp Ala Val
            260                 265                 270

Thr Thr Ala Ala Ala Val Thr Ser Ser Ala Ser Val Glu Val Val
            275                 280                 285

Pro Thr Thr Thr Pro Ser Ser Ile Val Ser Ala Phe Pro Thr Trp
            290                 295                 300

Ser Pro Ser Ser Thr Pro Pro Phe Ser Asn Ser Ser Asn Gly Trp Arg
305                 310                 315                 320

Pro Ser Phe Ser Arg Gly Pro Gly Gly Pro Arg Phe Thr Ser Ala Pro
                325                 330                 335

Ala Pro Gln Phe Ser Ala Pro Ser Gly Ala Gln Gln Lys Gln Ser Ala
            340                 345                 350

Thr Ala Thr Pro Ile Val Ala Thr Pro Val Val Ile Thr Met Thr Glu
            355                 360                 365

Thr Ser Thr Ser Trp Val Thr Glu Met Val Thr Leu Thr Asp Lys Ser
370                 375                 380

Val Val Gln Thr Thr Ser Ala Val Pro Val Val Val Ala Ala Thr Thr
385                 390                 395                 400

Thr Leu Thr Glu Gly Ser Glu Pro Ala Gln Thr Ala Ser Pro Ser Val
            405                 410                 415
```

Val Ser Gly Ser Ser Ser Gly Ser Ser Ser Thr Thr Thr
        420                 425             430

Thr Ser Lys Thr Ser Thr Gly Ser Asp Tyr Val Ser Asp Trp Met
            435             440             445

Ser Tyr Leu Ser Ser Leu Ser Ala Ala Glu Val Leu Gln Met Leu Arg
    450                 455                 460

Gln Thr Phe Arg Trp Met Val Ser Asn Asp Lys Val His Ala Arg Asp
465             470                 475                 480

Ile Thr Ile Asn

<210> SEQ ID NO 95
<211> LENGTH: 1021
<212> TYPE: DNA
<213> ORGANISM: Talaromyces stipitatus

<400> SEQUENCE: 95

```
atgccttcca ctaaagttgc tgctctatct gccgtcctgg ctttggcctc cacggttgct      60
ggccatggct ttgtgcaaaa tattgtcatt gacggtaaat cgtaagtgac ttgcttttgt     120
actatagagc tagataaata cttatactaa ataattcagc tacactggct acctcgtgaa     180
ccagtatcct taccagtcca acccaccagc tgttattggg tggtcaacca ctgcaaccga     240
cttgggattt gtcgatggat ctggatacac caacccggat atcatctgcc acaaaaacgc     300
caaacccggt cagcttttctg ctccggttgc cgcaggagga aaggttgagc tcgaatggac     360
aacatggccc gagagccatc acggccctgt catcagctat ctcgccaatt gcaatggcga     420
ttgtactacc gtggataaga cgaagctcga atttgtcaaa atcgatcagc ggggtctgat     480
cgacgacagc aatcctcccg gtacatgggc cgccgaccag ctcatcgccg ccaacaacag     540
ctggactgta actattcccg agagcatcgc gcctggaaac tacgtccttc gccacgaaat     600
catcgctctt cactccgcca caacgcaac cggagctcaa aactaccctc aatgcatcaa     660
cttgcaaatc actggcagcg ggacggccaa cccatctggt acccctggcg agaaactcta     720
taccccaact gacccaggta tcttggtcaa catctaccag tcattgtcgt cttatgttat     780
tcccggtccg actttgtgga gtggtgctgc agcgcacgtt gttgccactg cagccggttc     840
tgctactggg gttgcttctg ccaccgctac tccgaccact cttgtgactg ccgtttcatc     900
gcctaccggt gctccttcag tggtgactcc tgaggctcct tcagtaacct cgttcgcccc     960
agtggtgact gttactgatg tcgttactgt gactaccgtc atcactacta ctatctctta    1020
g                                                                    1021
```

<210> SEQ ID NO 96
<211> LENGTH: 320
<212> TYPE: PRT
<213> ORGANISM: Talaromyces stipitatus

<400> SEQUENCE: 96

Met Pro Ser Thr Lys Val Ala Ala Leu Ser Ala Val Leu Ala Leu Ala
1               5                   10                  15

Ser Thr Val Ala Gly His Gly Phe Val Gln Asn Ile Val Ile Asp Gly
            20                  25                  30

Lys Ser Tyr Thr Gly Tyr Leu Val Asn Gln Tyr Pro Tyr Gln Ser Asn
        35                  40                  45

Pro Pro Ala Val Ile Gly Trp Ser Thr Thr Ala Thr Asp Leu Gly Phe
    50                  55                  60

Val Asp Gly Ser Gly Tyr Thr Asn Pro Asp Ile Ile Cys His Lys Asn

```
                65                  70                  75                  80
Ala Lys Pro Gly Gln Leu Ser Ala Pro Val Ala Ala Gly Gly Lys Val
                    85                  90                  95

Glu Leu Glu Trp Thr Thr Trp Pro Glu Ser His His Gly Pro Val Ile
                100                 105                 110

Ser Tyr Leu Ala Asn Cys Asn Gly Asp Cys Thr Val Asp Lys Thr
                115                 120                 125

Lys Leu Glu Phe Val Lys Ile Asp Gln Arg Gly Leu Ile Asp Asp Ser
130                 135                 140

Asn Pro Pro Gly Thr Trp Ala Ala Asp Gln Leu Ile Ala Ala Asn Asn
145                 150                 155                 160

Ser Trp Thr Val Thr Ile Pro Glu Ser Ile Ala Pro Gly Asn Tyr Val
                165                 170                 175

Leu Arg His Glu Ile Ile Ala Leu His Ser Ala Asn Asn Ala Thr Gly
                180                 185                 190

Ala Gln Asn Tyr Pro Gln Cys Ile Asn Leu Gln Ile Thr Gly Ser Gly
                195                 200                 205

Thr Ala Asn Pro Ser Gly Thr Pro Gly Glu Lys Leu Tyr Thr Pro Thr
210                 215                 220

Asp Pro Gly Ile Leu Val Asn Ile Tyr Gln Ser Leu Ser Ser Tyr Val
225                 230                 235                 240

Ile Pro Gly Pro Thr Leu Trp Ser Gly Ala Ala His Val Val Ala
                245                 250                 255

Thr Ala Ala Gly Ser Ala Thr Gly Val Ala Ser Ala Thr Ala Thr Pro
                260                 265                 270

Thr Thr Leu Val Thr Ala Val Ser Ser Pro Thr Gly Ala Pro Ser Val
                275                 280                 285

Val Thr Pro Glu Ala Pro Ser Val Thr Ser Phe Ala Pro Val Val Thr
                290                 295                 300

Val Thr Asp Val Val Thr Val Thr Thr Val Ile Thr Thr Thr Ile Ser
305                 310                 315                 320

<210> SEQ ID NO 97
<211> LENGTH: 821
<212> TYPE: DNA
<213> ORGANISM: Humicola insolens

<400> SEQUENCE: 97
atgaagctca gcgttgtcct cacaggcctg gcggcagccc tcgccgaggc tcattgtcag      60
tccatacgac agcgaaaccc ctggatgatc acgagactaa ccagtcctac agacaccctt    120
ccccagcgtc ggcaacaccg ccgactggca ggtcgtgcgc cagacgacca acttccagag    180
caacggcccc gtgacggacg tcaactcgga ccagatccgg tgctacgagc gcttccccgg    240
ccagggggcg cccggcatct acaacgtcac cgccggccag accatctcgt acaacgccaa    300
ggcctctatc tcccacccgg ccccatggc cttctacatc gccaaggtcc ctgccggcta    360
caccgccgcc aactgggatg caggggcgc cgtgtggtcc aagatctacc aggacatgcc    420
gcgcattgcg gggagtctga cctggcctac caatggtacg aaatcctctt ctatccttca    480
tacttgctat tcctccaact gcctggcagc tcacactaac ttccacacac caggcgccc    540 gttccgtctc ggtaaccatc ccccgctgcc tgcaagacgg ccactacctg ttgcgcgccg    600
agcacatcgg cctgcacagc gcgagcggcg tgggcggcgc agttctac atctcgtgtg    660 cccagctcta cgtcagcggc ggcaccggca cttggaaccc gcgcaacaag gtcgcgttcc    720
```

-continued

```
ccggcgccta cagcccgacg cacccgggca tcatgatcaa catctactgg ccggtgccga      780
cgagctacac gccgccgggg ccgccggttg agacgtgctg a                          821
```

<210> SEQ ID NO 98
<211> LENGTH: 227
<212> TYPE: PRT
<213> ORGANISM: Humicola insolens

<400> SEQUENCE: 98

```
Met Lys Leu Ser Val Val Leu Thr Gly Leu Ala Ala Leu Ala Glu
1               5                   10                  15

Ala His Tyr Thr Phe Pro Ser Val Gly Asn Thr Ala Asp Trp Gln Val
            20                  25                  30

Val Arg Gln Thr Thr Asn Phe Gln Ser Asn Gly Pro Val Thr Asp Val
        35                  40                  45

Asn Ser Asp Gln Ile Arg Cys Tyr Glu Arg Phe Pro Gly Gln Gly Ala
    50                  55                  60

Pro Gly Ile Tyr Asn Val Thr Ala Gly Gln Thr Ile Ser Tyr Asn Ala
65                  70                  75                  80

Lys Ala Ser Ile Ser His Pro Gly Pro Met Ala Phe Tyr Ile Ala Lys
                85                  90                  95

Val Pro Ala Gly Tyr Thr Ala Ala Asn Trp Asp Gly Arg Gly Ala Val
            100                 105                 110

Trp Ser Lys Ile Tyr Gln Asp Met Pro Arg Ile Ala Gly Ser Leu Thr
        115                 120                 125

Trp Pro Thr Asn Gly Ala Arg Ser Val Ser Val Thr Ile Pro Arg Cys
    130                 135                 140

Leu Gln Asp Gly His Tyr Leu Leu Arg Ala Glu His Ile Gly Leu His
145                 150                 155                 160

Ser Ala Ser Gly Val Gly Gly Ala Gln Phe Tyr Ile Ser Cys Ala Gln
                165                 170                 175

Leu Tyr Val Ser Gly Gly Thr Gly Thr Trp Asn Pro Arg Asn Lys Val
            180                 185                 190

Ala Phe Pro Gly Ala Tyr Ser Pro Thr His Pro Gly Ile Met Ile Asn
        195                 200                 205

Ile Tyr Trp Pro Val Pro Thr Ser Tyr Thr Pro Pro Gly Pro Pro Val
    210                 215                 220

Glu Thr Cys
225
```

<210> SEQ ID NO 99
<211> LENGTH: 1120
<212> TYPE: DNA
<213> ORGANISM: Humicola insolens

<400> SEQUENCE: 99

```
atgcgcccct tcctcgccgc cctcgccgcg gccaccacgg tccacgccca cggctgggtc      60
gacaacgcca ccatcgacgg cgtcttctac cagctctacc acccgtacat ggacccgtac     120
atgggcgagt cgccccgcc tcgcatctcg cgcaagctgg tgtggaacgg ctacgtgaac     180
gacgtgacgt ccatcgacct gcaatgcggc ggacacacgg ccgaagggca aatcggcacg     240
gaacccgcgc cgctgcacgc ccccgccacg gccgggtcga cggtcaacct ccgctggacg     300
ctgtggccgg actcgcacat ggggcccatc atgacgtaca tggcgcggtg tccggacgag     360
ggttgtgata agtggttgcc gggggaggag taagtgtttc ctggcgggaa tggctgtgta     420
```

-continued

```
tttgagaagg agatattatg agtgaaactg ggagaggcga gaagaagaga tgctgacgcg    480
ggttttgctc tcctcagacc agtctggttc aaaatccacg aagccggccg gtacaccacc    540
gacaagtctt accccgacga catctgggaa gttgtaagtg ccctgcctac ctatccatcc    600
ctaattccct ccctcccctc tccacctcct ccttccgcgc ccccctcccc cccttatt     660
gctaaccaac ccctcccctt acagacccgc ctcatgtacc ccgccaacga aggctacaac    720
tacaccatcc ccgcctgcct cgcatccggc cactacctgg tccggcacga gatcatcgcc    780
ttacactcgg cctgggccaa aggcgaagcg cagttctatc cctcgtgcca ccagctgacc    840
gtcacctcca tcggcggtaa cgtgcgcgaa gcgccggccg agtaccgcgt cagtttcccc    900
ggcgcgtaca aggacgatga tccgggtatt ttcatcaacg tttggaaccg taagttcttt    960
ttttgttccc cttcctccca acctacctag gtgtcgtaat gtggtccgta agggtttgtt   1020
tgttgttgag ggatatagct gacaatggat gtgtgataac acagctggcc cctacaccat   1080
tcccggaccg ccggtctgga cgtgccccga gtctgagtaa                         1120
```

<210> SEQ ID NO 100
<211> LENGTH: 257
<212> TYPE: PRT
<213> ORGANISM: Humicola insolens

<400> SEQUENCE: 100

```
Met Arg Pro Phe Leu Ala Ala Leu Ala Ala Ala Thr Thr Val His Ala
1               5                   10                  15

His Gly Trp Val Asp Asn Ala Thr Ile Asp Gly Val Phe Tyr Gln Leu
            20                  25                  30

Tyr His Pro Tyr Met Asp Pro Tyr Met Gly Glu Phe Ala Pro Pro Arg
        35                  40                  45

Ile Ser Arg Lys Leu Val Trp Asn Gly Tyr Val Asn Asp Val Thr Ser
    50                  55                  60

Ile Asp Leu Gln Cys Gly Gly His Thr Ala Glu Gly Gln Ile Gly Thr
65                  70                  75                  80

Glu Pro Ala Pro Leu His Ala Pro Ala Thr Ala Gly Ser Thr Val Asn
                85                  90                  95

Leu Arg Trp Thr Leu Trp Pro Asp Ser His Met Gly Pro Ile Met Thr
            100                 105                 110

Tyr Met Ala Arg Cys Pro Asp Glu Gly Cys Asp Lys Trp Leu Pro Val
        115                 120                 125

Trp Phe Lys Ile His Glu Ala Gly Arg Tyr Thr Thr Asp Lys Ser Tyr
    130                 135                 140

Pro Asp Asp Ile Trp Glu Val Thr Arg Leu Met Tyr Pro Ala Asn Glu
145                 150                 155                 160

Gly Tyr Asn Tyr Thr Ile Pro Ala Cys Leu Ala Ser Gly His Tyr Leu
                165                 170                 175

Val Arg His Glu Ile Ile Ala Leu His Ser Ala Trp Ala Lys Gly Glu
            180                 185                 190

Ala Gln Phe Tyr Pro Ser Cys His Gln Leu Thr Val Thr Ser Ile Gly
        195                 200                 205

Gly Asn Val Arg Glu Ala Pro Ala Glu Tyr Arg Val Ser Phe Pro Gly
    210                 215                 220

Ala Tyr Lys Asp Asp Asp Pro Gly Ile Phe Ile Asn Val Trp Asn Pro
225                 230                 235                 240

Gly Pro Tyr Thr Ile Pro Gly Pro Pro Val Trp Thr Cys Pro Glu Ser
                245                 250                 255
```

Glu

<210> SEQ ID NO 101
<211> LENGTH: 878
<212> TYPE: DNA
<213> ORGANISM: Humicola insolens

<400> SEQUENCE: 101

| | | | | |
|---|---|---|---|---|
| atgagactct | ccctgacaac | cctcctggcc | tctgccctgt | ccgtccaggg tcacgccatc | 60 |
| ttccaggtgc | gttcctttca | ccacccacat | catcatgatg | aacctcaaag ttgctaaccc | 120 |
| ccgctgggca | gagagttacc | gtcaacggcc | aggaccaagg | ctcgttgact ggtctccggg | 180 |
| ccccgaataa | caacaacccc | gtgcagaacg | tcaacagcca | ggacatcatc tgtggcgctc | 240 |
| ccgggtcgcg | gtcacagtcc | gtcatcaacg | tcaatgccgg | cgaccgcatc ggtgcctggt | 300 |
| accagcatgt | catcggcggc | gcccagttcc | ccggcgaccc | ggacaacccg atcgccaggt | 360 |
| cccacaaggg | ccccatctcc | gtctatctgg | ccaaggtgga | caacgctgcc acggcgaacc | 420 |
| accagggtct | gcaatggtaa | acatacctcg | ggtcaagtca | aacctctgt gatcgccgag | 480 |
| acgactaacc | cctctttccc | ataaacaggt | tcaagatctg | gcacgacggc ttcaacccct | 540 |
| ccacccggca | atgggccgtc | gacaccatga | tcaacaacaa | cggctgggtc tatttcaacc | 600 |
| tcccgcagtg | catcgctccc | ggccactatc | tcatgcgcgt | cgagctgctc gctctccact | 660 |
| cggccaccta | ccaaggccag | gcgcagttct | acatctcgtg | cgcccagatc aacgtccagt | 720 |
| cgggcggcaa | ctttactccc | tggcagacgg | ttagcttccc | cggcgcctac caggccaacc | 780 |
| accccggcat | tcaggtcaac | atttacggcg | ccatgggcca | gccggataac ggcggcaggc | 840 |
| cctaccagat | tccgggcccg | gagccgattc | agtgctga | | 878 |

<210> SEQ ID NO 102
<211> LENGTH: 246
<212> TYPE: PRT
<213> ORGANISM: Humicola insolens

<400> SEQUENCE: 102

Met Arg Leu Ser Leu Thr Thr Leu Leu Ala Ser Ala Leu Ser Val Gln
1               5                   10                  15

Gly His Ala Ile Phe Gln Arg Val Thr Val Asn Gly Gln Asp Gln Gly
                20                  25                  30

Ser Leu Thr Gly Leu Arg Ala Pro Asn Asn Asn Asn Pro Val Gln Asn
            35                  40                  45

Val Asn Ser Gln Asp Ile Ile Cys Gly Ala Pro Gly Ser Arg Ser Gln
        50                  55                  60

Ser Val Ile Asn Val Asn Ala Gly Asp Arg Ile Gly Ala Trp Tyr Gln
65                  70                  75                  80

His Val Ile Gly Gly Ala Gln Phe Pro Gly Asp Pro Asp Asn Pro Ile
                85                  90                  95

Ala Arg Ser His Lys Gly Pro Ile Ser Val Tyr Leu Ala Lys Val Asp
                100                 105                 110

Asn Ala Ala Thr Ala Asn His Gln Gly Leu Gln Trp Phe Lys Ile Trp
            115                 120                 125

His Asp Gly Phe Asn Pro Ser Thr Arg Gln Trp Ala Val Asp Thr Met
        130                 135                 140

Ile Asn Asn Asn Gly Trp Val Tyr Phe Asn Leu Pro Gln Cys Ile Ala
145                 150                 155                 160

Pro Gly His Tyr Leu Met Arg Val Glu Leu Leu Ala Leu His Ser Ala
            165                 170                 175
Thr Tyr Gln Gly Gln Ala Gln Phe Tyr Ile Ser Cys Ala Gln Ile Asn
        180                 185                 190
Val Gln Ser Gly Gly Asn Phe Thr Pro Trp Gln Thr Val Ser Phe Pro
    195                 200                 205
Gly Ala Tyr Gln Ala Asn His Pro Gly Ile Gln Val Asn Ile Tyr Gly
210                 215                 220
Ala Met Gly Gln Pro Asp Asn Gly Gly Arg Pro Tyr Gln Ile Pro Gly
225                 230                 235                 240
Pro Glu Pro Ile Gln Cys
            245

<210> SEQ ID NO 103
<211> LENGTH: 1067
<212> TYPE: DNA
<213> ORGANISM: Humicola insolens

<400> SEQUENCE: 103

```
atgggaccga cctgggcagt gattctgggg ctgattgctc cttctgtgct cagtcacagt    60
tgcgtctccc aacagacctc tcgactttta tcaagctggt actgactcat aacccaactc   120
acctagatat ccatgggatc ctcctggtca atggcacaga gaccccagag tggaaatacg   180
tcctgtatgt ttcctcatat cctagccca ttgtacgagt tgttgacgtg atacagcgat    240
gttgcgccgg cggttccaat ttcaaaccca gactctctcc ccctggata ccaaggctat    300
aaggttgatc ccatcatcgg atccgggaac cccaacatca cttgtggccg gctagcattt   360
gactcggcac ccaagacgca aatcgccgat gtgctagccg gctccgaggt aggattccga   420
gtctcggctg atggcttggg aaatcgggat ctggagaagg ctacatccc gacgttctgg    480
cacccaggtc cggcccaggc atacttgtca cgtgccccga cgacgacct gtacagctac    540
aaaggcgacg gggactggtt caagattgcc tacgctggcc cggtggacga cctgacgtgg   600
tccctttggc cgggagtttc agatgtatgt tcatcctcca tagtcctgtt tttgccctct   660
ccaggaccaa attattaata tcgagtcgca gttcaacttc accattccgt tgtcgacacc   720
ccctggcaag tatttgctcc gaatcgagaa cttcatgcca acggcctcga caggatatct   780
tcagttctac gtcaattgtg catttgtcaa catcattgga ccaggaggtg ggaccccgac   840
cgagttcatt cgaattcccg gggattacac cgacgaggat ccaggtgagt ttgtgttatg   900
agacatgttc aactcgcacc gacgaatgct tgtttcctga cagagatttg taaaaactag   960
gctttctcgt tcccccggag caaagctcct tggatggcag agtcccaagg gaccagttga  1020
aactgatgag ctacacgcca ccaggtcctg cggtgtggac ggggtga              1067
```

<210> SEQ ID NO 104
<211> LENGTH: 265
<212> TYPE: PRT
<213> ORGANISM: Humicola insolens

<400> SEQUENCE: 104

Met Gly Pro Thr Trp Ala Val Ile Leu Gly Leu Ile Ala Pro Ser Val
1               5                   10                  15
Leu Asn Ile His Gly Ile Leu Leu Val Asn Gly Thr Glu Thr Pro Glu
            20                  25                  30
Trp Lys Tyr Val Leu Asp Val Ala Pro Ala Val Pro Ile Ser Asn Pro
        35                  40                  45

Asp Ser Leu Pro Pro Gly Tyr Gln Gly Tyr Lys Val Asp Pro Ile Ile
 50                  55                  60

Gly Ser Gly Asn Pro Asn Ile Thr Cys Gly Arg Leu Ala Phe Asp Ser
 65                  70                  75                  80

Ala Pro Lys Thr Gln Ile Ala Asp Val Leu Ala Gly Ser Glu Val Gly
                 85                  90                  95

Phe Arg Val Ser Ala Asp Gly Leu Gly Asn Arg Asp Leu Glu Lys Gly
            100                 105                 110

Tyr Ile Pro Thr Phe Trp His Pro Gly Pro Ala Gln Ala Tyr Leu Ser
        115                 120                 125

Arg Ala Pro Asn Asp Asp Leu Tyr Ser Tyr Lys Gly Asp Gly Asp Trp
130                 135                 140

Phe Lys Ile Ala Tyr Ala Gly Pro Val Asp Asp Leu Thr Trp Ser Leu
145                 150                 155                 160

Trp Pro Gly Val Ser Asp Phe Asn Phe Thr Ile Pro Leu Ser Thr Pro
                165                 170                 175

Pro Gly Lys Tyr Leu Leu Arg Ile Glu Asn Phe Met Pro Thr Ala Ser
            180                 185                 190

Thr Gly Tyr Leu Gln Phe Tyr Val Asn Cys Ala Phe Val Asn Ile Ile
        195                 200                 205

Gly Pro Gly Gly Gly Thr Pro Thr Glu Phe Ile Arg Ile Pro Gly Asp
    210                 215                 220

Tyr Thr Asp Glu Asp Pro Gly Phe Leu Val Pro Glu Gln Ser Ser
225                 230                 235                 240

Leu Asp Gly Arg Val Pro Arg Asp Gln Leu Lys Leu Met Ser Tyr Thr
                245                 250                 255

Pro Pro Gly Pro Ala Val Trp Thr Gly
            260                 265

<210> SEQ ID NO 105
<211> LENGTH: 1035
<212> TYPE: DNA
<213> ORGANISM: Humicola insolens

<400> SEQUENCE: 105
atgaaggccc tcaccctcct cgccgccgcg accgcggcct cggcgcacac catcttcgtg      60
cagctcgagg ccgacggcac gcgctacccc gtctcgcacg gcgtgcgcac cccgcagtac     120
gacggcccca tcaccgacgt ctcgtccaac gacctggcct gcaacggcgg gcccaacccg     180
accatgaaga cggacaagat catcaccgtg acggcgggca gcaccgtcaa ggccatctgg     240
cggcacacgc tgcagtcggg ccccaacgac gtcatggacc cagccacaa gggcccgacg      300 ctggcgtacc tgaagaaggt ggacaacgcg ctgacggatt cgggcgtggg cggcggctgg     360
ttcaagatcc aggaggacgg gcacagcaat gggaattggg gcacgctcaa ggtaatcaac     420
aaccagggca ttcactatat cgatatcccc gactgcatcg acagcgggca gtatttgttg     480
cgggccgaga tgatcgctct gcacgctgcc gggtcgccgg gcgtgcgca gctttatgtg      540 agtttcttcc ttcttttctt cttctctccc tttgtgataa gaataaagat ccacaccaca     600
gtcaaaccaa agcatcctaa cctcggcatc tactcacaga tggaatgcgc ccaaatcgaa     660
atcgtcggcg gcaagggcac cgtcaagccc cagacctact ccatcccggg catctacaag     720
tccaacgacc cgggcatcct catcaacatc tactccatgt cgccctcgag ccagtacatc     780
atccccggcc cgcccctctt cacctgcaac ggcggcggcg cagcaacaa cggcggcggc       840 aacaacggcg gcagcaaccc cccgtccag cagccccccg ccaccaccct caccaccgcc      900

```
atcgcccagc ccacgcccat ctgctccgtc cagcagtggg gtcagtgcgg cggccagggc    960
tatagcggct gcaccacctg cgcgtcgccg tataggtgta acgagatcaa cgcgtggtat   1020
tcgcagtgct tgtaa                                                    1035
```

<210> SEQ ID NO 106
<211> LENGTH: 310
<212> TYPE: PRT
<213> ORGANISM: Humicola insolens

<400> SEQUENCE: 106

```
Met Lys Ala Leu Thr Leu Leu Ala Ala Thr Ala Ala Ser Ala His
1               5                   10                  15

Thr Ile Phe Val Gln Leu Glu Ala Asp Gly Thr Arg Tyr Pro Val Ser
            20                  25                  30

His Gly Val Arg Thr Pro Gln Tyr Asp Gly Pro Ile Thr Asp Val Ser
        35                  40                  45

Ser Asn Asp Leu Ala Cys Asn Gly Gly Pro Asn Pro Thr Met Lys Thr
    50                  55                  60

Asp Lys Ile Ile Thr Val Thr Ala Gly Ser Thr Val Lys Ala Ile Trp
65                  70                  75                  80

Arg His Thr Leu Gln Ser Gly Pro Asn Asp Val Met Asp Pro Ser His
                85                  90                  95

Lys Gly Pro Thr Leu Ala Tyr Leu Lys Val Asp Asn Ala Leu Thr
            100                 105                 110

Asp Ser Gly Val Gly Gly Gly Trp Phe Lys Ile Gln Glu Asp Gly His
        115                 120                 125

Ser Asn Gly Asn Trp Gly Thr Leu Lys Val Ile Asn Asn Gln Gly Ile
    130                 135                 140

His Tyr Ile Asp Ile Pro Asp Cys Ile Asp Ser Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Glu Ile Val Gly Gly Lys Gly
            180                 185                 190

Thr Val Lys Pro Gln Thr Tyr Ser Ile Pro Gly Ile Tyr Lys Ser Asn
        195                 200                 205

Asp Pro Gly Ile Leu Ile Asn Ile Tyr Ser Met Ser Pro Ser Ser Gln
    210                 215                 220

Tyr Ile Ile Pro Gly Pro Pro Leu Phe Thr Cys Asn Gly Gly Gly Gly
225                 230                 235                 240

Ser Asn Asn Gly Gly Gly Asn Gly Gly Ser Asn Pro Val Gln
                245                 250                 255

Gln Pro Pro Ala Thr Thr Leu Thr Thr Ala Ile Ala Gln Pro Thr Pro
            260                 265                 270

Ile Cys Ser Val Gln Gln Trp Gly Gln Cys Gly Gly Gln Gly Tyr Ser
        275                 280                 285

Gly Cys Thr Thr Cys Ala Ser Pro Tyr Arg Cys Asn Glu Ile Asn Ala
    290                 295                 300

Trp Tyr Ser Gln Cys Leu
305                 310
```

<210> SEQ ID NO 107
<211> LENGTH: 1065
<212> TYPE: DNA

<213> ORGANISM: Humicola insolens

<400> SEQUENCE: 107

```
atggctccca agacctcgac gttccttgcc tccctcacgg gcgccgccct cgtggctgcc      60
cacggccatg tcagccacat cattgtcaat ggcgtccagt accggaacta cgaccccacc     120
accgacttct acagcggcaa ccctccgacc gtgatcggct ggtcggccct caaccaggac     180
aacggcttca tcgagcccaa caacttcggc acccccgaca tcatctgcca taagtcggcc     240
aagcccggcg gcggccacgt cacggtgagg gccggtgaca agatcagcat cgtctggacc     300
cccgagtggc ccgagtcgca cgtcggcccc gtcatcgact accttgccgc gtgcaacggc     360
gactgcgaga cggtcgacaa gacctccctc cgcttcttca agatcgacgg cgccggctac     420
gacgccgcgg ccggccgctg ggccgccgac gctctgcgcg ccaacggcaa ctcgtggctt     480
gtgcagatcc ccgccgacct caaggccggc aactacgtgc tccggcacga gatcatcgcc     540
ctgcacggcg ccgccaaccc caacggcgcc caggcctacc gcagtgcat caacatccgc      600
gtcaccggcg gcggcaacaa ccagccctcg ggcgtccccg caccccagct ctacaaggcc     660
tcggacccgg gcatcctctt caaccccctgg gtcgccaacc ctcagtaccc cgtcccgggc    720
ccggccctca tccccggcgc cgtgagctcc atccctcaga gccgctcgac cgccaccgcc    780
acgggcaccg ccacccgccc cggcgccgac acggacccga cgggcgtccc tcccgtcgtc    840
accaccactt ctgccccggc tcaggtgacc accaccacca gcagccgcac cacctccctc    900
cctcagatca ccaccacctt cgcgaccagc accaccccgc cgcccccggc cgctacccag    960
agcaagtggg gccagtgcgg cggcaacggc tggaccggcc cgaccgtctg cgcgccgggc    1020
tcgagctgca acaagctcaa cgactggtac tcgcagtgca tctaa                    1065
```

<210> SEQ ID NO 108
<211> LENGTH: 354
<212> TYPE: PRT
<213> ORGANISM: Humicola insolens

<400> SEQUENCE: 108

```
Met Ala Pro Lys Thr Ser Thr Phe Leu Ala Ser Leu Thr Gly Ala Ala
1               5                  10                  15

Leu Val Ala Ala His Gly His Val Ser His Ile Ile Val Asn Gly Val
                20                  25                  30

Gln Tyr Arg Asn Tyr Asp Pro Thr Thr Asp Phe Tyr Ser Gly Asn Pro
            35                  40                  45

Pro Thr Val Ile Gly Trp Ser Ala Leu Asn Gln Asp Asn Gly Phe Ile
        50                  55                  60

Glu Pro Asn Asn Phe Gly Thr Pro Asp Ile Ile Cys His Lys Ser Ala
65                  70                  75                  80

Lys Pro Gly Gly Gly His Val Thr Val Arg Ala Gly Asp Lys Ile Ser
                85                  90                  95

Ile Val Trp Thr Pro Glu Trp Pro Glu Ser His Val Gly Pro Val Ile
                100                 105                 110

Asp Tyr Leu Ala Ala Cys Asn Gly Asp Cys Glu Thr Val Asp Lys Thr
            115                 120                 125

Ser Leu Arg Phe Phe Lys Ile Asp Gly Ala Gly Tyr Asp Ala Ala Ala
        130                 135                 140

Gly Arg Trp Ala Ala Asp Ala Leu Arg Ala Asn Gly Asn Ser Trp Leu
145                 150                 155                 160

Val Gln Ile Pro Ala Asp Leu Lys Ala Gly Asn Tyr Val Leu Arg His
```

```
                165                 170                 175
Glu Ile Ile Ala Leu His Gly Ala Ala Asn Pro Asn Gly Ala Gln Ala
            180                 185                 190
Tyr Pro Gln Cys Ile Asn Ile Arg Val Thr Gly Gly Asn Asn Gln
        195                 200                 205
Pro Ser Gly Val Pro Gly Thr Gln Leu Tyr Lys Ala Ser Asp Pro Gly
        210                 215                 220
Ile Leu Phe Asn Pro Trp Val Ala Asn Pro Gln Tyr Pro Val Pro Gly
225                 230                 235                 240
Pro Ala Leu Ile Pro Gly Ala Val Ser Ser Ile Pro Gln Ser Arg Ser
            245                 250                 255
Thr Ala Thr Ala Thr Gly Thr Ala Thr Arg Pro Gly Ala Asp Thr Asp
            260                 265                 270
Pro Thr Gly Val Pro Pro Val Val Thr Thr Ser Ala Pro Ala Gln
        275                 280                 285
Val Thr Thr Thr Thr Ser Ser Arg Thr Thr Ser Leu Pro Gln Ile Thr
            290                 295                 300
Thr Thr Phe Ala Thr Ser Thr Thr Pro Pro Pro Ala Ala Thr Gln
305                 310                 315                 320
Ser Lys Trp Gly Gln Cys Gly Gly Asn Gly Trp Thr Gly Pro Thr Val
            325                 330                 335
Cys Ala Pro Gly Ser Ser Cys Asn Lys Leu Asn Asp Trp Tyr Ser Gln
            340                 345                 350
Cys Ile

<210> SEQ ID NO 109
<211> LENGTH: 804
<212> TYPE: DNA
<213> ORGANISM: Humicola insolens

<400> SEQUENCE: 109
atgtatcttt tacctatcgc cgcggccgcc ctagcgttca ccaccaccgc atacgcccac        60
gcccaagtct acggcttgcg tgtcaacgac caacaccaag gcgatgggcg caacaaatac       120
atccgctcgc ccagcagcaa ttcccccatc cggtgggacc acgtaaccca cccattcctc       180
atctgcaaca tccgcgacga caaccaaccc ccgggtcccg cgcctgactt tgtccgcgcc       240
ttcgccggcg accgcgtggc gttccaatgg taccacgccc gccccaacga cccgacggat       300
tacgtcctcg acagctccca cctcggcgtc ctcgttacct ggatcgcgcc gtacacggac       360
gggcccggga ccggccccat ttggaccaag atccaccagg acgggtggaa cggcacgcac       420
tgggccacga gccggctcat cagcaacggc gggttcgtcg agttccggct gcccggctcg       480
ctaaagcccg ggaagtacct ggtgcggcag gagattatcg ctctgcacca ggccgacatg       540
cccggtccga accgcgggcc tgagttctac cccagctgcg cgcaattgga ggttttgggg       600
tctggtgagg cggcgccgcc gcaggggtat gatatcaaca aggggtatgc ggagagcggg       660
gataagttgt ggttcaacat ttacatcaac aagaatgatg agttcaaaat gcctggaccg       720
gaggtttggg atggtgggtg tcggtttgga gagcgatggg caaccgagga accaggcaag       780
cccaaggtga accaacacgg ataa                                              804

<210> SEQ ID NO 110
<211> LENGTH: 267
<212> TYPE: PRT
<213> ORGANISM: Humicola insolens
```

<400> SEQUENCE: 110

Met Tyr Leu Leu Pro Ile Ala Ala Ala Leu Ala Phe Thr Thr Thr
1               5                   10                  15

Ala Tyr Ala His Ala Gln Val Tyr Gly Leu Arg Val Asn Asp Gln His
            20                  25                  30

Gln Gly Asp Gly Arg Asn Lys Tyr Ile Arg Ser Pro Ser Ser Asn Ser
        35                  40                  45

Pro Ile Arg Trp Asp His Val Thr His Pro Phe Leu Ile Cys Asn Ile
    50                  55                  60

Arg Asp Asp Asn Gln Pro Pro Gly Pro Ala Pro Asp Phe Val Arg Ala
65                  70                  75                  80

Phe Ala Gly Asp Arg Val Ala Phe Gln Trp Tyr His Ala Arg Pro Asn
                85                  90                  95

Asp Pro Thr Asp Tyr Val Leu Asp Ser Ser His Leu Gly Val Leu Val
            100                 105                 110

Thr Trp Ile Ala Pro Tyr Thr Asp Gly Pro Gly Thr Gly Pro Ile Trp
        115                 120                 125

Thr Lys Ile His Gln Asp Gly Trp Asn Gly Thr His Trp Ala Thr Ser
    130                 135                 140

Arg Leu Ile Ser Asn Gly Gly Phe Val Glu Phe Arg Leu Pro Gly Ser
145                 150                 155                 160

Leu Lys Pro Gly Lys Tyr Leu Val Arg Gln Glu Ile Ile Ala Leu His
                165                 170                 175

Gln Ala Asp Met Pro Gly Pro Asn Arg Gly Pro Glu Phe Tyr Pro Ser
            180                 185                 190

Cys Ala Gln Leu Glu Val Phe Gly Ser Gly Glu Ala Ala Pro Pro Gln
        195                 200                 205

Gly Tyr Asp Ile Asn Lys Gly Tyr Ala Glu Ser Gly Asp Lys Leu Trp
    210                 215                 220

Phe Asn Ile Tyr Ile Asn Lys Asn Asp Glu Phe Lys Met Pro Gly Pro
225                 230                 235                 240

Glu Val Trp Asp Gly Gly Cys Arg Phe Gly Glu Arg Trp Ala Thr Glu
                245                 250                 255

Glu Pro Gly Lys Pro Lys Val Asn Gln His Gly
            260                 265

<210> SEQ ID NO 111
<211> LENGTH: 843
<212> TYPE: DNA
<213> ORGANISM: Humicola insolens

<400> SEQUENCE: 111
atgaagctcc tcgctcctct gatgctggct ggcgccgcca cgcccgtga gtaaccctg      60 gctggatctc atgctggtgc cagtgttcca tgactgacaa ccaccctcag acaccatctt    120
cacctccctc gaggttgatg ccgcaactac ggcacgggc aacggcgtcc gcgtcccctc    180
ctacaacggc cccgtcgagg atgtcacgtc caactcgatc gcctgcaacg gcccgccgaa    240
cccgaccagc ccgaccgaca cggtcatcac cgtccaggct ggccagaacg tgactgccat    300
ctggcggtac atgctcaaca cccagggcac ctcgcccaac gacatcatgg acagcagcca    360
caagggtcct actctcgcct acctcaagaa ggtcaacgat gcccggactg actcgggcgt    420
cggcgatggc tggttcaaga tccagcacga cggcttcgac ggcaccacct ggggcaccga    480
gcgcgtcatc ttcggccagg gccgtcacac catcaagatc cccgagtgca tcgagcccgg    540

```
ccagtacctg ctgcgtgctg agatgatcgc cctccacggc gcccagaact acccgggtgc    600
tcagttctac atggagtgcg cccagctcaa cattgtcggt ggcaccggca ccaagaaacc    660
cagcaccgtc agcttccctg gcgcttacaa ggtatgtccg agtttggtac cgagataact    720
ggagatgaga aaagtgatgc taacaaacca tgacagggca ccgacccgg cgtcaagctc    780 agcatctggt ggccgcccgt caccaactac gtcattcccg gccccgatgt cttcaagtgc    840
taa                                                                  843
```

```
<210> SEQ ID NO 112
<211> LENGTH: 237
<212> TYPE: PRT
<213> ORGANISM: Humicola insolens

<400> SEQUENCE: 112

Met Lys Leu Leu Ala Pro Leu Met Leu Ala Gly Ala Ala Ser Ala His
1               5                   10                  15

Thr Ile Phe Thr Ser Leu Glu Val Asp Gly Arg Asn Tyr Gly Thr Gly
            20                  25                  30

Asn Gly Val Arg Val Pro Ser Tyr Asn Gly Pro Val Glu Asp Val Thr
        35                  40                  45

Ser Asn Ser Ile Ala Cys Asn Gly Pro Pro Asn Pro Thr Ser Pro Thr
    50                  55                  60

Asp Thr Val Ile Thr Val Gln Ala Gly Gln Asn Val Thr Ala Ile Trp
65                  70                  75                  80

Arg Tyr Met Leu Asn Thr Gln Gly Thr Ser Pro Asn Asp Ile Met Asp
                85                  90                  95

Ser Ser His Lys Gly Pro Thr Leu Ala Tyr Leu Lys Lys Val Asn Asp
            100                 105                 110

Ala Arg Thr Asp Ser Gly Val Gly Asp Gly Trp Phe Lys Ile Gln His
        115                 120                 125

Asp Gly Phe Asp Gly Thr Thr Trp Gly Thr Glu Arg Val Ile Phe Gly
    130                 135                 140

Gln Gly Arg His Thr Ile Lys Ile Pro Glu Cys Ile Glu Pro Gly Gln
145                 150                 155                 160

Tyr Leu Leu Arg Ala Glu Met Ile Ala Leu His Gly Ala Gln Asn Tyr
                165                 170                 175

Pro Gly Ala Gln Phe Tyr Met Glu Cys Ala Gln Leu Asn Ile Val Gly
            180                 185                 190

Gly Thr Gly Thr Lys Lys Pro Ser Thr Val Ser Phe Pro Gly Ala Tyr
        195                 200                 205

Lys Gly Thr Asp Pro Gly Val Lys Leu Ser Ile Trp Trp Pro Pro Val
    210                 215                 220

Thr Asn Tyr Val Ile Pro Gly Pro Asp Val Phe Lys Cys
225                 230                 235
```

```
<210> SEQ ID NO 113
<211> LENGTH: 705
<212> TYPE: DNA
<213> ORGANISM: Humicola insolens

<400> SEQUENCE: 113
atgaagctcc tctcaaccct cgccgccatt gcggccacct tggccacggc ggatgcgcac     60
tacatcttca acatcctgta cgtcaacggc cagcgcatgg gcggcgagta cacctacgtg    120
cggcgcaact ccaactcgta cttccccgtg ttccccgaca tcctcaactc caacgacatg    180
```

```
cgttgcaacg tgggtgccag accgggcaac acccaaaccg ccaccgtcag ggccggcgac    240
aggatcggct tcaaggtctt caacaacgag gtcatcgagc accctggtcc cggcttcatc    300
tacatgtcca agccccgggg cagcgtcaac aactatgacg gcagcgggga ctggttcaag    360
gtttacgaga ccggtctctg ccgcggtggt ggcaacgtcg acaccaactg gtgctcgtac    420
tacaaggacc ggctcgagtt taccatcccg cccaagactc ctcccggcga gtatctggtg    480
cgtatcgagc atatcggtct gcacgagggc cacgtcaaca gggcgcagtt ctacatcacc    540
tgcgcgcagc tcaagattga ggggcccggc ggcggcaacc cgaacccact cgtgaagatc    600
ccgggcatct acagggccaa cgaccccggc atcgcctaca acaagtggac caacaacccg    660
gcgccgtaca tcatgccggg tcccaaggtg tgggatggca actaa                    705
```

<210> SEQ ID NO 114
<211> LENGTH: 234
<212> TYPE: PRT
<213> ORGANISM: Humicola insolens

<400> SEQUENCE: 114

```
Met Lys Leu Leu Ser Thr Leu Ala Ala Ile Ala Ala Thr Leu Ala Thr
1               5                   10                  15

Ala Asp Ala His Tyr Ile Phe Asn Ile Leu Tyr Val Asn Gly Gln Arg
                20                  25                  30

Met Gly Gly Glu Tyr Thr Tyr Val Arg Arg Asn Ser Asn Ser Tyr Phe
            35                  40                  45

Pro Val Phe Pro Asp Ile Leu Asn Ser Asn Asp Met Arg Cys Asn Val
        50                  55                  60

Gly Ala Arg Pro Gly Asn Thr Gln Thr Ala Thr Val Arg Ala Gly Asp
65                  70                  75                  80

Arg Ile Gly Phe Lys Val Phe Asn Asn Glu Val Ile Glu His Pro Gly
                85                  90                  95

Pro Gly Phe Ile Tyr Met Ser Lys Ala Pro Gly Ser Val Asn Asn Tyr
            100                 105                 110

Asp Gly Ser Gly Asp Trp Phe Lys Val Tyr Glu Thr Gly Leu Cys Arg
        115                 120                 125

Gly Gly Gly Asn Val Asp Thr Asn Trp Cys Ser Tyr Tyr Lys Asp Arg
130                 135                 140

Leu Glu Phe Thr Ile Pro Pro Lys Thr Pro Pro Gly Glu Tyr Leu Val
145                 150                 155                 160

Arg Ile Glu His Ile Gly Leu His Glu Gly His Val Asn Arg Ala Gln
                165                 170                 175

Phe Tyr Ile Thr Cys Ala Gln Leu Lys Ile Glu Gly Pro Gly Gly Gly
            180                 185                 190

Asn Pro Asn Pro Leu Val Lys Ile Pro Gly Ile Tyr Arg Ala Asn Asp
        195                 200                 205

Pro Gly Ile Ala Tyr Asn Lys Trp Thr Asn Asn Pro Ala Pro Tyr Ile
    210                 215                 220

Met Pro Gly Pro Lys Val Trp Asp Gly Asn
225                 230
```

<210> SEQ ID NO 115
<211> LENGTH: 753
<212> TYPE: DNA
<213> ORGANISM: Humicola insolens

<400> SEQUENCE: 115

```
atgctgggaa gcgctcttct gctcctgggc actgccctgg gcgccaccgc ccactacacg    60
ttccctagga tcaacagcgg cggcgactgg cagtatgtcc gccgggccga caactggcag   120
gacaacggct tcgttggcaa cgtcaactcg cctcagatcc ggtgcttcca gagcaggcac   180
caggccgccc cggccaccct caacgtcacc gccggctcca cggtgaccta ctacgccaat   240
cccaacgtct atcaccccgg cccgatggcc ttctacatgg cccgcgtccc cgatggccag   300
gatatcaact cgtggaccgg cgagggtgcc gtgtggttca agatctacca cgagcagcct   360
accggcctgg gccagcagct gaggtggtct agcgatggta cgtgaatggt gatcctgtgg   420
catctcaacc tcttccagac ttctgacccg agccccgcg gccctacagg caagaactcg   480
ttccaggttc agatccccg ctgcatccgc tctggctact acctgctccg tgctgagcac   540
atcggcttgc acagcgccgg cagccctggt ggcgctcagt tctacatctc ttgcgcccag   600
ctcgccgtca acggcggtgg cagcaccgag ccccccaaca aggtgtcctt ccctggtgcc   660
tacagcccgt ccgaccccgg cattcagatc aacatctact ggcctgttcc gacctcgtac   720
aagaaccccg gccccccggt cttccagtgc taa                                753
```

<210> SEQ ID NO 116
<211> LENGTH: 226
<212> TYPE: PRT
<213> ORGANISM: Humicola insolens

<400> SEQUENCE: 116

```
Met Leu Gly Ser Ala Leu Leu Leu Gly Thr Ala Leu Gly Ala Thr
1               5                   10                  15

Ala His Tyr Thr Phe Pro Arg Ile Asn Ser Gly Gly Asp Trp Gln Tyr
                20                  25                  30

Val Arg Arg Ala Asp Asn Trp Gln Asp Asn Gly Phe Val Gly Asn Val
            35                  40                  45

Asn Ser Pro Gln Ile Arg Cys Phe Gln Ser Arg His Gln Ala Ala Pro
50                  55                  60

Ala Thr Leu Asn Val Thr Ala Gly Ser Thr Val Thr Tyr Tyr Ala Asn
65                  70                  75                  80

Pro Asn Val Tyr His Pro Gly Pro Met Ala Phe Tyr Met Ala Arg Val
                85                  90                  95

Pro Asp Gly Gln Asp Ile Asn Ser Trp Thr Gly Glu Gly Ala Val Trp
            100                 105                 110

Phe Lys Ile Tyr His Glu Gln Pro Thr Gly Leu Gly Gln Gln Leu Arg
        115                 120                 125

Trp Ser Ser Asp Gly Lys Asn Ser Phe Gln Val Gln Ile Pro Arg Cys
130                 135                 140

Ile Arg Ser Gly Tyr Tyr Leu Leu Arg Ala Glu His Ile Gly Leu His
145                 150                 155                 160

Ser Ala Gly Ser Pro Gly Gly Ala Gln Phe Tyr Ile Ser Cys Ala Gln
                165                 170                 175

Leu Ala Val Asn Gly Gly Gly Ser Thr Glu Pro Asn Lys Val Ser
            180                 185                 190

Phe Pro Gly Ala Tyr Ser Pro Ser Asp Pro Gly Ile Gln Ile Asn Ile
        195                 200                 205

Tyr Trp Pro Val Pro Thr Ser Tyr Lys Asn Pro Gly Pro Pro Val Phe
    210                 215                 220

Gln Cys
225
```

<210> SEQ ID NO 117
<211> LENGTH: 854
<212> TYPE: DNA
<213> ORGANISM: Humicola insolens

<400> SEQUENCE: 117

```
atgaagctgc ttcctgggtt gcttctggca gccacggctg cccaagccca ttgtacgttt      60
ccgatcccca agaccatctt cgagaatttt cgagccagat ctttctgaga gagttgctga    120
caattcctgc tagacacatt ccccaggctc gttgtcaacg gcagcctga ggagagggac      180
tggtcggtca ctcggatgac aaagaaccac cagagcaagt cgggaattga aacccaact    240
agcccccgaca tccgttgcta cagctcgcag actgcccctca acgtggcgat gtgccggcc    300
gggtctacca tccactacat ctcgacccaa caaatcaacc atcctggccc gactcagtac    360
tatctcgcca aggtcccagc tggtcagtca gccaagacct gggatggctc tggcaacgtg    420
tggttcaaga tcgccacgag catgccggag tacgatcaaa acaggcagct ggtttggccc    480
ggtcatagta aggactcact ctcgtccgat catctctttt gagtgagtct tgggcatacc    540
cactgactac gtctgctatg acagatacct atcagaccat caacgccacc atcccggcca    600
acacgccgag cggagagtac ctcctgcgtg tcgagcaaat tgcccctccac atggccagcc    660
agccgaacaa ggcccagttc tacatctcgt gctctcagat tcagattacc aatggcggaa    720
acggcactcc gggccctcta gttgcattcc cgggggcata caggagcaac gaccctggca    780
tcctggtcaa tctctacagc ggcatgcagc cttcgcagta ccagccccct ggaccggccg    840
tgtggcgtgg ctga                                                        854
```

<210> SEQ ID NO 118
<211> LENGTH: 231
<212> TYPE: PRT
<213> ORGANISM: Humicola insolens

<400> SEQUENCE: 118

Met Lys Leu Leu Pro Gly Leu Leu Leu Ala Ala Thr Ala Ala Gln Ala
1               5                   10                  15

His Tyr Thr Phe Pro Arg Leu Val Val Asn Gly Gln Pro Glu Glu Arg
            20                  25                  30

Asp Trp Ser Val Thr Arg Met Thr Lys Asn His Gln Ser Lys Ser Gly
        35                  40                  45

Ile Glu Asn Pro Thr Ser Pro Asp Ile Arg Cys Tyr Ser Ser Gln Thr
    50                  55                  60

Ala Pro Asn Val Ala Ile Val Pro Ala Gly Ser Thr Ile His Tyr Ile
65                  70                  75                  80

Ser Thr Gln Gln Ile Asn His Pro Gly Pro Thr Gln Tyr Tyr Leu Ala
            85                  90                  95

Lys Val Pro Ala Gly Gln Ser Ala Lys Thr Trp Asp Gly Ser Gly Asn
            100                 105                 110

Val Trp Phe Lys Ile Ala Thr Ser Met Pro Glu Tyr Asp Gln Asn Arg
        115                 120                 125

Gln Leu Val Trp Pro Gly His Asn Thr Tyr Gln Thr Ile Asn Ala Thr
    130                 135                 140

Ile Pro Ala Asn Thr Pro Ser Gly Glu Tyr Leu Leu Arg Val Glu Gln
145                 150                 155                 160

Ile Ala Leu His Met Ala Ser Gln Pro Asn Lys Ala Gln Phe Tyr Ile
                165                 170                 175

Ser Cys Ser Gln Ile Gln Ile Thr Asn Gly Gly Asn Gly Thr Pro Gly
            180                 185                 190

Pro Leu Val Ala Phe Pro Gly Ala Tyr Arg Ser Asn Asp Pro Gly Ile
        195                 200                 205

Leu Val Asn Leu Tyr Ser Gly Met Gln Pro Ser Gln Tyr Gln Pro Pro
    210                 215                 220

Gly Pro Ala Val Trp Arg Gly
225                 230

<210> SEQ ID NO 119
<211> LENGTH: 863
<212> TYPE: DNA
<213> ORGANISM: Humicola insolens

<400> SEQUENCE: 119
atgctcctga actcggtcat cggctcggcc gtcctcctgg ccaccggcgc cgccgcccac      60
ggtgccgtga ccagctacgt cattgccggg aagaactacc ctgggtaggt aacctcgtgg     120
aagcgaatgc aggcagttca ttcactaaca catacctccg ttagctacaa cggctacgcc     180
ccgtccacca cccccaacac gatccagtgg caatggtcga cctacgaccc catctactcc     240
gccaccgacc caagctccg ctgcaacggc ggccgctcgg ccacgcagtc cgccccggct     300
gctccgggcg acaacatcac cgccatctgg cagcagtgga cgcatagcca gggccccatc     360
ctcgtctgga tgtacaagtg tcccggcgcc ttcagctcgt cgacggctc gggccagggc     420 tggttcaaga ttgacgaggc cggcttcaat ggcgacggca agaccgtgtt cctcgacacc     480
gagcgcccct ccggctggga gatcgccaag ctggttggcg gcaacaaggg ctggaccagc     540
accatcccca gaacctggc cccgggcaac tacctggtcc gccacgagtt gattgccctt     600
caccaggcca acgcccgca gtggtaccct gagtgcgcgc aggtcgtgat caccggctcg     660
ggcactaagg agccgcctgc gtcgtacaag gctgccattc ccggctactg caaccagaac     720
gatcccaaca ttcgggtatg tgaggcctat ttggagttcg gctaaggcat gatactaact     780 ctaccccca ggttcctatc aacgaccact ccatccccca gacctacaag atccctggcc     840
ctccggtctg gcgcggcgag taa                                            863

<210> SEQ ID NO 120
<211> LENGTH: 248
<212> TYPE: PRT
<213> ORGANISM: Humicola insolens

<400> SEQUENCE: 120

Met Leu Leu Asn Ser Val Ile Gly Ser Ala Val Leu Leu Ala Thr Gly
1               5                   10                  15

Ala Ala Ala His Gly Ala Val Thr Ser Tyr Val Ile Ala Gly Lys Asn
            20                  25                  30

Tyr Pro Gly Tyr Asn Gly Tyr Ala Pro Ser Thr Thr Pro Asn Thr Ile
        35                  40                  45

Gln Trp Gln Trp Ser Thr Tyr Asp Pro Ile Tyr Ser Ala Thr Asp Pro
    50                  55                  60

Lys Leu Arg Cys Asn Gly Gly Arg Ser Ala Thr Gln Ser Ala Pro Ala
65                  70                  75                  80

Ala Pro Gly Asp Asn Ile Thr Ala Ile Trp Gln Gln Trp Thr His Ser
            85                  90                  95

Gln Gly Pro Ile Leu Val Trp Met Tyr Lys Cys Pro Gly Ala Phe Ser
        100                 105                 110

```
Ser Cys Asp Gly Ser Gly Gln Gly Trp Phe Lys Ile Asp Glu Ala Gly
        115                 120                 125

Phe Asn Gly Asp Gly Lys Thr Val Phe Leu Asp Thr Glu Arg Pro Ser
    130                 135                 140

Gly Trp Glu Ile Ala Lys Leu Val Gly Gly Asn Lys Gly Trp Thr Ser
145                 150                 155                 160

Thr Ile Pro Lys Asn Leu Ala Pro Gly Asn Tyr Leu Val Arg His Glu
                165                 170                 175

Leu Ile Ala Leu His Gln Ala Asn Ala Pro Gln Trp Tyr Pro Glu Cys
            180                 185                 190

Ala Gln Val Val Ile Thr Gly Ser Gly Thr Lys Glu Pro Pro Ala Ser
        195                 200                 205

Tyr Lys Ala Ala Ile Pro Gly Tyr Cys Asn Gln Asn Asp Pro Asn Ile
    210                 215                 220

Arg Val Pro Ile Asn Asp His Ser Ile Pro Gln Thr Tyr Lys Ile Pro
225                 230                 235                 240

Gly Pro Pro Val Trp Arg Gly Glu
                245
```

```
<210> SEQ ID NO 121
<211> LENGTH: 883
<212> TYPE: DNA
<213> ORGANISM: Humicola insolens

<400> SEQUENCE: 121
atgaagctca ccacctccat cgccctgctg gctgcggccg gcgcgcaggc tcactgtacg      60
tgctccctca tctcatccat ctcctcagac catgttttac ctattggtta ctaacaagct     120
ctcacgcaga caccttcccc cgcaccaagg tcgacggcgt cacctcgggc gagtgggaga     180
cgatccgcat caccgagaac cactggtcgc acggccccgt gacggacgtg acctcgcagg     240
ccatgacgtg ctacgagaag acgcccggcc agggcgcgcc caagacggtt aacgtgaagg     300
ccggcggcac cgtcaccttc accgtcgaca cggacgtggg ccacccgggc ccgctgcact     360
tctacttggc caaggtgccc gcgggcaaga cggccgcgac gtttgacggc aagggcgccg     420
tgtggttcaa gatttaccag gacggccccg gcgggttggg gaccagctcg ttgacttggc     480
ctagctttgg tgagctttct tttctttatt ttcttcaatc ctcccataat tacctcccga     540
cgaggaaata aatataccttt acctgatatt aacccatccc ccccaccctc ctccaggcaa     600
gaaggaagtc tctgtccaaa tcccccctg cgtgcaggac ggcgagtacc tgctgcgcgt     660
cgagcacatt gcgctgcaca cgccgcgag cgtcggcggc gcgcagctct acatttcgtg     720
cgcgcaaatc aacgtcaccg gcggcaccgg cacgctcaac ccgggccagc tcgtctcgtt     780
cccgggcgcc tacaagccca ccgacccggg catcctgttc cagctctact ggccgccgcc     840
gacccagtac atcaaccccg gtccggcgcc ggtgaagtgc tga                       883
```

```
<210> SEQ ID NO 122
<211> LENGTH: 233
<212> TYPE: PRT
<213> ORGANISM: Humicola insolens

<400> SEQUENCE: 122

Met Lys Leu Thr Thr Ser Ile Ala Leu Leu Ala Ala Gly Ala Gln
1               5                   10                  15

Ala His Tyr Thr Phe Pro Arg Thr Lys Val Asp Gly Val Thr Ser Gly
                20                  25                  30
```

Glu Trp Glu Thr Ile Arg Ile Thr Glu Asn His Trp Ser His Gly Pro
         35                  40                  45

Val Thr Asp Val Thr Ser Gln Ala Met Thr Cys Tyr Glu Lys Thr Pro
 50                  55                  60

Gly Gln Gly Ala Pro Lys Thr Val Asn Val Lys Ala Gly Gly Thr Val
 65                  70                  75                  80

Thr Phe Thr Val Asp Thr Asp Val Gly His Pro Gly Pro Leu His Phe
                 85                  90                  95

Tyr Leu Ala Lys Val Pro Ala Gly Lys Thr Ala Ala Thr Phe Asp Gly
             100                 105                 110

Lys Gly Ala Val Trp Phe Lys Ile Tyr Gln Asp Gly Pro Gly Gly Leu
             115                 120                 125

Gly Thr Ser Ser Leu Thr Trp Pro Ser Phe Gly Lys Lys Glu Val Ser
130                 135                 140

Val Gln Ile Pro Pro Cys Val Gln Asp Gly Glu Tyr Leu Leu Arg Val
145                 150                 155                 160

Glu His Ile Ala Leu His Ser Ala Ala Ser Val Gly Gly Ala Gln Leu
                 165                 170                 175

Tyr Ile Ser Cys Ala Gln Ile Asn Val Thr Gly Gly Thr Gly Thr Leu
             180                 185                 190

Asn Pro Gly Gln Leu Val Ser Phe Pro Gly Ala Tyr Lys Pro Thr Asp
             195                 200                 205

Pro Gly Ile Leu Phe Gln Leu Tyr Trp Pro Pro Thr Gln Tyr Ile
             210                 215                 220

Asn Pro Gly Pro Ala Pro Val Lys Cys
225                 230

<210> SEQ ID NO 123
<211> LENGTH: 928
<212> TYPE: DNA
<213> ORGANISM: Humicola insolens

<400> SEQUENCE: 123
atgaagactc tcgcatccgc cctcattgcc gcgggccttc tggcccagta cgccgctgcc    60
catgccattt tccagtttgc cagcagcggt ggcactgact tgggacgtc ctgtgttagg    120
atgccggtga gtgaacgggt gccctgaac atgtgttgct cacgaaacaa ggttatgttg    180
actctataca gcccaacaac tctcccgtca cgagcgtcac cagcagtgac atggcttgca    240
atgttggcgg atctcgcggt gtatctggca tttgcgaggt gaacggtaag agttctcctc    300
agccttttct ctgtcaagca ctaaacagca ctcgctaacc atttcaatct cagccggctc    360
cgacttcacc gtcgagatgc acgcgcagcc caacgaccgg tcgtgcgcca gcgaagccat    420
tggcggcaac cacttcgggc ccgtcatggt gtacatggcc aaggtggacg acgcgacgcg    480
ggcggacggt gcgtcggcgt cttggttcaa ggtggacgag ttcggctacg acgccggctc    540
caagacatgg gaaccgaca tgctcaacaa gaactgcggc aagcggacgt ccgcatccc    600
gagcaaaatc ccgtctgggg actatctggt gcgtgcggag gctattgctt tgcacaccgc    660
gggccagccg tcgggtgcgc agtttttatat gagctgctat gtgagttctt ccatgcttcc    720
ccttgtggtg tcactgtata aagatgctaa atatctccca cagcaagttc gcatcaaggg    780
cagcaacaac ggtcagcttc cggctggtgt tcggattcct ggcgcctaca gcgcgacgga    840
cccgggcatc ctcgtcgata tctggggcaa tggtttcagc cagtacacta ttcctggccc    900
tcgtgtcatt gatgggagct tttctga                                       928

<210> SEQ ID NO 124
<211> LENGTH: 243
<212> TYPE: PRT
<213> ORGANISM: Humicola insolens

<400> SEQUENCE: 124

Met Lys Thr Leu Ala Ser Ala Leu Ile Ala Ala Gly Leu Leu Ala Gln
1               5                   10                  15

Tyr Ala Ala Ala His Ala Ile Phe Gln Phe Ala Ser Ser Gly Gly Thr
            20                  25                  30

Asp Phe Gly Thr Ser Cys Val Arg Met Pro Pro Asn Asn Ser Pro Val
        35                  40                  45

Thr Ser Val Thr Ser Ser Asp Met Ala Cys Asn Val Gly Gly Ser Arg
    50                  55                  60

Gly Val Ser Gly Ile Cys Glu Val Asn Ala Gly Ser Asp Phe Thr Val
65                  70                  75                  80

Glu Met His Ala Gln Pro Asn Asp Arg Ser Cys Ala Ser Glu Ala Ile
                85                  90                  95

Gly Gly Asn His Phe Gly Pro Val Met Val Tyr Met Ala Lys Val Asp
            100                 105                 110

Asp Ala Thr Arg Ala Asp Gly Ala Ser Ala Ser Trp Phe Lys Val Asp
        115                 120                 125

Glu Phe Gly Tyr Asp Ala Gly Ser Lys Thr Trp Gly Thr Asp Met Leu
    130                 135                 140

Asn Lys Asn Cys Gly Lys Arg Thr Phe Arg Ile Pro Ser Lys Ile Pro
145                 150                 155                 160

Ser Gly Asp Tyr Leu Val Arg Ala Glu Ala Ile Ala Leu His Thr Ala
                165                 170                 175

Gly Gln Pro Ser Gly Ala Gln Phe Tyr Met Ser Cys Tyr Gln Val Arg
            180                 185                 190

Ile Lys Gly Ser Asn Asn Gly Gln Leu Pro Ala Gly Val Arg Ile Pro
        195                 200                 205

Gly Ala Tyr Ser Ala Thr Asp Pro Gly Ile Leu Val Asp Ile Trp Gly
    210                 215                 220

Asn Gly Phe Ser Gln Tyr Thr Ile Pro Gly Pro Arg Val Ile Asp Gly
225                 230                 235                 240

Ser Phe Phe

<210> SEQ ID NO 125
<211> LENGTH: 1092
<212> TYPE: DNA
<213> ORGANISM: Humicola insolens

<400> SEQUENCE: 125
atgcctcgct tcaccaagtc cattgtctcg gccctggccg gcgcttccct ggtcgcagcc      60
cacggccatg tcacccacat cgtcatcaac ggcgtgctgt acccgaactt cgaccctaca     120
tcccaccctt acctgcagaa cccgccgacc gttgtgggct ggaccgccgc caacaccgac     180
aacggcttcg ttgctcccga ccagttcgcc tcgggcgata tcatctgcca caaccaggcc     240
accaacgcgg cgccacacgc cgtggtcgcg ccggcgaca agatttggat ccagtgggac     300
cagtggcctg agagccacca cggccccgtc ctcgactacc tcgcctcctg cggcagctcg     360
ggctgcgagt cggtcaacaa gctcgacctc gagttcttca agatcggcga aaagggcctg     420
atcgacggct cctccgcgcc gggccggtgg gcgtcggacg agctgatcgc caacaacgcc     480

-continued

```
ggctggctgg tccagatccc cgccgacatt gcgcccggcc actacgtcct gcgccacgaa    540
atcatcgccc tccacgccgc cggccagccc aacggcgccc agaactaccc gcagtgcttc    600
aacctcctcg tcacgggctc cggcaccgcg cggccgcagg gcgtcaaggg aacagcgctg    660
tacaccccca acgacaaggg catcttggcg ggcatctaca atgcccccgt ctcgtacgag    720
attcccggcc ccgcgctcta ctccggcgcc gccaggaact tgcagcagag ctcgtcccag    780
gccacgtcga ctgccacggc tttgactggg gacgcggtgc ctgttccgac ccaagccccc    840
gtcactacca cttcctcttc ttcggccgat gccgccaccg ccacctccac caccgtccag    900
ccgccccagc aaaccaccct cacgaccgcc atcgccacgt cgaccgctgc tgctgccccg    960
acgaccaccg ccggcagcgg aaacggtggc aaccggccct ccaacccg ctgccctggc      1020 ctggctgggc tcgggtttga caagcgccgt cgccagctcc gcgctgagga gggtgtgcag    1080
gtggttgctt ga                                                        1092
```

<210> SEQ ID NO 126
<211> LENGTH: 363
<212> TYPE: PRT
<213> ORGANISM: Humicola insolens

<400> SEQUENCE: 126

```
Met Pro Arg Phe Thr Lys Ser Ile Val Ser Ala Leu Ala Gly Ala Ser
1               5                   10                  15

Leu Val Ala Ala His Gly His Val Thr His Ile Val Ile Asn Gly Val
            20                  25                  30

Leu Tyr Pro Asn Phe Asp Pro Thr Ser His Pro Tyr Leu Gln Asn Pro
        35                  40                  45

Pro Thr Val Val Gly Trp Thr Ala Ala Asn Thr Asp Asn Gly Phe Val
    50                  55                  60

Ala Pro Asp Gln Phe Ala Ser Gly Asp Ile Ile Cys His Asn Gln Ala
65                  70                  75                  80

Thr Asn Ala Gly Gly His Ala Val Val Ala Ala Gly Asp Lys Ile Trp
                85                  90                  95

Ile Gln Trp Asp Gln Trp Pro Glu Ser His His Gly Pro Val Leu Asp
            100                 105                 110

Tyr Leu Ala Ser Cys Gly Ser Ser Gly Cys Glu Ser Val Asn Lys Leu
        115                 120                 125

Asp Leu Glu Phe Phe Lys Ile Gly Glu Lys Gly Leu Ile Asp Gly Ser
    130                 135                 140

Ser Ala Pro Gly Arg Trp Ala Ser Asp Glu Leu Ile Ala Asn Asn Ala
145                 150                 155                 160

Gly Trp Leu Val Gln Ile Pro Ala Asp Ile Ala Pro Gly His Tyr Val
                165                 170                 175

Leu Arg His Glu Ile Ile Ala Leu His Ala Ala Gly Gln Pro Asn Gly
            180                 185                 190

Ala Gln Asn Tyr Pro Gln Cys Phe Asn Leu Leu Val Thr Gly Ser Gly
        195                 200                 205

Thr Ala Arg Pro Gln Gly Val Lys Gly Thr Ala Leu Tyr Thr Pro Asn
    210                 215                 220

Asp Lys Gly Ile Leu Ala Gly Ile Tyr Asn Ala Pro Val Ser Tyr Glu
225                 230                 235                 240

Ile Pro Gly Pro Ala Leu Tyr Ser Gly Ala Ala Arg Asn Leu Gln Gln
                245                 250                 255

Ser Ser Ser Gln Ala Thr Ser Thr Ala Thr Ala Leu Thr Gly Asp Ala
```

```
                260              265                270
Val Pro Val Pro Thr Gln Ala Pro Val Thr Thr Thr Ser Ser Ser Ser
            275              280              285

Ala Asp Ala Ala Thr Ala Thr Ser Thr Thr Val Gln Pro Pro Gln Gln
            290              295              300

Thr Thr Leu Thr Thr Ala Ile Ala Thr Ser Thr Ala Ala Ala Ala Pro
305              310              315              320

Thr Thr Thr Ala Gly Ser Gly Asn Gly Gly Asn Arg Pro Phe Pro Thr
            325              330              335

Arg Cys Pro Gly Leu Ala Gly Leu Gly Phe Asp Lys Arg Arg Arg Gln
            340              345              350

Leu Arg Ala Glu Glu Gly Val Gln Val Val Ala
            355              360
```

```
<210> SEQ ID NO 127
<211> LENGTH: 1086
<212> TYPE: DNA
<213> ORGANISM: Humicola insolens

<400> SEQUENCE: 127
atgaagggac ttctcagcat cgccgccctt tccctggcgg ttggtgaggc ttcggcccac     60
tacatcttcc agcagctctc gacgggtggc accaagcacc ccatgtggaa gtacatccgc    120
cagcacacca actacaactc tcccgtcatc gacctcgact ccaacgacct ccgctgcaat    180
gtcggtgccc ggggtgctgg aactgagacc gttacggtcg ctgctggctc gagcctgacc    240
ttccacctcg acacccccgt ctaccaccag ggccctgtgt cggtgtaagt agaagttctc    300
agacgaacca ccaatgtcgg cagataattt ctaactccga tgtccagcta tatgtccaag    360
gctcccggct ccgtgtcgga ctatgacggc agcggcggct ggttcaagat tcaagactgg    420
ggcccgacct tcaccggcag cggcgccacc tggaagctgg atgactccta caccttcaac    480 atccctcgt gcattcccga cggcgagtac ctcgtccgca tccagtccct gggtatccac    540 aaccctggc cggcgggtat ccgcagttc tatatctcgt gcgctcaggt gcgcgtcacc    600
ggcggtggca acgcgaaccc gagcccgcag gtgtcgatcc caggtgcctt caaggagacc    660
gacccgggct acactgccaa cgtgagtttc catccatgct acatatccct tttacgctct    720
cgatcccatg actaaccccc ccctgaaaag atctacaaca acttccgcag ctacaccgtc    780
cccggcccgt ccgtcttcac ctgcagcggc aacagcggcg gcggctccaa ccccagcaac    840
cctaaccccc cgaccccgac gaccttcacc acccaggtga ccaccccgac cccggcgtct    900
ccgccctctt gcaccgtcgc gaagtggtac gtctgaaaaa aaatctcctc caggccggac    960
atgagaaaac taacatgaac gaaaaacagg ggccagtgcg gtggccaggg ctacagcggc   1020
tgcaccaact gcgaggccgg ctcgacctgc aggcagcaga acgcttacta ttctcagtgc   1080
atctaa                                                              1086
```

```
<210> SEQ ID NO 128
<211> LENGTH: 296
<212> TYPE: PRT
<213> ORGANISM: Humicola insolens

<400> SEQUENCE: 128

Met Lys Gly Leu Leu Ser Ile Ala Ala Leu Ser Leu Ala Val Gly Glu
1               5                  10                  15

Ala Ser Ala His Tyr Ile Phe Gln Gln Leu Ser Thr Gly Gly Thr Lys
            20                  25                  30
```

His Pro Met Trp Lys Tyr Ile Arg Gln His Thr Asn Tyr Asn Ser Pro
         35                  40                  45

Val Ile Asp Leu Asp Ser Asn Asp Leu Arg Cys Asn Val Gly Ala Arg
     50                  55                  60

Gly Ala Gly Thr Glu Thr Val Thr Val Ala Ala Gly Ser Ser Leu Thr
 65                  70                  75                  80

Phe His Leu Asp Thr Pro Val Tyr His Gln Gly Pro Val Ser Val Tyr
                 85                  90                  95

Met Ser Lys Ala Pro Gly Ser Val Ser Asp Tyr Asp Gly Ser Gly Gly
                100                 105                 110

Trp Phe Lys Ile Gln Asp Trp Gly Pro Thr Phe Thr Gly Ser Gly Ala
            115                 120                 125

Thr Trp Lys Leu Asp Asp Ser Tyr Thr Phe Asn Ile Pro Ser Cys Ile
130                 135                 140

Pro Asp Gly Glu Tyr Leu Val Arg Ile Gln Ser Leu Gly Ile His Asn
145                 150                 155                 160

Pro Trp Pro Ala Gly Ile Pro Gln Phe Tyr Ile Ser Cys Ala Gln Val
                165                 170                 175

Arg Val Thr Gly Gly Gly Asn Ala Asn Pro Ser Pro Val Ser Ile
            180                 185                 190

Pro Gly Ala Phe Lys Glu Thr Asp Pro Gly Tyr Thr Ala Asn Ile Tyr
            195                 200                 205

Asn Asn Phe Arg Ser Tyr Thr Val Pro Gly Pro Ser Val Phe Thr Cys
210                 215                 220

Ser Gly Asn Ser Gly Gly Ser Asn Pro Ser Asn Pro Asn Pro Pro
225                 230                 235                 240

Thr Pro Thr Thr Phe Thr Thr Gln Val Thr Thr Pro Thr Pro Ala Ser
                245                 250                 255

Pro Pro Ser Cys Thr Val Ala Lys Trp Gly Gln Cys Gly Gly Gln Gly
            260                 265                 270

Tyr Ser Gly Cys Thr Asn Cys Glu Ala Gly Ser Thr Cys Arg Gln Gln
        275                 280                 285

Asn Ala Tyr Tyr Ser Gln Cys Ile
        290                 295

<210> SEQ ID NO 129
<211> LENGTH: 1032
<212> TYPE: DNA
<213> ORGANISM: Humicola insolens

<400> SEQUENCE: 129
atgaggccct tctcactcgt cgctctggcg acggccgtca gcggccacgc catcttccag      60
cgcgtgtcgg ttaacggcgt cgaccaaggc cagctcaagg gcgtccgcgc tccctcgagc     120
aactacccca tcgagaacgt caaccacccc gactttgcct gcaacaccaa catccagcac     180
cgcgacggca ccgtcatcaa gatccccgcc ggcgccaccg tcggcgcctg gtggcagcac     240
gagatcggcg ggccctcgtt cccgggtgac ccggataacc cgatcgctgc ttcgcacaag     300
ggtgagttcc catagataga tctcttctct cccgacccct tgtatcctct cataactaac     360
cacctcaacc ccccaggccc tatccaagtc tacctcgcca aggtcgacaa cgccgcgacc     420
gcctccccca acggcctgcg gtggttcaag attgccgaga agggcctgtc gggcggcgtc     480
tgggccgtcg acgagatgat ccgcaacaac ggctggcact acttcaccat gccgcagtgc     540
atcgcgcccg ccactacct gatgcgcgtc gagctgttgg cgctgcactc ggccagcttc     600

```
cccggcggcg cccagttcta catggagtgc gcccagatcg aggtcaccgg ctcgggcaac      660
ttctcgccct ccgagacggt cagcttcccc ggcgcctacc cggccaacca cccgggtatc      720
gtcgtcagca tctacgacgc ccagggtaac gccaacaacg gcgggcgcga gtaccagatc      780 cccggccgc ggccgatcac ctgctccggc ggtggaagca acaatggtgg cgggaacaac       840
aatggtggtg aaacaacaa cggcggcggc aacaacaacg gcggtgggaa caacaacggt       900
ggtggtaaca ccgtggcgg ctcggcgccg ctctggggcc agtgcggcgg caatgggtat       960
accggcccga cgacttgtgc cgagggtact tgcaagaagc agaatgactg gtactcgcag     1020
tgtacgcctt ag                                                         1032

<210> SEQ ID NO 130
<211> LENGTH: 318
<212> TYPE: PRT
<213> ORGANISM: Humicola insolens

<400> SEQUENCE: 130

Met Arg Pro Phe Ser Leu Val Ala Leu Ala Thr Ala Val Ser Gly His
 1               5                  10                  15

Ala Ile Phe Gln Arg Val Ser Val Asn Gly Val Asp Gln Gly Gln Leu
            20                  25                  30

Lys Gly Val Arg Ala Pro Ser Ser Asn Tyr Pro Ile Glu Asn Val Asn
        35                  40                  45

His Pro Asp Phe Ala Cys Asn Thr Asn Ile Gln His Arg Asp Gly Thr
    50                  55                  60

Val Ile Lys Ile Pro Ala Gly Ala Thr Val Ala Trp Trp Gln His
 65                  70                  75                  80

Glu Ile Gly Gly Pro Ser Phe Pro Gly Asp Pro Asp Asn Pro Ile Ala
                85                  90                  95

Ala Ser His Lys Gly Pro Ile Gln Val Tyr Leu Ala Lys Val Asp Asn
           100                 105                 110

Ala Ala Thr Ala Ser Pro Asn Gly Leu Arg Trp Phe Lys Ile Ala Glu
        115                 120                 125

Lys Gly Leu Ser Gly Gly Val Trp Ala Val Asp Glu Met Ile Arg Asn
    130                 135                 140

Asn Gly Trp His Tyr Phe Thr Met Pro Gln Cys Ile Ala Pro Gly His
145                 150                 155                 160

Tyr Leu Met Arg Val Glu Leu Leu Ala Leu His Ser Ala Ser Phe Pro
                165                 170                 175

Gly Gly Ala Gln Phe Tyr Met Glu Cys Ala Gln Ile Glu Val Thr Gly
            180                 185                 190

Ser Gly Asn Phe Ser Pro Ser Glu Thr Val Ser Phe Pro Gly Ala Tyr
        195                 200                 205

Pro Ala Asn His Pro Gly Ile Val Val Ser Ile Tyr Asp Ala Gln Gly
    210                 215                 220

Asn Ala Asn Asn Gly Gly Arg Glu Tyr Gln Ile Pro Gly Pro Arg Pro
225                 230                 235                 240

Ile Thr Cys Ser Gly Gly Ser Asn Asn Gly Gly Asn Asn
                245                 250                 255

Gly Gly Gly Asn Asn Asn Gly Gly Asn Asn Gly Gly Asn
            260                 265                 270

Asn Asn Gly Gly Gly Asn Thr Gly Gly Gly Ser Ala Pro Leu Trp Gly
    275                 280                 285
```

Gln Cys Gly Gly Asn Gly Tyr Thr Gly Pro Thr Thr Cys Ala Glu Gly
    290                 295                 300

Thr Cys Lys Lys Gln Asn Asp Trp Tyr Ser Gln Cys Thr Pro
305                 310                 315

<210> SEQ ID NO 131
<211> LENGTH: 1113
<212> TYPE: DNA
<213> ORGANISM: Humicola insolens

<400> SEQUENCE: 131

```
atggtgttgc ggtctctctc tatcctggcc ttcgtagcca gaggcgtctt cgcccacggt      60
ggcctctcca actacacggt cggcgacacg tggtatagcg ggtgcgtcca tgaacaactc     120
ctatatcttc cccccctcca cattgcgacc gctgcacatc tcactcgtcc ataaacaaca     180
acatcaatcg gtagacactg tccaaaagct aaccaccgta cctcctgaac acagctacga     240
cccctttcacc cccgccgccg cccaactctc ccaaccctgg ctgatccaac gccaatggac     300
cagcatcgac ccgctcttct ccccgacctc tccctacctc gctgcaact tccccggcac     360
cgcgccacca tcttacatcc ctctccgcgc cggcgacatc ctcaccgcgg tttactggtt     420
ctggctgcac cccgtggggc cgatgagcgt ttggctggcg cggtgcgcag gggactgccg     480
cgacgaggac gtgacgcggg cgcgctggtt caagatctgg catgcggggt ttctggaggg     540
gccgaatttg gagctcggga tgtggtatca gaagaagttc cagcggtggg atggcgggcc     600
ggcgctctgg cgggtgagga taccgagggg gttgaagaag gggttgtaca tggtcaggca     660
tgagattttg tcgattcatg tgggtggacg gccccagttt atcccgagt gtgcgcactt      720
gaatgtgacg gagggtggtg aggtggtagt gccgggggag tggacgagaa ggttccctgg     780
ggcgtatgac gatgatggtg agtgccttgc tagacgggaa ggctctatgg atggggcgga     840
tgagacgaaa ggctggtgtg agactgtcag cactgacggc ctgcagacaa gtcagtcttc     900
atcgatatct accggccgga acatgaaaac aggacggtac gtgggacaag caagcctcgg     960
atttttcaga ttttcgactc tgacaacgaa caggactatg agatccctgg aggcccgatt    1020
tgggaaaggt acgtacaatc gcatcatctt gactctgtat tcaggggcta acataaacac    1080
agcttggggg agatggagtt atggcctgaa tga                                 1113
```

<210> SEQ ID NO 132
<211> LENGTH: 259
<212> TYPE: PRT
<213> ORGANISM: Humicola insolens

<400> SEQUENCE: 132

Met Val Leu Arg Ser Leu Ser Ile Leu Ala Phe Val Ala Arg Gly Val
1               5                   10                  15

Phe Ala His Gly Gly Leu Ser Asn Tyr Thr Val Gly Asp Thr Trp Tyr
                20                  25                  30

Ser Gly Tyr Asp Pro Phe Thr Pro Ala Ala Ala Gln Leu Ser Gln Pro
            35                  40                  45

Trp Leu Ile Gln Arg Gln Trp Thr Ser Ile Asp Pro Leu Phe Ser Pro
        50                  55                  60

Thr Ser Pro Tyr Leu Ala Cys Asn Phe Pro Gly Thr Ala Pro Pro Ser
65                  70                  75                  80

Tyr Ile Pro Leu Arg Ala Gly Asp Ile Leu Thr Ala Val Tyr Trp Phe
                85                  90                  95

Trp Leu His Pro Val Gly Pro Met Ser Val Trp Leu Ala Arg Cys Ala 100                 105                 110
Gly Asp Cys Arg Asp Glu Asp Val Thr Arg Ala Arg Trp Phe Lys Ile
            115                 120                 125

Trp His Ala Gly Phe Leu Glu Gly Pro Asn Leu Glu Leu Gly Met Trp
    130                 135                 140

Tyr Gln Lys Lys Phe Gln Arg Trp Asp Gly Pro Ala Leu Trp Arg
145                 150                 155                 160

Val Arg Ile Pro Arg Gly Leu Lys Lys Gly Leu Tyr Met Val Arg His
                165                 170                 175

Glu Ile Leu Ser Ile His Val Gly Gly Arg Pro Gln Phe Tyr Pro Glu
            180                 185                 190

Cys Ala His Leu Asn Val Thr Glu Gly Gly Glu Val Val Val Pro Gly
        195                 200                 205

Glu Trp Thr Arg Arg Phe Pro Gly Ala Tyr Asp Asp Asp Lys Ser
    210                 215                 220

Val Phe Ile Asp Ile Tyr Arg Pro Glu His Glu Asn Arg Thr Asp Tyr
225                 230                 235                 240

Glu Ile Pro Gly Gly Pro Ile Trp Glu Ser Leu Gly Glu Met Glu Leu
                245                 250                 255

Trp Pro Glu

<210> SEQ ID NO 133
<211> LENGTH: 1103
<212> TYPE: DNA
<213> ORGANISM: Humicola insolens

<400> SEQUENCE: 133
atgaggaccg tcttcgccgc cgcactggca gcactcgctg cccgggaagt cgccggccat    60
gccacgttcc agcaactctg ggttgacgga accgattata taagtgcccc ccttttctcg   120
gttccatttg atatcatgat gctgacaccc ccagcacggc agcacctgcg tccgcctccc   180
cgccagcaac agccccctga ccgacgtcac cagcagcgac ttcgcctgca acatcggcgg   240
ccggcgcggc gtgggcggca aatgccccgt caaagccggc ggcgtggtca cgatcgagat   300
gcatcagcag cccaacgacc ggaactgccg cagcgaggcc atcggcggca tgcactgggg   360
tccggtgcag gtctacctca gcaaggtccc cgacgcgtcg accgccgagc gacgcaggt   420 gggctggttc aagatcttct ccaacgcgtg ggccaagaag cccggcggca actcgggcga   480
cgacgactac tggggcacgc gcgagctcaa cggctgctgc gggcgcatgg acgtgccgat   540
ccccaccgac ctggaagacg gcgactacct gctgcgcgcc gaggcgctgg cgctgcacgc   600
catgccgggc cagttctaca tgtcgtgcta ccagatcacc atcacgggcg gcacgggcac   660
cgcgaagccg cgcgactgtc cgcttccccgg agcgtacacc aacaacgacg ccggcatccg   720
cgccaacatc cacgccccgc tgagcaccta catcgcgccc ggcccggagg tgtactccgg   780
cggtaccacc cggcgcccg gtgagggctg cccgggatgt gctacgacct gccaggttgg   840
ctcgtcgccc agcgcgcagg ctccaggcca tggcacggcc gtgggcggcg agctggtgg    900 cccgtctgct tgcaccgtcc aggcgtatgg ccagtgcggt ggccagggat acacgggttg   960
caccgagtgc gcggtaagtt gggacttcct tgtcattaaa atcgcaaatg aacggatgg   1020 gctaacattt gcgggtgcag gatggttcg tttgccgcga cgtctcggct ccgtggtact   1080
ctcagtgcca gcctgctttc taa                                           1103

<210> SEQ ID NO 134

<211> LENGTH: 325
<212> TYPE: PRT
<213> ORGANISM: Humicola insolens

<400> SEQUENCE: 134

Met Arg Thr Val Phe Ala Ala Leu Ala Ala Leu Ala Ala Arg Glu
1               5                   10                  15

Val Ala Gly His Ala Thr Phe Gln Gln Leu Trp Val Asp Gly Thr Asp
            20                  25                  30

Tyr Gly Ser Thr Cys Val Arg Leu Pro Ala Ser Asn Ser Pro Leu Thr
        35                  40                  45

Asp Val Thr Ser Ser Asp Phe Ala Cys Asn Ile Gly Gly Arg Arg Gly
    50                  55                  60

Val Gly Gly Lys Cys Pro Val Lys Ala Gly Gly Val Val Thr Ile Glu
65                  70                  75                  80

Met His Gln Gln Pro Asn Asp Arg Asn Cys Arg Ser Glu Ala Ile Gly
                85                  90                  95

Gly Met His Trp Gly Pro Val Gln Val Tyr Leu Ser Lys Val Pro Asp
            100                 105                 110

Ala Ser Thr Ala Glu Pro Thr Gln Val Gly Trp Phe Lys Ile Phe Ser
        115                 120                 125

Asn Ala Trp Ala Lys Lys Pro Gly Gly Asn Ser Gly Asp Asp Asp Tyr
    130                 135                 140

Trp Gly Thr Arg Glu Leu Asn Gly Cys Cys Gly Arg Met Asp Val Pro
145                 150                 155                 160

Ile Pro Thr Asp Leu Glu Asp Gly Asp Tyr Leu Leu Arg Ala Glu Ala
                165                 170                 175

Leu Ala Leu His Ala Met Pro Gly Gln Phe Tyr Met Ser Cys Tyr Gln
            180                 185                 190

Ile Thr Ile Thr Gly Gly Thr Gly Thr Ala Lys Pro Ala Thr Val Arg
        195                 200                 205

Phe Pro Gly Ala Tyr Thr Asn Asn Asp Ala Gly Ile Arg Ala Asn Ile
    210                 215                 220

His Ala Pro Leu Ser Thr Tyr Ile Ala Pro Gly Pro Glu Val Tyr Ser
225                 230                 235                 240

Gly Gly Thr Thr Arg Ala Pro Gly Glu Gly Cys Pro Gly Cys Ala Thr
                245                 250                 255

Thr Cys Gln Val Gly Ser Ser Pro Ser Ala Gln Ala Pro Gly His Gly
            260                 265                 270

Thr Ala Val Gly Gly Gly Ala Gly Gly Pro Ser Ala Cys Thr Val Gln
        275                 280                 285

Ala Tyr Gly Gln Cys Gly Gly Gln Gly Tyr Thr Gly Cys Thr Glu Cys
    290                 295                 300

Ala Asp Gly Phe Val Cys Arg Asp Val Ser Ala Pro Trp Tyr Ser Gln
305                 310                 315                 320

Cys Gln Pro Ala Phe
                325

<210> SEQ ID NO 135
<211> LENGTH: 1039
<212> TYPE: DNA
<213> ORGANISM: Humicola insolens

<400> SEQUENCE: 135
atgaggctcc cccaagtggc ttccgttctg gccctcgcgg cccaggtcca cggtcacggc      60

```
tacatctacc gtgtcaccgc cgacaacatt gtgtaagcgc cctcagattc cggacctctt    120
cctacctggt ggctaacctt ctctcaactc ttcagctacc cgggatacga catctatgtc    180
gatcccctcc tccaaccgcc cccgtaccgc attgcctacg tggtggccca gacgggtccc    240
gtctatgata tcaacagcaa ggatatcgcc tgccagcgcg tccacagccc cgctccgggt    300
ctgattgccc aggctcgcgc gggcagcaac atcaccttct ggtggtcgcg gtggctgtac    360
agccacaagg gtcccatctc ggcatggatg gctccgtatg agggcgacat tgccaatgtg    420
gacgtcaacc agctcgagtt cttcaagatt ggcgaggagt tccacgatga accggcaag    480
tgggcgacgg agaagctggt ggacgacccc gagggcaagt ggaccgtcaa gatccccgcc    540
gatatcaagc ccggtctcta tgtcgtgcgg aacgaggtaa gtttcatccg tcccaaaaaa    600
ggggtcccat cccatgcatg gtgcatgccc agtctaatca tcatctcccg gatagatcat    660
cgccctccac ttcgccgtcc gcatgcctcc cttctttgcc gccttcaccc cctcggacc    720
gcagttctac atgaccctgct tcgccttcaa catcaccggc gacggcacgg ccactcccca    780
gggctacaag ttccctggcg cctacagcaa ggacgatccg gccctgtggt gggatctgga    840
ggagaacaag aacccgtacc ccggcgccgg ccccaagccc cacgtctcgg cctacgatgt    900
cgacctcgtc cccaacgagt tgtacatcgt cagcccgacg aacaacgcga cggctgatga    960
gctctactgg gaggcccaga ggcaggcgct tgctgcccag gcggcgacga cggagtactt   1020
tgactcgatt ggtggctaa                                                1039
```

<210> SEQ ID NO 136
<211> LENGTH: 298
<212> TYPE: PRT
<213> ORGANISM: Humicola insolens

<400> SEQUENCE: 136

```
Met Arg Leu Pro Gln Val Ala Ser Val Leu Ala Leu Ala Ala Gln Val
1               5                   10                  15

His Gly His Gly Tyr Ile Tyr Arg Val Thr Ala Asp Asn Ile Val Tyr
            20                  25                  30

Pro Gly Tyr Asp Ile Tyr Val Asp Pro Leu Leu Gln Pro Pro Tyr
        35                  40                  45

Arg Ile Ala Tyr Gly Gly Gln Thr Gly Pro Val Tyr Asp Ile Asn
    50                  55                  60

Ser Lys Asp Ile Ala Cys Gln Arg Val His Ser Pro Ala Pro Gly Leu
65                  70                  75                  80

Ile Ala Gln Ala Arg Ala Gly Ser Asn Ile Thr Phe Trp Trp Ser Arg
                85                  90                  95

Trp Leu Tyr Ser His Lys Gly Pro Ile Ser Ala Trp Met Ala Pro Tyr
            100                 105                 110

Glu Gly Asp Ile Ala Asn Val Asp Val Asn Gln Leu Glu Phe Phe Lys
        115                 120                 125

Ile Gly Glu Glu Phe His Asp Glu Thr Gly Lys Trp Ala Thr Glu Lys
    130                 135                 140

Leu Val Asp Asp Pro Glu Gly Lys Trp Thr Val Lys Ile Pro Ala Asp
145                 150                 155                 160

Ile Lys Pro Gly Leu Tyr Val Val Arg Asn Glu Ile Ile Ala Leu His
                165                 170                 175

Phe Ala Val Arg Met Pro Pro Phe Ala Ala Phe Thr Pro Leu Gly
            180                 185                 190

Pro Gln Phe Tyr Met Thr Cys Phe Ala Phe Asn Ile Thr Gly Asp Gly
```

```
                195                 200                 205
Thr Ala Thr Pro Gln Gly Tyr Lys Phe Pro Gly Ala Tyr Ser Lys Asp
    210                 215                 220

Asp Pro Ala Leu Trp Trp Asp Leu Glu Glu Asn Lys Asn Pro Tyr Pro
225                 230                 235                 240

Gly Ala Gly Pro Lys Pro His Val Ser Ala Tyr Asp Val Asp Leu Val
                245                 250                 255

Pro Asn Glu Leu Tyr Ile Val Ser Pro Thr Asn Asn Ala Thr Ala Asp
            260                 265                 270

Glu Leu Tyr Trp Glu Ala Gln Arg Gln Ala Leu Ala Ala Gln Ala Ala
        275                 280                 285

Thr Thr Glu Tyr Phe Asp Ser Ile Gly Gly
    290                 295

<210> SEQ ID NO 137
<211> LENGTH: 1025
<212> TYPE: DNA
<213> ORGANISM: Humicola insolens

<400> SEQUENCE: 137
atgcacgtcc agtctctcct tgccggagcg ctcgctctgg ctccgtcggc gtctgctcac        60
ttcctcttcc cgcacctgat gctgaacggt gtccgcacgg gagcctacga gtatgtccgg       120
gagcacgact tcggcttcat gccgcacaac aacgactgga tcaactcgcc cgatttccgt       180
tgcaacgagg ggtcctggcg tcatcgccgc gagcccaaga ccgccgtagt cactgccggc       240
gttgacgtcg tgggcttcaa cctgcacctg gactttgacc tgtaccatcc gggcccgtg        300 acggtaagca catctgagtc agaacatacc tccctgtgac gtagactaat gagtctctta       360
ccgcagatct atctctcccg cgccccggc gacgtgcgtg actacgacgg atctggtgac        420
tggttcaagg tgtaccagct gggcacccgc caacccttca acggcactga cgagggctgg       480
gccacttgga agatgaagaa ctggcagttc cgcctgcccg ctgagatccc ggcgggcgag       540
tacctgatgc gcatcgagca gatgagcgtg cacctcctt accgccagaa ggagtggtac        600
gtgcagtgcg cccacctaaa gatcaacagc aactacaacg cccccgcgcc cggcccgacc       660
atcaagattc ccggagggta caagatcagc gatcctgcga ttcaatatga ccagtgggcg       720
cagccgccgc cgacgtacgc gcccatgccg ggaccgccgc tgtggcccaa caacaatcct       780
cagcagggca acccgaatca gggcggaaat aacggcggtg caaccaggg cggcggcaat       840 ggtggctgca ccgttccgaa gtggtatgta gagttcttca ctattatcat gagatgcagc       900
gttggacttg tgcttacacc tagaacaggg gccaatgcgg tggtcagggt tacagcgggt       960
gcaggaactg cgagtctggc tcgacatgcc gtgcccagaa cgactggtac tcgcagtgcc      1020
tgtaa                                                                  1025

<210> SEQ ID NO 138
<211> LENGTH: 298
<212> TYPE: PRT
<213> ORGANISM: Humicola insolens

<400> SEQUENCE: 138

Met His Val Gln Ser Leu Leu Ala Gly Ala Leu Ala Leu Ala Pro Ser
1               5                   10                  15

Ala Ser Ala His Phe Leu Phe Pro His Leu Met Leu Asn Gly Val Arg
            20                  25                  30

Thr Gly Ala Tyr Glu Tyr Val Arg Glu His Asp Phe Gly Phe Met Pro
```

```
                35                  40                  45
His Asn Asn Asp Trp Ile Asn Ser Pro Asp Phe Arg Cys Asn Glu Gly
 50                  55                  60

Ser Trp Arg His Arg Arg Glu Pro Lys Thr Ala Val Val Thr Ala Gly
 65                  70                  75                  80

Val Asp Val Val Gly Phe Asn Leu His Leu Asp Phe Asp Leu Tyr His
                 85                  90                  95

Pro Gly Pro Val Thr Ile Tyr Leu Ser Arg Ala Pro Gly Asp Val Arg
            100                 105                 110

Asp Tyr Asp Gly Ser Gly Asp Trp Phe Lys Val Tyr Gln Leu Gly Thr
        115                 120                 125

Arg Gln Pro Phe Asn Gly Thr Asp Glu Gly Trp Ala Thr Trp Lys Met
    130                 135                 140

Lys Asn Trp Gln Phe Arg Leu Pro Ala Glu Ile Pro Ala Gly Glu Tyr
145                 150                 155                 160

Leu Met Arg Ile Glu Gln Met Ser Val His Pro Pro Tyr Arg Gln Lys
                165                 170                 175

Glu Trp Tyr Val Gln Cys Ala His Leu Lys Ile Asn Ser Asn Tyr Asn
            180                 185                 190

Gly Pro Ala Pro Gly Pro Thr Ile Lys Ile Pro Gly Gly Tyr Lys Ile
        195                 200                 205

Ser Asp Pro Ala Ile Gln Tyr Asp Gln Trp Ala Gln Pro Pro Thr
    210                 215                 220

Tyr Ala Pro Met Pro Gly Pro Pro Leu Trp Pro Asn Asn Pro Gln
225                 230                 235                 240

Gln Gly Asn Pro Asn Gln Gly Gly Asn Asn Gly Gly Asn Gln Gly
                245                 250                 255

Gly Gly Asn Gly Gly Cys Thr Val Pro Lys Trp Gly Gln Cys Gly Gly
            260                 265                 270

Gln Gly Tyr Ser Gly Cys Arg Asn Cys Glu Ser Gly Ser Thr Cys Arg
        275                 280                 285

Ala Gln Asn Asp Trp Tyr Ser Gln Cys Leu
    290                 295
```

<210> SEQ ID NO 139
<211> LENGTH: 1035
<212> TYPE: DNA
<213> ORGANISM: Humicola insolens

<400> SEQUENCE: 139

```
atgccaccac cactactggc caccgtcctc tccttgctag ccctcacccg cggcgccctt     60
tcccattccc acctagccca cgtcatcatc aacggccagc tctaccacgg cttcgaccca    120
cgtccaaacc aaaacaacca tccagcccgt gtcggctggt ccacgaccgc cacagatgac    180
ggcttcgtca ccccgggcaa ttactccatc ccgacatca tctgccaccg cggcggcgtc    240
agcccgcgcg cccacgctcc cgtcaccgcc ggcggcaagg tccaggtcca atggaacggc    300
tggccgatcg gacacgtcgg gccgatcctg acctacatcg cgccgtgcgg cggactgccg    360
ggcgccgaag aagggtgtac gggcgtggac aaaaccgacc tgcggtggac caagatcgac    420
gactcgatgc cgccgttccg gtttaccgac gccaccaagc cagtctctgg cagagcgcag    480
ttcccgatag ccaggtctg ggcgacggat gcgctggtcg aggcgaataa tagctggtcg    540
gtggtcattc ccaggaatat cccgccgggg ccgtacgttt tgaggcagga gattgtggcc    600
ctgcattacg cggcgaagtt gaacgggcg cagaactatc cgttgtgtct gaacctctgg    660
```

```
gtggaaaagg ggcagcagga tcagggagag cccttcaaat tcgatgctta cgacgcgagg    720
gagttttaca gcgaggacca tccgggtgtg ttgattgatg ttatgacgat ggttgggccg    780
agagccgtgt accggatacc tggaccgacc gtggccagtg gtgccacgag aattccgcac    840
tcattgcaga cgagcgccga gacgtgggtg aagggacgc cggtggccgt gacgagggcg     900
acggaaacgg ttcagatgga gataactacg acacctgcag gtcagggagc tggtgtgagg    960
acagctaccc ctgccatgcc aacaccaaca gtgacgaaga ggtggaaggg aagatttgag   1020
atgggtaggc catga                                                    1035
```

<210> SEQ ID NO 140
<211> LENGTH: 344
<212> TYPE: PRT
<213> ORGANISM: Humicola insolens

<400> SEQUENCE: 140

```
Met Pro Pro Leu Leu Ala Thr Val Leu Ser Leu Ala Leu Thr
1               5                   10                  15

Arg Gly Ala Leu Ser His Ser His Leu Ala His Val Ile Ile Asn Gly
            20                  25                  30

Gln Leu Tyr His Gly Phe Asp Pro Arg Pro Asn Gln Asn Asn His Pro
        35                  40                  45

Ala Arg Val Gly Trp Ser Thr Thr Ala Thr Asp Asp Gly Phe Val Thr
    50                  55                  60

Pro Gly Asn Tyr Ser His Pro Asp Ile Ile Cys His Arg Gly Val
65                  70                  75                  80

Ser Pro Arg Ala His Ala Pro Val Thr Ala Gly Lys Val Gln Val
                85                  90                  95

Gln Trp Asn Gly Trp Pro Ile Gly His Val Gly Pro Ile Leu Thr Tyr
            100                 105                 110

Ile Ala Pro Cys Gly Gly Leu Pro Gly Ala Glu Glu Gly Cys Thr Gly
        115                 120                 125

Val Asp Lys Thr Asp Leu Arg Trp Thr Lys Ile Asp Asp Ser Met Pro
    130                 135                 140

Pro Phe Arg Phe Thr Asp Ala Thr Lys Pro Val Ser Gly Arg Ala Gln
145                 150                 155                 160

Phe Pro Ile Gly Gln Val Trp Ala Thr Asp Ala Leu Val Glu Ala Asn
                165                 170                 175

Asn Ser Trp Ser Val Val Ile Pro Arg Asn Ile Pro Pro Gly Pro Tyr
            180                 185                 190

Val Leu Arg Gln Glu Ile Val Ala Leu His Tyr Ala Ala Lys Leu Asn
        195                 200                 205

Gly Ala Gln Asn Tyr Pro Leu Cys Leu Asn Leu Trp Val Glu Lys Gly
    210                 215                 220

Gln Gln Asp Gln Gly Glu Pro Phe Lys Phe Asp Ala Tyr Asp Ala Arg
225                 230                 235                 240

Glu Phe Tyr Ser Glu Asp His Pro Gly Val Leu Ile Asp Val Met Thr
                245                 250                 255

Met Val Gly Pro Arg Ala Val Tyr Arg Ile Pro Gly Pro Thr Val Ala
            260                 265                 270

Ser Gly Ala Thr Arg Ile Pro His Ser Leu Gln Thr Ser Ala Glu Thr
        275                 280                 285

Trp Val Glu Gly Thr Pro Val Ala Val Thr Arg Ala Thr Glu Thr Val
    290                 295                 300
```

```
Gln Met Glu Ile Thr Thr Thr Pro Ala Gly Gln Gly Ala Gly Val Arg
305                 310                 315                 320

Thr Ala Thr Pro Ala Met Pro Thr Pro Thr Val Thr Lys Arg Trp Lys
                325                 330                 335

Gly Arg Phe Glu Met Gly Arg Pro
            340

<210> SEQ ID NO 141
<211> LENGTH: 1057
<212> TYPE: DNA
<213> ORGANISM: Humicola insolens

<400> SEQUENCE: 141
atgaagtccc tgacctacgc cgcgctggcc gccctctggg cccagcagac cgctgctcat     60
gccaccttcc agcaactctg ggtcgacggc gtcgactacg gcagtcagtg cgcccgcctg    120
ccgccgtcca actcccccat cgccagcgtc acctcgaccg ccatgcgctg caacaacggt    180
ccccgcgctg ccgccaagtg ccccgtcaag gctggcggca ccgtcaccat cgagatgcac    240
caggttggtt ccttgaagt gttccctac cacatataca accgtagct aacacaccca       300 tccttagcaa cccggtgacc ggtcctgcaa ccaggacgcc attggcggtg cccaccacgg    360
ccccgtgatg gtgtacatgt ccaaggtctc tgatgccttc accgccgacg gctcgtcagg    420
ctggttcaag atcttccagg acggctgggc caagaacccc aacggccgcg ttggcgacga    480
cgacttctgg ggcaccaagg acctcaacac ctgctgcggc aagatgaacg tcaagatccc    540
cgccgacatc gccccggcg actacctgct ccgcgccgag gccatcgcgc tgcacgccgc     600
cggccccagc ggtggcgccc agccctacgt cacctgctac cagctcaccg tcacgggcgg    660
cggcaacgcc aacccgccca ccgtcaactt ccccggcgcc tacagcgagc gtgaccctgg    720
catcgccgtc agcatccacg gcgctctgtc caactacgtc gtccccggtc tccggtcta    780 ctcgggcggc agcgagaagc gcgctggcag ccctgcgag ggctgcgagg ccacctgcaa     840
ggtcggctcg agcccagcc agactcttgc tccttccaac ccggccccga cctctcccgc     900
caacggcggc ggcaacaacg tggtggcaa cactggcggc ggctgcaccg tgcccaagtg     960
gcagcagtgc ggcggccagg gctactcggg ctgcaccgtc tgcgagtctg gctcgacttg   1020
ccgcgctcag aaccagtggt actctcagtg cgtgtaa                            1057

<210> SEQ ID NO 142
<211> LENGTH: 330
<212> TYPE: PRT
<213> ORGANISM: Humicola insolens

<400> SEQUENCE: 142

Met Lys Ser Leu Thr Tyr Ala Ala Leu Ala Ala Leu Trp Ala Gln Gln
1               5                   10                  15

Thr Ala His Ala Thr Phe Gln Gln Leu Trp Val Asp Gly Val Asp
            20                  25                  30

Tyr Gly Ser Gln Cys Ala Arg Leu Pro Pro Ser Asn Ser Pro Ile Ala
        35                  40                  45

Ser Val Thr Ser Thr Ala Met Arg Cys Asn Asn Gly Pro Arg Ala Ala
    50                  55                  60

Ala Lys Cys Pro Val Lys Ala Gly Gly Thr Val Thr Ile Glu Met His
65                  70                  75                  80

Gln Gln Pro Gly Asp Arg Ser Cys Asn Gln Asp Ala Ile Gly Gly Ala
                85                  90                  95
```

His His Gly Pro Val Met Val Tyr Met Ser Lys Val Ser Asp Ala Phe
              100                 105                 110

Thr Ala Asp Gly Ser Ser Gly Trp Phe Lys Ile Phe Gln Asp Gly Trp
              115                 120                 125

Ala Lys Asn Pro Asn Gly Arg Val Gly Asp Asp Phe Trp Gly Thr
130                 135                 140

Lys Asp Leu Asn Thr Cys Cys Gly Lys Met Asn Val Lys Ile Pro Ala
145                 150                 155                 160

Asp Ile Ala Pro Gly Asp Tyr Leu Leu Arg Ala Glu Ala Ile Ala Leu
                165                 170                 175

His Ala Ala Gly Pro Ser Gly Gly Ala Gln Pro Tyr Val Thr Cys Tyr
              180                 185                 190

Gln Leu Thr Val Thr Gly Gly Gly Asn Ala Asn Pro Pro Thr Val Asn
              195                 200                 205

Phe Pro Gly Ala Tyr Ser Glu Arg Asp Pro Gly Ile Ala Val Ser Ile
              210                 215                 220

His Gly Ala Leu Ser Asn Tyr Val Val Pro Gly Pro Pro Val Tyr Ser
225                 230                 235                 240

Gly Gly Ser Glu Lys Arg Ala Gly Ser Pro Cys Glu Gly Cys Glu Ala
                245                 250                 255

Thr Cys Lys Val Gly Ser Ser Pro Ser Gln Thr Leu Ala Pro Ser Asn
              260                 265                 270

Pro Ala Pro Thr Ser Pro Ala Asn Gly Gly Asn Asn Gly Gly Gly
              275                 280                 285

Asn Thr Gly Gly Gly Cys Thr Val Pro Lys Trp Gln Gln Cys Gly Gly
              290                 295                 300

Gln Gly Tyr Ser Gly Cys Thr Val Cys Glu Ser Gly Ser Thr Cys Arg
305                 310                 315                 320

Ala Gln Asn Gln Trp Tyr Ser Gln Cys Val
              325                 330

<210> SEQ ID NO 143
<211> LENGTH: 772
<212> TYPE: DNA
<213> ORGANISM: Humicola insolens

<400> SEQUENCE: 143
atgaagctcc tcctccccgc cctcctggct ctggccgccg agtccgtctc ggcgcactac     60
atcttccaac aactcaccgt cgccggcacc aagtaccccg tgtggaagta catccggcgc    120
aacagcaatc cggcgtggct tcaaaacggc cctgtgaccg acctcgcctc gaccgacctg    180
cgctgcaacg tgggcgggca ggtcagcaac ggcaccgaga ctctcaccgt ccgcgcgggc    240
gaccagttca cgttccacct cgacacggcg gtgtaccacc agggcccgac ctcgctgtac    300
atgtcgcgcg ctccgggcaa ggtggaggac tatgatggca gcgggccgtg gtttaagatt    360
tatgattggg ggccgacagg gaataattgg gtcatgaggg gtatggtttc ccctattaat    420
tattattatt gtttacttgg ggcatcatct ggtggtggtg ctggtgacga tgataagagt    480
gatggagaag gacctggctg acgacctaaa aacccgatca gattcgtaca cgtacaacat    540 ccccgctgc atccccgacg gcgagtatct cctgcgcatc agcagctgg gtctgcacaa    600 tccgggcgcc gcgccgcagt ctacatcag ctgcgcccag atcaaggtca ccggcggcgg    660
cactaccaac ccgaccccca cggctctgat tccgggagcg ttcagggcta cggatccggg    720
atacactgtc aacgtaagtc aaactttgag caactccata tcaacctcgt ga           772

<210> SEQ ID NO 144
<211> LENGTH: 216
<212> TYPE: PRT
<213> ORGANISM: Humicola insolens

<400> SEQUENCE: 144

```
Met Lys Leu Leu Leu Pro Ala Leu Leu Ala Leu Ala Ala Glu Ser Val
1               5                   10                  15
Ser Ala His Tyr Ile Phe Gln Gln Leu Thr Val Ala Gly Thr Lys Tyr
            20                  25                  30
Pro Val Trp Lys Tyr Ile Arg Arg Asn Ser Asn Pro Ala Trp Leu Gln
        35                  40                  45
Asn Gly Pro Val Thr Asp Leu Ala Ser Thr Asp Leu Arg Cys Asn Val
    50                  55                  60
Gly Gly Gln Val Ser Asn Gly Thr Glu Thr Leu Thr Val Arg Ala Gly
65                  70                  75                  80
Asp Gln Phe Thr Phe His Leu Asp Thr Ala Val Tyr His Gln Gly Pro
                85                  90                  95
Thr Ser Leu Tyr Met Ser Arg Ala Pro Gly Lys Val Glu Asp Tyr Asp
            100                 105                 110
Gly Ser Gly Pro Trp Phe Lys Ile Tyr Asp Trp Gly Pro Thr Gly Asn
        115                 120                 125
Asn Trp Val Met Arg Asp Ser Tyr Thr Tyr Asn Ile Pro Arg Cys Ile
    130                 135                 140
Pro Asp Gly Glu Tyr Leu Leu Arg Ile Gln Gln Leu Gly Leu His Asn
145                 150                 155                 160
Pro Gly Ala Ala Pro Gln Phe Tyr Ile Ser Cys Ala Gln Ile Lys Val
                165                 170                 175
Thr Gly Gly Gly Thr Thr Asn Pro Thr Pro Thr Ala Leu Ile Pro Gly
            180                 185                 190
Ala Phe Arg Ala Thr Asp Pro Gly Tyr Thr Val Asn Val Ser Gln Thr
        195                 200                 205
Leu Ser Asn Ser Ile Ser Thr Ser
    210                 215
```

<210> SEQ ID NO 145
<211> LENGTH: 1536
<212> TYPE: DNA
<213> ORGANISM: Humicola insolens

<400> SEQUENCE: 145

```
atgcgttctg tttcccttct tgcggccgct ttcgcgccgc tggctacggc acacacggtc      60
tttacagctc ttttcatcaa caatgtccac cagggcgacg gcacttgcgt ccgtatggct     120
aagcagggca acctcgccac ccatcccgtc agtctgaaca gcaatgagat ggcctgcggt     180
gggtaggccc cgttcctcga gcagctgatc tcgaactaac atgttgattc ttgaactcca     240
ggtcgcgatg gccaacaacc agtggcattt acttgcccag cacctgcggg agccaagctg     300
accttattgt ttcgtatgtg gcagatggc tctcagccag gttccatcga caagtctcac     360
gttggtccca tgtccatcta cctcaagaaa gtctcagata tgaacaccga ctcggccgca     420
gggcccgggt ggttcaagat ctggagtgag ggctacgacg ctgcgacgaa gaaatgggcc     480
acggagaaac tcatcgccaa caacggtttg ctcagcgtca acctacctcc cggcctccct     540
gcaggctact acctcgcccg ccacgaaatc gtcactctcc aaaacgtcac caacaacaag     600
```

```
gccgatccgc agttctacgt cggctgtgcg cagctgttcg tccaagggtt gggcaccgcc    660
gcctccgtgc ctgctgacaa aaccgtttcc atccccggcc atctgaaccc caacgacccg    720
gcgctggtat tcaaccccta tacccaaaac gctgcgacat acccaagctt cggcccaccg    780
ctcttcttcc caaatgctgc ttcggcggga tcaaacaagg cccagtcaac actcaagcaa    840
acctccggcg tcatccccct cgactgcctc atcaaaaacg ccaactggtg cggccgtgaa    900
gttccagact ataccaacga ggcgggatgc tggacggcgg cggggaactg ttgggagcag    960
gctgatcaat gctacaagac agccccgcca tcgggccata agggatgcaa gacctgggag   1020
gagcagaagt gcaacgtcat ccagaactcc tgtgaagcga agaggttttc gggcccgcca   1080
aacaggggg tcaagtttgc tgatatggat gtgaatcagc ttgttccggg ggcgatccct    1140
gaagcagtga acgccggtca gaatggggag gcggttgttg ttgacggcac aacgagctct   1200
gcagatgaga aggcgagtgt ggatttgaca acatcgtctc taccgacgcc gacgcctgcg   1260
gctgaagaaa acgggaagga ggatgaaaga ctggctcttg atccgaccct gacggaggac   1320
gagtcgtttt tctcagttga gccaacgtct gagcccactg tgttcaggt tgaggtgcct    1380
ttgacaactg tggtcctcct tccaacgctc acctcatctt tgaatccatt gccaaccccg   1440
acctcaattt cccagccggc tcacccggga agaccatgca caggtcgccg tcgtaggccg   1500
aggccagggt ttccgaaaca cccgcgcgat ttttaa                             1536
```

```
<210> SEQ ID NO 146
<211> LENGTH: 490
<212> TYPE: PRT
<213> ORGANISM: Humicola insolens

<400> SEQUENCE: 146

Met Arg Ser Val Ser Leu Leu Ala Ala Ala Phe Ala Pro Leu Ala Thr
1               5                   10                  15

Ala His Thr Val Phe Thr Ala Leu Phe Ile Asn Asn Val His Gln Gly
            20                  25                  30

Asp Gly Thr Cys Val Arg Met Ala Lys Gln Gly Asn Leu Ala Thr His
        35                  40                  45

Pro Val Ser Leu Asn Ser Asn Glu Met Ala Cys Gly Arg Asp Gly Gln
    50                  55                  60

Gln Pro Val Ala Phe Thr Cys Pro Ala Pro Gly Ala Lys Leu Thr
65                  70                  75                  80

Leu Leu Phe Arg Met Trp Ala Asp Gly Ser Gln Pro Gly Ser Ile Asp
                85                  90                  95

Lys Ser His Val Gly Pro Met Ser Ile Tyr Leu Lys Lys Val Ser Asp
            100                 105                 110

Met Asn Thr Asp Ser Ala Ala Gly Pro Gly Trp Phe Lys Ile Trp Ser
        115                 120                 125

Glu Gly Tyr Asp Ala Ala Thr Lys Lys Trp Ala Thr Glu Lys Leu Ile
    130                 135                 140

Ala Asn Asn Gly Leu Leu Ser Val Asn Leu Pro Gly Leu Pro Ala
145                 150                 155                 160

Gly Tyr Tyr Leu Ala Arg His Glu Ile Val Thr Leu Gln Asn Val Thr
                165                 170                 175

Asn Asn Lys Ala Asp Pro Gln Phe Tyr Val Gly Cys Ala Gln Leu Phe
            180                 185                 190

Val Gln Gly Leu Gly Thr Ala Ala Ser Val Pro Ala Asp Lys Thr Val
        195                 200                 205
```

```
Ser Ile Pro Gly His Leu Asn Pro Asn Asp Pro Ala Leu Val Phe Asn
    210                 215                 220
Pro Tyr Thr Gln Asn Ala Ala Thr Tyr Pro Ser Phe Gly Pro Pro Leu
225                 230                 235                 240
Phe Phe Pro Asn Ala Ala Ser Ala Gly Ser Asn Lys Ala Gln Ser Thr
            245                 250                 255
Leu Lys Gln Thr Ser Gly Val Ile Pro Ser Asp Cys Leu Ile Lys Asn
                260                 265                 270
Ala Asn Trp Cys Gly Arg Glu Val Pro Asp Tyr Thr Asn Glu Ala Gly
            275                 280                 285
Cys Trp Thr Ala Ala Gly Asn Cys Trp Glu Gln Ala Asp Gln Cys Tyr
290                 295                 300
Lys Thr Ala Pro Pro Ser Gly His Lys Gly Cys Lys Thr Trp Glu Glu
305                 310                 315                 320
Gln Lys Cys Asn Val Ile Gln Asn Ser Cys Glu Ala Lys Arg Phe Ser
                325                 330                 335
Gly Pro Pro Asn Arg Gly Val Lys Phe Ala Asp Met Asp Val Asn Gln
            340                 345                 350
Leu Val Pro Gly Ala Ile Pro Glu Ala Val Asn Ala Gly Gln Asn Gly
                355                 360                 365
Glu Ala Val Val Val Asp Gly Thr Thr Ser Ser Ala Asp Glu Lys Ala
370                 375                 380
Ser Val Asp Leu Thr Thr Ser Ser Leu Pro Thr Pro Thr Pro Ala Ala
385                 390                 395                 400
Glu Glu Asn Gly Lys Glu Asp Glu Arg Leu Ala Leu Asp Pro Thr Leu
                405                 410                 415
Thr Glu Asp Glu Ser Phe Phe Ser Val Glu Pro Thr Ser Glu Pro Thr
            420                 425                 430
Gly Val Gln Val Glu Val Pro Leu Thr Thr Val Val Leu Leu Pro Thr
            435                 440                 445
Leu Thr Ser Ser Leu Asn Pro Leu Pro Thr Pro Thr Ser Ile Ser Gln
            450                 455                 460
Pro Ala His Pro Gly Arg Pro Cys Thr Gly Arg Arg Arg Pro Arg
465                 470                 475                 480
Pro Gly Phe Pro Lys His Pro Arg Asp Phe
                485                 490

<210> SEQ ID NO 147
<211> LENGTH: 921
<212> TYPE: DNA
<213> ORGANISM: Humicola insolens

<400> SEQUENCE: 147
atgttcttcc gcaacgccgc cactcttgct ctggcctacg ccaccaccgg cgtctcggcc        60
cacgcgctca tgtacggcgt ctgggtcaac ggcgtcgacc aaggcgacgg ccgcaacgtc       120
tacatccgca cgcccccccaa caacagcccg gtcaaagacc tcgccagccc ggacatcgtc      180
tgcaacgtca acggcgggcg cgccgttccg gacttcgtcc aggcctcggc ggggacacc        240 ctcaccttcg agtggctgca caacaccgc ggcgacgaca tcatcgaccg ctcccacctc         300
ggccccatca tcacctacat cgccccttttt accacgggca acccgacggg gcccgtctgg       360
accaaaatcg ccgaacaggg cttcaaccct tccacccgcc gctgggccgt cgacgatctg       420
atcgacaacg gcggcaagac cgacttcgtc ctgcccgcgt ccctcgcgcc gggcaggtac       480
atcatccggc aggagatcat cgcgcaccac gagtccgaaa ccacgttcga atccaacccg       540
```

```
gcgcggggtg cccagttcta cccgtcgtgc gtgcagatcc aagtctcttc tggctcgggc    600
accgccgtgc cggatcagaa ctttgacttc aacacgggct acacgtacgc cgaccccggc    660
atccacttca acatctacac ctcgttcaac agctactcca tccccggccc ggaggtttgg    720
acgggcgcta gcaccggcgg cggcaacggc aacggcaacg gcaacggcaa tgccacgcct    780
acgcagccta ctcccactcc cactgtcact cccactccca tcgagaccgc ccagccggtt    840
accacgacga ccacctcgac ccggccgttc cctacccgct gccctggccg ccgcctcaag    900
cgtgaggagc ccaaggcttg a                                              921
```

<210> SEQ ID NO 148
<211> LENGTH: 306
<212> TYPE: PRT
<213> ORGANISM: Humicola insolens

<400> SEQUENCE: 148

```
Met Phe Phe Arg Asn Ala Ala Thr Leu Ala Leu Ala Tyr Ala Thr Thr
1               5                   10                  15

Gly Val Ser Ala His Ala Leu Met Tyr Gly Val Trp Val Asn Gly Val
            20                  25                  30

Asp Gln Gly Asp Gly Arg Asn Val Tyr Ile Arg Thr Pro Asn Asn
        35                  40                  45

Ser Pro Val Lys Asp Leu Ala Ser Pro Asp Ile Val Cys Asn Val Asn
    50                  55                  60

Gly Gly Arg Ala Val Pro Asp Phe Val Gln Ala Ser Ala Gly Asp Thr
65                  70                  75                  80

Leu Thr Phe Glu Trp Leu His Asn Thr Arg Gly Asp Asp Ile Ile Asp
                85                  90                  95

Arg Ser His Leu Gly Pro Ile Ile Thr Tyr Ile Ala Pro Phe Thr Thr
            100                 105                 110

Gly Asn Pro Thr Gly Pro Val Trp Thr Lys Ile Ala Glu Gln Gly Phe
        115                 120                 125

Asn Pro Ser Thr Arg Arg Trp Ala Val Asp Asp Leu Ile Asp Asn Gly
    130                 135                 140

Gly Lys Thr Asp Phe Val Leu Pro Ala Ser Leu Ala Pro Gly Arg Tyr
145                 150                 155                 160

Ile Ile Arg Gln Glu Ile Ile Ala His His Glu Ser Glu Thr Thr Phe
                165                 170                 175

Glu Ser Asn Pro Ala Arg Gly Ala Gln Phe Tyr Pro Ser Cys Val Gln
            180                 185                 190

Ile Gln Val Ser Ser Gly Ser Gly Thr Ala Val Pro Asp Gln Asn Phe
        195                 200                 205

Asp Phe Asn Thr Gly Tyr Thr Tyr Ala Asp Pro Gly Ile His Phe Asn
    210                 215                 220

Ile Tyr Thr Ser Phe Asn Ser Tyr Ser Ile Pro Gly Pro Glu Val Trp
225                 230                 235                 240

Thr Gly Ala Ser Thr Gly Gly Gly Asn Gly Asn Gly Asn Gly Asn Gly
                245                 250                 255

Asn Ala Thr Pro Thr Gln Pro Thr Pro Thr Pro Thr Val Thr Pro Thr
            260                 265                 270

Pro Ile Glu Thr Ala Gln Pro Val Thr Thr Thr Thr Ser Thr Arg
        275                 280                 285

Pro Phe Pro Thr Arg Cys Pro Gly Arg Arg Leu Lys Arg Glu Glu Pro
    290                 295                 300
```

Lys Ala
305

<210> SEQ ID NO 149
<211> LENGTH: 1092
<212> TYPE: DNA
<213> ORGANISM: Humicola insolens

<400> SEQUENCE: 149

| | | |
|---|---|---|
| atggctcatc catgggcacg ttgcgtctat acagccatct ggctcgctgc ctccgcttct | 60 |
| ggacgtaggt acaagactcc ggcagtgcca tttatgaacc acaacgtgg actggtcccg | 120 |
| tgctaacaca tcacagactc gcgcgtttgg agtgtctcgg tcaatggacg ctaccaggga | 180 |
| ccgggtgttg atgactacct gcgcgcaccg ccaagtgact ctccggtggt ggacctggac | 240 |
| tcaccaaccc tcaactgcaa tgtcaatgga aacaagcctg ttccagggtt tgttgaggtg | 300 |
| tctgcgggag attctctgga atggaagtgg tactacatca acccgtacaa cccaagcgac | 360 |
| atgatcatcg cggcagaaca ccgcggaccg atcatcacct acatcacgaa ttacaccgat | 420 |
| ggccagcctc aaggagctgt ctggaccaag attgatcacg aaggctacga tcctgtgaca | 480 |
| gaccggttcg ccgtcgacaa cttgatcgcc aacaggggat ggaaagcaat caagcttccc | 540 |
| atgctcgccg acgggaagta catcctgcga caggagatca tcgcactcca cagcgcacac | 600 |
| aaccaaggcg gggcccagct gtatccgaac tgcattcaga tcaaggtcgt tggtggcaag | 660 |
| ggaagcgcgg tgcccaacca gaactttgat ctcaacaagg ggtacacatc cgatcacccg | 720 |
| ggacttcggt tcaacctgtg caaccattc aacaattaca ccattcccgg tcctgaggtc | 780 |
| tggaagggag ttgtggttgc gagcaatggt acaacgaaca gcaccacaaa tctcaccaac | 840 |
| aacaccggca ccggttttgc gaacagcact atggccactg gtgaaacaag gaccgagagg | 900 |
| agttttatga cacttaccgc atcacattca gacactggcg tccccgccaa atctcatact | 960 |
| gtggctgtaa gctggacaac atccgccgcc gttgttgggt ctccgattag cgttaccaca | 1020 |
| actttcagtt cctttaccac aacaccggtt ccgacgaact ctaccggtgc ttatctctac | 1080 |
| cggtacaagt ga | 1092 |

<210> SEQ ID NO 150
<211> LENGTH: 339
<212> TYPE: PRT
<213> ORGANISM: Humicola insolens

<400> SEQUENCE: 150

Met Ala His Pro Trp Ala Arg Cys Val Tyr Thr Ala Ile Trp Leu Ala
1               5                   10                  15

Ala Ser Ala Ser Gly His Ser Arg Val Trp Ser Val Ser Val Asn Gly
            20                  25                  30

Arg Tyr Gln Gly Pro Gly Val Asp Asp Tyr Leu Arg Ala Pro Pro Ser
        35                  40                  45

Asp Ser Pro Val Val Asp Leu Asp Ser Pro Thr Leu Asn Cys Asn Val
    50                  55                  60

Asn Gly Asn Lys Pro Val Pro Gly Phe Val Glu Val Ser Ala Gly Asp
65                  70                  75                  80

Ser Leu Glu Trp Lys Trp Tyr Tyr Ile Asn Pro Tyr Asn Pro Ser Asp
                85                  90                  95

Met Ile Ile Ala Ala Glu His Arg Gly Pro Ile Ile Thr Tyr Ile Thr
            100                 105                 110

Asn Tyr Thr Asp Gly Gln Pro Gln Gly Ala Val Trp Thr Lys Ile Asp
            115                 120                 125

His Glu Gly Tyr Asp Pro Val Thr Asp Arg Phe Ala Val Asp Asn Leu
    130                 135                 140

Ile Ala Asn Arg Gly Trp Lys Ala Ile Lys Leu Pro Met Leu Ala Asp
145                 150                 155                 160

Gly Lys Tyr Ile Leu Arg Gln Glu Ile Ile Ala Leu His Ser Ala His
                165                 170                 175

Asn Gln Gly Gly Ala Gln Leu Tyr Pro Asn Cys Ile Gln Ile Lys Val
            180                 185                 190

Val Gly Gly Lys Gly Ser Ala Val Pro Asn Gln Asn Phe Asp Leu Asn
        195                 200                 205

Lys Gly Tyr Thr Ser Asp His Pro Gly Leu Arg Phe Asn Leu Trp Gln
    210                 215                 220

Pro Phe Asn Asn Tyr Thr Ile Pro Gly Pro Glu Val Trp Lys Gly Val
225                 230                 235                 240

Val Val Ala Ser Asn Gly Thr Thr Asn Ser Thr Thr Asn Leu Thr Asn
                245                 250                 255

Asn Thr Gly Thr Gly Phe Ala Asn Ser Thr Met Ala Thr Gly Glu Thr
            260                 265                 270

Arg Thr Glu Arg Ser Phe Met Thr Leu Thr Ala Ser His Ser Asp Thr
        275                 280                 285

Gly Val Pro Ala Lys Ser His Thr Val Ala Val Ser Trp Thr Thr Ser
    290                 295                 300

Ala Ala Val Val Gly Ser Pro Ile Ser Val Thr Thr Thr Phe Ser Ser
305                 310                 315                 320

Phe Thr Thr Thr Pro Val Pro Thr Asn Ser Thr Gly Ala Tyr Leu Tyr
                325                 330                 335

Arg Tyr Lys

<210> SEQ ID NO 151
<211> LENGTH: 1089
<212> TYPE: DNA
<213> ORGANISM: Trichoderma reesei

<400> SEQUENCE: 151

```
atgatccaga agctttccaa cctccttgtc accgcactgg cggtggctac tggcgttgtc    60
ggacatggac atattaatga cattgtcatc aacggggtgt ggtatcaggc ctatgatcct   120
acaacgtttc atacgagtc aaaccccccc atagtagtgg gctggacggc tgccgacctt   180
gacaacggta cgtgatcctc atctctatct gtacaacgct catgctaatc caactcaata   240
ggcttcgttt cacccgacgc ataccaaaac cctgacatca tctgccacaa gaatgctacg   300
aatgccaagg ggcacgcgtc tgtcaaggcc ggagacacta ttctcttcca gtgggtgcca   360
gttccatggc cgcacccctg tcccattgtc gactacctgg ccaactgcaa tggtgactgc   420
gagaccgttg acaagacgac gcttgagttc ttcaagatcg atggcgttgg tctcctcagc   480
ggcggggatc cgggcaccct ggcctcagac gtgctgatct ccaacaacaa cacctgggtc   540
gtcaagatcc ccgacaatct tgcgccaggc aattacgtgc ccgccacga gatcatcgcg   600
ttacacagcg ccgggcaggc aaacggcgct cagaactacc ccagtgcttt caacattgcc   660
gtctcaggct cgggttctct gcagcccagc ggcgttctag gaccgaccct ctatacgcg   720
acggaccctg tgttctcat caacatctac accagcccgc tcaactacat catccctgga   780
cctaccgtgg tatcaggcct gccaacgagt gttgcccagg ggagctccgc cgcgacggcc   840
```

```
accgccagcg ccactgttcc tggaggcggt agcggcccga ccagcagaac cacgacaacg      900
gcgaggacga cgcaggcctc aagcaggccc agctctacgc ctcccgcaac cacgtcggca      960
cctgctggcg gcccaaccca gactctgtac ggccagtgtg gtggcagcgg ttacagcggg     1020
cctactcgat gcgcgccgcc agccacttgc tctaccttga accctactac gcccagtgc      1080
cttaactag                                                              1089
```

<210> SEQ ID NO 152
<211> LENGTH: 344
<212> TYPE: PRT
<213> ORGANISM: Trichoderma reesei

<400> SEQUENCE: 152

```
Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
            20                  25                  30

Val Trp Tyr Gln Ala Tyr Asp Pro Thr Thr Phe Pro Tyr Glu Ser Asn
        35                  40                  45

Pro Pro Ile Val Val Gly Trp Thr Ala Ala Asp Leu Asp Asn Gly Phe
    50                  55                  60

Val Ser Pro Asp Ala Tyr Gln Asn Pro Asp Ile Ile Cys His Lys Asn
65                  70                  75                  80

Ala Thr Asn Ala Lys Gly His Ala Ser Val Lys Ala Gly Asp Thr Ile
                85                  90                  95

Leu Phe Gln Trp Val Pro Val Pro Trp Pro His Pro Gly Pro Ile Val
            100                 105                 110

Asp Tyr Leu Ala Asn Cys Asn Gly Asp Cys Glu Thr Val Asp Lys Thr
        115                 120                 125

Thr Leu Glu Phe Phe Lys Ile Asp Gly Val Gly Leu Leu Ser Gly Gly
    130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
            180                 185                 190

Gln Asn Tyr Pro Gln Cys Phe Asn Ile Ala Val Ser Gly Ser Gly Ser
        195                 200                 205

Leu Gln Pro Ser Gly Val Leu Gly Thr Asp Leu Tyr His Ala Thr Asp
    210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Val Pro Gly Gly Gly
            260                 265                 270

Ser Gly Pro Thr Ser Arg Thr Thr Thr Ala Arg Thr Thr Gln Ala
        275                 280                 285

Ser Ser Arg Pro Ser Ser Thr Pro Ala Thr Thr Ser Ala Pro Ala
    290                 295                 300

Gly Gly Pro Thr Gln Thr Leu Tyr Gly Gln Cys Gly Gly Ser Gly Tyr
305                 310                 315                 320
```

Ser Gly Pro Thr Arg Cys Ala Pro Pro Ala Thr Cys Ser Thr Leu Asn
            325                 330                 335

Pro Tyr Tyr Ala Gln Cys Leu Asn
            340

<210> SEQ ID NO 153
<211> LENGTH: 1398
<212> TYPE: DNA
<213> ORGANISM: Penicillium emersonii

<400> SEQUENCE: 153

```
atgtttggat tcaagtctac taccttggct gtttggatgc tcagtcttcc ggcaacatcg      60
catgcccaca ctgtcatgac cacactgttt gtcgatggcg tcaaccaggg agacggtgtc     120
tgtatccgta tgaacaagaa cggctctacg tccaatttct tcgtcagtcc tgtcagtagc     180
agggacgttg cttgtggtag ggaaaaagag caccaatccc tacatgtact ctacttttgt     240
tttcaaaaca taagaactga caagcaaaaa ggaatcgatg agaaatcgg tgtcgcaaga      300
gtctgtccgg ccaaggcctc gtcgatcctg accttcgagt ccgcgaaca tcccgacaac      360
gtgagctctg cacctctcga tccctcacac aagggtcccg cgtcggtgta cttgaagaag     420
gtcgattccg ccatcgccag caacaacgcc gcaggagacg gtggttcaa gatctgggaa      480
tccgtctacg acgagacgtc agacaaatgg ggcacgacga agatgatcga gaacgatgga     540
cacatctccg ttcagatccc ggaggagatt gaggagggt actatctcgc gcgaacggag      600
cttctggcgc ttcacgcggc gagctcgaat ccgcccaatc cgcagttctt gtcggctgc      660
gcgcagctct tcatcgagtc gaatgggacc gcaaagccgt cgactgttcg catcggtgag     720
ggtacctata acctgtccat gccgggactg acctacaata tctgggaaaa gccgctgtcc     780
ctgccgtatg cgatggttgg tccgacggtt tacagagctg gctcggggc tagctcatca      840
gcagtcgctc ccacggcagc gagtgctact gctgctgcta ccgttacgca ggcggtagct     900
ccattaccaa ctaccagtgc tccaagttca acaaaatg tcggctcatg cggagttgtt      960
gttgcggacg agatagaaaa gcgagacact ctcgttcaga cggaaggact caagccagaa    1020
ggctgcatct tgtcaatgg taactggtgc ggtttcgaag tgccttcgta cacggaccaa     1080
gacagctgct gggccgtaag tctcttgctt tcaccttact actttttttt ttcttttcgaa   1140
agaaaaatga aaaatgtgac caagctgaca acctgtctcc atataatata gtcatcgaac    1200
aactgctggg cccaatccga cgactgctgg aacaagacac aaccgacggg atacaacctc    1260
tgtccgatct ggcaggccaa atgccgagag atctccaacg ggtgcgagaa agggacttgg   1320
acggggcctc ctcatcaggg agaggacatg actccgtcgt ggccgtcgtt gaggggggaa   1380
ttgaagatct ttacctga                                                  1398
```

<210> SEQ ID NO 154
<211> LENGTH: 408
<212> TYPE: PRT
<213> ORGANISM: Penicillium emersonii

<400> SEQUENCE: 154

Met Phe Gly Phe Lys Ser Thr Thr Leu Ala Val Trp Met Leu Ser Leu
1               5                   10                  15

Pro Ala Thr Ser His Ala His Thr Val Met Thr Thr Leu Phe Val Asp
            20                  25                  30

Gly Val Asn Gln Gly Asp Gly Val Cys Ile Arg Met Asn Lys Asn Gly
        35                  40                  45

```
Ser Thr Ser Asn Phe Phe Val Ser Pro Val Ser Ser Arg Asp Val Ala
    50                  55                  60

Cys Gly Ile Asp Gly Glu Ile Gly Val Ala Arg Val Cys Pro Ala Lys
65                  70                  75                  80

Ala Ser Ser Ile Leu Thr Phe Glu Phe Arg Glu His Pro Asp Asn Val
                85                  90                  95

Ser Ser Ala Pro Leu Asp Pro Ser His Lys Gly Pro Ala Ser Val Tyr
            100                 105                 110

Leu Lys Lys Val Asp Ser Ala Ile Ala Ser Asn Asn Ala Ala Gly Asp
        115                 120                 125

Gly Trp Phe Lys Ile Trp Glu Ser Val Tyr Asp Glu Thr Ser Asp Lys
    130                 135                 140

Trp Gly Thr Thr Lys Met Ile Glu Asn Asp Gly His Ile Ser Val Gln
145                 150                 155                 160

Ile Pro Glu Glu Ile Glu Gly Gly Tyr Tyr Leu Ala Arg Thr Glu Leu
                165                 170                 175

Leu Ala Leu His Ala Ala Ser Ser Asn Pro Pro Asn Pro Gln Phe Phe
            180                 185                 190

Val Gly Cys Ala Gln Leu Phe Ile Glu Ser Asn Gly Thr Ala Lys Pro
        195                 200                 205

Ser Thr Val Arg Ile Gly Glu Gly Thr Tyr Asn Leu Ser Met Pro Gly
    210                 215                 220

Leu Thr Tyr Asn Ile Trp Glu Lys Pro Leu Ser Leu Pro Tyr Ala Met
225                 230                 235                 240

Val Gly Pro Thr Val Tyr Arg Ala Gly Ser Gly Ala Ser Ser Ser Ala
                245                 250                 255

Val Ala Pro Thr Ala Ala Ser Ala Thr Ala Ala Thr Val Thr Gln
            260                 265                 270

Ala Val Ala Pro Leu Pro Thr Thr Ser Ala Pro Ser Ser Gln Gln Asn
        275                 280                 285

Val Gly Ser Cys Gly Val Val Ala Asp Glu Ile Glu Lys Arg Asp
    290                 295                 300

Thr Leu Val Gln Thr Glu Gly Leu Lys Pro Glu Gly Cys Ile Phe Val
305                 310                 315                 320

Asn Gly Asn Trp Cys Gly Phe Glu Val Pro Ser Tyr Thr Asp Gln Asp
                325                 330                 335

Ser Cys Trp Ala Ser Ser Asn Asn Cys Trp Ala Gln Ser Asp Asp Cys
            340                 345                 350

Trp Asn Lys Thr Gln Pro Thr Gly Tyr Asn Leu Cys Pro Ile Trp Gln
        355                 360                 365

Ala Lys Cys Arg Glu Ile Ser Asn Gly Cys Lys Gly Thr Trp Thr
    370                 375                 380

Gly Pro Pro His Gln Gly Glu Asp Met Thr Pro Ser Trp Pro Ser Leu
385                 390                 395                 400

Arg Gly Glu Leu Lys Ile Phe Thr
                405

<210> SEQ ID NO 155
<211> LENGTH: 902
<212> TYPE: DNA
<213> ORGANISM: Malbranchea cinnamomea

<400> SEQUENCE: 155
atgagaattg aaaagcttct aaacgctgcg ctcctcgctg agcagtatc tgctcacacc    60
```

-continued

```
atcatgacca gcttggttgt tgatggaacc gaatatcgta tgttcaatct caccttgagc    120
tttcttttca cactagtttg ttgagaatct ggccattttc agctcctgga catgctgtcc    180
gcatcccaag ttacaacggg gtatgcatgt ggatgggctc tgtttcctat taagagcccc    240
atgagctgat cgccttgaca tagcccatta ccgatgtcac ctccaacagc gtggcttgca    300
atggtccccc taatcccact acccctagct ccgagatcat catggtccgg ctggatcga    360 ctatccaggg gaaatggaga cataccgaga ccgacgtgat tgacccaagc cacaaggtat    420
gactataccg ccacgagaga tatccttgac tcacttacac cctctttcta acctctctat    480
attagggccc cgtaatggcg tacctgaaga aagtcgacga cgccatcaac gaccctggaa    540
cgggtgacgg ctggttcaag atttgggaag acggcctgca cgacgatggc acctgggccg    600
tcgacgacct catcgccgcc aacggttacc aggacattcc catcccccca tgtctcgcgg    660
acggccagta cttgctgcgg gctgagatca ttgctctgca tggtgctagc cagccgggtg    720
gtgcgcaact gtatatggaa tgcgcccaga tcggagttgt gggtggctct ggaacagcta    780
acccgtccac agttgcgttc cccggcgcct acaaggccga tgatcctggc atcactgtca    840
acatttattg gccgcctctt gaggaataca tcattcctgg tcctgaccca ttcacctgct    900
aa                                                                   902
```

<210> SEQ ID NO 156
<211> LENGTH: 234
<212> TYPE: PRT
<213> ORGANISM: Malbranchea cinnamomea

<400> SEQUENCE: 156

```
Met Arg Ile Glu Lys Leu Leu Asn Ala Ala Leu Leu Ala Gly Ala Val
1               5                   10                  15

Ser Ala His Thr Ile Met Thr Ser Leu Val Val Asp Gly Thr Glu Tyr
            20                  25                  30

Pro Pro Gly His Ala Val Arg Ile Pro Ser Tyr Asn Gly Pro Ile Thr
        35                  40                  45

Asp Val Thr Ser Asn Ser Val Ala Cys Asn Gly Pro Pro Asn Pro Thr
    50                  55                  60

Thr Pro Ser Ser Glu Ile Ile Met Val Arg Ala Gly Ser Thr Ile Gln
65                  70                  75                  80

Gly Lys Trp Arg His Thr Glu Thr Asp Val Ile Asp Pro Ser His Lys
                85                  90                  95

Gly Pro Val Met Ala Tyr Leu Lys Lys Val Asp Asp Ala Ile Asn Asp
            100                 105                 110

Pro Gly Thr Gly Asp Gly Trp Phe Lys Ile Trp Glu Asp Gly Leu His
        115                 120                 125

Asp Asp Gly Thr Trp Ala Val Asp Leu Ile Ala Ala Asn Gly Tyr
    130                 135                 140

Gln Asp Ile Pro Ile Pro Pro Cys Leu Ala Asp Gly Gln Tyr Leu Leu
145                 150                 155                 160

Arg Ala Glu Ile Ile Ala Leu His Gly Ala Ser Gln Pro Gly Gly Ala
                165                 170                 175

Gln Leu Tyr Met Glu Cys Ala Gln Ile Gly Val Val Gly Gly Ser Gly
            180                 185                 190

Thr Ala Asn Pro Ser Thr Val Ala Phe Pro Gly Ala Tyr Lys Ala Asp
        195                 200                 205

Asp Pro Gly Ile Thr Val Asn Ile Tyr Trp Pro Pro Leu Glu Glu Tyr
    210                 215                 220
```

Ile Ile Pro Gly Pro Asp Pro Phe Thr Cys
225                 230

<210> SEQ ID NO 157
<211> LENGTH: 810
<212> TYPE: DNA
<213> ORGANISM: Malbranchea cinnamomea

<400> SEQUENCE: 157

| | | |
|---|---|---|
| atgcttccga acgcagctgg tctgcttgta gcaggtgtcg tctctctttc tggagtagcc | 60 |
| gcacatggac atgtctcgaa aattttcctg gacggccagg agtaagccaa ttgtgcgtca | 120 |
| ttttttagt atccgttggt taatcattga tttgtattcc tcagatacgg tggttggatc | 180 |
| gccgatgtct atccgtacat gcccgaaccc cagagacaa ttggctggcc tacaaatgtg | 240 |
| accgacaatg gcttcgtgtc ccccgacagg ttcagctctc agaaatcat ctgtcaccgc | 300 |
| gggggcgttc caagcgccat ctcggcgccc gtttccgcgg cgggaccgt cgagttggaa | 360 |
| tggagcacgt ggcccgagag ccatcatggt cctgtgctca actaccttgc caaggtcgac | 420 |
| ggcgacttca gcacatcgg ccccagcacg ctccagttct tcaagtttga cgagaccggc | 480 |
| cttgtatccg gctcaaaccc agggtactgg ggtacggatg tgatgctcgc gaatggccgg | 540 |
| cggtactcca tgatgatccc aagcaccatc gctcccggga agtacgtctt cgccatgag | 600 |
| ctcgtcgccc tgcagaacgt cggcgccgcc cagctgtacc gcagtgtat caacattgaa | 660 |
| gtgacaagta ataccactgg aggagacgtc aaccccggcg gtacgcctgc taccgagctc | 720 |
| tactctcctg cggaccccgg tttcttgttc aacatctacg aacagtatga ttcgtaccca | 780 |
| attcccggtc cggatgtttt ccgcgattaa | 810 |

<210> SEQ ID NO 158
<211> LENGTH: 248
<212> TYPE: PRT
<213> ORGANISM: Malbranchea cinnamomea

<400> SEQUENCE: 158

Met Leu Pro Asn Ala Ala Gly Leu Leu Val Ala Gly Val Val Ser Leu
1               5                   10                  15

Ser Gly Val Ala Ala His Gly His Val Ser Lys Ile Phe Leu Asp Gly
                20                  25                  30

Gln Glu Tyr Gly Gly Trp Ile Ala Asp Val Tyr Pro Tyr Met Pro Glu
            35                  40                  45

Pro Pro Glu Thr Ile Gly Trp Pro Thr Asn Val Thr Asp Asn Gly Phe
        50                  55                  60

Val Ser Pro Asp Arg Phe Ser Ser Pro Glu Ile Ile Cys His Arg Gly
65                  70                  75                  80

Gly Val Pro Ser Ala Ile Ser Ala Pro Val Ser Ala Gly Gly Thr Val
                85                  90                  95

Glu Leu Glu Trp Ser Thr Trp Pro Glu Ser His Gly Pro Val Leu
            100                 105                 110

Asn Tyr Leu Ala Lys Val Asp Gly Asp Phe Ser Asp Ile Gly Pro Ser
        115                 120                 125

Thr Leu Gln Phe Phe Lys Phe Asp Glu Thr Gly Leu Val Ser Gly Ser
    130                 135                 140

Asn Pro Gly Tyr Trp Gly Thr Asp Val Met Leu Ala Asn Gly Arg Arg
145                 150                 155                 160

Tyr Ser Met Met Ile Pro Ser Thr Ile Ala Pro Gly Lys Tyr Val Leu

```
                165                 170                 175
Arg His Glu Leu Val Ala Leu Gln Asn Val Gly Ala Ala Gln Leu Tyr
            180                 185                 190

Pro Gln Cys Ile Asn Ile Glu Val Thr Ser Asn Thr Thr Gly Gly Asp
        195                 200                 205

Val Asn Pro Gly Gly Thr Pro Ala Thr Glu Leu Tyr Ser Pro Ala Asp
    210                 215                 220

Pro Gly Phe Leu Phe Asn Ile Tyr Glu Gln Tyr Asp Ser Tyr Pro Ile
225                 230                 235                 240

Pro Gly Pro Asp Val Phe Arg Asp
                245

<210> SEQ ID NO 159
<211> LENGTH: 729
<212> TYPE: DNA
<213> ORGANISM: Malbranchea cinnamomea

<400> SEQUENCE: 159
atggttcagt ttaagctgag cacggcctct cttctggctc ttgcctccta cgccgccgcc      60
cacggctacg tgagctcgat ccaagccgac ggacagacct atcccggcgc tgatccacac     120
aaccccaacc cagagtcccc cggctggcag gcggagaaca ccgatctggg cttcgtcgag     180
ccctccgcct tctcgacccc cgccatcgcc tgccacaaga cgcgcgggc tccgcccgcc     240 cacgcgaccg tccaggccgg gagcaccatc aagctgacgt ggaacacctg gccggagtcg     300
caccacggac ccgtgctcga ctacatcgcg ccgtgcaacg cgactgctc tagcgcgtcg      360 gcgggctcgc tgaacttcgt caagatcgcc gagaagggcc tgatctccgg ctccaaccca     420
ggcttctggg ccgccgacga gctgatccag aacggcaact cgtgggaggt caccatcccc     480
gcgaacctgg cgccgggcaa gtacgtgctg cgccacgaga tcatcgcgct gcactcggcc     540
ggcaacccca acggcgccca ggcctacccg cagtgcatca cctcgaggt cactggcggc     600 ggctccgcga ctccctctgg ccagccggcg acttcgttct actccccaa cgaccccggc      660 atcctgttca acctgtacca gtcgttcgac tcctacccga tccccggccc cgccgtgtgg     720
agcggttaa                                                             729

<210> SEQ ID NO 160
<211> LENGTH: 242
<212> TYPE: PRT
<213> ORGANISM: Malbranchea cinnamomea

<400> SEQUENCE: 160

Met Val Gln Phe Lys Leu Ser Thr Ala Ser Leu Leu Ala Leu Ala Ser
1               5                   10                  15

Tyr Ala Ala Ala His Gly Tyr Val Ser Ser Ile Gln Ala Asp Gly Gln
            20                  25                  30

Thr Tyr Pro Gly Ala Asp Pro His Asn Pro Asn Pro Glu Ser Pro Gly
        35                  40                  45

Trp Gln Ala Glu Asn Thr Asp Leu Gly Phe Val Glu Pro Ser Ala Phe
    50                  55                  60

Ser Thr Pro Ala Ile Ala Cys His Lys Asn Ala Arg Ala Pro Pro Ala
65                  70                  75                  80

His Ala Thr Val Gln Ala Gly Ser Thr Ile Lys Leu Thr Trp Asn Thr
                85                  90                  95

Trp Pro Glu Ser His His Gly Pro Val Leu Asp Tyr Ile Ala Pro Cys
            100                 105                 110
```

Asn Gly Asp Cys Ser Ser Ala Ser Ala Gly Ser Leu Asn Phe Val Lys
        115                 120                 125

Ile Ala Glu Lys Gly Leu Ile Ser Gly Ser Asn Pro Gly Phe Trp Ala
    130                 135                 140

Ala Asp Glu Leu Ile Gln Asn Gly Asn Ser Trp Glu Val Thr Ile Pro
145                 150                 155                 160

Ala Asn Leu Ala Pro Gly Lys Tyr Val Leu Arg His Glu Ile Ala
                165                 170                 175

Leu His Ser Ala Gly Asn Pro Asn Gly Ala Gln Ala Tyr Pro Gln Cys
            180                 185                 190

Ile Asn Leu Glu Val Thr Gly Gly Gly Ser Ala Thr Pro Ser Gly Gln
        195                 200                 205

Pro Ala Thr Ser Phe Tyr Ser Pro Asn Asp Pro Gly Ile Leu Phe Asn
    210                 215                 220

Leu Tyr Gln Ser Phe Asp Ser Tyr Pro Ile Pro Gly Pro Ala Val Trp
225                 230                 235                 240

Ser Gly

<210> SEQ ID NO 161
<211> LENGTH: 1081
<212> TYPE: DNA
<213> ORGANISM: Malbranchea cinnamomea

<400> SEQUENCE: 161

```
atgtcaccct ccttcaagtc cactgccatc ctcggagccg ttgctctggc cgcccgcgtg      60
cgcgcccacg gctacgtgtc tggaatcgtc gttgacggtg cttagtacgt ctgcatgttc     120
ctctcttcgt tacaggtaac atctttcttg gtattgctcg tgctgaccct tttctttcag     180
ccatggcggt tacatcgtcg acaagtaccc ctacatgccc aacccgcccg atgtggtcgg     240
ctggtcgact acggccacgg acctgggctt cgtcgcccct gacgcctttg gcgacccgga     300
catcatctgc caccgggacg gtgccccgg tgccatccac gccaaagtca acgccggtgc     360
caccatcgag ctgcagtgga cacctggcc cgagagccac cacggtcccg tcatcgacta     420
cctggctaac tgcaacggtg actgctcgtc cgtcgacaag acctcgctca agttcttcaa     480
gatcagcgag gccggcctaa cgacggctc caacgccccc ggccagtggg cgtccgacga     540
tctcattgcc aacaacaaca gctggactgt gaccatcccc aagtcgatcg ccccgggcaa     600
ctacgtgctg cgccacgaga tcatcgccct gcacagcgcc ggcaaccaga tggcgcgca     660
gaactacccc cagtgcttca acctcgagat caccagcaac ggcagcgaca cccggaggg     720
cgtgctggga accgagctgt acaaggccga cgacccgggc attctgttca acatctacca     780
gcccatggac tcgtacccga ttcccggccc tgctctctac accggcggct cttctcctc     840
ccctaatccg cccacctcta cccagtcgcc tgtgccccag cccacccagt ctcccccatc     900
gggcagcaac cccggcaacg caacggcga cgacgacaac gacaacggca acgagacccc     960
atccccgtct ctccccgtcg agatccctga cgacctgacc tcgcgcgagc tactcctcgt    1020
ggcccaggag atcattgccc gtctgcttga gctgcagaat cagctggtcg tctcgaacta    1080
a                                                                    1081
```

<210> SEQ ID NO 162
<211> LENGTH: 334
<212> TYPE: PRT
<213> ORGANISM: Malbranchea cinnamomea

<400> SEQUENCE: 162

| | | | | | | | | | | | | | | |
|---|---|---|---|---|---|---|---|---|---|---|---|---|---|---|
| Met | Ser | Pro | Ser | Phe | Lys | Ser | Thr | Ala | Ile | Leu | Gly | Ala | Val | Ala | Leu |
| 1 | | | | 5 | | | | | 10 | | | | | 15 | |
| Ala | Ala | Arg | Val | Arg | Ala | His | Gly | Tyr | Val | Ser | Gly | Ile | Val | Val | Asp |
| | | | 20 | | | | | 25 | | | | | 30 | | |
| Gly | Ala | Tyr | His | Gly | Gly | Tyr | Ile | Val | Asp | Lys | Tyr | Pro | Tyr | Met | Pro |
| | | 35 | | | | | 40 | | | | | 45 | | | |
| Asn | Pro | Pro | Asp | Val | Val | Gly | Trp | Ser | Thr | Thr | Ala | Thr | Asp | Leu | Gly |
| | 50 | | | | | 55 | | | | | 60 | | | | |
| Phe | Val | Ala | Pro | Asp | Ala | Phe | Gly | Asp | Pro | Asp | Ile | Ile | Cys | His | Arg |
| 65 | | | | | 70 | | | | | 75 | | | | | 80 |
| Asp | Gly | Ala | Pro | Gly | Ala | Ile | His | Ala | Lys | Val | Asn | Ala | Gly | Ala | Thr |
| | | | | 85 | | | | | 90 | | | | | 95 | |
| Ile | Glu | Leu | Gln | Trp | Asn | Thr | Trp | Pro | Glu | Ser | His | His | Gly | Pro | Val |
| | | | 100 | | | | | 105 | | | | | 110 | | |
| Ile | Asp | Tyr | Leu | Ala | Asn | Cys | Asn | Gly | Asp | Cys | Ser | Ser | Val | Asp | Lys |
| | | | | 115 | | | | | 120 | | | | | 125 | |
| Thr | Ser | Leu | Lys | Phe | Phe | Lys | Ile | Ser | Glu | Ala | Gly | Leu | Asn | Asp | Gly |
| | 130 | | | | | 135 | | | | | 140 | | | | |
| Ser | Asn | Ala | Pro | Gly | Gln | Trp | Ala | Ser | Asp | Asp | Leu | Ile | Ala | Asn | Asn |
| 145 | | | | | 150 | | | | | 155 | | | | | 160 |
| Asn | Ser | Trp | Thr | Val | Thr | Ile | Pro | Lys | Ser | Ile | Ala | Pro | Gly | Asn | Tyr |
| | | | | 165 | | | | | 170 | | | | | 175 | |
| Val | Leu | Arg | His | Glu | Ile | Ile | Ala | Leu | His | Ser | Ala | Gly | Asn | Gln | Asn |
| | | | 180 | | | | | 185 | | | | | 190 | | |
| Gly | Ala | Gln | Asn | Tyr | Pro | Gln | Cys | Phe | Asn | Leu | Glu | Ile | Thr | Ser | Asn |
| | | | | 195 | | | | | 200 | | | | | 205 | |
| Gly | Ser | Asp | Asn | Pro | Glu | Gly | Val | Leu | Gly | Thr | Glu | Leu | Tyr | Lys | Ala |
| | 210 | | | | | 215 | | | | | 220 | | | | |
| Asp | Asp | Pro | Gly | Ile | Leu | Phe | Asn | Ile | Tyr | Gln | Pro | Met | Asp | Ser | Tyr |
| 225 | | | | | 230 | | | | | 235 | | | | | 240 |
| Pro | Ile | Pro | Gly | Pro | Ala | Leu | Tyr | Thr | Gly | Gly | Ser | Ser | Pro | Ser | Pro |
| | | | | 245 | | | | | 250 | | | | | 255 | |
| Asn | Pro | Pro | Thr | Ser | Thr | Gln | Ser | Pro | Val | Pro | Gln | Pro | Thr | Gln | Ser |
| | | | 260 | | | | | 265 | | | | | 270 | | |
| Pro | Pro | Ser | Gly | Ser | Asn | Pro | Gly | Asn | Gly | Asn | Gly | Asp | Asp | Asp | Asn |
| | | 275 | | | | | 280 | | | | | 285 | | | |
| Asp | Asn | Gly | Asn | Glu | Thr | Pro | Ser | Pro | Ser | Leu | Pro | Val | Glu | Ile | Pro |
| | 290 | | | | | 295 | | | | | 300 | | | | |
| Asp | Asp | Leu | Thr | Ser | Arg | Glu | Leu | Leu | Leu | Val | Ala | Gln | Glu | Ile | Ile |
| 305 | | | | | 310 | | | | | 315 | | | | | 320 |
| Ala | Arg | Leu | Leu | Glu | Leu | Gln | Asn | Gln | Leu | Val | Val | Ser | Asn | | |
| | | | | 325 | | | | | 330 | | | | | | |

<210> SEQ ID NO 163
<211> LENGTH: 875
<212> TYPE: DNA
<213> ORGANISM: Malbranchea cinnamomea

<400> SEQUENCE: 163

```
atgaagacgc tctctgcggg tctccttgcg cttgccagcg ctgccagcgc tcactgtccg      60
tccagccttc ccttgctctc tcctgacatt cgcgccagca tttccatcag gtccaataaa     120
actaacacac gagccatggg acgacggtca tagacacctt cccctccctg atcgccaacg     180
```

```
gcgtcgtcac cggcgaatgg gagtatgtcc ggcagacgga gaaccattac tcaaacgccc    240
ccgtcaccga cgtctccagc gaggccatcc gctgctacga gaatcccggg cggcccgccg    300
caaagaccct gagcgttgcc gccggctcga ccgtgggctt caccgtctcc cccagcatct    360
accaccgggg cccactgcag ttctacatgg ccagggtgcc cgacggccag accgcggact    420
cgtgggacgg cagcgggcag gtgtggttca agatcttcga gcagggaccg cagatcgatc    480
cgtcgggatt gacgtggccg agtgacggtg cgacgagaaa accccctttt ttttttttt     540 tttttttttt tccctctcgc catctgctaa ctgcgagtga actggctcta ggactctccc    600
aggtccaagt caccatcccc agctccctcc cgtcgggcga ctacctgctg cgcgtcgagc    660
agattggcct gcactccgcg tcgtccgtca acggcgccca gttctacctc tcctgcgcac    720
agctcaccgt caccggcggc ggaaacggga acccaggccc gctcgtctcg ttcccgggcg    780
cgtacagccc cacggacccg ggtctgctga tcaacatcta ctggccgatt ccgaccagct    840
acgagctgcc cgggccaccg gtgtggcgcg gttag                                875
```

<210> SEQ ID NO 164
<211> LENGTH: 230
<212> TYPE: PRT
<213> ORGANISM: Malbranchea cinnamomea

<400> SEQUENCE: 164

Met Lys Thr Leu Ser Ala Gly Leu Leu Ala Leu Ala Ser Ala Ala Ser
1               5                   10                  15

Ala His Tyr Thr Phe Pro Ser Leu Ile Ala Asn Gly Val Val Thr Gly
                20                  25                  30

Glu Trp Glu Tyr Val Arg Gln Thr Glu Asn His Tyr Ser Asn Ala Pro
            35                  40                  45

Val Thr Asp Val Ser Ser Glu Ala Ile Arg Cys Tyr Glu Asn Pro Gly
        50                  55                  60

Arg Pro Ala Ala Lys Thr Leu Ser Val Ala Ala Gly Ser Thr Val Gly
65                  70                  75                  80

Phe Thr Val Ser Pro Ser Ile Tyr His Pro Gly Pro Leu Gln Phe Tyr
                85                  90                  95

Met Ala Arg Val Pro Asp Gly Gln Thr Ala Asp Ser Trp Asp Gly Ser
            100                 105                 110

Gly Gln Val Trp Phe Lys Ile Phe Glu Gln Gly Pro Gln Ile Asp Pro
        115                 120                 125

Ser Gly Leu Thr Trp Pro Ser Asp Gly Leu Ser Gln Val Gln Val Thr
130                 135                 140

Ile Pro Ser Ser Leu Pro Ser Gly Asp Tyr Leu Leu Arg Val Glu Gln
145                 150                 155                 160

Ile Gly Leu His Ser Ala Ser Ser Val Asn Gly Ala Gln Phe Tyr Leu
                165                 170                 175

Ser Cys Ala Gln Leu Thr Val Thr Gly Gly Gly Asn Gly Asn Pro Gly
            180                 185                 190

Pro Leu Val Ser Phe Pro Gly Ala Tyr Ser Pro Thr Asp Pro Gly Leu
        195                 200                 205

Leu Ile Asn Ile Tyr Trp Pro Ile Pro Thr Ser Tyr Glu Leu Pro Gly
    210                 215                 220

Pro Pro Val Trp Arg Gly
225                 230

<210> SEQ ID NO 165

<211> LENGTH: 1194
<212> TYPE: DNA
<213> ORGANISM: Malbranchea cinnamomea

<400> SEQUENCE: 165

```
atgcggttct cagccgtggc cgcggttggc tttctgatgg gcaccgccag cgcacacatg      60
aagatgaaga ctccatatcc atttggcccc gacacgctca acaccagccc cctccaggca     120
aacctgaccg acttcccctg caagcacaga cccggcgtct acgacccacc gctactccca     180
caccccgacg cgaataccct taccgtcggc gtccccgtca ccctcagctt catcggcagc     240
gccgtccacg gcggcggctc gtgtcagatc agcctgacca cggaccgaca gccgaccagg     300
gactcggtct ggaaggtcat ccactccatc gagggcggct gtcccgccaa caccgacggc     360
aacctgggag gcggcgcgga cgccgaggtc gccagcacct tcgagttcca gattccccc      420
agcattccgc ccggcgagta cacgctggcg tggacctggc tcaaccgcct cggcaaccgc     480
gagttctaca tgaactgcgc cccgatcacc gtcgtcgcgc caagaagcg atacgccccg      540
tcgtcgtcgt cgtcggaccc gcggcccctt gcgtccctcg cccagcgcca ggacctcccg     600
gacatgttca tcgcgaacat caacggctgc acgaccgagg agggcatcga cgtgcgcttc     660
cccgaccccg cccctccgt cgaacgcgca gggaaccca gcaggctcct ggcgagcggc       720
gaggtgatct gcaagatgcg cggcagcgac acgggaccca tcgcgggggg tggcagcggc     780
ggcggagacg aggcaacga ctcggaggcc agcccagctc ccagtcaaga tcctcacccc      840
agttcaaacc caagccccga cccgaatcca gacccggacc cgcagtgcct gccgccagcg     900
ccatcaacat caaccgcgtc gaccccgacg tctccgtcgg cgacaccacc cgcctccccg     960
tcctccaccg gcgacagcgg cgacggtggc ccggggctca ccggctcctg caccgagggc    1020
tggttcaact gcatcggcgg cacgcacttc cagcagtgca cggccagcgg gcagtggagc    1080
gtcgcgcggc ccgtggcccc gggcacggtc tgccgcgaag agtgggggcc tgatctgcag    1140
atcggttatg ccaaggggga cgacgttaga ggcgtccgtc gggcgcaccg ctga           1194
```

<210> SEQ ID NO 166
<211> LENGTH: 397
<212> TYPE: PRT
<213> ORGANISM: Malbranchea cinnamomea

<400> SEQUENCE: 166

```
Met Arg Phe Ser Ala Val Ala Val Gly Phe Leu Met Gly Thr Ala
1               5                   10                  15

Ser Ala His Met Lys Met Lys Thr Pro Tyr Pro Phe Gly Pro Asp Thr
            20                  25                  30

Leu Asn Thr Ser Pro Leu Gln Ala Asn Leu Thr Asp Phe Pro Cys Lys
        35                  40                  45

His Arg Pro Gly Val Tyr Asp Pro Pro Leu Leu Pro His Pro Asp Ala
    50                  55                  60

Asn Thr Phe Thr Val Gly Val Pro Val Thr Leu Ser Phe Ile Gly Ser
65                  70                  75                  80

Ala Val His Gly Gly Gly Ser Cys Gln Ile Ser Leu Thr Thr Asp Arg
                85                  90                  95

Gln Pro Thr Arg Asp Ser Val Trp Lys Val Ile His Ser Ile Glu Gly
            100                 105                 110

Gly Cys Pro Ala Asn Thr Asp Gly Asn Leu Gly Gly Gly Ala Asp Ala
        115                 120                 125

Glu Val Ala Ser Thr Phe Glu Phe Gln Ile Pro Pro Ser Ile Pro Pro
```

```
            130                 135                 140
Gly Glu Tyr Thr Leu Ala Trp Thr Trp Leu Asn Arg Leu Gly Asn Arg
145                 150                 155                 160

Glu Phe Tyr Met Asn Cys Ala Pro Ile Thr Val Ala Pro Lys Lys
                165                 170                 175

Arg Tyr Ala Pro Ser Ser Ser Ser Asp Pro Arg Pro Leu Ala Ser
            180                 185                 190

Leu Ala Gln Arg Gln Asp Leu Pro Asp Met Phe Ile Ala Asn Ile Asn
                195                 200                 205

Gly Cys Thr Thr Glu Glu Gly Ile Asp Val Arg Phe Pro Asp Pro Gly
            210                 215                 220

Pro Ser Val Glu Arg Ala Gly Asn Pro Ser Arg Leu Leu Ala Ser Gly
225                 230                 235                 240

Glu Val Ile Cys Lys Met Arg Gly Ser Asp Thr Gly Pro Ile Ala Gly
                245                 250                 255

Gly Gly Ser Gly Gly Gly Asp Gly Gly Asn Asp Ser Glu Ala Ser Pro
            260                 265                 270

Ala Pro Ser Gln Asp Pro His Pro Ser Ser Asn Pro Ser Pro Asp Pro
                275                 280                 285

Asn Pro Asp Pro Asp Pro Gln Cys Leu Pro Pro Ala Pro Ser Thr Ser
290                 295                 300

Thr Ala Ser Thr Pro Thr Ser Pro Ser Ala Thr Pro Pro Ala Ser Pro
305                 310                 315                 320

Ser Ser Thr Gly Asp Ser Gly Asp Gly Gly Pro Gly Leu Thr Gly Ser
                325                 330                 335

Cys Thr Glu Gly Trp Phe Asn Cys Ile Gly Gly Thr His Phe Gln Gln
            340                 345                 350

Cys Thr Ala Ser Gly Gln Trp Ser Val Ala Arg Pro Val Ala Pro Gly
                355                 360                 365

Thr Val Cys Arg Glu Gly Val Gly Pro Asp Leu Gln Ile Gly Tyr Ala
            370                 375                 380

Lys Gly Asp Asp Val Arg Gly Val Arg Arg Ala His Arg
385                 390                 395

<210> SEQ ID NO 167
<211> LENGTH: 1233
<212> TYPE: DNA
<213> ORGANISM: Malbranchea cinnamomea

<400> SEQUENCE: 167
atgcgtttct cggcttccac cgttgcagca gcggctgctt tcctgtccgc tggggttgtc      60
aacgcccata tgaacatgaa gtttccctat ccatatgggc ctgatactct gaacaacagc     120
cctcttcaga caacctcgc cgactttccc tgcaagcaac ggcctggagt gtatgaccct      180
ccagcgctcc ccagtcctga tgccaacacc ctcaccatcg cgtccctgc gaccctggag      240 ttccttggcg atgctgtcca tggtggtggt tcttgccaaa tcagcttgac aactgacaag     300
gagcctacca aagactctgt ctggaaggtt atccattcca ttgagggtgg atgccctgcc     360
aacactgaag gaaccttgg aagtgatcca aagggagaac gtgccagcaa gttccagttc      420
actatccctc ccagcatcgc accaggcgag tatactctgg cttggacctg atcaaccgc      480 attggtaacc gcgagtatta tatggactgc gccccaatca gagttcaaga agcgcccaag     540
aagcggtata ccccaacccc gccaactgag ccacgaagcc tgattccctt ggcgaaacgt     600
gacgaccttc ctgatatgtt tatcgccaac atcaacggct gcaataccccc tgaaggtatc     660
```

```
gacatccgtt acccaaaccc cggtccttct attgagtatg cgggcaatcc catgaacctt    720
atgaaggtcg gtgagccagt ttgcgtgtac gcagatggca ctcctggccc tcttgctgga    780
ggtgaagagg gtggtgacgg tggtaacact gagcaaccgc aaccgtcgaa caacgcgggc    840
ccttcgcctg gtgtcttcgc gcctctccag tccgagactt tgttcctcc agtgcccaca     900 ccacccactc cggctcccca gccgtcgacc ccgactgtcc agactcaggc cccggccccc    960
accgttccct ccaatccaac tccaacggtg gtgccagctc cggctcctaa cagcggcaac    1020
ggtggctctg ctttgactgg tccttgtact gaagagggca tttacaactg cattggcggc    1080
acttccttcc agcgatgtgc tagtggtgaa tggaccgcag ttctgccagt tgctgagggc    1140
actgtctgca aggaagggtt cagtactgat ttgggaatta cccatgcgaa aaagcgtggc    1200
attcatcgtc gccgtggcca ctttcgcgca taa                                 1233
```

<210> SEQ ID NO 168
<211> LENGTH: 410
<212> TYPE: PRT
<213> ORGANISM: Malbranchea cinnamomea

<400> SEQUENCE: 168

```
Met Arg Phe Ser Ala Ser Thr Val Ala Ala Ala Ala Phe Leu Ser
1               5                   10                  15

Ala Gly Val Val Asn Ala His Met Asn Met Lys Phe Pro Tyr Pro Tyr
            20                  25                  30

Gly Pro Asp Thr Leu Asn Asn Ser Pro Leu Gln Asn Asn Leu Ala Asp
            35                  40                  45

Phe Pro Cys Lys Gln Arg Pro Gly Val Tyr Asp Pro Pro Ala Leu Pro
    50                  55                  60

Ser Pro Asp Ala Asn Thr Leu Thr Ile Gly Val Pro Ala Thr Leu Glu
65                  70                  75                  80

Phe Leu Gly Asp Ala Val His Gly Gly Gly Ser Cys Gln Ile Ser Leu
                85                  90                  95

Thr Thr Asp Lys Glu Pro Thr Lys Asp Ser Val Trp Lys Val Ile His
            100                 105                 110

Ser Ile Glu Gly Gly Cys Pro Ala Asn Thr Glu Gly Asn Leu Gly Ser
        115                 120                 125

Asp Pro Lys Gly Glu Arg Ala Ser Lys Phe Gln Phe Thr Ile Pro Pro
    130                 135                 140

Ser Ile Ala Pro Gly Glu Tyr Thr Leu Ala Trp Thr Trp Ile Asn Arg
145                 150                 155                 160

Ile Gly Asn Arg Glu Tyr Tyr Met Asp Cys Ala Pro Ile Arg Val Gln
                165                 170                 175

Glu Ala Pro Lys Lys Arg Tyr Thr Pro Thr Pro Thr Glu Pro Arg
            180                 185                 190

Ser Leu Ile Pro Leu Ala Lys Arg Asp Asp Leu Pro Asp Met Phe Ile
        195                 200                 205

Ala Asn Ile Asn Gly Cys Asn Thr Pro Glu Gly Ile Asp Ile Arg Tyr
    210                 215                 220

Pro Asn Pro Gly Pro Ser Ile Glu Tyr Ala Gly Asn Pro Met Asn Leu
225                 230                 235                 240

Met Lys Val Gly Glu Pro Val Cys Val Tyr Ala Asp Gly Thr Pro Gly
                245                 250                 255

Pro Leu Ala Gly Gly Glu Gly Gly Asp Gly Gly Asn Thr Glu Gln
            260                 265                 270
```

```
Pro Gln Pro Ser Asn Asn Ala Gly Pro Ser Pro Gly Val Phe Ala Pro
        275                 280                 285

Leu Gln Ser Glu Thr Val Val Pro Pro Val Pro Thr Pro Pro Thr Pro
    290                 295                 300

Ala Pro Gln Pro Ser Thr Pro Thr Val Gln Thr Gln Ala Pro Ala Pro
305                 310                 315                 320

Thr Val Pro Ser Asn Pro Thr Pro Thr Val Val Pro Ala Pro Ala Pro
                325                 330                 335

Asn Ser Gly Asn Gly Gly Ser Ala Leu Thr Gly Pro Cys Thr Glu
            340                 345                 350

Gly Ile Tyr Asn Cys Ile Gly Gly Thr Ser Phe Gln Arg Cys Ala Ser
        355                 360                 365

Gly Glu Trp Thr Ala Val Leu Pro Val Ala Glu Gly Thr Val Cys Lys
    370                 375                 380

Glu Gly Phe Ser Thr Asp Leu Gly Ile Thr His Ala Lys Lys Arg Gly
385                 390                 395                 400

Ile His Arg Arg Arg Gly His Phe Arg Ala
                405                 410

<210> SEQ ID NO 169
<211> LENGTH: 699
<212> TYPE: DNA
<213> ORGANISM: Malbranchea cinnamomea

<400> SEQUENCE: 169
atgaaggcag cagtatcctt ggcccttctt gttgccgtag ctggagcagc ctctgctcac      60
aatatcttcc ccaacctcat cgtcgacggg acggttacgg agactgggga attcgtccgc     120
accaccgcca acaaatggtc ccgcgagggc ttaaccaacg tcaacagcga gagtatgaga     180
tgctacgagg aggccggccg tccacccctcg gaggtgaaaa ccgtcaaagc ggggtcgaga     240
gtcggtttcg cttcccaggc gcctattcgc catattgggc cagtgctctt ttacatggcc     300
cgtgttcccg atgggcagga tgtggactcg tggaccccat cggggggacgt ctggttcaag     360
atccatcagc agggaccgga gcggtctgag tcgggatgga cctggcctac gcaagaccaa     420
accgaactct tcgtcgacat cccagcctcc gtcccagacg caactatctc ctgcgaatc     480
gagcaaatcg cgctccacga cgcacagtac gttggtggtg cgcagtttta cctcgcatgc     540
ggccaaatca acgtcaccgg gggcggcagc ggggacccag gtcccaaggt ctcattccct     600
ggcgcgtata aacccaccga tcctggtatt ttgctggacc tccatggaca tccgccggcg     660
aattatcagt tcccgggacc agccgtatgg caaggctga                             699

<210> SEQ ID NO 170
<211> LENGTH: 232
<212> TYPE: PRT
<213> ORGANISM: Malbranchea cinnamomea

<400> SEQUENCE: 170

Met Lys Ala Ala Val Ser Leu Ala Leu Leu Val Ala Val Ala Gly Ala
1               5                   10                  15

Ala Ser Ala His Asn Ile Phe Pro Asn Leu Ile Val Asp Gly Thr Val
            20                  25                  30

Thr Gly Asp Trp Glu Phe Val Arg Thr Thr Ala Asn Lys Trp Ser Arg
        35                  40                  45

Glu Gly Leu Thr Asn Val Asn Ser Glu Ser Met Arg Cys Tyr Glu Glu
    50                  55                  60
```

```
Ala Gly Arg Pro Pro Ser Glu Val Lys Thr Val Lys Ala Gly Ser Arg
 65                  70                  75                  80

Val Gly Phe Ala Ser Gln Ala Pro Ile Arg His Ile Gly Pro Val Leu
                 85                  90                  95

Phe Tyr Met Ala Arg Val Pro Asp Gly Gln Asp Val Asp Ser Trp Thr
            100                 105                 110

Pro Ser Gly Asp Val Trp Phe Lys Ile His Gln Gln Gly Pro Glu Arg
        115                 120                 125

Ser Glu Ser Gly Trp Thr Trp Pro Thr Gln Asp Gln Thr Glu Leu Phe
130                 135                 140

Val Asp Ile Pro Ala Ser Val Pro Asp Gly Asn Tyr Leu Leu Arg Ile
145                 150                 155                 160

Glu Gln Ile Ala Leu His Asp Ala Gln Tyr Val Gly Ala Gln Phe
                165                 170                 175

Tyr Leu Ala Cys Gly Gln Ile Asn Val Thr Gly Gly Ser Gly Asp
            180                 185                 190

Pro Gly Pro Lys Val Ser Phe Pro Gly Ala Tyr Lys Pro Thr Asp Pro
        195                 200                 205

Gly Ile Leu Leu Asp Leu His Gly His Pro Ala Asn Tyr Gln Phe
210                 215                 220

Pro Gly Pro Ala Val Trp Gln Gly
225                 230

<210> SEQ ID NO 171
<211> LENGTH: 801
<212> TYPE: DNA
<213> ORGANISM: Malbranchea cinnamomea

<400> SEQUENCE: 171
atgaaggcca ccgttctagc tggcctcgcg gccgtgattg ctgctcaagg tgtagctggg     60
catgcgacat tccagcagct atgggttgat ggagaggata agggaggtgc ttgcgcaaga    120 ttgccttga gcaactcacc cgtgacagat gtcaatagcg cagagatcgc atgcaacgcg    180
aacagcggtc ctgcggccga gaagtgtacc gtttccgcag gcgagtcgt caccgtcgag    240 atgcaccagc agcccggaga tcggtcgtgt gacaacgaag ccattggagg caaccactgg    300
ggtcccgtgc tcgtatacat gagtaaagtc gacgactccg ccaccgcaga cgggtccggc    360
gggtggttca agatcttcga agacacctgg gctcccgcac ccgactccaa ttccggctcc    420
gacgactact ggggcgtcaa ggatctgaac gcccactgcg ccgcatggaa cgtgccaatc    480
cccgctgacc tggcgccagg agactacctg ctgagagcgg aggtgattgc gctgcacacc    540
gcgtcgtcgc ccggcggtgc gcagttctac atgacctgct accagctcac ggttgatgga    600
gaggggtcac agagcccgca aaccgtgtcg ttccccggcg cttattcgcc aagtgaccct    660
gggattcaga tcaatatcta tcagaagttg acggaatatg tctctcctgg accagctgtg    720
attgagggtg aaccaccgt tgaggccggc acaggcggta gcaccattcc cggcaaacta    780
aatgacgtgt tcttgtcttg a                                              801

<210> SEQ ID NO 172
<211> LENGTH: 266
<212> TYPE: PRT
<213> ORGANISM: Malbranchea cinnamomea

<400> SEQUENCE: 172

Met Lys Ala Thr Val Leu Ala Gly Leu Ala Ala Val Ile Ala Ala Gln
```

```
  1               5                   10                  15
Gly Val Ala Gly His Ala Thr Phe Gln Gln Leu Trp Val Asp Gly Glu
            20                  25                  30
Asp Lys Gly Gly Ala Cys Ala Arg Leu Pro Leu Ser Asn Ser Pro Val
        35                  40                  45
Thr Asp Val Asn Ser Ala Glu Ile Ala Cys Asn Ala Asn Ser Gly Pro
    50                  55                  60
Ala Ala Glu Lys Cys Thr Val Ser Ala Gly Val Val Thr Val Glu
65                  70                  75                  80
Met His Gln Gln Pro Gly Asp Arg Ser Cys Asp Asn Glu Ala Ile Gly
                85                  90                  95
Gly Asn His Trp Gly Pro Val Leu Val Tyr Met Ser Lys Val Asp Asp
            100                 105                 110
Ser Ala Thr Ala Asp Gly Ser Gly Gly Trp Phe Lys Ile Phe Glu Asp
        115                 120                 125
Thr Trp Ala Pro Ala Pro Asp Ser Asn Ser Gly Ser Asp Asp Tyr Trp
    130                 135                 140
Gly Val Lys Asp Leu Asn Ala His Cys Gly Arg Met Asp Val Pro Ile
145                 150                 155                 160
Pro Ala Asp Leu Ala Pro Gly Asp Tyr Leu Leu Arg Ala Glu Val Ile
                165                 170                 175
Ala Leu His Thr Ala Ser Ser Pro Gly Gly Ala Gln Phe Tyr Met Thr
            180                 185                 190
Cys Tyr Gln Leu Thr Val Asp Gly Glu Gly Ser Gln Ser Pro Gln Thr
        195                 200                 205
Val Ser Phe Pro Gly Ala Tyr Ser Pro Ser Asp Pro Gly Ile Gln Ile
    210                 215                 220
Asn Ile Tyr Gln Lys Leu Thr Glu Tyr Val Ser Pro Gly Pro Ala Val
225                 230                 235                 240
Ile Glu Gly Gly Thr Thr Val Glu Ala Gly Thr Gly Gly Ser Thr Ile
                245                 250                 255
Pro Gly Lys Leu Asn Asp Val Phe Leu Ser
            260                 265
```

<210> SEQ ID NO 173
<211> LENGTH: 975
<212> TYPE: DNA
<213> ORGANISM: Corynascus thermophilus

<400> SEQUENCE: 173

| | | |
|---|---|---|
| atgcccctc cacggctaca cacgttcctt gccctcttgg ccctggtatc agccccacc | 60 |
| gcacggggc attccatct cgcatacatc atcatcaacg gcgaggtgta ccacggattc | 120 |
| gacccgcggc cggggagga gaactcgccg gcgcgcgtgg gctggtcgac ggggcggtc | 180 |
| gacgacgggt tcgtggggcc ggccgactac tcgtcgcccg acataatctg ccacgtcgag | 240 |
| ggggccagcc cgccggcgca cgcgcccgtc cgggccggcg accgggttca cgtgcagtgg | 300 |
| aacggctggc cgctcgggca tgtggggccg gtgctgtcgt acctggcccc ctgcggcggc | 360 |
| ctggaggggg ccgagcgcgg gtgtgccgga tggacaagc ggcagctgcg gtggaccaag | 420 |
| gtggacgact cgctgccggc gatggagaga ctgtccacca cggtcggggc gcggacggc | 480 |
| ggcggcgtgc ccgggcagcg ctgggccacc gacgtgctgg tcgcggccaa caacagctgg | 540 |
| caggtcgaga tcccgcgcgg gctccgggac gggccgtacg tgctgcggca cgagatcgtc | 600 |
| gcgctgcact tcgcggccga ccgcggcggc gcgcagaact acccggtctg cgtcaacctc | 660 |

```
tgggtcgagg gcggcgacgg caccatggag ctggacggct tcgacgccac cgagctctac      720
cggcccgacg acccgggcat cctgctcgac gtgacggccg gcccgcgctc gtacgtcgtg      780
cccggcccga cgctggtcgc gggggccacg cgggtgccgt acgcgcagca gaacagcagc      840
tcggcgaggg cggagggaac ccccgtgatg gtcatcagga gcacagagac ggtgcccctg      900
acggtagcac ctaccccgac caatagtacg ggtcgggctt acggaggag gtacggaagc       960 aggtttcagg ggtag                                                      975
```

<210> SEQ ID NO 174
<211> LENGTH: 324
<212> TYPE: PRT
<213> ORGANISM: Corynascus thermophilus

<400> SEQUENCE: 174

```
Met Pro Pro Pro Arg Leu His Thr Phe Leu Ala Leu Leu Ala Leu Val
1               5                   10                  15

Ser Ala Pro Thr Ala Arg Gly His Ser His Leu Ala Tyr Ile Ile Ile
            20                  25                  30

Asn Gly Glu Val Tyr His Gly Phe Asp Pro Arg Pro Gly Glu Glu Asn
        35                  40                  45

Ser Pro Ala Arg Val Gly Trp Ser Thr Gly Ala Val Asp Asp Gly Phe
    50                  55                  60

Val Gly Pro Ala Asp Tyr Ser Ser Pro Asp Ile Ile Cys His Val Glu
65                  70                  75                  80

Gly Ala Ser Pro Pro Ala His Ala Pro Val Arg Ala Gly Asp Arg Val
                85                  90                  95

His Val Gln Trp Asn Gly Trp Pro Leu Gly His Val Gly Pro Val Leu
            100                 105                 110

Ser Tyr Leu Ala Pro Cys Gly Gly Leu Glu Gly Ala Glu Arg Gly Cys
        115                 120                 125

Ala Gly Val Asp Lys Arg Gln Leu Arg Trp Thr Lys Val Asp Asp Ser
    130                 135                 140

Leu Pro Ala Met Glu Arg Leu Ser Thr Thr Val Gly Ala Ala Asp Gly
145                 150                 155                 160

Gly Gly Val Pro Gly Gln Arg Trp Ala Thr Asp Val Leu Val Ala Ala
                165                 170                 175

Asn Asn Ser Trp Gln Val Glu Ile Pro Arg Gly Leu Arg Asp Gly Pro
            180                 185                 190

Tyr Val Leu Arg His Glu Ile Val Ala Leu His Phe Ala Ala Asp Arg
        195                 200                 205

Gly Gly Ala Gln Asn Tyr Pro Val Cys Val Asn Leu Trp Val Glu Gly
    210                 215                 220

Gly Asp Gly Thr Met Glu Leu Asp Gly Phe Asp Ala Thr Glu Leu Tyr
225                 230                 235                 240

Arg Pro Asp Asp Pro Gly Ile Leu Leu Asp Val Thr Ala Gly Pro Arg
                245                 250                 255

Ser Tyr Val Val Pro Gly Pro Thr Leu Val Ala Gly Ala Thr Arg Val
            260                 265                 270

Pro Tyr Ala Gln Gln Asn Ser Ser Ala Arg Ala Glu Gly Thr Pro
        275                 280                 285

Val Met Val Ile Arg Ser Thr Glu Thr Val Pro Leu Thr Val Ala Pro
    290                 295                 300

Thr Pro Thr Asn Ser Thr Gly Arg Ala Tyr Gly Arg Arg Tyr Gly Ser
```

Arg Phe Gln Gly

<210> SEQ ID NO 175
<211> LENGTH: 1115
<212> TYPE: DNA
<213> ORGANISM: Corynascus thermophilus
<400> SEQUENCE: 175

```
atggctccat taacgtccgc agccctgatc ctgggcaccc ttatcagctt ggtctcgggc      60
catggctatc tgaagagcat caccgtcaac ggcaaggagt acctcgcttg caggttggc     120
caggacgact atatcaaccc gactccggtc cgatatgccc gcaggcttgc aaacaacggg    180
ccagtcccgg atttcaccac caaggatatc acgtacgttt ccgtggaggc cggcactggc    240
tgtggcggaa gagggcaaga ccgccggact gacgcgtgcc atgactttac agctgcggcg    300
ccggtggtaa tgagccggct gagggaatca tcgagctgaa ggctggcgac actgtgtacg    360
cgccgtcccc tccccagcta acgttacccg atcgacctca tctggacggt tagctgacag    420
ggtcgtcttc tctcgcacac gcaaatagga ccctcaactg gaccagtgg ggtagcagcc     480
actccggccc agtcatgaag tgagtcttgc ggccttcccg cgacggacc gtaccagagg     540
ttattacggg agtagcagtc gtaatcagcg aacccattcg aactaaccc tcccgcacca     600
gctatctcgc ccattgcacc aacgacgact gcaagtcgtt caaggcgac agcggcaacg     660
tctgggtcaa gatcgagcag ctcgcgtaca accgtcggc caacccccc tgggcgtccg      720
acctcctccg cgagcagggc gccaagtgga aggtgacgat cccgcccacc ctcgcccccg   780
gcgagtacct gctgcggcac gagatcctgg gcctgcacgt cgccggaacc gtgatgggcg   840
cccagttcta ccccagctgc acccagatca gggtcaccca gggcgggaac acgcagctgc   900
cctccggcat cgcgcttccc ggtgcttacg acccgcatga cggggtgta agtctcggat   960
gtatgatctg gaattgtctc gacgcttgct gacagtgttt attccagatc ttggtcgagt  1020
tgtggagggt taaccagggc aggtcaact acaccgcgcc tggaggaccc gtctggagcg  1080
cggcggcgcc ggatcccaac cgctctggcc cctga                              1115
```

<210> SEQ ID NO 176
<211> LENGTH: 240
<212> TYPE: PRT
<213> ORGANISM: Corynascus thermophilus
<400> SEQUENCE: 176

```
Met Ala Pro Leu Thr Ser Ala Ala Leu Ile Leu Gly Thr Leu Ile Ser
1               5                   10                  15

Leu Val Ser Gly His Gly Tyr Leu Lys Ser Ile Thr Val Asn Gly Lys
            20                  25                  30

Glu Tyr Leu Ala Trp Gln Val Gly Gln Asp Asp Tyr Ile Asn Pro Thr
        35                  40                  45

Pro Val Arg Tyr Ala Arg Arg Leu Ala Asn Asn Gly Pro Val Pro Asp
    50                  55                  60

Phe Thr Thr Lys Asp Ile Thr Cys Gly Ala Gly Asn Glu Pro Ala
65                  70                  75                  80

Glu Gly Ile Ile Glu Leu Lys Ala Gly Asp Thr Val Thr Leu Asn Trp
                85                  90                  95

Asp Gln Trp Gly Ser Ser His Ser Gly Pro Val Met Asn Tyr Leu Ala
            100                 105                 110
```

His Cys Thr Asn Asp Asp Cys Lys Ser Phe Lys Gly Asp Ser Gly Asn
            115                 120                 125

Val Trp Val Lys Ile Glu Gln Leu Ala Tyr Asn Pro Ser Ala Asn Pro
        130                 135                 140

Pro Trp Ala Ser Asp Leu Leu Arg Glu Gln Gly Ala Lys Trp Lys Val
145                 150                 155                 160

Thr Ile Pro Pro Thr Leu Ala Pro Gly Glu Tyr Leu Leu Arg His Glu
                165                 170                 175

Ile Leu Gly Leu His Val Ala Gly Thr Val Met Gly Ala Gln Phe Tyr
                180                 185                 190

Pro Ser Cys Thr Gln Ile Arg Val Thr Gln Gly Gly Asn Thr Gln Leu
        195                 200                 205

Pro Ser Gly Ile Ala Leu Pro Gly Ala Tyr Asp Pro His Asp Gly Gly
        210                 215                 220

Gly Pro Val Trp Ser Ala Ala Pro Asp Pro Asn Arg Ser Gly Pro
225                 230                 235                 240

<210> SEQ ID NO 177
<211> LENGTH: 988
<212> TYPE: DNA
<213> ORGANISM: Corynascus thermophilus

<400> SEQUENCE: 177
atgaaatacg ccctccagct cgctgcggcc gcggcttttg cggtgaacag cgcggccggc      60
cactacatct tccagcagtt tgcgacaggc gggacgacgt accgccctg gaagtacatc      120
cgccgcaaca ccaaccccgga ctggctgcag aacgggccgg tgacggacct gtcgtcgacc   180
gacctgcgct gtaacgtggg cgggcaggtc agcaacggga ccgagaccat caccgtcaac   240
gccggcgacg aattcacctt catcctcgac acgcccgtct accacgccgg ccccaccctcg   300
ctctacatgt ccaaggcgcc cggcgcggcg ccgactacg acggcagcgg gtcctggttc    360
aagatctatg actggggccc gcagggaacg agctggacgc tgagcggtac gtgtgcctgt    420
ttctcatcat caccacgacc atcctcatga tgattaccgc tctcgttatg attatgctgc    480
tgttgcggtt ctgctggaag agtatctgac ccgtctaccg tatccaggct cgtacaccca    540
gagaattccc aggtgcatcc ctgacggcga atacctcctc cgcatccagc agatcggact    600
tcacaacccc ggcgccgagc acaggtacg gtcctggact ccgggtctc ctcttgcgca     660
ccgtcgctga cgcaggacga acaaaaacag ttctacatca gctgcgccca agtcaaggtg   720
gtcaatggcg gcagcaccaa cccgagcccg accgccagaa ttccgggagc cttccacagc   780
aacgatcccg gcttgaccgt caacgtaagc ccggcctcgc atcatttccc cgggaaccga   840
aatagcaatg agctgacaac cgatcgtaga tctacaccga ccctctcaac aactacgtcg   900
tccccggacc ccgggttgta agtctctccg gatgccctcc tccgttgatg gtcacgcctt   960
gctaatgtcg tccaagttct cctgctag                                                            988

<210> SEQ ID NO 178
<211> LENGTH: 225
<212> TYPE: PRT
<213> ORGANISM: Corynascus thermophilus

<400> SEQUENCE: 178

Met Lys Tyr Ala Leu Gln Leu Ala Ala Ala Ala Phe Ala Val Asn
1               5                   10                  15

Ser Ala Ala Gly His Tyr Ile Phe Gln Gln Phe Ala Thr Gly Gly Thr
                20                  25                  30

```
          Thr Tyr Pro Pro Trp Lys Tyr Ile Arg Arg Asn Thr Asn Pro Asp Trp
                       35                  40                  45

Leu Gln Asn Gly Pro Val Thr Asp Leu Ser Ser Thr Asp Leu Arg Cys
           50                  55                  60

Asn Val Gly Gly Gln Val Ser Asn Gly Thr Glu Thr Ile Thr Val Asn
           65                  70                  75                  80

Ala Gly Asp Glu Phe Thr Phe Ile Leu Asp Thr Pro Val Tyr His Ala
                           85                  90                  95

Gly Pro Thr Ser Leu Tyr Met Ser Lys Ala Pro Gly Ala Ala Ala Asp
                          100                 105                 110

Tyr Asp Gly Ser Gly Ser Trp Phe Lys Ile Tyr Asp Trp Gly Pro Gln
                          115                 120                 125

Gly Thr Ser Trp Thr Leu Ser Gly Ser Tyr Thr Gln Arg Ile Pro Arg
                      130                 135                 140

Cys Ile Pro Asp Gly Glu Tyr Leu Leu Arg Ile Gln Gln Ile Gly Leu
          145                 150                 155                 160

His Asn Pro Gly Ala Glu Pro Gln Phe Tyr Ile Ser Cys Ala Gln Val
                              165                 170                 175

Lys Val Val Asn Gly Gly Ser Thr Asn Pro Ser Pro Thr Ala Gln Ile
                          180                 185                 190

Pro Gly Ala Phe His Ser Asn Asp Pro Gly Leu Thr Val Asn Ile Tyr
                          195                 200                 205

Thr Asp Pro Leu Asn Asn Tyr Val Val Pro Gly Pro Arg Val Phe Ser
                      210                 215                 220

Cys
          225

<210> SEQ ID NO 179
<211> LENGTH: 859
<212> TYPE: DNA
<213> ORGANISM: Corynascus thermophilus

<400> SEQUENCE: 179
atgaaggccc tctctctcct tgcggctgcc tcggcggtct ctgcccacac catcttcgtc       60
cagctcgaag cggacggcac gaggtacccg gtctcgtacg gcatccggac gccgacgtac      120
gacggcccca tcaccgacgt cacgtccaac gacgttgcct gcaacggcgg gccgaacccg      180
acgaccccgt ccggcgacgt catcacggtc acggcgggca ccacggtcaa ggccatctgg      240
agacacacgc tccagtccgg cccggacgac gtcatggacg ccagccacaa gggcccgacc      300
ctggcctacc tcaagaaggt cgacgacgcc accacggact cgggcatcgg cggcggctgg      360
ttcaagattc aggaggacgg ctacaacaac ggcgagtggg gcaccagcaa ggtgatctcc      420
aacggcggcg agcactacat gtgagtcctt tctccgacag agcgaggaga acacagaga      480 gggagagaga gagaggccga ccaatctcgc tgacccgctg caacagcgac atcccggcct      540
gcattccccc gggccagtac ctcctccgcg ccgagatgat tgctctccac agcgccgggt      600
ctcccggcgg tgctcagctc tacgtaagcc tctctgccct tcttattac cacccccccc       660 ccaaacctct gactgacacg cttggcagat ggaatgcgcc cagatcaaca tcgtcggcag      720
ctccggctcc ctgcccagct cgaccgtcag cttccccggc gcgtacagcg ccaacgaccc      780 ggcatcctc atcaacatct actccatgtc ccctcggac acgtacatca ttccgggccc        840
ggaggtcttc acttgctag                                                   859
```

<210> SEQ ID NO 180
<211> LENGTH: 235
<212> TYPE: PRT
<213> ORGANISM: Corynascus thermophilus

<400> SEQUENCE: 180

```
Met Lys Ala Leu Ser Leu Leu Ala Ala Ala Ser Ala Val Ser Ala His
1               5                   10                  15

Thr Ile Phe Val Gln Leu Glu Ala Asp Gly Thr Arg Tyr Pro Val Ser
            20                  25                  30

Tyr Gly Ile Arg Thr Pro Thr Tyr Asp Gly Pro Ile Thr Asp Val Thr
        35                  40                  45

Ser Asn Asp Val Ala Cys Asn Gly Gly Pro Asn Pro Thr Thr Pro Ser
    50                  55                  60

Gly Asp Val Ile Thr Val Thr Ala Gly Thr Thr Val Lys Ala Ile Trp
65                  70                  75                  80

Arg His Thr Leu Gln Ser Gly Pro Asp Asp Val Met Asp Ala Ser His
                85                  90                  95

Lys Gly Pro Thr Leu Ala Tyr Leu Lys Lys Val Asp Asp Ala Thr Thr
            100                 105                 110

Asp Ser Gly Ile Gly Gly Gly Trp Phe Lys Ile Gln Glu Asp Gly Tyr
        115                 120                 125

Asn Asn Gly Glu Trp Gly Thr Ser Lys Val Ile Ser Asn Gly Gly Glu
    130                 135                 140

His Tyr Ile Asp Ile Pro Ala Cys Ile Pro Gly Gln Tyr Leu Leu
145                 150                 155                 160

Arg Ala Glu Met Ile Ala Leu His Ser Ala Gly Ser Pro Gly Gly Ala
                165                 170                 175

Gln Leu Tyr Met Glu Cys Ala Gln Ile Asn Ile Val Gly Ser Ser Gly
            180                 185                 190

Ser Leu Pro Ser Ser Thr Val Ser Phe Pro Gly Ala Tyr Ser Ala Asn
        195                 200                 205

Asp Pro Gly Ile Leu Ile Asn Ile Tyr Ser Met Ser Pro Ser Asp Thr
    210                 215                 220

Tyr Ile Ile Pro Gly Pro Glu Val Phe Thr Cys
225                 230                 235
```

<210> SEQ ID NO 181
<211> LENGTH: 1011
<212> TYPE: DNA
<213> ORGANISM: Corynascus thermophilus

<400> SEQUENCE: 181

| | | |
|---|---|---|
| atggccaaga cctctgctct cctcgccggc ctgacgggcg cggccctcgt cgctgcccac | | 60 |
| ggccacgtca gccacatcat cgtcaacggc gtgtactaca ggaactacga cccgacgacc | | 120 |
| gactcgtacc agaccaaccc gccgagggtc atcggctggg cggccgccca gcaggacaat | | 180 |
| ggcttcgtcg agcccaacaa ctttggctcg ccggatgtca tctgccacaa gagcgccact | | 240 |
| cccggcggcg ccacgccac cgtcgctgcc ggagacaaga tcagcctcgt ctggacgccc | | 300 |
| gagtggcccg agtccacat cggcccggtc atcgactatc tggcggcctg caacggcgac | | 360 |
| tgcgagacgg tcgacaagac gtcgctgcgc tggttcaaga tcgacggcgc cggctacgac | | 420 |
| aagtcgaccg gccgctgggc cgccgacgcc ctgcgcgcca acggcaacag ctggctcgtc | | 480 |
| cagatcccgt cggacctcaa ggcgggcaac tacgtgctcc gccacgagat catcgccctc | | 540 |
| cacggcgcca acaacgccaa cggcgcccag tcgtacccgc agtgcatcaa cctccgcgtc | | 600 |

```
acgggcggcg caacaacct gcccagcggc gtgcccggca cctcgctgta cagggccaac    660
gacccgggca tcctcttcaa ccctacgtc ccctcgcccg actacccggt ccccggcccg    720
tccctcattc ccggcgccgt cagctccatc gcccagagca agtcggtcgc cacggccacg    780
gccacggcca cccctcccgg cggcggcaac aacaacccc ccgccaccac cacggccggc    840
ggccccacca gcaccaccag cagcccctcc cagcagacca ccaccccgcc gtcgggcagc    900
gtgcagacca agtacggcca gtgcggcggc aacggctgga ccggcccgac cctgtgcgcc    960
cccggctcga gctgcaccgt tctcaacgag tggtactccc agtgcgtgta a            1011
```

<210> SEQ ID NO 182
<211> LENGTH: 336
<212> TYPE: PRT
<213> ORGANISM: Corynascus thermophilus

<400> SEQUENCE: 182

```
Met Ala Lys Thr Ser Ala Leu Leu Ala Gly Leu Thr Gly Ala Ala Leu
1               5                   10                  15

Val Ala Ala His Gly His Val Ser His Ile Ile Val Asn Gly Val Tyr
                20                  25                  30

Tyr Arg Asn Tyr Asp Pro Thr Thr Asp Ser Tyr Gln Thr Asn Pro Pro
            35                  40                  45

Arg Val Ile Gly Trp Ala Ala Gln Gln Asp Asn Gly Phe Val Glu
        50                  55                  60

Pro Asn Asn Phe Gly Ser Pro Asp Val Ile Cys His Lys Ser Ala Thr
65                  70                  75                  80

Pro Gly Gly Gly His Ala Thr Val Ala Ala Gly Asp Lys Ile Ser Leu
                85                  90                  95

Val Trp Thr Pro Glu Trp Pro Glu Ser His Ile Gly Pro Val Ile Asp
                100                 105                 110

Tyr Leu Ala Ala Cys Asn Gly Asp Cys Glu Thr Val Asp Lys Thr Ser
            115                 120                 125

Leu Arg Trp Phe Lys Ile Asp Gly Ala Gly Tyr Asp Lys Ser Thr Gly
        130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
                165                 170                 175

Ile Ile Ala Leu His Gly Ala Asn Asn Ala Asn Gly Ala Gln Ser Tyr
            180                 185                 190

Pro Gln Cys Ile Asn Leu Arg Val Thr Gly Gly Gly Asn Asn Leu Pro
        195                 200                 205

Ser Gly Val Pro Gly Thr Ser Leu Tyr Arg Ala Asn Asp Pro Gly Ile
    210                 215                 220

Leu Phe Asn Pro Tyr Val Pro Ser Pro Asp Tyr Pro Val Pro Gly Pro
225                 230                 235                 240

Ser Leu Ile Pro Gly Ala Val Ser Ser Ile Ala Gln Ser Lys Ser Val
                245                 250                 255

Ala Thr Ala Thr Ala Thr Ala Pro Pro Gly Gly Gly Asn Asn Asn
            260                 265                 270

Pro Pro Ala Thr Thr Thr Ala Gly Gly Pro Thr Ser Thr Thr Ser Ser
        275                 280                 285

Pro Ser Gln Gln Thr Thr Thr Pro Pro Ser Gly Ser Val Gln Thr Lys
    290                 295                 300
```

```
Tyr Gly Gln Cys Gly Gly Asn Gly Trp Thr Gly Pro Thr Leu Cys Ala
305                 310                 315                 320

Pro Gly Ser Ser Cys Thr Val Leu Asn Glu Trp Tyr Ser Gln Cys Val
                325                 330                 335
```

<210> SEQ ID NO 183
<211> LENGTH: 1315
<212> TYPE: DNA
<213> ORGANISM: Corynascus thermophilus

<400> SEQUENCE: 183

```
atgaaaacgc ttgccgccct cctcgtctcc gccggcctcg tggctgcgca cggctatgtt      60
gaccgtgcca cgatcggcgg caaggagtac caggtaatga caacaaacac ggctactccc     120
gtgtggatgc gtcgtcgaag agtagctaac aatacggtcc ctatagttct accaggtggg     180
ctcggtaccg gccagttggc tctccatgcc ggcagttcct gacatgcatc tcgcatattt     240
agccgtacgt tgatccgtac atgggcgaca caaggtaac aacaaacctt aatataacaa     300
gaacaaccta tccatcctcc ctccccccc ctctccacac cccccccctc tctctctctt     360
tctctccttt ctcctctgat gcaccggtcg agcacgcact aaacaggggg taattacggg     420
gggcatttca gcccgacagg gtctcccgct cgatcccggg caacggcccc gtggaggacg     480
tcaactcgct cgacatccag tgcaacgcgg gcgcgcagcc ggccaagctc acgccccccg     540
ccgccgccgg ctcgaccgtg acgctcaact ggaccctctg gcccgactcg cacgtcggcc     600
ccgtcatcac ctacatggcg cgctgccccg acagcggctg ccagaactgg tcgcccggaa     660
cccagtatgg cccattccaa tcctgtttgt tgatattgat ggggggtaaa gacggaggg     720
atggttggcg gtgctaaatg gtttactttc ctgatgacag gccgtctgg ttcaagatca     780
aggagggcgg ccgtgagggc acgtccaacg tctgggcggc cgtacgtgat cacacccgt     840
tccgaaaaca acgaggcaca caccaaagcc aactaacccc tccttctttt cgctctctat     900
ctctctcgac agaccccgct catgaaggcg ccgtcggcgt acacgtacac gatcccggcc     960
tgcctcaaga gcggctacta cctggtgcgg cacgagatca tcgcgctgca ctcggcctgg    1020
cagtaccccg gcgcgcagtt ctacccgggc tgccaccagc tccaggtcac ggcggcggc    1080
tcgaccgtgc cctcggccaa cctggtcgcc ttccccggcg cctacaaggg cagcgacccc    1140
ggcatcacct acgacgcgta caaggtgag ccatctctt ctctctttct ctctgtctcg    1200
cttttctctt tccttgtgcc tcttggttgt ccgtcttgga gcagggcagg gcgactgacg    1260
cggagtggca gcgcaacctt acacgatccc gggcccgccc gtgtttactt gctaa         1315
```

<210> SEQ ID NO 184
<211> LENGTH: 253
<212> TYPE: PRT
<213> ORGANISM: Corynascus thermophilus

<400> SEQUENCE: 184

```
Met Lys Thr Leu Ala Ala Leu Leu Val Ser Ala Gly Leu Val Ala Ala
1               5                   10                  15

His Gly Tyr Val Asp Arg Ala Thr Ile Gly Gly Lys Glu Tyr Gln Phe
            20                  25                  30

Tyr Gln Val Gly Ser Val Pro Ala Ser Trp Leu Ser Met Pro Ala Val
        35                  40                  45

Pro Asp Met His Leu Ala Tyr Leu Ala Pro Asp Arg Val Ser Arg Ser
    50                  55                  60
```

Ile Pro Gly Asn Gly Pro Val Glu Asp Val Asn Ser Leu Asp Ile Gln
65                  70                  75                  80

Cys Asn Ala Gly Ala Gln Pro Ala Lys Leu His Ala Pro Ala Ala Ala
                85                  90                  95

Gly Ser Thr Val Thr Leu Asn Trp Thr Leu Trp Pro Asp Ser His Val
            100                 105                 110

Gly Pro Val Ile Thr Tyr Met Ala Arg Cys Pro Asp Ser Gly Cys Gln
            115                 120                 125

Asn Trp Ser Pro Gly Thr Gln Pro Val Trp Phe Lys Ile Lys Glu Gly
        130                 135                 140

Gly Arg Glu Gly Thr Ser Asn Val Trp Ala Ala Thr Pro Leu Met Lys
145                 150                 155                 160

Ala Pro Ser Ala Tyr Thr Tyr Thr Ile Pro Ala Cys Leu Lys Ser Gly
                165                 170                 175

Tyr Tyr Leu Val Arg His Glu Ile Ile Ala Leu His Ser Ala Trp Gln
            180                 185                 190

Tyr Pro Gly Ala Gln Phe Tyr Pro Gly Cys His Gln Leu Gln Val Thr
            195                 200                 205

Gly Gly Gly Ser Thr Val Pro Ser Ala Asn Leu Val Ala Phe Pro Gly
210                 215                 220

Ala Tyr Lys Gly Ser Asp Pro Gly Ile Thr Tyr Asp Ala Tyr Lys Ala
225                 230                 235                 240

Gln Pro Tyr Thr Ile Pro Gly Pro Val Phe Thr Cys
                245                 250

<210> SEQ ID NO 185
<211> LENGTH: 924
<212> TYPE: DNA
<213> ORGANISM: Corynascus thermophilus

<400> SEQUENCE: 185

```
atgtaccgca cgctcggttc ccttgccctg ctcgctggag gcgctgctgc ccacggtgcc     60
gtgaccagct acaacatcgc gggcaaggac taccctgggt aaggaaggag atctctctct    120
ctctctctct ctctctctct ctctctctct ctcgttctct tgctaacaca aaggcacctc    180
tgcagatact cgggctttgc cccgaccggc gaacccgtca tccagtggca atggcccgac    240
tacaaccccg tcatgtccgc tagcgacttc aagctccgct gcaacggcgg caccaacgcg    300
cagctgtatg ctgaggcggc ccccggcgat accatcacgg ccacctgggc ccagtggacg    360
cacgcccagg gcccgatcct ggtgtggatg tacaagtgcc ccggcgactt cagctcctgc    420
gacggctccg gcgagggctg gttcaagatc gacgaggccg gcttccacgg cgacggccag    480
actgtcttcc tcgacagcga gaaccccctcg gctgggaca tcgccaagct ggtcggcggc    540
aacaagtcgt ggagcagcaa gatccccgag ggcctcgctc cgggcaacta cctggtccgc    600
cacgagctca tcgccctgca ccaggccaac gccccgcagt tctacccccga gtgcgcccag    660
gtcaaggtta ccggctccgg caccgccgag cccgactcct cgtacaaggc cgccatcccc    720
ggctactgct cgcagagcga ccccaacatt tcggtaagga gggactcccg gccgagagag    780
agagaggact cattcctggt gctaacccgt tcacttccgc agttcaacat caacgaccac    840
tccctcccgc aggagtacaa gatccccggc ccgccggtct tcaagggcac tgcctccgcc    900
aaggctcgct ccttccaggc ctaa                                          924
```

<210> SEQ ID NO 186
<211> LENGTH: 255

```
<212> TYPE: PRT
<213> ORGANISM: Corynascus thermophilus

<400> SEQUENCE: 186

Met Tyr Arg Thr Leu Gly Ser Leu Ala Leu Leu Ala Gly Gly Ala Ala
1               5                   10                  15

Ala His Gly Ala Val Thr Ser Tyr Asn Ile Ala Gly Lys Asp Tyr Pro
            20                  25                  30

Gly Tyr Ser Gly Phe Ala Pro Thr Gly Glu Pro Val Ile Gln Trp Gln
        35                  40                  45

Trp Pro Asp Tyr Asn Pro Val Met Ser Ala Ser Asp Phe Lys Leu Arg
    50                  55                  60

Cys Asn Gly Gly Thr Asn Ala Gln Leu Tyr Ala Glu Ala Ala Pro Gly
65                  70                  75                  80

Asp Thr Ile Thr Ala Thr Trp Ala Gln Trp Thr His Ala Gln Gly Pro
                85                  90                  95

Ile Leu Val Trp Met Tyr Lys Cys Pro Gly Asp Phe Ser Ser Cys Asp
            100                 105                 110

Gly Ser Gly Glu Gly Trp Phe Lys Ile Asp Glu Ala Gly Phe His Gly
        115                 120                 125

Asp Gly Gln Thr Val Phe Leu Asp Ser Glu Asn Pro Ser Gly Trp Asp
    130                 135                 140

Ile Ala Lys Leu Val Gly Gly Asn Lys Ser Trp Ser Ser Lys Ile Pro
145                 150                 155                 160

Glu Gly Leu Ala Pro Gly Asn Tyr Leu Val Arg His Glu Leu Ile Ala
                165                 170                 175

Leu His Gln Ala Asn Ala Pro Gln Phe Tyr Pro Glu Cys Ala Gln Val
            180                 185                 190

Lys Val Thr Gly Ser Gly Thr Ala Glu Pro Asp Ser Ser Tyr Lys Ala
        195                 200                 205

Ala Ile Pro Gly Tyr Cys Ser Gln Ser Asp Pro Asn Ile Ser Phe Asn
    210                 215                 220

Ile Asn Asp His Ser Leu Pro Gln Glu Tyr Lys Ile Pro Gly Pro Pro
225                 230                 235                 240

Val Phe Lys Gly Thr Ala Ser Ala Lys Ala Arg Ser Phe Gln Ala
                245                 250                 255

<210> SEQ ID NO 187
<211> LENGTH: 742
<212> TYPE: DNA
<213> ORGANISM: Corynascus thermophilus

<400> SEQUENCE: 187
atgctggcga caaccttcgc tctcctgacg gccgctctcg gcgtcagcgc ccattatacc        60
ctcccccggg tcgggtccgg ctccgagtgg cagcacgtgc gccgggctga caactggcaa      120
aacaacggct tcgtcgacaa cgtctactcg cagcagatcc gctgcttcca gtcgagcaat      180
gccggcgccc cggatgtcta caccgtccag gcgggctcga gcgtgaccta ctacgccaac      240
cccagcatct accaccccgg ccccatgcag ttctacctcg cccgcgttcc ggacggacag      300
gacgtcaagt cgtggaacgg cgacggcgct gtgtggttca aggtgtacga ggagcagcct      360
cagttcggct cccagcttac ctggcctagc aacggtgcgt cgaccatgct ctctcgtttg      420
gcccgttgcc aggtgctaac tgtccttccc gtccgcaggc aagaactcgt tccaggttcc      480
catccccagc tgcatccgcc cgggcaagta cctcctccgc gccgagcaca tcgccctgca      540
```

```
cgttgcccag agccagggcg gtgcccagtt ctacatctcg tgcgcccagc tcgacgtcac    600
tggcggcggc agcaccgagc cttcccagaa ggttgccttc ccgggtgcct actcgcccac    660
cgaccccggc attctcatca acatcaactg gcccatcccg acctcgtaca agaaccccgg    720
cccgccggtc ttccgctgct aa                                            742
```

<210> SEQ ID NO 188
<211> LENGTH: 225
<212> TYPE: PRT
<213> ORGANISM: Corynascus thermophilus

<400> SEQUENCE: 188

```
Met Leu Ala Thr Thr Phe Ala Leu Leu Thr Ala Ala Leu Gly Val Ser
1               5                   10                  15

Ala His Tyr Thr Leu Pro Arg Val Gly Ser Gly Ser Glu Trp Gln His
            20                  25                  30

Val Arg Arg Ala Asp Asn Trp Gln Asn Asn Gly Phe Val Asp Asn Val
        35                  40                  45

Tyr Ser Gln Gln Ile Arg Cys Phe Gln Ser Ser Asn Ala Gly Ala Pro
    50                  55                  60

Asp Val Tyr Thr Val Gln Ala Gly Ser Ser Val Thr Tyr Tyr Ala Asn
65                  70                  75                  80

Pro Ser Ile Tyr His Pro Gly Pro Met Gln Phe Tyr Leu Ala Arg Val
                85                  90                  95

Pro Asp Gly Gln Asp Val Lys Ser Trp Asn Gly Asp Gly Ala Val Trp
            100                 105                 110

Phe Lys Val Tyr Glu Glu Gln Pro Gln Phe Gly Ser Gln Leu Thr Trp
        115                 120                 125

Pro Ser Asn Gly Lys Asn Ser Phe Gln Val Pro Ile Pro Ser Cys Ile
    130                 135                 140

Arg Pro Gly Lys Tyr Leu Leu Arg Ala Glu His Ile Ala Leu His Val
145                 150                 155                 160

Ala Gln Ser Gln Gly Gly Ala Gln Phe Tyr Ile Ser Cys Ala Gln Leu
                165                 170                 175

Asp Val Thr Gly Gly Gly Ser Thr Glu Pro Ser Gln Lys Val Ala Phe
            180                 185                 190

Pro Gly Ala Tyr Ser Pro Thr Asp Pro Gly Ile Leu Ile Asn Ile Asn
        195                 200                 205

Trp Pro Ile Pro Thr Ser Tyr Lys Asn Pro Gly Pro Pro Val Phe Arg
    210                 215                 220

Cys
225
```

<210> SEQ ID NO 189
<211> LENGTH: 901
<212> TYPE: DNA
<213> ORGANISM: Corynascus thermophilus

<400> SEQUENCE: 189

```
atgaaggttc tcgcgcccct ggttctggcc ggcgccgcca gcgcccacac catcttcacg     60
tcgctcgagg tgggcggcgt caaccatggc gtcggccagg cgtccgcgt gccgtcgtac    120 aacggcccga tcgaggacgt gacgtccaac tcgatcgcct gcaacggccc cccaacccg    180 acgacgccga cggacaaggt gatcacggtc caggccggcc agacggtgac ggccatctgg    240
cggtacatgc tcagcaccac cggctcggcc cccaacgacg tcatggacag cagccacaag    300
```

```
ggcccgacca tgqcctacct caagaaggtc ggcaacgcca ccaccgactc gggcgtcggc    360
ggcggctggt tcaagatcca ggaggacggg ctgaacaacg gcgtctgggg cacggagcgc    420
gtcatcaacg ccagggccg ccacaacatc aagatccccg agtgcatcgc ccccggccag    480
tacctcctcc gcgccgagat gctcgccctg cacggagcct ccaactaccc cggcgcccag    540
ttctacatgg agtgcgctca gctcaacagt acgtttgtcc acgagagacg gaaaaacaaa    600
acagaagcaa gggaggcgg ggcagatgtg atggctaaca ttgatgcttt cttcttcagt     660
cgtcggcggc agcggcagca agaccccgtc caccgtcagc ttcccgggtg cttacagcgt    720
acgttgttcc aaaaggcttt tcttcgcgt tttttttct ttgaactgat acagccccct      780
ctgtgacgac tactaacacg gccacaatca acagggcaac gaccccggtg tcaagatcaa    840
catctactgg cctcccgtca ccgaatacaa ggttcccggc cccagcgtct tcacttgcta    900
a                                                                    901
```

<210> SEQ ID NO 190
<211> LENGTH: 237
<212> TYPE: PRT
<213> ORGANISM: Corynascus thermophilus

<400> SEQUENCE: 190

```
Met Lys Val Leu Ala Pro Leu Val Leu Ala Gly Ala Ser Ala His
1               5                   10                  15

Thr Ile Phe Thr Ser Leu Glu Val Gly Val Asn His Gly Val Gly
                20                  25                  30

Gln Gly Val Arg Val Pro Ser Tyr Asn Gly Pro Ile Glu Asp Val Thr
            35                  40                  45

Ser Asn Ser Ile Ala Cys Asn Gly Pro Pro Asn Pro Thr Thr Pro Thr
        50                  55                  60

Asp Lys Val Ile Thr Val Gln Ala Gly Gln Thr Val Thr Ala Ile Trp
65                  70                  75                  80

Arg Tyr Met Leu Ser Thr Thr Gly Ser Ala Pro Asn Asp Val Met Asp
                85                  90                  95

Ser Ser His Lys Gly Pro Thr Met Ala Tyr Leu Lys Lys Val Gly Asn
            100                 105                 110

Ala Thr Thr Asp Ser Gly Val Gly Gly Gly Trp Phe Lys Ile Gln Glu
        115                 120                 125

Asp Gly Leu Asn Asn Gly Val Trp Gly Thr Glu Arg Val Ile Asn Gly
    130                 135                 140

Gln Gly Arg His Asn Ile Lys Ile Pro Glu Cys Ile Ala Pro Gly Gln
145                 150                 155                 160

Tyr Leu Leu Arg Ala Glu Met Leu Ala Leu His Gly Ala Ser Asn Tyr
                165                 170                 175

Pro Gly Ala Gln Phe Tyr Met Glu Cys Ala Gln Leu Asn Ile Val Gly
            180                 185                 190

Gly Ser Gly Ser Lys Thr Pro Ser Thr Val Ser Phe Pro Gly Ala Tyr
        195                 200                 205

Ser Gly Asn Asp Pro Gly Val Lys Ile Asn Ile Tyr Trp Pro Pro Val
    210                 215                 220

Thr Glu Tyr Lys Val Pro Gly Pro Ser Val Phe Thr Cys
225                 230                 235
```

<210> SEQ ID NO 191
<211> LENGTH: 944
<212> TYPE: DNA

<213> ORGANISM: Corynascus thermophilus

<400> SEQUENCE: 191

```
atgaagctga gcgctgccat cgccgtgctc gcggccgccc ttgccgaggc gcactgtaag      60
ctggcttgcc ggtcctcccc cttctcaacg acgccgagct cgagcgcgtg ggactaatga     120
cgatgtgacg acgacatcaa gatacctttc ccagcatcgc caacacgccc gactggcagt     180
atgtgcgcat cacgaccaac taccagagca acggccccgt gacggacgtc aactcggacc     240
agatccgctg ctacgagcgc aacccgggca cgggcgcgcc cggcatctac aacgtcaccg     300
ccggcaccac catcaactac aacgccaagt cgtccatctc ccacccgggc cccatggcct     360
tctacatcgc caaggtcccc gccggccagt cggccgccac ctgggacggc aagggcgccg     420
tctggtccaa gatctaccag gagatgccgc actttggctc gagcctgacc tgggactcga     480
acggtatgat gagttctctc tctccttctc tctttgatgc tctccttgtg atgctaaacg     540
acgaccccg ccaggccgcg tctccatgcc cgtcaccatc cccgctgtc tgcagaacgg      600
cgagtacctg ctgcgtgccg agcacattgc cctccacagc gccggcagcg tcggcggcgc     660
ccagttctac atctcgtgcg ctcagatctc gggtatgcat tatatacttc catattgtcc     720
acccactcac cccccatccc ccacgcttaa tagctcgagc agcggaacca tctgaagcta     780
acacgtcccc cccagtcacc ggcggcaccg gcacctggaa ccccgcaac aaggtgtcct      840
tccccggcgc ctacaaggcc accgacccgg gcatcctgat caacatctac tggcccatcc     900
cgaccagcta cacgcccgcc ggcccggccg tcgacacctg ctag                      944
```

<210> SEQ ID NO 192
<211> LENGTH: 227
<212> TYPE: PRT
<213> ORGANISM: Corynascus thermophilus

<400> SEQUENCE: 192

```
Met Lys Leu Ser Ala Ala Ile Ala Val Leu Ala Ala Leu Ala Glu
1               5                   10                  15

Ala His Tyr Thr Phe Pro Ser Ile Ala Asn Thr Pro Asp Trp Gln Tyr
            20                  25                  30

Val Arg Ile Thr Thr Asn Tyr Gln Ser Asn Gly Pro Val Thr Asp Val
        35                  40                  45

Asn Ser Asp Gln Ile Arg Cys Tyr Glu Arg Asn Pro Gly Thr Gly Ala
    50                  55                  60

Pro Gly Ile Tyr Asn Val Thr Ala Gly Thr Thr Ile Asn Tyr Asn Ala
65                  70                  75                  80

Lys Ser Ser Ile Ser His Pro Gly Pro Met Ala Phe Tyr Ile Ala Lys
                85                  90                  95

Val Pro Ala Gly Gln Ser Ala Ala Thr Trp Asp Gly Lys Gly Ala Val
            100                 105                 110

Trp Ser Lys Ile Tyr Gln Glu Met Pro His Phe Gly Ser Ser Leu Thr
        115                 120                 125

Trp Asp Ser Asn Gly Arg Val Ser Met Pro Val Thr Ile Pro Arg Cys
    130                 135                 140

Leu Gln Asn Gly Glu Tyr Leu Leu Arg Ala Glu His Ile Ala Leu His
145                 150                 155                 160

Ser Ala Gly Ser Val Gly Gly Ala Gln Phe Tyr Ile Ser Cys Ala Gln
                165                 170                 175

Ile Ser Val Thr Gly Gly Thr Gly Thr Trp Asn Pro Arg Asn Lys Val
            180                 185                 190
```

Ser Phe Pro Gly Ala Tyr Lys Ala Thr Asp Pro Gly Ile Leu Ile Asn
        195                 200                 205

Ile Tyr Trp Pro Ile Pro Thr Ser Tyr Thr Pro Ala Gly Pro Ala Val
    210                 215                 220

Asp Thr Cys
225

<210> SEQ ID NO 193
<211> LENGTH: 948
<212> TYPE: DNA
<213> ORGANISM: Corynascus thermophilus

<400> SEQUENCE: 193

```
atgtcttcct tcacctccaa gggcctcctt tccgccctca tgggcgctgc cacggttgcc    60
gcccacggcc acgtcaccaa tatcgtcatc aacggcgtct cgtaccagaa ctacgatccg   120
ttcagccacc cttacatgcg aaccccccg acggttgtcg gctggacggg agcaacacg    180
gacaacggct tcgtcggccc cgagtccttc tctagcccgg acatcatctg ccacaagtcg   240
gccaccaacg ccggcggtca tgccgttgtt gccgccggcg acaagatttc catccagtgg   300
gacacctggc ccgagtcgca ccacggtccg gtcatcgact acctcgccga ctgcggcgac   360
gcgggctgcg agaaggtcga caagaccacg ctcgagttct tcaagatcag cgagaagggc   420
ctgatcgacg cagcagcgc gcccggcagg tgggcgtccg acgagctgat cgccaacaac   480
aactcgtggc tggtccagat cccgccccgac atcgcccccg caactacgt cctgcgccac   540
gagatcatcg ccctgcacag cgccggccag cagaacggcg cgcagaacta ccccagtgc    600
gtcaacctgc acatcaccgg ctccggcacc cggaaaccct cgggcgtccc cggcaccgag   660
ctctaccggc cgaccgaccc cggcatcctg ccaacatct acacctcccc cgtcgcctac   720
cagatccccg gccggccat catcccgggc gcctccgccg tcgagcagac cacctcggcc   780
atcaccgcct ccgccagcgc ggttcttccc ggcttcgcta ccgccgcgcc ccggctgcg    840
accaccacaa ccaccaccgc ctccgctacc agtgctcccc gcccgaccgg ctgtgccggt   900
ctgaggaagc gccgtcgcca cgcccgtgat gtcaaggttg ccctctag             948
```

<210> SEQ ID NO 194
<211> LENGTH: 315
<212> TYPE: PRT
<213> ORGANISM: Corynascus thermophilus

<400> SEQUENCE: 194

Met Ser Ser Phe Thr Ser Lys Gly Leu Leu Ser Ala Leu Met Gly Ala
1               5                   10                  15

Ala Thr Val Ala Ala His Gly His Val Thr Asn Ile Val Ile Asn Gly
            20                  25                  30

Val Ser Tyr Gln Asn Tyr Asp Pro Phe Ser His Pro Tyr Met Arg Asn
        35                  40                  45

Pro Pro Thr Val Val Gly Trp Thr Ala Ser Asn Thr Asp Asn Gly Phe
    50                  55                  60

Val Gly Pro Glu Ser Phe Ser Ser Pro Asp Ile Ile Cys His Lys Ser
65                  70                  75                  80

Ala Thr Asn Ala Gly Gly His Ala Val Val Ala Ala Gly Asp Lys Ile
                85                  90                  95

Ser Ile Gln Trp Asp Thr Trp Pro Glu Ser His Gly Pro Val Ile
            100                 105                 110

| | | | | | | | | | | | | |
|---|---|---|---|---|---|---|---|---|---|---|---|---|
|Asp|Tyr|Leu|Ala|Asp|Cys|Gly|Asp|Ala|Gly|Cys|Glu|Lys|Val|Asp|Lys|
| | |115| | | |120| | | |125| | | |

Asp Tyr Leu Ala Asp Cys Gly Asp Ala Gly Cys Glu Lys Val Asp Lys
          115                 120                 125

Thr Thr Leu Glu Phe Phe Lys Ile Ser Glu Lys Gly Leu Ile Asp Gly
    130                 135                 140

Ser Ser Ala Pro Gly Arg Trp Ala Ser Asp Glu Leu Ile Ala Asn Asn
145                 150                 155                 160

Asn Ser Trp Leu Val Gln Ile Pro Pro Asp Ile Ala Pro Gly Asn Tyr
                165                 170                 175

Val Leu Arg His Glu Ile Ile Ala Leu His Ser Ala Gly Gln Gln Asn
            180                 185                 190

Gly Ala Gln Asn Tyr Pro Gln Cys Val Asn Leu His Ile Thr Gly Ser
        195                 200                 205

Gly Thr Arg Lys Pro Ser Gly Val Pro Gly Thr Glu Leu Tyr Arg Pro
    210                 215                 220

Thr Asp Pro Gly Ile Leu Ala Asn Ile Tyr Thr Ser Pro Val Ala Tyr
225                 230                 235                 240

Gln Ile Pro Gly Pro Ala Ile Ile Pro Gly Ala Ser Ala Val Glu Gln
                245                 250                 255

Thr Thr Ser Ala Ile Thr Ala Ser Ala Ser Val Leu Pro Gly Phe
            260                 265                 270

Ala Thr Ala Ala Pro Pro Ala Ala Thr Thr Thr Thr Thr Thr Ala Ser
        275                 280                 285

Ala Thr Ser Ala Pro Arg Pro Thr Gly Cys Ala Gly Leu Arg Lys Arg
    290                 295                 300

Arg Arg His Ala Arg Asp Val Lys Val Ala Leu
305                 310                 315

<210> SEQ ID NO 195
<211> LENGTH: 1380
<212> TYPE: DNA
<213> ORGANISM: Corynascus thermophilus

<400> SEQUENCE: 195

```
atgcatcctc ccatctttgt tcttgggctt gcgagcctgc tttgccccct ctcgtctgca    60
cacactactt tcaccaccct cttcatcaat gatgtcaacc aaggtgacgg aacctgcatt   120
cgcatggcga aggagggcaa cgtcgctact catcctctcg cgggcggcct cgactctgaa   180
gacatggcct gtggtacgtt gacacgtcct tgaccccgcc gagactgtcc cgtgtatcta   240
aacttctcat caggccggga tggccaagaa cccgttgcat ttacctgccc ggccccagct   300
ggtgccaagt tgaccttcga gtttcgcatg tgggccgacg cttcgcagcc cggatcgatc   360
gacccgtccc atcttggcgc tatggccatc tacctcaaga aggtttctaa catgaaatct   420
gacgcggccg ctgggccggg ctggttcaag atttgggacc aaggctacga cacggaggcc   480
aagaagtggg ccaccgagaa tctcattgag aacaacggcc tgctgagcgt caaccttccc   540
tcgggcttgt cgaccggcta ctacctcgtc cgtcaggaga ccattacctt ccaaaacgtc   600
accaatgaca tgccagatcc ccagttctac gtcggttgcg cgcagctcta cgtcgaaggc   660
acctcggact cacccatccc ccagacaag accgtctcca ttcccggcca catcagcgac   720
ccggccgacc cgggcctgac ctttaacatc tacacggacg acgtgtccgc ctacaagccc   780
cccggcccgg aggtttactt ccccaccgcc atcacctcct ccggaagcag cgacgacagg   840
ggggccgcgc gccagcagac tcccgccgac aagcaggccg agaaggcct cgttcccacc   900
gactgcgtcg tcaagaacgc aaactggtgc gccgccgccc tgccgcccta caccgacgag   960
```

```
gccggctgct gggccgccgt ggaggactgc aacaggcagc tggacgagtg ctacaccagc   1020 gcgccccct  cgggcagcag ggggtgcaag atctgggagg agcaggtatg catcgtcgtc   1080
tcgcggaagt gcgaggcccg ggatttccag cccctcccgc ggctgtggaa ggatctaaga   1140
gagggaattg atgagccgat cccgggtggg aagttgcctc cggcgctcaa cgcgggagag   1200
agcggggatc atggcggaag aggctgcggc caccatggtg gcgaggagga ggctggggct   1260
ggggcggcct ccactcctgc ttttgctgct cccccatgcgg ccaggattca caacccaaat  1320
ttcaagaggg gccggcgccg tgagtcgcgt tggcggcgac tggcatctgg tgagcaatag   1380
```

<210> SEQ ID NO 196
<211> LENGTH: 439
<212> TYPE: PRT
<213> ORGANISM: Corynascus thermophilus

<400> SEQUENCE: 196

```
Met His Pro Pro Ile Phe Val Leu Gly Leu Ala Ser Leu Leu Cys Pro
1               5                   10                  15

Leu Ser Ser Ala His Thr Thr Phe Thr Thr Leu Phe Ile Asn Asp Val
            20                  25                  30

Asn Gln Gly Asp Gly Thr Cys Ile Arg Met Ala Lys Glu Gly Asn Val
        35                  40                  45

Ala Thr His Pro Leu Ala Gly Leu Asp Ser Glu Asp Met Ala Cys
    50                  55                  60

Gly Arg Asp Gly Gln Glu Pro Val Ala Phe Thr Cys Pro Ala Pro Ala
65                  70                  75                  80

Gly Ala Lys Leu Thr Phe Glu Phe Arg Met Trp Ala Asp Ala Ser Gln
                85                  90                  95

Pro Gly Ser Ile Asp Pro Ser His Leu Gly Ala Met Ala Ile Tyr Leu
            100                 105                 110

Lys Lys Val Ser Asn Met Lys Ser Asp Ala Ala Ala Gly Pro Gly Trp
        115                 120                 125

Phe Lys Ile Trp Asp Gln Gly Tyr Asp Thr Glu Ala Lys Lys Trp Ala
    130                 135                 140

Thr Glu Asn Leu Ile Glu Asn Asn Gly Leu Leu Ser Val Asn Leu Pro
145                 150                 155                 160

Ser Gly Leu Ser Thr Gly Tyr Tyr Leu Val Arg Gln Glu Thr Ile Thr
                165                 170                 175

Phe Gln Asn Val Thr Asn Asp Met Pro Asp Pro Gln Phe Tyr Val Gly
            180                 185                 190

Cys Ala Gln Leu Tyr Val Glu Gly Thr Ser Asp Ser Pro Ile Pro Pro
        195                 200                 205

Asp Lys Thr Val Ser Ile Pro Gly His Ile Ser Asp Pro Ala Asp Pro
    210                 215                 220

Gly Leu Thr Phe Asn Ile Tyr Thr Asp Asp Val Ser Ala Tyr Lys Pro
225                 230                 235                 240

Pro Gly Pro Glu Val Tyr Phe Pro Thr Ala Ile Thr Ser Ser Gly Ser
                245                 250                 255

Ser Asp Asp Arg Gly Ala Ala Arg Gln Gln Thr Pro Ala Asp Lys Gln
            260                 265                 270

Ala Gly Glu Gly Leu Val Pro Thr Asp Cys Val Val Lys Asn Ala Asn
        275                 280                 285

Trp Cys Ala Ala Ala Leu Pro Pro Tyr Thr Asp Glu Ala Gly Cys Trp
    290                 295                 300
```

```
Ala Ala Val Glu Asp Cys Asn Arg Gln Leu Asp Glu Cys Tyr Thr Ser
305                 310                 315                 320

Ala Pro Pro Ser Gly Ser Arg Gly Cys Lys Ile Trp Glu Glu Gln Val
            325                 330                 335

Cys Ile Val Val Ser Arg Lys Cys Glu Ala Arg Asp Phe Gln Pro Leu
                340                 345                 350

Pro Arg Leu Trp Lys Asp Leu Arg Glu Gly Ile Asp Glu Pro Ile Pro
            355                 360                 365

Gly Gly Lys Leu Pro Pro Ala Leu Asn Ala Gly Ser Gly Asp His
        370                 375                 380

Gly Gly Arg Gly Cys Gly His His Gly Gly Glu Glu Ala Gly Ala
385                 390                 395                 400

Gly Ala Ala Ser Thr Pro Ala Phe Ala Ala Pro His Ala Ala Arg Ile
                405                 410                 415

His Asn Pro Asn Phe Lys Arg Gly Arg Arg Glu Ser Arg Trp Arg
            420                 425                 430

Arg Leu Ala Ser Gly Glu Gln
        435
```

<210> SEQ ID NO 197
<211> LENGTH: 821
<212> TYPE: DNA
<213> ORGANISM: Corynascus thermophilus

<400> SEQUENCE: 197

```
atgaagctct ctctcttttc cgtcctggcc gctgccctca ccgtcgaggg gcatgccatc      60
ttccagaagg tctccgtcaa cggggcggac cagggctccc tcaccggcct ccgcgctccc     120
aacaacaaca accgggtgca ggatgtcagc agccaggaca tgatctgcgg ccagccggga     180
tcgacgtcga gcacggtcat cgaggtcaag gccggcgaca ggatcggcgc ctggtaccag     240
cacgtcatcg gcggtgccca gttccccggc gaccctgaca cccgatcgc cgcgtcgcac      300
aagggccccg tcatggccta cctcgccaag gttgacaatg ccgcaaccgc cgacaagacg     360
ggcctgcagt ggtatgtgtt cccgccgccc gagggacgtc agcttggggc aagtcgcgtc     420
tgaccgggct cgcttctttc tctctgtata ggttcaagat ctgggaggac acctttgatc     480
ccagcagcaa gacctggggt gtcgacaacc tcatcaacaa caacggctgg gtgtacttca     540
acatcccgca gtgcatcgcc gacgccact acctcctccg ggttgaggtc ctcgccctgc      600
actcggccta ccagaccggc ggggctcagt tctaccagtc ctgcgcccag atcagcgtgt     660
ccggcggcg ctccttcacg ccgtcgtcga ctgtgagctt cccgggcgcc tacaacgcca      720
acgaccccgg catcacgatc aacatctacg gcgctaccgg tcagcccgac aacaacggcc     780
agccgtacac tgcccctggc cccgcgccca tctcctgctg a                         821
```

<210> SEQ ID NO 198
<211> LENGTH: 246
<212> TYPE: PRT
<213> ORGANISM: Corynascus thermophilus

<400> SEQUENCE: 198

```
Met Lys Leu Ser Leu Phe Ser Val Leu Ala Ala Leu Thr Val Glu
1               5                   10                  15

Gly His Ala Ile Phe Gln Lys Val Ser Val Asn Gly Ala Asp Gln Gly
            20                  25                  30

Ser Leu Thr Gly Leu Arg Ala Pro Asn Asn Asn Pro Val Gln Asp
        35                  40                  45
```

```
Val Ser Ser Gln Asp Met Ile Cys Gly Gln Pro Gly Ser Thr Ser Ser
     50                  55                  60

Thr Val Ile Glu Val Lys Ala Gly Asp Arg Ile Gly Ala Trp Tyr Gln
 65                  70                  75                  80

His Val Ile Gly Gly Ala Gln Phe Pro Gly Asp Pro Asp Asn Pro Ile
                 85                  90                  95

Ala Ala Ser His Lys Gly Pro Val Met Ala Tyr Leu Ala Lys Val Asp
            100                 105                 110

Asn Ala Ala Thr Ala Asp Lys Thr Gly Leu Gln Trp Phe Lys Ile Trp
            115                 120                 125

Glu Asp Thr Phe Asp Pro Ser Ser Lys Thr Trp Gly Val Asp Asn Leu
130                 135                 140

Ile Asn Asn Gly Trp Val Tyr Phe Asn Ile Pro Gln Cys Ile Ala
145                 150                 155                 160

Asp Gly His Tyr Leu Leu Arg Val Glu Val Leu Ala Leu His Ser Ala
                165                 170                 175

Tyr Gln Thr Gly Gly Ala Gln Phe Tyr Gln Ser Cys Ala Gln Ile Ser
            180                 185                 190

Val Ser Gly Gly Ser Phe Thr Pro Ser Ser Thr Val Ser Phe Pro
            195                 200                 205

Gly Ala Tyr Asn Ala Asn Asp Pro Gly Ile Thr Ile Asn Ile Tyr Gly
            210                 215                 220

Ala Thr Gly Gln Pro Asp Asn Asn Gly Gln Pro Tyr Thr Ala Pro Gly
225                 230                 235                 240

Pro Ala Pro Ile Ser Cys
                245

<210> SEQ ID NO 199
<211> LENGTH: 1125
<212> TYPE: DNA
<213> ORGANISM: Corynascus thermophilus

<400> SEQUENCE: 199
atgaagtcct tcaccctcac cgccctggcc gccctggccg caacgccgc cgcccacgcg      60
accttccagg ccctctgggt cgacggcgtc gactacggct cgcagtgcgc ccgtcttccc    120
ggatccaact ccccgatcac cgacgtgagc tcgacggcca tccgctgcaa tgccaacgcc    180
ggccgcgccc agggcaagtg cccggtcaag gccggctcga ccgtgacgat cgagatgcac    240
caggtatgtt ccactaaaag gaggaaaaga aaaaaaacag agtggaacgg tcaggctgac    300
tgaggctctc tcgctacgat cagcaacccg gtgaccggtc gtgcggcagc gacgccatcg    360
gcggcgccca ccacggcccc gtcctcgtgt acatgtccaa ggtgtcggat gcggcgtcgg    420
ccgacggctc gtccggctgg ttcaaggtgt tcgaggacgg ctgggccaag aacccgtcgg    480
gcggctccgg cgacgacgac tactgggca ccaaggacct caacgcctgc tgcggcaaga    540
tgaacgtcaa gatcccgtcc gacctgccgt cgggcgacta cctgctccgt gccgaggcca    600
tcgccctgca cacggccggc ggctcgggcg cgcccagtt ctacatcacc tgctaccagc    660
tcaccgtcga gggttccggc aacgccagcc cggccaccgt ctccttccct ggcgcctaca    720
aggcctccga cccgggcatc ctggtcaaca tccacgccgc catgtccggc tacaccgtgc    780
ccggcccgtc cgtctactcg ggcggcagca ccaagaaggc cggcagcggc tgctccggct    840
gcgaggccac ctgcgccgtc ggctctagcc cagcgccac cgtcacctcg tcgcccggca    900
gccagcccac ctcccccggc ggcggcgacg gcggcggctg caccgtcccc aagtaccagc    960
```

```
agtgcggtgg ccagggctac agcggctgca ccaactgcga ggtgagttcc cctgcttact   1020
tgttgtcctc tgtaccoctt ccatgttttc gatgctgact ttctgcgtta gtctggctct   1080
acttgcagcg ccgtctcgcc gccgtactac taccagtgcg tgtaa                  1125
```

<210> SEQ ID NO 200
<211> LENGTH: 324
<212> TYPE: PRT
<213> ORGANISM: Corynascus thermophilus

<400> SEQUENCE: 200

```
Met Lys Ser Phe Thr Leu Thr Ala Leu Ala Ala Leu Ala Gly Asn Ala
1               5                   10                  15

Ala Ala His Ala Thr Phe Gln Ala Leu Trp Val Asp Gly Val Asp Tyr
            20                  25                  30

Gly Ser Gln Cys Ala Arg Leu Pro Gly Ser Asn Ser Pro Ile Thr Asp
        35                  40                  45

Val Ser Ser Thr Ala Ile Arg Cys Asn Ala Asn Ala Gly Arg Ala Gln
    50                  55                  60

Gly Lys Cys Pro Val Lys Ala Gly Ser Thr Val Thr Ile Glu Met His
65                  70                  75                  80

Gln Gln Pro Gly Asp Arg Ser Cys Gly Ser Asp Ala Ile Gly Gly Ala
                85                  90                  95

His His Gly Pro Val Leu Val Tyr Met Ser Lys Val Ser Asp Ala Ala
            100                 105                 110

Ser Ala Asp Gly Ser Ser Gly Trp Phe Lys Val Phe Glu Asp Gly Trp
        115                 120                 125

Ala Lys Asn Pro Ser Gly Gly Ser Gly Asp Asp Tyr Trp Gly Thr
    130                 135                 140

Lys Asp Leu Asn Ala Cys Cys Gly Lys Met Asn Val Lys Ile Pro Ser
145                 150                 155                 160

Asp Leu Pro Ser Gly Asp Tyr Leu Leu Arg Ala Glu Ala Ile Ala Leu
                165                 170                 175

His Thr Ala Gly Gly Ser Gly Gly Ala Gln Phe Tyr Ile Thr Cys Tyr
            180                 185                 190

Gln Leu Thr Val Glu Gly Ser Gly Asn Ala Ser Pro Ala Thr Val Ser
        195                 200                 205

Phe Pro Gly Ala Tyr Lys Ala Ser Asp Pro Gly Ile Leu Val Asn Ile
    210                 215                 220

His Ala Ala Met Ser Gly Tyr Thr Val Pro Gly Pro Ser Val Tyr Ser
225                 230                 235                 240

Gly Gly Ser Thr Lys Lys Ala Gly Ser Gly Cys Ser Gly Cys Glu Ala
                245                 250                 255

Thr Cys Ala Val Gly Ser Ser Pro Ser Ala Thr Val Thr Ser Ser Pro
            260                 265                 270

Gly Ser Gln Pro Thr Ser Pro Gly Gly Asp Gly Gly Gly Cys Thr
        275                 280                 285

Val Pro Lys Tyr Gln Gln Cys Gly Gly Gln Gly Tyr Ser Gly Cys Thr
    290                 295                 300

Asn Cys Glu Ser Gly Ser Thr Cys Ser Ala Val Ser Pro Pro Tyr Tyr
305                 310                 315                 320

Tyr Gln Cys Val
```

<210> SEQ ID NO 201

<211> LENGTH: 1037
<212> TYPE: DNA
<213> ORGANISM: Corynascus thermophilus

<400> SEQUENCE: 201

```
atgaagtcgt tcacctcagc cttgttcgcc gctgggctcc ttgctcagca tgccgcagcc    60
cactccatct tccagcaggc aagcagcggc tcgatcgact cgacacgct gtgcacccgg    120
atgccggtca gtcccgaggg cccttgggtg atggatcatc tgcccataga cttgttaccg   180
acgagctgac gggttctcgt tattaatagc ccaacaatag ccctgtcact agcgtgacca    240
gcggcgacat gacctgcaac gtcggcggca ccaacggagt gtcgggcttc tgcgaggtga    300
acggtatggt ttcccgagtt ttcgaccagt ccccccgttt gattttacc gccgcctgac    360
acgtgggctt cttgcttcgc tccttcggct agccggcgac gagtttacgg ttgagatgca    420
cgcgcagccc ggcgaccgct cgtgcgacaa cgaggccatc ggcgggaacc acttcggccc    480
ggtcctcatc tacatgagca aggtcgacga cgcctcgact gccgacgggt ccggcgactg    540
gttcaaggtg gacgagttcg gctacgaccc gagcaccaag acctggggca ccgacaagct    600
caacgagaac tgcggcaagc gcactttcaa gatccccgc aacatccctg cgggcgacta    660
tctcgtccgg gccgaggcca tcgcgctgca cactgccagc cagccgggcg gcgcgcagtt   720
ctacatgagc tgctatgtaa gtttctagag tctctctctc tctctcgctt tctctctctc   780
gctcgccccg tctctccatt tgtcttcgtt cttccttttc ccttccttca aatgatgtct    840
ccccgctaac tttctctctc cccacaactt agcaagtccg gatttccggc ggcaacggag    900
gccagctgcc tgccggagtc aagatcccgg gcgcgtacag tgccaacgac cccggtatcc    960
tcatcgacat ctggggcaac gacttcaacg agtacatcat cccgggcccg ccgttatcg   1020
acagcagcta cttctaa                                                  1037
```

<210> SEQ ID NO 202
<211> LENGTH: 242
<212> TYPE: PRT
<213> ORGANISM: Corynascus thermophilus

<400> SEQUENCE: 202

```
Met Lys Ser Phe Thr Ser Ala Leu Phe Ala Ala Gly Leu Leu Ala Gln
1               5                   10                  15
His Ala Ala His Ser Ile Phe Gln Gln Ala Ser Ser Gly Ser Ile
            20                  25                  30
Asp Phe Asp Thr Leu Cys Thr Arg Met Pro Pro Asn Asn Ser Pro Val
        35                  40                  45
Thr Ser Val Thr Ser Gly Asp Met Thr Cys Asn Val Gly Gly Thr Asn
    50                  55                  60
Gly Val Ser Gly Phe Cys Glu Val Asn Ala Gly Asp Glu Phe Thr Val
65                  70                  75                  80
Glu Met His Ala Gln Pro Gly Asp Arg Ser Cys Asp Asn Glu Ala Ile
                85                  90                  95
Gly Gly Asn His Phe Gly Pro Val Leu Ile Tyr Met Ser Lys Val Asp
            100                 105                 110
Asp Ala Ser Thr Ala Asp Gly Ser Gly Asp Trp Phe Lys Val Asp Glu
        115                 120                 125
Phe Gly Tyr Asp Pro Ser Thr Lys Thr Trp Gly Thr Asp Lys Leu Asn
    130                 135                 140
Glu Asn Cys Gly Lys Arg Thr Phe Lys Ile Pro Arg Asn Ile Pro Ala
145                 150                 155                 160
```

Gly Asp Tyr Leu Val Arg Ala Glu Ala Ile Ala Leu His Thr Ala Ser
            165                 170                 175

Gln Pro Gly Gly Ala Gln Phe Tyr Met Ser Cys Tyr Gln Val Arg Ile
        180                 185                 190

Ser Gly Gly Asn Gly Gly Gln Leu Pro Ala Gly Val Lys Ile Pro Gly
            195                 200                 205

Ala Tyr Ser Ala Asn Asp Pro Gly Ile Leu Ile Asp Ile Trp Gly Asn
        210                 215                 220

Asp Phe Asn Glu Tyr Ile Ile Pro Gly Pro Pro Val Ile Asp Ser Ser
225                 230                 235                 240

Tyr Phe

<210> SEQ ID NO 203
<211> LENGTH: 1200
<212> TYPE: DNA
<213> ORGANISM: Corynascus thermophilus

<400> SEQUENCE: 203

```
atgaaggcct ttagcctcgt cgccctggcg acggccgtga gcggccatac catcttccag     60
cgggtgtcgg tcaacgggca agaccagggc cagctcaagg gcgtgcgggc gccgtcgagc    120
aacttcccga tccagaacgt caacgattcc aacttcgcct gcaacgcaaa catcgtgtac    180
aaggacgaca ccatcatcaa gatccccgcg ggagcccgcg tgggttcgtg gtggcagcac    240
gtcatcggcg gcccgcaggg ctccaacgac ccggacaacc cgatcgccgc ctcccacaag    300
ggtatgctga gatggcgaac caacccgcgc ccccttcccc ccctcaacct cccggaaca    360
cgcgtagctg acgggcaaat ccaggcccca tccaggtcta cctggccaag gttgacaacg    420
cggcgacagc gtcgcccacg ggcctcaggt ggttcaaggt tgccgagcgc gggctgaaca    480
acggcgtgtg ggcggtcgac gagctcatcg ccaacaacgg ctggcactac ttcgacctgc    540
cgtcgtgcgt ggccccggc cagtacctga tgcgcgtcga gctgctcgcc ctgcacagcg    600
cctcgagccc cggcggcgcc cagttctaca tgggctgcgc ccagatcgaa ggtgggtgca    660
attctcgttc tgcttccccg tcccttccgg ccctttcttt ctctctctcc ccttgtgctt    720
tcttcgctcc ttgacgaacc cgaggaaaga gggaagagga agaggaaag agggaggaaa    780
cggggcggag agacagacgg gatcgaatga gagagacaag acaagatcgg ctgacgagga    840
caaccagtca ccggctcggg cacccacacg ggctccgact tcgtctcgtt cccgggcgcc    900
tactcggcca cgacccggg catcctgctg agcatctacg actcctcggg caagcccacc    960
aacggcgggc gggcgtacca gatccccggc ccgcgcccca tctcgtgctc gggcggcagc   1020
aacggcggcg gtgacaacgg cggcggcgac aacggcggcg caacaacgg cggcggcaac   1080
agcggcggca ccgtcccct ctacggccag tgcggcggca acggatacac cggcccgacc   1140
acctgcgccg agggaacctg caaggtgtcg aacgagtggt acagccagtg cctcccctag   1200
```

<210> SEQ ID NO 204
<211> LENGTH: 306
<212> TYPE: PRT
<213> ORGANISM: Corynascus thermophilus

<400> SEQUENCE: 204

Met Lys Ala Phe Ser Leu Val Ala Leu Ala Thr Ala Val Ser Gly His
1               5                   10                  15

Thr Ile Phe Gln Arg Val Ser Val Asn Gly Gln Asp Gln Gly Gln Leu
            20                  25                  30

Lys Gly Val Arg Ala Pro Ser Ser Asn Phe Pro Ile Gln Asn Val Asn
        35                  40                  45

Asp Ser Asn Phe Ala Cys Asn Ala Asn Ile Val Tyr Lys Asp Asp Thr
 50                  55                  60

Ile Ile Lys Ile Pro Ala Gly Ala Arg Val Gly Ser Trp Trp Gln His
 65                  70                  75                  80

Val Ile Gly Gly Pro Gln Gly Ser Asn Asp Pro Asp Asn Pro Ile Ala
                85                  90                  95

Ala Ser His Lys Gly Pro Ile Gln Val Tyr Leu Ala Lys Val Asp Asn
                100                 105                 110

Ala Ala Thr Ala Ser Pro Thr Gly Leu Arg Trp Phe Lys Val Ala Glu
                115                 120                 125

Arg Gly Leu Asn Asn Gly Val Trp Ala Val Asp Glu Leu Ile Ala Asn
        130                 135                 140

Asn Gly Trp His Tyr Phe Asp Leu Pro Ser Cys Val Ala Pro Gly Gln
145                 150                 155                 160

Tyr Leu Met Arg Val Glu Leu Leu Ala Leu His Ser Ala Ser Ser Pro
                165                 170                 175

Gly Gly Ala Gln Phe Tyr Met Gly Cys Ala Gln Ile Glu Val Thr Gly
                180                 185                 190

Ser Gly Thr His Thr Gly Ser Asp Phe Val Ser Phe Pro Gly Ala Tyr
                195                 200                 205

Ser Ala Asn Asp Pro Gly Ile Leu Leu Ser Ile Tyr Asp Ser Ser Gly
        210                 215                 220

Lys Pro Thr Asn Gly Gly Arg Ala Tyr Gln Ile Pro Gly Pro Arg Pro
225                 230                 235                 240

Ile Ser Cys Ser Gly Gly Ser Asn Gly Gly Asp Asn Gly Gly
                245                 250                 255

Asp Asn Gly Gly Gly Asn Asn Gly Gly Gly Asn Ser Gly Gly Thr Val
                260                 265                 270

Pro Leu Tyr Gly Gln Cys Gly Gly Asn Gly Tyr Thr Gly Pro Thr Thr
        275                 280                 285

Cys Ala Glu Gly Thr Cys Lys Val Ser Asn Glu Trp Tyr Ser Gln Cys
 290                 295                 300

Leu Pro
305

<210> SEQ ID NO 205
<211> LENGTH: 759
<212> TYPE: DNA
<213> ORGANISM: Acrophialophora fusispora

<400> SEQUENCE: 205
atgcgcatag aagctatcac aggcctcgtg ctggcctcgg ccggtgcagt gtctgcccat      60
ggctgggtcg atgtctgggc tattggcggc aagaactaca caggcttcaa ccccacggtg     120
gcgccatggg tcccggatca gggcaccatt gcgtggccgg cctggaacac cgacacagga     180
ccggtgtaca gcaaggacgt caacaccaca gacatcatct gctcaatcaa tgccaccaac     240
gccaagatct actccgaccc catcgccgct gggaacgtca tcaacctgca ctggacggtg     300
tggccagact cacaccacgg gcccatcctg tcgtacctgg ccgcgtgcaa cggcgactgc     360
gccaaggccg acaagaccaa gctcaagtgg ttcaagattg cccatgccgg tcaaatcagc     420
ctgggcaccg gcggcggcca ggttggctac tgggccagcg acaagctgca agacgacaac     480

```
ggcacctggc cgtcaccat tccggcctcc atcaagcccg gcaattacgt gctgcggaac    540
gagattattg ccctccattc ggcgtacgac gtcggcgccg cccagctcta cccgcagtgc    600
gttaatatca agatcacggg caacggccgc gtcaccctg ccggcgtggt gggaaccaag     660
ctctacaagg agaccgatcc tggcctgcat tataacatct ataacgacga gtctaagcct    720
gtctatcaga tccccggccc ggccttgtgt aagtgctaa                           759
```

```
<210> SEQ ID NO 206
<211> LENGTH: 252
<212> TYPE: PRT
<213> ORGANISM: Acrophialophora fusispora

<400> SEQUENCE: 206

Met Arg Ile Glu Ala Ile Thr Gly Leu Val Leu Ala Ser Ala Gly Ala
1               5                   10                  15
Val Ser Ala His Gly Trp Val Asp Val Trp Ala Ile Gly Gly Lys Asn
                20                  25                  30
Tyr Thr Gly Phe Asn Pro Thr Val Ala Pro Trp Val Pro Asp Gln Gly
            35                  40                  45
Thr Ile Ala Trp Pro Ala Trp Asn Thr Asp Thr Gly Pro Val Tyr Ser
        50                  55                  60
Lys Asp Val Asn Thr Thr Asp Ile Ile Cys Ser Ile Asn Ala Thr Asn
65                  70                  75                  80
Ala Lys Ile Tyr Ser Asp Pro Ile Ala Ala Gly Asn Val Ile Asn Leu
                85                  90                  95
His Trp Thr Val Trp Pro Asp Ser His His Gly Pro Ile Leu Ser Tyr
            100                 105                 110
Leu Ala Ala Cys Asn Gly Asp Cys Ala Lys Ala Asp Lys Thr Lys Leu
        115                 120                 125
Lys Trp Phe Lys Ile Ala His Ala Gly Gln Ile Ser Leu Gly Thr Gly
130                 135                 140
Gly Gly Gln Val Gly Tyr Trp Ala Ser Asp Lys Leu Gln Asp Asp Asn
145                 150                 155                 160
Gly Thr Trp Pro Val Thr Ile Pro Ala Ser Ile Lys Pro Gly Asn Tyr
                165                 170                 175
Val Leu Arg Asn Glu Ile Ile Ala Leu His Ser Ala Tyr Asp Val Gly
            180                 185                 190
Ala Ala Gln Leu Tyr Pro Gln Cys Val Asn Ile Lys Ile Thr Gly Asn
        195                 200                 205
Gly Arg Val Thr Pro Ala Gly Val Val Gly Thr Lys Leu Tyr Lys Glu
210                 215                 220
Thr Asp Pro Gly Leu His Tyr Asn Ile Tyr Asn Asp Glu Ser Lys Pro
225                 230                 235                 240
Val Tyr Gln Ile Pro Gly Pro Ala Leu Cys Lys Cys
                245                 250
```

```
<210> SEQ ID NO 207
<211> LENGTH: 1035
<212> TYPE: DNA
<213> ORGANISM: Corynascus sepedonium

<400> SEQUENCE: 207
atgtctaaga cttctgctct ccttgctggc ctaacggggcg cggccctcgt cgctgcccac    60
gggcacgtca gccatatcat tgtcaacggt gtctactatg agaactacga ccccacgaca   120
cactggtacc agcccaaccc accaacagtc atcggctgga cggcagccca gcaggacaac   180
```

```
ggcttcatcg agcccaacaa ctttggcacg tcggacatca tctgccacaa gagcggttct    240
ccaggcggcg gtcacgctac cgtcgctgcg ggcgacaaga tcaacatcgt ctggactccg    300
gagtggcccg actcccatat cggcccggtc attgactacc tggctgcctg caacggtgac    360
tgcgagaccg taaacaagga gtcgctgcgc ttctttaaga ttgacggggc cggctatgac    420
aaggccgctg gccgctgggc cgccgagact ctgcgccaga acggcaacag ctggctcgtc    480
cagatcccgt ctgaccttaa ggctggcaac tacgtgctcc gccacgaaat catcgccctc    540
cacggcgctg gaagcgccaa cggtgctcaa gcctaccgc agtgcatcaa ccttcgcgtg     600
acgggcggcg gcagcagcgt gcccagcggc gtggccggca cctcgctcta caaagcctcc    660
gacgcaggca tcctcttcaa cccctacgtc gcctctcccg attacccggt cccaggcccg    720
gcgctcattg ctggtgccgc cagctctatc gtacagagca cgtcggcagt gaccgctacc    780
gcctcggcca ccgctcccgg tggcggcggc gccaacccca accctacgcc caccaccacc    840
tcctcgagca tcccgcccc aagcaccacc ctcaggacaa ccacctcggc cgcgcaaacc     900
acgcccccgc ctaccaatgg caacgtccag acaaagtacg gtcagtgtgg tggtagggac    960
tggagcggcc caacggcgtg cgcggctggt tccagctgct cggtgctcaa cgactggtac   1020
tcccagtgcg tgtaa                                                     1035
```

<210> SEQ ID NO 208
<211> LENGTH: 344
<212> TYPE: PRT
<213> ORGANISM: Corynascus sepedonium

<400> SEQUENCE: 208

```
Met Ser Lys Thr Ser Ala Leu Leu Ala Gly Leu Thr Gly Ala Ala Leu
1               5                   10                  15

Val Ala Ala His Gly His Val Ser His Ile Ile Val Asn Gly Val Tyr
            20                  25                  30

Tyr Glu Asn Tyr Asp Pro Thr Thr His Trp Tyr Gln Pro Asn Pro
        35                  40                  45

Thr Val Ile Gly Trp Thr Ala Ala Gln Gln Asp Asn Gly Phe Ile Glu
    50                  55                  60

Pro Asn Asn Phe Gly Thr Ser Asp Ile Ile Cys His Lys Ser Gly Ser
65                  70                  75                  80

Pro Gly Gly Gly His Ala Thr Val Ala Ala Gly Asp Lys Ile Asn Ile
                85                  90                  95

Val Trp Thr Pro Glu Trp Pro Asp Ser His Ile Gly Pro Val Ile Asp
            100                 105                 110

Tyr Leu Ala Ala Cys Asn Gly Asp Cys Glu Thr Val Asn Lys Glu Ser
        115                 120                 125

Leu Arg Phe Phe Lys Ile Asp Gly Ala Gly Tyr Asp Lys Ala Ala Gly
    130                 135                 140

Arg Trp Ala Ala Glu Thr Leu Arg Gln Asn Gly Asn Ser Trp Leu Val
145                 150                 155                 160

Gln Ile Pro Ser Asp Leu Lys Ala Gly Asn Tyr Val Leu Arg His Glu
                165                 170                 175

Ile Ile Ala Leu His Gly Ala Gly Ser Ala Asn Gly Ala Gln Ala Tyr
            180                 185                 190

Pro Gln Cys Ile Asn Leu Arg Val Thr Gly Gly Gly Ser Ser Val Pro
        195                 200                 205

Ser Gly Val Ala Gly Thr Ser Leu Tyr Lys Ala Ser Asp Ala Gly Ile
```

```
Leu Phe Asn Pro Tyr Val Ala Ser Pro Asp Tyr Pro Val Pro Gly Pro
225                 230                 235                 240

Ala Leu Ile Ala Gly Ala Ala Ser Ser Ile Val Gln Ser Thr Ser Ala
            245                 250                 255

Val Thr Ala Thr Ala Ser Ala Thr Ala Pro Gly Gly Gly Ala Asn
            260                 265                 270

Pro Asn Pro Thr Pro Thr Thr Thr Ser Ser Ser Asn Pro Ala Pro Ser
        275                 280                 285

Thr Thr Leu Arg Thr Thr Thr Ser Ala Ala Gln Thr Thr Pro Pro Pro
        290                 295                 300

Thr Asn Gly Asn Val Gln Thr Lys Tyr Gly Gln Cys Gly Gly Arg Asp
305                 310                 315                 320

Trp Ser Gly Pro Thr Ala Cys Ala Ala Gly Ser Ser Cys Ser Val Leu
                325                 330                 335

Asn Asp Trp Tyr Ser Gln Cys Val
                340
```

<210> SEQ ID NO 209
<211> LENGTH: 1044
<212> TYPE: DNA
<213> ORGANISM: Corynascus sepedonium

<400> SEQUENCE: 209

```
atgccttctt ctacctccaa gggtctttc tccgccctca tgggcgcggc gtcggttgcc      60
gcccatggtc atgtcaccaa cattgtcatc aacggtgtgt cgtaccagaa ctacgacccg     120
accagcttcc cttacatgca gaacccgccg acggttgttg gctggacggc aagcaacact     180
gataacggct tcgtcgctcc tgatgcgttt gctagcggcg acatcatctg ccacagggac     240
gccaccaatg ctggtggtca tgccgtcgtt gctgctggtg acaaggtctt catccagtgg     300
gataccggc tgagtcgca ccatggcccc gtccttgatt acctcgccag ctgcggtgac      360
gccggctgcg aaacggtcga caagaacact ctcgagttct tcaagatcgg cgaggctggc     420
ctgatcgacg gcagcagtgc tcccggcaag tgggcgtcgg accagctgat tgagaacaat     480
aactcgtgga tggttcagat ccctgccaac cttgcgcccg aaactatgt gctgcggcat     540
gagattattg ctttgcacag cgctgggcaa gctaacggtg cccaaaacta cccccagtgc     600
ttcaacctgc aagttaccgg ctccggcacg acaagcctg ccggtgtgct cggcaccgag     660
ctctacactc ccaccgacgc cggcatcttg ccaacatct acacctcgcc tgttcagtac     720
gagattcctg gcccggctct gatctcgggc gcttcggccg ttgaacagtc ctcctcggct     780
atcaccgcct ccgccagcgc tgagaccggc tccgccacag caccccctgc cggctctgcc     840
acggccgccc ccaccactac cactaccacg gctggctcgg atgctagcgc tacgccctcg     900
tcctcgtcca gctctggtgc gagcaccacc gccgagccca ccccttcggc tactactacc     960
gccggcggca gcaccccgcg cccgacccgg tgccctggcc tgaagcgccg ccgccacgcc    1020
cgtgatgtca agctcgccct ctaa                                          1044
```

<210> SEQ ID NO 210
<211> LENGTH: 347
<212> TYPE: PRT
<213> ORGANISM: Corynascus sepedonium

<400> SEQUENCE: 210

Met Pro Ser Ser Thr Ser Lys Gly Leu Phe Ser Ala Leu Met Gly Ala

```
              1               5                  10                 15
            Ala Ser Val Ala Ala His Gly His Val Thr Asn Ile Val Ile Asn Gly
                           20                  25                 30

Val Ser Tyr Gln Asn Tyr Asp Pro Thr Ser Phe Pro Tyr Met Gln Asn
                           35                  40                 45

Pro Pro Thr Val Val Gly Trp Thr Ala Ser Asn Thr Asp Asn Gly Phe
                           50                  55                 60

Val Ala Pro Asp Ala Phe Ala Ser Gly Asp Ile Ile Cys His Arg Asp
             65                  70                  75                 80

Ala Thr Asn Ala Gly Gly His Ala Val Ala Ala Gly Asp Lys Val
                           85                  90                 95

Phe Ile Gln Trp Asp Thr Trp Pro Glu Ser His His Gly Pro Val Leu
                           100                 105                110

Asp Tyr Leu Ala Ser Cys Gly Asp Ala Gly Cys Glu Thr Val Asp Lys
                           115                 120                125

Asn Thr Leu Glu Phe Phe Lys Ile Gly Glu Ala Gly Leu Ile Asp Gly
                           130                 135                140

Ser Ser Ala Pro Gly Lys Trp Ala Ser Asp Gln Leu Ile Glu Asn Asn
            145                 150                 155                160

Asn Ser Trp Met Val Gln Ile Pro Ala Asn Leu Ala Pro Gly Asn Tyr
                           165                 170                175

Val Leu Arg His Glu Ile Ile Ala Leu His Ser Ala Gly Gln Ala Asn
                           180                 185                190

Gly Ala Gln Asn Tyr Pro Gln Cys Phe Asn Leu Gln Val Thr Gly Ser
                           195                 200                205

Gly Thr Asp Lys Pro Ala Gly Val Leu Gly Thr Glu Leu Tyr Thr Pro
                           210                 215                220

Thr Asp Ala Gly Ile Leu Ala Asn Ile Tyr Thr Ser Pro Val Gln Tyr
            225                 230                 235                240

Glu Ile Pro Gly Pro Ala Leu Ile Ser Gly Ala Ser Ala Val Glu Gln
                           245                 250                255

Ser Ser Ser Ala Ile Thr Ala Ser Ala Ser Glu Thr Gly Ser Ala
                           260                 265                270

Thr Ala Pro Pro Ala Gly Ser Ala Thr Ala Ala Pro Thr Thr Thr Thr
                           275                 280                285

Thr Thr Ala Gly Ser Asp Ala Ser Ala Thr Pro Ser Ser Ser Ser Ser
                           290                 295                300

Ser Gly Ala Ser Thr Thr Ala Glu Pro Thr Pro Ser Ala Thr Thr Thr
            305                 310                 315                320

Ala Gly Gly Ser Thr Pro Arg Pro Thr Arg Cys Pro Gly Leu Lys Arg
                           325                 330                335

Arg Arg His Ala Arg Asp Val Lys Leu Ala Leu
                           340                 345

<210> SEQ ID NO 211
<211> LENGTH: 1005
<212> TYPE: DNA
<213> ORGANISM: Malbranchea cinnamomea

<400> SEQUENCE: 211
atgtcaccct ccttcaagtc cactgccatc ctcggagccg ttgctctggc cgcccgcgtg      60
cgcgcccacg gctacgtgtc tggaatcgtc gttgacggtg cttaccatgg cggttacatc     120
gtcgacaagt accccctaca tgcccaaccca cccgatgtgg tcggctggtc gactacggcc    180
```

```
acggacctgg gcttcgtcgc ccctgacgcc tttggcgacc cggacatcat ctgccaccgg     240
gacggtgccc ccggtgccat ccacgccaaa gtcaacgccg gtgccaccat cgagctgcag     300
tggaacacct ggcccgaaag ccaccacggg cccgtcatcg actacctggc taactgcaac     360
ggtgactgct cgtccgtcga caagacctcg ctcaagttct tcaagatcag cgaggccggc     420
ctaaacgacg gctccaacgc ccccggccag tgggcgtccg acgatctcat tgccaacaac     480
aacagctgga ctgtgaccat ccccaagtcg atcgccccgg caactacgt gctgcgccac      540 gagatcatcg ccctgcacag cgccggcaac cagaatggcg cgcagaacta cccccagtgc    600
ttcaacctcg agatcaccag caacggcagc gacaacccgg agggcgtgct gggaaccgag    660
ctgtacaagg ccgacgaccc gggcattctg ttcaacatct accagcccat ggactcgtac    720
ccgattcccg ccctgctct ctacaccggc ggctcttctc cctcccctaa tccgcccacc     780
tctacccagt cgcctgtgcc ccagcccacc cagtctcccc catcgggcag caaccccggc    840
aacggcaacg cgacgacga caacgacaac ggcaacgaga ccccatcccc gtctctcccc    900
gtcgagatcc ctgacgacct gacctcgcgc gagctactcc ttgtggccca ggagatcatt    960
gcccgtctgc ttgagctgca gaatcagctg gtcgtctcga actaa                    1005
```

<210> SEQ ID NO 212
<211> LENGTH: 334
<212> TYPE: PRT
<213> ORGANISM: Malbranchea cinnamomea

<400> SEQUENCE: 212

```
Met Ser Pro Ser Phe Lys Ser Thr Ala Ile Leu Gly Ala Val Ala Leu
1               5                   10                  15

Ala Ala Arg Val Arg Ala His Gly Tyr Val Ser Gly Ile Val Val Asp
                20                  25                  30

Gly Ala Tyr His Gly Gly Tyr Ile Val Asp Lys Tyr Pro Tyr Met Pro
            35                  40                  45

Asn Pro Pro Asp Val Val Gly Trp Ser Thr Thr Ala Thr Asp Leu Gly
        50                  55                  60

Phe Val Ala Pro Asp Ala Phe Gly Asp Pro Asp Ile Ile Cys His Arg
65                  70                  75                  80

Asp Gly Ala Pro Gly Ala Ile His Ala Lys Val Asn Ala Gly Ala Thr
                85                  90                  95

Ile Glu Leu Gln Trp Asn Thr Trp Pro Glu Ser His His Gly Pro Val
            100                 105                 110

Ile Asp Tyr Leu Ala Asn Cys Asn Gly Asp Cys Ser Ser Val Asp Lys
        115                 120                 125

Thr Ser Leu Lys Phe Phe Lys Ile Ser Glu Ala Gly Leu Asn Asp Gly
    130                 135                 140

Ser Asn Ala Pro Gly Gln Trp Ala Ser Asp Asp Leu Ile Ala Asn Asn
145                 150                 155                 160

Asn Ser Trp Thr Val Thr Ile Pro Lys Ser Ile Ala Pro Gly Asn Tyr
                165                 170                 175

Val Leu Arg His Glu Ile Ile Ala Leu His Ser Ala Gly Asn Gln Asn
            180                 185                 190

Gly Ala Gln Asn Tyr Pro Gln Cys Phe Asn Leu Glu Ile Thr Ser Asn
        195                 200                 205

Gly Ser Asp Asn Pro Glu Gly Val Leu Gly Thr Glu Leu Tyr Lys Ala
    210                 215                 220

Asp Asp Pro Gly Ile Leu Phe Asn Ile Tyr Gln Pro Met Asp Ser Tyr
```

```
                225                 230                 235                 240
Pro Ile Pro Gly Pro Ala Leu Tyr Thr Gly Gly Ser Ser Pro Ser Pro
                245                 250                 255

Asn Pro Pro Thr Ser Thr Gln Ser Pro Val Pro Gln Pro Thr Gln Ser
                260                 265                 270

Pro Pro Ser Gly Ser Asn Pro Gly Asn Gly Asn Gly Asp Asp Asn
                275                 280                 285

Asp Asn Gly Asn Glu Thr Pro Ser Pro Ser Leu Pro Val Glu Ile Pro
                290                 295                 300

Asp Asp Leu Thr Ser Arg Glu Leu Leu Leu Val Ala Gln Glu Ile Ile
305                 310                 315                 320

Ala Arg Leu Leu Glu Leu Gln Asn Gln Leu Val Val Ser Asn
                325                 330

<210> SEQ ID NO 213
<211> LENGTH: 1101
<212> TYPE: DNA
<213> ORGANISM: Talaromyces leycettanus

<400> SEQUENCE: 213
atgcatcaac acttccgata cactgcgctc ctgacagcgt tgctgtcagc atcaacccga      60
gtcgcatccc acggccatgt cagcaacatt gtcattaatg gcgttcccta tcaaggatgg     120
gatatcgatt ccatgcccta cgagtcagac ccaccagtgg ttgtcgcctg ggagacacct     180
aacacgtcaa acggtttcat taccccggat cagtacggta cgagtgatat tatctgccat     240
ctgaacgcaa ccaacgcaaa gggccatgcc gtcgttgctg ccggagacaa gatcagcatt     300
caatggactg cctggcccag ctcccaccac ggccctgtca tcagctacct ggccaactgt     360
ggcgccagct gtgagacagt cgacaaaacg acgttgcaat tctttaagat cgacaacatc     420
ggtttcatag atgactcttc ccccccaggc atctgggcag ccgatcaatt ggaagcaaac     480
aacaacacct ggctcgtgga tcccccccg accatcgctc aggatacta cgtcctgcgc      540 aacgagatca tcgccctaca cggtgcagag aatcaggatg gcgcccagaa ctatccgcag     600
tgcttcaatc tgcaggtcac cggctcgggt accgataaac ccgccggcgt tcttggaact     660
cagctctatt ctcccactga cccgggcatt ctcgtgaaca tttacacgag cctttcgacc     720
tacatcgtcc ccgtccaac cccgtacagt ggttgggtgt ccgtcgtgca gtctagctct     780
gctatcaccg cttctggaac cccggtgacg ggcactggcg gagttagccc aaccacggct     840
gctactacga cttcttcttc tcactccacg acttctacta ctaccgggcc cactgtaacc     900
tcgactagcc acactactac cactactact cctactaccc tcagaaccac gactacaact     960
gcagctggtg gtggtgcgac acagaccgtc tacggccaat gcggcggtag tggttggact    1020
ggcgcaactg cctgcgcagc cggagctact tgcagcactc tgaatcccta ctatgcccaa    1080
tgccttccta ctggtgcttg a                                              1101

<210> SEQ ID NO 214
<211> LENGTH: 366
<212> TYPE: PRT
<213> ORGANISM: Talaromyces leycettanus

<400> SEQUENCE: 214

Met His Gln His Phe Arg Tyr Thr Ala Leu Leu Thr Ala Leu Leu Ser
1               5                   10                  15

Ala Ser Thr Arg Val Ala Ser His Gly His Val Ser Asn Ile Val Ile
                20                  25                  30
```

```
Asn Gly Val Pro Tyr Gln Gly Trp Asp Ile Asp Ser Met Pro Tyr Glu
         35                  40                  45

Ser Asp Pro Val Val Ala Trp Glu Thr Pro Asn Thr Ser Asn
 50                  55                  60

Gly Phe Ile Thr Pro Asp Gln Tyr Gly Thr Ser Asp Ile Ile Cys His
 65                  70                  75                  80

Leu Asn Ala Thr Asn Ala Lys Gly His Ala Val Ala Ala Gly Asp
                 85                  90                  95

Lys Ile Ser Ile Gln Trp Thr Ala Trp Pro Ser Ser His His Gly Pro
                100                 105                 110

Val Ile Ser Tyr Leu Ala Asn Cys Gly Ala Ser Cys Glu Thr Val Asp
            115                 120                 125

Lys Thr Thr Leu Gln Phe Phe Lys Ile Asp Asn Ile Gly Phe Ile Asp
        130                 135                 140

Asp Ser Ser Pro Pro Gly Ile Trp Ala Ala Asp Gln Leu Glu Ala Asn
145                 150                 155                 160

Asn Asn Thr Trp Leu Val Glu Ile Pro Pro Thr Ile Ala Pro Gly Tyr
                165                 170                 175

Tyr Val Leu Arg Asn Glu Ile Ile Ala Leu His Gly Ala Glu Asn Gln
                180                 185                 190

Asp Gly Ala Gln Asn Tyr Pro Gln Cys Phe Asn Leu Gln Val Thr Gly
            195                 200                 205

Ser Gly Thr Asp Lys Pro Ala Gly Val Leu Gly Thr Gln Leu Tyr Ser
        210                 215                 220

Pro Thr Asp Pro Gly Ile Leu Val Asn Ile Tyr Thr Ser Leu Ser Thr
225                 230                 235                 240

Tyr Ile Val Pro Gly Pro Thr Pro Tyr Ser Gly Trp Val Ser Val Val
                245                 250                 255

Gln Ser Ser Ser Ala Ile Thr Ala Ser Gly Thr Pro Val Thr Gly Thr
            260                 265                 270

Gly Gly Val Ser Pro Thr Thr Ala Ala Thr Thr Ser Ser Ser His
        275                 280                 285

Ser Thr Thr Ser Thr Thr Thr Gly Pro Thr Val Thr Ser Thr Ser His
        290                 295                 300

Thr Thr Thr Thr Thr Thr Pro Thr Thr Leu Arg Thr Thr Thr Thr
305                 310                 315                 320

Ala Ala Gly Gly Gly Ala Thr Gln Thr Val Tyr Gly Gln Cys Gly Gly
                325                 330                 335

Ser Gly Trp Thr Gly Ala Thr Ala Cys Ala Ala Gly Ala Thr Cys Ser
            340                 345                 350

Thr Leu Asn Pro Tyr Tyr Ala Gln Cys Leu Pro Thr Gly Ala
        355                 360                 365

<210> SEQ ID NO 215
<211> LENGTH: 1091
<212> TYPE: DNA
<213> ORGANISM: Chaetomium thermophilum
<220> FEATURE:
<221> NAME/KEY: misc_feature
<222> LOCATION: (522)..(524)
<223> OTHER INFORMATION: n is a, c, g, or t

<400> SEQUENCE: 215
atgccttcct tcgcttcgaa gactctcatt tctgccctcg ccggcgctgc cagcgtcgcc      60
gctcacggcc acgtcaagaa cttcgtcatc aacggtctgt cgtaccaggc ctacgacccg     120
```

```
accgtcttcc cgtacatgca gaaccctccc atcgtcgccg gctggacggc ctccaacact      180
gacaacggct tcgtgggccc cgagtcctac tcgagcccg atatcatctg ccacaagtcg       240
gccacgaacg ccaagggcca tgccgtcatc aaggccggtg actctgtcta catccagtgg     300
gacacctggc ccgagtcgca ccacggcccg gtcatcgact acctcgccag ctgcggcagc     360
gccggctgcg agacggtcga caagacccag ctcgagttct tcaagatcgc cgaggccggt     420
ctgattgacg gctcccaggc tcccggaaag tgggctgccg atcagctcat cgcccagaac     480
aactcgtggc tggtcaccat ccccgagaat atcaagccgc tnnnggctcc tacgtcctcc    540
gccacgagat catcgccctg cacagcgctg ccagaccaa cggtgcccag aactaccccg     600
tctgcatcaa cctcgaggtc actggtggcg gcagcgacgt ccctcgggt gtcaagggta    660 ctgagctcta caagcccacc gaccccggca tcctcatcaa catctaccag tcgctctcga     720
actacaccat ccctggccct gctctgatgc ccggcgccaa gccagtcacc cagcacacct    780
cagccatcat cggcagcacc accgccatca ctggcaccgc caccgctgct ccggccgcgc    840
cgacctcgac cgccgctgcc atcaccacca gctctgctaa tgccaacccc gccccgacca    900
ccacccgcgg caacgccaac cccgtcccga ctaccaccct ccgacgagc accatcgctc     960 ctcagcccac tgctgccccc atccagaccc cgacctccag cgtcggccgg cccccgcgcc   1020
cgacccgctg ccctggtctg acaacttca gcgcgctcg tcgccacgct cgtgaccttg    1080
ctgcccacta a                                                             1091
```

<210> SEQ ID NO 216
<211> LENGTH: 364
<212> TYPE: PRT
<213> ORGANISM: Chaetomium thermophilum
<220> FEATURE:
<221> NAME/KEY: misc_feature
<222> LOCATION: (174)..(176)
<223> OTHER INFORMATION: Xaa can be any naturally occurring amino acid

<400> SEQUENCE: 216

```
Met Pro Ser Phe Ala Ser Lys Thr Leu Ile Ser Ala Leu Ala Gly Ala
1               5                   10                  15

Ala Ser Val Ala Ala His Gly His Val Lys Asn Phe Val Ile Asn Gly
                20                  25                  30

Leu Ser Tyr Gln Ala Tyr Asp Pro Thr Val Phe Pro Tyr Met Gln Asn
            35                  40                  45

Pro Pro Ile Val Ala Gly Trp Thr Ala Ser Asn Thr Asp Asn Gly Phe
        50                  55                  60

Val Gly Pro Glu Ser Tyr Ser Pro Asp Ile Ile Cys His Lys Ser
65                  70                  75                  80

Ala Thr Asn Ala Lys Gly His Ala Val Ile Lys Ala Gly Asp Ser Val
                85                  90                  95

Tyr Ile Gln Trp Asp Thr Trp Pro Glu Ser His His Gly Pro Val Ile
            100                 105                 110

Asp Tyr Leu Ala Ser Cys Gly Ser Ala Gly Cys Glu Thr Val Asp Lys
        115                 120                 125

Thr Gln Leu Glu Phe Phe Lys Ile Ala Glu Ala Gly Leu Ile Asp Gly
    130                 135                 140

Ser Gln Ala Pro Gly Lys Trp Ala Ala Asp Gln Leu Ile Ala Gln Asn
145                 150                 155                 160

Asn Ser Trp Leu Val Thr Ile Pro Glu Asn Ile Lys Pro Xaa Xaa Xaa
                165                 170                 175
```

```
Gly Ser Tyr Val Leu Arg His Glu Ile Ile Ala Leu His Ser Ala Gly
            180                 185                 190

Gln Thr Asn Gly Ala Gln Asn Tyr Pro Val Cys Ile Asn Leu Glu Val
        195                 200                 205

Thr Gly Gly Ser Asp Val Pro Ser Gly Val Lys Gly Thr Glu Leu
    210                 215                 220

Tyr Lys Pro Thr Asp Pro Gly Ile Leu Ile Asn Ile Tyr Gln Ser Leu
225                 230                 235                 240

Ser Asn Tyr Thr Ile Pro Gly Pro Ala Leu Met Pro Gly Ala Lys Pro
            245                 250                 255

Val Thr Gln His Thr Ser Ala Ile Ile Gly Ser Thr Ala Ile Thr
        260                 265                 270

Gly Thr Ala Thr Ala Pro Ala Ala Pro Thr Ser Thr Ala Ala Ala
    275                 280                 285

Ile Thr Thr Ser Ser Ala Asn Ala Asn Pro Ala Pro Thr Thr Thr Arg
290                 295                 300

Gly Asn Ala Asn Pro Val Pro Thr Thr Thr Leu Arg Thr Ser Thr Ile
305                 310                 315                 320

Ala Pro Gln Pro Thr Ala Ala Pro Ile Gln Thr Pro Thr Ser Ser Val
            325                 330                 335

Gly Arg Pro Pro Arg Pro Thr Arg Cys Pro Gly Leu Asp Asn Phe Lys
            340                 345                 350

Arg Ala Arg Arg His Ala Arg Asp Leu Ala Ala His
            355                 360
```

```
<210> SEQ ID NO 217
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 217
cacaactggg gatccatgac tttgtccaag atcacttcca                    40

<210> SEQ ID NO 218
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 218
ggcctccgcg gccgcttaag cgttgaacag tgcaggacca                    40

<210> SEQ ID NO 219
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 219
cacaactggg gatccatgac tttgtccaag atcacttcca                    40

<210> SEQ ID NO 220
<211> LENGTH: 40
<212> TYPE: DNA
<213> ORGANISM: Artificial Sequence
<220> FEATURE:
```

<223> OTHER INFORMATION: Artificial DNA Primer

<400> SEQUENCE: 220
ggcctccgcg gccgcttaag cgttgaacag tgcaggacca        40

<210> SEQ ID NO 221
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 221
cacaactggg gatccatgct gtcttcgacg actcgcaccc        40

<210> SEQ ID NO 222
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 222
ggcctccgcg gccgcctaga acgtcggctc aggcggcccc        40

<210> SEQ ID NO 223
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 223
ctggggatcc atgtcctttt ccaagat        27

<210> SEQ ID NO 224
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 224
ctccgcggcc gcttaaccag tatacagag        29

<210> SEQ ID NO 225
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 225
actcaattta cctctatcca cactt        25

<210> SEQ ID NO 226
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 226
gaattgtgag cggataacaa tttca        25

```
<210> SEQ ID NO 227
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 227
cggactgcgc accatgctgt cttcgacgac tcgcac                                 36

<210> SEQ ID NO 228
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 228
tcgccacgga gcttatcgac ttcttctaga acgtc                                  35

<210> SEQ ID NO 229
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 229
atcatcgccc ttcactctgc ggccaacctg aacggcgcgc agaac                       45

<210> SEQ ID NO 230
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 230
gttctgcgcg ccgttcaggt tggccgcaga gtgaagggcg atgat                       45

<210> SEQ ID NO 231
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 231
atcatcgccc ttcactctgc gtggaacctg aacggcgcgc agaac                       45

<210> SEQ ID NO 232
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 232
gttctgcgcg ccgttcaggt tccacgcaga gtgaagggcg atgat                       45

<210> SEQ ID NO 233
<211> LENGTH: 49
<212> TYPE: DNA
<213> ORGANISM: Artificial Sequence
<220> FEATURE:
<223> OTHER INFORMATION: Artificial DNA Primer
```

```
<400> SEQUENCE: 233
acaagaatac tgatcctggc atctggtttg acatctactc ggatctgag            49

<210> SEQ ID NO 234
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 234
ctcagatccg agtagatgtc aaaccagatg ccaggatcag tattcttgt            49

<210> SEQ ID NO 235
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 235
tcgcccttca ctctgcgggt aagctgaacg gcgcgcagaa ctac                 44

<210> SEQ ID NO 236
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 236
gtagttctgc gcgccgttca gcttacccgc agagtgaagg gcga                 44

<210> SEQ ID NO 237
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 237
atcatcgccc ttcactctgc gtttaacctg aacggcgcgc agaac                45

<210> SEQ ID NO 238
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 238
gttctgcgcg ccgttcaggt taaacgcaga gtgaagggcg atgat                45

<210> SEQ ID NO 239
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 239
tcgcccttca ctctgcgggt aagctgaacg gcgcgcagaa ctac                 44

<210> SEQ ID NO 240
<211> LENGTH: 44
```

```
<212> TYPE: DNA
<213> ORGANISM: Artificial Sequence
<220> FEATURE:
<223> OTHER INFORMATION: Artificial DNA Primer

<400> SEQUENCE: 240
gtagttctgc gcgccgttca gcttacccgc agagtgaagg gcga                    44

<210> SEQ ID NO 241
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 241
gtgctcaggg atctggcacc tacggcacgt ccctgtacaa gaata                   45

<210> SEQ ID NO 242
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 242
tattcttgta cagggacgtg ccgtaggtgc cagatccctg agcac                   45

<210> SEQ ID NO 243
<211> LENGTH: 3060
<212> TYPE: DNA
<213> ORGANISM: Aspergillus fumigatus

<400> SEQUENCE: 243
atgagattcg gttggctcga ggtggccgct ctgacggccg cttctgtagc caatgcccag    60
gtttgtgatg ctttcccgtc attgtttcgg atatagttga caatagtcat ggaaataatc   120
aggaattggc tttctctcca ccattctacc cttcgccttg ggctgatggc cagggagagt   180
gggcagatgc ccatcgacgc gccgtcgaga tcgtttctca gatgacactg gcggagaagg   240
ttaaccttac aacgggtact gggtgggttg cgactttttt gttgacagtg agctttcttc   300
actgaccatc tacacagatg ggaaatggac cgatgcgtcg gtcaaaccgg cagcgttccc   360
aggtaagctt gcaattctgc aacaacgtgc aagtgtagtt gctaaaacgc ggtggtgcag   420
acttggtatc aactggggtc tttgtggcca ggattcccct tgggtatccc gtttctgtga   480
gctatacccg cggagtcttt cagtccttgt attatgtgct gatgattgtc tctgtatagc   540
tgacctcaac tccgccttcc ctgctggtac taatgtcgcc gcgacatggg acaagacact   600
cgcctacctt cgtggcaagg ccatgggtga ggaattcaac gacaagggcg tggacatttt   660
gctggggcct gctgctggtc ctctcggcaa atacccggac ggcggcagaa tctgggaagg   720
cttctctcct gatccggttc tcactggtgt acttttcgcc gaaactatca agggtatcca   780
agacgcgggt gtgattgcta ctgccaagca ttacattctg aatgaacagg agcatttccg   840
acaggttggc gaggcccagg atatggttta acaacatcacg gagacgatca gctccaacgt   900
ggatgacaag accatgcacg agttgtacct tggtgagta gttgacactg caaatgagga   960
ccttgattga tttgactgac ctggaatgca ggccctttgc agatgctgtg cgcggtaaga  1020 tttccgtag acttgacctc gcgacgaaga aatcgctgac gaaccatcgt agctggcgtt  1080
ggcgctgtca tgtgttccta caatcaaatc aacaacagct acggttgtca aaacagtcaa  1140
```

```
actctcaaca agctcctcaa ggctgagctg ggcttccaag gcttcgtcat gagtgactgg    1200
agcgctcacc acagcggtgt cggcgctgcc ctcgctgggt tggatatgtc gatgcctgga    1260
gacatttcct tcgacgacgg actctccttc tggggcacga acctaactgt cagtgttctt    1320
aacggcaccg ttccagcctg cgtgtcgat gacatggctg ttcgtatcat gaccgcgtac     1380
tacaaggttg gtcgtgaccg tcttcgtatt cccctaact tcagctcctg gacccgggat     1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga cacggggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctggggtagt ggtactgcca acttccctta ccttgtcacc    1740
cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggccttgagc tacaccacct tggttactct    2400
caccttcggg ttcaggccct caatagttcg agttcggcat atgtcccgac tagcggagag    2460
accaagcctg cgccaaccta tgtgagatc ggtagtgccg ccgactacct gtatcccgag     2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaacccct cctgaaggct ggcggcgctc ctggtggtaa ccctacccct    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caagtaccc caagaaagtg     3000 cacgtcggca gctcctcgcg taagctgcct ctgagagcgc ctctgccccg tgtctactag    3060
```

<210> SEQ ID NO 244
<211> LENGTH: 863
<212> TYPE: PRT
<213> ORGANISM: Aspergillus fumigatus

<400> SEQUENCE: 244

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val

```
            35                  40                  45
Glu Ile Val Ser Gln Met Thr Leu Ala Glu Lys Val Asn Leu Thr Thr
 50                  55                  60
Gly Thr Gly Trp Glu Met Asp Arg Cys Val Gly Gln Thr Gly Ser Val
 65                  70                  75                  80
Pro Arg Leu Gly Ile Asn Trp Gly Leu Cys Gly Gln Asp Ser Pro Leu
                 85                  90                  95
Gly Ile Arg Phe Ser Asp Leu Asn Ser Ala Phe Pro Ala Gly Thr Asn
                100                 105                 110
Val Ala Ala Thr Trp Asp Lys Thr Leu Ala Tyr Leu Arg Gly Lys Ala
                115                 120                 125
Met Gly Glu Glu Phe Asn Asp Lys Gly Val Asp Ile Leu Leu Gly Pro
130                 135                 140
Ala Ala Gly Pro Leu Gly Lys Tyr Pro Asp Gly Gly Arg Ile Trp Glu
145                 150                 155                 160
Gly Phe Ser Pro Asp Pro Val Leu Thr Gly Val Leu Phe Ala Glu Thr
                165                 170                 175
Ile Lys Gly Ile Gln Asp Ala Gly Val Ile Ala Thr Ala Lys His Tyr
                180                 185                 190
Ile Leu Asn Glu Gln Glu His Phe Arg Gln Val Gly Glu Ala Gln Gly
                195                 200                 205
Tyr Gly Tyr Asn Ile Thr Glu Thr Ile Ser Ser Asn Val Asp Asp Lys
210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Gln Asn Ser Gln Thr Leu Asn Lys Leu Leu Lys Ala Glu Leu
                260                 265                 270
Gly Phe Gln Gly Phe Val Met Ser Asp Trp Ser Ala His His Ser Gly
                275                 280                 285
Val Gly Ala Ala Leu Ala Gly Leu Asp Met Ser Met Pro Gly Asp Ile
                290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                325                 330                 335
Arg Ile Met Thr Ala Tyr Tyr Lys Val Gly Arg Asp Arg Leu Arg Ile
                340                 345                 350
Pro Pro Asn Phe Ser Ser Trp Thr Arg Asp Glu Tyr Gly Trp Glu His
                355                 360                 365
Ser Ala Val Ser Glu Gly Ala Trp Thr Lys Val Asn Asp Phe Val Asn
                370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
                420                 425                 430
Ala Asn Gly Cys Pro Asp Arg Gly Cys Asp Asn Gly Thr Leu Ala Met
                435                 440                 445
Ala Trp Gly Ser Gly Thr Ala Asn Phe Pro Tyr Leu Val Thr Pro Glu
                450                 455                 460
```

Gln Ala Ile Gln Arg Glu Val Ile Ser Asn Gly Asn Val Phe Ala
465                 470                 475                 480

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
                500                 505                 510

Ile Ser Val Asp Gly Asn Glu Gly Asp Arg Lys Asn Leu Thr Leu Trp
                515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
                595                 600                 605

Gly Ala Pro Leu Leu Thr Glu Pro Asn Gly Asn Gly Ala Pro Gln
610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
                660                 665                 670

Ser Ala Tyr Val Pro Thr Ser Gly Glu Thr Lys Pro Ala Pro Thr Tyr
                675                 680                 685

Gly Glu Ile Gly Ser Ala Ala Asp Tyr Leu Tyr Pro Glu Gly Leu Lys
690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
                740                 745                 750

Gly Ala Pro Gly Gly Asn Pro Thr Leu Tyr Gln Asp Leu Val Arg Val
                755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
                820                 825                 830

Gln Asp Trp Val Ile Thr Lys Tyr Pro Lys Lys Val His Val Gly Ser
                835                 840                 845

Ser Ser Arg Lys Leu Pro Leu Arg Ala Pro Leu Pro Arg Val Tyr
850                 855                 860

<210> SEQ ID NO 245
<211> LENGTH: 1599

<212> TYPE: DNA
<213> ORGANISM: Aspergillus fumigatus

<400> SEQUENCE: 245

```
atgctggcct ccaccttctc ctaccgcatg tacaagaccg cgctcatcct ggccgccctt      60
ctgggctctg gccaggctca gcaggtcggt acttcccagg cggaagtgca tccgtccatg     120
acctggcaga gctgcacggc tgcggcagc tgcaccacca caacggcaa ggtggtcatc      180
gacgcgaact ggcgttgggt gcacaaagtc ggcgactaca ccaactgcta caccggcaac     240
acctgggaca cgactatctg ccctgacgat gcgacctgcg catccaactg cgccttgag     300
ggtgccaact acgaatccac ctatggtgtg accgccagcg gcaattccct ccgcctcaac     360
ttcgtcacca ccagccagca aagaacatt ggctcgcgtc tgtacatgat gaaggacgac     420
tcgacctacg agatgtttaa gctgctgaac caggagttca ccttcgatgt cgatgtctcc     480
aacctcccct gcggtctcaa cggtgctctg tactttgtcg ccatggacgc cgacggtggc     540
atgtccaagt acccaaccaa caaggccggt gccaagtacg gtactggata ctgtgactcg     600
cagtgccctc gcgacctcaa gttcatcaac ggtcaggcca acgtcgaagg gtggcagccc     660
tcctccaacg atgccaatgc gggtaccggg aaccacgggt cctgctgcgc ggagatggat     720
atctgggagg ccaacagcat ctccacggcc ttcacccccc atccgtgcga cacgcccggc     780
caggtgatgt gcaccggtga tgcctgcggt ggcacctaca gctccgaccg ctacggcggc     840
acctgcgacc ccgacggatg tgatttcaac tccttccgcc agggcaacaa gaccttctac     900
ggccctggca tgaccgtcga caccaagagc aagtttaccg tcgtcaccca gttcatcacc     960
gacgacggca cctccagcgg caccctcaag gagatcaagc gcttctacgt gcagaacggc    1020
aaggtgatcc ccaactcgga gtcgacctgg accggcgtca gcggcaactc catcaccacc    1080
gagtactgca ccgcccagaa gagcctgttc caggaccaga acgtcttcga aaagcacggc    1140
ggcctcgagg gcatgggtgc tgccctcgcc cagggtatgg ttctcgtcat gtccctgtgg    1200
gatgatcact cggccaacat gctctggctc gacagcaact accgaccac tgcctcttcc     1260
accactcccg gcgtcgcccg tggtacctgc gacatctcct ccggcgtccc tgcggatgtc    1320
gaggcgaacc accccgacgc ctacgtcgtc tactccaaca tcaaggtcgg ccccatcggc    1380
tcgaccttca acagcggtgg ctcgaacccc ggtggcggaa ccaccacgac aactaccacc    1440
cagcctacta ccaccacgac cacggctgga aaccctggcg caccggagt cgcacagcac    1500
tatggccagt gtggtggaat cggatggacc ggacccacaa cctgtgccag cccttatacc    1560
tgccagaagc tgaatgatta ttactctcag tgcctgtag                           1599
```

<210> SEQ ID NO 246
<211> LENGTH: 532
<212> TYPE: PRT
<213> ORGANISM: Aspergillus fumigatus

<400> SEQUENCE: 246

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60
```

-continued

```
Arg Trp Val His Lys Val Gly Asp Tyr Thr Asn Cys Tyr Thr Gly Asn
 65                  70                  75                  80

Thr Trp Asp Thr Thr Ile Cys Pro Asp Ala Thr Cys Ala Ser Asn
                 85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Thr Thr Thr Thr Thr Thr
465                 470                 475                 480

Gln Pro Thr Thr Thr Thr Thr Ala Gly Asn Pro Gly Gly Thr Gly
```

|  |  | 485 |  |  | 490 |  |  | 495 |  |  |
| --- | --- | --- | --- | --- | --- | --- | --- | --- | --- | --- |
| Val | Ala | Gln | His | Tyr | Gly | Gln | Cys | Gly | Gly | Ile | Gly | Trp | Thr | Gly | Pro |
|  |  |  |  | 500 |  |  |  |  | 505 |  |  |  |  | 510 |  |

Thr Thr Cys Ala Ser Pro Tyr Thr Cys Gln Lys Leu Asn Asp Tyr Tyr
          515                 520                 525

Ser Gln Cys Leu
    530

<210> SEQ ID NO 247
<211> LENGTH: 1713
<212> TYPE: DNA
<213> ORGANISM: Aspergillus fumigatus

<400> SEQUENCE: 247

```
atgaagcacc ttgcatcttc catcgcattg actctactgt tgcctgccgt gcaggcccag      60
cagaccgtat ggggccaatg tatgttctgg ctgtcactgg aataagactg tatcaactgc     120
tgatatgctt ctaggtggcg gccaaggctg gtctggcccg acgagctgtg ttgccggcgc     180
agcctgtagc acactgaatc cctgtatgtt agatatcgtc ctgagtggag acttatactg     240
acttccttag actacgctca gtgtatcccg ggagccaccg cgacgtccac caccctcacg     300
acgacgacgg cggcgacgac gacatcccag accaccacca aacctaccac gactggtcca     360
actacatccg cacccaccgt gaccgcatcc ggtaaccctt tcagcggcta ccagctgtat     420
gccaacccct actactcctc cgaggtccat actctggcca tgccttctct gcccagctcg     480
ctgcagccca aggctagtgc tgttgctgaa gtgccctcat tgtttggct gtaagtggcc      540
ttatcccaat actgagacca actctctgac agtcgtagcg acgttgccgc caaggtgccc     600
actatgggaa cctacctggc cgacattcag gccaagaaca aggccggcgc caaccctcct     660
atcgctggta tcttcgtggt ctacgacttg ccggaccgtg actgcgccgc tctggccagt     720
aatggcgagt actcaattgc caacaacggt gtggccaact acaaggcgta cattgacgcc     780
atccgtgctc agctggtgaa gtactctgac gttcacacca tcctcgtcat cggtaggccg     840
tacacctccg ttgcgcgccg ccttttctctg acatcttgca gaacccgaca gcttggccaa     900
cctggtgacc aacctcaacg tcgccaaatg cgccaatgcg cagagcgcct acctggagtg     960
tgtcgactat gctctgaagc agctcaacct gcccaacgtc gccatgtacc tcgacgcagg    1020
tatgcctcac ttcccgcatt ctgtatccct tccagacact aactcatcag gccatgcggg    1080
ctggctcgga tggcccgcca acttgggccc cgccgcaaca ctcttcgcca agtctacac     1140
cgacgcgggt tcccccgcgg ctgttcgtgg cctggccacc aacgtcgcca actacaacgc    1200
ctggtcgctc agtacctgcc cctcctacac ccagggagac cccaactgcg acgagaagaa    1260
gtacatcaac gccatggcgc ctcttctcaa ggaagccggc ttcgatgccc acttcatcat    1320
ggatacctgt aagtgcttat tccaatcgcc gatgtgtgcc gactaatcaa tgtttcagcc    1380
cggaatggcg tccagcccac gaagcaaaac gcctggggtg actggtgcaa cgtcatcggc    1440
accggcttcg gtgttcgccc ctcgactaac accggcgatc cgctccagga tgcctttgtg    1500
tggatcaagc ccggtggaga gagtgatggc acgtccaact cgacttcccc ccggtatgac    1560
gcgcactgcg gatatagtga tgctctgcag cctgctcctg aggctggtac ttggttccag    1620
gtatgtcatc cattagccag atgagggata agtgactgac ggacctaggc ctactttgag    1680
cagcttctga ccaacgctaa cccgtccttt taa                                 1713
```

<210> SEQ ID NO 248

```
<211> LENGTH: 454
<212> TYPE: PRT
<213> ORGANISM: Aspergillus fumigatus

<400> SEQUENCE: 248

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly
                20                  25                  30

Ser Gly Pro Thr Ser Cys Val Ala Gly Ala Ala Cys Ser Thr Leu Asn
                35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Ser Ala Pro Thr Val Thr Ala Ser
                85                  90                  95

Gly Asn Pro Phe Ser Gly Tyr Gln Leu Tyr Ala Asn Pro Tyr Tyr Ser
                100                 105                 110

Ser Glu Val His Thr Leu Ala Met Pro Ser Leu Pro Ser Ser Leu Gln
            115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
```

```
                385                 390                 395                 400
Trp Ile Lys Pro Gly Gly Glu Ser Asp Gly Thr Ser Asn Ser Thr Ser
                    405                 410                 415

Pro Arg Tyr Asp Ala His Cys Gly Tyr Ser Asp Ala Leu Gln Pro Ala
                420                 425                 430

Pro Glu Ala Gly Thr Trp Phe Gln Ala Tyr Phe Glu Gln Leu Leu Thr
            435                 440                 445

Asn Ala Asn Pro Ser Phe
    450

<210> SEQ ID NO 249
<211> LENGTH: 1849
<212> TYPE: DNA
<213> ORGANISM: Trichoderma reesei

<400> SEQUENCE: 249
tgccatttct gacctggata ggttttccta tggtcattcc tataagagac acgctctttc      60
gtcggcccgt agatatcaga ttggtattca gtcgcacaga cgaaggtgag ttgatcctcc     120
aacatgagtt ctatgagccc cccccttgcc ccccccgtt caccttgacc tgcaatgaga      180
atcccacctt ttacaagagc atcaagaagt attaatggcg ctgaatagcc tctgctcgat     240
aatatctccc cgtcatcgac aatgaacaag tccgtggctc cattgctgct tgcagcgtcc     300
atactatatg gcggcgccgt cgcacagcag actgtctggg ccagtgtgg aggtattggt      360
tggagcggac ctacgaattg tgctcctggc tcagcttgtt cgaccctcaa tccttattat     420
gcgcaatgta ttccgggagc cactactatc accacttcga cccggccacc atccggtcca     480
accaccacca ccagggctac ctcaacaagc tcatcaactc cacccacgag ctctggggtc     540
cgatttgccg gcgttaacat cgcgggtttt gactttggct gtaccacaga gtgagtaccc     600
ttgtttcctg gtgttgctgg ctggttgggc gggtatacag cgaagcggac gcaagaacac     660
cgccggtccg ccaccatcaa gatgtgggtg gtaagcggcg tgttttgta caactacctg      720
acagctcact caggaaatga gaattaatgg aagtcttgtt acagtggcac ttgcgttacc     780
tcgaaggttt atcctccgtt gaagaacttc accggctcaa acaactaccc cgatggcatc     840
ggccagatgc agcacttcgt caacgaggac gggatgacta ttttccgctt acctgtcgga     900
tggcagtacc tcgtcaacaa caatttgggc ggcaatcttg attccacgag catttccaag     960
tatgatcagc ttgttcaggg gtgcctgtct ctgggcgcat actgcatcgt cgacatccac    1020
aattatgctc gatggaacgg tgggatcatt ggtcagggcg ccctactaa tgctcaattc     1080
acgagccttt ggtcgcagtt ggcatcaaag tacgcatctc agtcgagggt gtggttcggc    1140
atcatgaatg agccccacga cgtgaacatc aacacctggg ctgccacggt ccaagaggtt    1200
gtaaccgcaa tccgcaacgc tggtgctacg tcgcaattca tctctttgcc tggaaatgat    1260
tggcaatctg ctggggcttt catatccgat ggcagtgcag ccgccctgtc tcaagtcacg    1320
aacccggatg ggtcaacaac gaatctgatt tttgacgtgc acaaatactt ggactcagac    1380
aactccggta ctcacgccga atgtactaca ataacattg acggcgcctt ttctccgctt     1440
gccacttggc tccgacagaa caatcgccag gctatcctga cagaaaccgg tggtggcaac    1500
gttcagtcct gcatacaaga catgtgccag caaatccaat atctcaacca gaactcagat    1560
gtctatcttg gctatgttgg ttggggtgcc ggatcatttg atagcacgta tgtcctgacg    1620
gaaacaccga ctggcagtgg taactcatgg acggacacat ccttggtcag ctcgtgtctc    1680
gcaagaaagt agcactctga gctgaatgca gaagcctcgc caacgtttgt atctcgctat    1740
```

```
caaacatagt agctactcta tgaggctgtc tgttctcgat ttcagcttta tatagtttca   1800
tcaaacagta catattccct ctgtggccac gcaaaaaaaa aaaaaaaaa              1849
```

<210> SEQ ID NO 250
<211> LENGTH: 418
<212> TYPE: PRT
<213> ORGANISM: Trichoderma reesei

<400> SEQUENCE: 250

```
Met Asn Lys Ser Val Ala Pro Leu Leu Ala Ala Ser Ile Leu Tyr
 1               5                  10                  15

Gly Gly Ala Val Ala Gln Gln Thr Val Trp Gly Gln Cys Gly Gly Ile
                20                  25                  30

Gly Trp Ser Gly Pro Thr Asn Cys Ala Pro Gly Ser Ala Cys Ser Thr
            35                  40                  45

Leu Asn Pro Tyr Tyr Ala Gln Cys Ile Pro Gly Ala Thr Thr Ile Thr
        50                  55                  60

Thr Ser Thr Arg Pro Pro Ser Gly Pro Thr Thr Thr Arg Ala Thr
 65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
                100                 105                 110

Cys Val Thr Ser Lys Val Tyr Pro Pro Leu Lys Asn Phe Thr Gly Ser
            115                 120                 125

Asn Asn Tyr Pro Asp Gly Ile Gly Gln Met Gln His Phe Val Asn Glu
        130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350
```

| Gly | Gly | Asn | Val | Gln | Ser | Cys | Ile | Gln | Asp | Met | Cys | Gln | Gln | Ile | Gln |
| | | 355 | | | | 360 | | | | | 365 | | | | |

| Tyr | Leu | Asn | Gln | Asn | Ser | Asp | Val | Tyr | Leu | Gly | Tyr | Val | Gly | Trp | Gly |
| | 370 | | | | | 375 | | | | | 380 | | | | |

| Ala | Gly | Ser | Phe | Asp | Ser | Thr | Tyr | Val | Leu | Thr | Glu | Thr | Pro | Thr | Gly |
| 385 | | | | | 390 | | | | | 395 | | | | | 400 |

| Ser | Gly | Asn | Ser | Trp | Thr | Asp | Thr | Ser | Leu | Val | Ser | Ser | Cys | Leu | Ala |
| | | | | 405 | | | | | 410 | | | | | 415 | |

Arg Lys

<210> SEQ ID NO 251
<211> LENGTH: 1415
<212> TYPE: DNA
<213> ORGANISM: Aspergillus fumigatus

<400> SEQUENCE: 251

```
atggtccatc tatcttcatt ggcagcagcc ctggctgctc tgcctctgta tgtttaccca      60
ctcacgagag gaggaacagc tttgacattg ctatagtgta tatggagctg gcctgaacac     120
agcagccaaa gccaaaggac taaagtactt tggttccgcc acggacaatc agagctcac     180
ggactctgcg tatgtcgcgc aactgagcaa caccgatgat tttggtcaaa tcacacccgg     240
aaactccatg aaggttttgct tacgtctgcc tccctggagc attgcctcaa agctaattg     300
gttgttttgt ttggatagtg ggatgccacc gagccttctc agaattcttt ttcgttcgca     360
aatggagacg ccgtggtcaa tctggcgaac aagaatggcc agctgatgcg atgccatact     420
ctggtctggc acagtcagct accgaactgg ggtatgtaaa cgtcttgtct attctcaaat     480
actctctaac agttgacagt ctctagcggg tcatggacca atgcgaccct tttggcggcc     540
atgaagaatc atatcaccaa tgtggttact cactacaagg ggaagtgcta cgcctgggat     600
gttgtcaatg aaggtttgtt gctccatcta tcctcaatag ttcttttgaa actgacaagc     660
ctgtcaatct agccctgaac gaggacggta ctttccgtaa ctctgtcttc taccagatca     720
tcggcccagc atacattcct attgcgttcg ccacggctgc tgccgcagat cccgacgtga     780
aactctacta caacgactac aacattgaat actcaggcgc caaagcgact gctgcgcaga     840
atatcgtcaa gatgatcaag gcctacggcg cgaagatcga cggcgtcggc ctccaggcac     900
actttatcgt cggcagcact ccgagtcaat cggatctgac gaccgtcttg aagggctaca     960
ctgctctcgg cgttgaggtg gcctataccg aacttgacat ccgcatgcag ctgccctcga    1020
ccgccgcaaa gctggcccag cagtccactg acttccaagg cgtggccgca gcatgcgtta    1080
gcaccactgg ctgcgtgggt gtcactatct gggactggac cgacaagtac tcctgggtcc    1140
ccagcgtgtt ccaaggctac ggcgcccat tgccttggga tgagaactat gtgaagaagc    1200
cagcgtacga tggcctgatg gcgggtcttg agcaagcgg ctccggcacc acaacgacca    1260
ctactactac ttctactacg acaggaggta cggaccctac tggagtcgct cagaaatggg    1320
gacagtgtgg cggtattggc tggaccgggc caacaacttg tgtcagtggt accacttgcc    1380
aaaagctgaa tgactggtac tcacagtgcc tgtaa                               1415
```

<210> SEQ ID NO 252
<211> LENGTH: 397
<212> TYPE: PRT
<213> ORGANISM: Aspergillus fumigatus

<400> SEQUENCE: 252

Met Val His Leu Ser Ser Leu Ala Ala Ala Leu Ala Ala Leu Pro Leu

```
1               5                   10                  15
Val Tyr Gly Ala Gly Leu Asn Thr Ala Ala Lys Ala Lys Gly Leu Lys
                    20                  25                  30
Tyr Phe Gly Ser Ala Thr Asp Asn Pro Glu Leu Thr Asp Ser Ala Tyr
                35                  40                  45
Val Ala Gln Leu Ser Asn Thr Asp Asp Phe Gly Gln Ile Thr Pro Gly
            50                  55                  60
Asn Ser Met Lys Trp Asp Ala Thr Glu Pro Ser Gln Asn Ser Phe Ser
65                  70                  75                  80
Phe Ala Asn Gly Asp Ala Val Val Asn Leu Ala Asn Lys Asn Gly Gln
                    85                  90                  95
Leu Met Arg Cys His Thr Leu Val Trp His Ser Gln Leu Pro Asn Trp
                100                 105                 110
Val Ser Gly Ser Trp Thr Asn Ala Thr Leu Leu Ala Ala Met Lys
                115                 120                 125
Asn His Ile Thr Asn Val Val Thr His Tyr Lys Gly Lys Cys Tyr Ala
            130                 135                 140
Trp Asp Val Val Asn Glu Ala Leu Asn Glu Asp Gly Thr Phe Arg Asn
145                 150                 155                 160
Ser Val Phe Tyr Gln Ile Ile Gly Pro Ala Tyr Ile Pro Ile Ala Phe
                165                 170                 175
Ala Thr Ala Ala Ala Asp Pro Asp Val Lys Leu Tyr Tyr Asn Asp
                180                 185                 190
Tyr Asn Ile Glu Tyr Ser Gly Ala Lys Ala Thr Ala Ala Gln Asn Ile
            195                 200                 205
Val Lys Met Ile Lys Ala Tyr Gly Ala Lys Ile Asp Gly Val Gly Leu
        210                 215                 220
Gln Ala His Phe Ile Val Gly Ser Thr Pro Ser Gln Ser Asp Leu Thr
225                 230                 235                 240
Thr Val Leu Lys Gly Tyr Thr Ala Leu Gly Val Glu Val Ala Tyr Thr
                245                 250                 255
Glu Leu Asp Ile Arg Met Gln Leu Pro Ser Thr Ala Ala Lys Leu Ala
                260                 265                 270
Gln Gln Ser Thr Asp Phe Gln Gly Val Ala Ala Cys Val Ser Thr
            275                 280                 285
Thr Gly Cys Val Gly Val Thr Ile Trp Asp Trp Thr Asp Lys Tyr Ser
        290                 295                 300
Trp Val Pro Ser Val Phe Gln Gly Tyr Gly Ala Pro Leu Pro Trp Asp
305                 310                 315                 320
Glu Asn Tyr Val Lys Lys Pro Ala Tyr Asp Gly Leu Met Ala Gly Leu
                325                 330                 335
Gly Ala Ser Gly Ser Gly Thr Thr Thr Thr Thr Thr Ser Thr
                340                 345                 350
Thr Thr Gly Gly Thr Asp Pro Thr Gly Val Ala Gln Lys Trp Gly Gln
            355                 360                 365
Cys Gly Gly Ile Gly Trp Thr Gly Pro Thr Thr Cys Val Ser Gly Thr
        370                 375                 380
Thr Cys Gln Lys Leu Asn Asp Trp Tyr Ser Gln Cys Leu
385                 390                 395

<210> SEQ ID NO 253
<211> LENGTH: 2376
<212> TYPE: DNA
<213> ORGANISM: Aspergillus fumigatus
```

<400> SEQUENCE: 253

```
atggcggttg ccaaatctat tgctgccgtg ctggtagcac tgttgcctgg tgcgcttgct    60
caggcgaata caagctatgt tgattacaat gtggaggcga atccggatct caccccctcag   120
tcggtcgcta cgattgacct gtcctttccc gactgcgaga atggaccgct cagcaagact   180
ctcgtttgcg acacgtcggc tcggccgcat gaccgagctg ctgccctggt ttccatgttc   240
accttcgagg agctggtgaa caacacaggc aacactagcc ctggtgttcc aagacttggt   300
ctccctccgt accaagtatg gagcgaggct ctccatggac ttgaccgcgc caacttcaca   360
aacgagggag agtacagctg gccaccteg ttccccatgc ctatcctgac aatgtcggcc    420
ttgaaccgaa ccctgatcaa ccagatcgcg accatcatcg caactcaagg acgagctttc   480
aataacgttg gcggtatgg gctggacgtg tacgccccga atataaatgc attcagatcg    540
gctatgtggg gaagaggtca agagacccc ggagaagacg cttactgcct ggcatcggcg    600
tatgcgtacg agtatatcac tggcatccag gtggtgttg atccggaaca cctcaagttg    660
gtggccactg ccaaacacta tgcgggctac gatcttgaga actgggacgg tcactcccgt   720
ttgggcaacg atatgaacat tacacagcag gaactttccg aatactacac ccctcagttc   780
cttgttgcag ccagagacgc caaagtgcac agtgtcatgt gctcctacaa cgcggtaaat   840
ggggtgccca gctgcgcaaa ctcgttcttc ctccagaccc tcctccgtga cacattcggc   900
ttcgtcgagg atggttatgt atccagcgac tgcgactcgg cgtacaatgt ctggaacccg   960
cacgagtttg cggccaacat cacgggggcc gctgcagact ctatccgggc ggggacggac  1020
attgattgcg gcactactta tcaatactat ttcggcgaag cctttgacga gcaagaggtc  1080
acccgtgcag aaatcgaaag aggtgtgatc cgcctgtaca gcaacttggt gcgtctcggc  1140
tatttcgatg gcaatggaag cgtgtatcgg gacctgacgt ggaatgatgt cgtgaccacg  1200
gatgcctgga atatctcata cgaagccgct gtagaaggca ttgtcctact gaagaacgat  1260
ggaaccttgc ctctcgccaa gtcggtccgc agtgttgcat tgattgggcc ctggatgaat  1320
gtgacgactc agcttcaggg caactacttt ggaccggcgc cttatctgat tagtccgttg  1380
aatgccttcc agaattctga cttcgacgtg aactacgctt tcggcacgaa catttcatcc  1440
cactccacag atgggttttc cgaggcgttg tctgctgcga agaaatccga cgtcatcata  1500
ttcgcgggcg ggattgacaa cacttttgga gcagaagcca tggatcgcat gaatatcaca  1560
tggcccggca atcagctaca gctcatcgac cagttgagcc aactcggcaa accgctgatc  1620
gtcctccaga tgggcggcgg ccaagtcgac tcctcctcgc tcaagtccaa caagaatgtc  1680
aactccctga tctggggtgg ataccccgga caatccggcg ggcaggctct cctagacatc  1740
atcaccggca agcgcgcccc cgccggccga ctcgtggtca cgcagtaccc ggccgaatac  1800
gcaacccagt tccccgccac cgacatgagc ctgcggcctc acggcaataa tcccggccag  1860
acctacatgt ggtacaccgg cacccccgtc tacgagtttg ccacgggct cttctacacg  1920
accttccacg cctccctccc tggcaccggc aaggacaaga cctccttcaa catccaagac  1980
ctcctcacgc agccgcatcc gggcttcgca aacgtcgagc aaatgccttt gctcaacttc  2040
accgtgacga tcaccaatac cggcaaggtc gcttccgact acactgctat gctcttcgcg  2100
aacaccaccg cgggacctgc tccataccg aacaagtggc tcgtcggctt cgaccggctg  2160
gcgagcctgg aaccgcacag gtcgcagact atgaccatcc ccgtgactat cgacagcgtg  2220
gctcgtacgg atgaggccgg caatcgggtt ctctacccgg gaaagtacga gttggccctg  2280
```

```
aacaatgagc ggtcggttgt ccttcagttt gtgctgacag gccgagaggc tgtgattttc    2340
aagtggcctg tagagcagca gcagatttcg tctgcg                              2376
```

<210> SEQ ID NO 254
<211> LENGTH: 792
<212> TYPE: PRT
<213> ORGANISM: Aspergillus fumigatus

<400> SEQUENCE: 254

```
Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
            20                  25                  30

Ala Asn Pro Asp Leu Thr Pro Gln Ser Val Ala Thr Ile Asp Leu Ser
        35                  40                  45

Phe Pro Asp Cys Glu Asn Gly Pro Leu Ser Lys Thr Leu Val Cys Asp
    50                  55                  60

Thr Ser Ala Arg Pro His Asp Arg Ala Ala Leu Val Ser Met Phe
65                  70                  75                  80

Thr Phe Glu Glu Leu Val Asn Asn Thr Gly Asn Thr Ser Pro Gly Val
                85                  90                  95

Pro Arg Leu Gly Leu Pro Pro Tyr Gln Val Trp Ser Glu Ala Leu His
            100                 105                 110

Gly Leu Asp Arg Ala Asn Phe Thr Asn Glu Gly Glu Tyr Ser Trp Ala
        115                 120                 125

Thr Ser Phe Pro Met Pro Ile Leu Thr Met Ser Ala Leu Asn Arg Thr
    130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
        195                 200                 205

Ile Gln Gly Gly Val Asp Pro Glu His Leu Lys Leu Val Ala Thr Ala
    210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
            260                 265                 270

Met Cys Ser Tyr Asn Ala Val Asn Gly Val Pro Ser Cys Ala Asn Ser
        275                 280                 285

Phe Phe Leu Gln Thr Leu Leu Arg Asp Thr Phe Gly Phe Val Glu Asp
    290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Asp Ser Ile Arg
                325                 330                 335

Ala Gly Thr Asp Ile Asp Cys Gly Thr Thr Tyr Gln Tyr Tyr Phe Gly
            340                 345                 350

Glu Ala Phe Asp Glu Gln Glu Val Thr Arg Ala Glu Ile Glu Arg Gly
```

```
            355                 360                 365
Val Ile Arg Leu Tyr Ser Asn Leu Val Arg Leu Gly Tyr Phe Asp Gly
            370                 375                 380

Asn Gly Ser Val Tyr Arg Asp Leu Thr Trp Asn Asp Val Val Thr Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ala Lys Ser Val Arg Ser Val
            420                 425                 430

Ala Leu Ile Gly Pro Trp Met Asn Val Thr Thr Gln Leu Gln Gly Asn
            435                 440                 445

Tyr Phe Gly Pro Ala Pro Tyr Leu Ile Ser Pro Leu Asn Ala Phe Gln
            450                 455                 460

Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Ala Lys Lys Ser
                485                 490                 495

Asp Val Ile Ile Phe Ala Gly Gly Ile Asp Asn Thr Leu Glu Ala Glu
            500                 505                 510

Ala Met Asp Arg Met Asn Ile Thr Trp Pro Gly Asn Gln Leu Gln Leu
            515                 520                 525

Ile Asp Gln Leu Ser Gln Leu Gly Lys Pro Leu Ile Val Leu Gln Met
530                 535                 540

Gly Gly Gly Gln Val Asp Ser Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
            580                 585                 590

Val Thr Gln Tyr Pro Ala Glu Tyr Ala Thr Gln Phe Pro Ala Thr Asp
            595                 600                 605

Met Ser Leu Arg Pro His Gly Asn Asn Pro Gly Gln Thr Tyr Met Trp
610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
            660                 665                 670

Glu Gln Met Pro Leu Leu Asn Phe Thr Val Thr Ile Thr Asn Thr Gly
            675                 680                 685

Lys Val Ala Ser Asp Tyr Thr Ala Met Leu Phe Ala Asn Thr Thr Ala
            690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
            740                 745                 750

Pro Gly Lys Tyr Glu Leu Ala Leu Asn Asn Glu Arg Ser Val Val Leu
            755                 760                 765

Gln Phe Val Leu Thr Gly Arg Glu Ala Val Ile Phe Lys Trp Pro Val
770                 775                 780
```

Glu Gln Gln Gln Ile Ser Ser Ala
785                 790

<210> SEQ ID NO 255
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 255
gcagtggacg ccgtggccgc cgagccacca cggacccgtc at                42

<210> SEQ ID NO 256
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 256
atgacgggtc cgtggtggct cggcggccac ggcgtccact gc                42

<210> SEQ ID NO 257
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 257
gcagtggacg ccgtggccga agagccacca cggacccgtc at                42

<210> SEQ ID NO 258
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 258
atgacgggtc cgtggtggct cttcggccac ggcgtccact gc                42

<210> SEQ ID NO 259
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 259
catcgccctg cactcggccg ccaacaagga cggcgcccag aac               43

<210> SEQ ID NO 260
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 260
gttctgggcg ccgtccttgt tggcggccga gtgcagggcg atg               43

<210> SEQ ID NO 261
<211> LENGTH: 43

<210> SEQ ID NO 261
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 261
catcgccctg cactcggcct ggaacaagga cggcgcccag aac          43

<210> SEQ ID NO 262
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 262
gttctgggcg ccgtccttgt tccaggccga gtgcagggcg atg          43

<210> SEQ ID NO 263
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 263
cgccctgcac tcggccaaca agaaggacgg cgcccagaac tac          43

<210> SEQ ID NO 264
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 264
gtagttctgg gcgccgtcct tcttgttggc cgagtgcagg gcg          43

<210> SEQ ID NO 265
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 265
gcttcaatgg actccatggc ctaaatctca ccatggccca gttatca      47

<210> SEQ ID NO 266
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 266
tgataactgg gccatggtga gatttaggcc atggagtcca ttgaagc      47

<210> SEQ ID NO 267
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 267
gcttcaatgg actccatggc ctccttctca ccatggccca gttatca     47

<210> SEQ ID NO 268
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 268
tgataactgg gccatggtga gaaggaggcc atggagtcca ttgaagc     47

<210> SEQ ID NO 269
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 269
gagattattg ctcttcactc agcttggaac caggatggtg cccagaac     48

<210> SEQ ID NO 270
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 270
gttctgggca ccatcctggt tccaagctga gtgaagagca ataatctc     48

<210> SEQ ID NO 271
<211> LENGTH: 27
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (10)..(10)
<223> OTHER INFORMATION: N=URACIL

<400> SEQUENCE: 271
atgcagcgcn gccataacca tgagtga     27

<210> SEQ ID NO 272
<211> LENGTH: 28
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (10)..(10)
<223> OTHER INFORMATION: N=URACIL

<400> SEQUENCE: 272
agcgctgcan aattctctta ctgtcatg     28

<210> SEQ ID NO 273
<211> LENGTH: 36
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature

```
<222> LOCATION: (8)..(8)
<223> OTHER INFORMATION: N=URACIL

<400> SEQUENCE: 273
aattaagncc tcagcgtgat ttaaaacgcc attgct                              36

<210> SEQ ID NO 274
<211> LENGTH: 41
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=URACIL

<400> SEQUENCE: 274
acttaatnaa accctcagcg cagttaggtt ggtgttcttc t                        41

<210> SEQ ID NO 275
<211> LENGTH: 29
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (11)..(11)
<223> OTHER INFORMATION: N=URACIL

<400> SEQUENCE: 275
agctcaagga nacctacagt tattcgaaa                                      29

<210> SEQ ID NO 276
<211> LENGTH: 35
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (11)..(11)
<223> OTHER INFORMATION: N=URACIL

<400> SEQUENCE: 276
atccttgagc ngtttcctgt gtgaaattgt tatcc                               35

<210> SEQ ID NO 277
<211> LENGTH: 37
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (9)..(9)
<223> OTHER INFORMATION: N=URACIL

<400> SEQUENCE: 277
atctcctcng ctggtctggt taagccagcc ccgacac                             37

<210> SEQ ID NO 278
<211> LENGTH: 27
<212> TYPE: DNA
<213> ORGANISM: Artificial Sequence
<220> FEATURE:
<223> OTHER INFORMATION: Artificial DNA Primer
<220> FEATURE:
```

<221> NAME/KEY: misc_feature
<222> LOCATION: (9)..(9)
<223> OTHER INFORMATION: N=URACIL

<400> SEQUENCE: 278
agaggagana atactctgcg ctccgcc                                    27

<210> SEQ ID NO 279
<211> LENGTH: 32
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (9)..(9)
<223> OTHER INFORMATION: N=URACIL

<400> SEQUENCE: 279
gggtttaanc ctcacacagg aaacagctat ga                              32

<210> SEQ ID NO 280
<211> LENGTH: 46
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (12)..(12)
<223> OTHER INFORMATION: N=URACIL

<400> SEQUENCE: 280
agtgtctgcg ancgctctca ctgcccccag ttgtgtatat agagga               46

<210> SEQ ID NO 281
<211> LENGTH: 36
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (12)..(12)
<223> OTHER INFORMATION: N=URACIL

<400> SEQUENCE: 281
atcgcagaca cngctggcgg tagacaatca atccat                          36

<210> SEQ ID NO 282
<211> LENGTH: 32
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (9)..(9)
<223> OTHER INFORMATION: N=URACIL

<400> SEQUENCE: 282
ggacttaang gatctaagat gagctcatgg ct                              32

<210> SEQ ID NO 283
<211> LENGTH: 24
<212> TYPE: DNA
<213> ORGANISM: Artificial Sequence
<220> FEATURE:
<223> OTHER INFORMATION: Artificial DNA Primer

```
<400> SEQUENCE: 283
acgccattgc tatgatgctt gaag                                           24

<210> SEQ ID NO 284
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 284
tggtgaggtg ctatcgtcct t                                              21

<210> SEQ ID NO 285
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 285
cttcctgtag gtgcaccgaa g                                              21

<210> SEQ ID NO 286
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 286
acagaacgat atcggacctc g                                              21

<210> SEQ ID NO 287
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 287
tcgttatgtt aagtcttcta tca                                            23

<210> SEQ ID NO 288
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 288
agagctcgaa gttcctccga g                                              21

<210> SEQ ID NO 289
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 289
tatcacgagg ccctttcgtc tc                                             22

<210> SEQ ID NO 290
```

```
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 290
tccgtcggct cctctccttc gt                                             22

<210> SEQ ID NO 291
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 291
tgcatatcct ctgacagtat atga                                           24

<210> SEQ ID NO 292
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 292
cagtgaagag ggcagtcgat agt                                            23

<210> SEQ ID NO 293
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 293
acgaggaaca tggctatctg ga                                             22

<210> SEQ ID NO 294
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 294
tcagctcatt ctgggaggtg gga                                            23

<210> SEQ ID NO 295
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 295
actccaggat cctttaaatc ca                                             22

<210> SEQ ID NO 296
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 296
```
actggcaagg gatgccatgc t                    21

<210> SEQ ID NO 297
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 297
tgatcatata accaattgcc ct                   22

<210> SEQ ID NO 298
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 298
agttgtgtat atagaggatt ga                   22

<210> SEQ ID NO 299
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 299
tggtccttcg ctcgtgatgt gga                  23

<210> SEQ ID NO 300
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 300
agtcctcagc gttaccggca                      20

<210> SEQ ID NO 301
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 301
accctcagct gtgtccggga                      20

<210> SEQ ID NO 302
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 302
tggtatgtga acgccagtct g                    21

<210> SEQ ID NO 303
<211> LENGTH: 28
<212> TYPE: DNA

<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=URACIL

<400> SEQUENCE: 303
agagcganat gtccttttcc aagataat                                28

<210> SEQ ID NO 304
<211> LENGTH: 49
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=URACIL

<400> SEQUENCE: 304
tctgcgantt agtgatggtg gtgatgatga ccagtataca gaggaggac        49

<210> SEQ ID NO 305
<211> LENGTH: 28
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=URACIL

<400> SEQUENCE: 305
agagcganat gctgtcttcg acgactcg                                28

<210> SEQ ID NO 306
<211> LENGTH: 49
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=URACIL

<400> SEQUENCE: 306
tctgcganct agtgatggtg gtgatgatgg aacgtcggct caggcggcc        49

<210> SEQ ID NO 307
<211> LENGTH: 33
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=URACIL

<400> SEQUENCE: 307
agagcganat gtctgttgct aagtttgctg gtg                          33

<210> SEQ ID NO 308
<211> LENGTH: 49

```
<212> TYPE: DNA
<213> ORGANISM: Artificial Sequence
<220> FEATURE:
<223> OTHER INFORMATION: Artificial DNA Primer
<220> FEATURE:
<221> NAME/KEY: misc_feature
<222> LOCATION: (8)..(8)
<223> OTHER INFORMATION: N=URACIL

<400> SEQUENCE: 308
tctgcgantt agtgatggtg gtgatgatgg gcggagaggt cacgggcgt          49

<210> SEQ ID NO 309
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 309
cccagttatc aactaccttg                                          20

<210> SEQ ID NO 310
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 310
ctcaatttac ctctatccac                                          20

<210> SEQ ID NO 311
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 311
tataaccaat tgccctcatc                                          20

<210> SEQ ID NO 312
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 312
gcaccgtcga gctgcagtgg                                          20

<210> SEQ ID NO 313
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 313
ccttgccaac tgcaatggtg                                          20

<210> SEQ ID NO 314
<211> LENGTH: 20
<212> TYPE: DNA
<213> ORGANISM: Artificial Sequence
<220> FEATURE:
```

<223> OTHER INFORMATION: Artificial DNA Primer

<400> SEQUENCE: 314
gcaccgtcga gctgcagtgg                                                    20

<210> SEQ ID NO 315
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 315
attattgctc ttcactcagc tttcaaccag gatggtgccc agaac                        45

<210> SEQ ID NO 316
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 316
gttctgggca ccatcctggt tgaaagctga gtgaagagca ataat                        45

<210> SEQ ID NO 317
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 317
attattgctc ttcactcagc tatgaaccag gatggtgccc agaac                        45

<210> SEQ ID NO 318
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 318
gttctgggca ccatcctggt tcatagctga gtgaagagca ataat                        45

<210> SEQ ID NO 319
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 319
ccctgcactc ggccatgaac aaggacggcg c                                       31

<210> SEQ ID NO 320
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 320
gcgccgtcct tgttcatggc cgagtgcagg g                                       31

```
<210> SEQ ID NO 321
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 321
gcactcggcc aaccacaagg acggcgccc                                    29

<210> SEQ ID NO 322
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 322
gggcgccgtc cttgtggttg gccgagtgc                                    29

<210> SEQ ID NO 323
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 323
ccagaccagc agaggagata atact                                        25

<210> SEQ ID NO 324
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 324
caaggatacc tacagttatt cga                                          23

<210> SEQ ID NO 325
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 325
ccagaccagc agaggagata atactctgcg                                   30

<210> SEQ ID NO 326
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 326
caaggatacc tacagttatt cgaaacctcc tg                                32

<210> SEQ ID NO 327
<211> LENGTH: 42
<212> TYPE: DNA
<213> ORGANISM: Artificial Sequence
<220> FEATURE:
<223> OTHER INFORMATION: Artificial DNA Primer
```

```
<400> SEQUENCE: 327
tccagtggac tacctggccc aagagccacc acggccctgt cc                42

<210> SEQ ID NO 328
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 328
gggccaggta gtccactgga gctcaacagt ac                           32

<210> SEQ ID NO 329
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 329
tccagtggac tacctggccc cccagccacc acggccctgt cc                42

<210> SEQ ID NO 330
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 330
gggccaggta gtccactgga gctcaacagt ac                           32

<210> SEQ ID NO 331
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 331
ccggtacctg ggccagtgat atcttgatcg ccaacaacaa cagctg             46

<210> SEQ ID NO 332
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 332
atcactggcc caggtaccgg ggacgtcgtc                              30

<210> SEQ ID NO 333
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 333
ccggtacctg ggccagtgat ctcttgatcg ccaacaacaa cagctg             46
```

<210> SEQ ID NO 334
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 334
atcactggcc caggtaccgg ggacgtcgtc                             30

<210> SEQ ID NO 335
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 335
aaatcattgc ccttcactct gctttcaaca aggatggtgc tcagaacta         49

<210> SEQ ID NO 336
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 336
agcagagtga agggcaatga tttcgtgacg gag                          33

<210> SEQ ID NO 337
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 337
aaatcattgc ccttcactct gctatgaaca aggatggtgc tcagaacta         49

<210> SEQ ID NO 338
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 338
agcagagtga agggcaatga tttcgtgacg gag                          33

<210> SEQ ID NO 339
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 339
aaatcattgc ccttcactct gctgccaaca aggatggtgc tcagaacta         49

<210> SEQ ID NO 340
<211> LENGTH: 33
<212> TYPE: DNA
<213> ORGANISM: Artificial Sequence

```
<220> FEATURE:
<223> OTHER INFORMATION: Artificial DNA Primer

<400> SEQUENCE: 340
agcagagtga agggcaatga tttcgtgacg gag                          33

<210> SEQ ID NO 341
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 341
aaatcattgc ccttcactct gcttggaaca aggatggtgc tcagaacta         49

<210> SEQ ID NO 342
<211> LENGTH: 33
<212> TYPE: DNA
<213> ORGANISM: Artificial Sequence
<220> FEATURE:
<223> OTHER INFORMATION: Artificial DNA Primer

<400> SEQUENCE: 342
agcagagtga agggcaatga tttcgtgacg gag                          33

<210> SEQ ID NO 343
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 343
cattgccctt cactctgctg gtcacaagga tggtgctcag aactacc           47

<210> SEQ ID NO 344
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 344
accagcagag tgaagggcaa tgatttcgtg acgg                         34

<210> SEQ ID NO 345
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 345
cattgccctt cactctgctg gtaagaagga tggtgctcag aactacc           47

<210> SEQ ID NO 346
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 346
accagcagag tgaagggcaa tgatttcgtg acgg                         34
```

GH61 POLYPEPTIDE VARIANTS AND POLYNUCLEOTIDES ENCODING SAME

CROSS-REFERENCE TO RELATED APPLICATIONS

This application is a 35 U.S.C. § 371 national application of PCT/US2012/066278 filed Nov. 21, 2012, which claims priority or the benefit under 35 U.S.C. § 119 of U.S. Provisional Application No. 61/562,277 filed Nov. 21, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to GH61 polypeptide variants, polynucleotides encoding the variants, methods of producing the variants, and methods of using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars can easily be fermented by yeast into ethanol.

WO 2005/074647, WO 2008/148131, and WO 2011/035027 disclose isolated GH61 polypeptides having cellulolytic enhancing activity and the polynucleotides thereof from *Thielavia terrestris*. WO 2005/074656 and WO 2010/065830 disclose isolated GH61 polypeptides having cellulolytic enhancing activity and the polynucleotides thereof from *Thermoascus aurantiacus*. WO 2007/089290 and WO 2012/149344 disclose isolated GH61 polypeptides having cellulolytic enhancing activity and the polynucleotides thereof from *Trichoderma reesei*. WO 2009/085935, WO 2009/085859, WO 2009/085864, and WO 2009/085868 disclose isolated GH61 polypeptides having cellulolytic enhancing activity and the polynucleotides thereof from *Myceliophthora thermophila*. WO 2010/138754 discloses an isolated GH61 polypeptide having cellulolytic enhancing activity and the polynucleotide thereof from *Aspergillus fumigatus*. WO 2011/005867 discloses an isolated GH61 polypeptide having cellulolytic enhancing activity and the polynucleotide thereof from *Penicillium pinophilum*. WO 2011/039319 discloses an isolated GH61 polypeptide having cellulolytic enhancing activity and the polynucleotide thereof from *Thermoascus* sp. WO 2011/041397 discloses an isolated GH61 polypeptide having cellulolytic enhancing activity and the polynucleotide thereof from *Penicillium* sp. (*emersonii*). WO 2011/041504 discloses isolated GH61 polypeptides having cellulolytic enhancing activity and the polynucleotides thereof from *Thermoascus crustaceus*. WO 2012/030799 discloses GH61 polypeptides having cellulolytic enhancing activity and the polynucleotides thereof from *Aspergillus aculeatus*. WO 2012/113340 discloses GH61 polypeptides having cellulolytic enhancing activity and the polynucleotides thereof from *Thermomyces lanuginosus*. WO 2012/146171 discloses GH61 polypeptides having cellulolytic enhancing activity and the polynucleotides thereof from *Humicola insolens*. WO 2008/151043 discloses methods of increasing the activity of a GH61 polypeptide having cellulolytic enhancing activity by adding a soluble activating divalent metal cation to a composition comprising the polypeptide.

WO 2012/044835 and WO 2012/044836 disclose GH61 polypeptide variants having cellulolytic enhancing activity with improved thermal activity and thermostability.

The present invention provides GH61 polypeptide variants with increased thermostability.

SUMMARY OF THE INVENTION

The present invention relates to isolated GH61 polypeptide variants, comprising a substitution at one or more (e.g., several) positions corresponding to positions 105, 154, 188, 189, 216, and 229 of the mature polypeptide of SEQ ID NO: 30, wherein the variants have cellulolytic enhancing activity.

The present invention also relates to isolated polynucleotides encoding the variants; nucleic acid constructs, vectors, and host cells comprising the polynucleotides; and methods of producing the variants.

The present invention also relates to processes for degrading or converting a cellulosic material, comprising: treating the cellulosic material with an enzyme composition in the presence of a GH61 polypeptide variant of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a GH61 polypeptide variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a GH61 polypeptide variant of the present invention. In one aspect, the fermenting of the cellulosic material produces a fermentation product. In another aspect, the processes further comprise recovering the fermentation product from the fermentation.

BRIEF DESCRIPTION OF THE FIGURES

FIG. 1 shows the genomic DNA sequence (SEQ ID NO: 29) and the deduced amino acid sequence (SEQ ID NO: 30) of an *Aspergillus fumigatus* gene encoding a GH61B polypeptide having cellulolytic enhancing activity.

DEFINITIONS

Figure 2:
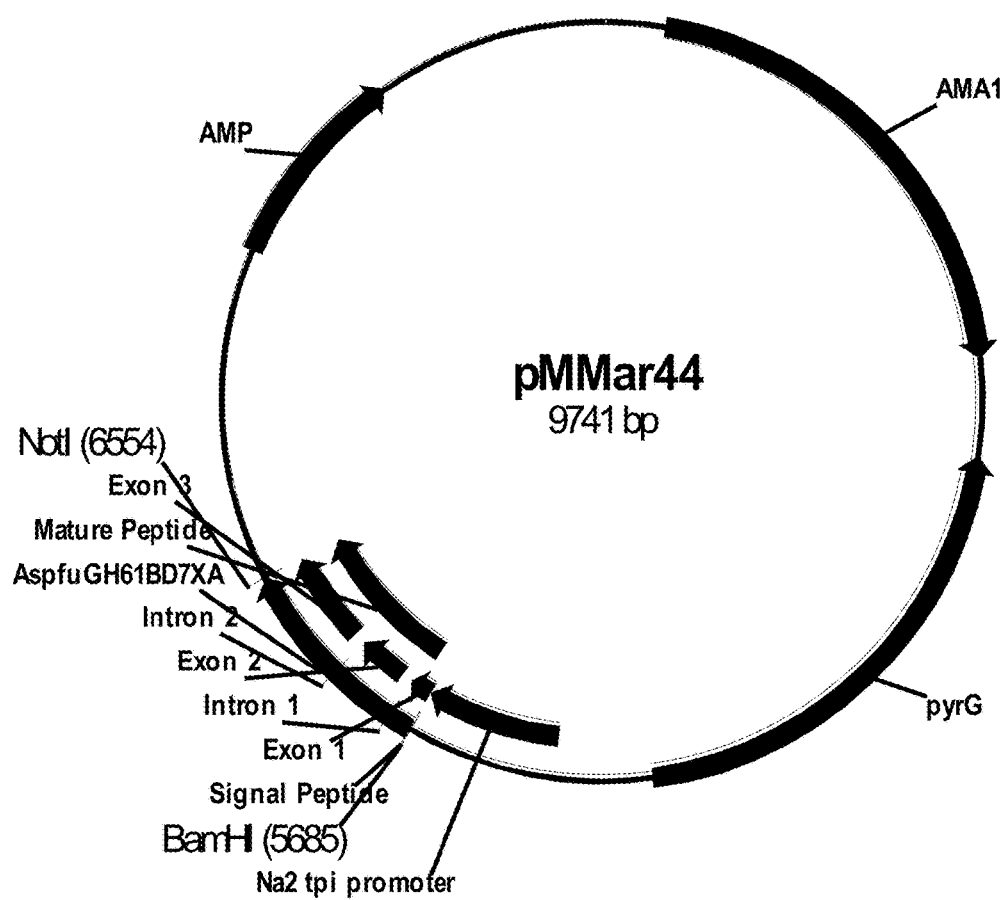
FIG. 2 shows a restriction map of plasmid pMMar44.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed pretreated corn stover (PCS), 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA). 40° C.-80° C., e.g., 50° C., 55° C., 60° C., 65° C., or 70° C.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of the mature polypeptide thereof, wherein the fragment has cellulolytic enhancing activity. In one aspect, a fragment contains at least 85% of the amino acid residues, e.g., at least 90% of the amino acid residues or at least 95% of the amino acid residues of the mature polypeptide of a GH61 polypeptide.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such an improved property includes, but is not limited to, increased thermostability.

Increased thermostability: The term "increased thermostability" means a higher retention of cellulolytic enhancing activity of a GH61 polypeptide variant after a period of incubation at a temperature relative to the parent. The increased thermostability of the variant relative to the parent can be assessed, for example, under conditions of one or more (e.g., several) temperatures. For example, the one or more (e.g., several) temperatures can be any temperature or temperatures in the range of 45° C. to 95° C., e.g., 45, 50, 55, 60, 65, 70, 75, 80, 85, or 95° C. (or in between, e.g., 62° C., 68° C., 72° C., etc.) at one or more (e.g., several) pHs in the range of 3 to 9, e.g., 3.0, 3.5, 4.0, 4.5, 5.0, 5.5, 6.0, 6.5, 7.0, 7.5, 8.0, 8.5, or 9.0 (or in between) for a suitable period (time) of incubation, e.g., 1 minute, 5 minutes, 10 minutes, 15 minutes, 20 minutes, 25 minutes, 30 minutes, 45 minutes, or 60 minutes (or in between, e.g., 23 minutes, 37 minutes, etc.), such that the variant retains residual activity. However, longer periods of incubation can also be used. The term "increased thermostability" can be used interchangeably with "improved thermostability".

The increased thermostability of the variant relative to the parent can be determined by differential scanning calorimetry (DSC) using methods standard in the art (see, for example, Sturtevant, 1987, *Annual Review of Physical*

*Chemistry* 38: 463-488; Examples 9 and 17). The increased thermostability of the variant relative to the parent can also be determined using protein thermal unfolding analysis (see, for example, Examples 10, 18, and 23 herein). The increased thermostability of the variant relative to the parent can also be determined using any enzyme assay known in the art for GH61 polypeptides having cellulolytic enhancing activity to measure residual activity after a temperature treatment. See for example, WO 2005/074647, WO 2008/148131 WO 2005/074656, WO 2010/065830, WO 2007/089290, WO 2009/085935, WO 2009/085859, WO 2009/085864, WO 2009/085868, and WO 2008/151043, which are incorporated herein by reference. Alternatively, the increased thermostability of the variant relative to the parent can be determined using any application assay for the variant where the performance of the variant is compared to the parent. For example, the application assays described in Examples 5, 12, and 13 can be used.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 326 of SEQ ID NO: 2 based on the SignalP program (Nielsen et al., 1997, *Protein Engineering* 10:1-6) that predicts amino acids 1 to 19 of SEQ ID NO: 2 are a signal peptide. In another aspect, the mature polypeptide is amino acids 18 to 239 of SEQ ID NO: 4 based on the SignalP program that predicts amino acids 1 to 17 of SEQ ID NO: 4 are a signal peptide. In another aspect, the mature polypeptide is amino acids 20 to 258 of SEQ ID NO: 6 based on the SignalP program that predicts amino acids 1 to 19 of SEQ ID NO: 6 are a signal peptide. In another aspect, the mature polypeptide is amino acids 19 to 226 of SEQ ID NO: 8 based on the SignalP program that predicts amino acids 1 to 18 of SEQ ID NO: 8 are a signal peptide. In another aspect, the mature polypeptide is amino acids 20 to 304 of SEQ ID NO: 10 based on the SignalP program that predicts amino acids 1 to 19 of SEQ ID NO: 10 are a signal peptide. In another aspect, the mature polypeptide is amino acids 16 to 317 of SEQ ID NO: 12 based on the SignalP program that predicts amino acids 1 to 15 of SEQ ID NO: 12 are a signal peptide. In another aspect, the mature polypeptide is amino acids 22 to 249 of SEQ ID NO: 14 based on the SignalP program that predicts amino acids 1 to 21 of SEQ ID NO: 14 are a signal peptide. In another aspect, the mature polypeptide is amino acids 20 to 249 of SEQ ID NO: 16 based on the SignalP program that predicts amino acids 1 to 19 of SEQ ID NO: 16 are a signal peptide. In another aspect, the mature polypeptide is amino acids 18 to 232 of SEQ ID NO: 18 based on the SignalP program that predicts amino acids 1 to 17 of SEQ ID NO: 18 are a signal peptide. In another aspect, the mature polypeptide is amino acids 16 to 235 of SEQ ID NO: 20 based on the SignalP program that predicts amino acids 1 to 15 of SEQ ID NO: 20 are a signal peptide. In another aspect, the mature polypeptide is amino acids 19 to 323 of SEQ ID NO: 22 based on the SignalP program that predicts amino acids 1 to 18 of SEQ ID NO: 22 are a signal peptide. In another aspect, the mature polypeptide is amino acids 16 to 310 of SEQ ID NO: 24 based on the SignalP program that predicts amino acids 1 to 15 of SEQ ID NO: 24 are a signal peptide. In another aspect, the mature polypeptide is amino acids 20 to 246 of SEQ ID NO: 26 based on the SignalP program that predicts amino acids 1 to 19 of SEQ ID NO: 26 are a signal peptide. In another aspect, the mature polypeptide is amino acids 22 to 354 of SEQ ID NO: 28 based on the SignalP program that predicts amino acids 1 to 21 of SEQ ID NO: 28 are a signal peptide. In another aspect, the mature polypeptide is amino acids 22 to 250 of SEQ ID NO: 30 based on the SignalP program that predicts amino acids 1 to 21 of SEQ ID NO: 30 are a signal peptide. In another aspect, the mature polypeptide is amino acids 22 to 322 of SEQ ID NO: 32 based on the SignalP program that predicts amino acids 1 to 21 of SEQ ID NO: 32 are a signal peptide. In another aspect, the mature polypeptide is amino acids 24 to 444 of SEQ ID NO: 34 based on the SignalP program that predicts amino acids 1 to 23 of SEQ ID NO: 34 are a signal peptide. In another aspect, the mature polypeptide is amino acids 26 to 253 of SEQ ID NO: 36 based on the SignalP program that predicts amino acids 1 to 25 of SEQ ID NO: 36 are a signal peptide. In another aspect, the mature polypeptide is amino acids 18 to 246 of SEQ ID NO: 38 based on the SignalP program that predicts amino acids 1 to 17 of SEQ ID NO: 38 are a signal peptide. In another aspect, the mature polypeptide is amino acids 20 to 334 of SEQ ID NO: 40 based on the SignalP program that predicts amino acids 1 to 19 of SEQ ID NO: 40 are a signal peptide. In another aspect, the mature polypeptide is amino acids 18 to 227 of SEQ ID NO: 42 based on the SignalP program that predicts amino acids 1 to 17 of SEQ ID NO: 42 are a signal peptide. In another aspect, the mature polypeptide is amino acids 20 to 223 of SEQ ID NO: 44 based on the SignalP program that predicts amino acids 1 to 19 of SEQ ID NO: 44 are a signal peptide. In another aspect, the mature polypeptide is amino acids 22 to 368 of SEQ ID NO: 46 based on the SignalP program that predicts amino acids 1 to 21 of SEQ ID NO: 46 are a signal peptide. In another aspect, the mature polypeptide is amino acids 25 to 330 of SEQ ID NO: 48 based on the SignalP program that predicts amino acids 1 to 24 of SEQ ID NO: 48 are a signal peptide. In another aspect, the mature polypeptide is amino acids 17 to 236 of SEQ ID NO: 50 based on the SignalP program that predicts amino acids 1 to 16 of SEQ ID NO: 50 are a signal peptide. In another aspect, the mature polypeptide is amino acids 19 to 250 of SEQ ID NO: 52 based on the SignalP program that predicts amino acids 1 to 18 of SEQ ID NO: 52 are a signal peptide. In another aspect, the mature polypeptide is amino acids 23 to 478 of SEQ ID NO: 54 based on the SignalP program that predicts amino acids 1 to 22 of SEQ ID NO: 54 are a signal peptide. In another aspect, the mature polypeptide is amino acids 17 to 230 of SEQ ID NO: 56 based on the SignalP program that predicts amino acids 1 to 16 of SEQ ID NO: 56 are a signal peptide. In another aspect, the mature polypeptide is amino acids 20 to 257 of SEQ ID NO: 58 based on the SignalP program that predicts amino acids 1 to 19 of SEQ ID NO: 58 are a signal peptide. In another aspect, the mature polypeptide is amino acids 23 to 251 of SEQ ID NO: 60 based on the SignalP program that predicts amino acids 1 to 22 of SEQ ID NO: 60 are a signal peptide. In another aspect, the mature polypeptide is amino acids 19 to 349 of SEQ ID NO: 62 based on the SignalP program that predicts amino acids 1 to 18 of SEQ ID NO: 62 are a signal peptide. In another aspect, the mature polypeptide is amino acids 24 to 436 of SEQ ID NO: 64 based on the SignalP program that predicts amino acids 1 to 23 of SEQ ID NO: 64 are a signal peptide. In another aspect, the mature polypeptide is amino acids 21 to 344 of SEQ ID NO: 66 based on the SignalP program that predicts amino acids 1 to 23 of SEQ ID NO: 66 are a signal peptide. In another aspect, the mature polypeptide is amino acids 26 to 400 of SEQ ID NO: 68 based on the SignalP program that predicts amino acids 1 to 25 of SEQ ID NO: 68 are a signal peptide. In another aspect, the mature polypeptide is amino acids 21 to 389 of SEQ ID NO: 70 based on the SignalP program that predicts amino acids 1 to 20 of SEQ ID NO: 70 are a signal peptide. In another aspect, the mature polypeptide is amino acids 22 to 406 of SEQ ID NO: 72 based on the SignalP program that predicts amino acids 1 to 21 of SEQ ID NO: 72 are a signal peptide. In another aspect, the mature polypeptide is amino acids 20 to 427 of SEQ ID NO: 74 based on the SignalP program that predicts amino acids 1 to 19 of SEQ ID NO: 74 are a signal peptide. In another aspect, the mature polypeptide is amino acids 18 to 267 of SEQ ID NO: 76 based on the SignalP program that predicts amino acids 1 to 17 of SEQ ID NO: 76 are a signal peptide. In another aspect, the mature polypeptide is amino acids 21 to 273 of SEQ ID NO: 78 based on the SignalP program that predicts amino acids 1 to 20 of SEQ ID NO: 78 are a signal peptide. In another aspect, the mature polypeptide is amino acids 23 to 272 of SEQ ID NO: 80 based on the SignalP program that predicts amino acids 1 to 22 of SEQ ID NO: 80 are a signal peptide. In another aspect, the mature polypeptide is amino acids 22 to 327 of SEQ ID NO: 82 based on the SignalP program that predicts amino acids 1 to 21 of SEQ ID NO: 82 are a signal peptide. In another aspect, the mature polypeptide is amino acids 23 to 274 of SEQ ID NO: 84 based on the SignalP program that predicts amino acids 1 to 22 of SEQ ID NO: 84 are a signal peptide. In another aspect, the mature polypeptide is amino acids 21 to 322 of SEQ ID NO: 86 based on the SignalP program that predicts amino acids 1 to 20 of SEQ ID NO: 86 are a signal peptide. In another aspect, the mature polypeptide is amino acids 18 to 234 of SEQ ID NO: 88 based on the SignalP program that predicts amino acids 1 to 17 of SEQ ID NO: 88 are a signal peptide. In another aspect, the mature polypeptide is amino acids 24 to 233 of SEQ ID NO: 90 based on the SignalP program that predicts amino acids 1 to 23 of SEQ ID NO: 90 are a signal peptide. In another aspect, the mature polypeptide is amino acids 17 to 237 of SEQ ID NO: 92 based on the SignalP program that predicts amino acids 1 to 16 of SEQ ID NO: 92 are a signal peptide. In another aspect, the mature polypeptide is amino acids 20 to 484 of SEQ ID NO: 94 based on the SignalP program that predicts amino acids 1 to 19 of SEQ ID NO: 94 are a signal peptide. In another aspect, the mature polypeptide is amino acids 22 to 329 of SEQ ID NO: 96 based on the SignalP program that predicts amino acids 1 to 21 of SEQ ID NO: 96 are a signal peptide. In another aspect, the mature polypeptide is amino acids 18 to 227 of SEQ ID NO: 98 based on the SignalP program that predicts amino acids 1 to 17 of SEQ ID NO: 98 are a signal peptide. In another aspect, the mature polypeptide is amino acids 17 to 257 of SEQ ID NO: 100 based on the SignalP program that predicts amino acids 1 to 16 of SEQ ID NO: 100 are a signal peptide. In another aspect, the mature polypeptide is amino acids 20 to 246 of SEQ ID NO: 102 based on the SignalP program that predicts amino acids 1 to 19 of SEQ ID NO: 102 are a signal peptide. In another aspect, the mature polypeptide is amino acids 28 to 265 of SEQ ID NO: 104 based on the SignalP program that predicts amino acids 1 to 27 of SEQ ID NO: 104 are a signal peptide. In another aspect, the mature polypeptide is amino acids 16 to 310 of SEQ ID NO: 106 based on the SignalP program that predicts amino acids 1 to 15 of SEQ ID NO: 106 are a signal peptide. In one aspect, the mature polypeptide is amino acids 21 to 354 of SEQ ID NO: 108 based on the SignalP program that predicts amino acids 1 to 20 of SEQ ID NO: 108 are a signal peptide. In another aspect, the mature polypeptide is amino acids 22 to 267 of SEQ ID NO: 110 based on the SignalP program that predicts amino acids 1 to 21 of SEQ ID NO: 110 are a signal peptide. In another aspect, the mature polypeptide is amino acids 16 to 237 of SEQ ID NO: 112 based on the SignalP program that predicts amino acids 1 to 15 of SEQ ID NO: 112 are a signal peptide. In another aspect, the mature polypeptide is amino acids 20 to 234 of SEQ ID NO: 114 based on the SignalP program that predicts amino acids 1 to 19 of SEQ ID NO: 114 are a signal peptide. In another aspect, the mature polypeptide is amino acids 18 to 226 of SEQ ID NO: 116 based on the SignalP program that predicts amino acids 1 to 17 of SEQ ID NO: 116 are a signal peptide. In one aspect, the mature polypeptide is amino acids 17 to 231 of SEQ ID NO: 118 based on the SignalP program that predicts amino acids 1 to 16 of SEQ ID NO: 118 are a signal peptide. In another aspect, the mature polypeptide is amino acids 22 to 248 of SEQ ID NO: 120 based on the SignalP program that predicts amino acids 1 to 21 of SEQ ID NO: 120 are a signal peptide. In another aspect, the mature polypeptide is amino acids 18 to 233 of SEQ ID NO: 122 based on the SignalP program that predicts amino acids 1 to 17 of SEQ ID NO: 122 are a signal peptide. In another aspect, the mature polypeptide is amino acids 21 to 243 of SEQ ID NO: 124 based on the SignalP program that predicts amino acids 1 to 20 of SEQ ID NO: 124 are a signal peptide. In another aspect, the mature polypeptide is amino acids 21 to 363 of SEQ ID NO: 126 based on the SignalP program that predicts amino acids 1 to 20 of SEQ ID NO: 126 are a signal peptide. In one aspect, the mature polypeptide is amino acids 20 to 296 of SEQ ID NO: 128 based on the SignalP program that predicts amino acids 1 to 19 of SEQ ID NO: 128 are a signal peptide. In another aspect, the mature polypeptide is amino acids 16 to 318 of SEQ ID NO: 130 based on the SignalP program that predicts amino acids 1 to 15 of SEQ ID NO: 130 are a signal peptide. In another aspect, the mature polypeptide is amino acids 19 to 259 of SEQ ID NO: 132 based on the SignalP program that predicts amino acids 1 to 18 of SEQ ID NO: 132 are a signal peptide. In another aspect, the mature polypeptide is amino acids 20 to 325 of SEQ ID NO: 134 based on the SignalP program that predicts amino acids 1 to 19 of SEQ ID NO: 134 are a signal peptide. In another aspect, the mature polypeptide is amino acids 19 to 298 of SEQ ID NO: 136 based on the SignalP program that predicts amino acids 1 to 18 of SEQ ID NO: 136 are a signal peptide. In one aspect, the mature polypeptide is amino acids 20 to 298 of SEQ ID NO: 138 based on the SignalP program that predicts amino acids 1 to 19 of SEQ ID NO: 138 are a signal peptide. In another aspect, the mature polypeptide is amino acids 22 to 344 of SEQ ID NO: 140 based on the SignalP program that predicts amino acids 1 to 21 of SEQ ID NO: 140 are a signal peptide. In another aspect, the mature polypeptide is amino acids 20 to 330 of SEQ ID NO: 142 based on the SignalP program that predicts amino acids 1 to 19 of SEQ ID NO: 142 are a signal peptide. In another aspect, the mature polypeptide is amino acids 19 to 216 of SEQ ID NO: 144 based on the SignalP program that predicts amino acids 1 to 18 of SEQ ID NO: 144 are a signal peptide. In another aspect, the mature polypeptide is amino acids 18 to 490 of SEQ ID NO: 146 based on the SignalP program that predicts amino acids 1 to 17 of SEQ ID NO: 146 are a signal peptide. In one aspect, the mature polypeptide is amino acids 21 to 306 of SEQ ID NO: 148 based on the SignalP program) that predicts amino acids 1 to 20 of SEQ ID NO: 148 are a signal peptide. In another aspect, the mature polypeptide is amino acids 22 to 339 of SEQ ID NO: 150 based on the SignalP program that predicts amino acids 1 to 21 of SEQ ID NO: 150 are a signal peptide. In another aspect, the mature polypeptide is amino acids 22 to 344 of SEQ ID NO: 152 based on the SignalP program that predicts amino acids 1 to 21 of SEQ ID NO: 152 are a signal peptide. In another aspect, the mature polypeptide is amino acids 23 to 408 of SEQ ID NO: 154 based on the SignalP program that predicts amino acids 1 to 22 of SEQ ID NO: 154 are a signal peptide. In another aspect, the mature polypeptide is amino acids 19 to 234 of SEQ ID NO: 156 based on the SignalP program that predicts amino acids 1 to 18 of SEQ ID NO: 156 are a signal peptide. In another aspect, the mature polypeptide is amino acids 22 to 248 of SEQ ID NO: 158 based on the SignalP program that predicts amino acids 1 to 21 of SEQ ID NO: 158 are a signal peptide. In another aspect, the mature polypeptide is amino acids 21 to 242 of SEQ ID NO: 160 based on the SignalP program that predicts amino acids 1 to 20 of SEQ ID NO: 160 are a signal peptide. In another aspect, the mature polypeptide is amino acids 23 to 334 of SEQ ID NO: 162 based on the SignalP program that predicts amino acids 1 to 22 of SEQ ID NO: 162 are a signal peptide. In another aspect, the mature polypeptide is amino acids 18 to 230 of SEQ ID NO: 164 based on the SignalP program that predicts amino acids 1 to 17 of SEQ ID NO: 164 are a signal peptide. In another aspect, the mature polypeptide is amino acids 19 to 397 of SEQ ID NO: 166 based on the SignalP program that predicts amino acids 1 to 18 of SEQ ID NO: 166 are a signal peptide. In another aspect, the mature polypeptide is amino acids 23 to 410 of SEQ ID NO: 168 based on the SignalP program that predicts amino acids 1 to 22 of SEQ ID NO: 168 are a signal peptide. In another aspect, the mature polypeptide is amino acids 20 to 232 of SEQ ID NO: 170 based on the SignalP program that predicts amino acids 1 to 19 of SEQ ID NO: 170 are a signal peptide. In another aspect, the mature polypeptide is amino acids 21 to 266 of SEQ ID NO: 172 based on the SignalP program that predicts amino acids 1 to 20 of SEQ ID NO: 172 are a signal peptide. In another aspect, the mature polypeptide is amino acids 24 to 324 of SEQ ID NO: 174 based on the SignalP program that predicts amino acids 1 to 23 of SEQ ID NO: 174 are a signal peptide. In another aspect, the mature polypeptide is amino acids 21 to 240 of SEQ ID NO: 176 based on the SignalP program that predicts amino acids 1 to 20 of SEQ ID NO: 176 are a signal peptide. In another aspect, the mature polypeptide is amino acids 21 to 225 of SEQ ID NO: 178 based on the SignalP program that predicts amino acids 1 to 20 of SEQ ID NO: 178 are a signal peptide.

In another aspect, the mature polypeptide is amino acids 16 to 235 of SEQ ID NO: 180 based on the SignalP program that predicts amino acids 1 to 15 of SEQ ID NO: 180 are a signal peptide. In another aspect, the mature polypeptide is amino acids 20 to 336 of SEQ ID NO: 182 based on the SignalP program that predicts amino acids 1 to 19 of SEQ ID NO: 182 are a signal peptide. In another aspect, the mature polypeptide is amino acids 17 to 253 of SEQ ID NO: 184 based on the SignalP program that predicts amino acids 1 to 16 of SEQ ID NO: 184 are a signal peptide. In another aspect, the mature polypeptide is amino acids 18 to 255 of SEQ ID NO: 186 based on the SignalP program that predicts amino acids 1 to 17 of SEQ ID NO: 186 are a signal peptide. In another aspect, the mature polypeptide is amino acids 18 to 225 of SEQ ID NO: 188 based on the SignalP program that predicts amino acids 1 to 17 of SEQ ID NO: 188 are a signal peptide. In another aspect, the mature polypeptide is amino acids 16 to 237 of SEQ ID NO: 190 based on the SignalP program that predicts amino acids 1 to 15 of SEQ ID NO: 190 are a signal peptide. In another aspect, the mature polypeptide is amino acids 18 to 227 of SEQ ID NO: 192 based on the SignalP program that predicts amino acids 1 to 17 of SEQ ID NO: 192 are a signal peptide. In another aspect, the mature polypeptide is amino acids 22 to 315 of SEQ ID NO: 194 based on the SignalP program that predicts amino acids 1 to 21 of SEQ ID NO: 194 are a signal peptide. In another aspect, the mature polypeptide is amino acids 21 to 439 of SEQ ID NO: 196 based on the SignalP program that predicts amino acids 1 to 20 of SEQ ID NO: 196 are a signal peptide. In another aspect, the mature polypeptide is amino acids 18 to 246 of SEQ ID NO: 198 based on the SignalP program that predicts amino acids 1 to 17 of SEQ ID NO: 198 are a signal peptide. In another aspect, the mature polypeptide is amino acids 19 to 324 of SEQ ID NO: 200 based on the SignalP program that predicts amino acids 1 to 18 of SEQ ID NO: 200 are a signal peptide. In another aspect, the mature polypeptide is amino acids 21 to 242 of SEQ ID NO: 202 based on the SignalP program that predicts amino acids 1 to 20 of SEQ ID NO: 202 are a signal peptide. In another aspect, the mature polypeptide is amino acids 16 to 306 of SEQ ID NO: 204 based on the SignalP program that predicts amino acids 1 to 15 of SEQ ID NO: 204 are a signal peptide. In another aspect, the mature polypeptide is amino acids 20 to 252 of SEQ ID NO: 206 based on the SignalP program that predicts amino acids 1 to 19 of SEQ ID NO: 206 are a signal peptide. In another aspect, the mature polypeptide is amino acids 20 to 344 of SEQ ID NO: 208 based on the SignalP program that predicts amino acids 1 to 19 of SEQ ID NO: 208 are a signal peptide. In another aspect, the mature polypeptide is amino acids 22 to 347 of SEQ ID NO: 210 based on the SignalP program that predicts amino acids 1 to 21 of SEQ ID NO: 210 are a signal peptide. In another aspect, the mature polypeptide is amino acids 23 to 334 of SEQ ID NO: 212 based on the SignalP program that predicts amino acids 1 to 22 of SEQ ID NO: 212 are a signal peptide. In another aspect, the mature polypeptide is amino acids 24 to 366 of SEQ ID NO: 214 based on the SignalP program that predicts amino acids 1 to 23 of SEQ ID NO: 214 are a signal peptide. In another aspect, the mature polypeptide is amino acids 21 to 364 of SEQ ID NO: 216 based on the SignalP program that predicts amino acids 1 to 20 of SEQ ID NO: 216 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 388 to 1332 of SEQ ID NO: 1 based on the SignalP program (Nielsen et al., 1997, supra) that predicts nucleotides 330 to 387 of SEQ ID NO: 1 encode a signal peptide. In another aspect, the mature polypeptide coding sequence is nucleotides 98 to 821 of SEQ ID NO: 3 based on the SignalP program that predicts nucleotides 47 to 97 of SEQ ID NO: 3 encode a signal peptide. In another aspect, the mature polypeptide coding sequence is nucleotides 126 to 978 of SEQ ID NO: 5 based on the SignalP program that predicts nucleotides 69 to 125 of SEQ ID NO: 5 encode a signal peptide. In another aspect, the mature polypeptide coding sequence is nucleotides 55 to 678 of SEQ ID NO: 7 based on the SignalP program that predicts nucleotides 1 to 54 of SEQ ID NO: 7 encode a signal peptide. In another aspect, the mature polypeptide coding sequence is nucleotides 58 to 912 of SEQ ID NO: 9 based on the SignalP program that predicts nucleotides 1 to 57 of SEQ ID NO: 9 encode a signal peptide. In another aspect, the mature polypeptide coding sequence is nucleotides 46 to 951 of SEQ ID NO: 11 based on the SignalP program that predicts nucleotides 1 to 45 of SEQ ID NO: 11 encode a signal peptide. In another aspect, the mature polypeptide coding sequence is nucleotides 64 to 796 of SEQ ID NO: 13 based on the SignalP program that predicts nucleotides 1 to 63 of SEQ ID NO: 13 encode a signal peptide. In another aspect, the mature polypeptide coding sequence is nucleotides 77 to 766 of SEQ ID NO: 15 based on the SignalP program that predicts nucleotides 20 to 76 of SEQ ID NO: 15 encode a signal peptide. In another aspect, the mature polypeptide coding sequence is nucleotides 52 to 921 of SEQ ID NO: 17 based on the SignalP program that predicts nucleotides 1 to 51 of SEQ ID NO: 17 encode a signal peptide. In another aspect, the mature polypeptide coding sequence is nucleotides 46 to 851 of SEQ ID NO: 19 based on the SignalP program that predicts nucleotides 1 to 45 of SEQ ID NO: 19 encode a signal peptide. In another aspect, the mature polypeptide coding sequence is nucleotides 55 to 1239 of SEQ ID NO: 21 based on the SignalP program that predicts nucleotides 1 to 54 of SEQ ID NO: 21 encode a signal peptide. In another aspect, the mature polypeptide coding sequence is nucleotides 46 to 1250 of SEQ ID NO: 23 based on the SignalP program that predicts nucleotides 1 to 45 of SEQ ID NO: 23 encode a signal peptide. In another aspect, the mature polypeptide coding sequence is nucleotides 58 to 811 of SEQ ID NO: 25 based on the SignalP program that predicts nucleotides 1 to 57 of SEQ ID NO: 25 encode a signal peptide. In another aspect, the mature polypeptide coding sequence is nucleotides 64 to 1112 of SEQ ID NO: 27 based on the SignalP program that predicts nucleotides 1 to 63 of SEQ ID NO: 27 encode a signal peptide. In another aspect, the mature polypeptide coding sequence is nucleotides 64 to 859 of SEQ ID NO: 29 based on the SignalP program that predicts nucleotides 1 to 63 of SEQ ID NO: 29 encode a signal peptide. In another aspect, the mature polypeptide coding sequence is nucleotides 64 to 1018 of SEQ ID NO: 31 based on the SignalP program that predicts nucleotides 1 to 63 of SEQ ID NO: 31 encode a signal peptide. In another aspect, the mature polypeptide coding sequence is nucleotides 70 to 1483 of SEQ ID NO: 33 based on the SignalP program that predicts nucleotides 1 to 69 of SEQ ID NO: 33 encode a signal peptide. In another aspect, the mature polypeptide coding sequence is nucleotides 76 to 832 of SEQ ID NO: 35 based on the SignalP program that predicts nucleotides 1 to 75 of SEQ ID NO: 35 encode a signal peptide. In another aspect, the mature polypeptide coding sequence is nucleotides 52 to 875 of SEQ ID NO: 37 based on the SignalP program that predicts nucleotides 1 to 51 of SEQ ID NO: 37 encode a signal peptide. In another aspect, the mature polypeptide coding sequence is nucleotides 58 to 1250 of SEQ ID NO: 39 based on the SignalP program that predicts nucleotides 1 to 57 of SEQ ID NO: 39 encode a signal peptide. In another aspect, the mature polypeptide coding sequence is nucleotides 52 to 795 of SEQ ID NO: 41 based on the SignalP program that predicts nucleotides 1 to 51 of SEQ ID NO: 41 encode a signal peptide. In another aspect, the mature polypeptide coding sequence is nucleotides 58 to 974 of SEQ ID NO: 43 based on the SignalP program that predicts nucleotides 1 to 57 of SEQ ID NO: 43 encode a signal peptide. In another aspect, the mature polypeptide coding sequence is nucleotides 64 to 1104 of SEQ ID NO: 45 based on the SignalP program that predicts nucleotides 1 to 63 of SEQ ID NO: 45 encode a signal peptide. In another aspect, the mature polypeptide coding sequence is nucleotides 73 to 990 of SEQ ID NO: 47 based on the SignalP program that predicts nucleotides 1 to 72 of SEQ ID NO: 47 encode a signal peptide. In another aspect, the mature polypeptide coding sequence is nucleotides 49 to 1218 of SEQ ID NO: 49 based on the SignalP program that predicts nucleotides 1 to 48 of SEQ ID NO: 49 encode a signal peptide. In another aspect, the mature polypeptide coding sequence is nucleotides 55 to 930 of SEQ ID NO: 51 based on the SignalP program that predicts nucleotides 1 to 54 of SEQ ID NO: 51 encode a signal peptide. In another aspect, the mature polypeptide coding sequence is nucleotides 67 to 1581 of SEQ ID NO: 53 based on the SignalP program that predicts nucleotides 1 to 66 of SEQ ID NO: 53 encode a signal peptide. In another aspect, the mature polypeptide coding sequence is nucleotides 49 to 865 of SEQ ID NO: 55 based on the SignalP program that predicts nucleotides 1 to 48 of SEQ ID NO: 55 encode a signal peptide. In another aspect, the mature polypeptide coding sequence is nucleotides 58 to 1065 of SEQ ID NO: 57 based on the SignalP program that predicts nucleotides 1 to 57 of SEQ ID NO: 57 encode a signal peptide. In another aspect, the mature polypeptide coding sequence is nucleotides 67 to 868 of SEQ ID NO: 59 based on the SignalP program that predicts nucleotides 1 to 66 of SEQ ID NO: 59 encode a signal peptide. In another aspect, the mature polypeptide coding sequence is nucleotides 55 to 1099 of SEQ ID NO: 61 based on the SignalP program that predicts nucleotides 1 to 54 of SEQ ID NO: 61 encode a signal peptide. In another aspect, the mature polypeptide coding sequence is nucleotides 70 to 1490 of SEQ ID NO: 63 based on the SignalP program that predicts nucleotides 1 to 69 of SEQ ID NO: 63 encode a signal peptide. In another aspect, the mature polypeptide coding sequence is nucleotides 61 to 1032 of SEQ ID NO: 65 based on the SignalP program that predicts nucleotides 1 to 60 of SEQ ID NO: 65 encode a signal peptide. In another aspect, the mature polypeptide coding sequence is nucleotides 76 to 1200 of SEQ ID NO: 67 based on the SignalP program that predicts nucleotides 1 to 75 of SEQ ID NO: 67 encode a signal peptide. In another aspect, the mature polypeptide coding sequence is nucleotides 61 to 1167 of SEQ ID NO: 69 based on the SignalP program that predicts nucleotides 1 to 60 of SEQ ID NO: 69 encode a signal peptide. In another aspect, the mature polypeptide coding sequence is nucleotides 64 to 1218 of SEQ ID NO: 71 based on the SignalP program that predicts nucleotides 1 to 63 of SEQ ID NO: 71 encode a signal peptide. In another aspect, the mature polypeptide coding sequence is nucleotides 58 to 1281 of SEQ ID NO: 73 based on the SignalP program that predicts nucleotides 1 to 57 of SEQ ID NO: 73 encode a signal peptide. In another aspect, the mature polypeptide coding sequence is nucleotides 52 to 801 of SEQ ID NO: 75 based on the SignalP program that predicts nucleotides 1 to 51 of SEQ ID NO: 75 encode a signal peptide. In another aspect, the mature polypeptide coding sequence is nucleotides 61 to 819 of SEQ ID NO: 77 based on the SignalP program that predicts nucleotides 1 to 60 of SEQ ID NO: 77 encode a signal peptide. In another aspect, the mature polypeptide coding sequence is nucleotides 67 to 869 of SEQ ID NO: 79 based on the SignalP program that predicts nucleotides 1 to 66 of SEQ ID NO: 79 encode a signal peptide. In another aspect, the mature polypeptide coding sequence is nucleotides 64 to 1036 of SEQ ID NO: 81 based on the SignalP program that predicts nucleotides 1 to 63 of SEQ ID NO: 81 encode a signal peptide. In another aspect, the mature polypeptide coding sequence is nucleotides 67 to 878 of SEQ ID NO: 83 based on the SignalP program that predicts nucleotides 1 to 66 of SEQ ID NO: 83 encode a signal peptide. In another aspect, the mature polypeptide coding sequence is nucleotides 61 to 966 of SEQ ID NO: 85 based on the SignalP program that predicts nucleotides 1 to 60 of SEQ ID NO: 85 encode a signal peptide. In another aspect, the mature polypeptide coding sequence is nucleotides 52 to 702 of SEQ ID NO: 87 based on the SignalP program that predicts nucleotides 1 to 51 of SEQ ID NO: 87 encode a signal peptide. In another aspect, the mature polypeptide coding sequence is nucleotides 70 to 699 of SEQ ID NO: 89 based on the SignalP program that predicts nucleotides 1 to 69 of SEQ ID NO: 89 encode a signal peptide. In another aspect, the mature polypeptide coding sequence is nucleotides 49 to 711 of SEQ ID NO: 91 based on the SignalP program that predicts nucleotides 1 to 48 of SEQ ID NO: 91 encode a signal peptide. In another aspect, the mature polypeptide coding sequence is nucleotides 58 to 1452 of SEQ ID NO: 93 based on the SignalP program that predicts nucleotides 1 to 57 of SEQ ID NO: 93 encode a signal peptide. In another aspect, the mature polypeptide coding sequence is nucleotides 64 to 1018 of SEQ ID NO: 95 based on the SignalP program that predicts nucleotides 1 to 63 of SEQ ID NO: 95 encode a signal peptide. In another aspect, the mature polypeptide coding sequence is nucleotides 52 to 818 of SEQ ID NO: 97 based on the SignalP program that predicts nucleotides 1 to 51 of SEQ ID NO: 97 encode a signal peptide. In another aspect, the mature polypeptide coding sequence is nucleotides 49 to 1117 of SEQ ID NO: 99 based on the SignalP program that predicts nucleotides 1 to 48 of SEQ ID NO: 99 encode a signal peptide. In another aspect, the mature polypeptide coding sequence is nucleotides 58 to 875 of SEQ ID NO: 101 based on the SignalP program that predicts nucleotides 1 to 57 of SEQ ID NO: 101 encode a signal peptide. In another aspect, the mature polypeptide coding sequence is nucleotides 82 to 1064 of SEQ ID NO: 103 based on the SignalP program that predicts nucleotides 1 to 81 of SEQ ID NO: 103 encode a signal peptide. In another aspect, the mature polypeptide coding sequence is nucleotides 46 to 1032 of SEQ ID NO: 105 based on the SignalP program that predicts nucleotides 1 to 45 of SEQ ID NO: 105 encode a signal peptide. In one aspect, the mature polypeptide coding sequence is nucleotides 61 to 1062 of SEQ ID NO: 107 based on the SignalP program that predicts nucleotides 1 to 60 of SEQ ID NO: 107 encode a signal peptide. In another aspect, the mature polypeptide coding sequence is nucleotides 64 to 801 of SEQ ID NO: 109 based on the SignalP program that predicts nucleotides 1 to 63 of SEQ ID NO: 109 encode a signal peptide. In another aspect, the mature polypeptide coding sequence is nucleotides 46 to 840 of SEQ ID NO: 111 based on the SignalP program that predicts nucleotides 1 to 45 of SEQ ID NO: 111 encode a signal peptide. In another aspect, the mature polypeptide coding sequence is nucleotides 58 to 702 of SEQ ID NO: 113 based on the SignalP program that predicts nucleotides 1 to 57 of SEQ ID NO: 113 encode a signal peptide. In another aspect, the mature polypeptide coding sequence is nucleotides 52 to 750 of SEQ ID NO: 115 based on the SignalP program that predicts nucleotides 1 to 51 of SEQ ID NO: 115 encode a signal peptide. In one aspect, the mature polypeptide coding sequence is nucleotides 49 to 851 of SEQ ID NO: 117 based on the SignalP program that predicts nucleotides 1 to 48 of SEQ ID NO: 117 encode a signal peptide. In another aspect, the mature polypeptide coding sequence is nucleotides 64 to 860 of SEQ ID NO: 119 based on the SignalP program that predicts nucleotides 1 to 63 of SEQ ID NO: 119 encode a signal peptide. In another aspect, the mature polypeptide coding sequence is nucleotides 52 to 830 of SEQ ID NO: 121 based on the SignalP program that predicts nucleotides 1 to 51 of SEQ ID NO: 121 encode a signal peptide. In another aspect, the mature polypeptide coding sequence is nucleotides 61 to 925 of SEQ ID NO: 123 based on the SignalP program that predicts nucleotides 1 to 60 of SEQ ID NO: 123 encode a signal peptide. In another aspect, the mature polypeptide coding sequence is nucleotides 61 to 1089 of SEQ ID NO: 125 based on the SignalP program that predicts nucleotides 1 to 60 of SEQ ID NO: 125 encode a signal peptide. In one aspect, the mature polypeptide coding sequence is nucleotides 58 to 1083 of SEQ ID NO: 127 based on the SignalP program that predicts nucleotides 1 to 57 of SEQ ID NO: 127 encode a signal peptide. In another aspect, the mature polypeptide coding sequence is nucleotides 46 to 1029 of SEQ ID NO: 129 based on the SignalP program that predicts nucleotides 1 to 45 of SEQ ID NO: 129 encode a signal peptide. In another aspect, the mature polypeptide coding sequence is nucleotides 55 to 1110 of SEQ ID NO: 131 based on the SignalP program that predicts nucleotides 1 to 54 of SEQ ID NO: 131 encode a signal peptide. In another aspect, the mature polypeptide coding sequence is nucleotides 58 to 1100 of SEQ ID NO: 133 based on the SignalP program that predicts nucleotides 1 to 57 of SEQ ID NO: 133 encode a signal peptide. In another aspect, the mature polypeptide coding sequence is nucleotides 55 to 1036 of SEQ ID NO: 135 based on the SignalP program that predicts nucleotides 1 to 54 of SEQ ID NO: 135 encode a signal peptide. In one aspect, the mature polypeptide coding sequence is nucleotides 58 to 1022 of SEQ ID NO: 137 based on the SignalP program that predicts nucleotides 1 to 57 of SEQ ID NO: 137 encode a signal peptide. In another aspect, the mature polypeptide coding sequence is nucleotides 64 to 1032 of SEQ ID NO: 139 based on the SignalP program that predicts nucleotides 1 to 63 of SEQ ID NO: 139 encode a signal peptide. In another aspect, the mature polypeptide coding sequence is nucleotides 58 to 1054 of SEQ ID NO: 141 based on the SignalP program that predicts nucleotides 1 to 57 of SEQ ID NO: 141 encode a signal peptide. In another aspect, the mature polypeptide coding sequence is nucleotides 55 to 769 of SEQ ID NO: 143 based on the SignalP program that predicts nucleotides 1 to 54 of SEQ ID NO: 143 encode a signal peptide. In another aspect, the mature polypeptide coding sequence is nucleotides 52 to 1533 of SEQ ID NO: 145 based on the SignalP program that predicts nucleotides 1 to 51 of SEQ ID NO: 145 encode a signal peptide. In one aspect, the mature polypeptide coding sequence is nucleotides 61 to 918 of SEQ ID NO: 147 based on the SignalP program that predicts nucleotides 1 to 60 of SEQ ID NO: 147 encode a signal peptide. In another aspect, the mature polypeptide coding sequence is nucleotides 64 to 1089 of SEQ ID NO: 149 based on the SignalP program that predicts nucleotides 1 to 63 of SEQ ID NO: 149 encode a signal peptide. In another aspect, the mature polypeptide coding sequence is nucleotides 64 to 1086 of SEQ ID NO: 151 based on the SignalP program that predicts nucleotides 1 to 63 of SEQ ID NO: 151 encode a signal peptide. In another aspect, the mature polypeptide coding sequence is nucleotides 67 to 1395 of SEQ ID NO: 153 based on the SignalP program that predicts nucleotides 1 to 66 of SEQ ID NO: 155 encode a signal peptide. In another aspect, the mature polypeptide coding sequence is nucleotides 55 to 899 of SEQ ID NO: 155 based on the SignalP program that predicts nucleotides 1 to 54 of SEQ ID NO: 155 encode a signal peptide. In another aspect, the mature polypeptide coding sequence is nucleotides 64 to 807 of SEQ ID NO: 157 based on the SignalP program that predicts nucleotides 1 to 63 of SEQ ID NO: 157 encode a signal peptide. In another aspect, the mature polypeptide coding sequence is nucleotides 61 to 726 of SEQ ID NO: 159 based on the SignalP program that predicts nucleotides 1 to 60 of SEQ ID NO: 159 encode a signal peptide. In another aspect, the mature polypeptide coding sequence is nucleotides 67 to 1078 of SEQ ID NO: 161 based on the SignalP program that predicts nucleotides 1 to 66 of SEQ ID NO: 161 encode a signal peptide. In another aspect, the mature polypeptide coding sequence is nucleotides 52 to 872 of SEQ ID NO: 163 based on the SignalP program that predicts nucleotides 1 to 51 of SEQ ID NO: 163 encode a signal peptide. In another aspect, the mature polypeptide coding sequence is nucleotides 55 to 1191 of SEQ ID NO: 165 based on the SignalP program that predicts nucleotides 1 to 54 of SEQ ID NO: 165 encode a signal peptide. In another aspect, the mature polypeptide coding sequence is nucleotides 67 to 1230 of SEQ ID NO: 167 based on the SignalP program that predicts nucleotides 1 to 66 of SEQ ID NO: 167 encode a signal peptide. In another aspect, the mature polypeptide coding sequence is nucleotides 58 to 696 of SEQ ID NO: 169 based on the SignalP program that predicts nucleotides 1 to 57 of SEQ ID NO: 169 encode a signal peptide. In another aspect, the mature polypeptide coding sequence is nucleotides 61 to 798 of SEQ ID NO: 171 based on the SignalP program that predicts nucleotides 1 to 60 of SEQ ID NO: 171 encode a signal peptide. In one aspect, the mature polypeptide coding sequence is nucleotides 70 to 972 of SEQ ID NO: 173 based on the SignalP program that predicts nucleotides 1 to 69 of SEQ ID NO: 173 encode a signal peptide. In another aspect, the mature polypeptide coding sequence is nucleotides 61 to 1112 of SEQ ID NO: 175 based on the SignalP program that predicts nucleotides 1 to 60 of SEQ ID NO: 175 encode a signal peptide. In another aspect, the mature polypeptide coding sequence is nucleotides 61 to 985 of SEQ ID NO: 177 based on the SignalP program that predicts nucleotides 1 to 60 of SEQ ID NO: 177 encode a signal peptide. In another aspect, the mature polypeptide coding sequence is nucleotides 46 to 856 of SEQ ID NO: 179 based on the SignalP program that predicts nucleotides 1 to 45 of SEQ ID NO: 179 encode a signal peptide. In another aspect, the mature polypeptide coding sequence is nucleotides 58 to 1008 of SEQ ID NO: 181 based on the SignalP program that predicts nucleotides 1 to 57 of SEQ ID NO: 181 encode a signal peptide. In another aspect, the mature polypeptide coding sequence is nucleotides 49 to 1312 of SEQ ID NO: 183 based on the SignalP program that predicts nucleotides 1 to 48 of SEQ ID NO: 183 encode a signal peptide. In another aspect, the mature polypeptide coding sequence is nucleotides 52 to 921 of SEQ ID NO: 185 based on the SignalP program that predicts nucleotides 1 to 51 of SEQ ID NO: 185 encode a signal peptide. In another aspect, the mature polypeptide coding sequence is nucleotides 52 to 739 of SEQ ID NO: 187 based on the SignalP program that predicts nucleotides 1 to 51 of SEQ ID NO: 187 encode a signal peptide. In another aspect, the mature polypeptide coding sequence is nucleotides 46 to 898 of SEQ ID NO: 189 based on the SignalP program that predicts nucleotides 1 to 45 of SEQ ID NO: 189 encode a signal peptide. In another aspect, the mature polypeptide coding sequence is nucleotides 52 to 941 of SEQ ID NO: 191 based on the SignalP program that predicts nucleotides 1 to 51 of SEQ ID NO: 191 encode a signal peptide. In another aspect, the mature polypeptide coding sequence is nucleotides 64 to 945 of SEQ ID NO: 193 based on the SignalP program that predicts nucleotides 1 to 63 of SEQ ID NO: 193 encode a signal peptide. In another aspect, the mature polypeptide coding sequence is nucleotides 61 to 1377 of SEQ ID NO: 195 based on the SignalP program that predicts nucleotides 1 to 60 of SEQ ID NO: 195 encode a signal peptide. In another aspect, the mature polypeptide coding sequence is nucleotides 52 to 818 of SEQ ID NO: 197 based on the SignalP program that predicts nucleotides 1 to 51 of SEQ ID NO: 197 encode a signal peptide. In another aspect, the mature polypeptide coding sequence is nucleotides 55 to 1122 of SEQ ID NO: 199 based on the SignalP program that predicts nucleotides 1 to 54 of SEQ ID NO: 199 encode a signal peptide. In another aspect, the mature polypeptide coding sequence is nucleotides 60 to 1034 of SEQ ID NO: 201 based on the SignalP program that predicts nucleotides 1 to 61 of SEQ ID NO: 201 encode a signal peptide. In another aspect, the mature polypeptide coding sequence is nucleotides 46 to 1197 of SEQ ID NO: 203 based on the SignalP program that predicts nucleotides 1 to 45 of SEQ ID NO: 203 encode a signal peptide. In another aspect, the mature polypeptide coding sequence is nucleotides 58 to 756 of SEQ ID NO: 205 based on the SignalP program that predicts nucleotides 1 to 57 of SEQ ID NO: 205 encode a signal peptide. In another aspect, the mature polypeptide coding sequence is nucleotides 58 to 1032 of SEQ ID NO: 207 based on the SignalP program that predicts nucleotides 1 to 57 of SEQ ID NO: 207 encode a signal peptide. In another aspect, the mature polypeptide coding sequence is nucleotides 64 to 1041 of SEQ ID NO: 209 based on the SignalP program that predicts nucleotides 1 to 63 of SEQ ID NO: 209 encode a signal peptide. In another aspect, the mature polypeptide coding sequence is nucleotides 67 to 1002 of SEQ ID NO: 211 based on the SignalP program that predicts nucleotides 1 to 66 of SEQ ID NO: 211 encode a signal peptide. In another aspect, the mature polypeptide coding sequence is nucleotides 70 to 1098 of SEQ ID NO: 213 based on the SignalP program that predicts nucleotides 1 to 69 of SEQ ID NO: 213 encode a signal peptide. In another aspect, the mature polypeptide coding sequence is nucleotides 61 to 1088 of SEQ ID NO: 215 based on the SignalP program that predicts nucleotides 1 to 60 of SEQ ID NO: 215 encode a signal peptide. In each of the aspects above, the term "mature polypeptide coding sequence" shall be understood to include the cDNA sequence of the genomic DNA sequence or the genomic DNA sequence of the cDNA sequence.

Medium stringency conditions: The term "medium stringency conditions" means for probes of at least 100 nucleotides in length, prehybridization and hybridization at 42° C.

in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent GH61 polypeptide: The term "parent" or "parent GH61 polypeptide" means a GH61 polypeptide to which an alteration is made to produce the GH61 polypeptide variants of the present invention. The parent may be a naturally occurring (wild-type) polypeptide or a variant or fragment thereof.

Polypeptide having cellulolytic enhancing activity: The term "polypeptide having cellulolytic enhancing activity" means a GH61 polypeptide or variant thereof that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide or variant thereof for 1-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

Another assay for determining the cellulolytic enhancing activity of a GH61 polypeptide or variant thereof is to incubate the GH61 polypeptide or variant with 0.5% phosphoric acid swollen cellulose (PASC), 100 mM sodium acetate pH 5, 1 mM MnSO$_4$, 0.1% gallic acid, 0.025 mg/ml of *Aspergillus fumigatus* beta-glucosidase, and 0.01% TRITON® X100 for 24-96 hours at 40° C. followed by determination of the glucose released from the PASO.

The GH61 polypeptides or variants thereof having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Subsequence: The term "subsequence" means a polynucleotide having one or more (e.g., several) nucleotides absent from the 5' and/or 3' end of a mature polypeptide coding sequence, wherein the subsequence encodes a fragment having cellulolytic enhancing activity. In one aspect, a subsequence contains at least 85% of the nucleotides, e.g., at least 90% of the nucleotides or at least 95% of the nucleotides of the mature polypeptide coding sequence of a GH61 polypeptide.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the cellulolytic enhancing activity of their parent GH61 polypeptides.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type GH61 polypeptide: The term "wild-type" GH61 polypeptide means a GH61 polypeptide expressed by a naturally occurring microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, Recent progress in the assays of xylanolytic enzymes, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

Conventions for Designation of Variants

For purposes of the present invention, the mature polypeptide disclosed in SEQ ID NO: 30 is used to determine the corresponding amino acid residue in another GH61 polypeptide. The amino acid sequence of another GH61 polypeptide is aligned with the mature polypeptide disclosed in SEQ ID NO: 30, and based on the alignment, the amino acid position number corresponding to any amino acid residue in the mature polypeptide disclosed in SEQ ID NO: 30 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. Numbering of the amino acid positions is based on the full-length polypeptide (e.g., including the signal peptide) of SEQ ID NO: 30 wherein position 1 is the first amino acid of the signal peptide (e.g., Met).

Identification of the corresponding amino acid residue in another GH61 polypeptide can be determined by alignment of multiple polypeptide sequences using several computer programs including, but not limited to MUSCLE (multiple sequence comparison by log-expectation; version 3.5 or later; Edgar, 2004, *Nucleic Acids Research* 32: 1792-1797); MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

For example, the position corresponding to position 105 of the *Aspergillus fumigatus* GH61 polypeptide (SEQ ID NO: 30) is position 109 in the *Penicillium emersonii* GH61 polypeptide (SEQ ID NO: 36), position 105 in the *Thermoascus aurantiacus* GH61 polypeptide (SEQ ID NO: 14), and position 103 in the *Aspergillus aculeatus* GH61 polypeptide (SEQ ID NO: 68); the position corresponding to position 188 of the *Aspergillus fumigatus* GH61 polypeptide is position 192 in the *Penicillium emersonii* GH61 polypeptide, position 188 in the *Thermoascus aurantiacus* GH61 polypeptide, and position 186 in the *Aspergillus aculeatus* GH61 polypeptide; the position corresponding to position 154 of the *Aspergillus fumigatus* GH61 polypeptide is position 152 in the *Aspergillus aculeatus* GH61 polypeptide; and the position corresponding to position 189 of the *Aspergillus fumigatus* GH61 polypeptide is position 193 in the *Penicillium emersonii* GH61 polypeptide and position 187 in the *Aspergillus aculeatus* GH61 polypeptide.

When another GH61 polypeptide has diverged from the mature polypeptide of SEQ ID NO: 30 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the GH61 polypeptide variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 95 195a 195b |
| G       | G - K - A |

Multiple Substitutions.

Variants comprising multiple substitutions are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Substitutions.

Where different substitutions can be introduced at a position, the different substitutions are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated GH61 polypeptide variants, comprising a substitution at one or more (e.g., several) positions corresponding to positions 105, 154, 188, 189, 216, and 229 of the mature polypeptide of SEQ ID NO: 30, wherein the variants have cellulolytic enhancing activity.

Variants

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent GH61 polypeptide.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216.

In one aspect, the number of substitutions in the variants of the present invention is 1-6, e.g., 1, 2, 3, 4, 5, or 6 substitutions.

In another aspect, a variant comprises a substitution at one or more (e.g., several) positions corresponding to positions 105, 154, 188, 189, 216, and 229. In another aspect, a variant comprises a substitution at two positions corresponding to any of positions 105, 154, 188, 189, 216, and 229. In another aspect, a variant comprises a substitution at three positions corresponding to any of positions 105, 154, 188, 189, 216, and 229. In another aspect, a variant comprises a substitution at four positions corresponding to any of positions 105, 154, 188, 189, 216, and 229. In another aspect, a variant comprises a substitution at five positions corresponding to any of positions 105, 154, 188, 189, 216, and 229. In another aspect, a variant comprises a substitution at each position corresponding to positions 105, 154, 188, 189, 216, and 229.

In another aspect, the variant comprises or consists of a substitution at a position corresponding to position 105. In another aspect, the amino acid at a position corresponding to position 105 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro or Lys. In another aspect, the variant comprises or consists of the substitution E105P or E105K of the mature polypeptide of SEQ ID NO: 30.

In another aspect, the variant comprises or consists of a substitution at a position corresponding to position 154. In another aspect, the amino acid at a position corresponding to position 154 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile or Leu. In another aspect, the variant comprises or consists of the substitution E154I or E154L of the mature polypeptide of SEQ ID NO: 30.

In another aspect, the variant comprises or consists of a substitution at a position corresponding to position 188. In another aspect, the amino acid at a position corresponding to position 188 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Met, Phe, or Trp. In another aspect, the variant comprises or consists of the substitution G188A, G188F, G188M, or G188W of the mature polypeptide of SEQ ID NO: 30.

In another aspect, the variant comprises or consists of a substitution at a position corresponding to position 189. In another aspect, the amino acid at a position corresponding to position 189 is substituted with Ala, Arg, Asn, Asp, Cys, Gln, Glu, Gly, His, Ile, Leu, Lys, Met, Phe, Pro, Ser, Thr, Trp, Tyr, or Val, preferably with His or Lys. In another aspect, the variant comprises or consists of the substitution N189H or N189K of the mature polypeptide of SEQ ID NO: 30.

In another aspect, the variant comprises or consists of a substitution at a position corresponding to position 216. In another aspect, the amino acid at a position corresponding to position 216 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu or Tyr. In another aspect, the variant comprises or consists of the substitution A216L or A216Y of the mature polypeptide of SEQ ID NO: 30.

In another aspect, the variant comprises or consists of a substitution at a position corresponding to position 229. In another aspect, the amino acid at a position corresponding to position 229 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, His, Ile, or Tyr. In another aspect, the variant comprises or consists of the substitution K229W, K229H, K229I, or K229Y of the mature polypeptide of SEQ ID NO: 30.

In another aspect, the variant comprises or consists of substitutions at positions corresponding to positions 105 and 154, such as those described above.

In another aspect, the variant comprises or consists of substitutions at positions corresponding to positions 105 and 188, such as those described above.

In another aspect, the variant comprises or consists of substitutions at positions corresponding to positions 105 and 189, such as those described above.

In another aspect, the variant comprises or consists of substitutions at positions corresponding to positions 105 and 216, such as those described above.

In another aspect, the variant comprises or consists of substitutions at positions corresponding to positions 105 and 229, such as those described above.

In another aspect, the variant comprises or consists of substitutions at positions corresponding to positions 154 and 188, such as those described above.

In another aspect, the variant comprises or consists of substitutions at positions corresponding to positions 154 and 189, such as those described above.

In another aspect, the variant comprises or consists of substitutions at positions corresponding to positions 154 and 216, such as those described above.

In another aspect, the variant comprises or consists of substitutions at positions corresponding to positions 154 and 229, such as those described above.

In another aspect, the variant comprises or consists of substitutions at positions corresponding to positions 188 and 189, such as those described above.

In another aspect, the variant comprises or consists of substitutions at positions corresponding to positions 188 and 216, such as those described above.

In another aspect, the variant comprises or consists of substitutions at positions corresponding to positions 188 and 229, such as those described above.

In another aspect, the variant comprises or consists of substitutions at positions corresponding to positions 189 and 216, such as those described above.

In another aspect, the variant comprises or consists of substitutions at positions corresponding to positions 189 and 229, such as those described above.

In another aspect, the variant comprises or consists of substitutions at positions corresponding to positions 216 and 229, such as those described above.

In another aspect, the variant comprises or consists of substitutions at positions corresponding to positions 105, 154, and 188, such as those described above.

In another aspect, the variant comprises or consists of substitutions at positions corresponding to positions 105, 154, and 189, such as those described above.

In another aspect, the variant comprises or consists of substitutions at positions corresponding to positions 105, 154, and 216, such as those described above.

In another aspect, the variant comprises or consists of substitutions at positions corresponding to positions 105, 154, and 229, such as those described above.

In another aspect, the variant comprises or consists of substitutions at positions corresponding to positions 105, 188, and 189, such as those described above.

In another aspect, the variant comprises or consists of substitutions at positions corresponding to positions 105, 188, and 216, such as those described above.

In another aspect, the variant comprises or consists of substitutions at positions corresponding to positions 105, 188, and 229, such as those described above.

In another aspect, the variant comprises or consists of substitutions at positions corresponding to positions 105, 189, and 216, such as those described above.

In another aspect, the variant comprises or consists of substitutions at positions corresponding to positions 105, 189, and 229, such as those described above.

In another aspect, the variant comprises or consists of substitutions at positions corresponding to positions 105, 216, and 229, such as those described above.

In another aspect, the variant comprises or consists of substitutions at positions corresponding to positions 154, 188, and 189, such as those described above.

In another aspect, the variant comprises or consists of substitutions at positions corresponding to positions 154, 188, and 216, such as those described above.

In another aspect, the variant comprises or consists of substitutions at positions corresponding to positions 154, 188, and 229, such as those described above.

In another aspect, the variant comprises or consists of substitutions at positions corresponding to positions 154, 189, and 216, such as those described above.

In another aspect, the variant comprises or consists of substitutions at positions corresponding to positions 154, 189, and 229, such as those described above.

In another aspect, the variant comprises or consists of substitutions at positions corresponding to positions 154, 216, and 229, such as those described above.

In another aspect, the variant comprises or consists of substitutions at positions corresponding to positions 188, 189, and 216, such as those described above.

In another aspect, the variant comprises or consists of substitutions at positions corresponding to positions 188, 189, and 229, such as those described above.

In another aspect, the variant comprises or consists of substitutions at positions corresponding to positions 188, 216, and 229, such as those described above.

In another aspect, the variant comprises or consists of substitutions at positions corresponding to positions 189, 216, and 229, such as those described above.

In another aspect, the variant comprises or consists of substitutions at positions corresponding to positions 105, 154, 188, and 216, such as those described above.

In another aspect, the variant comprises or consists of substitutions at positions corresponding to positions 105, 154, 188, and 229, such as those described above.

In another aspect, the variant comprises or consists of substitutions at positions corresponding to positions 105, 154, 189, and 216, such as those described above.

In another aspect, the variant comprises or consists of substitutions at positions corresponding to positions 105, 154, 189, and 229, such as those described above.

In another aspect, the variant comprises or consists of substitutions at positions corresponding to positions 105, 154, 216, and 229, such as those described above.

In another aspect, the variant comprises or consists of substitutions at positions corresponding to positions 105, 188, 189, and 216, such as those described above.

In another aspect, the variant comprises or consists of substitutions at positions corresponding to positions 105, 188, 189, and 229, such as those described above.

In another aspect, the variant comprises or consists of substitutions at positions corresponding to positions 105, 188, 216, and 229, such as those described above.

In another aspect, the variant comprises or consists of substitutions at positions corresponding to positions 105, 189, 216, and 229, such as those described above.

In another aspect, the variant comprises or consists of substitutions at positions corresponding to positions 154, 188, 189, and 216, such as those described above.

In another aspect, the variant comprises or consists of substitutions at positions corresponding to positions 154, 188, 189, and 229, such as those described above.

In another aspect, the variant comprises or consists of substitutions at positions corresponding to positions 154, 188, 216, and 229, such as those described above.

In another aspect, the variant comprises or consists of substitutions at positions corresponding to positions 154, 189, 216, and 229, such as those described above.

In another aspect, the variant comprises or consists of substitutions at positions corresponding to positions 188, 189, 216, and 229, such as those described above.

In another aspect, the variant comprises or consists of substitutions at positions corresponding to positions 105, 154, 188, 189, and 216, such as those described above.

In another aspect, the variant comprises or consists of substitutions at positions corresponding to positions 105, 154, 188, 189, and 229, such as those described above.

In another aspect, the variant comprises or consists of substitutions at positions corresponding to positions 105, 154, 188, 216, and 229, such as those described above.

In another aspect, the variant comprises or consists of substitutions at positions corresponding to positions 105, 154, 189, 216, and 229, such as those described above.

In another aspect, the variant comprises or consists of substitutions at positions corresponding to positions 105, 188, 189, 216, and 229, such as those described above.

In another aspect, the variant comprises or consists of substitutions at positions corresponding to positions 154, 188, 189, 216, and 229, such as those described above.

In another aspect, the variant comprises or consists of substitutions at positions corresponding to positions 105, 154, 188, 189, 216, and 229, such as those described above.

In another aspect, the variant comprises or consists of one or more (e.g., several) substitutions selected from the group consisting of E105P,K; E154I,L; G188A,F,M,W; A216L,Y; and K229W,H,I,Y, or the one or more (e.g., several) substitutions selected from the group consisting of E105P,K; E154I,L; G188A,F,M,W; A216L,Y; and K229W,H,I,Y at positions corresponding to SEQ ID NO: 30 in other GH61 polypeptides described herein.

In each of the aspects below, the variant comprises or consists of the one or more (e.g., several) substitutions described below at positions corresponding to SEQ ID NO: 30 in other GH61 polypeptides described herein.

In another aspect, the variant comprises or consists of the substitutions E105P,K and E154I,L of the mature polypeptide of SEQ ID NO: 30.

In another aspect, the variant comprises or consists of the substitutions E105P,K and G188A,F,M,W of the mature polypeptide of SEQ ID NO: 30.

In another aspect, the variant comprises or consists of the substitutions E105P,K and N189H,K of the mature polypeptide of SEQ ID NO: 30.

In another aspect, the variant comprises or consists of the substitutions E105P,K and A216L,Y of the mature polypeptide of SEQ ID NO: 30.

In another aspect, the variant comprises or consists of the substitutions E105P,K and K229W,H,I,Y of the mature polypeptide of SEQ ID NO: 30.

In another aspect, the variant comprises or consists of the substitutions E154I,L and G188A,F,M,W of the mature polypeptide of SEQ ID NO: 30.

In another aspect, the variant comprises or consists of the substitutions E154I,L and N189H,K of the mature polypeptide of SEQ ID NO: 30.

In another aspect, the variant comprises or consists of the substitutions E154I,L and A216L,Y of the mature polypeptide of SEQ ID NO: 30.

In another aspect, the variant comprises or consists of the substitutions E154I,L and K229W,H,I,Y of the mature polypeptide of SEQ ID NO: 30.

In another aspect, the variant comprises or consists of the substitutions G188A,F,M,W and N189H,K of the mature polypeptide of SEQ ID NO: 30.

In another aspect, the variant comprises or consists of the substitutions G188A,F,M,W and A216L,Y of the mature polypeptide of SEQ ID NO: 30.

In another aspect, the variant comprises or consists of the substitutions G188A,F,M,W and K229W,H,I,Y of the mature polypeptide of SEQ ID NO: 30.

In another aspect, the variant comprises or consists of the substitutions N189H,K and A216L,Y of the mature polypeptide of SEQ ID NO: 30.

In another aspect, the variant comprises or consists of the substitutions N189H,K and K229W,H,I,Y of the mature polypeptide of SEQ ID NO: 30.

In another aspect, the variant comprises or consists of the substitutions A216L,Y and K229W,H,I,Y of the mature polypeptide of SEQ ID NO: 30.

In another aspect, the variant comprises or consists of the substitutions E105P,K; E154I,L; and G188A,F,M,W of the mature polypeptide of SEQ ID NO: 30.

In another aspect, the variant comprises or consists of the substitutions E105P,K; E154I,L; and N189H,K of the mature polypeptide of SEQ ID NO: 30.

In another aspect, the variant comprises or consists of the substitutions E105P,K; E154I,L; and A216L,Y of the mature polypeptide of SEQ ID NO: 30.

In another aspect, the variant comprises or consists of the substitutions E105P,K; E154I,L; and K229W,H,I,Y of the mature polypeptide of SEQ ID NO: 30.

In another aspect, the variant comprises or consists of the substitutions E105P,K; G188A,F,M,W; and N189H,K of the mature polypeptide of SEQ ID NO: 30.

In another aspect, the variant comprises or consists of the substitutions E105P,K; G188A,F,M,W; and A216L,Y of the mature polypeptide of SEQ ID NO: 30.

In another aspect, the variant comprises or consists of the substitutions E105P,K; G188A,F,M,W; and K229W,H,I,Y of the mature polypeptide of SEQ ID NO: 30.

In another aspect, the variant comprises or consists of the substitutions E105P,K; N189H,K; and A216L,Y of the mature polypeptide of SEQ ID NO: 30.

In another aspect, the variant comprises or consists of the substitutions E105P,K; N189H,K; and K229W,H,I,Y of the mature polypeptide of SEQ ID NO: 30.

In another aspect, the variant comprises or consists of the substitutions E105P,K; A216L,Y; and K229W,H,I,Y of the mature polypeptide of SEQ ID NO: 30.

In another aspect, the variant comprises or consists of the substitutions E154I,L; G188A,F,M,W; and N189H,K of the mature polypeptide of SEQ ID NO: 30.

In another aspect, the variant comprises or consists of the substitutions E154I,L; G188A,F,M,W; and A216L,Y of the mature polypeptide of SEQ ID NO: 30.

In another aspect, the variant comprises or consists of the substitutions E154I,L; G188A,F,M,W; and K229W,H,I,Y of the mature polypeptide of SEQ ID NO: 30.

In another aspect, the variant comprises or consists of the substitutions E154I,L; N189H,K; and A216L,Y of the mature polypeptide of SEQ ID NO: 30.

In another aspect, the variant comprises or consists of the substitutions E154I,L; N189H,K; and K229W,H,I,Y of the mature polypeptide of SEQ ID NO: 30.

In another aspect, the variant comprises or consists of the substitutions E154I,L; A216L,Y; and K229W,H,I,Y of the mature polypeptide of SEQ ID NO: 30.

In another aspect, the variant comprises or consists of the substitutions G188A,F,M,W; N189H,K; and A216L,Y of the mature polypeptide of SEQ ID NO: 30.

In another aspect, the variant comprises or consists of the substitutions G188A,F,M,W; N189H,K; and K229W,H,I,Y of the mature polypeptide of SEQ ID NO: 30.

In another aspect, the variant comprises or consists of the substitutions G188A,F,M,W; A216L,Y; and K229W,H,I,Y of the mature polypeptide of SEQ ID NO: 30.

In another aspect, the variant comprises or consists of the substitutions N189H,K; A216L,Y; and K229W,H,I,Y of the mature polypeptide of SEQ ID NO: 30.

In another aspect, the variant comprises or consists of the substitutions E105P,K; E154I,L; G188A,F,M,W; and N189H,K of the mature polypeptide of SEQ ID NO: 30.

In another aspect, the variant comprises or consists of the substitutions E105P,K; E154I,L; G188A,F,M,W; and A216L,Y of the mature polypeptide of SEQ ID NO: 30.

In another aspect, the variant comprises or consists of the substitutions E105P,K; E154I,L; G188A,F,M,W; and K229W,H,I,Y of the mature polypeptide of SEQ ID NO: 30.

In another aspect, the variant comprises or consists of the substitutions E105P,K; E154I,L; N189H,K; and A216L,Y of the mature polypeptide of SEQ ID NO: 30.

In another aspect, the variant comprises or consists of the substitutions E105P,K; E154I,L; N189H,K; and K229W,H,I,Y of the mature polypeptide of SEQ ID NO: 30.

In another aspect, the variant comprises or consists of the substitutions E105P,K; E154I,L; A216L,Y; and K229W,H,I,Y of the mature polypeptide of SEQ ID NO: 30.

In another aspect, the variant comprises or consists of the substitutions E105P,K; G188A,F,M,W; N189H,K; and A216L,Y of the mature polypeptide of SEQ ID NO: 30.

In another aspect, the variant comprises or consists of the substitutions E105P,K; G188A,F,M,W; N189H,K; and K229W,H,I,Y of the mature polypeptide of SEQ ID NO: 30.

In another aspect, the variant comprises or consists of the substitutions E105P,K; G188A,F,M,W; A216L,Y; and K229W,H,I,Y of the mature polypeptide of SEQ ID NO: 30.

In another aspect, the variant comprises or consists of the substitutions E105P,K; N189H,K; A216L,Y; and K229W,H,I,Y of the mature polypeptide of SEQ ID NO: 30.

In another aspect, the variant comprises or consists of the substitutions E154I,L; G188A,F,M,W; N189H,K; and A216L,Y of the mature polypeptide of SEQ ID NO: 30.

In another aspect, the variant comprises or consists of the substitutions E154I,L; G188A,F,M,W; N189H,K; and K229W,H,I,Y of the mature polypeptide of SEQ ID NO: 30.

In another aspect, the variant comprises or consists of the substitutions E154I,L; G188A,F,M,W; A216L,Y; and K229W,H,I,Y of the mature polypeptide of SEQ ID NO: 30.

In another aspect, the variant comprises or consists of the substitutions E154I,L; N189H,K; A216L,Y; and K229W,H,I,Y of the mature polypeptide of SEQ ID NO: 30.

In another aspect, the variant comprises or consists of the substitutions G188A,F,M,W; N189H,K; A216L,Y; and K229W,H,I,Y of the mature polypeptide of SEQ ID NO: 30.

In another aspect, the variant comprises or consists of the substitutions E105P,K; E154I,L; G188A,F,M,W; N189H,K; and A216L,Y of the mature polypeptide of SEQ ID NO: 30.

In another aspect, the variant comprises or consists of the substitutions E105P,K; E154I,L; G188A,F,M,W; N189H,K; and K229W,H,I,Y of the mature polypeptide of SEQ ID NO: 30.

In another aspect, the variant comprises or consists of the substitutions E105P,K; E154I,L; G188A,F,M,W; A216L,Y; and K229W,H,I,Y of the mature polypeptide of SEQ ID NO: 30.

In another aspect, the variant comprises or consists of the substitutions E105P,K; E154I,L; N189H,K; A216L,Y; and K229W,H,I,Y of the mature polypeptide of SEQ ID NO: 30.

In another aspect, the variant comprises or consists of the substitutions E105P,K; G188A,F,M,W; N189H,K; A216L,Y; and K229W,H,I,Y of the mature polypeptide of SEQ ID NO: 30.

In another aspect, the variant comprises or consists of the substitutions E154I,L; G188A,F,M,W; N189H,K; A216L,Y; and K229W,H,I,Y of the mature polypeptide of SEQ ID NO: 30.

In another aspect, the variant comprises or consists of the substitutions E105P,K; E154I,L; G188A,F,M,W; N189H,K; A216L,Y; and K229W,H,I,Y of the mature polypeptide of SEQ ID NO: 30.

In another aspect, the variant comprises or consists of the substitutions D105K,P of the mature polypeptide of SEQ ID NO: 14. In another aspect, the variant comprises or consists of the substitutions Q188W,F,M of the mature polypeptide of SEQ ID NO: 14.

In another aspect, the variant comprises or consists of the substitution D109P,K of the mature polypeptide of SEQ ID NO: 36. In another aspect, the variant comprises or consists of the substitution N192A,W,M of the mature polypeptide of SEQ ID NO: 36. In another aspect the variant comprises or consists of the substitution N193K,H of the mature polypeptide of SEQ ID NO: 36. In another aspect, the variant comprises or consists of the substitution D109P,K of the mature polypeptide of SEQ ID NO: 36. In another aspect, the substitution is N192A,W,M of the mature polypeptide of SEQ ID NO: 36. In another aspect, the variant comprises or consists of the substitution N193K,H of the mature polypeptide of SEQ ID NO: 36.

In another aspect, the variant comprises or consists of the substitution D103K,P of the mature polypeptide of SEQ ID NO: 68. In another aspect, the variant comprises or consists of the substitution N152I,L of the mature polypeptide of SEQ ID NO: 68. In another aspect the variant comprises or consists of the substitution G186A,F,M,W of the mature polypeptide of SEQ ID NO: 68. In another aspect, the variant comprises or consists of the substitution N187H,K of the mature polypeptide of SEQ ID NO: 68.

The variants may further comprise one or more additional alterations, e.g., substitutions, insertions, or deletions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

The variants of the present invention may further comprise a substitution at one or more (e.g., several) positions corresponding to positions 111, 152, 155, and 162 of the mature polypeptide of SEQ ID NO: 30, wherein the variants have cellulolytic enhancing activity (WO 2012/044835).

In one aspect, the number of additional substitutions in the variants of the present invention is 1-4, such as 1, 2, 3, or 4 substitutions.

In another aspect, the variant further comprises a substitution at one or more (e.g., several) positions corresponding to positions 111, 152, 155, and 162. In another aspect, the variant further comprises a substitution at two positions corresponding to any of positions 111, 152, 155, and 162. In another aspect, the variant further comprises a substitution at three positions corresponding to any of positions 111, 152, 155, and 162. In another aspect, the variant further comprises a substitution at each position corresponding to positions 111, 152, 155, and 162.

In another aspect, the variant further comprises a substitution at a position corresponding to position 111. In another aspect, the amino acid at a position corresponding to position 111 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further comprises the substitution L111V of the mature polypeptide of SEQ ID NO: 30.

In another aspect, the variant further comprises a substitution at a position corresponding to position 152. In another aspect, the amino acid at a position corresponding to position 152 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant further comprises the substitution D152S of the mature polypeptide of SEQ ID NO: 30.

In another aspect, the variant further comprises a substitution at a position corresponding to position 155. In another aspect, the amino acid at a position corresponding to position 155 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further comprises the substitution M155L of the mature polypeptide of SEQ ID NO: 30.

In another aspect, the variant further comprises a substitution at a position corresponding to position 162. In another aspect, the amino acid at a position corresponding to position 162 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp. In another aspect, the variant further comprises the substitution A162W of the mature polypeptide of SEQ ID NO: 30.

In another aspect, the variant further comprises substitutions at positions corresponding to positions 111 and 152, such as those described above.

In another aspect, the variant further comprises substitutions at positions corresponding to positions 111 and 155, such as those described above.

In another aspect, the variant further comprises substitutions at positions corresponding to positions 111 and 162, such as those described above.

In another aspect, the variant further comprises substitutions at positions corresponding to positions 152 and 155, such as those described above.

In another aspect, the variant further comprises substitutions at positions corresponding to positions 152 and 162, such as those described above.

In another aspect, the variant further comprises substitutions at positions corresponding to positions 155 and 162, such as those described above.

In another aspect, the variant further comprises substitutions at positions corresponding to positions 111, 152, and 155, such as those described above.

In another aspect, the variant further comprises substitutions at positions corresponding to positions 111, 152, and 162, such as those described above.

In another aspect, the variant further comprises substitutions at positions corresponding to positions 111, 155, and 162, such as those described above.

In another aspect, the variant further comprises substitutions at positions corresponding to positions 152, 155, and 162, such as those described above.

In another aspect, the variant further comprises substitutions at positions corresponding to positions 111, 152, 155, and 162, such as those described above.

In another aspect, the variant further comprises one or more (e.g., several) substitutions selected from the group consisting of L111V, D152S, M155L, and A162W, or the one or more (e.g., several) substitutions selected from the group consisting of L111V, D152S, M155L, and A162W at positions corresponding to SEQ ID NO: 30 in other GH61 polypeptides described herein.

In another aspect, the variant comprises substitutions L111V, D152S, M155L, A162W, and G188A, or the same substitutions at corresponding positions thereof. In another aspect, the variant comprises substitutions L111V, D152S, M155L, A162W, G188F, and K229W, or the same substitutions at corresponding positions thereof. In another aspect, the variant comprises substitutions L111V, D152S, M155L, A162W, and K229W, or corresponding substitutions thereof. In another aspect, the variant comprises substitutions L111V, D152S, M155L, A162W, A216Y, and K229W, or the same substitutions at corresponding positions thereof. In another aspect, the variant comprises substitutions L111V, D152S, M155L, A162W, N189K, and K229W, or the same substitutions at corresponding positions thereof. In another aspect, the variant comprises substitutions L111V, D152S, M155L, A162W, and N189K, or the same substitutions at corresponding positions thereof. In another aspect, the variant comprises substitutions L111V, D152S, M155L, A162W, and G188W, or the same substitutions at corresponding positions thereof.

In each of the aspects below, the variant further comprises the one or more (e.g., several) substitutions described below at positions corresponding to SEQ ID NO: 30 in other GH61 polypeptides described herein.

In another aspect, the variant further comprises the substitutions L111V+D152S of the mature polypeptide of SEQ ID NO: 30, or corresponding substitutions thereof.

In another aspect, the variant further comprises the substitutions L111V+M155L of the mature polypeptide of SEQ ID NO: 30, or corresponding substitutions thereof.

In another aspect, the variant further comprises the substitutions L111V+A162W of the mature polypeptide of SEQ ID NO: 30, or corresponding substitutions thereof.

In another aspect, the variant further comprises the substitutions D152S+M155L of the mature polypeptide of SEQ ID NO: 30, or corresponding substitutions thereof.

In another aspect, the variant further comprises the substitutions D152S+A162W of the mature polypeptide of SEQ ID NO: 30, or corresponding substitutions thereof.

In another aspect, the variant further comprises the substitutions M155L+A162W of the mature polypeptide of SEQ ID NO: 30, or corresponding substitutions thereof.

In another aspect, the variant further comprises the substitutions L111V+D152S+M155L of the mature polypeptide of SEQ ID NO: 30, or corresponding substitutions thereof.

In another aspect, the variant further comprises the substitutions L111V+D152S+A162W of the mature polypeptide of SEQ ID NO: 30, or corresponding substitutions thereof.

In another aspect, the variant further comprises the substitutions L111V+M155L+A162W of the mature polypeptide of SEQ ID NO: 30, or corresponding substitutions thereof.

In another aspect, the variant further comprises the substitutions D152S+M155L+A162W of the mature polypeptide of SEQ ID NO: 30, or corresponding substitutions thereof.

In another aspect, the variant further comprises the substitutions L111V+D152S+M155L+A162W of the mature polypeptide of SEQ ID NO: 30, or corresponding substitutions thereof.

In each of the aspects above, the variants of the present invention may further comprise a substitution at one or more (e.g., several) positions corresponding to positions 96, 98, 200, 202, and 204 of the mature polypeptide of SEQ ID NO: 30, wherein the variants have cellulolytic enhancing activity (WO 2012/044836).

In one aspect, the number of additional substitutions in the variants of the present invention is 1-5, such as 1, 2, 3, 4, or 5 substitutions.

In another aspect, the variant further comprises a substitution at one or more (e.g., several) positions corresponding to positions 96, 98, 200, 202, and 204. In another aspect, the variant further comprises a substitution at two positions corresponding to any of positions 96, 98, 200, 202, and 204. In another aspect, the variant further comprises a substitution at three positions corresponding to any of positions 96, 98, 200, 202, and 204. In another aspect, the variant further comprises a substitution at four positions corresponding to any of positions 96, 98, 200, 202, and 204. In another aspect, the variant further comprises a substitution at each position corresponding to positions 96, 98, 200, 202, and 204.

In another aspect, the variant further comprises a substitution at a position corresponding to position 96. In another aspect, the amino acid at a position corresponding to position 96 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further comprises the substitution I96V of the mature polypeptide of SEQ ID NO: 30.

In another aspect, the variant further comprises a substitution at a position corresponding to position 98. In another aspect, the amino acid at a position corresponding to position 98 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further comprises the substitution F98L of the mature polypeptide of SEQ ID NO: 30.

In another aspect, the variant further comprises a substitution at a position corresponding to position 200. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant further comprises the substitution F200I of the mature polypeptide of SEQ ID NO: 30.

In another aspect, the variant further comprises a substitution at a position corresponding to position 202. In another aspect, the amino acid at a position corresponding to position 202 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further comprises the substitution I202L of the mature polypeptide of SEQ ID NO: 30.

In another aspect, the variant further comprises a substitution at a position corresponding to position 204. In another aspect, the amino acid at a position corresponding to position 204 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant further comprises the substitution I204V of the mature polypeptide of SEQ ID NO: 30.

In another aspect, the variant further comprises substitutions at positions corresponding to positions 96 and 98, such as those described above.

In another aspect, the variant further comprises substitutions at positions corresponding to positions 96 and 200, such as those described above.

In another aspect, the variant further comprises substitutions at positions corresponding to positions 96 and 202, such as those described above.

In another aspect, the variant further comprises substitutions at positions corresponding to positions 96 and 204, such as those described above.

In another aspect, the variant further comprises substitutions at positions corresponding to positions 98 and 200, such as those described above.

In another aspect, the variant further comprises substitutions at positions corresponding to positions 98 and 202, such as those described above.

In another aspect, the variant further comprises substitutions at positions corresponding to positions 98 and 204, such as those described above.

In another aspect, the variant further comprises substitutions at positions corresponding to positions 200 and 202, such as those described above.

In another aspect, the variant further comprises substitutions at positions corresponding to positions 200 and 204, such as those described above.

In another aspect, the variant further comprises substitutions at positions corresponding to positions 202 and 204, such as those described above.

In another aspect, the variant further comprises substitutions at positions corresponding to positions 96, 98, and 200, such as those described above.

In another aspect, the variant further comprises substitutions at positions corresponding to positions 96, 98, and 202, such as those described above.

In another aspect, the variant further comprises substitutions at positions corresponding to positions 96, 98, and 204, such as those described above.

In another aspect, the variant further comprises substitutions at positions corresponding to positions 96, 200, and 202, such as those described above.

In another aspect, the variant further comprises substitutions at positions corresponding to positions 96, 200, and 204, such as those described above.

In another aspect, the variant further comprises substitutions at positions corresponding to positions 96, 202, and 204, such as those described above.

In another aspect, the variant further comprises substitutions at positions corresponding to positions 98, 200, and 202, such as those described above.

In another aspect, the variant further comprises substitutions at positions corresponding to positions 98, 200, and 204, such as those described above.

In another aspect, the variant further comprises substitutions at positions corresponding to positions 200, 202, and 204, such as those described above.

In another aspect, the variant further comprises substitutions at positions corresponding to positions 98, 202, and 204, such as those described above.

In another aspect, the variant further comprises substitutions at positions corresponding to positions 96, 98, 200, and 202, such as those described above.

In another aspect, the variant further comprises substitutions at positions corresponding to positions 96, 200, 202, and 204, such as those described above.

In another aspect, the variant further comprises substitutions at positions corresponding to positions 96, 98, 202, and 204, such as those described above.

In another aspect, the variant further comprises substitutions at positions corresponding to positions 96, 98, 200, and 204, such as those described above.

In another aspect, the variant further comprises substitutions at positions corresponding to positions 98, 200, 202, and 204, such as those described above.

In another aspect, the variant further comprises substitutions at positions corresponding to positions 96, 98, 200, 202, and 204, such as those described above.

In another aspect, the variant further comprises one or more (e.g., several) substitutions selected from the group consisting of I96V, F98L, F200I, I202L, and I204V, or the one or more (e.g., several) substitutions selected from the group consisting of I96V, F98L, F200I, I202L, and I204V at positions corresponding to SEQ ID NO: 30 in other GH61 polypeptides described herein.

In each of the aspects below, the variant further comprises the one or more (e.g., several) substitutions described below at positions corresponding to SEQ ID NO: 30 in other GH61 polypeptides described herein.

In another aspect, the variant further comprises the substitutions I96V+F98L of the mature polypeptide of SEQ ID NO: 30, or corresponding substitutions thereof.

In another aspect, the variant further comprises the substitutions I96V+F200I of the mature polypeptide of SEQ ID NO: 30, or corresponding substitutions thereof.

In another aspect, the variant further comprises the substitutions I96V+I202L of the mature polypeptide of SEQ ID NO: 30, or corresponding substitutions thereof.

In another aspect, the variant further comprises the substitutions I96V+I204V of the mature polypeptide of SEQ ID NO: 30, or corresponding substitutions thereof.

In another aspect, the variant further comprises the substitutions F98L+F200I of the mature polypeptide of SEQ ID NO: 30, or corresponding substitutions thereof.

In another aspect, the variant further comprises the substitutions F98L+I202L of the mature polypeptide of SEQ ID NO: 30, or corresponding substitutions thereof.

In another aspect, the variant further comprises the substitutions F98L+I204V of the mature polypeptide of SEQ ID NO: 30, or corresponding substitutions thereof.

In another aspect, the variant further comprises the substitutions F200I+I202L of the mature polypeptide of SEQ ID NO: 30, or corresponding substitutions thereof.

In another aspect, the variant further comprises the substitutions F200I+I204V of the mature polypeptide of SEQ ID NO: 30, or corresponding substitutions thereof.

In another aspect, the variant further comprises the substitutions I202L+I204V of the mature polypeptide of SEQ ID NO: 30, or corresponding substitutions thereof.

In another aspect, the variant further comprises the substitutions I96V+F98L+F200I of the mature polypeptide of SEQ ID NO: 30, or corresponding substitutions thereof.

In another aspect, the variant further comprises the substitutions I96V+F98L+I202L of the mature polypeptide of SEQ ID NO: 30, or corresponding substitutions thereof.

In another aspect, the variant further comprises the substitutions I96V+F98L+I204V of the mature polypeptide of SEQ ID NO: 30, or corresponding substitutions thereof.

In another aspect, the variant further comprises the substitutions I96V+F200I+I202L of the mature polypeptide of SEQ ID NO: 30, or corresponding substitutions thereof.

In another aspect, the variant further comprises the substitutions I96V+F200I+I204V of the mature polypeptide of SEQ ID NO: 30, or corresponding substitutions thereof.

In another aspect, the variant further comprises the substitutions I96V+I202L+I204V of the mature polypeptide of SEQ ID NO: 30, or corresponding substitutions thereof.

In another aspect, the variant further comprises the substitutions F98L+F200I+I202L of the mature polypeptide of SEQ ID NO: 30, or corresponding substitutions thereof.

In another aspect, the variant further comprises the substitutions F98L+F200I+I204V of the mature polypeptide of SEQ ID NO: 30, or corresponding substitutions thereof.

In another aspect, the variant further comprises the substitutions F200I+I202L+I204V of the mature polypeptide of SEQ ID NO: 30, or corresponding substitutions thereof.

In another aspect, the variant further comprises the substitutions F98L+I202L+I204V of the mature polypeptide of SEQ ID NO: 30, or corresponding substitutions thereof.

In another aspect, the variant further comprises the substitutions I96V+F98L+F200I+I202L of the mature polypeptide of SEQ ID NO: 30, or corresponding substitutions thereof.

In another aspect, the variant further comprises the substitutions I96V+F200I+I202L+I204V of the mature polypeptide of SEQ ID NO: 30, or corresponding substitutions thereof.

In another aspect, the variant further comprises the substitutions I96V+F98L+I202L+I204V of the mature polypeptide of SEQ ID NO: 30, or corresponding substitutions thereof.

In another aspect, the variant further comprises the substitutions I96V+F98L+F200I+I204V of the mature polypeptide of SEQ ID NO: 30, or corresponding substitutions thereof.

In another aspect, the variant further comprises the substitutions F98L+F200I+I202L+I204V of the mature polypeptide of SEQ ID NO: 30, or corresponding substitutions thereof.

In another aspect, the variant further comprises the substitutions I96V+F98L+F200I+I202L+I204V of the mature polypeptide of SEQ ID NO: 30, or corresponding substitutions thereof.

The variants may consist of at least 85% of the amino acid residues, e.g., at least 90% of the amino acid residues or at least 95% of the amino acid residues of the mature polypeptides of the corresponding parent GH61 polypeptides.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. Essential amino acids in GH61 polypeptides correspond to positions 22, 107, 194, and/or 196 of the mature polypeptide of SEQ ID NO: 30.

In an embodiment, the variants have increased thermostability compared to their parent GH61 polypeptides.

In one aspect, the thermostability of the variant relative to the parent is determined at pH 3.0 and 45° C. In another aspect, the thermostability of the variant relative to the parent is determined at pH 3.0 and 50° C. In another aspect, the thermostability of the variant relative to the parent is determined at pH 3.0 and 55° C. In another aspect, the thermostability of the variant relative to the parent is determined at pH 3.0 and 60° C. In another aspect, the thermostability of the variant relative to the parent is determined at pH 3.0 and 62° C. In another aspect, the thermostability of the variant relative to the parent is determined at pH 3.0 and 65° C. In another aspect, the thermostability of the variant relative to the parent is determined at pH 3.0 and 68° C. In another aspect, the thermostability of the variant relative to the parent is determined at pH 3.0 and 70° C. In another aspect, the thermostability of the variant relative to the parent is determined at pH 3.0 and 72° C. In another aspect, the thermostability of the variant relative to the parent is determined at pH 3.0 and 75° C. In another aspect, the thermostability of the variant relative to the parent is determined at pH 3.0 and 80° C. In another aspect, the thermostability of the variant relative to the parent is determined at pH 3.0 and 85° C. In another aspect, the thermostability of the variant relative to the parent is determined at pH 3.0 and 90° C. In another aspect, the thermostability of the variant relative to the parent is determined at pH 3.0 and 95° C.

In another aspect, the thermostability of the variant relative to the parent is determined at pH 3.5 and 45° C. In another aspect, the thermostability of the variant relative to the parent is determined at pH 3.5 and 50° C. In another aspect, the thermostability of the variant relative to the parent is determined at pH 3.5 and 55° C. In another aspect, the thermostability of the variant relative to the parent is determined at pH 3.5 and 60° C. In another aspect, the thermostability of the variant relative to the parent is determined at pH 3.5 and 62° C. In another aspect, the thermostability of the variant relative to the parent is determined at pH 3.5 and 65° C. In another aspect, the thermostability of the variant relative to the parent is determined at pH 3.5 and 68° C. In another aspect, the thermostability of the variant relative to the parent is determined at pH 3.5 and 70° C. In another aspect, the thermostability of the variant relative to the parent is determined at pH 3.5 and 72° C. In another aspect, the thermostability of the variant relative to the parent is determined at pH 3.5 and 75° C. In another aspect, the thermostability of the variant relative to the parent is determined at pH 3.5 and 80° C. In another aspect, the thermostability of the variant relative to the parent is determined at pH 3.5 and 85° C. In another aspect, the thermostability of the variant relative to the parent is determined at pH 3.5 and 90° C. In another aspect, the thermostability of the variant relative to the parent is determined at pH 3.5 and 95° C.

In another aspect, the thermostability of the variant relative to the parent is determined at pH 4.0 and 45° C. In another aspect, the thermostability of the variant relative to the parent is determined at pH 4.0 and 50° C. In another aspect, the thermostability of the variant relative to the parent is determined at pH 4.0 and 55° C. In another aspect, the thermostability of the variant relative to the parent is determined at pH 4.0 and 60° C. In another aspect, the thermostability of the variant relative to the parent is determined at pH 4.0 and 62° C. In another aspect, the thermostability of the variant relative to the parent is determined at pH 4.0 and 65° C. In another aspect, the thermostability of the variant relative to the parent is determined at pH 4.0 and 68° C. In another aspect, the thermostability of the variant relative to the parent is determined at pH 4.0 and 70° C. In another aspect, the thermostability of the variant relative to the parent is determined at pH 4.0 and 72° C. In another aspect, the thermostability of the variant relative to the parent is determined at pH 4.0 and 75° C. In another aspect, the thermostability of the variant relative to the parent is determined at pH 4.0 and 80° C. In another aspect, the thermostability of the variant relative to the parent is determined at pH 4.0 and 85° C. In another aspect, the thermostability of the variant relative to the parent is determined at pH 4.0 and 90° C. In another aspect, the thermostability of the variant relative to the parent is determined at pH 4.0 and 95° C.

In another aspect, the thermostability of the variant relative to the parent is determined at pH 4.5 and 45° C. In another aspect, the thermostability of the variant relative to the parent is determined at pH 4.5 and 50° C. In another aspect, the thermostability of the variant relative to the parent is determined at pH 4.5 and 55° C. In another aspect, the thermostability of the variant relative to the parent is determined at pH 4.5 and 60° C. In another aspect, the thermostability of the variant relative to the parent is determined at pH 4.5 and 62° C. In another aspect, the thermostability of the variant relative to the parent is determined at pH 4.5 and 65° C. In another aspect, the thermostability of the variant relative to the parent is determined at pH 4.5 and 68° C. In another aspect, the thermostability of the variant relative to the parent is determined at pH 4.5 and 70° C. In another aspect, the thermostability of the variant relative to the parent is determined at pH 4.5 and 72° C. In another aspect, the thermostability of the variant relative to the parent is determined at pH 4.5 and 75° C. In another aspect, the thermostability of the variant relative to the parent is determined at pH 4.5 and 80° C. In another aspect, the thermostability of the variant relative to the parent is determined at pH 4.5 and 85° C. In another aspect, the thermostability of the variant relative to the parent is determined at pH 4.5 and 90° C. In another aspect, the thermostability of the variant relative to the parent is determined at pH 4.5 and 95° C.

In another aspect, the thermostability of the variant relative to the parent is determined at pH 5.0 and 45° C. In another aspect, the thermostability of the variant relative to the parent is determined at pH 5.0 and 50° C. In another aspect, the thermostability of the variant relative to the parent is determined at pH 5.0 and 55° C. In another aspect, the thermostability of the variant relative to the parent is determined at pH 5.0 and 60° C. In another aspect, the thermostability of the variant relative to the parent is determined at pH 5.0 and 62° C. In another aspect, the thermostability of the variant relative to the parent is determined at pH 5.0 and 65° C. In another aspect, the thermostability of the variant relative to the parent is determined at pH 5.0 and 68° C. In another aspect, the thermostability of the variant relative to the parent is determined at pH 5.0 and 70° C. In another aspect, the thermostability of the variant relative to the parent is determined at pH 5.0 and 72° C. In another aspect, the thermostability of the variant relative to the parent is determined at pH 5.0 and 75° C. In another aspect, the thermostability of the variant relative to the parent is determined at pH 5.0 and 80° C. In another aspect, the thermostability of the variant relative to the parent is determined at pH 5.0 and 85° C. In another aspect, the thermostability of the variant relative to the parent is determined at pH 5.0 and 90° C. In another aspect, the thermostability of the variant relative to the parent is determined at pH 5.0 and 95° C.

In another aspect, the thermostability of the variant relative to the parent is determined at pH 5.5 and 45° C. In another aspect, the thermostability of the variant relative to the parent is determined at pH 5.5 and 50° C. In another aspect, the thermostability of the variant relative to the parent is determined at pH 5.5 and 55° C. In another aspect, the thermostability of the variant relative to the parent is determined at pH 5.5 and 60° C. In another aspect, the thermostability of the variant relative to the parent is determined at pH 5.5 and 62° C. In another aspect, the thermostability of the variant relative to the parent is determined at pH 5.5 and 65° C. In another aspect, the thermostability of the variant relative to the parent is determined at pH 5.5 and 68° C. In another aspect, the thermostability of the variant relative to the parent is determined at pH 5.5 and 70° C. In another aspect, the thermostability of the variant relative to the parent is determined at pH 5.5 and 72° C. In another aspect, the thermostability of the variant relative to the parent is determined at pH 5.5 and 75° C. In another aspect, the thermostability of the variant relative to the parent is determined at pH 5.5 and 80° C. In another aspect, the thermostability of the variant relative to the parent is determined at pH 5.5 and 85° C. In another aspect, the thermostability of the variant relative to the parent is determined at pH 5.5 and 90° C. In another aspect, the thermostability of the variant relative to the parent is determined at pH 5.5 and 95° C.

In another aspect, the thermostability of the variant relative to the parent is determined at pH 6.0 and 45° C. In another aspect, the thermostability of the variant relative to the parent is determined at pH 6.0 and 50° C. In another aspect, the thermostability of the variant relative to the parent is determined at pH 6.0 and 55° C. In another aspect, the thermostability of the variant relative to the parent is determined at pH 6.0 and 60° C. In another aspect, the thermostability of the variant relative to the parent is determined at pH 6.0 and 62° C. In another aspect, the thermostability of the variant relative to the parent is determined at pH 6.0 and 65° C. In another aspect, the thermostability of the variant relative to the parent is determined at pH 6.0 and 68° C. In another aspect, the thermostability of the variant relative to the parent is determined at pH 6.0 and 70° C. In another aspect, the thermostability of the variant relative to the parent is determined at pH 6.0 and 72° C. In another aspect, the thermostability of the variant relative to the parent is determined at pH 6.0 and 75° C. In another aspect, the thermostability of the variant relative to the parent is determined at pH 6.0 and 80° C. In another aspect, the thermostability of the variant relative to the parent is determined at pH 6.0 and 85° C. In another aspect, the thermostability of the variant relative to the parent is determined at pH 6.0 and 90° C. In another aspect, the thermostability of the variant relative to the parent is determined at pH 6.0 and 95° C.

In another aspect, the thermostability of the variant relative to the parent is determined at pH 6.5 and 45° C. In another aspect, the thermostability of the variant relative to the parent is determined at pH 6.5 and 50° C. In another aspect, the thermostability of the variant relative to the parent is determined at pH 6.5 and 55° C. In another aspect, the thermostability of the variant relative to the parent is determined at pH 6.5 and 60° C. In another aspect, the thermostability of the variant relative to the parent is determined at pH 6.5 and 62° C. In another aspect, the thermostability of the variant relative to the parent is determined at pH 6.5 and 65° C. In another aspect, the thermostability of the variant relative to the parent is determined at pH 6.5 and 68° C. In another aspect, the thermostability of the variant relative to the parent is determined at pH 6.5 and 70° C. In another aspect, the thermostability of the variant relative to the parent is determined at pH 6.5 and 72° C. In another aspect, the thermostability of the variant relative to the parent is determined at pH 6.5 and 75° C. In another aspect, the thermostability of the variant relative to the parent is determined at pH 6.5 and 80° C. In another aspect, the thermostability of the variant relative to the parent is determined at pH 6.5 and 85° C. In another aspect, the thermostability of the variant relative to the parent is determined at pH 6.5 and 90° C. In another aspect, the thermostability of the variant relative to the parent is determined at pH 6.5 and 95° C.

In another aspect, the thermostability of the variant relative to the parent is determined at pH 7.0 and 45° C. In another aspect, the thermostability of the variant relative to the parent is determined at pH 7.0 and 50° C. In another aspect, the thermostability of the variant relative to the parent is determined at pH 7.0 and 55° C. In another aspect, the thermostability of the variant relative to the parent is determined at pH 7.0 and 60° C. In another aspect, the thermostability of the variant relative to the parent is determined at pH 7.0 and 62° C. In another aspect, the thermostability of the variant relative to the parent is determined at pH 7.0 and 65° C. In another aspect, the thermostability of the variant relative to the parent is determined at pH 7.0 and 68° C. In another aspect, the thermostability of the variant relative to the parent is determined at pH 7.0 and 70° C. In another aspect, the thermostability of the variant relative to the parent is determined at pH 7.0 and 72° C. In another aspect, the thermostability of the variant relative to the parent is determined at pH 7.0 and 75° C. In another aspect, the thermostability of the variant relative to the parent is determined at pH 7.0 and 80° C. In another aspect, the thermostability of the variant relative to the parent is determined at pH 7.0 and 85° C. In another aspect, the thermostability of the variant relative to the parent is determined at pH 7.0 and 90° C. In another aspect, the thermostability of the variant relative to the parent is determined at pH 7.0 and 95° C.

In another aspect, the thermostability of the variant relative to the parent is determined at pH 7.5 and 45° C. In another aspect, the thermostability of the variant relative to the parent is determined at pH 7.5 and 50° C. In another aspect, the thermostability of the variant relative to the parent is determined at pH 7.5 and 55° C. In another aspect, the thermostability of the variant relative to the parent is determined at pH 7.5 and 60° C. In another aspect, the thermostability of the variant relative to the parent is determined at pH 7.5 and 62° C. In another aspect, the thermostability of the variant relative to the parent is determined at pH 7.5 and 65° C. In another aspect, the thermostability of the variant relative to the parent is determined at pH 7.5 and 68° C. In another aspect, the thermostability of the variant relative to the parent is determined at pH 7.5 and 70° C. In another aspect, the thermostability of the variant relative to the parent is determined at pH 7.5 and 72° C. In another aspect, the thermostability of the variant relative to the parent is determined at pH 7.5 and 75° C. In another aspect, the thermostability of the variant relative to the parent is determined at pH 7.5 and 80° C. In another aspect, the thermostability of the variant relative to the parent is determined at pH 7.5 and 85° C. In another aspect, the thermostability of the variant relative to the parent is determined at pH 7.5 and 90° C. In another aspect, the thermostability of the variant relative to the parent is determined at pH 7.5 and 95° C.

In another aspect, the thermostability of the variant relative to the parent is determined at pH 8.0 and 45° C. In another aspect, the thermostability of the variant relative to the parent is determined at pH 8.0 and 50° C. In another aspect, the thermostability of the variant relative to the parent is determined at pH 8.0 and 55° C. In another aspect, the thermostability of the variant relative to the parent is determined at pH 8.0 and 60° C. In another aspect, the thermostability of the variant relative to the parent is determined at pH 8.0 and 62° C. In another aspect, the thermostability of the variant relative to the parent is determined at pH 8.0 and 65° C. In another aspect, the thermostability of the variant relative to the parent is determined at pH 8.0 and 68° C. In another aspect, the thermostability of the variant relative to the parent is determined at pH 8.0 and 70° C. In another aspect, the thermostability of the variant relative to the parent is determined at pH 8.0 and 72° C. In another aspect, the thermostability of the variant relative to the parent is determined at pH 8.0 and 75° C. In another aspect, the thermostability of the variant relative to the parent is determined at pH 8.0 and 80° C. In another aspect, the thermostability of the variant relative to the parent is determined at pH 8.0 and 85° C. In another aspect, the thermostability of the variant relative to the parent is determined at pH 8.0 and 90° C. In another aspect, the thermostability of the variant relative to the parent is determined at pH 8.0 and 95° C.

In another aspect, the thermostability of the variant relative to the parent is determined at pH 8.5 and 45° C. In another aspect, the thermostability of the variant relative to the parent is determined at pH 8.5 and 50° C. In another aspect, the thermostability of the variant relative to the parent is determined at pH 8.5 and 55° C. In another aspect, the thermostability of the variant relative to the parent is determined at pH 8.5 and 60° C. In another aspect, the thermostability of the variant relative to the parent is determined at pH 8.5 and 62° C. In another aspect, the thermostability of the variant relative to the parent is determined at pH 8.5 and 65° C. In another aspect, the thermostability of the variant relative to the parent is determined at pH 8.5 and 68° C. In another aspect, the thermostability of the variant relative to the parent is determined at pH 8.5 and 70° C. In another aspect, the thermostability of the variant relative to the parent is determined at pH 8.5 and 72° C. In another aspect, the thermostability of the variant relative to the parent is determined at pH 8.5 and 75° C. In another aspect, the thermostability of the variant relative to the parent is determined at pH 8.5 and 80° C. In another aspect, the thermostability of the variant relative to the parent is determined at pH 8.5 and 85° C. In another aspect, the thermostability of the variant relative to the parent is determined at pH 8.5 and 90° C. In another aspect, the thermostability of the variant relative to the parent is determined at pH 8.5 and 95° C.

In another aspect, the thermostability of the variant relative to the parent is determined at pH 9.0 and 45° C. In another aspect, the thermostability of the variant relative to the parent is determined at pH 9.0 and 50° C. In another aspect, the thermostability of the variant relative to the parent is determined at pH 9.0 and 55° C. In another aspect, the thermostability of the variant relative to the parent is determined at pH 9.0 and 60° C. In another aspect, the thermostability of the variant relative to the parent is determined at pH 9.0 and 62° C. In another aspect, the thermostability of the variant relative to the parent is determined at pH 9.0 and 65° C. In another aspect, the thermostability of the variant relative to the parent is determined at pH 9.0 and 68° C. In another aspect, the thermostability of the variant relative to the parent is determined at pH 9.0 and 70° C. In another aspect, the thermostability of the variant relative to the parent is determined at pH 9.0 and 72° C. In another aspect, the thermostability of the variant relative to the parent is determined at pH 9.0 and 75° C. In another aspect, the thermostability of the variant relative to the parent is determined at pH 9.0 and 80° C. In another aspect, the thermostability of the variant relative to the parent is determined at pH 9.0 and 85° C. In another aspect, the thermostability of the variant relative to the parent is determined at pH 9.0 and 90° C. In another aspect, the thermostability of the variant relative to the parent is determined at pH 9.0 and 95° C.

In each of the aspects above, the thermostability of the variant relative to the parent can be determined by incubating the variant and parent for 1 minute. In each of the aspects above, the thermostability of the variant relative to the parent can be determined by incubating the variant and parent for 5 minutes. In each of the aspects above, the thermostability of the variant relative to the parent can be determined by incubating the variant and parent for 10 minutes. In each of the aspects above, the thermostability of the variant relative to the parent can be determined by incubating the variant and parent for 15 minutes. In each of the aspects above, the thermostability of the variant relative to the parent can be determined by incubating the variant and parent for 20 minutes. In each of the aspects above, the thermostability of the variant relative to the parent can be determined by incubating the variant and parent for 25 minutes. In each of the aspects above, the thermostability of the variant relative to the parent can be determined by incubating the variant and parent for 30 minutes. In each of the aspects above, the thermostability of the variant relative to the parent can be determined by incubating the variant and parent for 45 minutes. In each of the aspects above, the thermostability of the variant relative to the parent can be determined by incubating the variant and parent for 60 minutes. A time period longer than 60 minutes can also be used.

In one aspect, the thermostability of the variant having cellulolytic enhancing activity is increased at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 50-fold, at least 75-fold, or at least 100-fold compared to the parent.

Parent GH61 Polypeptides

The parent GH61 polypeptide may be any GH61 polypeptide having cellulolytic enhancing activity.

The parent GH61 polypeptide may be (a) a polypeptide having at least 60% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215; (b) a polypeptide encoded by a polynucleotide that hybridizes under at least low stringency conditions with (i) the mature polypeptide coding sequence of 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, or (ii) the full-length complement of (i); or (c) a polypeptide encoded by a polynucleotide having at least 60% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

In one aspect, the parent has a sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellulolytic enhancing activity.

In another aspect, the amino acid sequence of the parent differs by up to 10 amino acids, e.g., 1, 2, 3, 4, 5, 6, 7, 8, 9, or 10 from the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216.

In another aspect, the parent comprises or consists of the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216.

In another aspect, the parent comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216.

In another aspect, the parent is a fragment containing at least 85% of the amino acid residues, e.g., at least 90% of the amino acid residues or at least 95% of the amino acid residues of the mature polypeptide of a GH61 polypeptide.

In another embodiment, the parent is an allelic variant of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, or the full-length complements thereof (Sambrook et al., 1989, *Molecular Cloning, A Laboratory Manual*, 2d edition, Cold Spring Harbor, N.Y.).

The polynucleotide of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, or subsequences thereof, as well as the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216, or fragments thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, or subsequences thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215; (ii) the mature polypeptide coding sequence thereof; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

In another aspect, the nucleic acid probe is a polynucleotide that encodes the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216; the mature polypeptide thereof; or a fragment thereof.

In another aspect, the nucleic acid probe is SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

In another embodiment, the parent is encoded by a polynucleotide having a sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The parent may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial GH61 polypeptide. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* GH61 polypeptide, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* GH61 polypeptide.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* GH61 polypeptide.

In another aspect, the parent is a *Streptococcus equisimilis, Streptococcus pyogenes, Streptococcus uberis,* or *Streptococcus equi* subsp. *Zooepidemicus* GH61 polypeptide.

In another aspect, the parent is a *Streptomyces achromogenes, Streptomyces avermitilis, Streptomyces coelicolor, Streptomyces griseus,* or *Streptomyces lividans* GH61 polypeptide.

The parent may be a fungal GH61 polypeptide. For example, the parent may be a yeast GH61 polypeptide such as a *Candida, Kluyveromyces, Pichia, Saccharomyces, Schizosaccharomyces,* or *Yarrowia* GH61 polypeptide; or a filamentous fungal GH61 polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* GH61 polypeptide.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* GH61 polypeptide.

In another aspect, the parent is an *Acremonium cellulolyticus, Aspergillus aculeatus, Aspergillus awamori, Aspergillus foetidus, Aspergillus fumigatus, Aspergillus japonicus, Aspergillus lentulus, Aspergillus nidulans, Aspergillus niger, Aspergillus oryzae, Aspergillus terreus, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fennellia nivea, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium emersonii, Penicillium funiculosum, Penicillium pinophilum, Penicillium purpurogenum, Phanerochaete chrysosporium, Talaromyces leycettanus, Thermoascus aurantiacus, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* GH61 polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a GH61 polypeptide variant having cellulolytic enhancing activity, comprising: (a) introducing into a parent GH61 polypeptide a substitution at one or more (e.g., several) positions corresponding to positions 105, 154, 188, 189, 216, and 229 of the mature polypeptide of SEQ ID NO: 30, wherein the variant has cellulolytic enhancing activity; and optionally (b) recovering the variant. In one aspect, the methods further comprise introducing into the parent GH61 polypeptide a substitution at one or more (e.g., several) positions corresponding to positions 111, 152, 155, and 162 of the mature polypeptide of SEQ ID NO: 30, wherein the variant has cellulolytic enhancing activity. In another aspect, the methods further or even further comprise introducing into the parent GH61 polypeptide a substitution at one or more (e.g., several) positions corresponding to positions 96, 98, 200, 202, and 204 of the mature polypeptide of SEQ ID NO: 30, wherein the variant has cellulolytic enhancing activity.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding GH61 polypeptide variants of the present invention.

Nucleic Acid Constructs

The present invention also relates to nucleic acid constructs comprising a polynucleotide encoding a GH61 polypeptide variant of the present invention operably linked to one or more control sequences that direct the expression of the coding sequence in a suitable host cell under conditions compatible with the control sequences.

The polynucleotide may be manipulated in a variety of ways to provide for expression of a GH61 polypeptide variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the GH61 polypeptide variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* ctyIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the GH61 polypeptide variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* ctyIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the GH61 polypeptide variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the GH61 polypeptide variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a GH61 polypeptide variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a GH61 polypeptide variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the GH61 polypeptide variant and the signal peptide sequence is positioned next to the N-terminus of the propeptide sequence.

It may also be desirable to add regulatory sequences that regulate expression of the GH61 polypeptide variant relative to the growth of the host cell. Examples of regulatory sequences are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a GH61 polypeptide variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the GH61 polypeptide variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a GH61 polypeptide variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a GH61 polypeptide variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a GH61 polypeptide variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium* zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a GH61 polypeptide variant, comprising: (a) cultivating a host cell of the present invention under conditions suitable for expression of the variant; and optionally (b) recovering the variant.

The host cells are cultivated in a nutrient medium suitable for production of the GH61 polypeptide variant using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The GH61 polypeptide variant may be detected using methods known in the art that are specific for the variant. These detection methods include, but are not limited to, use of specific antibodies, formation of an enzyme product, or disappearance of an enzyme substrate. For example, an enzyme assay may be used to determine the activity of the variant. See, for example, the assay described in Example 5.

The GH61 polypeptide variant may be recovered using methods known in the art. For example, the variant may be recovered from the nutrient medium by conventional procedures including, but not limited to, collection, centrifugation, filtration, extraction, spray-drying, evaporation, or precipitation. In one aspect, a whole fermentation broth comprising a variant of the present invention is recovered.

The GH61 polypeptide variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the GH61 polypeptide variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a variant of the present invention. Preferably, the compositions are enriched in such a variant. The term "enriched" indicates that the cellulolytic enhancing activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the GH61 polypeptide variants having cellulolytic enhancing activity, or compositions thereof.

The present invention also relates to processes for degrading or converting a cellulosic material, comprising: treating the cellulosic material with an enzyme composition in the presence of a GH61 polypeptide variant of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a GH61 polypeptide variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a GH61 polypeptide variant of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a GH61 polypeptide variant of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 80° C., e.g., about 30° C. to about 65° C., about 40° C. to about 60° C., or about 50° C. to about 55° C. The pH is in the range of preferably about 3 to about 9, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another preferred aspect, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and the GH61 polypeptide variants depend on several factors including, but not limited to, the mixture of component cellulolytic enzymes and/or hemicellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a GH61 polypeptide variant to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a GH61 polypeptide variant to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram-positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram-negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus*

*japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an Acidothermus cellulolyticus endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In the processes of the present invention, any GH61 polypeptide having cellulolytic enhancing activity can be used as a component of the enzyme composition.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), *Thermoascus crustaceus* (WO 2011/041504), *Aspergillus aculeatus* (WO 2012/0307990), and *Thermomyces lanuginosus* (WO 2012/113340). WO 2012/146171 discloses GH61 polypeptides having cellulolytic enhancing activity and the polynucleotides thereof from *Humicola insolens*.

In one aspect, the GH61 polypeptide variant and GH61 polypeptide having cellulolytic enhancing activity is used in the presence of a soluble activating divalent metal cation according to WO 2008/151043, e.g., manganese or copper.

In another aspect, the GH61 polypeptide variant and GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide or variant can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide or variant during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces,* and *Saccharomyces,* e.g., *Candida sonorensis, Kluyveromyces marxianus,* and *Saccharomyces cerevisiae.*

Examples of fermenting organisms that can ferment pentose sugars in their native state include bacterial and fungal organisms, such as some yeast. Preferred xylose fermenting yeast include strains of *Candida,* preferably *C. sheatae* or *C. sonorensis*; and strains of *Pichia,* preferably *P. stipitis,* such as *P. stipitis* CBS 5773. Preferred pentose fermenting yeast include strains of *Pachysolen,* preferably *P. tannophilus.* Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum,* and *Zymomonas mobilis* (Philippidis, 1996, supra).

Other fermenting organisms include strains of *Bacillus,* such as *Bacillus coagulans; Candida,* such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium,* such as *C. acetobutylicum, C. thermocellum,* and *C. phytofermentans; E. coli,* especially *E. coli* strains that have been genetically modified to improve the yield of ethanol; *Geobacillus* sp.; *Hansenula,* such as *Hansenula anomala; Klebsiella,* such as *K. oxytoca; Kluyveromyces,* such as *K. marxianus, K. lactis, K. thermotolerans,* and *K. fragilis; Schizosaccharomyces,* such as *S. pombe; Thermoanaerobacter,* such as *Thermoanaerobacter saccharolyticum*; and *Zymomonas,* such as *Zymomonas mobilis.*

In a preferred aspect, the yeast is a *Bretannomyces.* In a more preferred aspect, the yeast is *Bretannomyces clausenii.* In another preferred aspect, the yeast is a *Candida.* In another more preferred aspect, the yeast is *Candida sonorensis.* In another more preferred aspect, the yeast is *Candida boidinii.* In another more preferred aspect, the yeast is *Candida blankii.* In another more preferred aspect, the yeast is *Candida brassicae.* In another more preferred aspect, the yeast is *Candida diddensii.* In another more preferred aspect, the yeast is *Candida entomophiliia.* In another more preferred aspect, the yeast is *Candida pseudotropicalis.* In another more preferred aspect, the yeast is *Candida scehatae.* In another more preferred aspect, the yeast is *Candida utilis.* In another preferred aspect, the yeast is a *Clavispora.* In another more preferred aspect, the yeast is *Clavispora lusitaniae.* In another more preferred aspect, the yeast is *Clavispora opuntiae.* In another preferred aspect, the yeast is a *Kluyveromyces.* In another more preferred aspect, the yeast is *Kluyveromyces fragilis.* In another more preferred aspect, the yeast is *Kluyveromyces marxianus.* In another more preferred aspect, the yeast is *Kluyveromyces thermotolerans.* In another preferred aspect, the yeast is a *Pachysolen.* In another more preferred aspect, the yeast is *Pachysolen tannophilus.* In another preferred aspect, the yeast is a *Pichia.* In another more preferred aspect, the yeast is a *Pichia stipitis.* In another preferred aspect, the yeast is a *Saccharomyces* spp. In another more preferred aspect, the yeast is *Saccharomyces cerevisiae.* In another more preferred aspect, the yeast is *Saccharomyces distaticus.* In another more preferred aspect, the yeast is *Saccharomyces uvarum.*

In a preferred aspect, the bacterium is a *Bacillus.* In a more preferred aspect, the bacterium is *Bacillus coagulans.* In another preferred aspect, the bacterium is a *Clostridium.* In another more preferred aspect, the bacterium is *Clostridium acetobutylicum.* In another more preferred aspect, the bacterium is *Clostridium phytofermentans.* In another more preferred aspect, the bacterium is *Clostridium thermocellum.* In another more preferred aspect, the bacterium is *Geobacilus* sp. In another more preferred aspect, the bacterium is a *Thermoanaerobacter.* In another more preferred aspect, the bacterium is *Thermoanaerobacter saccharolyticum.* In another preferred aspect, the bacterium is a *Zymomonas.* In another more preferred aspect, the bacterium is *Zymomonas mobilis.*

Commercially available yeast suitable for ethanol production include, e.g., BIOFERM™ AFT and XR (NABC—

North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Detergent Compositions

The present invention also relates to detergent compositions comprising a GH61 polypeptide variant of the present invention and a surfactant. A GH61 polypeptide variant of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In one aspect, the present invention also relates to methods for cleaning or washing a hard surface or laundry, the method comprising contacting the hard surface or the laundry with a detergent composition of the present invention.

In a specific aspect, the present invention provides a detergent additive comprising a GH61 polypeptide variant of the invention. The detergent additive as well as the detergent composition may comprise one or more (e.g., several) enzymes selected from the group consisting of an amylase, arabinase, cutinase, carbohydrase, cellulase, galactanase, laccase, lipase, mannanase, oxidase, pectinase, peroxidase, protease, and xylanase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME™, and CAREZYME™ (Novozymes A/S), CLAZINASE™, and PURADAX HA™ (Genencor International Inc.), and KAC-500(B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include ALCALASE™ SAVINASE™, PRIMASE™, DURALASE™, ESPERASE™, and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus lipase*, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases:

Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), RAPIDASE™ and PURASTAR™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S).

The detergent enzyme(s) may be included in a detergent composition by adding separate additives containing one or more (e.g., several) enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste, or a liquid. A liquid detergent may be aqueous, typically containing up to 70% water and 0-30% organic solvent, or non-aqueous.

The detergent composition comprises one or more (e.g., several) surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more (e.g., several) polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a GH61 polypeptide variant of the present invention having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A GH61 polypeptide variant of the present invention having cellulolytic enhancing activity may also be incorporated in the detergent formulations disclosed in WO 97/07202, which is hereby incorporated by reference.

Plants

The present invention also relates to plants, e.g., a transgenic plant, plant part, or plant cell, comprising a polynucleotide of the present invention so as to express and produce a GH61 polypeptide variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3:

1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and optionally (b) recovering the variant.

The present invention is further described by the following examples that should not be construed as limiting the scope of the invention.

EXAMPLES

Strains

*Aspergillus oryzae* strain PFJO218 (amy$^-$, alp$^-$, Npl$^-$, CPA$^-$, KA$^-$, pyrG$^-$, ku70$^-$; U.S. Patent Application 20100221783) was used as an expression host for the GH61 polypeptide variants.

*Aspergillus oryzae* strain COLs1300 was also used as an expression host for GH61 polypeptide variants. *A. niger* COLs1300 (amyA, amyB, amyC, alpA, nprA, kusA, niaD, niiA, amdS+) was created from *A. oryzae* PFJ0220 (EP 2 147 107 B1) by deleting the promoter and 5' part of both the nitrite reductase (niiA) gene and nitrate reductase (niaD) gene.

Media and Reagents

AMG trace metals solution was composed of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, 3 g of citric acid, and deionized water to 1 liter.

COLs1300 cultivating medium was composed of 100 ml of sucrose medium and 1 ml of 1 M urea.

COLs1300 protoplasting solution was composed of 80 mg of GLUCANEX® (Novozymes A/S, Bagsvaerd, Denmark), 0.5 mg/ml of chitinase (Sigma Chemical Co., Inc., St. Louis, Mo., USA), 10 ml of 1.2 M $MgSO_4$, and 100 µl of 1 M $NaH_2PO_4$ pH 5.8.

COVE-N-Gly plates were composed of 50 ml of COVE salt solution, 218 g of sorbitol, 10 g of glycerol, 2.02 g of $KNO_3$, 25 g of Noble agar, and deionized water to 1 liter.

COVE-N-Gly plates with 10 mM uridine were composed of 50 ml of COVE salt solution, 218 g of sorbitol, 10 g of glycerol, 2.02 g of $KNO_3$, 25 g of Noble agar, and deionized water to 1 liter; uridine was then added at a concentration of 10 mM to individual plates.

COVE salt solution was composed of 26 g of KCl, 26 g of $MgSO_4.7H_2O$, 76 g of $KH_2PO_4$, 50 ml of COVE trace elements solution, and deionized water to 1 liter.

COVE trace elements solution was composed of 40 mg of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

LB medium was composed of 10 g of tryptone, 5 g of yeast extract, 5 g of NaCl, and deionized water to 1 liter.

LB+Amp medium was composed of LB medium supplemented with 100 µg of ampicillin per ml.

M400 medium was composed of 50 g of maltodextrin, 2 g of $MgSO_4.7H_2O$, 2 g of $KH_2PO_4$, 4 g of citric acid, 8 g of yeast extract, 2 g of urea, 0.5 ml of AMG trace metals solution, 0.5 g of $CaCl_2$, and deionized water to 1 liter; adjusted with NaOH to pH 6. After pH adjustment 0.7 ml of antifoam was added.

Magnificent Broth was composed of 50 g of Magnificent Broth powder (MacConnell Research Corp. San Diego, Calif., USA) and deionized water to 1 liter.

MaltV1 medium was composed of 20 g of maltose, 10 g of Bacto Peptone, 1 g of yeast extract, 1.45 g of $(NH_4)_2SO_4$, 2.08 g of $KH_2PO_4$, 0.28 g of $CaCl_2$, 0.42 g of $MgSO_4.7H_2O$, 0.42 ml of Trichoderma trace metals solution, 0.48 g of citric acid, 19.52 g of 2-(N-morpholino)ethanesulfonic acid (MES), and deionized water to 1 liter; adjusted with NaOH to pH 5.5.

MDU2BP medium (pH 5.0) was composed of 135 g of maltose, 3 g of $MgSO_4.7H_2O$, 3 g of NaCl, 6 g of $K2SO_4$, 36 g of $KH_2PO_4$, 21 g of yeast extract, 6 g of urea, 1.5 ml of AMG trace metals solution, and deionized water up to 1 liter.

PEG solution was composed of 6 g of polyethylene glycol 4000 (PEG 4000), 100 µl of 1 M Tris pH 7.5, 100 µl of 1 M $CaCl_2$, and deionized water to 10 ml.

Protoplasting cultivation medium was composed of 92 ml of transformation sucrose medium, 2 ml of 1 M uridine, 1 ml of 1 M $NaNO_3$, and 10 ml of YP medium.

Protoplasting solution was composed of 15 ml of 1.2 M $MgSO_4$, 150 µl of 1 M $NaH_2PO_4$ (pH 5.8), 100 mg of GLUCANEX® (Novozymes A/S, Bagsvaerd, Denmark), and 10 mg of chitinase (Sigma Chemical Co., Inc., St. Louis, Mo., USA).

ST solution was composed of 1.5 ml of 2 M sorbitol, 500 µl of 1 M Tris pH 7.5, and deionized water to 5 ml.

STC solution was composed of 60 ml of 2 M sorbitol, 1 ml of 1 M Tris pH 7.5, 1 ml of 1 M $CaCl_2$, and deionized water to 100 ml.

Sucrose medium was composed of 20 ml of COVE salt solution, 342 g of sucrose, and deionized water to 1 liter.

Sucrose agar plate was composed of 20 ml of Trichoderma trace element solution, 20 g of Noble agar, 342 g of sucrose, and deionized water to 1 liter.

TAE buffer was composed of 40 mM 2-amino-2-hydroxymethyl-propane-1,3-diol, 20 mM Glacial acetic acid, and 2 mM ethylenediaminetetraacetic acid at pH 8.0.

TBE buffer was composed of 10.8 g of Tris base, 5.5 g of boric acid, and 0.74 g of EDTA (pH 8) in deionized water to 1 liter.

TE buffer was composed of 10 mM Tris-0.1 mM EDTA pH 8.

Top agar was composed of 500 ml of sucrose medium, 5 g of low melting agarose, and 10 ml of 20 mM Tris pH 7.5.

Transformation sucrose medium was composed of 70 ml of 1 M sucrose and 20 ml of COVE salt solution.

Trichoderma trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

2XYT agar plates were composed of 16 g of tryptone, 10 g of yeast extract, 5 g of NaCl, 15 g of Bacto agar, and deionized water to 1 liter.

2XYT+Amp agar plates were composed of 2XYT agar supplemented with 100 µg of ampicillin per ml.

YP medium was composed of 10 g of Bacto yeast extract, 20 g of Bacto peptone, and deionized water to 1 liter.

Example 1: Construction of Expression Vectors pMMar44, pMMar49, pMMar45, and pDFng113

Plasmid pMMar44 was constructed as described below for expression of the *Aspergillus fumigatus* GH61B polypeptide, and generation of mutant gene libraries. Additionally, plasmids pMMar49, pMMar45, and pDFng113 were constructed as described below for expression of the *Aspergillus fumigatus* GH61B polypeptide mutant (WO 2012/044835), *Penicillium* sp. (*emersonii*) GH61A polypeptide (hereinafter *Penicillium emersonii* GH61A polypeptide), and *Thermoascus aurantiacus* GH61A polypeptide, respectively, and generation of variants.

Plasmid pENI2376 (U.S. Patent Application 20060234340) containing the AMA sequence for autonomous maintenance in *Aspergillus* was digested with Bam HI and Not I to linearize the plasmid and remove an 8 bp fragment. The digested plasmid was purified using a PCR Purification Kit (QIAGEN Inc., Valencia, Calif., USA) according to the manufacturer's instructions.

The *Aspergillus fumigatus* GH61B polypeptide coding sequence (FIG. 1; SEQ ID NO: 29 [genomic DNA sequence] and SEQ ID NO: 30 [deduced amino acid sequence]), mutated *Aspergillus fumigatus* GH61B polypeptide coding sequence (WO 2012/044835), *Penicillium emersonii* GH61A polypeptide coding sequence (SEQ ID NO: 35 [genomic DNA sequence] and SEQ ID NO: 36 [deduced amino acid sequence]), and *Thermoascus aurantiacus* GH61A polypeptide coding sequence (SEQ ID NO: 13 [genomic DNA sequence] and SEQ ID NO: 14 [deduced amino acid sequence]) were amplified from source plasmids described below using the primers shown in Table 1. Bold letters represent coding sequence. The remaining sequences are homologous to insertion sites of pENI2376 for expression of the GH61 polypeptide coding sequences.

TABLE 1

| GH61 Polypeptide origin | Source Template | Plasmid | Primer ID | Primer Sequence |
|---|---|---|---|---|
| Aspergillus fumigatus GH61B | pAG43 (WO 2010/138754) | pMMar44 | AspfuGH61Bp ENI2376F_2 | CACAACTGGGGATCCATGACT TTGTCCAAGATCACTTCCA (SEQ ID NO: 217) |
| | | | AspfuGH61Bp ENI2376R_2 | GGCCTCCGCGGCCGCTTAAG CGTTGAACAGTGCAGGACCA (SEQ ID NO: 218) |
| Mutated Aspergillus fumigatus GH61B | pTH230 (WO 2012/044835) | pMMar49 | AfumGH61SDMB 3pENI3376F | CACAACTGGGGATCCATGACT TTGTCCAAGATCACTTCCA (SEQ ID NO: 219) |
| | | | AfumGH61SDMB 3pENI3376R | GGCCTCCGCGGCCGCTTAAG CGTTGAACAGTGCAGGACCA (SEQ ID NO: 220) |
| Penicillium emersonii GH61A | pDM286 | pMMar45 | PenemGH61p ENI2376F | CACAACTGGGGATCCATGCTG TCTTCGACGACTCGCACCC (SEQ ID NO: 221) |
| | | | PenemGH61p ENI2376R | GGCCTCCGCGGCCGCCTAGA ACGTCGGCTCAGGCGGCCCC (SEQ ID NO: 222) |
| Thermo- ascusaur- antiacus GH61A | pDZA2 (WO 2005/074656) | pDFng113 | TaGH61aBaM HItagF | CTGGGGATCCATGTCCTTTTC CAAGAT (SEQ ID NO: 223) |
| | | | TaGH61aNcoIt agR | CTCCGCGGCCGCTTAACCAGT ATACAGAG (SEQ ID NO: 224) |

Construction of plasmid pMMar44 containing the *Aspergillus fumigatus* GH61B polypeptide coding sequence is described below. The *Aspergillus fumigatus* GH61B polypeptide coding sequence was amplified from plasmid pAG43 (WO 2010/138754) using the primers shown in Table 1 with overhangs designed for cloning into plasmid pENI2376.

Fifty picomoles of each of the primers listed in Table 1 were used in a PCR reaction composed of 90 ng of pAG43, 1× ADVANTAGE® 2 PCR Buffer (Clontech Laboratories, Inc., Mountain View, Calif., USA), 1 µl of a blend of dATP, dTTP, dGTP, and dCTP, each at 10 mM, and 1× ADVANTAGE® 2 DNA Polymerase Mix (Clontech Laboratories, Inc., Mountain View, Calif., USA), in a final volume of 50 µl. The amplification was performed using an EPPENDORF® MASTERCYCLER® 5333 (Eppendorf Scientific, Inc., Westbury, N.Y., USA) programmed for 1 cycle at 95° C. for 1 minute; 30 cycles each at 95° C. for 30 seconds, 60° C. for 30 seconds, and 72° C. for 1 minute; and a final elongation at 72° C. for 10 minutes. The heat block then went to a 4° C. soak cycle.

The reaction product was isolated by 1.0% agarose gel electrophoresis using TBE buffer where an approximately 862 bp PCR product band was excised from the gel and extracted using a QIAQUICK® Gel Extraction Kit (QIAGEN Inc., Valencia, Calif., USA).

The homologous ends of the 862 bp PCR product and the digested pENI2376 were joined together using an IN-FUSION™ ADVANTAGE® PCR Cloning Kit (Clontech Laboratories, Inc., Mountain View, Calif., USA). A total of 63 ng of the 862 bp PCR product and 200 ng of the Bam HI/Not I digested pENI2376 were used in a reaction composed of 4 µl of 5×IN-FUSION™ reaction buffer (Clontech Laboratories, Inc., Mountain View, Calif., USA) and 2 µl of IN-FUSION™ enzyme (Clontech Laboratories, Inc., Mountain View, Calif., USA), in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into *E. coli* XL10-GOLD® Super Competent Cells (Stratagene, La Jolla, Calif., USA) according to the manufacturer's instructions. *E. coli* transformants were selected on 2XYT+Amp agar plates. Plasmid DNA from several of the resulting *E. coli* transformants was prepared using a BIOROBOT® 9600 (QIAGEN Inc., Valencia, Calif., USA). The *Aspergillus fumigatus* GH61B polypeptide coding sequence insert was confirmed by DNA sequencing with a Model 377 XL Automated DNA Sequencer (Applied Biosystems Inc., Foster City, Calif., USA) using dye-terminator chemistry (Giesecke et al., 1992, *J. Virol. Methods* 38: 47-60). Sequencing primers used for verification of the gene insert and sequence are shown below.

Primer 996271:
(SEQ ID NO: 225)
ACTCAATTTACCTCTATCCACACTT

Primer pALLO2 3':
(SEQ ID NO: 226)
GAATTGTGAGCGGATAACAATTTCA

A plasmid containing the correct *A. fumigatus* GH61B polypeptide coding sequence was selected and designated pMMar44 (FIG. 2).

Construction of plasmid pMMar49 containing eight base-pair changes resulted in four amino acid mutations of the *Aspergillus fumigatus* GH61B polypeptide (WO 2012/044835) is described below. The mutated *Aspergillus fumigatus* GH61B polypeptide coding sequence (WO 2012/044835) was amplified from plasmid pTH230 using the primers shown in Table 1 with overhangs designed for cloning into plasmid pENI2376.

Fifty picomoles of each of the primers listed in Table 1 were used in a PCR reaction composed of 100 ng of pTH230, 1× ADVANTAGE® 2 PCR Buffer (Clontech Laboratories, Inc., Mountain View, Calif., USA), 1 µl of a blend of dATP, dTTP, dGTP, and dCTP, each at 10 mM, and 1× ADVANTAGE® 2 DNA Polymerase Mix (Clontech Laboratories, Inc., Mountain View, Calif., USA), in a final volume of 50 µl. The amplification was performed using an EPPENDORF® MASTERCYCLER® 5333 programmed for 1 cycle at 95° C. for 1 minute; 30 cycles each at 95° C. for 30 seconds, 60° C. for 30 seconds, and 72° C. for 1 minute; and a final elongation at 72° C. for 7 minutes. The heat block then went to a 4° C. soak cycle.

The reaction product was isolated by 1.0% agarose gel electrophoresis using TBE buffer where an approximately 862 bp PCR product band was excised from the gel and extracted using a QIAQUICK® Gel Extraction Kit.

The homologous ends of the 862 bp PCR product and the digested pENI2376 were joined together using an IN-FUSION™ ADVANTAGE® PCR Cloning Kit. A total of 90 ng of the 862 bp PCR product and 220 ng of the Bam HI/Not I digested pENI2376 were used in a reaction composed of 4 µl of 5×IN-FUSION™ reaction buffer and 2 µl of IN-FUSION™ enzyme in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into *E. coli* XL10-GOLD® Super Competent Cells according to the manufacturer's instructions. *E. coli* transformants were selected on 2XYT+ Amp agar plates. Plasmid DNA from several of the resulting *E. coli* transformants was prepared using a BIOROBOT® 9600. The mutated *Aspergillus fumigatus* GH61B polypeptide coding sequence insert was confirmed by DNA sequencing with a Model 377 XL Automated DNA Sequencer using dye-terminator chemistry (Giesecke et al., 1992, supra). The sequencing primers 996271 and pALLO2 3' were used for verification of the gene insert and sequence.

Figure 3:
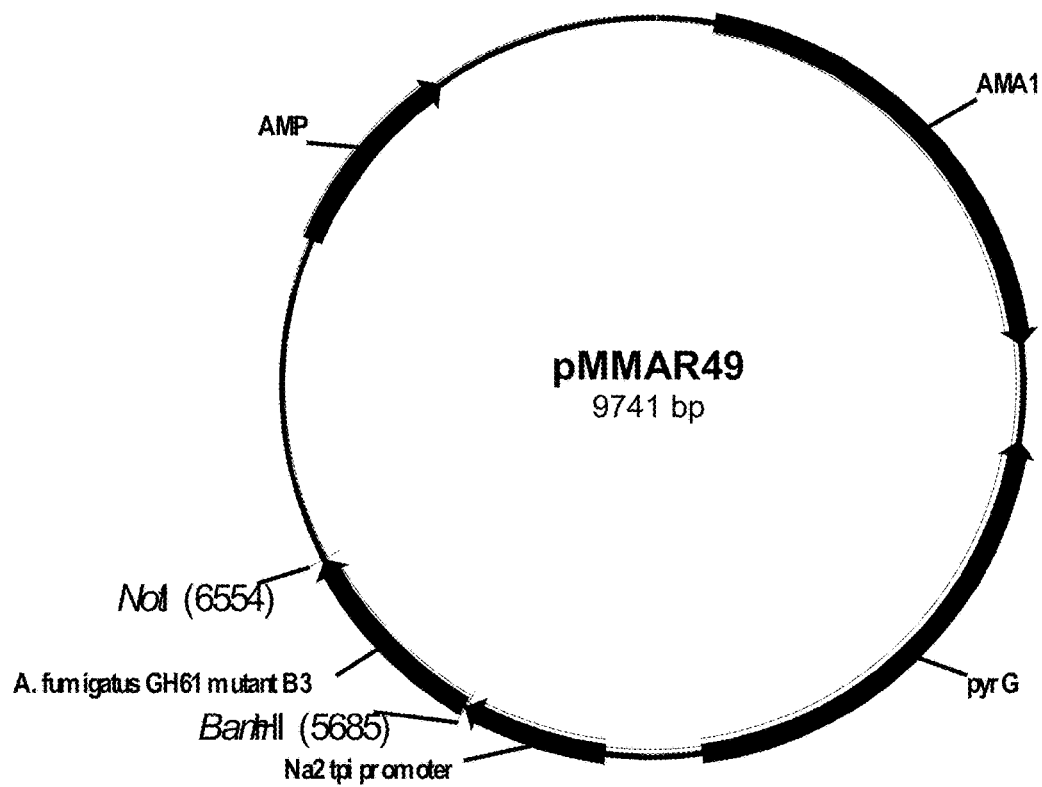
FIG. 3 shows a restriction map of plasmid pMMar49.

A plasmid containing the correct mutated *A. fumigatus* GH61B polypeptide coding sequence was selected and designated pMMar49 (FIG. 3).

Construction of plasmid pMMar45 containing the *Penicillium emersonii* GH61A polypeptide coding sequence is described below. The *Penicillium emersonii* GH61A polypeptide coding sequence was amplified from plasmid pDM286 containing the *Penicillium emersonii* GH61A polypeptide coding sequence using the primers shown in Table 1 with overhangs designed for cloning into plasmid pENI2376.

Plasmid pDM286 was constructed according to the following protocol. The *P. emersonii* GH61A polypeptide gene was amplified from plasmid pGH61D23Y4 (WO 2011/041397) using PHUSION™ High-Fidelity Hot Start DNA Polymerase (Finnzymes Oy, Espoo, Finland) and gene-specific forward and reverse primers shown below. The region in italics represents vector homology to the site of insertion.

```
Forward primer:
                                    (SEQ ID NO: 227)
5'-CGGACTGCGCACCATGCTGTCTTCGACGACTCGCAC-3'

Reverse primer:
                                    (SEQ ID NO: 228)
5'-TCGCCACGGAGCTTATCGACTTCTTCTAGAACGTC-3'
```

The amplification reaction contained 30 ng of plasmid pGH61D23Y4, 50 pmoles of each of the primers listed above, 1 µl of a 10 mM blend of dATP, dTTP, dGTP, and dCTP, 1× PHUSION™ High-Fidelity Hot Start DNA Polymerase buffer (Finnzymes Oy, Espoo, Finland) and 1 unit of PHUSION™ High-Fidelity Hot Start DNA Polymerase buffer (Finnzymes Oy, Espoo, Finland) in a final volume of 50 µl.

The amplification reaction was incubated in an EPPENDORF® MASTERCYCLER® 5333 epgradient S (Eppendorf Scientific, Inc., Westbury, N.Y., USA) programmed for 1 cycle at 98° C. for 30 seconds; 35 cycles each at 98° C. for 10 seconds, 60° C. for 30 seconds, and 72° C. for 30 seconds, and 1 cycle at 72° C. for 10 minutes.

PCR products were separated by 1% agarose gel electrophoresis using TAE buffer. A 0.87 kb fragment was excised from the gel and extracted using a NUCLEOSPIN® Extract II Kit (Macherey-Nagel, Inc., Bethlehem, Pa., USA) according to the manufacturer's protocol.

Plasmid pMJ09 (US 2005/0214920 A1) was digested with Nco I and Pac I, and after digestion, the digested vector was isolated by 1.0% agarose gel electrophoresis using TBE buffer where an approximately 7.1 kb fragment was excised from the gel and extracted using a QIAQUICK® Gel Extraction Kit. The 0.87 kb PCR product was inserted into Nco I/Pac I-digested pMJ09 using an IN-FUSION™ ADVANTAGE® PCR Cloning Kit according to the manufacturer's protocol. The IN-FUSION™ reaction was composed of 1×IN-FUSION™ Reaction buffer, 180 ng of Not I/Pac I digested plasmid pMJ09, 108 ng of the 0.87 kb PCR product, and 1 µl of IN-FUSION™ Enzyme in a 10 µl reaction volume. The reaction was incubated for 15 minutes at 37° C. and then for 15 minutes at 50° C. To the reaction 40 µl of TE were added and 2 µl were used to transform ONE SHOT® TOP10 competent cells (Invitrogen, Carlsbad, Calif., USA) according to the manufacturer's protocol. Transformants were screened by sequencing and one clone containing the insert with no PCR errors was identified and designated plasmid pDM286. Plasmid pDM286 can be digested with Pme I to generate an approximately 5.4 kb fragment for *T. reesei* transformation. This 5.4 kb fragment contains the expression cassette [*T. reesei* Cel7A cellobiohydrolase (CBHI) promoter, *P. emersonii* glycosyl hydrolase 61A (GH61A) gene, *T. reesei* Cel7A cellobiohydrolase (CBHI) terminator], and *Aspergillus nidulans* acetamidase (amdS) gene.

For construction of pMMar45, 50 picomoles of each of the primers listed in Table 1 were used in a PCR reaction composed of 120 ng of pDM286, 1× EXPAND® PCR Buffer (Roche Diagnostics, Inc., Indianapolis, Ind., USA), 1 µl of a blend of dATP, dTTP, dGTP, and dCTP, each at 10 mM, and 1× EXPAND® DNA Polymerase Mix (Roche Diagnostics, Inc., Indianapolis, Ind., USA), in a final volume of 50 µl. The amplification was performed using an EPPENDORF® MASTERCYCLER® 5333 programmed for 1 cycle at 95° C. for 1 minute; 30 cycles each at 95° C. for 30 seconds, 60° C. for 30 seconds, and 72° C. for 1 minute; and a final elongation at 72° C. for 10 minutes. The heat block then went to a 4° C. soak cycle.

The reaction product was isolated by 1.0% agarose gel electrophoresis using TBE buffer where an approximately 762 bp PCR product band was excised from the gel and extracted using a QIAQUICK® Gel Extraction Kit.

The homologous ends of the 762 bp PCR product and the Bam HI/Not I digested pENI2376 were joined together using an IN-FUSION™ ADVANTAGE® PCR Cloning Kit. A total of 90 ng of the 762 bp PCR product and 200 ng of the digested pENI2376 were used in a reaction composed of 4 µl of 5×IN-FUSION™ reaction buffer and 2 µl of IN-FUSION™ enzyme, in a final volume of 20 µl. The reaction was incubated for 15 minutes at 37° C., followed by 15 minutes at 50° C., and then placed on ice. The reaction volume was increased to 100 µl with TE buffer and 2 µl of the reaction were transformed into *E. coli* XL10-GOLD® Super Competent Cells according to the manufacturer's instructions. *E. coli* transformants were selected on 2XYT+ Amp agar plates. Plasmid DNA from several of the resulting *E. coli* transformants was prepared using a BIOROBOT® 9600. The *P. emersonii* GH61A polypeptide coding sequence insert was confirmed by DNA sequencing with a Model 377 XL Automated DNA Sequencer using dye-terminator chemistry (Giesecke et al., 1992, supra). The sequencing primers 996271 and pALLO2 3' were used for verification of the gene insert and sequence.

Figure 4:
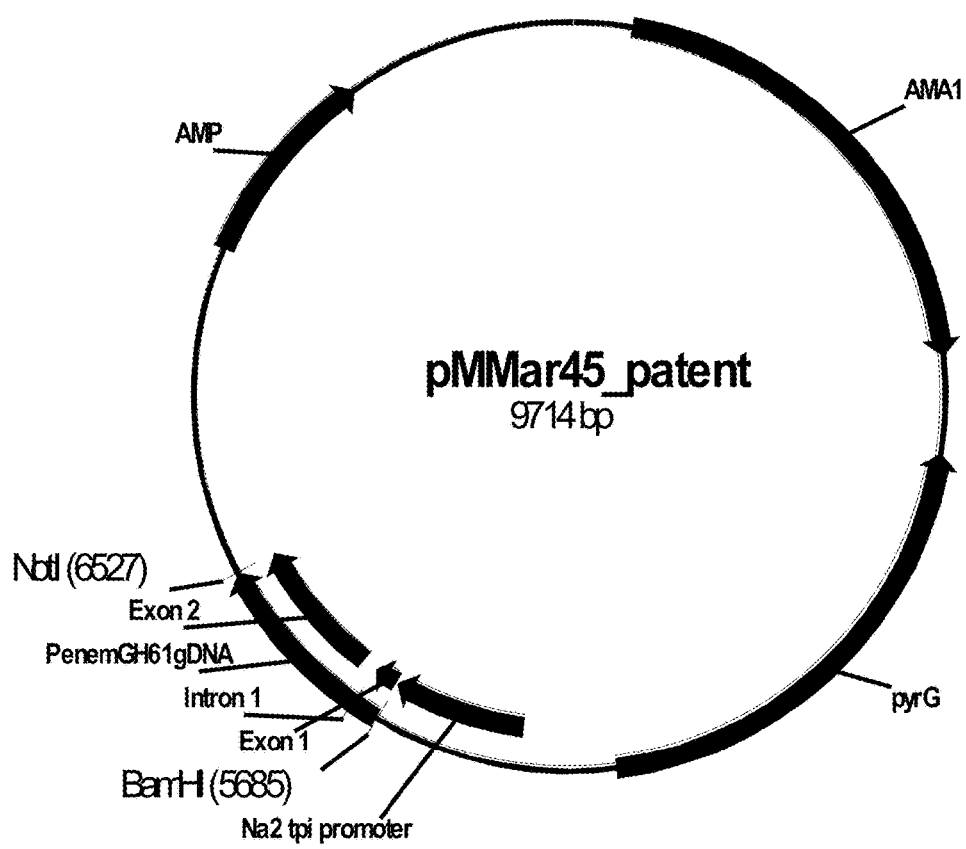
FIG. 4 shows a restriction map of plasmid pMMar45.

A plasmid containing the correct *P. emersonii* GH61A polypeptide coding sequence was selected and designated pMMar45 (FIG. 4).

Construction of plasmid pDFng113 containing the *Thermoascus aurantiacus* GH61A polypeptide coding sequence is described below. The *Thermoascus aurantiacus* GH61A polypeptide coding sequence was amplified from plasmid pDZA2 (WO 2005/074656) using the primers shown in Table 1 with overhangs designed for cloning into plasmid pENI2376.

Fifty picomoles of each of the primers listed in Table 1 were used in a PCR reaction composed of 100 ng of pDZA2, 1× EXPAND® PCR Buffer, 1 µl of a blend of dATP, dTTP, dGTP, and dCTP, each at 10 mM, and 1× EXPAND® DNA Polymerase Mix, in a final volume of 50 µl. The amplification was performed using an EPPENDORF® MASTERCYCLER® 5333 programmed for 1 cycle at 94° C. for 2 minutes; 30 cycles each at 94° C. for 15 seconds, 59.9° C. for 30 seconds, and 72° C. for 1 minute; and a final elongation at 72° C. for 7 minutes. The heat block then went to a 4° C. soak cycle.

The reaction product was isolated by 1.0% agarose gel electrophoresis using TBE buffer where an approximately 822 bp PCR product band was excised from the gel and extracted using a QIAQUICK® Gel Extraction Kit.

The homologous ends of the 822 bp PCR product and the Bam HI/Not I digested pENI2376 were joined together using an IN-FUSION™ ADVANTAGE® PCR Cloning Kit. A total of 37 ng of the 799 bp PCR product and 200 ng of the digested pENI2376 were used in a reaction composed of 4 µl of 5×IN-FUSION™ reaction buffer and 2 µl of IN-FUSION™ enzyme in a final volume of 20 µl. The reaction was incubated for 15 minutes at 37° C., followed by 15 minutes at 50° C., and then placed on ice. The reaction volume was increased to 50 µl with TE buffer and 2 µl of the reaction were transformed into *E. coli* XL10-GOLD® Ultra Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *T. aurantiacus* GH61A polypeptide coding sequence insert was confirmed by DNA sequencing with a Model 377 XL Automated DNA Sequencer using dye-terminator chemistry (Giesecke et al., 1992, supra). The sequencing primers 996271 and pALLO2 3' were used for verification of the gene insert and sequence.

Figure 5:
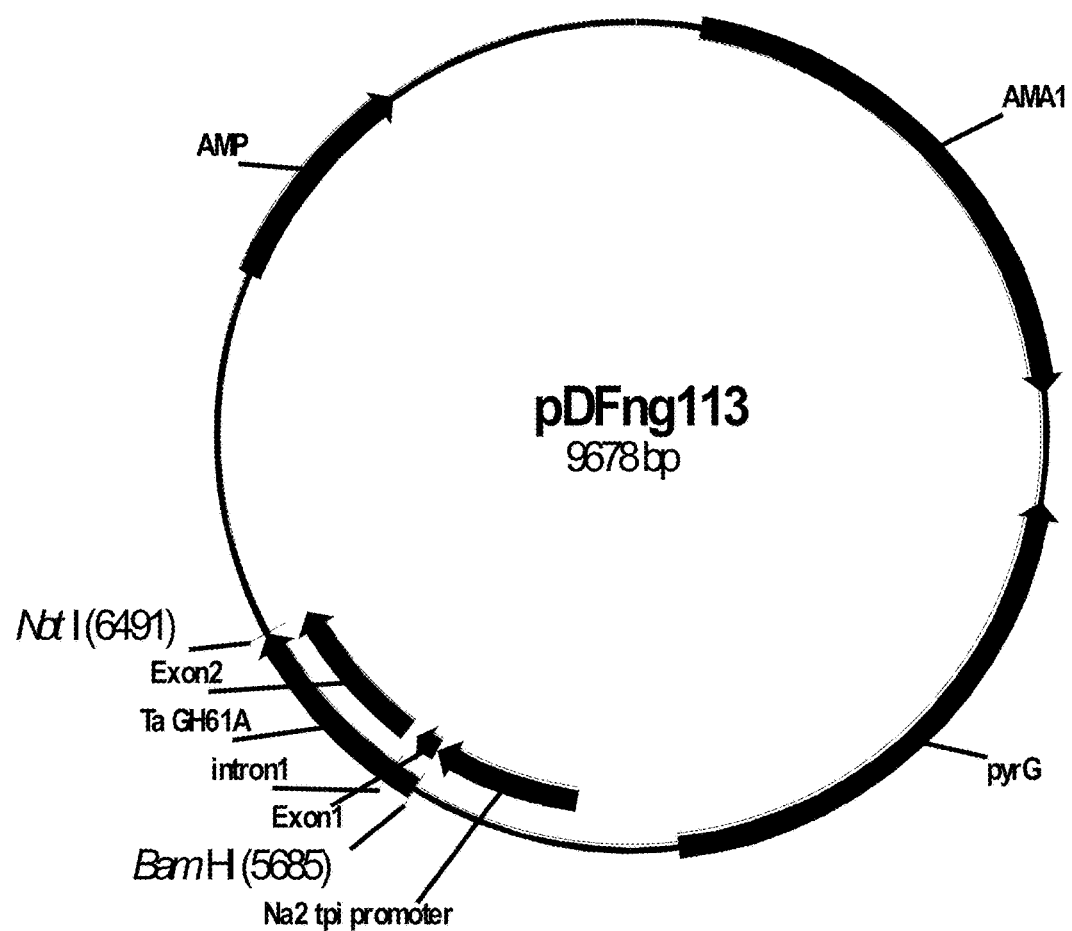
FIG. 5 shows a restriction map of plasmid pDFng113.

A plasmid containing the correct *T. aurantiacus* GH61A polypeptide coding sequence was selected and designated pDFng113 (FIG. 5).

Example 2: Construction of an *Aspergillus fumigatus* GH61B Polypeptide Site Saturation Library A site saturation library of the *Aspergillus fumigatus* GH61B polypeptide coding sequence was synthesized by GeneArt AG (Regensburg, Germany). An average of 16.8 mutations per position was synthesized for a total of 165 residues, excluding the most conserved residues, resulting in a total of 2768 mutants. *E. coli* DH10B (Invitrogen, Carlsbad, Calif., USA) strains containing mutant plasmids with known mutations were arrayed in 96 well plates as 50 µl glycerol stocks, and stored at −80° C.

DNA was generated from a thawed GeneArt plate by using a sterile 96 well replicator to stamp the GeneArt plate onto a 2XYT+Amp agar plate. The agar plate was incubated overnight at 37° C. Resulting colonies from the agar plate were used to inoculate a 96 deep well block with each well containing 1 ml of Magnificent broth supplemented with 400 µg of ampicillin per ml. The block was covered with an airpore breathable lid and then incubated in a humidified box at 37° C. overnight at 350 rpm. The block was centrifuged at 1100×g for 10 minutes and the supernatant discarded. Plasmids were extracted from the cell pellets using a BIOROBOT® 9600.

Example 3: Expression of the *A. fumigatus* GH61B, *P. emersonii* GH61A, and *T. aurantiacus* GH61A Polypeptide Variants in *Aspergillus oryzae* PFJO218

*Aspergillus oryzae* PFJO218 was inoculated onto a COVE-N-Gly plate with 10 mM uridine and incubated at 34° C. until confluent. Spores were collected from the plate by washing with 8 ml of 0.01% TWEEN® 20. One ml of the spore suspension was used to inoculate 103 ml of the Protoplasting cultivation medium in a 500 ml polycarbonate shake flask. The shake flask was incubated at 30° C. with agitation at 180 rpm for 17-20 hours. Mycelia were filtered through a funnel lined with MIRACLOTH® (Calbiochem, La Jolla, Calif., USA) and washed with 200 ml of 0.6 M MgSO$_4$. Washed mycelia were resuspended in 15 ml of Protoplasting solution in a 125 ml sterile polycarbonate shake flask and incubated on ice for 5 minutes. One ml of a solution of 12 mg of bovine serum albumin per ml of deionized water was added to the shake flask and the shake flask was then incubated at 37° C. with mixing at 70 rpm for 1-3 hours until protoplasting was complete. The mycelia/protoplast mixture was filtered through a funnel lined with MIRACLOTH® into a 50 ml conical tube and overlayed with 5 ml of ST. The 50 ml conical tube was centrifuged at 1050×g for 15 minutes with slow acceleration/deceleration. After centrifugation, the liquid was separated into 3 phases. The interphase which contained the protoplasts was transferred to a new 50 ml conical tube. Two volumes of STC were added to the protoplasts followed by a brief centrifugation at 1050×g for 5 minutes. The supernatant was discarded. The protoplasts were washed twice with 20 ml of STC with resuspension of the protoplast pellet, centrifugation at 1050×g for 10 minutes, and decanting of the supernatant each time. After the final decanting, the protoplast pellet was resuspended in STC at a concentration of 1×10$^8$/ml. Protoplasts were frozen at −80° C. until transformation.

A 1.3 µl volume of each mutant plasmid was used to transform 3.5 µl of *A. oryzae* PFJO218 protoplasts with 3.5 µl of PEG solution per well in a 24 well plate. Plasmid pMMar44, pMMar45, or pDFng113 (Table 1) was also transformed as above into *A. oryzae* PFJO218 protoplasts to provide broth comprising the *A. fumigatus*, *P. emersonii*, or *T. aurantiacus* wild-type GH61 polypeptides. The 24 well plate was incubated at 37° C. stationary for 30 minutes followed by addition of 28.6 µl of Transformation sucrose medium containing 10 mM NaNO$_3$ and 14.3 µl of STC. The 24 well plate was then placed in a humidified box at 37° C. stationary for 7 days. On day 7, 1 ml of MaltV1 medium was added to each well. The plate was returned to the humidified box at 39° C. stationary and incubated for an additional 5 days. At least 550 μl of broth for each variant or the wild-type *A. fumigatus, P. emersonii*, or *T. aurantiacus* GH61 polypeptide were harvested using a pipette to remove the mycelia mat and aspirate the liquid, for assay using PASC as a substrate. Mutant plasmids resulting in variants with improved thermostability using a PASC assay (Example 5) were transformed again and retested using the protocols described above.

Some of the variants were spore-purified for further characterization. After a 7 day incubation of the transformation and prior to the addition of 1 ml of MaltV1 expression medium, a loop was swiped over the initial growth from the transformation to collect spores in the well. The spores were then streaked onto a COVE-N-Gly plate and incubated at 37° C. for approximately 36 hours. Single individual transformants were excised from the plate and transferred onto fresh COVE-N-Gly plates. The plates were stored at 34° C. until confluent. Once confluent, a loop dipped in 0.01% TWEEN® 20 was swiped over the spores which was then used to inoculate a 24 well plate with each well containing 1 ml of MaltV1 expression medium. The 24 well plate was placed in a humidified box at 39° C. Samples were harvested on the fifth day by removing the mycelia mat and pipetting up the broth.

Example 4: Preparation of *Aspergillus fumigatus* Beta-Glucosidase

*Aspergillus fumigatus* NN055679 Cel3A beta-glucosidase (SEQ ID NO: 243 [DNA sequence] and SEQ ID NO: 244 [deduced amino acid sequence]) was recombinantly prepared according to WO 2005/047499 using *Aspergillus oryzae* as a host.

The filtered broth was adjusted to pH 8.0 with 20% sodium acetate, which made the solution turbid. To remove the turbidity, the solution was centrifuged at 20,000×g for 20 minutes, and the supernatant was filtered through a 0.2 μm filtration unit (Nalgene, Rochester, N.Y., USA). The filtrate was diluted with deionized water to reach the same conductivity as 50 mM Tris/HCl pH 8.0. The adjusted enzyme solution was applied to a Q SEPHAROSE® Fast Flow column (GE Healthcare, Piscataway, N.J., USA) equilibrated with 50 mM Tris-HCl pH 8.0 and eluted with a linear gradient from 0 to 500 mM sodium chloride. Fractions were pooled and treated with 1% (w/v) activated charcoal to remove color from the beta-glucosidase pool. The charcoal was removed by filtration of the suspension through a 0.2 μm filtration unit (Nalgene, Rochester, N.Y., USA). The filtrate was adjusted to pH 5.0 with 20% acetic acid and diluted 10 times with deionized water. The adjusted filtrate was applied to a SP SEPHAROSE® Fast Flow column (GE Healthcare, Piscataway, N.J., USA) equilibrated with 10 mM succinic acid pH 5.0 and eluted with a linear gradient from 0 to 500 mM sodium chloride. Protein concentration was determined using a Microplate BCA™ Protein Assay Kit (Thermo Fischer Scientific, Waltham, Mass., USA) in which bovine serum albumin was used as a protein standard.

Example 5: Screening of *Aspergillus fumigatus* GH61B Polypeptide Variant Libraries Using a BIOMEK® FX Laboratory Automation Workstation (Beckman Coulter, Fullerton, Calif., USA) with a DYAD® Thermal Cycler (Bio-Rad Laboratories, Inc., Richmond, Calif., USA), 80 μl of each broth sample from the library plates of the *Aspergillus fumigatus* GH61B variants and parent (wild-type) polypeptide grown in MaltV1 medium (Example 3) were mixed with 20 μl of 1 M sodium acetate-10 mM $MnSO_4$ pH 5.0 buffer. The samples were then heat challenged at 62° C., 65° C., and 68° C. for 20 minutes and compared to ambient temperature controls. After the heat challenge, the broth samples were diluted 1.25, 2.5, 6.25, and 15.625-fold in 2 mM $MnSO_4$-200 mM sodium acetate pH 5 and 12.5 μl of the dilutions were then transferred to 384-well polypropylene assay plates containing 25 μl of 1% phosphoric acid swollen cellulose (PASC) and 12.5 μl of a cofactor solution (400 mM sodium acetate pH 5, 4 mM $MnSO_4$, 0.4% gallic acid, 0.1 mg/ml of *Aspergillus fumigatus* beta-glucosidase, and 0.04% TRITON® X100). The plates were heat-sealed using an ALPS-300™ (Abgene, Epsom, United Kingdom) with a plastic sheet and incubated at 40° C. for 4 days.

Background glucose concentration of the buffer-treated broth samples was determined prior to incubation by performing a glucose assay using the following reagents per liter: 0.9951 g of ATP, 0.5176 g of NAD, 0.5511 g of $MgSO_4 \cdot 7H_2O$, 20.9 g of MOPS, 1000 units of hexokinase, 1000 units of glucose-6-phosphate dehydrogenase, and 0.01% TRITON® X-100, pH 7.5. The BIOMEK® FX Laboratory Automation Workstation was used for this assay. Four 2-fold serial dilutions were performed in 384-well polystyrene plates using water as diluent. Five μl of the dilutions were added to a new 384-well polystyrene plate, followed by addition of 60 μl of the above reagents. The plate was incubated at ambient temperature (22° C.±2° C.) for 30 to 45 minutes. Relative fluorescent units (RFU) were determined using a DTX 880 plate reader (Beckman Coulter, Fullerton, Calif., USA) with excitation at 360 nm and emission at 465 nm and compared to glucose standards (1 mg/ml and 0.125 mg/ml) diluted in the same plate as the samples. At the end of four days, the 40° C. incubated PASO plates were analyzed for glucose concentration using the glucose assay described above. Any background glucose was subtracted from the appropriate samples and then residual activity was calculated by comparing the glucose released in the PASO assay of the ambient sample treatment to the glucose released in the PASO assay of the heat challenge sample treatment. Only data that fits in the linear part of the curve (defined as less than or equal to 1 mg/ml glucose produced in an assay containing 5 mg/ml PASO) was used in the calculation. The formula for calculating the residual activity of the heat treatment was as follows: (mg/ml glucose produced for heat treated sample/mg/ml glucose produced for ambient treated sample)×100%. Improved variants were those having a higher % residual activity as compared to wild-type *A. fumigatus* GH61A polypeptide broth from MaltV1 medium in at least one heat treatment condition. MICROSOFT® EXCEL® (Microsoft Corporation, Redmond, Wash., USA) was used for all calculations.

Example 6: Thermostability of *Aspergillus fumigatus* GH61B Polypeptide Variants Measured by Residual Activity after Heat Treatment Based on the residual activity ratios as described in Example 5, screening of libraries constructed in the previous Examples generated the results listed in Tables 2 and 3.

Table 2 shows average % Residual Activity (from 3-5 samples of each variant and the wild type control) after treatment at 62, 65, or 68° C. The parent *Aspergillus fumigatus* GH61B polypeptide showed decreased residual activity of 70%, 45%, and 22% when the temperature was increased from 62° C. to 65° C. to 68° C., respectively. The increase in thermostability of the *Aspergillus fumigatus* GH61B polypeptide variants ranged from 1.03- to 1.1-fold increase at 62° C., 1.09- to 1.4-fold increase at 65° C., and 1.5- to 2.5-fold increase at 68° C. treatment compared to the wild-type *A. fumigatus* GH61 polypeptide. The results showed that improvements were most significant at 68° C. treatment.

TABLE 2

Variants with improved thermostability at 62° C., 65° C., and 68° C. treatment

| Variant | Avg % Res. Act. 62° C. treatment | Standard Deviation | Avg % Res. Act. 65° C. treatment | Standard Deviation | Avg % Res. Act. 68° C. treatment | Standard Deviation |
|---|---|---|---|---|---|---|
| Parent (Wild-Type) | 70% | 9% | 45% | 4% | 22% | 6% |
| E105K | 72% | 6% | 54% | 3% | 39% | 4% |
| E105P | 80% | 11% | 54% | 3% | 33% | 4% |
| E154L | 78% | 8% | 64% | 3% | 47% | 4% |
| G188A | 77% | 7% | 62% | 8% | 55% | 8% |
| G188W | 75% | 13% | 63% | 8% | 46% | 7% |
| N189K | 73% | 1% | 61% | 6% | 46% | 8% |
| A216L | 75% | 8% | 62% | 4% | 42% | 3% |
| A216Y | 77% | 6% | 59% | 3% | 42% | 3% |
| K229H | 76% | 13% | 59% | 2% | 40% | 3% |
| K229I | 76% | 3% | 56% | 2% | 36% | 6% |
| K229W | 66% | 8% | 49% | 9% | 43% | 10% |
| K229Y | 75% | 3% | 54% | 4% | 31% | 2% |

Table 3 shows average % Residual Activity (from 3-5 samples of each variant and 110 samples of the wild type control) after treatment at 62° C., 65° C., or 68° C. The parent *Aspergillus fumigatus* GH61B polypeptide showed decreased residual activity of 56%, 35%, and 12% when the temperature was increased from 62° C. to 65° C. to 68° C., respectively. The increase in thermostability of the *Aspergillus fumigatus* GH61B polypeptide variants ranged from 1.02-fold to 1.2-fold increase at 62° C., 1.14-fold to 1.6-fold increase at 65° C., and 2.08-fold to 3.25-fold increase at 68° C. treatment compared to the wild-type *A. fumigatus* GH61 polypeptide. The results showed that improvements were most significant at 68° C. treatment.

Example 7: Thermostability of *Aspergillus fumigatus* GH61B Combinatorial Variants Four variants of the *Aspergillus fumigatus* GH61B polypeptide were constructed by performing site-directed mutagenesis on pMMar49 (Example 1) using a QUIKCHANGE® II XL Site-Directed Mutagenesis Kit (Stratagene, La Jolla, Calif., USA). Two mutagenic primers were designed for each construct to insert the desired mutation. 125 ng of each primer (Table 4) was used in a PCR reaction containing approximately 25 ng of template plasmid, 1× QUIKCHANGE® reaction buffer, 3 µl of QUIK-SOLUTION®, 1 µl of XL dNTP mix, and 1 µl of 2.5 U/µl Pfu Ultra enzyme in a final volume of 50 µl. An EPPENDORF® MASTERCYCLER® thermocycler was used with the following settings: 95° C. hot start, one cycle at 95° C. for 1 minute; 18 cycles each at 95° C. for 50 seconds, 60° C. for 50 seconds, and 68° C. for 10 minutes; and 4° C. hold. One microliter of Dpn I was directly added to the amplification reaction and incubated at 37° C. for 1 hour. A 2 µl

TABLE 3

*Aspergillus fumigatus* GH61B polypeptide variants with improved thermostability at 62° C., 65° C., and 68° C. treatment

| Variant | Avg % Res. Act. 62° C. treatment | Standard Deviation | Avg % Res. Act. 65° C. treatment | Standard Deviation | Avg % Res. Act. 68° C. treatment | Standard Deviation |
|---|---|---|---|---|---|---|
| Parent (Wild-Type) | 56% | 13% | 35% | 16% | 12% | 10% |
| E105K | 61% | 24% | 50% | 23% | 38% | 21% |
| E105P | 57% | 23% | 44% | 21% | 32% | 21% |
| E154I | 68% | 13% | 57% | 16% | 34% | 9% |
| E154L | 56% | 26% | 41% | 23% | 25% | 20% |
| G188F | 56% | 21% | 45% | 22% | 33% | 27% |
| G188M | 61% | 13% | 51% | 13% | 34% | 15% |
| G188A | 57% | 24% | 44% | 25% | 39% | 24% |
| G188W | 52% | 24% | 40% | 25% | 31% | 26% |
| N189H | 60% | 18% | 44% | 19% | 26% | 18% |
| N189K | 51% | 23% | 41% | 24% | 30% | 21% |
| A216Y | 56% | 27% | 43% | 27% | 32% | 23% |
| A216L | 56% | 24% | 46% | 25% | 33% | 21% |
| K229W | 51% | 22% | 41% | 21% | 39% | 26% |
| K229H | 58% | 24% | 46% | 22% | 31% | 21% |
| K229I | 58% | 25% | 45% | 24% | 30% | 21% |
| K229Y | 55% | 23% | 43% | 22% | 28% | 18% | volume of the DpnI digested reaction was used to transform *E. coli* XL10-Gold Ultracompetent Cells (Stratagene, La Jolla, Calif.) according to the manufacturer's instructions. *E. coli* transformants were selected on 2XYT+Amp agar plates. One of the clones with the desired mutation was designated as each plasmid listed below.

Mutations G188A, G188W, K229W, and N189K were added individually on top of the *A. fumigatus* GH61B polypeptide variant containing mutations L111V, D152S, M155L, and A162W (pMMar49, Example 1), resulting in pLSBF09-1, pLSBF09-2, pLSBF09-3, and pLSBF09-4, respectively. A summary of the oligos used for the site-directed mutagenesis reactions are shown below in Table 4.

Three additional variants of *Aspergillus fumigatus* GH61B were constructed by performing site-directed mutagenesis on pLSBF09-3 using a QUIKCHANGE® 11 XL Site-Directed Mutagenesis Kit as described above. Mutations G188F, N189K, and A216Y were individually added as described, resulting in pDFNG146, pDFNG147, and pLSBF21. A summary of the oligos used for the site-directed mutagenesis reactions are shown below in Table 4.

The seven variant plasmids above were prepared using a BIOROBOT® 9600. The variant plasmid constructs were then sequenced using a 3130xl Genetic Analyzer (Applied Biosystems, Foster City, Calif., USA) to verify the changes.

Based on the residual activity ratios determined according to Example 5, screening of libraries constructed in the previous Examples generated the results listed in Table 5. Table 5 shows an average % Residual Activity (from 1-14 samples each for the combinatorial variants and 23 samples of the wild type) after treatment at 65° C., 68° C., or 72° C.

The parent *Aspergillus fumigatus* GH61B polypeptide showed decreased residual activity of 33%, 3%, and 1% when the temperature of treatment was increased from 65° C. to 68° C. to 72° C., respectively. The increase in thermostability of the *Aspergillus fumigatus* GH61B polypeptide combinatorial variants ranged from 1.66-fold to 2.42-fold increase at 65° C., 14.36-fold to 19.57-fold increase at 68° C., and 31.45-fold to 80.07-fold increase at 72° C. compared to the wild-type *A. fumigatus* GH61 polypeptide. The results showed that improvements were most significant at 72° C. treatment.

TABLE 4

| Plasmid | Mutation | Oligo ID # | Sequence |
|---|---|---|---|
| pLSBF09-1 | L111V, D152S, M155L, A162W, G188A | 615626 | ATCATCGCCCTTCACTCTGCGGCCAACCTGA ACGGCGCGCAGAAC (SEQ ID NO: 229) |
| | | 615630 | GTTCTGCGCGCCGTTCAGGTTGGCCGCAGA GTGAAGGGCGATGAT (SEQ ID NO: 230) |
| pLSBF09-2 | L111V, D152S, M155L, A162W, G188W | 615627 | ATCATCGCCCTTCACTCTGCGTGGAACCTGA ACGGCGCGCAGAAC (SEQ ID NO: 231) |
| | | 615631 | GTTCTGCGCGCCGTTCAGGTTCCACGCAGA GTGAAGGGCGATGAT (SEQ ID NO: 232) |
| pLSBF09-3 | L111V, D152S, M155L, A162W, K229W | 615628 | ACAAGAATACTGATCCTGGCATCTGGTTTGA CATCTACTCGGATCTGAG (SEQ ID NO: 233) |
| | | 615632 | CTCAGATCCGAGTAGATGTCAAACCAGATGC CAGGATCAGTATTCTTGT (SEQ ID NO: 234) |
| pLSBF09-4 | L111V, D152S, M155L, A162W, N189K | 615629 | TCGCCCTTCACTCTGCGGGTAAGCTGAACGG CGCGCAGAACTAC (SEQ ID NO: 235) |
| | | 615633 | GTAGTTCTGCGCGCCGTTCAGCTTACCCGCA GAGTGAAGGGCGA (SEQ ID NO: 236) |
| pDFng146 | L111V, D152S, M155L, A162W, G188F, K229W | 1200378 | ATCATCGCCCTTCACTCTGCGTTTAACCTGAA CGGCGCGCAGAAC (SEQ ID NO: 237) |
| | | 1200379 | GTTCTGCGCGCCGTTCAGGTTAAACGCAGAG TGAAGGGCGATGAT (SEQ ID NO: 238) |
| pDFng147 | L111V, D152S, M155L, A162W, N189K, K229W | 1200380 | TCGCCCTTCACTCTGCGGGTAAGCTGAACGG CGCGCAGAACTAC (SEQ ID NO: 239) |
| | | 1200381 | GTAGTTCTGCGCGCCGTTCAGCTTACCCGCA GAGTGAAGGGCGA (SEQ ID NO: 240) |
| pLSBF21 | L111V, D152S, M155L, A162W, A216Y, K229W | 1200277 | GTGCTCAGGGATCTGGCACCTACGGCACGT CCCTGTACAAGAATA (SEQ ID NO: 241) |
| | | 1200278 | TATTCTTGTACAGGGACGTGCCGTAGGTGCC AGATCCCTGAGCAC (SEQ ID NO: 242) |

TABLE 5

*Aspergillus fumigatus* GH61B polypeptide variants with improved thermostability at 65° C., 68° C., and 72° C. treatment

| Mutations | Avg % Res. Act. 65° C. | Standard Deviation | Avg % Res. Act. 68° C. | Standard Deviation | Avg % Res. Act. 72° C. | Standard Deviation |
|---|---|---|---|---|---|---|
| L111V, D152S, M155L, A162W, G188F, K229W | 55% | 10% | 56% | 2% | 51% | 7% |
| L111V, D152S, M155L, A162W, G188A | 77% | 8% | 56% | 6% | 30% | 5% |
| L111V, D152S, M155L, A162W, A216Y, K229W | 78% | 15% | 64% | 16% | 30% | 6% |
| L111V, D152S, M155L, A162W, K229W | 66% | 16% | 54% | 18% | 25% | 10% |
| L111V, D152S, M155L, A162W, N189K, K229W | 58% | ND | 47% | ND | 24% | ND |
| L111V, D152S, M155L, A162W, N189K | 67% | 8% | 52% | 4% | 20% | 18% |
| L111V, D152S, M155L, A162W, G188W | 80% | 10% | 57% | 10% | 20% | 11% |
| L111V, D152S, M155L, A162W | 53% | 11% | 34% | 7% | 7% | 6% |
| Wild-Type | 33% | 12% | 3% | 9% | 0.6% | 3% |

Example 8: Purification of *Aspergillus fumigatus* GH61B Polypeptide Variants

Expression and purification of the wild-type *Aspergillus fumigatus* GH61B polypeptide was conducted as previously described in WO 2012/044835.

The *Aspergillus fumigatus* GH61B polypeptide variant strains were grown to recover culture broths for purification. Following isolation of single colonies, *Aspergillus oryzae* PFJO218 transformants were cultured for 4 days at 34° C. on COVE-N-GLY plates in preparation for larger scale fermentation. Spores were recovered from each plate using 0.01% TWEEN® 20. Each spore suspension (500 µl) was inoculated into 25 ml of M400 medium in 125 ml plastic shake flasks. The transformants were fermented for 3 days at 39° C. with agitation at 150 rpm and the broths were collected and filtered using 0.22 µm filters. The filtered culture broths were then concentrated by centrifugal ultrafiltration using VIVACELL® 100 5 kDa MWCO centrifugal concentration devices (Sartorius Stedim, Goettingen, Germany) and then buffer exchanged into 20 mM Tris-HCl pH 8.5.

The concentrated and buffer exchanged *Aspergillus fumigatus* GH61B polypeptide variants were further purified by one of two chromatographic methods. In one method, the concentrated and buffer exchanged broths were then each applied to a MONO Q® HR 16/10 column (GE Healthcare, Piscataway, N.J., USA) equilibrated with 20 mM Tris-HCl pH 8.0. Bound proteins were eluted with a linear gradient of 0-600 mM sodium chloride in 20 mM Tris-HCl pH 8.0. Fractions were analyzed by SDS-PAGE using a CRITERION® Stain-Free Tris-HCl 8-16% SDS-PAGE gel (Bio-Rad Laboratories, Inc., Hercules, Calif., USA), pooled based on the abundance of an approximately 25 kDa band, and concentrated using VIVASPIN® 5 kDa MWCO centrifugal concentration devices (GE Healthcare, Buckinghamshire, United Kingdom). Alternatively, the concentrated and desalted broths were then each applied to a HILOAD® 26/60 SUPERDEX® 75 (GE Healthcare, Piscataway, N.J., USA) size exclusion column which had been equilibrated with 20 mM Tris-HCl pH 8.0 and 150 mM NaCl. Applied proteins were eluted isocraticly using 20 mM Tris-HCl pH 8.0 and 150 mM NaCl as the mobile phase. Fractions were analyzed by SDS-PAGE using a CRITERION® Stain-Free Tris-HCl 8-16% SDS-PAGE gel, pooled based on the abundance of an approximately 25 kDa band, and concentrated using VIVASPIN® 5 kDa MWCO centrifugal concentration devices.

Protein concentrations were determined using a Microplate BCA™ Protein Assay Kit in which bovine serum albumin was used as a protein standard.

Example 9: Determination of Tm (Melting Temperature) of the *Aspergillus fumigatus* Wild-Type GH61B Polypeptide and *Aspergillus fumigatus* GH61B Polypeptide Variants by Differential Scanning Calorimetry The thermostabilities of the *A. fumigatus* wild-type GH61B polypeptide and the *Aspergillus fumigatus* GH61B polypeptide variants, which were purified as described in Example 8, were determined by Differential Scanning calorimetry (DSC) using a VP Differential Scanning calorimeter (MicroCal Inc., GE Healthcare, Piscataway, N.J., USA). The melting temperature, Tm (° C.), was taken as the top of denaturation peak (major endothermic peak) in thermograms (Cp vs. T) obtained after heating a 1 mg protein per ml solution of the enzyme in 50 mM sodium acetate pH 5.0, 100 µM $CuSO_4$, or a 1 mg protein per ml solution of the enzyme in 50 mM sodium acetate pH 5.0, 10 mM EDTA pH 5.0, at a constant programmed heating rate. One ml of sample and reference-solutions were degassed at 25° C. using a ThermoVac (MicroCal Inc., GE Healthcare, Piscataway, N.J., USA) prior to loading of sample and reference cells of the calorimeter. Sample and reference (reference: degassed water) solutions were manually loaded into the DSC and thermally pre-equilibrated to 25° C. before the DSC scan was performed from 25° C. to 95° C. at a scan rate of 90 K/hour. Denaturation temperatures were determined at an accuracy of approximately +/−1° C. The results of the thermostability determination of the *A. fumigatus* GH61B polypeptide variants are shown in Table 6.

TABLE 6

Melting temperatures (° C.) of the *A. fumigatus* GH61B polypeptide and variants of the *A. fumigatus* GH61B polypeptide, as determined by differential scanning calorimetry

| Mutations | Tm + 100 μm CuSO$_4$ | Tm + 10 mM EDTA pH 5 |
|---|---|---|
| Wild-Type | 69 | 59 |
| G188A | 75 | n.d. |
| G188W | 75 | 63 |
| N189K | 74 | 63 |
| K229W | 74 | 63 |
| L111V + D152S + M155L + A162W | 76 | 66 |
| L111V + D152S + M155L + A162W + K229W | n.d. | 70 |
| L111V + D152S + M155L + A162W + G188F + K229W | 83 | 73 |

Example 10: Determination of Tm (Melting Temperature) of the *Aspergillus fumigatus* Wild-Type GH61B Polypeptide and *Aspergillus fumigatus* GH61B Polypeptide Variants by Protein Thermal Unfolding Analysis Protein thermal unfolding of the *Aspergillus fumigatus* GH61B polypeptide variants was monitored using SYPRO® Orange Protein Stain (Invitrogen, Naerum, Denmark) using a StepOnePlus™ Real-Time PCR System (Applied Biosystems Inc., Foster City, Calif., USA). In a 96-well white PCR-plate, 15 μl of a protein sample (prepared as described in Example 8) in 100 mM sodium acetate pH 5.0 was mixed (1:1) with Sypro Orange (resulting concentration=10×; stock solution=5000× in DMSO) in 20 mM EDTA. The plate was sealed with an optical PCR seal. The PCR instrument was set at a scan-rate of 76° C. per hour, starting at 25° C. and finishing at 96° C. Fluorescence was monitored every 20 seconds using a built-in LED blue light for excitation and ROX-filter (610 nm, emission). Tm-values were calculated as the maximum value of the first derivative (dF/dK) (Gregory et al., 2009, *J. Biomol. Screen.* 14: 700). The results of the thermostability determinations are shown in Table 7.

TABLE 7

Melting temperatures (° C.) of the *A. fumigatus* GH61B polypeptide and variants determined by thermal unfolding analysis

| Mutations | Tm |
|---|---|
| Wild-Type | 59 |
| E105P | 62 |
| E154L | 61 |
| A216Y | 60 |
| A216L | 63 |
| K229H | 61 |
| K229I | 60 |

Example 11: Preparation of a High-Temperature Cellulase Composition

*Aspergillus fumigatus* GH7A cellobiohydrolase I (SEQ ID NO: 245 [genomic DNA sequence] and SEQ ID NO: 246 [deduced amino acid sequence]) was prepared recombinantly in *Aspergillus oryzae* as described in WO 2011/057140. The filtered broth of the *Aspergillus fumigatus* GH7A cellobiohydrolase I was concentrated and buffer exchanged with 20 mM Tris-HCl pH 8.0 using a tangential flow concentrator (Pall Filtron, Northborough, Mass., USA) equipped with a 10 kDa polyethersulfone membrane (Pall Filtron, Northborough, Mass., USA).

*Aspergillus fumigatus* GH6A cellobiohydrolase II (SEQ ID NO: 247 [genomic DNA sequence] and SEQ ID NO: 248 [deduced amino acid sequence]) was prepared recombinantly in *Aspergillus oryzae* as described in WO 2011/057140. The filtered broth of the *Aspergillus fumigatus* GH6A cellobiohydrolase II was concentrated and buffer exchanged with 20 mM Tris-HCl pH 8.0 using a tangential flow concentrator equipped with a 10 kDa polyethersulfone membrane.

*Trichoderma reesei* GH5 endoglucanase II (SEQ ID NO: 249 [genomic DNA sequence] and SEQ ID NO: 250 [deduced amino acid sequence]) was prepared recombinantly in *Aspergillus oryzae* as described in WO 2011/057140. Filtered broth of the *Trichoderma reesei* GH5 endoglucanase II was concentrated and buffer exchanged with 20 mM Tris-HCl pH 8.0 using a tangential flow concentrator equipped with a 10 kDa polyethersulfone membrane.

*Aspergillus fumigatus* GH10 xylanase (xyn3) (SEQ ID NO: 251 [genomic DNA sequence] and SEQ ID NO: 252 [deduced amino acid sequence]) was prepared recombinantly according to WO 2006/078256 using *Aspergillus oryzae* BECh2 (WO 2000/39322) as a host. Filtered broth of the *Aspergillus fumigatus* NN055679 GH10 xylanase (xyn3) was desalted and buffer-exchanged with 50 mM sodium acetate pH 5.0 using a HIPREP® 26/10 Desalting column (GE Healthcare, Piscataway, N.J., USA) according to the manufacturer's instructions.

*Aspergillus fumigatus* Cel3A beta-glucosidase was prepared as described in Example 4.

*Aspergillus fumigatus* GH3 beta-xylosidase (SEQ ID NO: 253 [genomic DNA sequence] and SEQ ID NO: 254 [deduced amino acid sequence]) was prepared recombinantly in *Aspergillus oryzae* as described in WO 2011/057140 and purified according to WO 2011/057140.

The protein concentration for each of the monocomponents described above was determined using a Microplate BCA™ Protein Assay Kit in which bovine serum albumin was used as a protein standard. The cellulase composition was composed of 44.7% *Aspergillus fumigatus* Cel7A cellobiohydrolase I, 29.4% *Aspergillus fumigatus* Cel6A cellobiohydrolase II, 11.8% *Trichoderma reesei* GH5 endoglucanase II, 5.9% *Aspergillus fumigatus* GH10 xylanase (xyn3), 5.9% *Aspergillus fumigatus* beta-glucosidase, and 2.3% *Aspergillus fumigatus* beta-xylosidase. The cellulase composition is designated herein as a "high-temperature cellulase composition".

Example 12: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained approximately 59% cellulose, 5% hemicelluloses, and 28% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

The hydrolysis of PCS was conducted using 2.2 ml deep-well plates (Axygen, Union City, Calif., USA) in a total reaction volume of 1.0 ml. The hydrolysis was performed with 50 mg of PCS per ml of 50 mM sodium acetate pH 5.0 buffer containing 1 mM manganese sulfate and a protein loading of the high-temperature cellulase composition (expressed as mg protein per gram of cellulose). Enzyme mixtures were prepared and then added simultaneously to all wells in a volume of 100 µl, for a final volume of 1 ml in each reaction. The plate was then sealed using an ALPS-300™ plate heat sealer (Abgene, Epsom, United Kingdom), mixed thoroughly, and incubated at 50° C., 55° C., and 60° C. for 72 hours. All experiments were performed in triplicate.

Following hydrolysis, samples were filtered with a 0.45 µm MULTISCREEN® 96-well filter plate (Millipore, Bedford, Mass., USA) and filtrates analyzed for sugar content as described below. When not used immediately, filtered sugary aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at a flow rate of 0.6 ml per minute at 65° C., and quantitation by integration of glucose and cellobiose signals using a refractive index detector (CHEMSTATION®, AGILENT® 1100 HPLC, Agilent Technologies, Santa Clara, Calif., USA) calibrated by pure sugar samples. The resultant equivalents were used to calculate the percentage of cellulose conversion for each reaction.

All HPLC data processing was performed using MICROSOFT EXCEL™ software (Microsoft, Richland, Wash., USA). Measured sugar concentrations were adjusted for the appropriate dilution factor. Glucose and cellobiose were measured individually. However, to calculate total conversion the glucose and cellobiose values were combined. Cellobiose concentration was multiplied by 1.053 in order to convert to glucose equivalents and added to the glucose concentration. The degree of cellulose conversion was calculated using the following equation:

% conversion=([sample glucose concentration]/[glucose concentration in a limit digest])×100

In order to calculate % conversion, a 100% conversion point was set based on a cellulase control of 50 mg of the cellulase composition per gram cellulose (CELLUCLAST PLUS™, Novozymes A/S, Bagsvaerd, Denmark), and all values were divided by this number and then multiplied by 100. Triplicate data points were averaged and standard deviation was calculated.

Example 13: Effect of Addition of *Aspergillus fumigatus* GH61B Polypeptide Variants in the Conversion of PCS by a High-Temperature Cellulase Composition at 50° C., 55° C., and 60° C.

*A. fumigatus* GH61B wild-type polypeptide and *Aspergillus fumigatus* GH61B polypeptide variants N189K, G188W, K229W, and G188A were evaluated for their ability to enhance the hydrolysis of PCS by the high temperature cellulase composition (Example 11) at 50° C., 55° C., or 60° C. The pretreated corn stover hydrolysis assay was performed as described in Example 12. The high temperature composition when loaded at 3 mg total protein per gram cellulose in the assay had the following enzyme loadings per gram cellulose: 1.34 mg of *A. fumigatus* cellobiohydrolase I per gram cellulose, 0.88 mg of *A. fumigatus* cellobiohydrolase II per gram cellulose, 0.18 mg of *A. fumigatus* beta-glucosidase per gram cellulose, 0.18 mg of *Aspergillus fumigatus* GH10 xylanase (Xyl3) per gram cellulose, 0.18 mg of *A. fumigatus* beta-xylosidase per gram cellulose, and 0.35 mg of *T. reesei* CEL5A endoglucanase II per gram cellulose.

Figure 6:
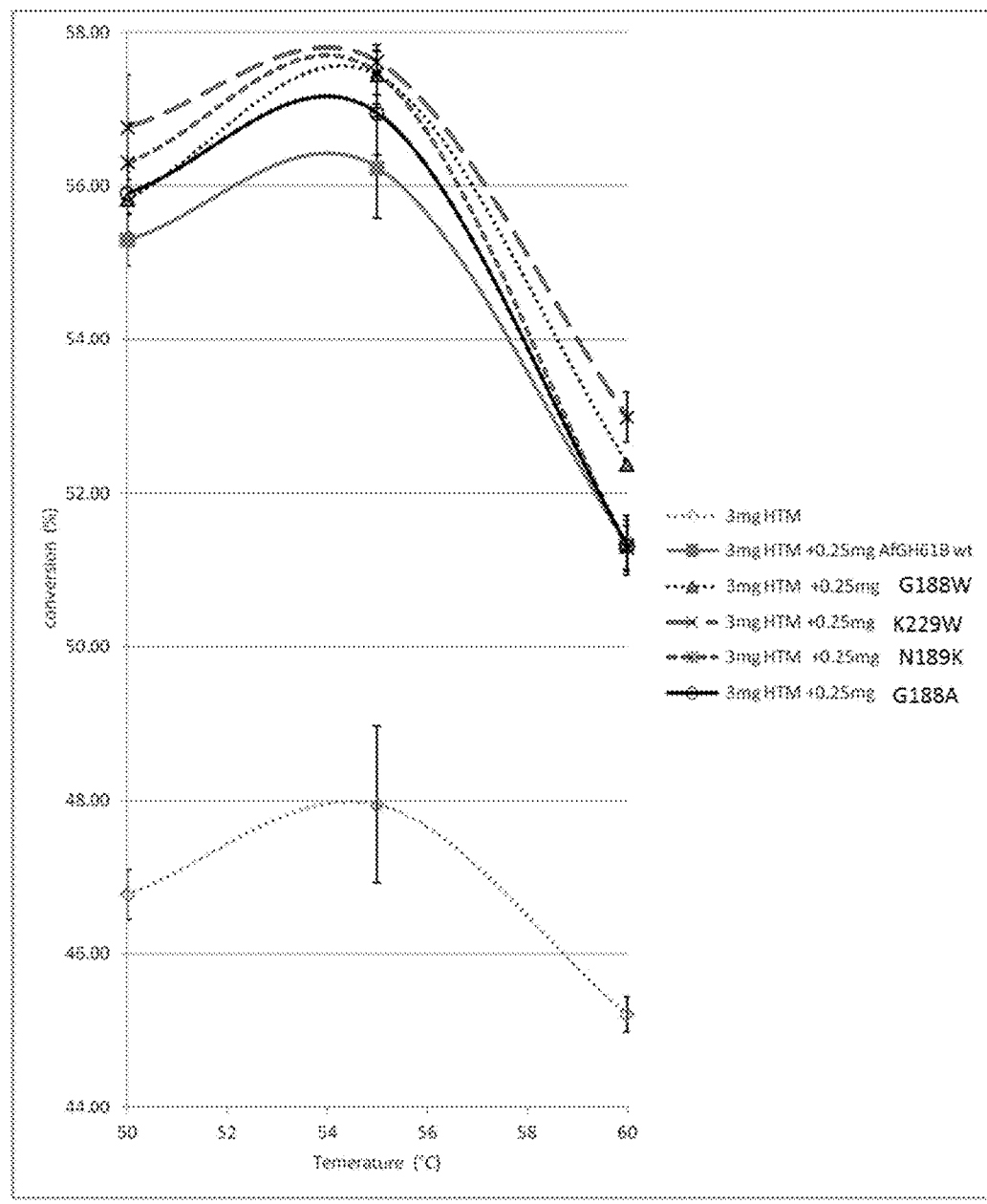
FIG. 6 shows the effect of addition of *Aspergillus fumigatus* GH61B polypeptide variants in the conversion of PCS by a high-temperature cellulase composition at 50° C., 55° C., and 60° C.

The conversion of pretreated corn stover by the high temperature cellulase composition (3 mg protein per gram cellulose); the combination of the high temperature cellulase composition (3 mg protein per gram cellulose) and *A. fumigatus* GH61B wild-type polypeptide (0.25 mg protein per gram cellulose); the combination of the high temperature cellulase composition (3 mg protein per gram cellulose) and *Aspergillus fumigatus* GH61B variant N168K polypeptide (0.25 mg protein per gram cellulose); the combination of the high temperature cellulase composition (3 mg protein per gram cellulose) and *Aspergillus fumigatus* GH61B variant G167W polypeptide (0.25 mg protein per gram cellulose); the combination of the high temperature cellulase composition (3 mg protein per gram cellulose) and *Aspergillus fumigatus* GH61B variant K208W polypeptide (0.25 mg protein per gram cellulose); and the combination of the high temperature cellulase composition (3 mg protein per gram cellulose) and *Aspergillus fumigatus* GH61B variant G167A polypeptide (0.25 mg protein per gram cellulose) were assayed as described in Example 12. Data were collected and analyzed, as described in Example 12, after 72 hours of incubation at 50° C., 55° C., or 60° C. These results are shown in FIG. 6.

The high temperature cellulase composition (3 mg protein per gram cellulose) resulted in conversions of 46.8±0.3%, 47.9±1.0%, and 45.2±0.2% at 50° C., 55° C., or 60° C., respectively, of the pretreated corn stover.

The combination of the high temperature cellulase composition (3 mg protein per gram cellulose) and *A. fumigatus* GH61B wild-type polypeptide (0.25 mg protein per gram cellulose) resulted in conversions of 55.3±0.3%, 56.2±0.7%, and 51.3±0.4% at 50° C., 55° C., or 60° C., respectively, of the pretreated corn stover.

The combination of the high temperature cellulase composition (3 mg protein per gram cellulose) and *A. fumigatus* GH61B variant N189K polypeptide (0.25 mg protein per gram cellulose) resulted in conversions of the pretreated corn stover of 56.3±0.5%, 57.5±0.3%, and 51.3±0.3% at 50° C., 55° C., or 60° C., respectively, of the pretreated corn stover.

The combination of the high temperature cellulase composition (3 mg protein per gram cellulose) and *A. fumigatus* GH61B variant G188W polypeptide (0.25 mg protein per gram cellulose) resulted in conversions of 55.8±0.4%, 57.5±0.4%, and 52.4±0.04% at 50° C., 55° C., or 60° C., respectively, of the pretreated corn stover.

The combination of the high temperature cellulase composition (3 mg protein per gram cellulose) and *A. fumigatus* GH61B variant K229W polypeptide (0.25 mg protein per gram cellulose) resulted in conversions of 56.8±0.7%, 57.6±0.1%, and 53.0±0.3% at 50° C., 55° C., or 60° C., respectively, of the pretreated corn stover.

The combination of the high temperature cellulase composition (3 mg protein per gram cellulose) and *A. fumigatus* GH61B variant G188A polypeptide (0.25 mg protein per gram cellulose) resulted in conversions of 55.9±0.3%, 56.9±0.5%, and 51.3±0.3% at 50° C., 55° C., or 60° C., respectively, of the pretreated corn stover.

Example 14: Construction of *Penicillium emersonii* GH61A and *Thermoascus aurantiacus* GH61A Polypeptide Variants Variants of the *Penicillium emersonii* GH61A polypeptide (SEQ ID NO: 35 [DNA sequence] and SEQ ID NO: 36 [amino acid sequence]), and *Thermoascus aurantiacus* GH61A polypeptide (SEQ ID NO: 13 [DNA sequence] and SEQ ID NO: 14 [amino acid sequence]) were constructed by performing site-directed mutagenesis on plasmids pMMar45 and pDFng113, respectively, using a QUIKCHANGE® Site-Directed Mutagenesis Kit (Stratagene, La Jolla, Calif., USA) as described in Example 7. A summary of the primers used for the site-directed mutagenesis and the variants obtained are shown in Table 8. The same protocol described in Example 7 was used.

The resulting mutant plasmid DNAs were prepared using a BIOROBOT® 9600. Each mutant plasmid was sequenced using a 3130xl Genetic Analyzer to verify the substitutions. The sequencing primers 996271 and pALLO2 3' were used for verification.

TABLE 8

| Variant Template Backbone | Amino Acid Substitution | Primer ID | Primer Sequence | Variant Plasmid Name |
|---|---|---|---|---|
| *Penicillium emersonii* GH61A | D109P | 615190 | GCAGTGGACGCCGTGGCCGCCGAG CCACCACGGACCCGTCAT (SEQ ID NO: 255) | pLSBF07-1 |
| | | 615201 | ATGACGGGTCCGTGGTGGCTCGGC GGCCACGGCGTCCACTGC (SEQ ID NO: 256) | |
| *Penicillium emersonii* GH61A | D109K | 615191 | GCAGTGGACGCCGTGGCCGAAGAG CCACCACGGACCCGTCAT (SEQ ID NO: 257) | pLSBF07-2 |
| | | 615202 | ATGACGGGTCCGTGGTGGCTCTTCG GCCACGGCGTCCACTGC (SEQ ID NO: 258) | |
| *Penicillium emersonii* GH61A | N192A | 615193 | CATCGCCCTGCACTCGGCCGCCAAC AAGGACGGCGCCCAGAAC (SEQ ID NO: 259) | pLSBF07-4 |
| | | 615204 | GTTCTGGGCGCCGTCCTTGTTGGCG GCCGAGTGCAGGGCGATG (SEQ ID NO: 260) | |
| *Penicillium emersonii* GH61A | N192W | 615194 | CATCGCCCTGCACTCGGCCTGGAAC AAGGACGGCGCCCAGAAC (SEQ ID NO: 261) | pLSBF07-5 |
| | | 615205 | GTTCTGGGCGCCGTCCTTGTTCCAG GCCGAGTGCAGGGCGATG (SEQ ID NO: 262) | |
| *Penicillium emersonii* GH61A | N193K | 615195 | CGCCCTGCACTCGGCCAACAAGAAG GACGGCGCCCAGAACTAC (SEQ ID NO: 263) | pLSBF07-6 |
| | | 615206 | GTAGTTCTGGGCGCCGTCCTTCTTG TTGGCCGAGTGCAGGGCG (SEQ ID NO: 264) | |
| *Thermoascus aurantiacus* GH61A | D105K | 615253 | GCTTCAATGGACTCCATGGCCTAAA TCTCACCATGGCCCAGTTATCA (SEQ ID NO: 265) | pDFng113-1 |
| | | 615254 | TGATAACTGGGCCATGGTGAGATTT AGGCCATGGAGTCCATTGAAGC (SEQ ID NO: 266) | |
| *Thermoascus aurantiacus* GH61A | D105P | 615255 | GCTTCAATGGACTCCATGGCCTCCT TCTCACCATGGCCCAGTTATCA (SEQ ID NO: 267) TGATAACTGGGCCATGGTGAGAAGG | pDFng113-3 |
| | | 615256 | AGGCCATGGAGTCCATTGAAGC (SEQ ID NO: 268) | |
| *Thermoascus aurantiacus* GH61A | Q188W | 615273 | GAGATTATTGCTCTTCACTCAGCTTG GAACCAGGATGGTGCCCAGAAC (SEQ ID NO: 269) | pDFng113-28 |
| | | 615275 | GTTCTGGGCACCATCCTGGTTCCAA GCTGAGTGAAGAGCAATAATCTC (SEQ ID NO: 270) | |

The *P. emersonii* GH61A polypeptide variants and *T. aurantiacus* GH61A polypeptide variants were expressed using *Aspergillus oryzae* PFJO218 as host was performed according to the procedure described in Example 3.

Example 15: Preparation of *Penicillium emersonii* Wild-Type GH61A Polypeptide and *P. emersonii* GH61A Polypeptide Variants The *P. emersonii* GH61A polypeptide wild-type and variant strains were grown as described in Example 8 to recover culture broths for purification.

The filtered culture broths were then concentrated by centrifugal ultrafiltration using VIVACELL® 20 5 kDa MWCO centrifugal concentration devices (Sartorius Stedim, Goettingen, Germany) and then buffer exchanged into 20 mM Tris-HCl pH 8.0. Protein concentrations were determined using a Microplate BCA™ Protein Assay Kit in which bovine serum albumin was used as a protein standard.

In the cases of *P. emersonii* GH61A wild-type polypeptide, *P. emersonii* GH61A polypeptide variant N192W, and *P. emersonii* GH61A polypeptide variant N193K, further purification was conducted by application of the concentrated and buffer exchanged broths to HITRAP® Q SEPHAROSE® Fast Flow columns (GE Healthcare, Piscataway, N.J., USA) equilibrated with 20 mM Tris-HCl pH 8.0. Bound proteins were eluted with a linear gradient of 0-500 mM sodium chloride in 20 mM Tris-HCl pH 8.0. Fractions were analyzed by SDS-PAGE using a CRITERION® Tris-HCl 8-16% SDS-PAGE gel (Bio-Rad Laboratories, Inc., Hercules, Calif., USA), pooled based on the abundance of an approximately 25 kDa band, and concentrated using VIVASPIN® 5 kDa MWCO centrifugal concentration devices. Protein concentrations were determined using a Microplate BCA™ Protein Assay Kit in which bovine serum albumin was used as a protein standard.

Example 16: Preparation of *Thermoascus aurantiacus* GH61A Polypeptide Variants The *T. aurantiacus* GH61A polypeptide wild-type and variant strains were grown as described in Example 8 to recover culture broths for purification.

The filtered culture broths were then concentrated by centrifugal ultrafiltration using VIVACELL® 20 5 kDa MWCO centrifugal concentration devices (Sartorius Stedim, Goettingen, Germany) and then buffer exchanged into 20 mM Tris-HCl pH 8.0. Protein concentrations were determined using a Microplate BCA™ Protein Assay Kit in which bovine serum albumin was used as a protein standard.

The purification was conducted by application of the concentrated and buffer exchanged broths to HITRAP® Q SEPHAROSE® Fast Flow columns equilibrated with 20 mM Tris-HCl pH 8.0. Bound proteins were eluted with a linear gradient of 0-500 mM sodium chloride in 20 mM Tris-HCl pH 8.0. Fractions were analyzed by SDS-PAGE using a CRITERION® Tris-HCl 8-16% SDS-PAGE gel, pooled based on the abundance of an approximately 25 kDa band, and concentrated using VIVASPIN® 5 kDa MWCO centrifugal concentration devices. Protein concentrations were determined using a Microplate BCA™ Protein Assay Kit in which bovine serum albumin was used as a protein standard.

Example 17: Determination of Tm (Melting Temperature) of the *P. emersonii* Wild-Type GH61A Polypeptide and *P. emersonii* GH61A Polypeptide Variants by Differential Scanning Calorimetry The thermostabilities of the *P. emersonii* wild-type GH61A polypeptide and the *P. emersonii* GH61A polypeptide variants, purified as described in Example 15, were determined by Differential Scanning calorimetry (DSC) using a VP Differential Scanning calorimeter. The melting temperature, Tm (° C.), was taken as the top of denaturation peak (major endothermic peak) in thermograms (Cp vs. T) obtained after heating a 1 mg protein per ml solution of the enzyme in 50 mM sodium acetate pH 5.0, 100 µM $CuSO_4$, or a 1 mg protein per ml solution of the enzyme in 50 mM sodium acetate pH 5.0, 10 mM EDTA pH 5.0, at a constant programmed heating rate. One ml of sample and reference-solutions were degassed at 25° C. using a ThermoVac prior to loading of sample and reference cells of the calorimeter. Sample and reference (reference: degassed water) solutions were manually loaded into the DSC and thermally pre-equilibrated to 25° C. before the DSC scan was performed from 25° C. to 95° C. at a scan rate of 90 K/hour. Denaturation temperatures were determined at an accuracy of approximately +/−1° C.

The results of the thermostability determination of the *P. emersonii* GH61A polypeptide variants are shown in Table 9.

TABLE 9

Melting temperatures (° C.) of *P. emersonii* GH61A polypeptide and variants of *P. emersonii* GH61A polypeptide, as determined by differential scanning calorimetry

| Enzyme sample | Tm + 100 µM $CuSO_4$ |
|---|---|
| *P. emersonii* GH61A | 82 |
| *P. emersonii* GH61A N192W | 84 |
| *P. emersonii* GH61A N193K | 83 |

Example 18: Determination of Tm (Melting Temperature) of *Penicillium emersonii* GH61A and *Thermoascus aurantiacus* GH61A Polypeptide Variants by Protein Thermal Unfolding Analysis Protein thermal unfolding of the *Penicillium emersonii* GH61A and *Thermoascus aurantiacus* GH61A polypeptide variants was monitored using SYPRO® Orange Protein Stain and was performed using a StepOnePlus™ Real-Time PCR System as described in Example 10. *P. emersonii* GH61A wild-type polypeptide and *P. emersonii* GH61A polypeptide variants were concentrated and buffer exchanged as described in Example 15. *T. aurantiacus* GH61A wild-type polypeptide and *T. aurantiacus* GH61A polypeptides variants were purified as described in Example 16. The results of the thermostability determination are shown in Table 10.

TABLE 10

Melting temperature (° C.) of *Penicillium emersonii* GH61A and *Thermoascus aurantiacus* GH61A polypeptide variants by protein thermal unfolding analysis

| Protein backbone | Sample type | Mutations | Tm |
|---|---|---|---|
| *P. emersonii* GH61A | Concentrated | Wild-Type | 69 |
| *P. emersonii* GH61A | Concentrated | D109P | 71 |
| *P. emersonii* GH61A | Concentrated | D109K | 70 |
| *P. emersonii* GH61A | Concentrated | N192A | 70 |
| *P. emersonii* GH61A | Concentrated | N192W | 71 |
| *P. emersonii* GH61A | Concentrated | N193K | 71 |
| *T. aurantiacus* GH61A | Purified | WT | 72 |
| *T. aurantiacus* GH61A | Purified | D105K | 74 |
| *T. aurantiacus* GH61A | Purified | D105P | 74 |
| *T. aurantiacus* GH61A | Purified | Q188W | 74 |

Example 19: Construction of Expression Vectors pDFng153-4, pDFng154-17, and pDFng155-33

Figure 7:
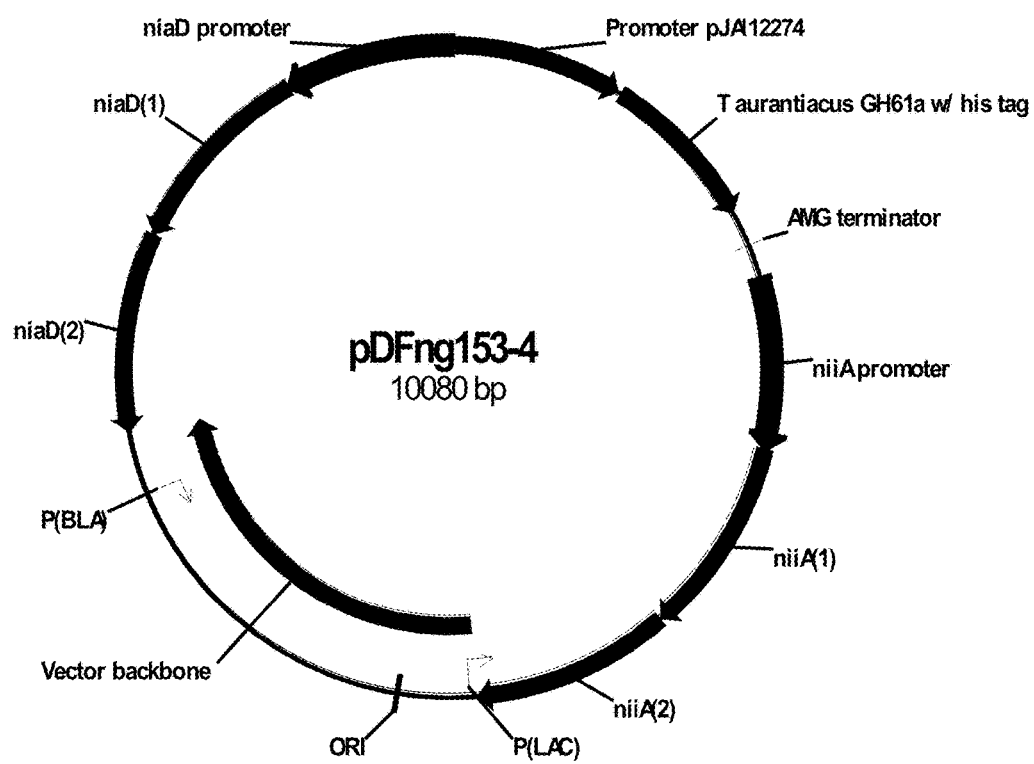
FIG. 7 shows a restriction map of plasmid pDFng153-4.
Figure 8:
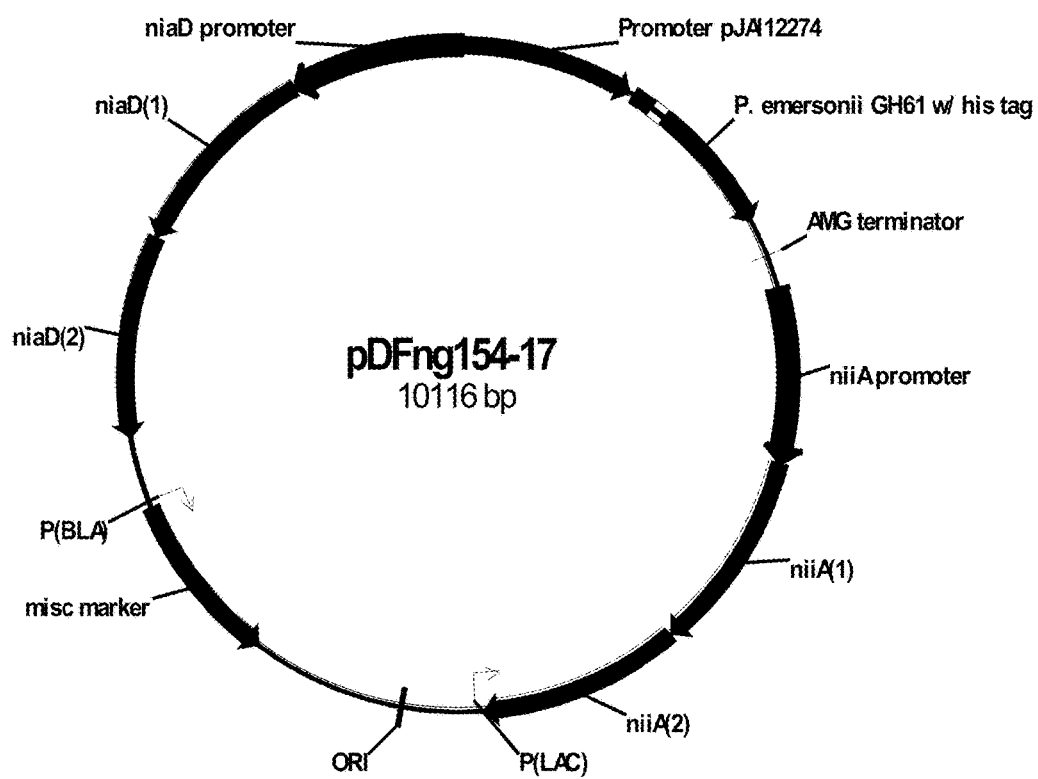
FIG. 8 shows a restriction map of plasmid pDFng154-17.
Figure 9:
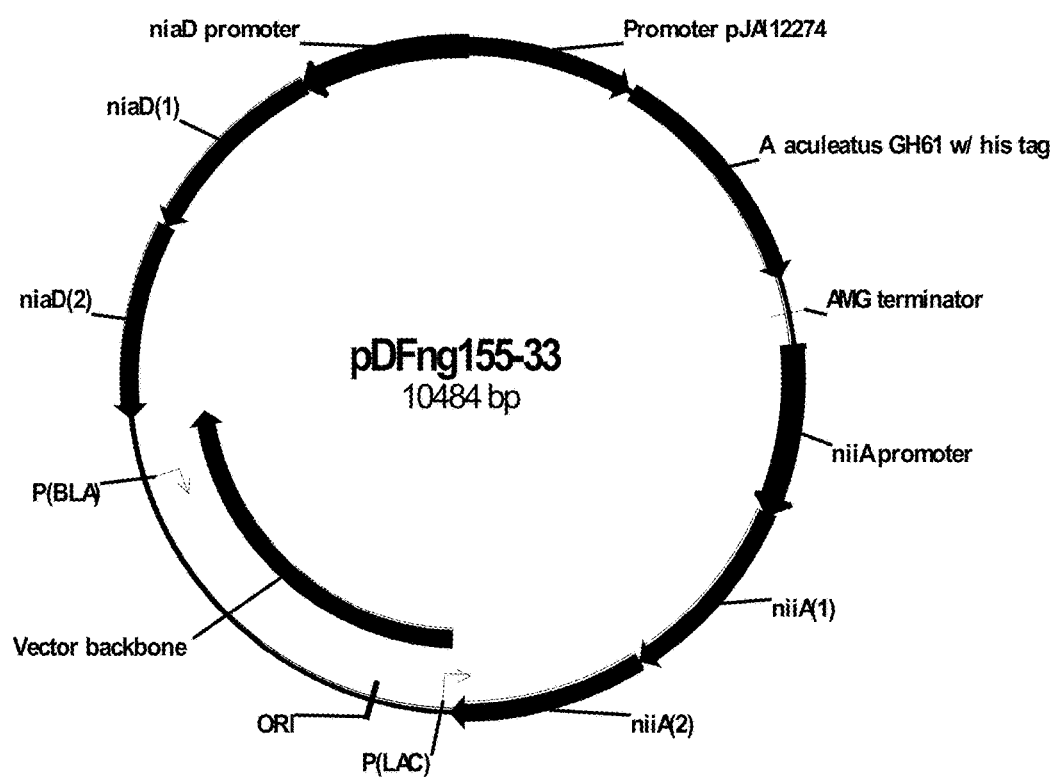
FIG. 9 shows a restriction map of plasmid pDFng155-33.
Figure 10:
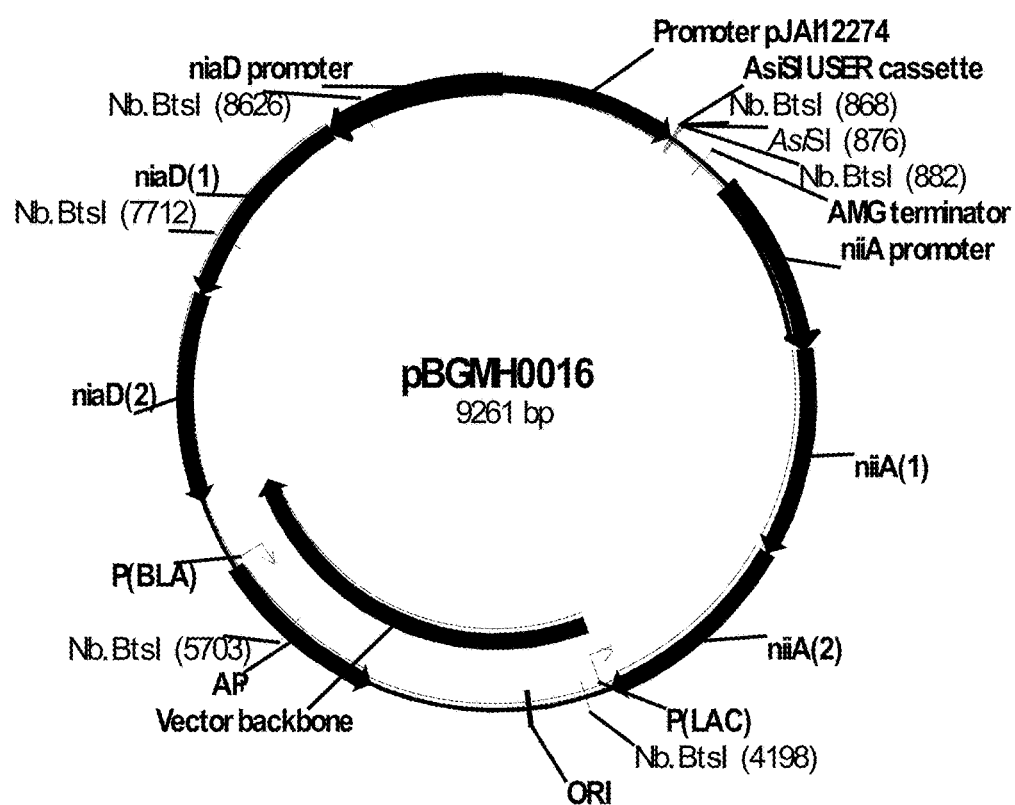
FIG. 10 shows a restriction map of plasmid pBGMH16.

Plasmids pDFng153-4 (FIG. 7), pDFng154-17 (FIG. 8), and pDFng155-33 (FIG. 9) were constructed as described below for expression of the *Thermoascus aurantiacus* GH61A polypeptide, *Penicillium emersonii* GH61A polypeptide, and *Aspergillus aculeatus* GH61 polypeptide, respectively, and generation of the variants listed in Table 11. The plasmids were constructed using plasmid pBGMH16 (FIG. 10).

Plasmid pBGMH16 was constructed according to the protocol described below. A Nb.BtsI recognition site in pUC19 was removed by PCR amplifying pUC19 with primer pair BGMH24/BGMH25 followed by the uracil-specific excision reagent USER™ based cloning (New England BioLabs, Ipswich, Mass., USA). Plasmid pUC19 is described in Yanisch-Perron et al., 1985, *Gene* 33(1):103-19.

BGMH 24
(SEQ ID NO: 271)
ATGCAGCGCUGCCATAACCATGAGTGA

BGMH 25
(SEQ ID NO: 272)
AGCGCTGCAUAATTCTCTTACTGTCATG

Underlined sequence is used in the USER™ assisted fusion of the PCR fragments creating pBGMH13. USER™ (Uracil-Specific Excision Reagent) Enzyme (New England Biolabs, Ipswich, Mass., USA) generates a single nucleotide gap at the location of a uracil. USER™ Enzyme is a mixture of Uracil DNA glycosylase (UDG) and the DNA glycosylase-lyase Endonuclease VIII. UDG catalyzes the excision of a uracil base, forming an abasic (apyrimidinic) site while leaving the phosphodiester backbone intact. The lyase activity of Endonuclease VIII breaks the phosphodiester backbone at the 3' and 5' sides of the basic site so that base-free deoxyribose is released.

The amplification reaction was composed of 100 ng of each primer, 10 ng of pUC19, 1×PfuTurbo® $C_x$ Reaction Buffer (Stratagene, La Jolla, Calif., USA), 2.5 µl of a blend of dATP, dTTP, dGTP, and dCTP, each at 10 mM, and 2.5 units of PfuTurbo® $C_x$ Hot Start DNA Polymerase (Stratagene, La Jolla, Calif., USA), in a final volume of 50 µl. The reaction was performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 3 minutes; and a final elongation at 72° C. for 7 minutes. Five µl of 10× NEBuffer 4 (New England Biolabs, Inc., Ipswich, Mass., USA), and 20 units of Dpn I were added and incubated 1 hour at 37° C. The Dpn I was inactivated at 80° C. for 20 minutes. A total of 100 ng of the PCR product and 1 unit of USER™ enzyme in a total volume of 10 µl were incubated 20 minutes at 37° C. followed by 20 minutes at 25° C. Ten µl were transformed into ONE SHOT® TOP10 competent cells. This resulted in plasmid pBHMG13.

Plasmid pBGMH14 contains part of pBGMH13 as vector backbone and a Pac I/Nt.BbvCI USER™ cassette (Hansen et al., 2011, *Appl. Environ. Microbiol.* 77(9): 3044-51) which is flanked by part of the *A. oryzae* niaD gene on one side and part of the *A. oryzae* niiA gene on the other side. The Pac I/Nt.BbvCI USER™ cassette can be linearized with Pac I and Nt.BbvCI and a PCR product with compatible overhangs can be cloned into this site (New England Biolabs, Ipswich, Mass., USA).

BGMH 27
(SEQ ID NO: 273)
AATTAAGUCCTCAGCGTGATTTAAAACGCCATTGCT

BGMH 28
(SEQ ID NO: 274)
ACTTAATUAAACCCTCAGCGCAGTTAGGTTGGTGTTCTTCT

BGMH 29
(SEQ ID NO: 275)
AGCTCAAGGAUACCTACAGTTATTCGAAA

BGMH 30
(SEQ ID NO: 276)
ATCCTTGAGCUGTTTCCTGTGTGAAATTGTTATCC

BGMH 31
(SEQ ID NO: 277)
ATCTCCTCUGCTGGTCTGGTTAAGCCAGCCCCGACAC

BGMH 32
(SEQ ID NO: 278)
AGAGGAGAUAATACTCTGCGCTCCGCC

Underlined sequence was used in the USER™ assisted fusion of the three fragments. The sequence marked in bold was used to introduce a PacI/Nt.BbvCI USER™ cassette (Hansen et al., 2011, supra) between the niiA and niaD fragments.

An *Aspergillus oryzae* niiA fragment was generated using primers BGMH27 and BGMH29. The primer pair BGMH28/BGMH32 was used to amplify the *Aspergillus oryzae* niaD gene region and primer-pair BGMH30/BGMH31 was used to amplify the plasmid backbone region.

Genomic DNA from *A. oryzae* BECH2 (WO 00/39322) was purified using a FASTDNA™ 2 ml SPIN Kit for Soil (MP Biomedicals, Santa Ana, Calif., USA).

The amplification reaction was composed of 100 ng of each primer, template DNA (pBGMH13 or *A. oryzae* BECH2 genomic DNA), 1×PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase, in a final volume of 50 µl. The reaction was performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 4 minutes; and a final elongation at 72° C. for 10 minutes. For PCR tubes where template DNA was a plasmid, 5 µl of 10× NEBuffer 4 and 20 units of Dpn I were added and incubated 1 hour at 37° C. The Dpn I was inactivated at 80° C. for 20 minutes. Fifty ng of each of the PCR products and 1 unit of USER™ enzyme in a total volume of 10 µl were incubated for 20 minutes at 37° C. followed by 20 minutes at 25° C. Then 10 µl were transformed into ONE SHOT® TOP10 competent cells. The three fragments were fused by uracil-specific excision reagent based cloning resulting in pBGMH14.

The promoter P13amy is a derivative of the NA-2tpi promoter from pJaL676 (WO 2003/008575). The *A. niger* AMG terminator used is described by Christensen et al., 1988, *Nature Biotechnology* 6: 141-1422.

The P13amy promoter and AMG terminator were cloned into the PacI/Nt.BbvCI USER™ cassette in pBGMH14. The primers were designed so that an AsiSI/Nb.BtsI USER™ cassette (Hansen et al., 2011, supra) was introduced between the promoter and terminator.

BGMH 49

(SEQ ID NO: 279)
GGGTTTAAUCCTCACACAGGAAACAGCTATGA

BGMH 50

(SEQ ID NO: 280)
AGTGTCTGCGAUCGCTCTCACTGCCCCCAGTTGTGTATATAGAGGA

BGMH 51

(SEQ ID NO: 281)
ATCGCAGACACUGCTGGCGGTAGACAATCAATCCAT

BGMH 52

(SEQ ID NO: 282)
GGACTTAAUGGATCTAAGATGAGCTCATGGCT

Underlined sequence was used in the USER™ assisted fusion of the two fragments into a PacI/Nt.BbvCI digested pBGMH14. The sequence marked in bold was used to introduce a AsiSI/Nb.BtsI USER™ cassette (Hansen et al., 2011, supra) between the promoter and terminator.

Promoter P13amy and AMG terminator was PCR amplified using the primer pair BGMH49/BGMH50 to amplify promoter P13amy and the primer pair BGMH51/BGMH52 to amplify the AMG terminator. The amplification reaction was composed of 100 ng of each primer, template DNA, 1×PfuTurbo® $C_x$ Reaction Buffer, 2.5 μl of a blend of dATP, dTTP, dGTP, and dCTP, each at 10 mM, and 2.5 units of PfuTurbo® $C_x$ Hot Start DNA Polymerase, in a final volume of 50 μl. The reaction was performed using a EPPENDORF® MASTERCYCLER® 5333 programmed for 1 cycle at 95° C. for 2 minutes; 32 cycles each at 95° C. for 30 seconds, 55° C. for 30 seconds, and 72° C. for 45 seconds; and a final elongation at 72° C. for 3 minutes. Then 5 μl of 10× NEBuffer 4 and 20 units of Dpn I were added and incubated 1 hour at 37° C. The Dpn I was inactivated at 80° C. for 20 minutes.

The two fragments were fused into PacI/Nt.BbvCI digested pBGMH14 by USER™ based cloning method in a reaction composed of 10 ng of PacI/Nt.BbvCI digested pBGMH14, 50 ng of each of the two PCR products, and 1 unit of USER™ enzyme in a total volume of 10 μl. The reaction was incubated for 20 minutes at 37° C. followed by 20 minutes at 25° C. Then 10 μl were transformed into ONE SHOT® TOP10 competent cells. E. coli transformants were selected on 2XYT+Amp agar plates and plasmid DNA was prepared using QIAPREP® Spin Miniprep Kit (QIAGEN Inc., Valencia, Calif., USA). Plasmid pBGMH16 was confirmed by sequencing analysis.

DNA sequencing was performed using a Model 377 XL Automated DNA Sequencer and dye-terminator chemistry (Giesecke et al., 1992, supra). Sequencing primers used for verification of niiA, niaD, the P13amy promoter, AsiSI/Nb.BtsI USER™ cassette, and AMG terminator sequence in BGMH16 are shown below.

(SEQ ID NO: 283)
BGMH 36 ACGCCATTGCTATGATGCTTGAAG (SEQ ID NO: 284)
BGMH 37 TGGTGAGGTGCTATCGTCCTT (SEQ ID NO: 285)
BGMH 38 CTTCCTGTAGGTGCACCGAAG (SEQ ID NO: 286)
BGMH 39 ACAGAACGATATCGGACCTCG (SEQ ID NO: 287)
BGMH 40 TCGTTATGTTAAGTCTTCTATCA (SEQ ID NO: 288)
BGMH 41 AGAGCTCGAAGTTCCTCCGAG (SEQ ID NO: 289)
BGMH 42 TATCACGAGGCCCTTTCGTCTC (SEQ ID NO: 290)
BGMH 43 TCCGTCGGCTCCTCTCCTTCGT (SEQ ID NO: 291)
BGMH 44 TGCATATCCTCTGACAGTATATGA (SEQ ID NO: 292)
BGMH 45 CAGTGAAGAGGGCAGTCGATAGT (SEQ ID NO: 293)
BGMH 46 ACGAGGAACATGGCTATCTGGA (SEQ ID NO: 294)
BGMH 47 TCAGCTCATTCTGGGAGGTGGGA (SEQ ID NO: 295)
BGMH 48 ACTCCAGGATCCTTTAAATCCA (SEQ ID NO: 296)
BGMH 53 ACTGGCAAGGGATGCCATGCT (SEQ ID NO: 297)
BGMH 54 TGATCATATAACCAATTGCCCT (SEQ ID NO: 298)
BGMH 55 AGTTGTGTATATAGAGGATTGA (SEQ ID NO: 299)
BGMH 56 TGGTCCTTCGCTCGTGATGTGGA (SEQ ID NO: 300)
BGMH 57 AGTCCTCAGCGTTACCGGCA (SEQ ID NO: 301)
BGMH 58 ACCCTCAGCTGTGTCCGGGA (SEQ ID NO: 302)
BGMH 59 TGGTATGTGAACGCCAGTCTG

Plasmid pBGMH16 contains flanking regions designed to repair the niiA gene and niaD gene in Aspergillus oryzae COLs1300. Plasmid pBGMH16 was digested with Asi Si and Nb. Bts I to linearize the plasmid and create single stranded overhangs so that a PCR product with compatible overhangs can be cloned into this site by USER™ cloning (New England Biolabs, Inc., Ipswich, Mass., USA). The digested plasmid was purified using a DNA Purification Kit (QIAGEN Inc., Valencia, Calif., USA) according to the manufacturer's instructions.

The T. aurantiacus GH61A polypeptide coding sequence (SEQ ID NO: 13 [genomic DNA sequence] and SEQ ID NO: 14 [deduced amino acid sequence]), P. emersonii GH61A polypeptide coding sequence (SEQ ID NO: 35 [genomic DNA sequence] and SEQ ID NO: 36 [deduced amino acid sequence]), and A. aculeatus GH61 polypeptide coding sequence (SEQ ID NO: 67 [genomic DNA sequence] and SEQ ID NO: 68 [deduced amino acid sequence]) were amplified from source plasmids described below using the primers shown in Table 11. Bold letters represent coding sequence. The single deoxyuridine (U) residue inserted into each primer is the U that is excised from the PCR products using the USER™ enzyme (New England Biolabs, Inc., Ipswich, Mass., USA) to obtain overhangs for the insertion site. The underline letters represent a His tag. The remaining sequences are homologous to insertion sites of pBGMH16 for expression of the GH61 polypeptides.

TABLE 11

| GH61 origin | Source Template | Plasmid | Primer ID | Primer Sequence |
|---|---|---|---|---|
| *Thermoascu-saurantiacus* GH61A | pDFng113 Example 1 | pDFng153-4 | TaGH61_USER tagF | AGAGCGA(U)ATGTCCTTTTCC AAGATAAT (SEQ ID NO: 303) |
|  |  |  | TaGH61_USER_ HIStagR | TCTGCGA(U)TTAGTGATGGTG GTGATGATGACCAGTATACAG AGGAGGAC (SEQ ID NO: 304) |
| *Penicillium emersonii* GH61A | pMMar45 Example 1 | pDFng154-17 | PeGH61_USER tagF | AGAGCGA(U)ATGCTGTCTTCG ACGACTCG (SEQ ID NO: 305) |
|  |  |  | PeGH61_USER_ HIStagR | TCTGCGA(U)CTAGTGATGGTG GTGATGATGGAACGTCGGCT CAGGCGGCC (SEQ ID NO: 306) |
| *Aspergillus aculeatus* GH61 | Xyz1566 (WO 2012/030799) | pDFng 155-33 | AaGH61_USER tagF | AGAGCGA(U)ATGTCTGTTGCT AAGTTTGCTGGTG (SEQ ID NO: 307) |
|  |  |  | AaGH61_USER_ HIStagR | TCTGCGA(U)TTAGTGATGGTG GTGATGATGGGCGGAGAGGT CACGGGCGT (SEQ ID NO: 308) |

Construction of plasmid pDFng153-4 containing the *Thermoascus aurantiacus* GH61A polypeptide coding sequence is described below. The *T. aurantiacus* GH61A polypeptide coding sequence was amplified from plasmid pDFng113 using the primers shown in Table 11 with overhangs designed for cloning into plasmid pBGMH16. The amplification was composed of 100 ng of each primer listed in Table 11, 30 ng of pDFng113, 1×PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase, in a final volume of 50 µl. The amplification was performed using an EPPENDORF® MASTERCYCLER® 5333 programmed for 1 cycle at 95° C. for 2 minutes; 30 cycles each at 95° C. for 30 seconds, 57.7° C. for 30 seconds, and 72° C. for 1.5 minutes; and a final elongation at 72° C. for 10 minutes. The heat block then went to a 10° C. soak cycle.

The PCR reaction was analyzed by 0.7% agarose gel electrophoresis using TBE buffer where an approximately 894 bp PCR product band was observed. The PCR reaction was then digested with 1 µl of Dpn I and 4.5 µl of NEBuffer 4 at 37° C. overnight and purified using a QIAGEN® Purification Kit according to the manufacturer's instructions.

The homologous ends of the 894 bp PCR reaction and the AsiSI and Nb.BtsI digested pBGMH16 were joined together in a reaction composed of 10 µl of the PCR containing the 894 bp PCR product, 1 µl of the AsiSI and Nb.BtsI digested plasmid pBGMH16, and 1 µl of USER™ enzyme (New England Biolabs, Inc., Ipswich, Mass., USA). The reaction was incubated for 15 minutes at 37° C., followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *T. aurantiacus* GH61A polypeptide coding sequence insert was confirmed by DNA sequencing using a Model 377 XL Automated DNA Sequencer and dye-terminator chemistry (Giesecke et al., 1992, supra). The sequencing primers shown below were used for verification of the gene insert and sequence.

Primer TaGH61seqF:
(SEQ ID NO: 309)
CCCAGTTATCAACTACCTTG

Primer pBGMH16seqF:
(SEQ ID NO: 310)
CTCAATTTACCTCTATCCAC

Primer pBGMH16seqR:
(SEQ ID NO: 311)
TATAACCAATTGCCCTCATC

A plasmid containing the correct *T. aurantiacus* GH61A polypeptide coding sequence was selected and designated pDFng153-4.

Construction of plasmid pDFng154-17 containing the *Penicillium emersonii* GH61A polypeptide coding sequence is described below. The *P. emersonii* GH61A polypeptide coding sequence was amplified from plasmid pMMar45 using the primers shown in Table 11 with overhangs designed for cloning into plasmid pBGMH16. The amplification was composed of 100 ng of each primer listed in Table 11, 30 ng of pMMar45, 1×PfuTurbo® $C_x$ Reaction Buffer, 2.5 µl of a blend of dATP, dTTP, dGTP, and dCTP, each at 10 mM, and 2.5 units of PfuTurbo® $C_x$ Hot Start DNA Polymerase, in a final volume of 50 µl. The amplification was performed using an EPPENDORF® MASTERCYCLER® 5333 programmed for 1 cycle at 95° C. for 2 minutes; 30 cycles each at 95° C. for 30 seconds, 64.1° C. for 30 seconds, and 72° C. for 1.5 minutes; and a final elongation at 72° C. for 10 minutes. The heat block then went to a 10° C. soak cycle.

The PCR reaction was analyzed by 0.7% agarose gel electrophoresis using TBE buffer where an approximately 930 bp PCR product band was observed. The PCR reaction was then digested with 1 µl of Dpn I and 4.5 µl of NEBuffer 4 at 37° C. overnight and purified using a QIAGEN® Purification Kit according to the manufacturer's instructions.

The homologous ends of the 930 bp PCR reaction and the AsiSI and Nb.BtsI digested pBGMH16 were joined together in a reaction composed of 10 µl of the PCR containing the 930 bp PCR product, 1 µl of the AsiSI and Nb.BtsI digested pBGMH16, and 1 µl of USER™ enzyme. The reaction was incubated for 15 minutes at 37° C., followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *P. emersonii* GH61A polypeptide coding sequence insert was confirmed by DNA sequencing using a Model 377 XL Automated DNA Sequencer and dye-terminator chemistry (Giesecke et al., 1992, supra). The sequencing primers pBGMH16seqF and pBGMH16seqR and primer PeGH61seqF shown below were used for verification of the gene insert and sequence.

```
PeGH61seqF:
                              (SEQ ID NO: 312)
GCACCGTCGAGCTGCAGTGG
```

A plasmid containing the correct *P. emersonii* GH61A polypeptide coding sequence was selected and designated pDFng154-17.

Construction of plasmid pDFng155-33 containing the *Aspergillus aculeatus* GH61A polypeptide coding sequence is described below. The *A. aculeatus* GH61A polypeptide coding sequence was amplified from plasmid Xyz1566 (WO 2012/030799 Example 3, P23NJ4 gene) using primers shown in Table 11 with overhangs designed for cloning into plasmid pBGMH16. The amplification reaction was composed of 100 ng of each primer listed in Table 11, 30 ng of plasmid Xyz1566, 1×PfuTurbo® C$_x$ Reaction Buffer, 2.5 µl of a blend of dATP, dTTP, dGTP, and dCTP, each at 10 mM, and 2.5 units of PfuTurbo® C$_x$ Hot Start DNA Polymerase, in a final volume of 50 µl. The amplification was performed using an EPPENDORF® MASTERCYCLER® 5333 programmed for 1 cycle at 95° C. for 2 minutes; 30 cycles each at 95° C. for 30 seconds, 63.4° C. for 30 seconds, and 72° C. for 1.5 minutes; and a final elongation at 72° C. for 10 minutes. The heat block then went to a 10° C. soak cycle.

The PCR reaction was analyzed by 0.7% agarose gel electrophoresis using TBE buffer where an approximately 1.3 kb PCR product band was observed. The PCR reaction was then digested with 1 µl of Dpn I and 4.5 µl of NEBuffer 4 at 37° C. overnight and purified using a QIAGEN® Purification Kit according to the manufacturer's instructions.

The homologous ends of the 1.3 kb PCR reaction and the digested pBGMH16 were joined together in a reaction composed of 10 µl of the PCR containing the 1.3 kb PCR product, 1 µl of the digested pBGMH16, and 1 µl of USER™ enzyme. The reaction was incubated for 15 minutes at 37° C., followed by 15 minutes at 25° C. Ten µl of the reaction were transformed into *E. coli* XL10-GOLD® Super Competent Cells according to the manufacturer's instructions. *E. coli* transformants were selected on 2XYT+Amp agar plates. Plasmid DNA from several of the resulting *E. coli* transformants was prepared using a BIOROBOT® 9600. The *A. aculeatus* GH61A polypeptide coding sequence insert was confirmed by DNA sequencing using a Model 377 XL Automated DNA Sequencer and dye-terminator chemistry (Giesecke et al., 1992, supra). The sequencing primers pBGMH16seqF and pBGMH16seqR and primer AaGH61seqF shown below were used for verification of the gene insert and sequence.

```
Primer AaGH61seqF:
                              (SEQ ID NO: 313)
CCTTGCCAACTGCAATGGTG
```

A plasmid containing the correct *A. aculeatus* GH61A polypeptide coding sequence was selected and designated pDFng155-33.

Example 20: Construction of the *Thermoascus aurantiacus* GH61A and *Penicillium emersonii* GH61A Polypeptide Variants Variants of the *T. aurantiacus* GH61A and *P. emersonii* GH61A polypeptides were constructed by performing site-directed mutagenesis on plasmids pDFng153-4 and pDFng154-17, respectively, according to the procedure described in Example 7 using the primers described in Table 12.

The sequencing primers pBGMH16seqF, pBGMH16seqR, and TaGH61seqF (used only for *T. aurantiacus* GH61A variants), and primer PeGH61seqR shown below (used only for *P. emersonii* GH61A variants) were used for verification.

```
PeGH61seqR (only used for P. emersonii GH61A
variants):
                              (SEQ ID NO: 314)
GCACCGTCGAGCTGCAGTGG
```

TABLE 12

| Variant Template Backbone | Amino Acid Substi- tution | Primer ID | Primer Sequence | Variant Plasmid Name |
|---|---|---|---|---|
| Thermoascu- saurantiacus GH61A (pDFng153-4) | Q188F | 1202295 | ATTATTGCTCTTCACTCAGCTTTCAACCAGGA TGGTGCCCAGAAC (SEQ ID NO: 315) | TaSDM2 |
| | | 1202296 | GTTCTGGGCACCATCCTGGTTGAAAGCTGAG TGAAGAGCAATAAT (SEQ ID NO: 316) | |
| | Q188M | 1202297 | ATTATTGCTCTTCACTCAGCTATGAACCAGGA TGGTGCCCAGAAC (SEQ ID NO: 317) | TaSDM3 |
| | | 1202298 | GTTCTGGGCACCATCCTGGTTCATAGCTGAG TGAAGAGCAATAAT (SEQ ID NO: 318) | |
| Penicillium emersonii GH61A (pDFng154- 17) | N192M | 1202305 | CCCTGCACTCGGCCATGAACAAGGACGGCG C (SEQ ID NO: 319) | PeSDM6 |
| | | 1202306 | GCGCCGTCCTTGTTCATGGCCGAGTGCAGG G (SEQ ID NO: 320) | |
| | N193H | 1202307 | GCACTCGGCCAACCACAAGGACGGCGCCC (SEQ ID NO: 321) | PeSDM7 |
| | | 1202308 | GGGCGCCGTCCTTGTGGTTGGCCGAGTGC (SEQ ID NO: 322) | |

PCR fragments were amplified from the mutant plasmids, the *T. aurantiacus* GH61A polypeptide plasmid pDFng153-4, and the *P. emersonii* GH61A polypeptide plasmid pDFng154-17 for *A. oryzae* COLs1300 transformation. The amplification was composed of 10 µM each of primers 1201513 and 1201514 (see below), 10 ng of either pDFng153-4, pDFng154-17, or one of the mutant plasmids, 5× PHUSION® High-Fidelity Buffer (New England Biolabs, Inc., Ipswich, Mass., USA), 1 µl of a blend of dATP, dTTP, dGTP, and dCTP, each at 10 mM, and 0.5 µl of PHUSION® High-Fidelity DNA polymerase (New England Biolabs, Inc., Ipswich, Mass., USA), in a final volume of 50 µl. For pDFng154-17 and the *P. emersonii* GH61 polypeptide mutant plasmids, 1.5 µl of DMSO were also added. The amplification was performed using an EPPENDORF® MASTERCYCLER® 5333 programmed for 1 cycle at 98° C. for 30 seconds; 10 cycles each at 98° C. for 10 seconds, 65° C. minus 1° C. per cycle for 30 seconds, and 72° C. for 3 minutes; 25 cycles each at 98° C. for 10 seconds, 55° C. at 30 seconds, and 72° C. for 3 minutes; and a final elongation at 72° C. for 10 minutes. The heat block then went to a 10° C. soak cycle.

```
Primer 1201513:
                              (SEQ ID NO: 323)
CCAGACCAGCAGAGGAGATAATACT Primer 1201514:
                              (SEQ ID NO: 324)
CAAGGATACCTACAGTTATTCGA
```

Each PCR reaction was analyzed by 0.7% agarose gel electrophoresis using TBE buffer where either a 7718 bp PCR product from *T. aurantiacus* or a 7754 bp PCR product band from *P. emersonii* was observed. The PCR reaction was then digested with 1 µl of Dpn 1 and 4.5 µl of NEBuffer 4 at 37° C. overnight and purified using a QIAGEN® Purification Kit according to the manufacturer's instructions.

Example 21: Construction of *Aspergillus aculeatus* GH61 Polypeptide Variants

The *Aspergillus aculeatus* GH61 polypeptide variants were constructed by SOE-PCR (Splicing by Overhang Extension Polymerase Chain Reaction) with plasmid pDFng155-33. In brief, the first PCR reaction used forward primer BGMH110V2F and a mutation specific reverse primer (Table 13). The second PCR reaction used a reverse primer BGMH109V2R and a mutation specific forward primer (Table 13) containing the sequence coding for the altered amino acid. The mutation specific forward and reverse primers contained 15-20 overlapping nucleotides. The third PCR reaction used the overlapping nucleotides to splice together the fragments produced in the first and second reaction. Finally, using forward primer BGMH110V2F and reverse primer BGMH109V2R, the spliced fragment was amplified by PCR.

```
Primer BGMH110V2F:
                              (SEQ ID NO: 325)
5'-CCAGACCAGCAGAGGAGATAATACTCTGCG-3'

Primer BGMH109V2R:
                              (SEQ ID NO: 326)
5'-CAAGGATACCTACAGTTATTCGAAACCTCCTG-3'
```

The first SOE-PCR reactions for the *A. aculeatus* GH61 polypeptide variants contained 0.5 picomole of the BGMH110V2F primer, 0.5 picomole of the reverse primer listed in Table 13, 50 ng of template (pDFng155-33), 5 nanomoles each dATP, dTTP, dGTP, and dCTP, 1× PHUSION® High-Fidelity Buffer, and 0.7 unit of PHUSION® High-Fidelity DNA Polymerase, in a final reaction volume of 50 µl. The amplification was performed using an EPPENDORF® MASTERCYCLER® Gradient (Eppendorf Scientific, Inc., Westbury, N.Y., USA) programmed for 1 cycle at 98° C. for 2 minutes; 35 cycles each at 98° C. for 25 seconds, 66° C. for 30 seconds, and 72° C. for 5 minute; and a final elongation at 72° C. for 10 minutes. The heat block then went to a 10° C. hold stage.

The second SOE-PCR reactions for the *A. aculeatus* GH61 variants contained 0.5 picomole of the forward primer listed in Table 13, 0.5 picomole of the BGMH109V2R primer, 50 ng of template (pDFng155-33), 5 nanomoles each dATP, dTTP, dGTP, and dCTP, 1× PHUSION® High-Fidelity Buffer, and 0.7 unit of PHUSION® High-Fidelity DNA Polymerase, in a final reaction volume of 50 µl. The amplification was performed using an EPPENDORF® MASTERCYCLER® Gradient programmed for 1 cycle at 98° C. for 2 minutes; 35 cycles each at 98° C. for 25 seconds, 66° C. for 30 seconds, and 72° C. for 5 minutes; and a final elongation at 72° C. for 10 minutes. The heat block then went to a 10° C. hold stage.

Each PCR reaction was analyzed by 1.0% agarose electrophoresis using TAE buffer where a 3.9 to 6.5 kb (as specified in Table 13) PCR product band was observed indicating proper amplification. The remaining 45 microliters were then treated with 10 units of Dpn I and 1×NEB4 to remove the remaining wild-type template. The reaction was incubated for 1 hour at 37° C. and then purified using a MINELUTE® 96 UF Purification Kit (QIAGEN Inc., Valencia, Calif., USA). The purified PCR products were resuspended in deionized water to a final volume equal to 20 µl. The concentration of each fragment was measured using a NanoDrop 2000 (Thermo Scientific, Wilmington, Del., USA).

The third PCR reaction for the *A. aculeatus* GH61 variants contained 100 to 200 ng of each fragment produced in the first and second SOE-PCR reactions, 5 nanomoles each dATP, dTTP, dGTP, and dCTP, 1× PHUSION® High-Fidelity Buffer, and 0.7 units PHUSION® High-Fidelity DNA Polymerase, in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage. Primer BGMH110V2F primer (0.5 picomole) and primer BGMH109V2R (0.5 picomole) were added during the annealing/elongation step of the fifth cycle to allow for the overlapping nucleotides to splice.

The wild-type fragment was produced using conditions similar to the third PCR reaction. The reaction was composed of 50 ng of template (pDFng155-33), 0.5 picomole of primer BGMH110V2F, 0.5 picomole of primer BGMH109V2R, 5 nanomoles each dATP, dTTP, dGTP, and dCTP, 1× PHUSION® High-Fidelity Buffer, and 0.7 units PHUSION® High-Fidelity DNA Polymerase, in a final reaction volume of 50 µl. The amplification was performed using an EPPENDORF® MASTERCYCLER® Gradient programmed for 1 cycle at 98° C. for 2 minutes; 35 cycles each at 98° C. for 15 seconds, 68° C. for 30 seconds, and 72° C. for 10 minutes; and a final elongation at 72° C. for 10 minutes. The heat block then went to a 10° C. hold stage.

Each PCR reaction was analyzed by 1.0% agarose electrophoresis using TAE buffer where an approximately 8 kb PCR product band was observed indicating proper amplification. The remaining 45 μl of each PCR reaction were then purified using a MINELUTE® 96 UF Purification Kit. The purified PCR products were resuspended in deionized water to a final volume equal to 20 μl. The concentration of each fragment was measured using a NanoDrop 2000. The entire volume was then transformed into the *Aspergillus oryzae* COLs1300 strain as described in Example 22.

suspension was used to inoculate 101 ml of COL1300 protoplasting cultivation medium in a 500 ml polycarbonate shake flask. The shake flask was incubated at 30° C. with agitation at 200 rpm for 18-24 hours. Mycelia were filtered through a funnel lined with MIRACLOTH® and washed with 200 ml of 0.6 M $MgSO_4$. Washed mycelia were resuspended in 10 ml of COLs1300 protoplasting solution in a 125 ml sterile polycarbonate shake flask and incubated at room temperature for 3 minutes. One ml of a solution of 12 mg of BSA per ml of deionized water was added to the shake

TABLE 13

| Template Backbone | Amino Acid Substitution | Primer ID | Primer Direction | Primer Sequence | PCR fragment size (kb) |
|---|---|---|---|---|---|
| *Aspergillus aculeatus* GH61 | D103K | 1202768 | Fwd | TCCAGTGGACTACCTGGCCCAAGAGCCACCA CGGCCCTGTCC (SEQ ID NO: 327) | 4.1 |
| | | 1202769 | Rev | GGGCCAGGTAGTCCACTGGAGCTCAACAGTA C (SEQ ID NO: 328) | 6.5 |
| *Aspergillus aculeatus* GH61 | D103P | 1202770 | Fwd | TCCAGTGGACTACCTGGCCCCCCAGCCACCA CGGCCCTGTCC (SEQ ID NO: 329) | 4.1 |
| | | 1202769 | Rev | GGGCCAGGTAGTCCACTGGAGCTCAACAGTA C (SEQ ID NO: 330) | 6.5 |
| *Aspergillus aculeatus* GH61 | N152I | 1202771 | Fwd | CCGGTACCTGGGCCAGTGATATCTTGATCGC CAACAACAACAGCTG (SEQ ID NO: 331) | 4.0 |
| | | 1202772 | Rev | ATCACTGGCCCAGGTACCGGGGACGTCGTC (SEQ ID NO: 332) | 6.4 |
| *Aspergillus aculeatus* GH61 | N152L | 1202773 | Fwd | CCGGTACCTGGGCCAGTGATCTCTTGATCGC CAACAACAACAGCTG (SEQ ID NO: 333) | 4.0 |
| | | 1202772 | Rev | ATCACTGGCCCAGGTACCGGGGACGTCGTC (SEQ ID NO: 334) | 6.4 |
| *Aspergillus aculeatus* GH61 | G186F | 1202774 | Fwd | AAATCATTGCCCTTCACTCTGCTTTCAACAAG GATGGTGCTCAGAACTA (SEQ ID NO: 335) | 3.9 |
| | | 1202775 | Rev | AGCAGAGTGAAGGGCAATGATTTCGTGACGG AG (SEQ ID NO: 336) | 6.3 |
| *Aspergillus aculeatus* GH61 | G186M | 1202776 | Fwd | AAATCATTGCCCTTCACTCTGCTATGAACAAG GATGGTGCTCAGAACTA (SEQ ID NO: 337) | 3.9 |
| | | 1202775 | Rev | AGCAGAGTGAAGGGCAATGATTTCGTGACGG AG (SEQ ID NO: 338) | 6.3 |
| *Aspergillus aculeatus* GH61 | G186A | 1202777 | Fwd | AAATCATTGCCCTTCACTCTGCTGCCAACAAG GATGGTGCTCAGAACTA (SEQ ID NO: 339) | 3.9 |
| | | 1202775 | Rev | AGCAGAGTGAAGGGCAATGATTTCGTGACGG AG (SEQ ID NO: 340) | 6.3 |
| *Aspergillus aculeatus* GH61 | G186W | 1202778 | Fwd | AAATCATTGCCCTTCACTCTGCTTGGAACAAG GATGGTGCTCAGAACTA (SEQ ID NO: 341) | 3.9 |
| | | 1202775 | Rev | AGCAGAGTGAAGGGCAATGATTTCGTGACGG AG (SEQ ID NO: 342) | 6.3 |
| *Aspergillus aculeatus* GH61 | N187H | 1202779 | Fwd | CATTGCCCTTCACTCTGCTGGTCACAAGGATG GTGCTCAGAACTACC (SEQ ID NO: 343) | 3.9 |
| | | 1202780 | Rev | ACCAGCAGAGTGAAGGGCAATGATTTCGTGA CGG (SEQ ID NO: 344) | 6.3 |
| *Aspergillus aculeatus* GH61 | N187K | 1202781 | Fwd | CATTGCCCTTCACTCTGCTGGTAAGAAGGATG GTGCTCAGAACTACC (SEQ ID NO: 345) | 3.9 |
| | | 1202780 | Rev | ACCAGCAGAGTGAAGGGCAATGATTTCGTGA CGG (SEQ ID NO: 346) | 6.3 |

Example 22: Expression of the *T. aurantiacus* GH61A, *P. emersonii* GH61A, and *A. aculeatus* GH61 Polypeptides Variants in *Aspergillus oryzae* COLs1300

*Aspergillus oryzae* COLs1300 was inoculated onto a COVE-N-Gly plate containing 10 mM urea and incubated at 34° C. until confluent. Spores were collected from the plate by washing with 10 ml of YP medium. The whole spore flask and the shake flask was then incubated at 37° C. with mixing at 65 rpm for 45-90 minutes until protoplasting was complete. The mycelia/protoplast mixture was filtered through a funnel lined with MIRACLOTH® in a 50 ml conical tube and overlayed with 5 ml of ST. The 50 ml conical tube was centrifuged at 1050×g for 15 minutes with slow acceleration/deceleration. After centrifugation, the liquid was separated in 3 phases. The interphase which contained the protoplasts was transferred to a new 50 ml conical tube. Two volumes of STC were added to the protoplasts followed by a brief centrifugation at 1050×g for 5 minutes. The supernatant was discarded and the protoplasts were washed twice with 5 ml of STC with resuspension of the protoplast pellet, centrifugation at 1050×g for 5 minutes, and decanting of the supernatant each time. After the final decanting, the protoplast pellet was resuspended in STC at a concentration of 5×10$^7$/ml. Protoplasts were frozen at −80° C. until transformation.

A 15 µl volume of each mutant fragment, as described in Example 21, was used to transform 100 µl of *A. oryzae* COLs1300 protoplasts in a 15 ml round bottom tube. After an initial incubation at room temperature for 15 minutes, 300 µl of PEG solution was added to the 15 ml round bottom tube containing the transformation mixture. The reaction was incubated for an additional 15 minutes at room temperature. Six ml of melted top agar were added to the reaction and the whole mixture was poured evenly onto a sucrose agar plate supplemented with 10 mM NaNO$_3$ and left at room temperature until the top agar was set. The plates were incubated at 37° C. for 4-6 days. Resulting transformants were picked using sterile inoculating loops and inoculated into a 96 well flat bottom plate contain 200 µl of MDU2BP per well. The plate was incubated at 34° C., stationary in a humidified box. Samples were harvested on the third day by removing the mycelia mat.

Example 23: Determination of Tm (Melting Temperature) of *Thermoascus aurantiacus* GH61A, *Penicillium emersonii* GH61A, and *Aspergillus aculeatus* GH61 Polypeptide Variants by Protein Thermal Unfolding Analysis Protein thermal unfolding of the *Thermoascus aurantiacus* GH61A, *Penicillium emersonii* GH61A, and *Aspergillus aculeatus* GH61 polypeptide variants was determined by protein thermal unfolding analysis described according to Example 10. The *Thermoascus aurantiacus* GH61A, *Penicillium emersonii* GH61A, and *Aspergillus aculeatus* GH61 polypeptide variants and wild type polypeptides thereof were prepared as described in Example 22. The results of the thermostability determinations are shown in Table 14.

TABLE 14

Melting temperatures (° C.) of *Thermoascus aurantiacus* GH61A, *Penicillium emersonii* GH61A, *Aspergillus aculeatus* GH61 polypeptide variants determined by protein thermal unfolding analysis

| Protein backbone | Mutations | Tm |
| --- | --- | --- |
| *T. aurantiacus* GH61 | Wild-Type | 75 |
| *T. aurantiacus* GH61 | Q188F | 78 |
| *T. aurantiacus* GH61 | Q188M | 76 |
| *P. emersonii* GH61 | Wild-Type | 71 |
| *P. emersonii* GH61 | N192M | 74 |
| *P. emersonii* GH61 | N193H | 73 |
| *A. aculeatus* GH61 | Wild-Type | 46 |
| *A. aculeatus* GH61 | D103K | 48 |
| *A. aculeatus* GH61 | D103P | 48 |
| *A. aculeatus* GH61 | N152I | 48 |
| *A. aculeatus* GH61 | N152L | 49 |
| *A. aculeatus* GH61 | G186F | 51 |
| *A. aculeatus* GH61 | G186M | 51 |
| *A. aculeatus* GH61 | G186A | 48 |
| *A. aculeatus* GH61 | G186W | 49 |
| *A. aculeatus* GH61 | N187H | 48 |
| *A. aculeatus* GH61 | N187K | 48 |

The present invention is further described by the following numbered paragraphs:

[1] A GH61 polypeptide variant, comprising a substitution at one or more positions corresponding to positions 105, 154, 188, 189, 216, and 229 of the mature polypeptide of 30, wherein the variant has cellulolytic enhancing activity.

[2] The variant of paragraph 1, which has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the amino acid sequence of a parent GH61 polypeptide.

[3] The variant of any of paragraphs 1 or 2, which is a variant of a parent GH61 polypeptide selected from the group consisting of: (a) a polypeptide having at least 60% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, or 179, 181, 183, 185, 187, 189, 191, 193, 195, 197, 199, 201, 203, 205, 207, 209, 211, 213, or 215, or (ii) the full-length complement of (i); (c) a polypeptide encoded by a polynucleotide having at least 60% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, or 179, 181, 183, 185, 187, 189, 191, 193, 195, 197, 199, 201, 203, 205, 207, 209, 211, 213, or 215; and (d) a fragment of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216, which has cellulolytic enhancing activity.

[4] The variant of paragraph 3, wherein the parent GH61 polypeptide has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99% or 100% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216.

[5] The variant of paragraph 3, wherein the parent GH61 polypeptide is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, or 179, 181, 183, 185, 187, 189, 191, 193, 195, 197, 199, 201, 203, 205, 207, 209, 211, 213, or 215, or (ii) the full-length complement of (i).

[6] The variant of paragraph 3, wherein the parent GH61 polypeptide is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, or 179, 181, 183, 185, 187, 189, 191, 193, 195, 197, 199, 201, 203, 205, 207, 209, 211, 213, or 215.

[7] The variant of paragraph 3, wherein the parent GH61 polypeptide comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216.

[8] The variant of paragraph 3, wherein the parent GH61 polypeptide is a fragment of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, or 179, 181, 183, 185, 187, 189, 191, 193, 195, 197, 199, 201, 203, 205, 207, 209, 211, 213, or 215, wherein the fragment has cellulolytic enhancing activity.

[9] The variant of any of paragraphs 1-8, which has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, or 180, 182, 184, 186, 188, 190, 192, 194, 196, 198, 200, 202, 204, 206, 208, 210, 212, 214, or 216.

[10] The variant of any of paragraphs 2-9, wherein the variant consists of at least 85% of the amino acid residues, e.g., at least 90% of the amino acid residues or at least 95% of the amino acid residues of the mature polypeptide of the parent GH61 polypeptide.

[11] The variant of any of paragraphs 1-10, wherein the number of substitutions is 1-6, e.g., 1, 2, 3, 4, 5, or 6 substitutions.

[12] The variant of any of paragraphs 1-11, which comprises a substitution at a position corresponding to position 105.

[13] The variant of paragraph 12, wherein the substitution is Pro or Lys.

[14] The variant of any of paragraphs 1-13, which comprises a substitution at a position corresponding to position 154.

[15] The variant of paragraph 14, wherein the substitution is Ile or Leu.

[16] The variant of any of paragraphs 1-15, which comprises a substitution at a position corresponding to position 188.

[17] The variant of paragraph 16, wherein the substitution is Ala, Met, Phe, or Trp.

[18] The variant of any of paragraphs 1-17, which comprises a substitution at a position corresponding to position 189.

[19] The variant of paragraph 18, wherein the substitution is His or Lys.

[20] The variant of any of paragraphs 1-19, which comprises a substitution at a position corresponding to position 216.

[21] The variant of paragraph 20, wherein the substitution is Leu or Tyr.

[22] The variant of any of paragraphs 1-21, which comprises a substitution at a position corresponding to position 229.

[23] The variant of paragraph 22, wherein the substitution is Trp, His, Ile, or Tyr.

[24] The variant of any of paragraphs 1-23, which comprises a substitution at two positions corresponding to any of positions 105, 154, 188, 189, 216, and 229.

[25] The variant of any of paragraphs 1-23, which comprises a substitution at three positions corresponding to any of positions 105, 154, 188, 189, 216, and 229.

[26] The variant of any of paragraphs 1-23, which comprises a substitution at four positions corresponding to any of positions 105, 154, 188, 189, 216, and 229.

[27] The variant of any of paragraphs 1-23, which comprises a substitution at five positions corresponding to any of positions 105, 154, 188, 189, 216, and 229.

[28] The variant of any of paragraphs 1-23, which comprises a substitution at each position corresponding to positions 105, 154, 188, 189, 216, and 229.

[29] The variant of any of paragraphs 1-28, which comprises one or more substitutions or corresponding substitutions selected from the group consisting of E105P,K; E154I,L; G188A,F,M,W; N189H,K; A216L,Y; and K229W,H,I,Y.

[30] The variant of any of paragraphs 1-29, which comprises the substitutions E105P,K and E154I,L; or corresponding substitutions thereof.

[31] The variant of any of paragraphs 1-29, which comprises the substitutions E105P,K and G188A,F,M,W; or corresponding substitutions thereof.

[32] The variant of any of paragraphs 1-29, which comprises the substitutions E105P,K and N189H,K; or corresponding substitutions thereof.

[33] The variant of any of paragraphs 1-29, which comprises the substitutions E105P,K and A216L,Y; or corresponding substitutions thereof.
[34] The variant of any of paragraphs 1-29, which comprises the substitutions E105P,K and K229W,H,I,Y; or corresponding substitutions thereof.
[35] The variant of any of paragraphs 1-29, which comprises the substitutions E154I,L and G188A,F,M,W; or corresponding substitutions thereof.
[36] The variant of any of paragraphs 1-29, which comprises the substitutions E154I,L and N189H,K; or corresponding substitutions thereof.
[37] The variant of any of paragraphs 1-29, which comprises the substitutions E154I,L and A216L,Y; or corresponding substitutions thereof.
[38] The variant of any of paragraphs 1-29, which comprises the substitutions E154I,L and K229W,H,I,Y; or corresponding substitutions thereof.
[39] The variant of any of paragraphs 1-29, which comprises the substitutions G188A,F,M,W and N189H,K; or corresponding substitutions thereof.
[40] The variant of any of paragraphs 1-29, which comprises the substitutions G188A,F,M,W and A216L,Y; or corresponding substitutions thereof.
[41] The variant of any of paragraphs 1-29, which comprises the substitutions G188A,F,M,W and K229W,H,I,Y; or corresponding substitutions thereof.
[42] The variant of any of paragraphs 1-29, which comprises the substitutions N189H,K and A216L,Y; or corresponding substitutions thereof.
[43] The variant of any of paragraphs 1-29, which comprises the substitutions N189H,K and K229W,H,I,Y; or corresponding substitutions thereof.
[44] The variant of any of paragraphs 1-29, which comprises the substitutions A216L,Y and K229W,H,I,Y; or corresponding substitutions thereof.
[45] The variant of any of paragraphs 1-29, which comprises the substitutions E105P,K; E154I,L; and G188A,F,M,W; or corresponding substitutions thereof.
[46] The variant of any of paragraphs 1-29, which comprises the substitutions E105P,K; E154I,L; and N189H,K; or corresponding substitutions thereof.
[47] The variant of any of paragraphs 1-29, which comprises the substitutions E105P,K; E154I,L; and A216L,Y; or corresponding substitutions thereof.
[48] The variant of any of paragraphs 1-29, which comprises the substitutions E105P,K; E154I,L; and K229W,H,I,Y; or corresponding substitutions thereof.
[49] The variant of any of paragraphs 1-29, which comprises the substitutions E105P,K; G188A,F,M,W; and N189H,K; or corresponding substitutions thereof.
[50] The variant of any of paragraphs 1-29, which comprises the substitutions E105P,K; G188A,F,M,W; and A216L,Y; or corresponding substitutions thereof.
[51] The variant of any of paragraphs 1-29, which comprises the substitutions E105P,K; G188A,F,M,W; and K229W,H,I,Y; or corresponding substitutions thereof.
[52] The variant of any of paragraphs 1-29, which comprises the substitutions E105P,K; N189H,K; and A216L,Y; or corresponding substitutions thereof.
[53] The variant of any of paragraphs 1-29, which comprises the substitutions E105P,K; N189H,K; and K229W,H,I,Y; or corresponding substitutions thereof.
[54] The variant of any of paragraphs 1-29, which comprises the substitutions E105P,K; A216L,Y; and K229W,H,I,Y; or corresponding substitutions thereof.
[55] The variant of any of paragraphs 1-29, which comprises the substitutions E154I,L; G188A,F,M,W; and N189H,K; or corresponding substitutions thereof.
[56] The variant of any of paragraphs 1-29, which comprises the substitutions E154I,L; G188A,F,M,W; and A216L,Y; or corresponding substitutions thereof.
[57] The variant of any of paragraphs 1-29, which comprises the substitutions E154I,L; G188A,F,M,W; and K229W,H,I,Y; or corresponding substitutions thereof.
[58] The variant of any of paragraphs 1-29, which comprises the substitutions E154I,L; N189H,K; and A216L,Y; or corresponding substitutions thereof.
[59] The variant of any of paragraphs 1-29, which comprises the substitutions E154I,L; N189H,K; and K229W,H,I,Y; or corresponding substitutions thereof.
[60] The variant of any of paragraphs 1-29, which comprises the substitutions E154I,L; A216L,Y; and K229W,H,I,Y; or corresponding substitutions thereof.
[61] The variant of any of paragraphs 1-29, which comprises the substitutions G188A,F,M,W; N189H,K; and A216L,Y; or corresponding substitutions thereof.
[62] The variant of any of paragraphs 1-29, which comprises the substitutions G188A,F,M,W; N189H,K; and K229W,H,I,Y; or corresponding substitutions thereof.
[63] The variant of any of paragraphs 1-29, which comprises the substitutions G188A,F,M,W; A216L,Y; and K229W,H,I,Y; or corresponding substitutions thereof.
[64] The variant of any of paragraphs 1-29, which comprises the substitutions N189H,K; A216L,Y; and K229W,H,I,Y; or corresponding substitutions thereof.
[65] The variant of any of paragraphs 1-29, which comprises the substitutions E105P,K; E154I,L; G188A,F,M,W; and N189H,K; or corresponding substitutions thereof.
[66] The variant of any of paragraphs 1-29, which comprises the substitutions E105P,K; E154I,L; G188A,F,M,W; and A216L,Y; or corresponding substitutions thereof.
[67] The variant of any of paragraphs 1-29, which comprises the substitutions E105P,K; E154I,L; G188A,F,M,W; and K229W,H,I,Y; or corresponding substitutions thereof.
[68] The variant of any of paragraphs 1-29, which comprises the substitutions E105P,K; E154I,L; N189H,K; and A216L,Y; or corresponding substitutions thereof.
[69] The variant of any of paragraphs 1-29, which comprises the substitutions E105P,K; E154I,L; N189H,K; and K229W,H,I,Y; or corresponding substitutions thereof.
[70] The variant of any of paragraphs 1-29, which comprises the substitutions E105P,K; E154I,L; A216L,Y; and K229W,H,I,Y; or corresponding substitutions thereof.
[71] The variant of any of paragraphs 1-29, which comprises the substitutions E105P,K; G188A,F,M,W; N189H,K; and A216L,Y; or corresponding substitutions thereof.
[72] The variant of any of paragraphs 1-29, which comprises the substitutions E105P,K; G188A,F,M,W; N189H,K; and K229W,H,I,Y; or corresponding substitutions thereof.
[73] The variant of any of paragraphs 1-29, which comprises the substitutions E105P,K; G188A,F,M,W; A216L,Y; and K229W,H,I,Y; or corresponding substitutions thereof.
[74] The variant of any of paragraphs 1-29, which comprises the substitutions E105P,K; N189H,K; A216L,Y; and K229W,H,I,Y; or corresponding substitutions thereof.
[75] The variant of any of paragraphs 1-29, which comprises the substitutions E154I,L; G188A,F,M,W; N189H,K; and A216L,Y; or corresponding substitutions thereof.
[76] The variant of any of paragraphs 1-29, which comprises the substitutions E154I,L; G188A,F,M,W; N189H,K; and K229W,H,I,Y; or corresponding substitutions thereof.

[77] The variant of any of paragraphs 1-29, which comprises the substitutions E154I,L; G188A,F,M,W; A216L,Y; and K229W,H,I,Y; or corresponding substitutions thereof.

[78] The variant of any of paragraphs 1-29, which comprises the substitutions E154I,L; N189H,K; A216L,Y; and K229W,H,I,Y; or corresponding substitutions thereof.

[79] The variant of any of paragraphs 1-29, which comprises the substitutions G188A,F,M,W; N189H,K; A216L,Y; and K229W,H,I,Y; or corresponding substitutions thereof.

[80] The variant of any of paragraphs 1-29, which comprises the substitutions E105P,K; E154I,L; G188A,F,M,W; N189H,K; and A216L,Y; or corresponding substitutions thereof.

[81] The variant of any of paragraphs 1-29, which comprises the substitutions E105P,K; E154I,L; G188A,F,M,W; N189H,K; and K229W,H,I,Y; or corresponding substitutions thereof.

[82] The variant of any of paragraphs 1-29, which comprises the substitutions E105P,K; E154I,L; G188A,F,M,W; A216L,Y; and K229W,H,I,Y; or corresponding substitutions thereof.

[83] The variant of any of paragraphs 1-29, which comprises the substitutions E105P,K; E154I,L; N189H,K; A216L,Y; and K229W,H,I,Y; or corresponding substitutions thereof.

[84] The variant of any of paragraphs 1-29, which comprises the substitutions E105P,K; G188A,F,M,W; N189H,K; A216L,Y; and K229W,H,I,Y; or corresponding substitutions thereof.

[85] The variant of any of paragraphs 1-29, which comprises the substitutions E154I,L; G188A,F,M,W; N189H,K; A216L,Y; and K229W,H,I,Y; or corresponding substitutions thereof.

[86] The variant of any of paragraphs 1-29, which comprises the substitutions E105P,K; E154I,L; G188A,F,M,W; N189H,K; A216L,Y; and K229W,H,I,Y; or corresponding substitutions thereof.

[87] The variant of any of paragraphs 1-86, which further comprises a substitution at one or more positions corresponding to positions 111, 152, 155, and 162 of the mature polypeptide of 30, wherein the variant has cellulolytic enhancing activity.

[88] The variant of paragraph 87, wherein the number of substitutions is 1-4, e.g., such as 1, 2, 3, or 4 substitutions.

[89] The variant of paragraph 87 or 88, which comprises a substitution at a position corresponding to position 111.

[90] The variant of paragraph 89, wherein the substitution is Val.

[91] The variant of any of paragraphs 87-90, which comprises a substitution at a position corresponding to position 152.

[92] The variant of paragraph 91, wherein the substitution is Ser.

[93] The variant of any of paragraphs 87-92, which comprises a substitution at a position corresponding to position 155.

[94] The variant of paragraph 93, wherein the substitution is Leu.

[95] The variant of any of paragraphs 87-94, which comprises a substitution at a position corresponding to position 162.

[96] The variant of paragraph 95, wherein the substitution is Trp.

[97] The variant of any of paragraphs 87-96, which comprises a substitution at two positions corresponding to any of positions 111, 152, 155, and 162.

[98] The variant of any of paragraphs 87-96, which comprises a substitution at three positions corresponding to any of positions 111, 152, 155, and 162.

[99] The variant of any of paragraphs 87-96, which comprises a substitution at each position corresponding to positions 111, 152, 155, and 162.

[100] The variant of any of paragraphs 87-99, which comprises one or more substitutions or corresponding substitutions selected from the group consisting of L111V, D152S, M155L, and A162W.

[101] The variant of any of paragraphs 87-100, which comprises the substitutions L111V+D152S; or corresponding substitutions thereof.

[102] The variant of any of paragraphs 87-100, which comprises the substitutions L111V+M155L; or corresponding substitutions thereof.

[103] The variant of any of paragraphs 87-100, which comprises the substitutions L111V+A162W; or corresponding substitutions thereof.

[104] The variant of any of paragraphs 87-100, which comprises the substitutions D152S+M155L; or corresponding substitutions thereof.

[105] The variant of any of paragraphs 87-100, which comprises the substitutions D152S+A162W; or corresponding substitutions thereof.

[106] The variant of any of paragraphs 87-100, which comprises the substitutions M155L+A162W; or corresponding substitutions thereof.

[107] The variant of any of paragraphs 87-100, which comprises the substitutions L111V+D152S+M155L; or corresponding substitutions thereof.

[108] The variant of any of paragraphs 87-100, which comprises the substitutions L111V+D152S+A162W; or corresponding substitutions thereof.

[109] The variant of any of paragraphs 87-100, which comprises the substitutions L111V+M155L+A162W; or corresponding substitutions thereof.

[110] The variant of any of paragraphs 87-100, which comprises the substitutions D152S+M155L+A162W; or corresponding substitutions thereof.

[111] The variant of any of paragraphs 87-100, which comprises the substitutions L111V+D152S+M155L+A162W; or corresponding substitutions thereof.

[112] The variant of any of paragraphs 1-111, which further comprises a substitution at one or more positions corresponding to positions 96, 98, 200, 202, and 204 of the mature polypeptide of 30, wherein the variant has cellulolytic enhancing activity.

[113] The variant of paragraph 112, wherein the number of substitutions is 1-5, e.g., such as 1, 2, 3, 4, or 5 substitutions.

[114] The variant of paragraph 112 or 113, which comprises a substitution at a position corresponding to position 96.

[115] The variant of paragraph 114, wherein the substitution is Val.

[116] The variant of any of paragraphs 112-115, which comprises a substitution at a position corresponding to position 98.

[117] The variant of paragraph 116 wherein the substitution is Leu.

[118] The variant of any of paragraphs 112-117, which comprises a substitution at a position corresponding to position 200.

[119] The variant of paragraph 118, wherein the substitution is Ile.

[120] The variant of any of paragraphs 112-119, which comprises a substitution at a position corresponding to position 202.

[121] The variant of paragraph 120, wherein the substitution is Leu.

[122] The variant of any of paragraphs 112-121, which comprises a substitution at a position corresponding to position 204.

[123] The variant of paragraph 120, wherein the substitution is Val.

[124] The variant of any of paragraphs 112-123, which comprises a substitution at two positions corresponding to any of positions 96, 98, 200, 202, and 204.

[125] The variant of any of paragraphs 112-123, which comprises a substitution at three positions corresponding to any of positions 96, 98, 200, 202, and 204.

[126] The variant of any of paragraphs 112-123, which comprises a substitution at four positions corresponding to any of positions 96, 98, 200, 202, and 204.

[127] The variant of any of paragraphs 112-123, which comprises a substitution at each position corresponding to positions 96, 98, 200, 202, and 204.

[128] The variant of any of paragraphs 112-127, which comprises one or more substitutions or corresponding substitutions selected from the group consisting of I96V, F98L, F200I, I202L, and I204V.

[129] The variant of any of paragraphs 112-128, which comprises the substitutions I96V+F98L; or corresponding substitutions thereof.

[130] The variant of any of paragraphs 112-128, which comprises the substitutions I96V+F200I; or corresponding substitutions thereof.

[131] The variant of any of paragraphs 112-128, which comprises the substitutions I96V+I202L; or corresponding substitutions thereof.

[132] The variant of any of paragraphs 112-128, which comprises the substitutions I96V+I204V; or corresponding substitutions thereof.

[133] The variant of any of paragraphs 112-128, which comprises the substitutions F98L+F200I; or corresponding substitutions thereof.

[134] The variant of any of paragraphs 112-128, which comprises the substitutions F98L+I202L; or corresponding substitutions thereof.

[135] The variant of any of paragraphs 112-128, which comprises the substitutions F98L+I204V; or corresponding substitutions thereof.

[136] The variant of any of paragraphs 112-128, which comprises the substitutions F200I+I202L; or corresponding substitutions thereof.

[137] The variant of any of paragraphs 112-128, which comprises the substitutions F200I+I204V; or corresponding substitutions thereof.

[138] The variant of any of paragraphs 112-128, which comprises the substitutions I202L+I204V; or corresponding substitutions thereof.

[139] The variant of any of paragraphs 112-128, which comprises the substitutions I96V+F98L+F200I; or corresponding substitutions thereof.

[140] The variant of any of paragraphs 112-128, which comprises the substitutions I96V+F98L+I202L; or corresponding substitutions thereof.

[141] The variant of any of paragraphs 112-128, which comprises the substitutions I96V+F98L+I204V; or corresponding substitutions thereof.

[142] The variant of any of paragraphs 112-128, which comprises the substitutions I96V+F200I+I202L; or corresponding substitutions thereof.

[143] The variant of any of paragraphs 112-128, which comprises the substitutions I96V+F200I+I204V; or corresponding substitutions thereof.

[144] The variant of any of paragraphs 112-128, which comprises the substitutions I96V+I202L+I204V; or corresponding substitutions thereof.

[145] The variant of any of paragraphs 112-128, which comprises the substitutions F98L+F200I+I202L; or corresponding substitutions thereof.

[146] The variant of any of paragraphs 112-128, which comprises the substitutions F98L+F200I+I204V; or corresponding substitutions thereof.

[147] The variant of any of paragraphs 112-128, which comprises the substitutions F200I+I202L+I204V; or corresponding substitutions thereof.

[148] The variant of any of paragraphs 112-128, which comprises the substitutions F98L+I202L+I204V; or corresponding substitutions thereof.

[149] The variant of any of paragraphs 112-128, which comprises the substitutions I96V+F98L+F200I+I202L; or corresponding substitutions thereof.

[150] The variant of any of paragraphs 112-128, which comprises the substitutions I96V+F200I+I202L+I204V; or corresponding substitutions thereof.

[151] The variant of any of paragraphs 112-128, which comprises the substitutions I96V+F98L+I202L+I204V; or corresponding substitutions thereof.

[152] The variant of any of paragraphs 112-128, which comprises the substitutions I96V+F98L+F200I+I204V; or corresponding substitutions thereof.

[153] The variant of any of paragraphs 112-128, which comprises the substitutions F98L+F200I+I202L+I204V; or corresponding substitutions thereof.

[154] The variant of any of paragraphs 112-128, which comprises the substitutions I96V+F98L+F200I+I202L+I204V; or corresponding substitutions thereof.

[155] The variant of any of paragraphs 1-154, wherein the thermostability of the variant is increased at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 50-fold, at least 75-fold, or at least 100-fold compared to the parent.

[156] An isolated polynucleotide encoding the variant of any of paragraphs 1-155.

[157] A nucleic acid construct comprising the polynucleotide of paragraph 156.

[158] An expression vector comprising the polynucleotide of paragraph 156.

[159] A host cell comprising the polynucleotide of paragraph 156.

[160] A method of producing a GH61 polypeptide variant, comprising: cultivating the host cell of paragraph 159 under conditions suitable for expression of the variant.

[161] The method of paragraph 160, further comprising recovering the variant.

[162] A transgenic plant, plant part or plant cell transformed with the polynucleotide of paragraph 156.

[163] A method of producing a variant of any of paragraphs 1-155, comprising: cultivating a transgenic plant or a plant cell comprising a polynucleotide encoding the variant under conditions conducive for production of the variant.

[164] The method of paragraph 163, further comprising recovering the variant.

[165] A method for obtaining a GH61 polypeptide variant, comprising introducing into a parent GH61 polypeptide a substitution at one or more positions corresponding to positions 105, 154, 188, 189, 216, and 229 of the mature polypeptide of 30, wherein the variant has cellulolytic enhancing activity; and optionally recovering the variant.

[166] The method of paragraph 165, further comprising introducing into the parent GH61 polypeptide a substitution at one or more (e.g., several) positions corresponding to positions 111, 152, 155, and 162 of the mature polypeptide of 30, wherein the variant has cellulolytic enhancing activity.

[167] The method of paragraph 165 or 166, further comprising introducing into the parent GH61 polypeptide a substitution at one or more (e.g., several) positions corresponding to positions 96, 98, 200, 202, and 204 of the mature polypeptide of 30, wherein the variant has cellulolytic enhancing activity.

[168] A process for degrading or converting a cellulosic material, comprising: treating the cellulosic material with an enzyme composition in the presence of the GH61 polypeptide variant having cellulolytic enhancing activity of any of paragraphs 1-155.

[169] The process of paragraph 168, wherein the cellulosic material is pretreated.

[170] The process of paragraph 168 or 169, further comprising recovering the degraded cellulosic material.

[171] The process of any of paragraphs 168-170, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[172] The process of paragraph 171, wherein the cellulase is one or more enzymes selected from the group consisting of an endoglucanase, a endoglucanase, and a beta-glucosidase.

[173] The process of paragraph 171, wherein the hemicellulase is one or more enzymes selected from the group consisting of a xylanase, an acetyxylan esterase, a feruloyl esterase, an arabinofuranosidase, a xylosidase, and a glucuronidase.

[174] The process of any of paragraphs 168-173, wherein the degraded cellulosic material is a sugar.

[175] The process of paragraph 174, wherein the sugar is selected from the group consisting of glucose, xylose, mannose, galactose, and arabinose.

[176] A process for producing a fermentation product, comprising: (a) saccharifying a cellulosic material with an enzyme composition in the presence of the GH61 polypeptide variant having cellulolytic enhancing activity of any of paragraphs 1-155; (b) fermenting the saccharified cellulosic material with one or more fermenting microorganisms to produce the fermentation product; and (c) recovering the fermentation product from the fermentation.

[177] The process of paragraph 176, wherein the cellulosic material is pretreated.

[178] The process of paragraph 176 or 177, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[179] The process of paragraph 178, wherein the cellulase is one or more enzymes selected from the group consisting of an endoglucanase, a endoglucanase, and a beta-glucosidase.

[180] The process of paragraph 178, wherein the hemicellulase is one or more enzymes selected from the group consisting of a xylanase, an acetyxylan esterase, a feruloyl esterase, an arabinofuranosidase, a xylosidase, and a glucuronidase.

[181] The process of any of paragraphs 176-180, wherein steps (a) and (b) are performed simultaneously in a simultaneous saccharification and fermentation.

[182] The process of any of paragraphs 176-181, wherein the fermentation product is an alcohol, an alkane, a cycloalkane, an alkene, an amino acid, a gas, isoprene, a ketone, an organic acid, or polyketide.

[183] A process of fermenting a cellulosic material, comprising: fermenting the cellulosic material with one or more fermenting microorganisms, wherein the cellulosic material is saccharified with an enzyme composition in the presence of the GH61 polypeptide variant having cellulolytic enhancing activity of any of paragraphs 1-155.

[184] The process of paragraph 183, wherein the cellulosic material is pretreated before saccharification.

[185] The process of paragraph 183 or 184, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[186] The process of paragraph 185, wherein the cellulase is one or more enzymes selected from the group consisting of an endoglucanase, a endoglucanase, and a beta-glucosidase.

[187] The process of paragraph 185, wherein the hemicellulase is one or more enzymes selected from the group consisting of a xylanase, an acetyxylan esterase, a feruloyl esterase, an arabinofuranosidase, a xylosidase, and a glucuronidase.

[188] The process of any of paragraphs 183-187, wherein the fermenting of the cellulosic material produces a fermentation product.

[189] The process of paragraph 189, further comprising recovering the fermentation product from the fermentation.

[190] The process of paragraph 188 or 189, wherein the fermentation product is an alcohol, an alkane, a cycloalkane, an alkene, an amino acid, a gas, isoprene, a ketone, an organic acid, or polyketide.

[191] A whole broth formulation or cell culture composition, comprising the variant of any of paragraphs 1-155.

[192] A detergent composition, comprising a surfactant and the variant of any of paragraphs 1-155.

[193] The composition of paragraph 192, further comprising one or more (e.g., several) enzymes selected from the group consisting of an amylase, arabinase, cutinase, carbohydrase, cellulase, galactanase, laccase, lipase, mannanase, oxidase, pectinase, peroxidase, protease, and xylanase.

[194] The composition of paragraph 192 or 193, which is formulated as a bar, a tablet, a powder, a granule, a paste, or a liquid.

[195] A method for cleaning or washing a hard surface or laundry, the method comprising contacting the hard surface or the laundry with the composition of any of paragraphs 192-194.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A variant GH61 polypeptide having cellulolytic enhancing activity, comprising a substitution at one or more positions corresponding to positions 105, 154, 188, 189, 216, and 229 of the mature polypeptide of SEQ ID NO: 30, wherein the substitution at position 105 is with Pro or Lys, the substitution at position 154 is with Ile or Leu, the substitution at position 188 is with Ala, Phe, Met, or Trp, the substitution at position 189 is with His or Lys, the substitution at position 216 is with Leu or Tyr, and the substitution at position 229 is with Trp, His, Ile, or Tyr, wherein the variant has cellulolytic enhancing activity, wherein the variant has increased thermostability relative to a GH61 polypeptide without the substitution at the one or more positions corresponding to positions 105, 154, 188, 189, 216, and 229 of the mature polypeptide of SEQ ID NO: 30, and wherein the variant has at least 95% sequence identity, but less than 100% sequence identity, to the mature polypeptide of SEQ ID NO: 30.

2. The variant of claim 1, wherein the variant comprises one or more of the substitution at position 105 with Pro or Lys, the substitution at position 154 with Be or Leu, the substitution at position 188 with Ala, Phe, Met, or Trp, the substitution at position 189 with His or Lys, the substitution at position 216 with Leu or Tyr, and the substitution at position 229 with Trp, His, Ile, or Tyr of the mature polypeptide of SEQ ID NO: 30.

3. The variant of claim 1, which further comprises a substitution at one or more positions corresponding to positions 111, 152, 155, and 162 of the mature polypeptide of SEQ ID NO: 30, wherein the substitution at position 111 is with Val, the substitution at position 152 is with Ser, the substitution at position 155 is with Leu, and the substitution at position 162 is with Trp, and wherein the variant has cellulolytic enhancing activity.

4. The variant of claim 1, wherein the thermostability of the variant is increased at least 1.01-fold compared to the parent.

5. An isolated polynucleotide encoding the GH61 polypeptide variant of claim 1.

6. A method of producing a GH61 polypeptide variant, comprising: (a) cultivating a host cell comprising the polynucleotide of claim 5 under conditions suitable for expression of the variant; and optionally (b) recovering the variant.

7. A transgenic plant, plant part or plant cell transformed with the polynucleotide of claim 5.

8. A method of producing the GH61 polypeptide variant of claim 1, comprising: (a) cultivating a transgenic plant or a plant cell comprising a polynucleotide encoding the variant under conditions conducive for production of the variant; and optionally (b) recovering the variant.

9. A process for degrading or converting a cellulosic material, comprising: treating the cellulosic material with an enzyme composition comprising the GH61 polypeptide variant having cellulolytic enhancing activity of claim 1.

10. A process for producing a fermentation product, comprising: (a) saccharifying a cellulosic material with an enzyme composition comprising the GH61 polypeptide variant having cellulolytic enhancing activity of claim 1; (b) fermenting the saccharified cellulosic material with one or more fermenting microorganisms to produce the fermentation product; and (c) recovering the fermentation product from the fermentation.

11. A process of fermenting a cellulosic material, comprising: fermenting the cellulosic material with one or more fermenting microorganisms, wherein the cellulosic material is saccharified with an enzyme composition comprising the GH61 polypeptide variant having cellulolytic enhancing activity of claim 1.

12. A whole broth formulation or cell culture composition, comprising the GH61 polypeptide variant of claim 1.

13. A detergent composition, comprising a surfactant and the GH61 polypeptide variant of claim 1.

14. The variant of claim 1, wherein the variant has at least 96% sequence identity, but less than 100% sequence identity, to the mature polypeptide of the GH61 polypeptide of SEQ ID NO: 30.

15. The variant of claim 1, wherein the variant has at least 97% sequence identity, but less than 100% sequence identity, to the mature polypeptide of the GH61 polypeptide of SEQ ID NO: 30.

16. The variant of claim 3, wherein said variant comprises one or more substitutions or corresponding substitutions selected from the group consisting of a substitution of Leu at position 111 with Val, a substitution of Asp at position 152 with Ser, a substitution of Met at position 155 with Leu, and a substitution of Ala at position 162 with Trp.

17. The variant of claim 1, wherein the variant has at least 98% sequence identity, but less than 100% sequence identity, to the mature polypeptide of the GH61 polypeptide of SEQ ID NO: 30.

18. The variant of claim 1, wherein the variant has at least 99% sequence identity, but less than 100% sequence identity, to the mature polypeptide of the GH61 polypeptide of SEQ ID NO: 30.

19. The variant of claim 1, wherein the substitution at or corresponding to position 105 is with Pro.

20. The variant of claim 1, wherein the substitution at or corresponding to position 105 is with Lys.

21. The variant of claim 1, wherein the substitution at or corresponding to position 154 is with Ile.

22. The variant of claim 1, wherein the substitution at or corresponding to position 154 is with Leu.

23. The variant of claim 1, wherein the substitution at or corresponding to position 188 is with Ala.

24. The variant of claim 1, wherein the substitution at or corresponding to position 188 is with Phe.

25. The variant of claim 1, wherein the substitution at or corresponding to position 188 is with Met.

26. The variant of claim 1, wherein the substitution at or corresponding to position 188 is with Trp.

27. The variant of claim 1, wherein the substitution at or corresponding to position 189 is with His.

28. The variant of claim 1, wherein the substitution at or corresponding to position 189 is with Lys.

29. The variant of claim 1, wherein the substitution at or corresponding to position 216 is with Leu.

30. The variant of claim 1, wherein the substitution at or corresponding to position 216 is with Tyr.

31. The variant of claim 1, wherein the substitution at or corresponding to position 229 is with Trp.

32. The variant of claim 1, wherein the substitution at or corresponding to position 229 is with His.

33. The variant of claim 1, wherein the substitution at or corresponding to position 229 is with Ile.

34. The variant of claim 1, wherein the substitution at or corresponding to position 229 is with Tyr.

* * * * *